(12) United States Patent
Amin et al.

US009856466B2

(10) Patent No.: US 9,856,466 B2
(45) Date of Patent: Jan. 2, 2018

(54) COMPOSITIONS AND METHODS COMPRISING SERINE PROTEASE VARIANTS

(75) Inventors: Neelam S. Amin, Palo Alto, CA (US); Katherine Augustyn, Menlo Park, CA (US); Joshua R. Basler, Palo Alto, CA (US); Luis G. Cascao-Pereira, Redwood City, CA (US); Katherine D. Collier, Los Altos, CA (US); Edward M. Concar, San Francisco, CA (US); David A. Estell, San Francisco, CA (US); James T. Kellis, Jr., San Carlos, CA (US); Euan John Magennis, Tynemouth (GB); Alexander Pisarchik, Belmont, CA (US); Ayrookaran J. Poulose, Belmont, CA (US); Philip Frank Souter, Morpeth (GB); Glenn Steven Ward, Newcastle Upon Tyne (GB); Jian Yao, Sunnyvale, CA (US)

(73) Assignee: DANISCO US INC., Palo Alto, CA (US)

( * ) Notice: Subject to any disclaimer, the term of this patent is extended or adjusted under 35 U.S.C. 154(b) by 12 days.

(21) Appl. No.: 14/115,801

(22) PCT Filed: May 4, 2012

(86) PCT No.: PCT/US2012/036608
§ 371 (c)(1),
(2), (4) Date: Nov. 5, 2013

(87) PCT Pub. No.: WO2012/151534
PCT Pub. Date: Nov. 8, 2012

(65) Prior Publication Data
US 2014/0154782 A1 Jun. 5, 2014

Related U.S. Application Data

(60) Provisional application No. 61/482,938, filed on May 5, 2011.

(51) Int. Cl.
*C12N 9/54* (2006.01)
*C11D 3/386* (2006.01)

(52) U.S. Cl.
CPC .............. *C12N 9/54* (2013.01); *C11D 3/386* (2013.01)

(58) Field of Classification Search
CPC .................................. C12N 9/54; C11D 3/386
See application file for complete search history.

(56) References Cited

U.S. PATENT DOCUMENTS

| 4,302,544 A | 11/1981 | Young et al. |
|---|---|---|
| 4,430,243 A | 2/1984 | Bragg |
| 4,435,307 A | 3/1984 | Barbesgaard et al. |
| 4,450,235 A | 5/1984 | Dean et al. |
| 4,515,705 A | 5/1985 | Moeddel |
| 4,515,707 A | 5/1985 | Brooks |
| 4,537,706 A | 8/1985 | Severson, Jr. |
| 4,550,862 A | 11/1985 | Barker et al. |
| 4,561,998 A | 12/1985 | Wertz et al. |
| 4,597,898 A | 7/1986 | Vander Meer |
| 4,683,195 A | 7/1987 | Mullis et al. |
| 4,683,202 A | 7/1987 | Mullis |
| 4,760,025 A | 7/1988 | Estell et al. |
| 4,765,916 A | 8/1988 | Ogar, Jr. et al. |
| 4,810,410 A | 3/1989 | Diakun et al. |
| 4,965,188 A | 10/1990 | Mullis et al. |
| 4,968,451 A | 11/1990 | Scheibel et al. |
| 4,972,017 A | 11/1990 | Smith et al. |
| 4,977,252 A | 12/1990 | Chiu |
| 5,227,084 A | 7/1993 | Martens et al. |
| 5,264,366 A | 11/1993 | Ferrari et al. |
| RE34,606 E | 5/1994 | Estell et al. |
| 5,340,735 A | 8/1994 | Christianson et al. |
| 5,352,603 A | 10/1994 | Vetter et al. |
| 5,354,559 A | 10/1994 | Morehouse |
| 5,427,936 A | 6/1995 | Moeller et al. |
| 5,486,303 A | 1/1996 | Capeci et al. |
| 5,489,392 A | 2/1996 | Capeci et al. |
| 5,500,364 A | 3/1996 | Christianson et al. |
| 5,516,448 A | 5/1996 | Capeci et al. |
| 5,565,145 A | 10/1996 | Watson et al. |

(Continued)

FOREIGN PATENT DOCUMENTS

| CA | 2162459 | 11/1994 |
|---|---|---|
| CA | 2162460 | 11/1994 |

(Continued)

OTHER PUBLICATIONS

U.S. Appl. No. 07/573,802, filed Aug. 29, 1990, Vetter et al.
Altschul, S.F., et al., "Basic Local Alignment Search Tool." *J. Mol. Biol.* 215: 403-410, 1990.
Altschul, S.F., et al., "Basic Local Alignment Statistics." *Meth. Enzymol.* 266: 460-480, 1996.
Altschul, S.F., et al., "Gapped BLAST and PSI-BLAST: a new generation of protein database search programs." *Nucleic Acids Res.* 25(17): 3389-3402, 1997.
Arigoni, F., et al., "The SpoIIE phosphatase, the sporulation septum and the establishment of forespore-specific transcription in *Bacillus subtilis*: a reassessment." *Mol. Microbiol.* 31: 1407-1415, 1999.

(Continued)

*Primary Examiner* — Kagnew H Gebreyesus

(57) ABSTRACT

The present invention provides serine protease variants, more specifically subtilisin variants produced there from. Specifically, the present invention provides serine protease variants, more specifically subtilisin variants having one or more substitutions as compared to a reference serine protease. In addition, the present invention provides compositions comprising these serine protease variants, more specifically subtilisin variants. In some embodiments, the present invention provides cleaning compositions comprising at least one of these serine protease variants, more specifically subtilisin variants.

19 Claims, 1 Drawing Sheet

(56) References Cited

U.S. PATENT DOCUMENTS

| | | | |
|---|---|---|---|
| 5,565,422 A | 10/1996 | Del Greco et al. | |
| 5,569,645 A | 10/1996 | Dinniwell et al. | |
| 5,574,005 A | 11/1996 | Welch et al. | |
| 5,576,282 A | 11/1996 | Miracle et al. | |
| 5,595,967 A | 1/1997 | Miracle et al. | |
| 5,597,936 A | 1/1997 | Perkins et al. | |
| 5,646,101 A | 7/1997 | MacBeath | |
| 5,686,014 A | 11/1997 | Baillely et al. | |
| 5,691,297 A | 11/1997 | Nassano et al. | |
| 5,695,679 A | 12/1997 | Christie et al. | |
| 5,698,504 A | 12/1997 | Christie et al. | |
| 5,700,676 A | 12/1997 | Bott et al. | |
| 5,705,464 A | 1/1998 | Scheper et al. | |
| 5,710,115 A | 1/1998 | Patel et al. | |
| 5,801,039 A | 9/1998 | Maurer et al. | |
| 5,855,625 A | 1/1999 | Maurer et al. | |
| 5,874,276 A | 2/1999 | Fowler et al. | |
| 5,879,584 A | 3/1999 | Bianchetti et al. | |
| 5,929,022 A | 7/1999 | Velazquez | |
| 5,935,826 A | 8/1999 | Blue et al. | |
| 5,955,340 A | 9/1999 | Bott et al. | |
| 6,225,464 B1 | 5/2001 | Hiler, II et al. | |
| 6,294,514 B1 | 9/2001 | Welling | |
| 6,306,812 B1 | 10/2001 | Perkins et al. | |
| 6,312,936 B1 | 11/2001 | Poulose et al. | |
| 6,326,348 B1 | 12/2001 | Vinson et al. | |
| 6,376,445 B1 | 4/2002 | Bettiol et al. | |
| 6,376,450 B1 | 4/2002 | Ghosh et al. | |
| 6,440,991 B1 | 8/2002 | Zhu et al. | |
| 6,472,184 B1 | 10/2002 | Hegemann | |
| 6,482,628 B1 | 11/2002 | Poulose et al. | |
| 6,509,021 B1 | 1/2003 | Weiss et al. | |
| 6,566,112 B2 | 5/2003 | Jones et al. | |
| 6,566,114 B1 | 5/2003 | Kaupinnen et al. | |
| 6,602,842 B2 | 8/2003 | Cuperus et al. | |
| 6,605,458 B1 | 8/2003 | Hansen et al. | |
| 6,610,642 B2 | 8/2003 | Ghosh et al. | |
| 6,632,646 B1* | 10/2003 | Aaslyng et al. | 435/220 |
| 8,224,578 B2 | 7/2012 | Raab et al. | |
| 8,728,790 B2* | 5/2014 | Basler et al. | 435/226 |
| 8,785,171 B2* | 7/2014 | Souter et al. | 435/212 |
| 2003/0073222 A1* | 4/2003 | Poulose | A23G 4/123 435/220 |
| 2003/0191039 A1* | 10/2003 | Aaslyng et al. | 510/226 |
| 2003/0228995 A1* | 12/2003 | Poulose | A23G 4/123 510/320 |
| 2005/0202535 A1 | 9/2005 | Collier et al. | |
| 2006/0089284 A1 | 4/2006 | Miracle et al. | |
| 2008/0090747 A1 | 4/2008 | Augustinus et al. | |
| 2010/0192985 A1* | 8/2010 | Aehle et al. | 134/26 |
| 2011/0262999 A1* | 10/2011 | Basler | C12N 9/52 435/221 |
| 2013/0123162 A1* | 5/2013 | Souter et al. | 510/295 |
| 2013/0260438 A1* | 10/2013 | Alekseyev et al. | 435/221 |
| 2014/0193888 A1* | 7/2014 | Souter et al. | 435/263 |
| 2014/0273177 A1* | 9/2014 | Basler et al. | 435/264 |
| 2015/0031589 A1* | 1/2015 | Aehle et al. | 510/218 |

FOREIGN PATENT DOCUMENTS

| | | |
|---|---|---|
| EP | 0134048 | 3/1985 |
| EP | 0200362 | 12/1986 |
| EP | 0201184 | 12/1986 |
| EP | 0214761 | 3/1987 |
| EP | 0218272 | 4/1987 |
| EP | 0238023 | 9/1987 |
| EP | 0258068 | 3/1988 |
| EP | 0305216 | 3/1989 |
| EP | 0331376 | 9/1989 |
| EP | 0415296 | 8/1990 |
| EP | 0495257 | 7/1992 |
| EP | 2100947 | 9/2009 |
| EP | 2100949 | 9/2009 |
| GB | 1296839 | 11/1972 |
| GB | 1372034 | 10/1974 |
| JP | 64/074992 | 3/1989 |
| WO | WO88/09367 | 12/1988 |
| WO | WO89/06270 | 7/1989 |
| WO | WO90/09446 | 8/1990 |
| WO | WO91/00345 | 1/1991 |
| WO | WO92/21760 | 12/1992 |
| WO | WO94/12621 | 6/1994 |
| WO | WO95/01426 | 1/1995 |
| WO | WO95/23221 | 8/1995 |
| WO | WO97/11151 | 3/1997 |
| WO | WO99/06521 | 2/1999 |
| WO | WO99/20727 | 4/1999 |
| WO | WO99/20771 | 4/1999 |
| WO | WO99/34011 | 7/1999 |
| WO | WO00/24924 | 5/2000 |
| WO | WO00/32601 | 6/2000 |
| WO | WO02/14490 | 2/2002 |
| WO | WO02/102955 | 12/2002 |
| WO | WO2004/041979 | 5/2004 |
| WO | WO2004/111178 | 12/2004 |
| WO | WO2005/056782 | 6/2005 |
| WO | WO2007/006305 | 1/2007 |
| WO | WO2007/044993 | 4/2007 |
| WO | WO2007/145964 | 12/2007 |
| WO | WO2009/149144 | 12/2009 |
| WO | WO2009/149200 | 12/2009 |
| WO | WO2011/140364 | 11/2011 |

OTHER PUBLICATIONS

Babé, L., et al., "Heterologous expression of human granzyme K in *Bacillus subtills* and characterization of its hydrolytic activity In vitro." *Biotech. Appl. Biochem.* 27: 117-124, 1998.

Beaucage, S.L., et al. "Deoxynucleoside Phosphoramioites—A New Class of Key Intermediates For Deoxypolynucleotide Synthesis." *Tetrahedron Letters* 22: 1859-69, 1981.

Bittker, J.A., et al., "Nucleic acid evolution and minimization by nonhomologous random recombination." *Nat. Biotechnol.* 20: 1024-1029, 2002.

Bittker, J.A., et al., "Directed evolution of protein enzymes using nonhomologous random recombination." *Proc Natl. Acad. Sci. USA* 101: 7011-7016, 2004.

Bron, S., "Plasmids." In *Molecular Biological Methods for Bacillus*, Chapter 3, pp. 140-145, Harwood, C.R., et al. (eds.), John Wiley & Sons; Chichester, England; 1990.

Bryan, P.N. "Protein Engineering of subtilisin." *Biochimica et Biophysica Acta* 1543(2): 203-222, 2000.

Caldwell, R., et al., "Correlation between *Bacillus subtilis* scoC Phenotype and Gene Expression Determined Using Microarrays for Transcriptome Analysis." *J. Bacteriol.* 183: 7329-7340, 2001.

Chang, S., et al., "High Frequency Transformation of *Bacillus subtilis* Protoplasts by Plasmid DNA." *Mol. Gen. Genet.* 168: 111-115, 1979.

Christianson, T., et al., "Peptide Mapping of Subtilisins as a Practical Tool for Locating Protein Sequence Errors during Extensive Protein Engineering Projects." *Anal. Biochem.* 223: 119-129, 1994.

Coco, W.M., et al., "Growth factor engineering by degenerate homoduplex gene family recombination." *Nat. Biotechnol.* 20: 1246-1250, 2002.

Contente, S., et al., "Marker Rescue Transformation by Linear Plasmid DNA in *Bacillus subtilis.*" *Plasmid* 2: 555-571, 1979.

Dartois, V., et al., "Cloning, nucleotide sequence and expression in *Escherichia coli* of a lipase gene from *Bacillus subtilis* 168." *Biochem. Biophys. Acta* 1131: 253-260, 1992.

Del Mar, E.G., et al., "A Sensitive New Substrate for Chymotrypsin." *Anal. Biochem.* 99: 316-320, 1979.

Devereux, J., et al., "A comprehensive set of sequence analysis programs for the VAX." *Nucl. Acid Res.* 12: 387-395, 1984.

Fahnestock, S.R., et al., "Expression of the Staphylococcal Protein A Gene in *Bacillus subtilis* by Gene Fusions Utilizing the Promoter from a *Bacillus amyloliquefaciens* α-Amylase Gene."*J. Bacteriol.* 165: 796-804, 1986.

(56) References Cited

OTHER PUBLICATIONS

Feng. D.-F., "Progressive Sequence Alignment as a Prerequisite to Correct Phylogenetic Trees." *J. Mol. Evol.* 25: 351-360, 1987.

Ferrari, E., et al., "Genetics." In Bacillus, Hardwood (ed.), Plenum Publishing Corp., pp. 57-72, 1989.

Fisher, H.M., et al., "Introduction of plasmid pC194 into *Bacillus thuringiensis* by protoplast transformation and plasmid transfer." *Arch. Microbiol.* 139: 213-217, 1981.

Glaser, S.M., et al., "Antibody Engineering by Codon-Based Mutagenesis in a Filamentous Phage Vector System." *J. Immunol.* 149(12): 3903-3913, 1992.

Haima, P., et al., "Novel plasmid marker rescue transformation system for molecular cloning in *Bacillus subtilis* enabling direct selection of recombinants." *Mol. Gen. Genet.* 223: 185-191, 1990.

Haas, M.J., et al., "Cloning, expression and characterization of a cDNA encoding a lipase from *Rhizopus delemar.*" *Gene* 109: 117-113, 1991.

Henikoff, S., et al, "Amino acid substitution matrices from protein blocks." *Proc. Natl. Acad. Sci. USA* 89: 10915-10919, 1992.

Higgins, D.G., et al., "Fast and sensitive multiple sequence alignments on a microcomputer." *CABIOS* 5: 151-153, 1989.

Hoch, J.A., et al., "Chromosomal Location of Pleiotropic Negative Sporulation Mutations in *Bacillus Subtilis.*" *Genetics* 73: 215-228, 1973.

Hoch, J.A., et al., "Transformation and Transduction in Recombination—Defective Mutants of *Bacillus subtilis.*" *J. Bacteriol.* 93: 1925 -1937, 1967.

Holubova, I., et al., "Transfer of Liposome-Encapsulated Plasmid DNA to *Bacillus subtilis* Protoplasts and Calcium-Treated *Escherichia coli* Cells." *Folia Microbiol.* 30: 97-109, 1985.

Hsia, C.Y., et al., "Active-Site Titration of Serine Proteases Using a Fluoride Ion Selective Electrode and Sulfonyl Fluoride Inhibitors." *Anal. Biochem.* 242: 221-227, 1999.

Itakura, K., et al., "Synthesis and Use of Synthetic Oligonucleotides." *Ann. Rev. Biochem.* 53: 323-326, 1984.

Itakura, K., et al., "Expression in *Escherichia coli* of a Chemically Synthesized Gene for the Hormone Somatostatin." *Science* 198: 1056-1063, 1977.

Kalisz, "Microbial Proteinases." In *Advances in Biochemical Engineering/Biotechnology*, vol. 36, Fiechter, A. (ed.), pp. 2-65, 1988.

Karlin, S., et al., "Applications and statistics for multiple high-scoring segment s in molecular sequences." *Proc. Natl. Acad. Sci. USA* 90: 5873-5877, 1993.

Kroll, D.J., et al., "A Multifunctional Prokaryotic Protein Expression System: Overproduction, Affinity Purjfication, and Selective Detection." *DNA Cell Biol.* 12(5) :441-453, 1993.

Kugimiya, W., et al., "Cloning and Sequence Analysis of cDNA encoding *Rhizopus niveus* Lipase." *Biosci. Biotech. Biochem.* 56(5): 716-719, 1992.

Lutz, S., et al. "Creating multiple-crossover DNA libraries independent of sequence identity." *Proc. Natl. Acad. Sci. USA* 98: 11248-11253, 2001.

Maddox, D.E., et al., "Elevated Serum Levels in Human Pregnancy of a Molecule Immunochemically Similar to Eosinophil Granule Major Basic Protein." *J. Exp. Med.* 158: 1211-1226, 1983.

Mann, S.P., et al., "Transformation of Bacillus Spp.: an Examination of the Transformation of Bacillus Protoplast by Plasmids pUB 110 and pHV33." *Current Microbiol.* 13: 191-195, 1986.

Matthes, H.W.D., et al., "Simultaneous rapid chemical synthesis of over one hundred oligonucleotides on a microscale." *EMBO J.* 3(4): 801-805, 1984.

McDonald, K.O., et al., "Plasmid Transformation of *Bacillus sphaericus* 1593." *J. Gen. Microbiol.* 130: 203-208, 1984.

McKenzie, T., et al., "The Nucleotide Sequence of pUB110: Some Salient Features in Relation to Replication and Its Regulation." *Plasmid* 15: 93-103, 1986.

Msadek, T., et al., "Signal Transduction Pathway Controlling Synthesis of a Class of Degradative Enzymes in *Bacillus subtilis*: Expression of the Regulatory Genes and Analysis of Mutations in degS and degU." *J. Bacteriol.* 172(2): 824-834, 1990.

Needleman, S.B., et al., "A General Method Applicable to the Search for Similarities in the Amino Add Sequence of Two Proteins." *J. Mol. Biol.* 48: 443-453, 1970.

Neidhardt, F.C., et al., "Culture Medium for Enterobacteria." *J. Bacteriol.*, 119: 736-747, 1974.

Ness, J.E., et al., "Synthetic shuffling expands functional protein diversity by allowing amino acids to recombine independently." *Nat. Biotechnol.* 20: 1251-1255, 2002.

Olmos, J., et al., "Effects of the *sinR* and *degtU32* (Hy) mutations on the regulation of the aprE gene in *Bacillus subtilis.*" *Mol. Gen. Genet.* 253: 562-567, 1997.

Ostermeier, M., et al., "Incremental Truncation as a Strategy in the Engineering of Novel Biocatalysts." *Bioorg. Med. Chem.* 7: 2139-2144, 1999.

Palmeros, B., et al., "A family of removable cassettes designed to obtain antibiotic-resistance-free genomic modifications of *Escherichia coli* and other bacteria." *Gene* 247: 255 -264, 2000.

Palva, I. "Molecular cloning of α-amylase gene from *Bacillus amyloliquefaciens* and its expression in *B. subtilis.*" *Gene* 19: 81-87, 1982.

Pearson, W.R., et al., "Improved tools for biological sequence comparison." *Proc. Natl. Acad. Sci. USA* 85: 2444-2448, 1988.

Perego, M., et al., "The oligopeptide transport system of *Bacillus subtilis* plays a role in the initiation of sporulation." *Mol. Microbiol.* 5(1): 173-185, 1991.

Perego, M., "Integrational Vectors for Genetic Manipulations in *Bacillus subtilis*." In *Bacillus Subtilis and Other Gram-Positive Bacteria*. Biochemistry, Physiology and Molecular Genetics, American Society for Microbiology, Sonenshein et al., (eds.) Washington, D.C., Chapter 42, pp. 615-624, 1993.

Porath, J., "Immobilized Metal Ion Affinity Chromatography." *Protein Expr. Purif.* 3: 263-281, 1992.

Rawlings, N.D., "Evolutionary families of peptidases." *Biochem J.*, 290: 205-218, 1993.

Rawlings, N.D., et al., "MEROPS: the peptidase database." *Nucl Acids Res*, 34: D270-D272, 2006.

Saunders, C.W., et al., "Use of Chromosomal Integration in the Establishment and Expression of blaZ, a *Staphylococcus aureus* β-Lactamase Gene, in *Bacillus subtilis.*" *J. Bacteriol.* 157: 718-726, 1984.

Schimada, Y., et al., "cDNA Molecular Cloning of *Geotrichum candidum* Lipase." *J. Biochem.* 106: 383-388, 1989.

Sieber, V., et al., "Libraries of hybrid proteins from distantly related sequences." *Nat. Biotechnol.* 19: 456-460, 2001.

Siezen, R.J. et al., "Subtilases: the Superfamily of Subtilisin-like Serine Proteases." *Protein Science* 6(3): 501-523, 1997.

Smith, T.F., et al., "Comparison of Biosequences." *Adv. Appl. Math.* 2: 482-489, 1981.

Smith, M.D., et al., "Protoplast Transformation in Coryneform Bacteria and Introduction of an α-Amylase Gene from *Bacillus amyloliquefaciens* into *Brevibacterium lactofermentum.*" *Appl. Env. Microbiol.* 51: 634-639, 1986.

Stahl, M.L., et al., "Replacement of the *Bacillus subtilis* Subtilisin Structural Gene with an In Vitro-Derived Deletion Mutation." *J. Bacteriol.* 158: 411-418, 1984.

Vorobjeva, I.P., et al., "Transformation of *Bacillus Megaterium* Protoplasts By Plasmid DNA." *FEMS Microbiol. Lett.* 7: 261-263, 1980.

Wang, L.-F., et al., "Expression and secretion of human atrial natriuretic α-factor in *Bacillus subtilis* using the subtilisin signal peptide." *Gene* 69: 39-47, 1988.

Ward, "Proteinases." In *Microbial Enzymes and Biotechnology*, Fogarty, W.M., (ed.), Applied Science Publishers, London, Chapter 6, pp. 251-317, 1983.

Weinrauch, Y., et al., "Plasmid Marker Rescue Transformation in *Bacillus subtilis.*" *J. Bacteriol.* 154(3): 1077-1087, 1983.

Weinrauch, Y., et al., "Plasmid Marker Rescue Transformation Proceeds by Breakage-Reunion in *Bacillus subtilis.*" *J. Bacteriol.* 169(3): 1205-1211, 1987.

Wells, J.A., et al., "Cloning, sequencing, and secretion of *Bacillus amyloliquefaciens* subtilisin in *Bacillus subtilis.*" *Nucleic Acids Res.* 11: 7911-7925, 1983.

(56) References Cited

OTHER PUBLICATIONS

Yamaguchi, S., et al., "Cloning and structure of the mono- and diacylglycerol lipase-encoding gene from *Penicillium camembertii* U-150." *Gene* 103: 61-67, 1991.

Zha, D., et al., "Assembly of Designed Oligonucleotides as an Efficient Method for Gene Recombination: A New Tool in Directed Evolution." *Chembiochem*. 4: 34-39, 2003.

International Search Report and the Written Opinion of the International Searching Authority for PCT/US2012/036608 dated Sep. 14, 2012.

International Preliminary Report on Patentability for PCT/US2012/036608 dated Nov. 5, 2013.

* cited by examiner

```
BPN'   1    AQSVPYGVSQ IKAPALHSQG YTGSNVKVAV IDSGIDSSHP DLKVAGGASM VPSETNPFQD

GG36   1    AQSVPWGISR VQAPAAHNRG LTGSGVKVAV LDTGIS-THP DLNIRGGASF VPGEPST-QD

BPN'  61    NNSHGTHVAG TVAALNNSIG VLGVAPSASL YAVKVLGADG SGQYSWIING IEWAIANNMD

GG36  59    GNGHGTHVAG TIAALNNSIG VLGVAPSAEL YAVKVLGASG SGSVSSIAQG LEWAGNNGMH

BPN' 121    VINMSLGGPS GSAALKAAVD KAVASGVVVV AAAGNEGTSG SSSTVGYPGK YPSVIAVGAV

GG36 119    VANLSLGSPS PSATLEQAVN SATSRGVLVV AASGNSGAGS ----ISYPAR YANAMAVGAT

BPN' 181    DSSNQRASFS SVGPELDVMA PGVSIQSTLP GNKYGAYNGT SMASPHVAGA AALILSKHPN

GG36 175    DQNNRASFS QYGAGLDIVA PGVNVQSTYP GSTYASLNGT SMATPHVAGA AALVKQKNPS

BPN' 241    WTNTQVRSSL ENTTTKLGDS FYYGKGLINV QAAAQ

GG36 235    WSNVQIRNHL KNTATSLGST NLYGSGLVNA EAATR
```

COMPOSITIONS AND METHODS COMPRISING SERINE PROTEASE VARIANTS

CROSS-REFERENCE TO RELATED APPLICATIONS

The present application is a U.S. National Stage Application of International Application No. PCT/US2012/036608, filed May 4, 2012, which claims the benefit of U.S. Provisional Application Ser. No. 61/482,938, filed May 5, 2011, which are hereby incorporated by reference in their entireties.

SEQUENCE LISTING

The sequence listing submitted via EFS, in compliance with 37 C.F.R. §1.52(e), is incorporated herein by reference. The sequence listing text file submitted via EFS contains the file "40015US-SEQ-LIST.txt" created on Sep. 25, 2013, which is 12,288 bytes in size.

FIELD OF THE INVENTION

The present invention provides serine protease variants. Specifically, the present invention provides serine protease variants having one or more substitutions as compared to a reference serine protease. In addition, the present invention provides compositions comprising these serine protease variants. In some embodiments, the present invention provides cleaning compositions comprising at least one of these serine protease variants, more specifically subtilisin variants.

BACKGROUND OF THE INVENTION

Although serine proteases have long been known in the art of industrial enzymes, there remains a need for engineered proteases that are suitable for particular conditions and uses.

SUMMARY OF THE INVENTION

In some embodiments, the present invention includes an isolated subtilisin variant, wherein said subtilisin variant is a mature form having proteolytic activity and comprises an amino acid sequence comprising a combination of amino acid substitutions at positions selected from Lists 1-19, and wherein amino acid positions of the subtilisin variant are numbered according to the numbering of corresponding amino acid positions in the amino acid sequence of Bacillus amyloliquefaciens subtilisin BPN' shown in SEQ ID NO:1.

In some embodiments, the present invention includes an isolated subtilisin variant of Bacillus lentus subtilisin GG36 protease, wherein said Bacillus lentus subtilisin GG36 protease has the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from Lists 1-19, and wherein amino acid positions of the subtilisin variant are numbered according to the numbering of corresponding amino acid positions in the amino acid sequence of Bacillus amyloliquefaciens subtilisin BPN' shown in SEQ ID NO:1. In some embodiments, the present invention is an expression vector, host cell or method for producing any of the aforementioned variants.

In some embodiments, the present invention includes nucleic acids encoding an isolated subtilisin variant of Bacillus lentus subtilisin GG36 protease, wherein said Bacillus lentus subtilisin GG36 protease has the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from Lists 1-19, and wherein amino acid positions of the subtilisin variant are numbered according to the numbering of corresponding amino acid positions in the amino acid sequence of Bacillus amyloliquefaciens subtilisin BPN' shown in SEQ ID NO:1. In some embodiments, the present invention is an expression vector, host cell or method for producing any of the aforementioned variants.

In each embodiment listed above, the variant can have improved cleaning compared to the GG36 protease having the amino acid sequence shown in SEQ ID NO:2.

In some embodiments, the present invention includes any of the above variants or nucleic acids encoding the variants, wherein the total net charge of the variant is 0, +1, +2, +3, +4, +5, −1, −2, −3, −4, or −5 relative to the total net charge of the Bacillus lentus subtilisin GG36 protease.

In some embodiments, the present invention includes compositions having at least one of the variants listed above, wherein said composition is not a fabric and home care product. In some embodiments, the present invention is a method of cleaning, using the aforementioned composition.

BRIEF DESCRIPTION OF THE DRAWINGS

FIG. 1 provides an alignment of the mature reference proteases including: BPN' (SEQ ID NO:1) and GG36 (SEQ ID NO:2). Each amino acid position of each protease variant, more specifically subtilisin variants described herein, including each cold water protease variant, is numbered according to the numbering of the corresponding amino acid position in the amino acid sequence of Bacillus amyloliquefaciens subtilisin protease BPN' (SEQ ID NO:1), as shown in FIG. 1, as determined by alignment of the protease variant amino acid sequence with the Bacillus amyloliquefaciens subtilisin protease BPN' amino acid sequence. Thus, unless otherwise specified herein, substitution positions are given in relationship to BPN'.

DESCRIPTION OF THE INVENTION

The present invention provides serine protease variants, more specifically subtilisin variants. Specifically, the present invention provides serine protease variants, more specifically subtilisin variants having one or more substitutions as compared to a reference serine protease. In addition, the present invention provides compositions comprising these serine protease variants, more specifically subtilisin variants. In some embodiments, the present invention provides cleaning compositions comprising at least one of these serine protease variants, more specifically subtilisin variants.

Definitions

Unless otherwise indicated, the practice of the present invention involves conventional techniques commonly used in molecular biology, protein engineering, microbiology, and recombinant DNA, which are within the skill of the art. Such techniques are known to those of skill in the art and are described in numerous texts and reference works well known to those of skill in the art. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. Many technical dictionaries are known to those of skill in the art. Although any methods and materials similar or equivalent to those described herein find use in the practice of the present invention, some suitable methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The practice of the present invention employs, unless otherwise indicated, conventional techniques of protein purification, molecular biology, microbiology, recombinant DNA techniques and protein sequencing, all of which are within the skill of those in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

As used herein, the terms "protease" and "proteinase" refer to an enzyme protein that has the ability to break down other proteins. A protease has the ability to conduct "proteolysis," which begins protein catabolism by hydrolysis of peptide bonds that link amino acids together in a peptide or polypeptide chain forming the protein. This activity of a protease as a protein-digesting enzyme is referred to as "proteolytic activity." Many well known procedures exist for measuring proteolytic activity (See e.g., Kalisz, "Microbial Proteinases," In: Fiechter (ed.), *Advances in Biochemical Engineering/Biotechnology*, (1988)). For example, proteolytic activity may be ascertained by comparative assays which analyze the respective protease's ability to hydrolyze a commercial substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011 and U.S. Pat. No. 6,376,450, both of which are incorporated herein by reference). The pNA assay (See e.g., Del Mar et al., Anal. Biochem. 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration. The active enzyme/total protein ratio gives the enzyme purity.

As used herein, the term "subtilisin" refers any member of the S8 serine protease family as described in MEROPS—The Peptidase Data base (See, Rawlings et al., MEROPS: the peptidase database, Nucl Acids Res, 34 Database issue, D270-272 [2006]). As described therein, the peptidase family S8 contains the serine endopeptidase subtilisin and its homologues (Rawlings and Barrett, Biochem J., 290:205-218, [1993]). Family S8, also known as the subtilase family, is the second largest family of serine peptidases. The tertiary structures for several members of family S8 have now been determined. A typical S8 protein structure consists of three layers with a seven-stranded 13 sheet sandwiched between two layers of helices. Subtilisin (S08.001) is the type structure for clan SB (SB). Despite the different structure, the active sites of subtilisin and chymotrypsin (S01.001) can be superimposed, which suggests the similarity is the result of convergent rather than divergent evolution.

As used herein, the terms "protease variant," "variant protease," "variant serine protease," "serine protease variant", "subtilisin variant", "mutant protease," are used in reference to proteases that are similar to a reference protease (which may be a wild-type subtilisin protease), particularly in their function, but have mutations in their amino acid sequence that make them different in sequence from the wild-type protease or any starting reference protease (i.e., "parent" protease) from which the variant protease is derived. In some embodiments, the present invention provides "GG36 variants," (or "GG36 subtilisin variants") wherein the mutations are present in the mature GG36 sequence set forth in SEQ ID NO:2. However, it is not intended that the reference protease be limited to any particular amino acid sequence. In addition, it is intended that the term encompass variants of a parent protease wherein the parent protease's sequence is at least 80%, at least 85%, at least 90%, at least 95%, at least 96%, at least 97%, at least 98%, at least 99%, or 100% identical to the amino acid sequence of SEQ ID NO:2.

As used herein, the term "cold water protease variant" means a protease variant, more specifically subtilisin variants of a parent protease, wherein the *B. lentus* subtilisin GG36 protease has the amino acid sequence of SEQ ID NO:2, wherein said protease variant, more specifically subtilisin variants has one or more of the following characteristics: a) a Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or e) Test Method 7 performance index of at least 1.1, at least 1.2, at least 1.3, at least 1.4, at least 1.5, at least 1.6, at least 1.7, at least 1.8, at least 1.9, at least 2, from 1.1 to about 15, from 1.1 to about 10, or even from 1.1 to about 7. Test Method 2, Test Method 3, Test Method 4, Test Method 6, and Test Method 7 are explicitly described infra in the section of Example 1 entitled "Test Methods". In addition, it is intended that the term encompass variants of a parent protease wherein the parent protease's sequence is at least 80%, at least 85%, at least 90%, at least 95%, at least 96%, at least 97%, at least 98%, at least 99%, or 100% identical to the amino acid sequence of SEQ ID NO:2.

In some embodiments of the present invention, the parent protease (i.e., "reference" or "starting" protease) is a commercially available protease, including but not limited to the proteases sold under the tradenames SAVINASE®, POLARZYME®, KANNASE®, LIQUINASE®, LIQUINASE ULTRA®, SAVINASE ULTRA®, OVOZYME®, (by Novozymes A/S); MAXACAL®, PROPERASE®, PURAFECT®, FN3®, FN4® and PURAFECT OXP®, PURAFAST™, PURAFECT® PRIME, PURAMAX® (by Danisco US, Genencor Division); and those available from Henkel/Kemira, namely BLAP (sequence shown in FIG. 29 of U.S. Pat. No. 5,352,604 with the following mutations S99D+S101R+S103A+V104I+G159S, hereinafter referred to as BLAP) and BLAP X (BLAP with S3T+V4I+V205I).

As used herein, the term "variant polypeptide" refers to a polypeptide comprising an amino acid sequence that differs in at least one amino acid residue from the amino acid sequence of a parent or reference polypeptide (including but not limited to wild-type polypeptides).

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Arnphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

The terms "polynucleotide" and "nucleic acid," which are used interchangeably herein, refer to a polymer of any length of nucleotide monomers covalently bonded in a chain. DNA (deoxyribonucleic acid), a polynucleotide comprising deoxyribonucleotides, and RNA (ribonucleic acid), a polymer of ribonucleotides, are examples of polynucleotides or nucleic acids having distinct biological function. Polynucleotides or nucleic acids include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, expressed sequence tag(s) (EST(s)), exons, introns, messenger RNA (mRNA), transfer RNA (tRNA), ribosomal RNA (rRNA), ribozymes, complementary DNA (cDNA), recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracyl, other sugars and linking groups such as fluororibose and thioate, and nucleotide branches. In a particular embodiment, a sequence of nucleotides is interrupted by non-nucleotide components.

As used herein, the term "mutation" refers to changes made in a starting amino acid or nucleic acid sequence. It is intended that the term encompass substitutions, insertions and deletions.

As used herein, the term "vector" refers to a nucleic acid construct or polynucleotide construct used to introduce or transfer nucleic acid(s) or polynucleotide(s) into a target cell or tissue. A vector is typically used to introduce foreign DNA into another cell or tissue. A vector generally comprises a DNA sequence that is a transgene and a larger polynucleotide sequence that serves as the "backbone" of the vector. The vector typically serves to transfers genetic information, such as the inserted transgene, to a target cell or tissue so as to isolate, multiply, or express the insert in the target cell or tissue. Vectors include plasmids, cloning vectors, bacteriophages, viruses (e.g., viral vector), cosmids, expression vectors, shuttle vectors, cassettes, and the like. A vector typically includes an origin of replication, a multi-cloning site, and a selectable marker. The process of inserting a vector into a target cell is typically referred to as transfection. The transfection of a cell with a viral vector is typically referred to as transduction. The present invention includes, in some embodiments, a vector that comprises a DNA sequence encoding a variant protease (e.g., precursor or mature variant protease) that is operably linked to a suitable prosequence (e.g., secretory, signal peptide sequence, etc.) capable of effecting the expression of the DNA sequence in a suitable host.

As used herein, the term "expression cassette," "expression plasmid" or "expression vector" refers to a nucleic acid construct or vector generated recombinantly or synthetically for the expression of a nucleic acid of interest (e.g., a foreign nucleic acid or transgene) in a target cell. The nucleic acid of interest typically expresses a protein of interest. An expression vector or expression cassette typically comprises a promoter nucleotide sequence that drives or promotes expression of the foreign nucleic acid. The expression vector or cassette also typically includes any other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Some expression vectors have the ability to incorporate and express heterologous DNA fragments in a host cell. Many prokaryotic and eukaryotic expression vectors are commercially available. Selection of appropriate expression vectors is within the knowledge of those of skill in the art. Selection of appropriate expression vectors for expression of a protein from a nucleic acid sequence incorporated into the expression vector is within the knowledge of those of skill in the art.

A DNA construct is an artificially constructed segment of nucleic acid that may be introduced into a target cell or tissue. A DNA construct typically comprises a DNA insert comprising a nucleotide sequence encoding a protein of interest that has been subcloned into a vector. The vector may contain bacterial resistance genes for growth in bacteria and a promoter for expression of the protein of interest in an organism. The DNA may be generated in vitro by PCR or any other suitable technique(s) known to those in the art. In some embodiments, the DNA construct comprises a nucleic acid sequence of interest. In some embodiments, the sequence is operably linked to additional elements such as control elements (e.g., promoters, etc.). The DNA construct may further comprise a selectable marker and may further comprise an incoming sequence flanked by homology boxes. The construct may comprise other non-homologous sequences, added to the ends (e.g., stuffer sequences or flanks). In some embodiments, the ends of the sequence are closed such that the DNA construct forms a closed circle. The nucleic acid sequence of interest, which is incorporated into the DNA construct, using techniques well known in the art, may be a wild-type, mutant, or modified nucleic acid. In some embodiments, the DNA construct comprises one or more nucleic acid sequences homologous to the host cell chromosome. In other embodiments, the DNA construct comprises one or more non-homologous nucleotide sequences. Once the DNA construct is assembled in vitro, it may be used, for example, to: 1) insert heterologous sequences into a desired target sequence of a host cell; and/or 2) mutagenize a region of the host cell chromosome (i.e., replace an endogenous sequence with a heterologous sequence); 3) delete target genes; and/or 4) introduce a replicating plasmid into the host. "DNA construct" is used interchangeably herein with "expression cassette."

As used herein, a "plasmid" refers to an extrachromosomal DNA molecule which is capable of replicating independently from the chromosomal DNA. A plasmid is double stranded (ds) and may be circular and is typically used as a cloning vector.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction (See e.g., Ferrari et al., "Genetics," in Hardwood et al. (eds.), *Bacillus*, Plenum Publishing Corp., pp. 57-72 [1989]).

Transformation refers to the genetic alteration of a cell which results from the uptake, genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "recombinant" when used with reference to a cell typically indicates that the cell has been modified by the introduction of a heterologous nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) but which has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination," "recombining," and "recombined" of polynucleotides or nucleic acids refer generally to the assembly or combining of two or more nucleic acid or polynucleotide strands or fragments to generate a new polynucleotide or nucleic acid. The recombinant polynucleotide or nucleic acid is sometimes referred to as a chimera. A nucleic acid or polypeptide is "recombinant" when it is artificial or engineered, or derived from an artificial or engineered protein or nucleic acid.

As used herein, the term nucleic acid or gene "amplification" refers to a process by which specific DNA sequences are disproportionately replicated such that the amplified nucleic acid or gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this nucleic acid or gene product or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide (a polymer of nucleotide residues), whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent such as DNA polymerase and at a suitable temperature and pH). A primer is preferably single stranded for maximum efficiency in amplification, but may alternatively be double stranded. If double stranded, the primer is first treated to separate its strands before being used to prepare extension products. In some embodiments, the primer is an oligodeoxyribonucleotide. The primer must be sufficiently long to prime the synthesis of extension products in the presence of the inducing agent. The exact length of a primer depends on a variety of factors, including temperature, source of primer, and the use of the method.

As used herein, the term "probe" refers to an oligonucleotide, whether occurring naturally as in a purified restriction digest or produced synthetically, recombinantly or by PCR amplification, which is typically capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. I t is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A nucleotide "segment" is a region of a nucleic acid within the target nucleic acid sequence.

As used herein, the term "polymerase chain reaction" (PCR) refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence is well known in the art.

As used herein, the term "amplification reagents" refers to those reagents (e.g., deoxyribonucleotide triphosphates, buffer, etc.) needed for amplification except for primers, nucleic acid template, and the amplification enzyme. Typically, amplification reagents along with other reaction components are placed and contained in a reaction vessel (test tube, microwell, etc.).

As used herein, the term "restriction endonuclease" or "restriction enzyme" refers to an enzyme (e.g., bacterial enzyme) that is capable of cutting double-stranded or single-stranded DNA at or near a specific sequence of nucleotides known as a restriction site. The nucleotide sequence comprising the restriction site is recognized and cleaved by a given restriction endonuclease or restriction enzyme and is frequently the site for insertion of DNA fragments. A restriction site can be engineered into an expression vector or DNA construct.

"Homologous recombination" refers to the exchange of DNA fragments between two DNA molecules or paired chromosomes at the site of identical or nearly identical nucleotide sequences. In some embodiments, chromosomal integration is homologous recombination.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

As is known in the art, a DNA sequence can be transcribed by an RNA polymerase to produce an RNA sequence, but an RNA sequence can be reverse transcribed by reverse transcriptase to produce a DNA sequence.

"Host strain" or "host cell" refers to a suitable host for an expression vector comprising a DNA sequence of interest.

The DNA sequence of interest may express a protein of interest in the host strain or host cell.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used through out this disclosure. The single letter X refers to any of the twenty amino acids. It is also understood that a polypeptide may be coded for by more than one nucleotide sequence due to the degeneracy of the genetic code. Mutations are named by the one letter code for the parent amino acid, followed by a three or two digit position number and then the one letter code for the variant amino acid. For example, mutating glycine (G) at position 87 to serine (S) is represented as "G087S" or "G87S". Multiple mutations are indicated by inserting a "-" between the mutations. Mutations at positions 87 and 90 are represented as either "G087S-A090Y" or "G87S-A90Y" or "G87S+A90Y" or "G087S+A090Y". For deletions, the one letter code "Z" is used. For an insertion relative to the parent sequence, the one letter code "Z" is on the left side of the position number. For a deletion, the one letter code "Z" is on the right side of the position number. For insertions, the position number is the position number before the inserted amino acid(s), plus 0.01 for each amino acid. For example, an insertion of three amino acids alanine (A), serine (S) and tyrosine (Y) between position 87 and 88 is shown as "Z087.01A-Z087.02S-Z087.03Y." Thus, combining all the mutations above plus a deletion at position 100 is: "G087S-Z087.01A-Z087.02S-Z087.03Y-A090Y-A100Z."

A "prosequence" or "propetide sequence" refers to an amino acid sequence between the signal peptide sequence and mature protease sequence that is necessary for the secretion of the protease. Cleavage of the prosequence or propeptide sequence results in a mature active protease.

The term "signal sequence" or "signal peptide" refers to a sequence of amino acid residues that may participate in the secretion or direct transport of the mature or precursor form of a protein. The signal sequence is typically located N-terminal to the precursor or mature protein sequence. The signal sequence may be endogenous or exogenous. One exemplary exogenous signal sequence comprises the first seven amino acid residues of the signal sequence from *Bacillus subtilis* subtilisin fused to the remainder of the signal sequence of the subtilisin from *Bacillus lentus* (ATCC 21536). A signal sequence is normally absent from the mature protein. A signal sequence is typically cleaved from the protein by a signal peptidase after the protein is transported.

The term "hybrid signal sequence" refers to signal sequences in which part of sequence is obtained from the expression host fused to the signal sequence of the gene to be expressed. In some embodiments, synthetic sequences are utilized.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polynucleotides that are involved in post-translational activity (e.g., polynucleotides cleaved therefrom to leave the mature form of a protein or peptide).

The term "wild-type" in reference to an amino acid sequence or nucleic acid sequence indicates that the amino acid sequence or nucleic acid sequence is native or naturally occurring sequence. As used herein, the term "naturally-occurring" refers to anything (e.g., proteins, amino acids, or nucleic acid sequences) that are found in nature (i.e., have not been manipulated by means of recombinant methods).

As used herein, the term "non-naturally occurring" refers to anything that is not found in nature (e.g., recombinant nucleic acids produced in the laboratory).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position along related proteins or a reference protein.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question. To exemplify, "proteases derived from *Bacillus*" refers to those enzymes having proteolytic activity which are naturally produced by *Bacillus*, as well as to serine proteases like those produced by *Bacillus* sources but which through the use of genetic engineering techniques are produced by non-*Bacillus* organisms transformed with a nucleic acid encoding the serine proteases.

The term "identical" in the context of two nucleic acids or polypeptide sequences refers to the residues in the two sequences that are the same when aligned for maximum correspondence, as measured using one of the following sequence comparison or analysis algorithms.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "homology" refers to sequence similarity or identity, with identity being preferred. Homology may be determined using standard techniques known in the art (See e.g., Smith and Waterman, Adv. Appl. Math. 2:482 [1981]; Needleman and Wunsch, J. Mol. Biol. 48:443 [1970\; Pearson and Lipman, Proc. Natl. Acad. Sci. USA 85:2444 [1988]; software programs such as GAP, BESTFIT, FASTA, and TFASTA in the Wisconsin Genetics Software Package (Genetics Computer Group, Madison, Wis.); and Devereux et al., Nucl. Acid Res. 12:387-395 [1984]). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (See, Feng and Doolittle, J. Mol. Evol. 35:351-360 [1987]). The method is similar to that described by Higgins and Sharp (See, Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (See, Altschul et al., J. Mol. Biol. 215:403-410 [1990]; and Karlin and Altschul, Proc. Natl. Acad. Sci. USA 90:5873-5787 [1993]). A particularly useful BLAST program is the WU-BLAST-2 program (See, Altschul et al., Meth. Enzymol. 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (See, Altschul, et al., J. Mol. Biol., 215:403-410 [1990]). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1992]) alignments (B) of 50, expectation (E) of 10, M'5, N'-4, and a comparison of both strands.

The BLAST algorithm then performs a statistical analysis of the similarity between two sequences (See e.g., Karlin and Altschul, supra). One measure of similarity provided by the BLAST algorithm is the smallest sum probability (P(N)), which provides an indication of the probability by which a match between two nucleotide or amino acid sequences would occur by chance. For example, a nucleic acid is considered similar to a serine protease nucleic acid of this invention if the smallest sum probability in a comparison of the test nucleic acid to a serine protease nucleic acid is less than about 0.1, more preferably less than about 0.01, and most preferably less than about 0.001. Where the test nucleic acid encodes a serine protease polypeptide, it is considered similar to a specified serine protease nucleic acid if the comparison results in a smallest sum probability of less than about 0.5, and more preferably less than about 0.2.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference (i.e., query) amino acid sequence means that the subject amino acid sequence is identical (i.e., on an amino acid-by-amino acid basis) by a specified percentage to the query amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

"Percent sequence identity" or "% identity" or "% sequence identity or "% nucleotide sequence identity" of a subject nucleic acid sequence to a reference (i.e. query) nucleic acid sequence means that the subject nucleic acid sequence is identical (i.e., on a nucleotide-by-nucleotide basis for a polynucleotide sequence) by a specified percentage to the query sequence over a comparison length when the sequences are optimally aligned. Thus, 80% nucleotide sequence identity or 80% identity with respect to two nucleic acid sequences means that 80% of the nucleotide residues in two optimally aligned nucleic acid sequences are identical.

In some embodiments, the "percent sequence identity" or "% sequence identity" or "% identity" of a subject sequence to a query sequence can be calculated by optimally aligning the two sequences and comparing the two optimally aligned sequences over the comparison length. The number of positions in the optimal alignment at which identical residues occur in both sequences is determined, thereby providing the number of matched positions, and the number of matched positions is then divided by the total number of positions of the comparison length (which, unless otherwise specified, is the length of the query sequence). The resulting number is multiplied by 100 to yield the percent sequence identity of the subject sequence to the query sequence.

"Optimal alignment" or "optimally aligned" refers to the alignment of two (or more) sequences giving the highest percent identity score. For example, optimal alignment of two protein sequences can be achieved by manually aligning the sequences such that the maximum number of identical amino acid residues in each sequence are aligned together or by using software programs or procedures described herein or known in the art. Optimal alignment of two nucleic acid sequences can be achieved by manually aligning the sequences such that the maximum number of identical nucleotide residues in each sequence are aligned together or by using software programs or procedures described herein or known in the art.

In some embodiments, two polypeptide sequences are deemed "optimally aligned" when they are aligned using defined parameters, such as a defined amino acid substitution matrix, gap existence penalty (also termed gap open penalty), and gap extension penalty, so as to achieve the highest similarity score possible for that pair of sequences. The BLOSUM62 scoring matrix (See, Henikoff and Henikoff, supra) is often used as a default scoring substitution matrix in polypeptide sequence alignment algorithms (e.g., BLASTP). The gap existence penalty is imposed for the introduction of a single amino acid gap in one of the aligned sequences, and the gap extension penalty is imposed for each residue position in the gap. Exemplary alignment parameters employed are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to achieve the highest possible similarity score.

Optimal alignment between two or more sequences can be determined manually by visual inspection or by using a computer, such as, but not limited to for example, the BLASTP program for amino acid sequences and the BLASTN program for nucleic acid sequences (See e.g., Altschul et al., Nucleic Acids Res. 25(17):3389-3402 (1997); See also, the National Center for Biotechnology Information (NCBI) website).

A polypeptide of interest may be said to be "substantially identical" to a reference polypeptide if the polypeptide of interest comprises an amino acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the reference polypeptide. The percent identity between two such polypeptides can be determined manually by inspection of the two optimally aligned polypeptide sequences or by using software programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative amino acid substitution or one or more conservative amino acid substitutions.

A nucleic acid of interest may be said to be "substantially identical" to a reference nucleic acid if the nucleic acid of interest comprises a nucleotide sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the nucleotide sequence of the reference nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the two nucleic acid molecules hybridize to each other under stringent conditions (e.g., within a range of medium to high stringency).

A nucleic acid or polynucleotide is "isolated" when it is partially or completely separated from other components, including but not limited to for example, other proteins, nucleic acids, cells, etc. Similarly, a polypeptide, protein or peptide is "isolated" when it is partially or completely separated from other components, including but not limited to for example, other proteins, nucleic acids, cells, etc. On a molar basis, an isolated species is more abundant than are other species in a composition. For example, an isolated species may comprise at least about 50%, about 70%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a protein or nucleic acid sample, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, the invention provides methods of enriching compositions for one or more molecules of the invention, such as one or more polypeptides or polynucleotides of the invention. A composition is enriched for a molecule when there is a substantial increase in the concentration of the molecule after application of a purification or enrichment technique. A substantially pure polypeptide or polynucleotide of the invention (e.g., substantially pure variant protease or polynucleotide encoding a variant protease of the invention, respectively) will typically comprise at least about 55%, about 60%, about 70%, about 80%, about 85%, about 90%, about 91%, about 92%, about 93%, about 94%, about 95%, about 96%, about 97%, about 98, about 99%, about 99.5% or more by weight (on a molar basis) of all macromolecular species in a particular composition.

In a related sense, the invention provides methods of enriching compositions for one or more molecules of the invention, such as one or more polypeptides of the invention (e.g., one or more variant proteases of the invention) or one or more nucleic acids of the invention (e.g., one or more nucleic acids encoding one or more variant proteases of the invention). A composition is enriched for a molecule when there is a substantial increase in the concentration of the molecule after application of a purification or enrichment technique. A substantially pure polypeptide or polynucleotide will typically comprise at least about 55%, about 60%, about 70%, about 80%, about 85%, about 90%, about 91%, about 92%, about 93%, about 94%, about 95%, about 96%, about 97%, about 98, about 99%, about 99.5% or more by weight (on a molar basis) of all macromolecular species in a particular composition.

As used herein, the term "combinatorial mutagenesis" or "combinatorial" refers to methods in which libraries of nucleic acid variants of a reference nucleic acid sequence are generated. In these libraries, the variants contain one or several mutations chosen from a predefined set of mutations. The methods also provide means to introduce random mutations which were not members of the predefined set of mutations. Some such methods include those set forth in U.S. Pat. No. 6,582,914, hereby incorporated by reference. Some such combinatorial mutagenesis methods include and/or encompass methods embodied in commercially available kits (e.g., QUIKCHANGE® Multi Site-Directed Mutagenesis Kit (Stratagene), PCR fusion/extension PCR).

As used herein, "having improved properties" used in connection with a variant protease refers to a variant protease with improved or enhanced wash or cleaning performance, and/or improved or enhanced stability optionally with retained wash or cleaning performance, relative to the corresponding reference protease (e.g., wild-type or naturally-occurring protease). The improved properties of a variant protease may comprise improved wash or cleaning performance and/or improved stability. In some embodiments, the invention provides variant proteases of the invention that exhibit one of more of the following properties: improved hand wash performance, improved hand or manual dishwashing performance, improved automatic dishwashing performance, improved laundry performance, and/or improved stability relative to a reference protease (e.g., wild-type protease, such as a wild-type subtilisin).

As used herein, the term "functional assay" refers to an assay that provides an indication of a protein's activity. In some embodiments, the term refers to assay systems in which a protein is analyzed for its ability to function in its usual capacity. For example, in the case of enzymes, a functional assay involves determining the effectiveness of the enzyme in catalyzing a reaction.

As used herein, the term "target property" refers to the property of the starting gene that is to be altered. It is not intended that the present invention be limited to any particular target property. However, in some embodiments, the target property is the stability of a gene product (e.g., resistance to denaturation, proteolysis or other degradative factors), while in other embodiments, the level of production in a production host is altered.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term "property" or grammatical equivalents thereof in the context of a polypeptide (including proteins), as used herein, refer to any characteristic or attribute of a polypeptide that can be selected or detected. These properties include, but are not limited to oxidative stability, substrate specificity, catalytic activity, enzymatic activity, thermal stability, alkaline stability, pH activity profile, resistance to proteolytic degradation, $K_M$, $k_{cat}$, $k_{cat}/k_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, and/or ability to treat disease, etc.

As used herein, the term "screening" has its usual meaning in the art. In one exemplary screening process, a mutant nucleic acid or variant polypeptide encoded therefrom is provided and a property of the mutant nucleic acid or variant polypeptide, respectively, is assessed or determined. The determined property of the mutant nucleic acid or variant polypeptide may be compared to a property of the corresponding precursor (parent) nucleic acid or to the property of the corresponding parent polypeptide, respectively.

It will be apparent to the skilled artisan that the screening procedure for obtaining a nucleic acid or protein with an altered property depends upon the property of the starting material the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH, specificity, etc., before and after mutation, wherein a change indicates an alteration. Preferably, the screens are performed in a high-throughput manner, including multiple samples being screened simultaneously, including, but not limited to assays utilizing chips, phage display, and multiple substrates and/or indicators.

As used herein, in some embodiments, a screening process encompasses one or more selection steps in which variants of interest are enriched from a population of variants. Examples of these embodiments include the selection of variants that confer a growth advantage to the host organism, as well as phage display or any other method of display, where variants can be captured from a population of variants based on their binding or catalytic properties. In some embodiments, a library of variants is exposed to stress (e.g., heat, denaturation, etc.) and subsequently variants that are still intact are identified in a screen or enriched by selection. It is intended that the term encompass any suitable means for selection. Indeed, it is not intended that the present invention be limited to any particular method of screening.

The terms "modified nucleic acid sequence" and "modified gene" are used interchangeably herein to refer to a nucleic acid sequence that includes a deletion, insertion or interruption of naturally occurring (i.e., wild-type) nucleic acid sequence. In some embodiments, the expression product of the modified nucleic acid sequence is a truncated protein (e.g., if the modification is a deletion or interruption of the sequence). In some embodiments, the truncated protein retains biological activity. In alternative embodiments, the expression product of the modified nucleic acid sequence is an elongated protein (e.g., modifications comprising an insertion into the nucleic acid sequence). In some embodiments, a nucleotide insertion in the nucleic acid sequence leads to a truncated protein (e.g., when the insertion results in the formation of a stop codon). Thus, an insertion may result in either a truncated protein or an elongated protein as an expression product.

A "mutant" nucleic acid sequence typically refers to a nucleic acid sequence that has an alteration in at least one codon occurring in a host cell's wild-type sequence such that the expression product of the mutant nucleic acid sequence is a protein with an altered amino acid sequence relative to the wild-type protein. The expression product may have an altered functional capacity (e.g., enhanced enzymatic activity).

As used herein, the phrase "alteration in substrate specificity" refers to changes in the substrate specificity of an enzyme. In some embodiments, a change in substrate specificity is defined as a change in $k_{cat}$ and/or $K_m$ for a particular substrate, resulting from mutations of the enzyme or alteration of reaction conditions. The substrate specificity of an enzyme is determined by comparing the catalytic efficiencies it exhibits with different substrates. These determinations find particular use in assessing the efficiency of mutant enzymes, as it is generally desired to produce variant enzymes that exhibit greater ratios of $k_{cat}/K_m$ for substrates of interest. However, it is not intended that the present invention be limited to any particular substrate composition or substrate specificity.

As used herein, "surface property" is used in reference to electrostatic charge, as well as properties such as the hydrophobicity and hydrophilicity exhibited by the surface of a protein.

As used herein, the term "net charge" is defined as the sum of all charges present in a molecule. "Net charge changes" are made to a parent protein molecule to provide a variant that has a net charge that differs from that of the parent molecule (i.e., the variant has a net charge that is not the same as that of the parent molecule). For example, substitution of a neutral amino acid with a negatively charged amino acid or a positively charged amino acid with a neutral amino acid results in net charge of −1 with respect to the parent molecule. Substitution of a positively charged amino acid with a negatively charged amino acid results in a net charge of −2 with respect to the parent. Substitution of a neutral amino acid with a positively charged amino acid or a negatively charged amino acid with a neutral amino acid results in net charge of +1 with respect to the parent. Substitution of a negatively charged amino acid with a positively charged amino acid results in a net charge of +2 with respect to the parent. The net charge of a parent protein can also be altered by deletion and/or insertion of charged amino acids The terms "thermally stable" and "thermostable" and "thermostability" refer to proteases that retain a specified amount of enzymatic activity after exposure to identified temperatures over a given period of time under conditions prevailing during the proteolytic, hydrolyzing, cleaning or other process of the invention, while being exposed to altered temperatures. "Altered temperatures" encompass increased or decreased temperatures. In some embodiments, the proteases retain at least about 50%, about 60%, about 70%, about 75%, about 80%, about 85%, about 90%, about 92%, about 95%, about 96%, about 97%, about 98%, or about 99% proteolytic activity after exposure to altered temperatures over a given time period, for example, at least about 60 minutes, about 120 minutes, about 180 minutes, about 240 minutes, about 300 minutes, etc.

The term "enhanced stability" in the context of an oxidation, chelator, thermal and/or pH stable protease refers to a higher retained proteolytic activity over time as compared to other proteases (e.g., subtilisin proteases) and/or wild-type enzymes.

The term "diminished stability" in the context of an oxidation, chelator, thermal and/or pH stable protease refers to a lower retained proteolytic activity over time as compared to other proteases (e.g., subtilisin proteases) and/or wild-type enzymes.

The term "cleaning activity" refers to a cleaning performance achieved by a variant protease or reference protease under conditions prevailing during the proteolytic, hydrolyzing, cleaning, or other process of the invention. In some embodiments, cleaning performance of a variant protease or reference protease may be determined by using various assays for cleaning one or more various enzyme sensitive stains on an item or surface (e.g., a stain resulting from food, grass, blood, ink, milk, oil, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO 99/34011 and U.S. Pat. No. 6,605,458, both of which are herein incorporated by reference, as well as those cleaning assays and methods included in the Examples provided below.

The term "cleaning effective amount" of a variant protease or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a variant protease of the invention. In some embodiments, the cleaning compositions of the present invention include one of more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

The term "enhanced performance" in the context of cleaning activity refers to an increased or greater cleaning activity by an enzyme on certain enzyme sensitive stains such as egg, milk, grass, ink, oil, and/or blood, as determined by usual evaluation after a standard wash cycle and/or multiple wash cycles.

The term "diminished performance" in the context of cleaning activity refers to a decreased or lesser cleaning activity by an enzyme on certain enzyme sensitive stains such as egg, milk, grass or blood, as determined by usual evaluation after a standard wash cycle.

The term "comparative performance" in the context of cleaning activity of a variant protease of the invention refers to at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.5% of the cleaning activity of a comparative or reference protease (e.g., commercially available proteases), including, but not limited to for example, OPTIMASE™ protease (Genencor), PURAFECT™ protease products (Genencor), SAVINASE™ protease (Novozymes), BPN'-variants (See e.g., U.S. Pat. No. Re 34,606), RELASE™, DURAZYME™, EVERLASE™, KANNASE™ protease (Novozymes), MAXACAL™, MAXAPEM™, PROPERASE™ proteases (Genencor; See also, U.S. Pat. No. Re 34,606, and U.S. Pat. Nos. 5,700,676; 5,955,340; 6,312,936; and 6,482,628), and B. lentus variant protease products (e.g., those described in WO 92/21760, WO 95/23221 and/or WO 97/07770). Cleaning performance can be determined by comparing the variant proteases of the present invention with reference subtilisin proteases in various cleaning assays concerning enzyme sensitive stains such as grass, blood, ink, oil, and/or milk as determined by usual spectrophotometric or analytical methodologies after standard wash cycle conditions.

As used herein, the term "consumer product" means fabric and home care product. As used herein, the term "fabric and home care product" or "fabric and household care product" includes products generally intended to be used or consumed in the form in which they are sold and that are for treating fabrics, hard surfaces and any other surfaces, and cleaning systems all for the care and cleaning of inanimate surfaces, as well as fabric conditioner products and other products designed specifically for the care and maintenance of fabrics, and air care products, including: air care including air fresheners and scent delivery systems, car care, pet care, livestock care, personal care, jewelry care, dishwashing, fabric conditioning (including softening and/or freshening), laundry detergency, laundry and rinse additive and/or care, pre-treatment cleaning compositions, hard surface cleaning and/or treatment including floor and toilet bowl cleaners, glass cleaners and/or treatments, tile cleaners and/or treatments, ceramic cleaners and/or treatments, and other cleaning for consumer or institutional use. In some embodiments, the fabric and home care products are suitable for use on wounds and/or skin. "Fabric and home care product" includes consumer and institutional products.

As used herein, the term "non-fabric and home care products" refers to compositions that are added to other compositions to produce an end product that may be a fabric and home care product.

As used herein, the term "institutional cleaning composition" refers to products suitable for use in institutions including but not limited to schools, hospitals, factories, stores, corporations, buildings, restaurants, office complexes and buildings, processing and/or manufacturing plants, veterinary hospitals, factory farms, factory ranches, etc.

As used herein, the term "cleaning and/or treatment composition" is a subset of fabric and home care products that includes, unless otherwise indicated, compositions suitable for cleaning and/or treating items. Such products include, but are not limited to, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use: car or carpet shampoos, bathroom cleaners including toilet bowl cleaners; as well as cleaning auxiliaries such as bleach additives and "stain-stick" or pre-treat types, substrate-laden products such as dryer added sheets.

Indeed, as used herein, "cleaning composition" or "cleaning formulation" of the invention refers to any composition of the invention useful for removing or eliminating a compound (e.g., undesired compound) from an object, item or surface to be cleaned, including, but not limited to for example, a fabric, fabric item, dishware item, tableware item, glassware item, contact lens, other solid substrate, hair (shampoo) (including human or animal hair), skin (soap or and cream), teeth (mouthwashes, toothpastes), surface of an item or object (e.g., hard surfaces, such as the hard surface of a table, table top, wall, furniture item, floor, ceiling, non-dishware item, non-tableware item, etc.), filters, membranes (e.g., filtration membranes, including but not limited to ultrafiltration membranes), etc. The term encompasses any material and/or added compound selected for the particular type of cleaning composition desired and the form of the product (e.g., liquid, gel, granule, spray, or other composition), as long as the composition is compatible with the protease and other enzyme(s) used in the composition. The specific selection of cleaning composition materials are readily made by considering the surface, object, item, or fabric to be cleaned, and the desired form of the composition for the cleaning conditions during use.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwash compositions (e.g., "hand" or "manual" dishwashing detergents) and automatic dishwashing compositions (e.g., "automatic dishwashing detergents").

Cleaning composition or cleaning formulations, as used herein, include, unless otherwise indicated, granular or powder-form all-purpose or heavy-duty washing agents, especially cleaning detergents; liquid, granular, gel, solid, tablet, or paste-form all-purpose washing agents, especially the so-called heavy-duty liquid (HDL) detergent or heavy-duty powder detergent (HDD) types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, and personal cleansing compositions.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners including toilet bowl cleaners; fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets. All of such products which are applicable may be in standard, concentrated or even highly concentrated form even to the extent that such products may in certain aspect be non-aqueous.

As used herein, the term "detergent composition" or "detergent formulation" is used in reference to a composition intended for use in a wash medium for the cleaning of soiled or dirty objects, including particular fabric and/or non-fabric objects or items. Such compositions of the present invention are not limited to any particular detergent composition or formulation. Indeed, in some embodiments, the detergents of the invention comprise at least one variant protease of the invention and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the invention, such as, but not limited to, cleaning compositions or detergent compositions, do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., a variant protease of the invention) refers to the contribution of a variant protease to washing that provides additional cleaning performance to the detergent as compared to the detergent without the addition of the variant protease to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

The term "improved wash performance" is used to indicate that a better end result is obtained in stain removal under relevant washing conditions, or that less variant protease, on weight basis, is needed to obtain the same end result relative to the corresponding wild-type or starting parent protease.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

The position of an amino acid residue in a given amino acid sequence is typically numbered herein using the numbering of the position of the corresponding amino acid residue of the *B. amyloliquefaciens* subtilisin BPN' amino acid sequence shown in SEQ ID NO:1. The *B. amyloliquefaciens* subtilisin BPN' amino acid sequence of SEQ ID NO:1, thus serves as a reference sequence. A given amino acid sequence, such as a variant protease amino acid sequence described herein, can be aligned with the BPN' sequence (SEQ ID NO:1) using an alignment algorithm as described herein, and an amino acid residue in the given amino acid sequence that aligns (preferably optimally aligns) with an amino acid residue in the BPN' sequence can be conveniently numbered by reference to the corresponding amino acid residue in the subtilisin BPN' sequence. Alternatively, if amino acid residue positions of the subtilisin variant protease sequences are numbered using the actual numbering of the amino acid residue positions in the GG36 amino acid sequence (SEQ ID NO:2), and not by reference to corresponding amino acid positions in the BPN' sequence upon alignment, the subtilisin variant protease can be described as a variant protease of the GG36 protease shown in SEQ ID NO:2

Generally, the nomenclature used herein and many of the laboratory procedures in cell culture, molecular genetics, molecular biology, nucleic acid chemistry, and protein chemistry described below are well known and commonly employed by those of ordinary skill in the art. Methods for production and manipulation of recombinant nucleic acid methods, nucleic acid synthesis, cell culture methods, and transgene incorporation (e.g., transfection, electroporation) are known to those skilled in the art and are described in numerous standard texts. Oligonucleotide synthesis and purification steps are typically performed according to specifications. Techniques and procedures are generally performed according to conventional methods well known in the art and various general references that are provided throughout this document. Procedures therein are believed to be well known to those of ordinary skill in the art and are provided for the convenience of the reader.

Polypeptides of the Invention

The present invention provides novel polypeptides, which may be collectively referred to as "polypeptides of the invention." Polypeptides of the invention include isolated, recombinant, substantially pure, or non-naturally occurring variant protease polypeptides, including for example, subtilisin variant polypeptides, having enzymatic activity (e.g., proteolytic activity). In some embodiments, the polypeptides of the invention, such as a subtilisin variant, or a variant of GG36 having the sequence of SEQ ID NO:2, has improved cleaning performance compared to the parent, e.g. GG36 protease having sequence of SEQ ID NO:2. In some embodiments, polypeptides of the invention are useful in cleaning applications and may be incorporated into cleaning compositions that are useful in methods of cleaning an item or a surface (e.g., of surface of an item) in need of cleaning.

In some embodiments, a variant protease of the invention comprises a "variant subtilisin." In some embodiments, the invention provides a "*Bacillus* sp. variant protease." In some embodiments, the invention provides a "*Bacillus* sp. variant subtilisin." In some embodiments, the invention provides an isolated subtilisin variant. In some embodiments, the invention provides an isolated subtilisin variant of *Bacillus lentus* subtilisin GG36 protease, wherein said *Bacillus lentus* subtilisin GG36 protease comprises the amino acid sequence shown in SEQ ID NO:2.

In any of the above embodiments, the invention includes an isolated, recombinant, substantially pure, or non-naturally occurring variant protease having proteolytic activity, which polypeptide comprises a polypeptide sequence having at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.5%, or 100% sequence identity to the amino acid sequences encoding the variant proteases provided herein.

As noted above, the variant protease polypeptides of the invention have enzymatic activities (e.g., proteolytic activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant protease polypeptides of the invention are described infra. The enzymatic activity (e.g., protease activity) of a variant protease polypeptide of the invention can be determined readily using procedures well known to those of ordinary skill in the art. The Examples presented infra describe methods for evaluating the enzymatic activity, cleaning performance, and/or washing performance. The performance of variant proteases of the invention in removing stains (e.g., a proteinaceous stain), cleaning hard surfaces, or cleaning laundry, dishware or tableware item(s) can be readily determined using procedures well known in the art and/or by using procedures set forth in the Examples.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleic acids in one or more codons such that a particular codon encodes the same or a different amino acid, resulting in either a silent variation (e.g., mutation in a nucleotide sequence results in a silent mutation in the amino acid sequence, for example when the encoded amino acid is not altered by the nucleic acid mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded variant protease compared to the variant protease encoded by the original nucleic acid sequence. A nucleic acid of the invention can also be modified to include one or more codons that provide for optimum expression in an expression system (e.g., bacterial expression system), while, if desired, said one or more codons still encode the same amino acid(s).

In some embodiments, the present invention provides a genus of polypeptides comprising variant protease polypeptides having the desired enzymatic activity (e.g., protease activity or cleaning performance activity) which comprise sequences having the amino acid substitutions described herein and also which comprise one or more additional amino acid substitutions, such as conservative and non-conservative substitutions, wherein the polypeptide exhibits, maintains, or approximately maintains the desired enzymatic activity (e.g., protease activity or subtilisin activity, as reflected in the cleaning activity or performance of the variant protease). Amino acid substitutions in accordance with the invention may include, but are not limited to, one or more non-conservative substitutions and/or one or more conservative amino acid substitutions. A conservative amino acid residue substitution typically involves exchanging a member within one functional class of amino acid residues for a residue that belongs to the same functional class (identical amino acid residues are considered functionally homologous or conserved in calculating percent functional homology). A conservative amino acid substitution typically involves the substitution of an amino acid in an amino acid sequence with a functionally similar amino acid. For example, alanine, glycine, serine, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine. Thus, for example, in some embodiments, the invention provides an isolated or recombinant variant protease polypeptide (e.g., variant subtilisin) having proteolytic activity, said variant protease polypeptide comprising an amino acid sequence having at least about 90%, about 95%, about 96%, about 97%, about 98%, about 99%, or about 99.5% sequence identity to the amino acid sequence of SEQ ID NO:2. A conservative substitution of one amino acid for another in a variant protease of the invention is not expected to alter significantly the enzymatic activity or cleaning performance activity of the variant protease. Enzymatic activity or cleaning performance activity of the resultant protease can be readily determined using the standard assays and the assays described herein.

Conservatively substituted variations of a polypeptide sequence of the invention (e.g., variant proteases of the invention) include substitutions of a small percentage, sometimes less than about 25%, about 20%, about 15%, about 14%, about 13%, about 12%, about 11%, about 10%, about 9%, about 8%, about 7%, or about 6% of the amino acids of the polypeptide sequence, or less than about 5%, about 4%, about 3%, about 2%, or about 1%, of the amino acids of the polypeptide sequence, with a conservatively selected amino acid of the same conservative substitution group.

As described elsewhere herein in greater detail and in the Examples provided herein, polypeptides of the invention may have cleaning abilities that may be compared to known proteases, including known subtilisins. Exemplary known subtilisin proteases include, but are not limited to, for example, *B. lentus* subtilisin GG36, *B. amyloliquefaciens* subtilisin BPN', *B. amyloliquefaciens* subtilisin BPN'-Y217L, and *B. clausii* PB92. The amino acid sequence of the mature *B. lentus* subtilisin GG36 protein is:

```
                                              (SEQ ID NO: 2)
AQSVPWGISRVQAPAAHNRGLTGSGVKVAVLDTGISTHPDLNIRGGASF

VPGEPSTQDGNGHGTHVAGTIAALNNSIGVLGVAPSAELYAVKVLGASG

SGSVSSIAQGLEWAGNNGMHVANLSLGSPSPSATLEQAVNSATSRGVLV

VAASGNSGAGSISYPARYANAMAVGATDQNNNRASFSQYGAGLDIVAPG

VNVQSTYPGSTYASLNGTSMATPHVAGAAALVKQKNPSWSNVQIRNHLK

NTATSLGSTNLYGSGLVNAEAATR
```

The amino acid sequence of mature *B. amyloliquefaciens* subtilisin BPN' protein is:

```
                                              (SEQ ID NO: 1)
AQSVPYGVSQIKAPALHSQGYTGSNVKVAVIDSGIDSSHPDLKVAGGA

SMVPSETNPFQDNNSHGTHVAGTVAALNNSIGVLGVAPSASLYAVKVL

GADGSGQYSWIINGIEWAIANNMDVINMSLGGPSGSAALKAAVDKAVA
```

-continued

SGVVVVAAAGNEGTSGSSSTVGYPGKYPSVIAVGAVDSSNQRASFSSV
GPELDVMAPGVSIQSTLPGNKYGAYNGTSMASPHVAGAAALILSKHPN
WTNTQVRSSLENTTTKLGDSFYYGKGLINVQAAAQ

The present invention provides an isolated subtilisin variant, wherein said subtilisin variant is a mature form having proteolytic activity and comprises an amino acid sequence comprising a combination of amino acid substitutions at positions selected from T022R+V104I+Q245R, G020R+S024R+S101A, T022R+S103A+V104I, T022R+V104I+A232V, T022R+S103A+Q245R, T022R+A232V+Q245R, T022R+S103A+A232V, T022R+S103A+V104I+A232V, T022R+V104I+A232V+Q245R, T022R+S103A+V104I+Q245R, T022R+S103A+A232V+Q245R, T022R+S103A+V104I+A232V+Q245R, T022A+N076D+S103A+V104I+A232V+Q245R, T022A+N076D+S103A+V104I+A232V, T022A+N076D+V104I+A232V+Q245R, T022A+N076D+S103A+A232V+Q245R, T022A+N076D+S103A+V104I+Q245R, T022A+N076D+V104I+Q245R, T022A+N076D+A232V+Q245R, T022A+N076D+V104I+A232V, T022A+N076D+S103A+Q245R, T022A+N076D+S103A+A232V, T022A+N076D+S103A+V104I, T022A+N076D+S103A, T022A+N076D+V104I, T022A+N076D+A232V, T022A+N076D+Q245R, G020R+S101A+T213A, G020R+R045T+S101A, G020R+S101A+G211Q, S024R+S101A+T213A, G020R+T022W+S101A, S024R+S101A+G211Q, N043R+S101A+T213A, N043R+R045T+S101A, S024R+N043R+S101A, S024R+R045T+S101A, S101A+G211Q+T213A, G020R+N043R+S101A, R045T+S101A+T213A, T022W+S024R+S101A, T022R+S101G+V104I, T022W+S101A+T213A, T022R+S101G+Q245R, T022W+S101A+G211Q, G020R+S024R+Q245R, T022R+S101G+V104I+Q245R, T022R+S101G+A232V, T022R+S101G+S103A, T022R+S101G+S103A+V104I, T022R+S101G+S103A+Q245R, T022R+S101G+A232V+Q245R, T022R+S101G+V104I+A232V, G020R+S024R+S101A+T213A, G020R+S024R+T213AS101N+V104I+A232V, S101N+S103A+V104I, S101N+S103A+A232V, S101N+S103A+V104I+A232V, G020R+S103A+A232V, G020R+V104I+A232V, G020R+S103A+V104I+A232V, G020R+S103A+V104I, N018R+N076D+N116A, N018R+N076D+T213A, N018R+N076D+S101A, N018R+N076D+A215F, or N018R+N076D+G211Q (List 1), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions T022A+N076D+S103A+V104I+A232V+Q245R (List 2), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from T022R+S103A+V104I+A232V+Q245R, T022A+N076D+S103A+V104I+A232V, T022A+N076D+V104I+A232V+Q245R, T022A+N076D+S103A+A232V+Q245R, or T022A+N076D+S103A+V104I+Q245R (List 3), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from T022R+S103A+V104I+A232V, T022R+V104I+A232V+Q245R, T022R+S103A+V104I+Q245R, T022R+S103A+A232V+Q245R, T022A+N076D+V104I+Q245R, T022A+N076D+A232V+Q245R, T022A+N076D+V104I+A232V, T022A+N076D+S103A+Q245R, T022A+N076D+S103A+A232V, T022A+N076D+S103A+V104I, T022R+S101G+V104I+Q245R, T022R+S101G+S103A+V104I, T022R+S101G+S103A+Q245R, T022R+S101G+A232V+Q245R, T022R+S101G+V104I+A232V, G020R+S024R+S101A+T213A, S101N+S103A+V104I+A232V or G020R+S103A+V104I+A232V (List 4), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from T022R+V104I+Q245R, G020R+S024R+S101A, T022R+S103A+V104I, T022R+V104I+A232V, T022R+S103A+Q245R, T022R+A232V+Q245R, T022R+S103A+A232V, T022A+N076D+S103A, T022A+N076D+V104I, T022A+N076D+A232V, T022A+N076D+Q245R, G020R+S101A+T213A, G020R+R045T+S101A, G020R+S101A+G211Q, S024R+S101A+T213A, G020R+T022W+S101A, S024R+S101A+G211Q, N043R+S101A+1213A, N043R+R045T+S101A, S024R+N043R+S101A, S024R+R045T+S101A, S101A+G211Q+T213A, G020R+N043R+S101A, R045T+S101A+T213A, T022W+S024R+S101A, T022R+S101G+V104I, T022W+S101A+T213A, T022R+S101G+Q245R, T022W+S101A+G211Q, G020R+S024R+Q245R, T022R+S101G+A232V, T022R+S101G+S103A, G020R+S024R+T213A, S101N+V104I+A232V, S101N+S103A+V104I, S101N+S103A+A232V, G020R+S103A+A232V, G020R+V104I+A232V, G020R+S103A+V104I, N018R+N076D+N116A, N018R+N076D+T213A, N018R+N076D+S101A, N018R+N076D+A215F, or N018R+N076D+G211Q (List 5), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from S101N+V104I+A232V, S101N+S103A+V104I, S101N+S103A+A232V, or S101N+S103A+V104I+A232V (List 6), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions S101N+S103A+V104I+A232V (List 7), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from S101N+V104I+A232V, S101N+S103A+V104I, or S101N+S103A+A232V (List 8), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from S103A+V104I+S188D, S188D+Q245R+N248D, S103A+S188D+Q245R, V104I+S188D+Q245R, S103A+V104I+S188D+Q245R, T022A+S103A+S188D, T022A+V104I+S188D, T022A+S103A+V104I+S188D, G159D+S188D+Q245R, S103A+S188D+A232V, S103A+G159D+S188D, V104I+S188D+A232V, V104I+G159D+S188D, S103A+V104I+S188D+A232V, S103A+V104I+G159D+S188D, S103A+S188D+N248D, V104I+S188D+N248D, S103A+V104I+S188D+N248D, G159D+S188D+N248D, S188D+A232V+Q245R, S103A+S188D+A232V+Q245R, V104I+S188D+A232V+Q245R, S103A+V104I+S188D+A232V+Q245R, T022A+S188D+Q245R, T022A+S103A+S188D+Q245R, T022A+V104I+S188D+Q245R, S103A+S188D+E271F, V104I+S188D+E271F, T022A+S103A+V104I+S188D+Q245R, S103A+V104I+S188D+E271F, T022A+S188D+N248D, T022A+S103A+S188D+N248D, T022A+V104I+S188D+N248D, S103A+S188D+Q245R+N248D, T022A+S103A+V104I+S188D+N248D, V104I+S188D+Q245R+N248D, S103A+V104I+S188D+Q245R+N248D, T022A+S188D+A232V, T022A+S103A+S188D+A232V, T022A+V104I+S188D+A232V, T022A+S103A+V104I+S188D+A232V, S188D+A232V+N248D, S188D+Q245R+E271F, T022A+S188D+E271F, T022A+S188D+Q245R+N248D, S103A+S188D+A232V+N248D, S103A+S188D+Q245R+E271F, S188D+N248D+E271F, V104I+S188D+A232V+N248D, V104I+S188D+Q245R+E271F, T022A+S103A+S188D+E271F, T022A+S103A+S188D+Q245R+N248D, S103A+S188D+N248D+E271F, T022A+V104I+S188D+E271F, T022A+V104I+S188D+Q245R+N248D, S103A+V104I+S188D+Q245R+E271F, S103A+V104I+S188D+A232V+N248D, V104I+S188D+N248D+E271F, S188D+A232V+E271F, T022A+S103A+V104I+S188D+E271F, T022A+S103A+V104I+S188D+Q245R+N248D, S103A+V104I+S188D+N248D+E271F, S103A+S188D+A232V+E271F, V104I+S188D+A232V+E271F, T022A+S188D+A232V+Q245R, T022A+S188D+Q245R+E271F, T022A+S188D+N248D+E271F, S103A+V104I+S188D+A232V+E271F, T022A+S103A+S188D+A232V+Q245R, S188D+A232V+Q245R+N248D, S188D+Q245R+N248D+E271F, T022A+S103A+S188D+Q245R+E271F, T022A+S103A+S188D+N248D+E271F, T022A+V104I+S188D+A232V+Q245R, S103A+S188D+A232V+Q245R+N248D, S103A+S188D+Q245R+N248D+E271F, T022A+S103A+S188D+A232V+N248D, T022A+V104I+S188D+N248D+E271F, T022A+V104I+S188D+Q245R+E271F, S188D+A232V+Q245R+E271F, S188D+A232V+Q245R+N248D+E271F, T022A+S103A+V104I+S188D+A232V+Q245R, V104I+S188D+A232V+Q245R+N248D, T022A+V104I+S188D+A232V+N248D, V104I+S188D+Q245R+N248D+E271F, T022A+S188D+A232V+E271F, T022A+S103A+V104I+S188D+Q245R+E271F, T022A+S103A+V104I+S188D+N248D+E271F, T022A+S188D+Q245R+N248D+E271F, S103A+S188D+A232V+Q245R+E271F, S103A+S188D+A232V+N248D+E271F, S103A+V104I+S188D+Q245R+N248D+E271F, T022A+S103A+V104I+S188D+A232V+N248D, S103A+V104I+S188D+A232V+Q245R+N248D, T022A+S103A+S188D+A232V+E271F, V104I+S188D+A232V+N248D+E271F, V104I+S188D+A232V+Q245R+E271F, T022A+S103A+S188D+Q245R+N248D+E271F, T022A+V104I+S188D+A232V+E271F, T022A+S188D+A232V+N248D+E271F, T022A+S188D+A232V+Q245R+N248D, S188D+A232V+Q245R+N248D+E271F, T022A+V104I+S188D+Q245R+N248D+E271F, S103A+V104I+S188D+A232V+N248D+E271F, S103A+V104I+S188D+A232V+Q245R+E271F, T022A+S188D+A232V+Q245R+E271F, T022A+S103A+V104I+S188D+A232V+E271F, T022A+S103A+S188D+A232V+N248D+E271F, T022A+S103A+S188D+A232V+Q245R+N248D, S103A+S188D+A232V+Q245R+N248D+E271F, T022A+V104I+S188D+A232V+Q245R+N248D, T022A+S103A+S188D+A232V+Q245R+E271F, T022A+V104I+S188D+A232V+N248D+E271F, T022A+S188D+A232V+Q245R+N248D+E271F, V104I+S188D+A232V+Q245R+N248D+E271F, T022A+V104I+S188D+A232V+Q245R+E271F, G159D+S188D+Q245R+N248D, T022A+G159D+S188D, T022A+S103A+G159D+S188D, T022A+V104I+G159D+S188D, T022A+S103A+V104I+G159D+S188D, S103A+G159D+S188D+Q245R, V104I+G159D+S188D+Q245R, S103A+V104I+G159D+S188D+Q245R, S103A+G159D+S188D+N248D, V104I+G159D+S188D+N248D, S103A+V104I+G159D+S188D+N248D, G159D+S188D+A232V, S103A+G159D+S188D+A232V, V104I+G159D+S188D+A232V, S103A+V104I+G159D+S188D+A232V, T022A+G159D+S188D+Q245R, G159D+S188D+E271F, T022A+S103A+G159D+S188D+Q245R, S103A+G159D+S188D+E271F, T022A+V104I+G159D+S188D+Q245R, V104I+G159D+S188D+E271F, T022A+S103A+V104I+G159D+S188D+Q245R, S103A+V104I+G159D+S188D+E271F, T022A+G159D+S188D+N248D, T022A+S103A+G159D+S188D+N248D, T022A+V104I+G159D+S188D+N248D, S103A+G159D+S188D+Q245R+N248D, T022A+S103A+V104I+G159D+S188D+N248D, V104I+G159D+S188D+Q245R+N248D, S103A+V104I+G159D+S188D+Q245R+N248D, T022A+G159D+S188D+A232V, T022A+S103A+0159D+S188D+A232V, T022A+V104I+G159D+S188D+A232V, G159D+S188D+A232V+Q245R, T022A+S103A+V104I+0159D+S188D+A232V, S103A+0159D+S188D+A232V+Q245R, G159D+S188D+Q245R+E271F, V104I+G159D+S188D+A232V+Q245R, G159D+S188D+A232V+N248D, T022A+G159D+S188D+E271F, S103A+0159D+S188D+Q245R+E271F, G159D+S188D+N248D+E271F, S103A+V104I+G159D+S188D+A232V+Q245R, S103A+0159D+S188D+A232V+N248D, T022A+G159D+S188D+Q245R+N248D, T022A+S103A+0159D+S188D+E271F, V104I+G159D+S188D+Q245R+E271F, T022A+V104I+G159D+S188D+E271F, V104I+G159D+S188D+E271F, V104I+G159D+S188D+A232V+N248D, S103A+0159D+S188D+N248D+E271F, T022A+S103A+0159D+S188D+Q245R+N248D, S103A+V104I+0159D+S188D+Q245R+E271F, V104I+G159D+S188D+N248D+E271F, G159D+S188D+A232V+E271F, T022A+S103A+V104I+G159D+S188D+E271F, S103A+ V104I+G159D+S188D+A232V+N248D, T022A+V104I+ G159D+S188D+Q245R+N248D, S103A+V104I+G159D+ S188D+N248D+E271F, S103A+0159D+S188D+A232V+ E271F, V104I+G159D+S188D+A232V+E271F, T022A+ 0159D+S188D+N248D+E271F, T022A+0159D+S188D+ A232V+Q245R, T022A+G159D+S188D+Q245R+E271F, S103A+V104I+0159D+S188D+A232V+E271F, G159D+ S188D+Q245R+N248D+E271F, T022A+S103A+0159D+ S188D+A232V+Q245R, T022A+S103A+0159D+S188D+ Q245R+E271F, T022A+S103A+0159D+S188D+N248D+ E271F, T022A+G159D+S188D+A232V+N248D, G159D+ S188D+A232V+Q245R+N248D, T022A+V104I+G159D+ S188D+Q245R+E271F, T022A+V104I+G159D+S188D+ N248D+E271F, T022A+V104I+G159D+S188D+A232V+ Q245R, S103A+0159D+S188D+Q245R+N248D+E271F, G159D+S188D+A232V+Q245R+E271F, G159D+S188D+ A232V+N248D+E271F, T022A+S103A+0159D+S188D+ A232V+N248D, V104I+G159D+S188D+Q245R+N248D+ E271F, S103A+0159D+S188D+A232V+Q245R+N248D, T022A+G159D+S188D+A232V+E271F, T022A+G159D+ S188D+Q245R+N248D+E271F, S103A+0159D+S188D+ A232V+Q245R+E271F, T022A+V104I+G159D+S188D+ A232V+N248D, V104I+G159D+S188D+A232V+Q245R+ N248D, S103A+G159D+S188D+A232V+N248D+E271F, T022A+S103A+0159D+S188D+A232V+E271F, V104I+ G159D+S188D+A232V+Q245R+E271F, V104I+G159D+ S188D+A232V+N248D+E271F, T022A+V104I+G159D+ S188D+A232V+E271F, G159D+S188D+A232V+Q245R+ N248D+E271F, T022A+G159D+S188D+A232V+N248D+ E271F, T022A+G159D+S188D+A232V+Q245R+E271F, T022A+G159D+S188D+A232V+Q245R+N248D, S101G+ S103A+S188D, S101G+V104I+S188D, S101G+S103A+ V104I+S188D (List 9), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides an isolated subtilisin variant, wherein said subtilisin variant is a mature form having proteolytic activity and comprises an amino acid sequence comprising a combination of amino acid substitutions at positions selected from T022A+S103A+V104I+S188D+ Q245R+N248D, T022A+S103A+V104I+S188D+A232V+ Q245R, T022A+S103A+V104I+S188D+Q245R+E271F, T022A+S103A+V104I+S188D+N248D+E271F, S103A+ V104I+S188D+Q245R+N248D+E271F, T022A+S103A+ V104I+S188D+A232V+N248D, S103A+V104I+S188D+ A232V+Q245R+N248D, T022A+S103A+S188D+Q245R+ N248D+E271F, T022A+V104I+S188D+Q245R+N248D+ E271F, S103A+V104I+S188D+A232V+N248D+E271F, S103A+V104I+S188D+A232V+Q245R+E271F, T022A+ S103A+V104I+S188D+A232V+E271F, T022A+S103A+ S188D+A232V+N248D+E271F, T022A+S103A+S188D+ A232V+Q245R+N248D, S103A+S188D+A232V+Q245R+ N248D+E271F, T022A+V104I+S188D+A232V+Q245R+ N248D, T022A+S103A+S188D+A232V+Q245R+E271F, T022A+V104I+S188D+A232V+N248D+E271F, T022A+ S188D+A232V+Q245R+N248D+E271F, V104I+S188D+ A232V+Q245R+N248D+E271F, T022A+V104I+S188D+ A232V+Q245R+E271F, T022A+S103A+V104I+G159D+ S188D+Q245R, T022A+S103A+V104I+G159D+S188D+ N248D, S103A+V104I+G159D+S188D+Q245R+N248D, T022A+S103A+V104I+G159D+S188D+A232V, S103A+ V104I+G159D+S188D+A232V+Q245R, T022A+S103A+ G159D+S188D+Q245R+N248D, S103A+V104I+G159D+ S188D+Q245R+E271F, T022A+S103A+V104I+0159D+ S188D+E271F, S103A+V104I+0159D+S188D+A232V+ N248D, T022A+V104I+G159D+S188D+Q245R+N248D, S103A+V104I+G159D+S188D+N248D+E271F, S103A+ V104I+G159D+S188D+A232V+E271F, T022A+S103A+ G159D+S188D+A232V+Q245R, T022A+S103A+G159D+ S188D+Q245R+E271F, T022A+S103A+G159D+S188D+ N248D+E271F, T022A+V104I+G159D+S188D+Q245R+ E271F, T022A+V104I+0159D+S188D+N248D+E271F, T022A+V104I+0159D+S188D+A232V+Q245R, S103A+ G159D+S188D+Q245R+N248D+E271F, T022A+S103A+ G159D+S188D+A232V+N248D, V104I+G159D+S188D+ Q245R+N248D+E271F, S103A+G159D+S188D+A232V+ Q245R+N248D, T022A+G159D+S188D+Q245R+N248D+ E271F, S103A+G159D+S188D+A232V+Q245R+E271F, T022A+V104I+G159D+S188D+A232V+N248D, V104I+ G159D+S188D+A232V+Q245R+N248D, S103A+G159D+ S188D+A232V+N248D+E271F, T022A+S103A+G159D+ S188D+A232V+E271F, V104I+G159D+S188D+A232V+ Q245R+E271F, V104I+0159D+S188D+A232V+N248D+ E271F, T022A+V104I+G159D+S188D+A232V+E271F, G159D+S188D+A232V+Q245R+N248D+E271F, T022A+ G159D+S188D+A232V+N248D+E271F, T022A+G159D+ S188D+A232V+Q245R+E271F, or T022A+G159D+ S188D+A232V+Q245R+N248D (List 10), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from S103A+V104I+ S188D+A232V+Q245R, T022A+S103A+V104I+S188D+ Q245R, T022A+S103A+V104I+S188D+N248D, S103A+ V104I+S188D+Q245R+N248D, T022A+S103A+V104I+ S188D+A232V, T022A+S103A+S188D+Q245R+N248D, T022A+V104I+S188D+Q245R+N248D, S103A+V104I+ S188D+Q245R+E271F, S103A+V104I+S188D+A232V+ N248D, T022A+S103A+V104I+S188D+E271F, S103A+ V104I+S188D+N248D+E271F, S103A+V104I+S188D+ A232V+E271F, T022A+S103A+S188D+A232V+Q245R, T022A+S103A+S188D+Q245R+E271F, T022A+S103A+ S188D+N248D+E271F, T022A+V104I+S188D+A232V+ Q245R, S103A+S188D+A232V+Q245R+N248D, S103A+ S188D+Q245R+N248D+E271F, T022A+S103A+S188D+ A232V+N248D, T022A+V104I+S188D+N248D+E271F, T022A+V104I+S188D+Q245R+E271F, V104I+S188D+ A232V+Q245R+N248D, T022A+V104I+S188D+A232V+ N248D, V104I+S188D+Q245R+N248D+E271F, T022A+ S188D+Q245R+N248D+E271F, S103A+S188D+A232V+ Q245R+E271F, S103A+S188D+A232V+N248D+E271F, T022A+S103A+S188D+A232V+E271F, V104I+S188D+ A232V+N248D+E271F, V104I+S188D+A232V+Q245R+ E271F, T022A+V104I+S188D+A232V+E271F, T022A+ S188D+A232V+N248D+E271F, T022A+S188D+A232V+ Q245R+N248D, S188D+A232V+Q245R+N248D+E271F, T022A+S188D+A232V+Q245R+E271F, T022A+S103A+ V104I+G159D+S188D, S103A+V104I+G159D+S188D+ Q245R, S103A+V104I+G159D+S188D+N248D, S103A+ V104I+G159D+S188D+A232V, T022A+S103A+G159D+ S188D+Q245R, T022A+V104I+G159D+S188D+Q245R, S103A+V104I+G159D+S188D+E271F, T022A+S103A+ G159D+S188D+N248D, T022A+V104I+G159D+S188D+ N248D, S103A+G159D+S188D+Q245R+N248D, V104I+ G159D+S188D+Q245R+N248D, T022A+S103A+G159D+ S188D+A232V, T022A+V104I+G159D+S188D+A232V, S103A+G159D+S188D+A232V+Q245R, V104I+G159D+ S188D+A232V+Q245R, S103A+G159D+S188D+Q245R+ E271F, S103A+G159D+S188D+A232V+N248D, T022A+ G159D+S188D+Q245R+N248D, T022A+S103A+G159D+ S188D+E271F, V104I+G159D+S188D+Q245R+E271F, T022A+V104I+G159D+S188D+E271F, V104I+G159D+ S188D+A232V+N248D, S103A+G159D+S188D+N248D+ E271F, V104I+G159D+S188D+N248D+E271F, S103A+ G159D+S188D+A232V+E271F, V104I+G159D+S188D+ A232V+E271F, T022A+G159D+S188D+N248D+E271F, T022A+G159D+S188D+A232V+Q245R, T022A+G159D+ S188D+Q245R+E271F, G159D+S188D+Q245R+N248D+ E271F, T022A+G159D+S188D+A232V+N248D, G159D+ S188D+A232V+Q245R+N248D, G159D+S188D+A232V+ Q245R+E271F, G159D+S188D+A232V+N248D+E271F, or T022A+G159D+S188D+A232V+E271F (List 11), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from S103A+V104I+ S188D+Q245R, T022A+S103A+V104I+S188D, S103A+ V104I+S188D+A232V, S103A+V104I+0159D+S188D, S103A+V104I+S188D+N248D, S103A+S188D+A232V+ Q245R, V104I+S188D+A232V+Q245R, T022A+S103A+ S188D+Q245R, T022A+V104I+S188D+Q245R, S103A+ V104I+S188D+E271F, T022A+S103A+S188D+N248D, T022A+V104I+S188D+N248D, S103A+S188D+Q245R+ N248D, V104I+S188D+Q245R+N248D, T022A+S103A+ S188D+A232V, T022A+V104I+S188D+A232V, T022A+ S188D+Q245R+N248D, S103A+S188D+A232V+N248D, S103A+S188D+Q245R+E271F, V104I+S188D+A232V+ N248D, V104I+S188D+Q245R+E271F, T022A+S103A+ S188D+E271F, S103A+S188D+N248D+E271F, T022A+ V104I+S188D+E271F, V104I+S188D+N248D+E271F, S103A+S188D+A232V+E271F, V104I+S188D+A232V+ E271F, T022A+S188D+A232V+Q245R, T022A+S188D+ Q245R+E271F, T022A+S188D+N248D+E271F, S188D+ A232V+Q245R+N248D, S188D+Q245R+N248D+E271F, T022A+S188D+A232V+N248D, S188D+A232V+Q245R+ E271F, S188D+A232V+N248D+E271F, T022A+S188D+ A232V+E271F, G159D+S188D+Q245R+N248D, T022A+ S103A+0159D+S188D, T022A+V104I+G159D+S188D, S103A+0159D+S188D+Q245R, V104I+G159D+S188D+ Q245R, S103A+G159D+S188D+N248D, V104I+G159D+ S188D+N248D, S103A+G159D+S188D+A232V, V104I+ 0159D+S188D+A232V, T022A+G159D+S188D+Q245R, S103A+0159D+S188D+E271F, V104I+G159D+S188D+ E271F, T022A+0159D+S188D+N248D, T022A+G159D+ S188D+A232V, G159D+S188D+A232V+Q245R, G159D+ S188D+Q245R+E271F, G159D+S188D+A232V+N248D, T022A+G159D+S188D+E271F, G159D+S188D+N248D+ E271F, G159D+S188D+A232V+E271F, or S101G+ S103A+V104I+S188D (List 12), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from S103A+V104I+ S188D, S188D+Q245R+N248D, S103A+S188D+Q245R, V104I+S188D+Q245R, T022A+S103A+S188D, T022A+ V104I+S188D, G159D+S188D+Q245R, S103A+S188D+ A232V, S103A+G159D+S188D, V104I+S188D+A232V, V104I+0159D+S188D, S103A+S188D+N248D, V104I+ S188D+N248D, G159D+S188D+N248D, S188D+A232V+ Q245R, T022A+S188D+Q245R, S103A+S188D+E271F, V104I+S188D+E271F, T022A+S188D+N248D, T022A+ S188D+A232V, S188D+A232V+N248D, S188D+Q245R+ E271F, T022A+S188D+E271F, S188D+N248D+E271F, S188D+A232V+E271F, T022A+0159D+S188D, G159D+ S188D+A232V, G159D+S188D+E271F, S101G+S103A+ S188D, or S101G+V104I+S188D (List 13), and wherein amino acid positions of the subtilisin variant are numbered according to the numbering of corresponding amino acid positions in the amino acid sequence of *Bacillus amyloliquefaciens* subtilisin BPN' shown in SEQ ID NO: 1.

The present invention further provides an isolated subtilisin variant, wherein said subtilisin variant is a mature form having proteolytic activity and comprises an amino acid sequence comprising a combination of amino acid substitutions at positions selected from S101G-S103A-V104I-G159D-S188D-A232V-Q245R-N248D-E271F, T022A-S103A-V104I-G159D-S188D-A232V-Q245R-N248D-E271F, T022A-S101G-V104I-G159D-S188D-A232V-Q245R-N248D-E271F, T022A-S101G-S103A-G159D-S188D-A232V-Q245R-N248D-E271F, T022A-S101G-S103A-V104I-S188D-A232V-Q245R-N248D-E271F, T022A-S101G-S103A-V104I-G159D-S188D-Q245R-N248D-E271F, T022A-S101G-S103A-V104I-G159D-S188D-A232V-N248D-E271F, T022A-S101G-S103A-V104I-G159D-S188D-A232V-Q245R-E271F, T022A-S101G-S103A-V104I-G159D-S188D-A232V-Q245R-N248D, S101G-S103A-V104I-N116L-G159D-S188D-A232V-Q245R-N248D-E271F, T022A-S103A-V104I-N116L-G159D-S188D-A232V-Q245R-N248D-E271F, T022A-S101G-V104I-N116L-G159D-S188D-A232V-Q245R-N248D-E271F, T022A-S101G-S103A-N116L-G159D-S188D-A232V-Q245R-N248D-E271F, T022A-S101G-S103A-V104I-N116L-S188D-A232V-Q245R-N248D-E271F, T022A-S101G-S103A-V104I-N116L-G159D-A232V-Q245R-N248D-E271F, T022A-S101G-S103A-V104I-N116L-G159D-S188D-Q245R-N248D-E271F, T022A-S101G-S103A-V104I-N116L-G159D-S188D-A232V-N248D-E271F, T022A-S101G-S103A-V104I-N116L-G159D-S188D-A232V-Q245R-E271F, T022A-S101G-S103A-V104I-N116L-G159D-S188D-A232V-Q245R-N248D-E271F, G020R-N062E-S078G-G118S-S188D-N248D-H249R, S024R-N062E-G118R-A158E-S188D, T022A-S024R-T033S-G118R-S166D-S188D, S024R-N062E-S078G-G118S-S188D-Q245R-N248D, G020R-S024R-N062E-S078D-G118S-P129E-G159D, G020R-S024R-N062E-S078G-G118D-P129E, G020R-S024R-N062E-S078G-G118S-P129E-G159D-S188D-Q245R-N248D, G020R-N062E-S078G-G118S-G159D-Q245R-N248D, S024R-N116L-A158E-S166D, G020R-N062E-S078G-G118S-G159D-S188D-H249R, G020R-S024R-S078G-G118D-P129E-G159D-S188D, S024R-G118R-S166D, T022A-S024R-T033S-G118R-A158E-S166D-A273V, G020R-N062E-S078G-G118S-P129E-G159D-S188D-Q245R, T022A-G118R-A158E-S166D, G020R-S024R-N062E-S078D-G118S-G159D-S188D-Q245R-N248D, T022A-S024R-G118R-S166D-S188D, N062E-S078G-G118S-G159D, T022A-S101G-S103A-V104I-G159D-S188D-A232V-Q245R-N248E-E271H, G020R-S024R-N062E-S078G-G118D-Q245R-N248D, S024R-T033S-N116L-A158E-S166D, S024R-N062E-S078G-G118D-P129E-G159D-Q245R, G020R-N062E-S078D-G118S-Q245R, T022A-S024R-N062E-N116L-A158E, G020R-N062E-S078G-G118D-P129E, S024R-T033S-N062E-N116L-G118R-S188D, G020R-N062E-S078G-G118D-P129E-G159D-S188D-H249R, S024R-S078G-G118S-P129E-G159D-Q245R-N248D, G020R-N062E-S078G-G118D-S188D-H249R, T022Q-S101G-S103A-V104I-G159D-S188D-A232L-Q245T-N248D-E271T, S078G-G118S-P129E-G159D-S188D-Q245R-N248D-H249R, T022Q-S101G-S103A-V104I-G159D-S188E-A232V-Q245T-N248H-E271T, G020R-S024R-S078D-G118S-G159D-S188D-H249R, G020R-S078D-G118S-P129E-G159D-Q245R-N248D-H249R, S024R-N062E-N116L-G118R, T022A-S024R-N116L-G118R-A158E-S188D, S024R-N062E-S078G-G118S-P129E-Q245R, S024R-N062E-G118R-A158E, G020R-N062E-S078G-G118S-G159D-S188D, G020R-S024R-S078D-G118S-G159D-S188D-Q245R-N248D-H249R, S024R-S078D-G118S-P129E-G159D-Q245R, A098Q-S099T-G102A-S103G, T022A-G118R-S166D-S188D, S024R-S078D-G118S-G159D-S188D-H249R, T022A-S024R-N116L-G118R-S166D-S188D, T022A-N062E-G118R-A158E, G020R-S078G-G118D-G159D-S188D-Q245R, S024R-N062E-S078G-G118D-G159D-S188D-Q245R, T022Q-S101G-S103A-V104I-G159D-S188D-A232V-Q245R-N248E-E271F, T022A-S101G-S103A-V104I-G159D-S188E-A232S-Q245R-N248E-E271F, G020R-N062E-S078G-G118S-P129E-N248D-H249R, S024R-N116L-G118R-S128I-S166D-S188D, G020R-S024R-N062E-S078G-G118D-P129E-G159D-S188D-H249R, G020R-S024R-N062E-S078G-G118D-G159D-S188D-N248D, G020R-S024R-S078G-G118D-P129E-S188D-Q245R-N248D, S024R-N062E-S078D-G118S-S188D-H249R, T033S-N062E-G118R, T022Q-S101G-S103A-V104I-G159D-S188D-A232S-Q245T-N248E-E271H, T033S-G118R-A158E-S166D, T022Q-S101G-S103A-V104I-G159D-S188E-A232S-Q245V-N248H, G020R-S024R-S078D-G118D-S188D-Q245R-N248D-H249R, T022A-S024R-N062E, G020R-S024R-N062E-S078D-G118D-G159D-S188D-R247L, T022Q-S101G-S103A-V104I-G159D-S188D-A232S-Q245R-N248E-E271T, G020R-N062E-S078G-G118S-P129E-G159D-Q245R-N248D, T022Q-S101G-S103A-V104I-G159D-S188E-A232S-Q245R-N248H, P014S-G020R-S024R-S078G-G118S-P129E-S188D-Q245R-N248D, T022A-S101G-S103A-V104I-G159D-S188E-A232V-Q245R-N248E-E271L, G020R-S078D-G118D-G159D-S188D-H249R, T022Q-S101G-S103A-V104I-G159D-S188E-A232L-Q245R-N248D-E271T, T022A-S101G-S103A-V104I-G159D-S188E-A232T-Q245T-N248E-E271L, S024R-N062E-S078D-G118S-S188D-Q245R, T022Q-S101G-S103A-V104I-G159D-S188E-A232L-Q245R-N248E-E271H, G020R-S078D-G118S-P129E-G159D-H249R, T022A-S101G-S103A-V104I-G159D-S188D-A232S-Q245R-N248H-E271F, T022A-S101G-S103A-V104I-G159D-S188D-A232L-Q245R-N248H-E271H, S024F-T033S-S101G-S103A-V104I-N116A-Y209A-T213A-A232V, S024F-S101G-S103A-V104I-N116L-S128N-Y209V-G211Q-T213A-A232V, S024R-S078G-G118S-G159D-S188D-Q245R-N248D, G020R-S024R-S078G-G118S-S188D-Q245R, G020R-S024R-N062E-S078D-G118D-P129E-G159D-Q245R, S024R-S078D-G118D-G159D-S188D-H249R, G020R-S078G-G118S-G159D-S188D-H249R, G020R-S024R-N062E-S078G-G118S-S188D-N248D, S078D-G118S-G159D-Q245R, G020R-S024R-N062E-S078G-G118D-P129E-G159D-N248D-H249R, S024R-N062E-S078G-G118S-P129E-Q245R-N248D, G020R-S078G-G118S-P129E-S188D-Q245R-N248D, S024R-N062E-S078G-G118S-G159D-Q245R, G020R-N062E-S078D-G118D-P129E-Q245R, T022A-S101G-S103A-V104I-G159D-S188E-P210L-A232T-Q245T-N248D-E271T, G020R-S024R-N062E-S078G-G118S-P129E, G020R-S024R-N062E-S078G-G118D-G159D-S188D-H249R, T022Q-S101G-S103A-V104I-G159D-S188D-A232T-Q245V-N248D-E271L, A016S-T022A-S101G-S103A-V104I-N116L-S128N-Y209V-A232V, T022A-S101G-S103A-V104I-G159D-S188E-A232S-Q245T-N248H-E271H, G020R-N062E-S078G-G118D-P129E-G159D-H249R, T022A-S101G-S103A-V104I-G159D-S188D-A232L-Q245R-N248E, G020R-S024R-S078G-G118D-G159D-S188D-Q245R, S024R-N062E-S078G-G118S-G159D-Q245R-N248D, G020R-S078G-G118S-G159D-S188D-Q245R, S024R-N062E-S078G-G118S-G159D-S188D, T022A-S101G-S103A-V104I-G159D-S188E-A232V-Q245R-N248H-E271H, G020R-S024R-N062E-S078G-G118D-G159D, T022A-S101G-S103A-V104I-G159D-S188D-A232T-V244A-Q245R-N248H-E271H, S024R-S078G-G118S-P129E-G159D-S188D-Q245R, T022Q-S101G-S103A-V104I-G159D-S188E-A232V-Q245V-N248D-E271F, G020R-S024R-N062E-S078G-G118D-G159D-S188D-Q245R, T022A-S024R-N062E-S128I-A158E, G020R-S024R-S078G-G118D-N248D-H249R, S024R-S078G-G118D-P129E-Q245R-H249R, T022A-S101G-S103A-V104I-G159D-S188D-A232T-Q236K-Q245T-N248E, N062E-S078G-G118S-G159D-Q245R-N248D, T033S-G118R-S166D, G020R-S024R-S078G-G118D-P129E-S188D-N248D, G020R-S078G-G118S-P129E-G159D-S188D-Q245R-N248D, A016S-T022A-S101G-S103A-V104I-L111V, T022Q-S101G-S103A-V104I-G159D-S188D-A232V-Q245R-N248E-E271H, S024R-N116L-G118R-S128I-A158E-S188D-V199I, G020R-S024R-S078D-G118D-G159D-H249R, T022A-S101G-S103A-V104I-G159D-S188E-A232S-Q245R-N248E-E271T, G020R-S024R-S078D-G118S-S188D-N248D-H249R, T022A-S101G-S103A-V104I-G159D-S188D-A232T-Q245R-N248D-E271T, G020R-S024R-S078G-G118D-P129E-S188D-H249R, S024R-N062E-S078G-G118S-S188D-N248D, T022A-S101G-S103A-V104I-N116L-S128N-Y209A-G211Q-T213A-A232V, T022Q-S101G-S103A-V104I-G159D-S188D-A232T-Q245R-N248D-E271L, S024R-A048V-S078G-G118D-G159D-S188D-H249R, G020R-S024R-N062E-S078D-G118D, G102A-S103G-V104I, G020R-S024R-S078D-G118D-G159D-Q245R-N248D-H249R, T022A-T033S-G118R-A158E, T022A-S024R-N116L-S128I-S188D, G020R-S024R-S078D-G118D-P129E-G159D-Q245R-N248D-H249R, T022Q-S101G-S103A-V104I-G159D-S188E-A232T-Q245T-N248E-E271F, S024R-N062E-S078G-G118S-S188D-Q245R, S024R-N062E-S078G-G118D-G159D, G020R-S024R-N062E-S078D-G118S-P129E-G159D-Q245R, T022Q-S101G-S103A-V104I-G159D-S188E-A232S-Q245V-N248E-E271T, G020R-S078G-G118D-S188D-N248D-H249R, T022A-S024R-N062E-N116L-G118R-A158E-S166D-S188D, S078G-G118S-G159D-S188D-H249R, T022Q-S101G-S103A-V104I-G159D-S188E-A232T-Q245V-N248H-E271F, G020R-S078G-G118S-P129E-G159D-S240E-N248D-H249R, S024F-T033S-S101G-S103A-V104I-N116A-Y209A-G211Q-T213A-A232V, N062E-S078D-G118S-S188D-H249R, T022A-S101G-S103A-V104I-G159D-S188E-A232V-Q245V-N248D-E271T, G020R-S078G-G118S-G159D-S188D-Q245R-N248D, T022Q-S101G-S103A-V104I-G159D-S188D-A232T-Q245R-N248D-E271F,

S024R-S078G-G118D-G159D-S188D-Q245R-N248D-H249R, G020R-S024R-N062E-S078D-G118D-Q245R, S024R-S078G-G118D-P129E-S188D-Q245R, N062E-S078G-G118S-S188D-Q245R-N248D-H249R, S024R-N062E-S078G-G118D-G159D-H249R, G020R-S078G-G118S-P129E-G159D-S188D-H249R, S024R-N062E-S078G-G118S-P129E-S188D-H249R, T022Q-S101G-S103A-V104I-G159D-S188E-A232L-Q245R-N248H, T022Q-S101G-S103A-V104I-G159D-S188D-A232V-Q245V-N248H-E271L, G020R-S101G-S103A-V104I-N116A-S128N-Y209V-G211Q-T213A-A232V, S024R-N062E-S078D-G118S-P129E-G159D-H249R, T022A-S101G-S103A-V104I-G159D-S188E-A232V-Q245R-N248D-E271H, G020R-N062E-S078G-G118D-P129E-S188D-H249R, T022Q-S101G-S103A-V104I-G159D-S188E-A232L-Q245V-N248E-E271L, G020K-T022L-S078D-G118S-P129E-G159D, G078G-G118S-S188D-Q245R-N248D, T022A-S024F-S101G-S103A-V104I-N116A-S128N-Y209A-A232V, G020R-S024R-N062E-S078G-G118S-G159D-N248D, N062E-G118R-S166D-S188D, T022Q-S101G-S103A-V104I-G159D-S188E-A232T-Q245R-N248E-E271T, T022A-S101G-S103A-V104I-G159D-S188D-A232S-Q245T-N248H-E271F, G020R-N062E-S078G-G118S-G159D-H249R, S024R-N062E-N116L-A158E, S024R-S078G-G118D-P129E-Q245R-N248D-H249R, G020R-S024R-N062E-S078D-G118S-P129E-S188D-Q245R, S024R-S078G-G118D-P129E-G159D-S188D-H249R, T022Q-S101G-S103A-V104I-G159D-S188E-A232L-Q245R-N248D-E271H, S024R-S078D-G118D-P129E-S188D-Q245R-N248D-H249R, G020R-S024R-S078G-G118D-P129E-G159D-N248D-H249R, T022A-S101G-S103A-V104I-G159D-S188E-A232V-Q245T-N248E-E271F, T022Q-S101G-S103A-V104I-G159D-S188D-A232L-Q245T-N248H-E271T, S024R-S078D-G118S-P129E-G159D, G020R-N062E-S078G-G118S-P129E-S188D-Q245R, T022A-S024R-N116L-G118R-S128I-S188D, T022A-S101G-S103A-V104I-G159D-S188E-A232L-Q245T-N248E-E271H, G020R-S024R-S078D-G118S-P129E-G159D-S188D-Q245R-N248D, G020R-S024R-N062E-S078G-G118S-P129E-S188D-N248D-H249R, T022A-S101G-S103A-V104I-G159D-S188E-A232V-Q245V-N248H-E271H, G020R-G078G-G118D-P129E-G159D-S188D-H249R, G020R-S024R-S078D-G118S-S188D-Q245R-H249R, T022A-S101G-S103A-V104I-G159D-S188D-A232V-Q245R-N248E-E271F, T022A-S101G-S103A-V104I-G159D-S188D-A232T-Q245R-N248D-E271F, S024R-N062E-S078G-G118S-S188D-N248D-H249R, G020R-N062E-S078G-G118S-G159D-Q245R, S024R-N062E-G118R-A158E-S166D-S188D, S024R-N062E-S078G-G118S-P129E-G159D-N248D-H249R, G020R-S024R-N062E-S078G-G118S-P129E-A158T-G159D-Q245R-N248D, T022Q-S101G-S103A-V104I-G159D-S188E-A232T-Q245R-N248E-E271L, G020R-S024R-N062E-S078D-G118S-S188D-H249R, S024R-S078G-G118S-S188D-N248D, T022A-S101G-S103A-V104I-G159D-S188E-A232L-Q245V-N248E-E271H, T022Q-S101G-S103A-V104I-G159D-S188D-A232L-Q245T-N248H-E271H, S099G-S101G, T022Q-S101G-S103A-V104I-G159D-S188D-A232T-Q245V-N248D-E271F, G020R-N062E-S078D-G118S-P129E-G159D-Q245R, T022A-S101G-S103A-V104I-G159D-S188E-A232T-Q245T-N248H-E271H, T022Q-S101G-S103A-V104I-G159D-S188E-A232V-Q245V-N248H-E271L, T022A-S101G-S103A-V104I-G159D-S188D-A232V-Q245R-N248E-E271T, T022Q-S101G-S103A-V104I-G159D-S188E-A232L-Q245T-N248E-E271T, T022Q-S101G-S103A-V104I-G159D-S188E-A232L-Q245V-N248E-E271H, T022Q-S101G-S103A-V104I-G159D-S188D-A232T-Q245R-N248H-E271L, G020R-S078G-G118S-P129E-G159D-S188D-Q245R-N248D-H249R, G020R-S024R-N062E-S078G-G118D-S188D-N248D, S024R-N062E-S078G-G118S-P129E-G159D, A016S-T022A-S101G-S103A-V104I-N116A-S128N-Y209V-G211Q-A232V, S024R-S078G-G118D-S188D-Q245R-N248D-H249R, G020R-S024R-S078D-G118D-G159D-S188D-Q245R-N248D-H249R, A016S-T022A-S101G-S103A-V104I-N116A-Y209V-G211Q-T213A-A232V, S024R-N062E-S078G-G118D-S188D-H249R, T022L-S078N-G118R-S166D-T213A-L217E, T022A-S101G-S103A-V104I-G159D-S188D-A232S-Q245R-N248E-E271H, S024R-S078G-G118D-G159D-N248D-H249R, S024R-S078G-G118D-P129E-S188D-Q245R-N248D, T022Q-S101G-S103A-V104I-G159D-S188E-A232T-Q245T-N248H-E271T, T022A-S101G-S103A-V104I-G159D-S188D-A232S-Q245R-N248H-E271H, G020R-S024R-S078G-G118S-G159D-S188D-Q245R-N248D, T022A-S101G-S103A-V104I-G159D-S188D-A232V-Q245R-N248D-E271L, S024R-N062E-S078G-G118D-P129E-G159D-H249R, T022A-S101G-S103A-V104I-G159D-S188E-A232T-Q245T-N248H-E271F, G020R-S024R-N062E-S078G-G118S-P129E-G159D-S188D-N248D-H249R, T022Q-S101G-S103A-V104I-G159D-S188E-A232T-Q245R-N248H-E271T, T022A-S101G-S103A-V104I-G159D-S188D-A232S-Q245R-N248E-E271F, G020R-S024R-S078D-G118S-P129E-G159D-H249R, S024R-N062E-S078G-G118S-P129E-G159D-S188D-Q245R, T022A-S101G-S103A-V104I-G159D-S188E-A232S-Q245R-N248D-E271H, G020R-S024R-S078D-G118S-S188D, T022A-S101G-S103A-V104I-G159D-S188D-A232T-Q245R-N248E, T022Q-S101G-S103A-V104I-G159D-S188D-A232T-Q245R-N248D-E271H, T022A-S101G-S103A-V104I-G159D-S188E-A232T-Q245R-N248H-E271F, T022Q-S101G-S103A-V104I-G159D-S188E-A232S-Q245T-N248H-E271T, T022A-S101G-S103A-V104I-G159D-S188D-A232S-Q245T-N248H-E271T, N062E-S078G-G118D-G159D-N248D-H249R, G020R-S078G-G118S-S188D-N248D, S024R-S078D-G118S-P129E-S188D, G020R-S078G-G118D-P129E-S188D-H249R, G020R-N062E-S078D-G118D-G159D-S188D-H249R, T022Q-S101G-S103A-V104I-G159D-S188D-A232T-Q245T-N248D-E271L, T022A-S101G-S103A-V104I-G159D-S188E-A232V-Q245V-N248H-E271T, G020R-N062E-S078G-G118S-P129E-G159D-Q245R, A001E-G020R-S024R-S078G-G118D-G159D-S188D, T022Q-S101G-S103A-V104I-G159D-S188D-A232S-Q245T-N248E-E271L, G020R-S078D-G118S-G159D-N248D-H249R, T022Q-S101G-S103A-V104I-G159D-S188E-A232T-Q245V-N248E-E271L, G020R-N062E-S078D-G118S-P129E-H249R, T022Q-S101G-S103A-V104I-G159D-S188D-A232S-Q245R-N248E-E271F, S024F-T033S-S101G-S103A-V104I-N116A-Y209V-A232V, S024R-N062E-N116L-G118R-S128I-A158E, S024R-S078G-G118D-P129E-G159D-S188D-Q245R, T022Q-S101G-S103A-V104I-G159D-S188E-A232L-Q245V-N248D-E271L, T022Q-S101G-S103A-V104I-G159D-S188D-A232S-Q245V-N248E-E271H, S024R-N062E-S078G-G118S-G159D-N248D, G020R-S078G-G118S-P129E-S188D-H249R, S024R-S078G-G118S-P129E-S188D-Q245R, S024R-N062E-S078D-G118D-G159D-H249R, T022Q-S101G-S103A-V104I-G159D-S188D-A232S-Q245T-N248H-E271H, S024R-S078G-G118S-P129E-Q245R-N248D, S024R-T033S-G118R-A158E, G020R-S024R-S078D-G118S-

S188D-Q245R-N248D, G020R-N062E-S078G-G118S-P129E-S188D-Q245R-N248D, T022A-S101G-S103A-V104I-G159D-S188E-A232S-Q245R-N248D-E271T, T022Q-S101G-S103A-V104I-G159D-S188D-A232S-Q245R-N248H-E271T, T022A-S101G-S103A-V104I-G159D-S188E-A232L-Q245T-N248D-E271H, G020R-S024R-N062E-S078G-G118D-P129E-S188D-Q245R-N248D, G020R-S024R-S078G-G118D-P129E-G159D-S188D-Q245R, T022A-S101G-S103A-V104I-G159D-S188D-A232S-Q245R-N248D-E271H, S024R-S078D-G118D-G159D-S188D-Q245R, G020R-S024R-S078G-G118D-P129E-S188D-N248D-H249R, S024R-S078G-G118S-G159D-S188D-Q245R-N248D-H249R, G020R-N062E-S078G-G118S-P129E, T022Q-S101G-S103A-V104I-G159D-S188E-A232V-Q245V-N248D, T022A-S101G-S103A-V104I-G159D-S188E-A232V-Q245R-N248D-E271L, A016S-T022A-S024F-S101G-S103A-V104I-N116L-Y209A-G211Q-T213A-A232V, T022A-S024R-T033S-S188D, G020R-S024R-S078D-G118S-G159D-Q245R-N248D, G020R-S024R-N062E-S078G-G118D-G159D-H249R, G020R-S024R-S078G-G118D-P129E-G159D-S188D-Q245R-N248D, T022Q-S101G-S103A-V104I-G159D-S188E-A232L-Q245T-N248D-E271H, N062E-S078G-G118S-N248D, T022A-S024R-N062E-S128I, G020R-S024R-N062E-S078D-G118D-G159D-S188D-Q245R-N248D, G020R-S024R-N062E-S078G-G118D-P129E-G159D-H249R, G020R-S024R-S078D-G118D-S188D-N248D-H249R, S024R-S078G-G118D-G159D-S188D, S024F-S101G-S103A-V104I-N116A-Y209A-G211Q-A232V, T022Q-S101G-S103A-V104I-G159D-S188D-A232L-Q245R-N248E-E271L, T022A-S024R-T033S-N062E-G118R-S188D, G020R-S078D-G118D-P129E-G159D-S188D-Q245R-H249R, T022Q-S101G-S103A-V104I-G159D-S188D-A232T-Q245R-N248D-T255M-E271T, S024R-N062E-S078D-G118S-N248D-H249R, T022A-S101G-S103A-V104I-G159D-S188E-A232L-Q245R-N248D-E271H, G020R-S024R-S078D-G118D-P129E-G159D-S188D-H249R, T022Q-S101G-S103A-V104I-G159D-S188E-A232S-Q245T-N248D-E271L, G020R-S024R-N062E-S078G-G118D-P129E-Q245R-N248D, T022A-S101G-S103A-V104I-G159D-S188D-A232L-Q245R-N248H-E271F, S024R-G118R-S128I-A158E-S188D, S024R-N062E-S078G-G118S-P129E-G159D-S188D-Q245R-N248D-H249R, T022Q-S101G-S103A-V104I-G159D-S188D-A232S-Q245V-N248H, T022A-S101G-S103A-V104I-G159D-S188D-A232L-Q245T-N248E-E271H, T022A-G118R-S128I-A158E-S188D, T022Q-S101G-S103A-V104I-G159D-S188E-A232V-Q245R-N248E-E271T, S078G-G118S-P129E-G159D-S188D-Q245R-H249R, S024R-N062E-S078G-G118D-P129E-G159D, N116L-G118R-S128I-A158E, T022A-S101G-S103A-V104I-G159D-S188E-A232T-Q245R-N248H-E271T, G020R-S024R-S078G-G118D-P129E-G159D-S188D-N248D-H249R, G020R-S024R-N062E-S078D-G118S-G159D-Q245R-N248D, S024R-S078D-G118S-P129E-G159D-Q245R-H249R, S024R-N062E-S078D-G118D-G159D, S024R-T033S-G118R-S188D, T022A-S101G-S103A-V104I-G159D-S188E-A232L-Q245R-N248H-E271L, T022Q-S101G-S103A-V104I-G159D-S188D-A232S-Q245V-N248E-E271L, S024R-S078G-G118D-P129E-S188D, S078G-G118D-G159D-S188D-H249R, T022A-S101G-S103A-V104I-G159D-S188E-A232V-Q245T-N248H-E271H, T022A-S101G-S103A-V104I-G159D-S188D-A232T-Q245V-N248D-E271L, A016S-T033S-S101G-S103A-V104I-N116A-Y209V-G211Q-T213A-A232V, T022A-S024R-N062E-N116L-S128I-A158E, T022Q-S101G-S103A-V104I-G159D-S188D-A232L-Q245T-N248H-E271F, S024R-G118R-S128I-S188D, G020R-S078G-G118D-G159D-Q245R-N248D-H249R, N062E-S101A-S103A-V104I-S188D-P210I-A232V-Q245R, S024R-N062E-S078G-G118S-P129E-G159D-S188D-Q245R-N248D, S024R-N062E-S078G-G118D-N248D-H249R, S024R-N062E-S078G-G118S-G159D-S188D-N248D, S024R-N062E-S078G-G118S-P129E-S188D-Q245R, T022A-T033S-G118R-S166D, T022Q-S101G-S103A-V104I-G159D-S188E-A232L-Q245R-N248E-E271T, 5078G-G118D-S188D-Q245R-N248D-H249R, T022A-S024R-G118R-S128I, T022Q-S101G-S103A-V104I-G159D-S188D-A232L-Q245T-N248E-E271L, G020R-N062E-S078D-G118S-S188D, T022A-T033S-S101G-S103A-V104I-N116L-G159D-S188D-T213A-A232V-Q245R-N248D-E271F, T022Q-S101G-S103A-V104I-G159D-S188D-A232V-Q245V-N248H-E271T, S024R-S078D-G118S-P129E-G159D-N248D-H249R, G020R-S078G-G118S-G159D-N248D-H249R, G020R-N062E-S078G-G118S-S188D, T022Q-S101G-S103A-V104I-G159D-S188D-A232T-Q245R-N248D-E271T, T022A-S101G-S103A-V104I-G159D-S188E-A232T-Q245T-N248H, G020R-S024R-N062E-S078D-G118S-P129E-G159D-Q245R-N248D, G020R-N062E-S078D-G118S-G159D-Q245R, S024R-S128I-A158E, T022Q-S101G-S103A-V104I-G159D-S188E-A232L-Q245R-N248H-E271H, S024R-N062E-S078D-G118S-S188D-N248D-H249R, A016S-S024F-S101G-S103A-V104I-N116L-Y209A-L217S-A232V, S003T-S024R-N062E-S078D-G118S-N248D, G020R-S024R-N062E-S078D-G118D-S188D, T022A-S101G-S103A-V104I-G159D-S188E-A232T-Q245V-N248D-E271H, T022Q-S101G-S103A-V104I-G159D-S188D-A232S-Q245V-N248D-E271H, G020R-N062E-S078D-G118S-P129E-S188D-Q245R, T022A-S101G-S103A-V104I-G159D-S188D-A232S-Q245R-N248D-S265G-E271H, G020R-S078G-G118D-P129E-G159D-Q245R-H249R, T022Q-S101G-S103A-V104I-G159D-S188D-A232L-Q245V-N248E-E271L, G020R-S024R-S078G-G118S-G159D-S188D-N248D, S078G-G118D-G159D-S188D-Q245R-N248D-H249R, G020R-N062E-S078D-G118S-G159D-Q245R-N248D, T022A-S101G-S103A-V104I-G159D-S188D-A232L-Q245T-N248H-E271H, S024R-N062E-S078D-G118S-P129E-S188D-Q245R-N248D-H249R, T022A-S101G-S103A-V104I-G159D-S188E-A232T-Q245R-N248E, T022Q-S101G-S103A-V104I-G159D-S188E-A232T-Q245R-N248D-E271L, G020K-T022L-S078N-S166D-T213A-L217E, G020R-S078D-G118S-P129E-G159D-Q245R, T022A-T033S-N116L-G118R-A158E, G020R-S024R-S078G-G118S-P129E-G159D-S188D-Q245R, A001G-T022A-S101G-S103A-V104I-G159D-S188D-A232L-Q245T-N248H-E271L, S024R-S078D-G118S-G159D-Q245R, G020K-T022L-S078N-G118R-S166D-T213A-L217E, S078G-G118S-P129E-S188D-Q245R, T022Q-S101G-S103A-V104I-G159D-S188E-A232L-Q245T-N248E, T022Q-S101G-S103A-V104I-G159D-S188D-A232V-Q245V-N248E-E271F, S024R-N062E-S078G-G118D-H249R, T022Q-S101G-S103A-V104I-G159D-S 88D-A232T-Q245T-N248H-E271L, T022A-S101G-S103A-V104I-G159D-S188E-A232T-Q245V-N248E-E271F, G020R-S024R-N062E-S078D-G118S-P129E-S188D, T022A-S101G-S103A-V104I-G159D-S188D-A232V-Q245T-N248H-E271L, S024R-S078D-G118D-P129E-S188D-H249R, T022A-S101G-S103A-V104I-G159D-S188D-A232V-Q245V-N248D-E271H, G020R-S078G-G118D-G159D, T022Q-S101G-S103A-V104I-G159D-S188E-A232V-Q245R-

N248D-E271L, T022A-N062E-G118R-S128I-S188D, T022A-N116L-G118R-A158E-S166D-S188D, S024R-N062E-S128I-N116L, T022A-S024R-N116L-S128I-S166D-S188D, T022Q-S101G-S103A-V104I-G159D-S188D-A232V-Q245T-N248D-E271F, N116L-A158E-S166D, G020R-S024R-S078D-G118S-P129E-N248D, T022A-S101G-S103A-V104I-G159D-S188D-A232S-Q245R-N248D-E271T, T022A-S101G-S103A-V104I-G159D-S188D-A232L-Q245R-N248E-E271H, T022Q-S101G-S103A-V104I-G159D-S188D-A232T-Q245R-N248H, T022A-S024R-N062E-N116L-A158E-S166D, G020R-N062E-S078D-G118S-P129E, T022A-S101G-S103A-V104I-N116L-H120Q-S128N-Y209A-G211Q-T213A-A232V, T022A-S101G-S103A-V104I-G159D-S188D-A232L-Q245V-N248E-E271F, A016S-S024F-S101G-S103A-V104I-N116L-S128N-Y209A-G211Q-T213A-A232V, T022Q-S101G-S103A-V104I-G159D-S188D-A232V-Q245T-N248H-E271L, G020R-S024R-N062E-S078G-G118D-P129E-S188D, T022Q-S101G-S103A-V104I-G159D-S188E-A232S-Q245R-N248E-E271F, N062E-S101A-S103A-V104I-A232V-Q245R, T022A-S101G-S103A-V104I-G159D-S188E-A232S-Q245R-N248H, T022A-S101G-S103A-V104I-G159D-S188D-A232L-Q245T-N248E-E271L, S024R-N062E-N116L-G118R-S128I, T022Q-S101G-S103A-V104I-G159D-S188E-A232T-Q245T-N248H-E271F, T022A-S101G-S103A-V104I-G159D-S188E-A232V-Q245T-N248E-E271H, T022A-S101G-S103A-V104I-G159D-S188E-A232V-Q245V-N248D-E271F, T022A-S101G-S103A-V104I-G159D-S188E-A232T-Q245R-N248E-E271F, T022A-S101G-S103A-V104I-G159D-S188E-A232S-Q245T-N248E-E271H, T022Q-S101G-S103A-V104I-G159D-S188D-A232T-Q245R-N248H-E271H, N062E-G118R-S128I-A158E, T022Q-S101G-S103A-V104I-G159D-S188E-A232T-Q245T-N248H-E271H, S078D-G118S-G159D-Q245R-H249R, S103A-V104I-S128N-L148I, G020R-S024R-N062E-S078D-G118D-P129E-S188D-H249R, T022Q-S101G-S103A-V104I-G159D-S188D-A232S-Q245R-N248H-E271H, S024R-G118R-S188D, T022Q-S101G-S103A-V104I-G159D-S188D-A232L-Q245V-N248E-E271F, T033S-N062E-G118R-A158E-S188D, T022A-S024F-S101G-S103A-V104I-N116A-S128N-Y209V-G211Q-T213A-A232V, S024R-N062E-S078G-G118S-P129E-G159D-S188D-H249R, S078G-G118S-P129E-G159D-H249R, T022A-S101G-S103A-V104I-G159D-S188D-A232T-Q245V-N248E-E271H, N062E-N076D-S101A-S103A-V104I-A232V-Q245R, G020K-S024F-S078N-L217E, S103A-S128N-L148I, S024F-S101G-S103A-V104I-N116L-Y209A-G211Q-T213A-A232V, G020R-S024R-S078D-G118S-P129E-G159D-S188D-Q245R-N248D-H249R, G020R-N062E-S078D-G118D-P129E-G159D-H249R, S078G-G118D-P129E-G159D-Q245R-H249R, G020R-N062E-S078D-G118S-G159D-Q245R-N248D-H249R, G020R-N062E-S078G-G118S-N248D-H249R, T022A-S101G-S103A-V104I-G159D-S188D-A232S-Q245R-N248E-E271L, G020R-S024R-S078D-G118D-G159D-S188D, T033S-N116L-A158E, G020K-S024F-S166D-L217E, S024R-S078D-G118D-G159D-S188D-Q245R-H249R, G020R-S024R-N062E-S078G-G118S-G159D-N248D-H249R, T022A-S101G-S103A-V104I-G159D-S188D-A232V-Q245T-N248H-E271H, T022A-S024R-T033S-G118R-A158E-S166D, N062E-S078D-G118D-G159D-Q245R, S078G-G118S-P129E-G159D-S188D-H249R, G020R-N062E-S078G-G118S-P129E-G159D, T022Q-S101G-S103A-V104I-G159D-S188E-A232L-Q245T-N248H-E271F, S078D-G118S-G159D-H249R, S078G-G118D-P129E-G159D-H249R, G020R-S024R-S078D-G118D-P129E-S188D-N248D-H249R, S024R-N062E-S078G-G118S-G159D-S188D-H249R, G020R-S078D-G118S-G159D-S188D-Q245R, G020R-N062E-S078D-G118S-G159D-S188D-H249R, G020R-S024R-N062E-S078G-G118S-P129E-Q245R-N248D, G020R-N062E-S078G-G118D-S188D-Q245R-N248D, S024R-N062E-S078D-G118S-G159D-S188D, G020R-S024R-N062E-S078G-G118S-P129E-Q245R, G020R-S024R-S078D-G118D-G159D, G020R-S078G-G118S-G159D-S188D-N248D-H249R, T022Q-S101G-S103A-V104I-G159D-S188E-A232T-Q245T-N248H, T022Q-S101G-S103A-V104I-G159D-S188D-A232S-Q245R-N248E-E271L, T022A-S101G-S103A-V104I-G159D-S188D-A232V-Q245R-N248H, T022A-S024R-N116L-G118R-S128I-S166D-S188D, S024R-N062E-S078G-G118S-G159D-S188D-Q245R-N248D, A016S-S024F-S101G-S103A-V104I-N116L-S128N-Y209V-G211Q-A232V, T022A-S101G-S103A-V104I-G159D-S188D-A232V-Q245V-N248H-E271L, S024R-S078G-G118S-P129E-S188D-Q245R-N248D-H249R, S024R-S078D-G118D-P129E-Q245R-H249R, T022Q-S101G-S103A-V104I-G159D-S188E-A232S-Q245V-N248D-E271F, G020K-S024F-S078N-G118R-S166D-L217E, S024F-G118R-S166D-T213A-L217E, G020R-S024R-S078D-G118S-P129E-S188D-Q245R-N248D-H249R: T022A-S024R-T033S-S078N-S166D-S188D, G020R-S024R-S078G-G118D-Q245R, G020K-S024F-S078N-G118R-S166D-T213A-L217E, G020K-T022L-S078G-G118S-G159D-S188D-H249R, T022A-S101G-S103A-V104I-G159D-S188E-A232V-Q245T-N248D-E271L, S024R-T033S-G118R-A158E-S166D-S188D, T022Q-S101G-S103A-V104I-G159D-S188D-A232L-Q245T-N248D-E271L, T022V-S024F-T033S-S101G-S103A-V104I-N116L-Y209A-G211Q-T213A-A232V, G020R-S024R-S078G-G118D-G159D-S188D, S078N-G118R-S166D-L217E, S024R-S078G-G118S-G159D-Q245R-N248D, T022A-S024R-G118R-S128I-A158E-S166D-S188D, T022A-S101G-S103A-V104I-G159D-S188E-A232L-Q245R-N248H-E271H, T022A-S101G-S103A-V104I-G159D-S188E-A232T-Q245T-N248H-E271T, G020R-S024R-S078G-G118D-G159D-N248D-H249R, T022Q-S101G-S103A-V104I-G159D-S188D-A232V-Q245V-N248D-E271F, A016S-T022A-S101G-S103A-V104L-L148I, G020R-S024R-N062E-S078D-G118S-G159D-N248D, T022Q-S101G-S103A-V104I-G159D-S188E-A232T-Q245R-N248E-E271H, S078G-G118D-P129E-G159D-Q245R, S024R-S078G-G118S-S188D-Q245R-N248D, G020R-N062E-S078G-G118D-G159D-S188D, G020R-S024R-N062E-S078D-G118D-G159D-S188D-Q245R, T022A-T033S-S101G-S103A-V104I-N116L-Y209A-G211Q-T213A-A232V, T022A-S101G-S103A-V104I-G159D-S188D-A232V-Q245R-N248H-E271H, T022A-S024R-T033S-S128I-S188D, T022Q-S101G-S103A-V104I-G159D-S188E-A232V-Q245T-N248D-E271H, T022Q-S101G-S103A-V104I-G159D-S188D-A232L-Q245R-N248E-E271F, S024R-S078G-G118S-P129E-S188D-N248D, G020R-N062E-S078D-G118S-P129E-Q245R, T022Q-S101G-S103A-V104I-G159D-S188D-A232T-Q245T-N248D-E271F, T022Q-S101G-S103A-V104I-G159D-S188D-A232T-Q245T-N248H, G020R-S024R-S078D-G118D-G159D-Q245R, T022Q-S101G-S103A-V104I-G159D-S188D-A232T-Q245T-N248E-E271L, S101A-N116L-P210I-T213A, T022Q-S101G-S103A-V104I-G159D-S188D-A232V-Q245R-N248H-E271F, G020R-S024R-N062E-S078D-G118D-P129E-Q245R-N248D, T022A-S024R-N062E-A158E, T022A-S101G-

S103A-V104I-G159D-S188E-A232V-Q245T-N248D-E271H, G020R-S024R-N062E-S078D-G118D-G159D-S188D-Q245R-N248D-H249R, G020R-N062E-S078D-G118S-G159D-S188D-Q245R-N248D, N062E-S078D-G118S-S188D-H249R, A016S-S024F-T033S-S101G-S103A-V104I-N116L-Y209V-G211Q-T213A-A232V, G020R-S078G-G118D-S188D-H249R, T022-S024F-S101G-S103A-V104I-N116L-S128N-Y209A-G211Q-A232V, G020R-N062E-S078D-G118D-G159D-N248D-H249R, T022A-S101G-S103A-V104I-G159D-S188D-A232T-Q245T-N248D-E271H, T022A-S024R-N116L-G118R-A158E-S166D-S188D, G020R-S024R-S078G-G118S-P129E-G159D-S188D-Q245R-N248D-H249R, S024R-N062E-N076D-S101A-S103A-V104I-P210I-A232V-Q245R, N062E-S078D-G118S-G159D-Q245R-N248D-H249R, G020R-S024R-S078G-G118D-G159D-S188D-N248D-H249R, T022Q-S101G-S103A-V104I-G159D-S188D-A232S-Q245V-N248E-E271T, T022A-S101G-S103A-V104I-G159D-S188D-A232L-Q245V-N248E-E271T, S024R-S101A-S103A-V104I-S188D-P210I-A232V-Q245R, S024R-N062E-N116L-G118R-A158E, G020R-S078G-G118D-S188D-Q245R, T022A-S101G-S103A-V104I-G159D-S188D-A232L-Q245V-N248E-E271L, T022Q-S101G-S103A-V104I-G159D-S188D-A232L-Q245R-N248E-E271H, S024R-S166D-S188D, T022A-S101G-S103A-V104I-G159D-S188D-A232V-Q245T-N248D-E271F, A016S-T022A-S024F-S101G-S103A-V104I-N116A-Y209V-G211Q-A232V, T022Q-S101G-S103A-V104I-G159D-S188E-A232L-Q245T-N248D-E271F, G020R-N062E-S078G-G118D-G159D-S188D-Q245R-N248D, T022A-N062E-N116L-G118R-A158E, S024R-N062E-N116L-G118R-S128I-S166D, T022Q-S101G-S103A-V104I-G159D-S188E-A232V-Q245R-N248H, G020R-S024R-N062E-S078D-G118D-H249R, T022A-S101G-S103A-V104I-G159D-S188E-A232T-Q245R-N248E-E271L, S024R-N062E-G118R-S128I-S188D, N062E-S078G-G118S-G159D-N248D-H249R, G020K-T022L-N062E-S078D-G118S-G159D-H249R, N062E-S078G-G118D-Q245R-N248D, G020R-S024R-N062E-S078D-G118D-G159D-S188D-H249R, T022A-S024F-S101G-S103A-V104I-N116L-Y209V-T213A-A232V, T022A-S101G-S103A-V104I-G159D-S188D-A232T-Q245R-N248D-E271L, S024R-N116L-G118R-S128I-A158E, T022A-S101G-S103A-V104I-G159D-S188E-A232V-Q245R-N248E-E271F, T022Q-S101G-S103A-V104I-G159D-S188D-A232V-Q245V-N248E-E271T, T022Q-S101G-S103A-V104I-G159D-S188D-A232S-Q245V-N248D-E271L, A016S-S101G-S103A-V104L-L148I, T022Q-S101G-S101G-S103A-V104I-G159D-S188E-A232L-Q245T-N248H-E271T, G020R-N062E-S078G-G118S-S188D-Q245R, T022A-S101G-S103A-V104I-G159D-S188E-A232V-Q245V-N248E-E271H, S024R-S078D-G118D-S188D-Q245R-N248D-H249R, G020R-S024R-S078D-G118S-P129E-Q245R-N248D, G020R-S078G-G118D-G159D-S188D, T022Q-S101G-S103A-V104I-G159D-S188D-A232L-Q245T-N248E-E271T, G020R-S024R-S078D-G118D-G159D-N248D-H249R, S024R-N062E-S078G-G118S-P129E-S188D-Q245R-N248D, T022A-S101G-S103A-V104I-G159D-S188E-A232L-Q245T-N248D-E271T, T022A-S101G-S103A-V104I-G159D-S188E-A232V-Q245R-N248E, T022Q-S101G-S103A-V104I-G159D-S188E-A232V-Q245T-N248H-E271F, T022Q-S101G-S103A-V104I-G159D-S188D-A232S-Q245T-N248E-E271F, T022A-S101G-S103A-V104I-G159D-S188D-A232L-Q245R-N248D-E271L, G020R-S024R-N062E-S078D-G118S-P129E-N248D, S024R-N062E-S078D-G118S-P129E-G159D-N248D-H249R, T022Q-S101G-S103A-V104I-G159D-S188E-S212L-A232S-Q245V-N248D-E271T, S024R-S078G-G118D-G159D-H249R, T022A-N116L-G118R-S128I-S188D, T022A-S101G-S103A-V104I-G159D-S188E-A232V-Q245R-N248D, N062E-S078G-G118D-S188D-Q245R, G020K-S078N-S166D-L217E, N062E-S078G-G118S-P129E-S188D-Q245R, T022Q-S101G-S103A-V104I-G159D-S188E-A232S-Q245V-N248E-E271F, N062E-N116L-G118R-S166D-S188D, G020R-S024R-S078D-G118S-G159D-N248D, T022A-S024F-S101G-S103A-V104I-N116L-S128N-Y209V-A232V, S078G-G118S-P129E-G159D-Q245R, T022A-T033S-S101G-S103A-V104I-N116L-Y209V-G211Q-T213A-A232V, S078D-G118S-P129E-G159D-S188D-Q245R-N248D-H249R, S101G-S103A-V104I-N116L-S128N-Y209A-G211Q-T213A-A232V, G097P-S101A-S103G, S024R-N062E-S078D-G118S-S188D, G020R-S024R-S078D-G118D-P129E-S188D-H249R, S024R-N062E-S078G-G118S-G159D, A016S-T022A-T033S-S101G-S103A-V104I-N116A-Y209A-A232V, T022A-N116L-G118R-S128I-A158E-S166D, T022Q-S101G-S103A-V104I-G159D-S188E-A232T-Q245R-N248D-E271T, S024R-G118R-S128I, T022A-S101G-S103A-V104I-G159D-S188E-A232L-Q245T-N248E-E271L, S024R-N062E-A158E, S024R-S078D-G118S-P129E, G020R-S024R-S078D-G118S-P129E-G159D-S188D-H249R, T022Q-S101G-S103A-V104I-G159D-S188E-A232V-Q245V-N248H-E271F, T022Q-S101G-S103A-V104I-G159D-S188E-A232V-Q245R-N248H-E271F, G020R-S024R-N062E-S078G-G118S-G159D, T022Q-S101G-S103A-V104I-G159D-S188D-A232S-Q245V-N248H-E271L, S024R-S078D-G118S-P129E-S188D-Q245R-N248D, N062E-S078G-G118S-S188D-Q245R-N248D, N062E-N116L-G118R-S128I-S188D, T022A-S101G-S103A-V104I-G159D-S188D-A232S-Q245V-N248D-E271F, G020R-S024R-S078D-G118S-G159D-S188D-Q245R-N248D, T022A-S101G-S103A-V104I-G159D-S188E-A232V-Q245T-N248D-E271T, T022A-S101G-S103A-V104I-G159D-S188D-A232S-Q245V-N248E-E271T, T022A-T033S-N116L-G118R-S188D, G020R-S024R-N062E-S078G-G118S-P129E-S188D-N248D, G020R-N062E-S078G-G118S-P129E-G159D-N248D, S078G-G118S-P129E-G159D-S188D-Q245R, N062E-S078D-G118S-G159D-H249R, T022A-S101G-S103A-V104I-G159D-S188E-A232T-Q245R-N248D, T022A-S024R-T033S-N062E-N116L, T022Q-S101G-S103A-V104I-G159D-S188E-A232S-Q245T-N248E-E271T, N062E-S078D-G118S-H249R, T022A-S024R-N062E-N116L-G118R-A158E, T022L-S078N-G118R-S166D-L217E, G020R-S024R-N062E-S078D-G118D-S188D-Q245R-N248D-H249R, T022A-S101G-S103A-V104I-G159D-S188E-A232S-Q245R-N248H-E271L, G020R-S024R-S078G-G118D-P129E-Q245R-N248D-H249R, T022A-S101G-S103A-V104I-G159D-S188E-A232T-Q245V-N248D-E271L, S078D-G118S-P129E-S188D-Q245R, S024R-S078G-G118D-G159D-S188D-Q245R-H249R, S078D-G118D-G159D-S188D-Q245R-H249R, S024F-T213A-L217E, S024F-T033S-S101G-S103A-V104I-N116L-S128N-Y209V-G211Q-A232V, T022Q-S101G-S103A-V104I-G159D-S188D-A232S-Q245T-N248D-E271H, T022Q-S101G-S103A-V104I-G159D-S188D-A232S-Q245T-N248E-E271T, T022Q-S101G-S103A-V104I-G159D-S188D-A232V-Q245R-N248H-E271H, G020R-S078D-G118D-P129E-G159D-Q245R-H249R, T022A-S101G-S103A-V104I-G159D-S188D-A232L-Q245R-N248D, T022A-S101G-S103A-V104I-G159D-S188D-A232L-

Q245R-N248D-E271T, N062E-S078G-G118S-P129E-Q245R, S078G-G118S-S188D-Q245R-N248D-H249R, S101A-S103G-V104I-L148I, T022A-S101G-S103A-V104I-G159D-S188E-A232V-Q245R-N248H-E271F, T022Q-S101G-S103A-V104I-G159D-S188E-A232T-Q245V-N248H-E271H, T022A-N116L-G118R-A158E, T022A-S024F-T033S-S101G-S103A-V104I-I107V-N116L-S128N-Y209A-G211Q-T213A-A232V, T022Q-S101G-S103A-V104I-G159D-S188E-A232S-Q245R-N248H-E271T, G020R-N062E-S078D-G118D-G159D, G020R-N062E-S078D-G118S, S024R-N062E-S078D-G118D-P129E-G159D-Q245R, T022A-S101G-S103A-V104I-G159D-S188E-A232T-Q245V-N248E-E271T, T022A-S101G-S103A-V104I-G159D-S188D-A232T-Q245V-N248D-E271H, S078G-G118S-G159D, S024F-G118R-T213A-L217E, S024R-N062E-S078D-G118S-P129E-Q245R-N248D, G020R-S024R-S078D-G118S-P129E-G159D-Q245R, S024R-S078D-G118D-G159D-H249R, S024R-N076D-S101A-S103A-V104I-S188D-P210I-A232V-Q245R, G020R-S024R-N062E-S078D-G118D-P129E-G159D-H249R, G020R-S024R-N062E-S078G-G118D-S188D-N248D-H249R, G020R-S024R-N062E-S078G-G118S-P129E-S188D-H249R, T022Q-S101G-S103A-V104I-G159D-S188E-A232S-Q245V-N248D, T022A-S101G-S103A-V104I-G159D-S188D-A232V-Q245T-N248E-E271H, T022Q-S101G-S103A-V104I-G159D-S188D-A232V-Q245V-N248D-E271T, G020R-S024R-S078D-G118D-P129E-G159D-N248D-H249R, G020R-S024R-N062E-S078D-G118S-P129E-G159D-N248D, N062E-S078G-G118D-P129E-H249R, G020K-T022L-S078N-G118R-T213A-L217E, G020R-S024R-N062E-S078G-G118D-P129E-S188D-H249R, T022A-S024R-T033S-N116L-S166D-S188D, S024R-S078G-G118D-G159D-S188D-H249R, T033S-N116L-G118R-A158E-S188D, T022A-S101G-S103A-V104I-G159D-S188E-A232V-Q245V-N248H, S101A-S103A-V104I-S188D-P210I-A232V-Q245R, G020R-S024R-N062E-S078G-G118D-S188D-Q245R, T022A-S024R-T033S-N062E-N116L-G118R-P129E-S188D, T022A-S101G-S103A-V104I-G159D-S188E-A232S-Q245T-N248E, S024R-S078G-G118S, N062E-S101A-S103A-V104I-P210I-A232V-Q245R, N062E-S078G-G118D-G159D, T022A-S024R-N062E-N116L-G118R-S128I-S166D-S188D, S024R-S078D-G118D-G159D-Q245R, G020R-N062E-S078G-G118S-G159D-S188D-N248D-H249R, T022Q-S101G-S103A-V104I-G159D-S188E-A232S-Q245R-N248E-E271H, T022Q-S101G-S103A-V104I-G159D-S188D-A232T-V244I-Q245R-N248H-E271L, S024R-S078G-G118S-P129E-G159D-N248D, S024R-N062E-S078G-G118S-G159D-H249R, T022A-S024F-T033S-S101G-S103A-V104I-N116L-Y209V-G211Q-A232V, A016S-S101G-S103A-V104I-N116A-S128N-Y209V-G211Q-T213A-A232V, G020R-N062E-S078G-G118D-S188D, T022A-S101G-S103A-V104I-G159D-S188E-A232S-Q245V-N248E-E271H, T022A-S101G-S103A-V104I-G159D-S188D-A232V-Q245V-N248E-E271L, G020K-S166D-L217E, T022A-S101G-S103A-V104I-G159D-S188D-A232S-Q245T-N248E-E271T, G020R-N062E-S078D-G118D-Q245R, S024R-N062E-S078D-G118S-P129E-S188D-Q245R-N248D, A016S-T022A-S024F-S101G-S103A-V104I-N116A-S128N-Y209A-G211Q-A232V, S024F-T033S-S101G-S103A-V104I-N116L-Y209A-A232V, T033S-G118R-S188D, T022A-S101G-S103A-V104I-G159D-S188D-A232S-Q245T-N248E-E271H, T022Q-S101G-S103A-V104I-G159D-S188D-A232S-Q245T-N248D-E271T, G020R-S024R-S078G-G118S-P129E-G159D-S188D-

N248D, T022Q-S101G-S103A-V104I-G159D-S188D-A232V-Q245T-N248H-E271F, G020R-S078G-G118D-P129E-S188D-Q245R, G020R-S078G-G118D-G159D-S188D-Q245R-N248D, S024R-S078G-G118D-P129E-N248D-H249R, G020R-S024R-S078D-G118D-P129E, N062E-S078D-G118S-S188D-Q245R, G020R-S024R-S078G-G118S-G159D-S188D, T022Q-S101G-S103A-V104I-G159D-S188D-A232T-Q245V-N248H-E271L, T022A-S101G-S103A-V104I-G159D-S188E-A232T-Q245R-N248D-E271L, N062E-S078G-G118S-G159D-H249R, G020R-S078D-G118S-P129E-G159D-N248D, G020R-S024R-S078D-G118S-G159D-S188D-Q245R, G020R-N062E-S078G-G118D-P129E-S188D-Q245R-N248D, T022Q-S101G-S103A-V104I-G159D-S188D-A232L-Q245R-N248H, G020R-S024R-S078D-G118S-G159D-V244L-Q245R-N248D, G020R-S024R-S078G-G118D-P129E-S188D-Q245R-N248D-H249R, T022A-S024F-T033S-S101G-S103A-V104I-N116A-Y209A-A232V, G020R-S024R-N062E-S078D-G118S-P129E-G159D-A272D, N116L-G118R-S128I-A158E-S166D, S024R-S078D-G118S-P129E-H249R, S024R-N062E-S078G-G118S-P129E-N248D, G020R-S078G-G118S-P129E-G159D-S188D, G020R-S024R-S078D-G118S-G159D-N248D-H249R, S024R-S078D-G118D-G159D-S188D-Q245R-N248D-H249R, T033S-S101G-S103A-V104I-N116L-Y209A-G211Q-T213A-A232V, T033S-S101G-S103A-V104I-N116A-Y209A-T213A-A232V, T022A-S101G-S103A-V104I-G159D-S188E-A232S-Q245V-N248H, N062E-S078G-G118S-N248D-H249R, G020R-N062E-S078D-G118D-G159D-S188D-Q245R, T022A-S024F-S101G-S103A-V104I-N116A-Y209A-T213A-A232V, N043F-S101G-S103A-V104I-G159D-S188D-A232V-Q245R-N248D-E271F, S024R-S078G-G118D-P129E-G159D, G020R-N062E-S078D-G118D-G159D-Q245R-N248D, S024R-S166D, S024R-S078G-G118S-P129E-N248D, N076D-S101A-S103A-V104I-S188D-P210I-A232V-Q245R, G020K-L217E, G118R-S166D-S188D, S024R-S078D-G118S-G159D-S188D, S024R-S078D-G118S-P129E-S188D-Q245R, A016S-S101G-S103A-V104I-N116A-S128N-Y209A-T213A-A232V, N116L-S166D, S024R-N062E-S078G-G118D-P129E-G159D-S188D-Q245R, G020R-S024R-S078D-G118D-P129E-N248D-H249R, N062E-S078G-G118S-G159D-S188D-Q245R, T022A-S101G-S103A-V104I-G159D-S188D-A232L-Q245V-N248E-E271H, S024R-N062E-S078D-G118S-P129E-H249R, G118R-S166D-T213A, G020R-S024R-N062E-S078G-G118S-P129E-G159D, G020R-S024R-S078D-G115W-G118D-G159D-N248D, A016S-S024F-S101G-S103A-V104I-N116A-Y209A-A232V, S024R-N062E-N116L-S128I-A158E, T022Q-S101G-S103A-V104I-G159D-S188E-A232V-Q245V-N248D-E271L, S024R-N062E-S078G-G118S-P129E-H249R, S024R-N062E-S078D-G118D-P129E-N248D-H249R, G020K-T022L-S024F-S078N-G118R-L217E, S101G-G102A-S103A, G020R-S078G-G118S-P129E-Q245R-N248D, G020K-S078N-S166D, T022A-G118R-A158E, G020K-T022L-S024F-S078N-S166D, T022A-T033S-N062E-N116L-G118R-A158E-S188D, S024R-S078G-G118S-P129E-G159D-H249R, S101G-S103A-V104I-N116L-Y209V-G211Q-A232V, A015D-A016S-S101G-S103A-V104I-N116L-S128N-Y209V-T213A-A232V, G020R-N062E-S078D-G118D-P129E-S188D-H249R, G020K-S024F-S078N-S128D, T033S-N116L-S166D-S188D, G020R-S078G-G118S-P129E-G159D, T022A-S024R-T033S-L082I-G118R-S128I-A158E-S188D, G020R-S024R-S078D-G118S-S188D-N248D, G020R-S078G-G118D-P129E-S188D-Q245R-

H249R, N062E-S078G-G118D-Q245R, G020K-T022L-S078N-L217E, T022A-S101G-S103A-V104I-G159D-S188D-A232T-Q245V-N248E-E271L, T022Q-S101G-S103A-V104I-G159D-S188E-A232S-Q245V-N248E-E271H, T022Q-S101G-S103A-V104I-G159D-S188E-A232T-Q245T-N248E-E271T, A016S-T033S-S101G-S103A-V104I-N116L-Y209V-G211Q-T213A-A232V, T022Q-S101G-S103A-V104I-G159D-S188E-A232L-Q245K-N248H, N062E-S078D-G118D-Q245R, T022A-S024R-G118R-A158E-S166D, A016S-S101A-S103A-S128N-L148I, T022A-S101G-S103A-V104I-G159D-S188D-A232S-Q245R-N248E, S024R-N062E-S078G-G118D, S024R-N062E-S078G-G118S-P129E-G159D-S188D, S078G-G118D-P129E-G159D-S188D-Q245R-N248D-H249R, G020R-S078D-G118D-P129E-G159D-Q245R, T022A-S101G-S103A-V104I-G159D-S188D-A232S-Q245V-N248H, T022Q-S101G-S103A-V104I-G159D-S188D-A232V-Q245R-N248D-E271H, G020R-S024R-N062E-S078G-G118D-H249R, S078D-G118S-P129E-G159D-H249R, T022Q-S101G-S103A-V104I-G159D-S188E-A232S-Q245T-N248D-E271H, S024R-S078D-G118D-P129E-G159D-S188D-Q245R, T022L-T213A-L217E, G020R-N062E-S078G-G118S-P129E-G159D-S188D-N248D-H249R, T022Q-S101G-S103A-V104I-G159D-S188D-A232T-Q245R-N248H-E271T, G020R-N062E-S078G-G118D-Q245R, G020R-S024R-N062E-S078G-G118D-N248D-H249R, T022A-S101G-S103A-V104I-G159D-S188D-A232V-Q245R-N248H-E271T, S024R-S078D-G118D-P129E-H249R, S024R-N062E-N116L-G118R-S188D, S024R-N062E-G118R, T022A-S101G-S103A-V104I-G159D-S188D-A232V-Q245R-N248E, G020R-S024R-S078G-G118S-P129E-G159D-S188D-H249R, T022A-S101G-S103A-V104I-G159D-S188E-A232L-Q245R-N248H, S024R-S078D-G118S-P129E-G159D-N248D, T022Q-S101G-S103A-V104I-G159D-S188D-A232L-Q245V-N248D-E271T, G020R-S078G-G118D-P129E-Q245R-N248D-H249R, G020R-S024R-N062E-S078D-G118D-P129E-S188D-Q245R-N248D, A016S-S024F-T033S-S101G-S103A-V104I-N116L-Y209V-A232V, G097P-A098Q-S099G-V104L, T022A-S101G-S103A-V104I-G159D-S188D-A232S-Q245T-N248D-E271F, G020R-S024R-N062E-S078G-G118S-N248D, A016S-S103A-S128N, S024R-S078G-G118D-P129E-Q245R, S078D-G118D-P129E-S188D-H249R, T022A-S024R-T033S-N062E-N116L-A158E, A016S-T022A-S101G-S103A-V104I-N116A-S128N-Y209V-T213A-A232V, S024R-S078G-G118S-G159D-S188D-Q245R, T033S-N062E-N116L-G118R-A158E-S188D, G020R-S024R-N062E-S078D-G118S-G159D-Q245R-A272V, G118R-S128I-A158E-S166D, G020K-T022L-S024F-S078N-S166D-D181E-L217E, N062E-G118R-S188D, S024F-S101G-S103A-V104I-N116L-S128N-Y209A-T213A-A232V, G020R-S078D-G118D-G159D-S188D-Q245R, S024R-N062E-S078G-G118D-P129E-N248D-H249R, G020R-S024R-N062E-S078G-G118D-N248D, T022A-V068A-S101G-S103A-V104I-G159D-S188D-T213A-A232V-Q245R-N248D-E271F, G020R-N062E-S078D-G118S-P129E-G159D-S188D-Q245R, S024R-S078G-G118S-P129E-N248D-H249R, T022Q-S101G-S103A-V104I-G159D-S188D-A232V-Q245R-N248H-E271L, T033S-N116L-G118R-S188D, N062E-S078G-G118S-S188D-N248D-H249R, A016S-T022A-S101G-S103A-V104I-S128N-L148I, G020R-S078G-G118S-S188D-N248D-H249R, G020R-S024R-S078D-G118D-P129E-G159D-Q245R-N248D, S024F-T033S-S101G-S103A-V104I-N116L-Y209A-T213A-A232V, S024R-N062E-G118R-S128I-A158E, G020R-S024R-S078D-G118S-G159D-S188D, S024R-N062E-S078G-G118D-G159D-Q245R-N248D-H249R, N062E-G118R-A158E-S166D, G020R-S024R-S078D-G118S-P129E-S188D, S078G-G118D-G159D, G020R-S024R-S078D-G118D-P129E-G159D-S188D-Q245R-N248D, G020R-S078G-G118D-S188D-N248D, G020K-T022L-S078G-G118D-G159D-N248D-H249R, S103G-L148I-M175T, G020R-S024R-S078G-G118S-P129E-Q245R-N248D, T022A-S101G-S103A-V104I-G159D-S188D-A232S-Q245R-N248D-H249R-E271F, T022A-S024F-S101G-S103A-V104I-N116A-S128N-Y209A-G211Q-T213A-A232V, A016S-T033S-S101G-S103A-V104I-N116A-Y209A-G211Q-A232V, T022A-S024R-N062E-S166D, G020R-S078D-G118S-G159D-S188D-Q245R-N248D-H249R, T022A-S024F-S101G-S103A-V104I-N116A-S128N-Y209V-A232V, T022A-S024R-N062E-N116L-A158E-S188D, T022Q-S101G-S103A-V104I-G159D-S188E-A232S-Q245T-N248E-E271L, S024R-T033S-N116L-G118R-A158E-S188D, T022Q-S101G-S103A-V104I-G159D-S188D-A232S-Q245V-N248H-E271H, G020R-N062E-S078D-G118S-G159D-N248D, T022A-S024R-N116L-G118R-A158E, G020K-T022L-S024F-G118R-L217E, S024R-S078D-G118S-G159D-S188D-N248D-H249R, G020R-S024R-N062E-S078G-G118D-P129E-S188D-N248D, T022Q-S101G-S103A-V104I-G159D-S188D-A232V-Q245R-N248D-E271L, G020R-S024R-N062E-S078D-G118S-P129E-G159D-S188D-N248D-H249R, N062E-G118R-S166D, T022Q-S101G-S103A-V104I-G159D-S188D-A232S-Q245R-N248D, G020R-N062E-S078D-G118S-P129E-G159D-N248D-H249R, T022A-S101G-S103A-V104I-G159D-S188D-A232T-Q245V-N248H-E271T, T022L-S024F-G118R-S166D, T022Q-S101G-S103A-V104I-G159D-S188D-A232V-Q245R-N248D, G020K-S024F-S166D-T213A-L217E, N062E-S078G-G118S-G159D-S188D, S024R-N062E-S078D-G118D-Q245R-N248D, G020K-T022L-S024F-S078N-T213A-L217E, T022A-V068A-S101G-S103A-V104I-N116L-G159D-S188D-T213A-A232V-Q245R-N248D-E271F, N062E-S078G-G118S-P129E-G159D, G020R-S024R-N062E-S078G-G118S-G159D-H249R, G020K-T022L-S024F-S078N-G118R-S166D-T213A-L217E, T022A-N062E-N116L-A158E, T022Q-S101G-S103A-V104I-G159D-S188D-A232T-Q245V-N248E-E271L, T022A-S024R-N062E-S128I-S166D, S024R-S078G-G118D-G159D-Q245R-N248D-H249R, G020R-S024R-N062E-S078G-G118S-P129E-G159D-H249R, G020R-S078G-G118D-S188D-Q245R-N248D, G020R-S024R-N062E-S078G-G118D-P129E-S188D-Q245R-N248D-H249R, S024R-S078G-G118S-G159D-Q245R, T022A-S024R-N062E-G118R-S128I-A158E, G020R-S078D-G118S-P129E-G159D-S188D-Q245R, S024R-S078G-G118S-Q245R-N248D-H249R, G118R-A158E-S188D, G020K-S024F-G118R-S166D-L217E, G020K-S024F-S078N-G118R-T213A-L217E, T022A-S101G-S103A-V104I-G159D-S188E-A232S-Q245V-N248D-E271L, T022A-S101G-S103A-V104I-G159D-S188D-A232S-Q245V-N248D, S024R-N062E-S078G-G118S-H249R, G020R-S024R-S078G-G118S-G159D-S188D-Q245R-N248D-H249R, A016S-S024F-S101G-S103A-V104I-N116L-S128N-Y209V-A232V, T033S-A158E-S166D, S024R-S078D-G118S-S188D-N248D-H249R, S024R-N062E-S078D-G118S-S188D-Q245R-N248D, N062E-S078G-G118D-G159D-Q245R-N248D, N062E-S078G-G118D-S188D-Q245R-N248D-H249R, S024R-N116L-G118R-S128I-A158E-S166D, G020R-N062E-S078D-G118S-P129E-G159D-Q245R-N248D, S024R-N062E-S101A-S103A-V104I-

S188D-P210I-A232V-Q245R, N062E-S078D-G118S-P129E-H249R, S024R-S078G-G118S-P129E-G159D-S188D, A016S-S101G-S103A-V104I-N116A-S128N-Y209V-T213A-A232V, G020K-T022L-S024F-S078N-S166D-T213A-L217E, G020R-S024R-N062E-S078D-G118D-S188D-N248D, G020R-S024R-N062E-S078G-G118S-G159D-A272D, T022A-S024R-A158E, G020R-S078G-G118S-G159D-N248D, T022A-S101A-S103A-V104I-G159D-S188E-A232V-Q245V-N248E-E271T, S101G-S103A-V104I-N116A-Y209A-G211Q-T213A-A232V, G020K-T022L-S024F-S166D-L217E, G020R-S024R-S078D-G118S-Q245R, G020R-S078D-G118D-P129E-S188D-Q245R, G020R-S024R-N062E-S078D-G118S-S188D-Q245R-N248D, G020R-S024R-S078D-G118D-G159D-N248D, T022A-S101G-S103A-V104I-G159D-S188D-A232S-Q245T-N248H, G020R-S024R-S078D-G118S-S188D-Q245R, 0020R-N062E-S078D-G118D-S188D-Q245R, G020R-S024R-S078D-G118D-G159D-S188D-Q245R-H249R, T022A-S128I-A158E-S188D, A016S-S024F-S101G-S103A-V104I-N116A-S128N-Y209V-T213A-A232V-V244G, T022L-S078N-T213A-L217E, S078D-G118S-P129E-H249R, G020K-T022L-S024F-S078N-G118R-T213A-L217E, N062E-S078D-G118S-S188D-Q245R, G020K-S024F-S166D, S024R-N062E-S078G-G118D-Q245R-N248D-H249R, G020K-S024F-S078N-G118R-L217E, T022L-S024F-S078N-G118R-S166D-L217E, T022A-S024R-T033S-A158E-S188D, T022Q-S101G-S103A-V104I-G159D-S188D-A232L-Q245T-N248D-E271H, S087R, T022A-S101G-S103A-V104I-G159D-S188E-A232T-Q245V-N248H, G020R-S078G-G118D-P129E-G159D-Q245R-N248D-H249R, S078G-G118S-P129E-G159D-Q245R-N248D, S024R-S078D-G118D-P129E-G159D-Q245R-N248D-H249R, 0020R-S078G-G118S-P129E, S024R-N116L-G118R-S166D-S188D, G020R-S024R-S078G-G118S-P129E-G159D-Q245R, T022A-S101G-S103G-V104I, G020R-S024R-N062E-S078D-G118D-P129E-G159D, G020R-S024R-N062E-S078D-G118D-P129E-Q245R-N248D-H249R, T022A-S024R-N062E-N116L-G118R-S188D, T022Q-S101G-S103A-V104I-G159D-S188E-A232L-Q245T-N248E-E271L, A016S-S101G-S103A-V104I-N116L-M119V-Y209V-G211Q-A232V, G020R-S024R-N062E-S078G-G118D, T022Q-S101G-S103A-V104I-G159D-S188E-A232V-Q245T-N248H-E271L, T022A-S101G-S103A-V104I-G159D-S188D-A232S-Q245T-N248D-E271T, T033S-S101G-S103A-V104I-N116L-Y209A-G211Q-A232V, G020R-S024R-N062E-S078D-G118S-P129E-G159D-N248D-H249R, G020R-S078G-G118S-P129E-N248D-H249R, G020K-T022L-G118R-S128D, T022Q-S101G-S103A-V104I-G159D-S188D-A232L-Q245V-N248D-E271L, G020R-S024R-S078D-G118S-G159D-S188D-N248D-H249R, S101G-S103A-V104I-N116L-Y209A-T213A-A232V, T022A-S101G-S103A-V104I-G159D-S188D-A232L-Q245T-N248E-E271T, S024R-N062E-S078D-G118D-G159D-Q245R-N248D-H249R, G020K-S024F-T213A-L217E, G118R-S128I-S188D, G020R-S078G-G118S-P129E-H249R, T022A-N062E-G118R-S188D, S024R-S078G-G118S-P129E-G159D-Q245R, T022A-S024F-S101G-S103A-V104I-N116L-Y209A-G211Q-T213A-A232V, T022A-S024R-N116L-A158E-S166D, T022A-S101G-S103A-V104I-G159D-S188D-A232L-Q245T-N248H-E271T, T022Q-S101G-S103A-V104I-G159D-S188D-A232L-Q245T-N248H-E271L, S024R-N062E-A158E-S188D, G020K-S024F-G118R-S166D-T213A-L217E, T022A-S101G-S103A-V104I-G159D-S188E-A232S-Q245T-N248H-E271T, S078D-G118D-P129E-G159D-Q245R, S101A-S103A-V104I-S188D-A232V-Q245R, N062E-N116L-G118R-A158E, T022A-T033S-S101G-S103A-V104I-N116L-Y209A-T213A-A232V, T022L-S024F-G118R-S128D-T213A, A016S-S024F-S101G-S103A-V104I-N116L-S128N-Y209A-A232V, S078D-G118S-G159D-S188D-N248D-H249R, G020R-S078G-G118S-P129E-S188D, T022A-T033S-N116L-S166D, S024R-N062E-G118R-S188D, S024R-T033S-N116L-G118R-S128I-A158E, S101A-S103A-V104I-P210I-A232V-Q245R, G020R-S024R-N062E-S078G-G118S-S188D-H249R, T022A-S024R-N116L-G118R-S128I-A158E-S166D-S188D, A016S-S024F-S101G-S103A-V104I-N116L-Y209V-G211Q-T213A-A232V, T022A-S101G-S103A-V104I-G159D-S188E-A232S-Q245V-N248D-E271H, S078G-G118S-G159D-S188D-N248D-H249R, S024R-S078D-G118D-P129E-G159D-S188D-H249R, T022Q-S101G-S103A-V104I-G159D-S188D-A232L-Q245T-N248E-E271F, G020R-N062E-S078D-G118D, S024R-T033S-N116L-G118R-S128I-A158E-S188D, T033S-N062E-N116L-G118R-S188D, T022A-T033S-N116L-G118R-A158E-S188D, S078N-G118R-S166D, T022Q-S101G-S103A-V104I-G159D-S188E-A232V-Q245T-N248E-E271L, T022Q-S101G-S103A-V104I-G159D-S188E-A232L-Q245T-N248H-E271L, S024F-S101G-S103A-V104I-N116A-Y209A-G211Q-T213A-A232V, G020R-S024R-S078D-G118D-G159D-S188D-Q245R-N248D, T022A-S101G-S103A-V104I-N116L-G159D-S188D-T213A-A232V-Q245R-N248D-E271F, T022A-G118R-A158E-S188D, S024R-S078D-G118S-G159D-H249R, S101G-S103A-V104I-N116L-Y209A-G211Q-A232V, T022A-S101G-S103A-V104I-G159D-S188E-A232S-Q245V-N248E-E271F, S024R-N062E-S078D-G118S-P129E-Q245R, G020K-S024F-S078N-T213A-L217E, G020R-S024R-S078G-G118D-P129E-G159D-H249R, G020R-S024R-S078D-G118S-G159D-S188D-N248D, T022A-S101G-S103A-V104I-G118R-G159D-S188D-A232V-Q245R-N248D-E271F, G020R-S078G-G118S-S188D-Q245R-N248D, G020R-S024R-N062E-S078G-G118D-P129E-S188D-N248D-H249R, G020R-S078D-G118S-P129E-G159D-S188D-Q245R-N248D, T022A-S101G-S103A-V104I-G159D-S188E-A232T-Q245V-N248D-E271T, T022A-S101G-S103A-V104I-G159D-S188E-A232V-Q245T-N248H, S024R-S078D-G118S-P129E-G159D-S188D-Q245R-N248D, S101G-S103A-L148I, T022A-S101G-S103A-V104I-G159D-S188E-A232S-Q245T-N248D-E271L, T022A-S101G-S103A-V104I-G159D-S188D-A232T-Q245T-N248D-S265G-E271L, V104I-L111V-L148I, T022A-G118R-S128I, G020R-S024R-S078G-G118D-P129E-G159D-N248D, G020K-T022L-G118R-S166D-T213A-L217E, G020R-S078D-G118D-P129E-Q245R-N248D, G097P-S099A-S101A-S103A, N062E-S078G-G118S-P129E-G159D-Q245R-N248D-H249R, A016S-V104L-L111V, T022Q-S101G-S103A-V104I-G159D-S188E-A232T-Q245V-N248D-E271T, N062E-S078G-G118D-P129E-Q245R-N248D, T022Q-S101G-S103A-V104I-G159D-S188E-A232L-Q245V-N248E, T022A-S024R-T033S-G118R-A158E-S188D, S078N-G118R-T213A-L217E, T022A-S024F-S101G-S103A-V104I-N116L-Y209A-G211Q-A232V, G020R-S024R-S078G-G118D-S188D-Q245R-H249R, T022A-S101G-S103A-V104I-N116L-S128L-G159D-S188D-A232V-Q245R-N248D-E271F, G020K-T022L-S078N-G118R-S128D-L217E, T022Q-S101G-S103A-V104I-G159D-S188E-A232V-Q245R-N248H-E271T, T022A-S024R-T033S-N116L-A158E-S188D, S024R-N062E-S128I-S188D, S024R-S078G-G118S-S188D, T022Q-S101G-

S103A-V104I-G159D-S188E-A232V-Q245T-N248D-E271L, G020K-S024F-G118R-T213A-L217E, T022A-S024R-S101G-S103A-V104I-P129E-G159D-S188D-A232V-Q245R-N248D-A270V-E271F-A272V, S103A-V104I-L111V-L148I, T022A-S024F-T033S-S101G-S103A-V104I-N116L-Y209V-G211Q-T213A-A232V, T022A-S101G-S103A-V104I-G159D-S188D-A232S-Q245V-N248H-E271T, S078D-G118D-G159D-Q245R, G020K-T022L-S078D-G118D-P129E-G159D-Q245R-H249R, A016S-T022A-T033S-S101G-S103A-V104I-N116A-Y209V-G211Q-T213A-A232V, T022A-S024R-T033S-S166D, S024R-S078D-G118D-G159D-S188D-N248D-H249R, A016S-S024F-S101G-S103A-V104I-N116L-Y209A-T213A-A232V, S024R-T033S-A158E, G020R-S024R-N062E-S078G-G118D-G159D-S188D-Q245R-N248D-H249R, T022Q-S101G-S103A-V104I-G159D-S188D-A232V-Q245T-N248D-E271T, G020R-N062E-S078D-G118D-S188D-Q245R-N248D, S078G-G118D-S188D-Q245R, T022Q-S101G-S103A-V104I-G159D-S188D-A232V-Q245T-N248D-E271L, G020R-S024R-N062E-S078G-G118D-P129E-G159D-S188D-N248D, S024R-N116L-S128I-S166D, S024R-S078D-G118D-G159D-Q245R-N248D, A016S-T022A-S024F-S101G-S103A-V104I-N116L-S128N-Y209A-G211Q-T213A-A232V, S078G-G118D-P129E-G159D-Q245V-N248E-E271F, G020K-S024F-S078N-G118R-S128D-T213A-L217E, T022L-S024F-T213A-L217E, T022A-S024F-S101G-S103A-V104I-N116L-G118V-Y209A-A232V, N062E-S101A-S103A-V104I-S188D-A232V-Q245R, S024R-T033S-S128I-A158E-S188D, S024R-S078D-G118S-S188D-Q245R, T022Q-S101G-S103A-V104I-G159D-S188E-A232L-Q245R-N248D, G020R-S024R-S078G-G118D-G159D-S188D-H249R, S024R-S078G-G118D-P129E-G159D-Q245R-H249R, S024R-N062E-S078G-G118D-P129E-G159D-S188D-N248D-H249R, S024R-T033S-A158E-S188D, T022A-S101G-S103A-V104I-L148I, N116L-G118R-S128I-S166D, S024R-N062E-S078D-G118S-S188D-N248D, S078G-G118S-P129E-H249R, S101A-S103A-V104I-S188D-P210I-Q245R, T022A-S101G-S103A-V104I-N116L-G118V-Y209V-T213A-A232V, G020K-T022L-S024F-S078N-G118R-S166D, T022A-G118R-S128I-S188D, G020R-N062E-S078G-G118S-N248D, G020R-S078D-G118D-S188D-H249R, N062E-S078G-G118D, G020K-T022L-G118R-S166D-T213A, G061E-S101G-S103A-V104I-N116A-Y209V-G211Q-T213A-A232V, T022A-S101G-S103A-V104I-G159D-S188E-A232S-Q245V-N248E-E271L, T022A-S024F-T033S-S101G-S103A-V104I-N116A-Y209V-T213A-A232V, T022A-S024R-N076D-S101G-S103A-V104I-G159D-S188D-A232V-Q245R-N248D-N269D-A270V-E271F-A272V, T022A-V068A-S101G-S103A-V104I-G159D-S188D-A232V-Q245R-N248D-E271F, T022A-S101G-S103A-V104I-G159D-S188E-A232L-Q245T-N248E-E271T, S078G-G118S-P129E-S188D-N248D-H249R, G020K-T022L-S166D-L217E, T213A-L217E, T022A-S101G-S103A-V104I-G159D-S188D-A232S-Q245V-N248D-E271T, T022A-S101G-S103A-V104I-G159D-S188D-A232S-Q245R-N248D, T022A-S101G-S103A-V104I-G159D-S188E-A232L-Q245V-N248H, G020R-S078D-G118S-G159D-Q245R-N248D-H249R, S024F-S101G-S103A-V104I-N116A-Y209V-A232V, T022L-S024F-G118R-S166D-L217E, S024R-T033S-S188D, G020R-N062E-S078G-G118D-G159D-S188D-H249R-A272D, T033S-A158E-S188D, S101G-S103A-V104I-N116L-S128N-Y209A-G211Q-A232V, T022Q-S101G-S103A-V104I-G159D-S188D-A232V-Q245T-N248E, G020R-S078D-G118D-G159D-Q245R, A016S-S024F-T033S-S101G-S103A-V104I-N116L-Y209V-G211Q-A232V, N062E-S078G-G118S-S188D, G020R-S024R-S078D-G118S-P129E-S188D-Q245R, A016S-S101G-S128N-L148I, G118R-S128I-S166D-S188D, N062E-S078G-G118D-P129E-G159D-H249R, T022A-T033S-N062E-N116L, N062E-S078G-G118D-P129E-Q245R, T022A-S024F-T033S-S101G-S103A-V104I-N116L-Y209V-T213A-A232V, T022A-S101G-S103A-V104I-G159D-S188D-A232T-Q245T-N248E-E271L, S078G-G118S-S188D-H249R, S024R-N062E-S078D-G118S-H249R, S078G-G118S-P129E-S188D-N248D, S101G-S103A-V104I-N116L-S128N-Y209V-T213A-A232V, T022A-S024R-N062E-N116L-G118R-A158E-S188D, G020K-S024F-S078N-S166D-L217E, S024R-S078G-G118S-P129E-H249R, T022A-S024R-S128I-A158E-S166D, S101G-S103A-V104I-N116L-Y209V-G211Q-T213A-A232V, T022A-S024F-T033S-S101G-S103A-V104I-N116L-Y209A-G211Q-A232V, G020R-S078D-G118D-P129E-G159D-S188D-Q245R, N062E-S078G-G118S-P129E-G159D-N248D-H249R, A016S-V104I-S128N-L148I, T022A-S101G-S103A-V104I-G159D-S188E-A232T-Q245V-N248E, T022A-G023A-T033S-S101G-S103A-V104I-N116A-Y209A-G211Q-T213A-A232V, T022A-N116L-S188D, G020R-N062E-S078D-G118D-P129E-G159D-S188D-Q245R, S024R-N062E-S078D-G118D-P129E-H249R, S024F-T033S-S101G-S103A-V104I-N116L-Y209V-T213A-A232V, S024R-S078G-G118S-G159D-S188D-N248D, T022A-S024F-S101G-S103A-V104I-N116L-Y209V-A232V, T022A-S101G-S103A-V104I-N116L-S128N-Y209V-G211Q-A232V, S024R-N062E-S166D-S188D, S024R-S078D-G118S-G159D-S188D-Q245R-N248D, S101G-S103A-V104I-N116A-Y209V-T213A-A232V, T022A-S024R-G118R-A158E-S166D-S188D, T022A-T033S-S101G-S103A-V104I-N116L-Y209A-A232V, G020K-T022L-S024F-S078N-G118R-S128D, A016S-T022A-S024F-T033S-S101G-S103A-V104I-N116A-Y209V-T213A-A232V, S024R-N062E-N116L-S128I, T022A-S024F-S101G-S103A-V104I-N116L-Y209A-T213A-A232V, T022A-V068A-S101G-S103A-V104I-N116L-G159D-S188D-A232V-Q245R-N248D-E271F, T022A-S024R-T033S-N062E-G118R-A158E, S024R-N062E-S078D-G118D-P129E-Q245R-N248D-H249R, T022Q-S101G-S103A-V104I-G159D-S188D-A232T-Q245R-N248D, T022A-S024R-A158E-S188D, G020K-T022L-S078N-G118R-S166D-L217E, G020R-S078D-G118D-P129E, A016S-S101G-S103A-V104I-N116A-S128N-Y209V-G211Q-A232V, G020K-T022L-S024F-G118R-S166D-T213A-L217E, G118R-T213A-L217E, T022L-S024F-S166D-T213A-L217E, S024R-N076D-S101A-S103A-V104I-S188D-A232V-Q245R, T022A-T033S-G118R-P129E, S024R-S078G-G118S-P129E-G159D-S188D-N248D, T022A-S024R-S101G-S103A-V104I-I107V-P129E-G159D-S188D-A232V-Q245R-N248D-A270V-E271F, T022A-S101G-S103A-V104I-N116L-Y209V-G211Q-T213A-A232V, T022A-S101A-S103G-V104I-S128N, T022A-S024R-N062E-N116L-G118R-S166D, A016S-T022A-S024F-S101G-S103A-V104I-N116L-Y209A-T213A-A232V, A016S-S101G-S103A-V164I-N116L-Y209V-G211Q-T213A-A232V, S024F-G118R-S128D-T213A-L217E, T022L-S024F-G118R-T213A-L217E, N062E-S078D-G118S, S024R-G118R-A158E-S188D, S024F-S101G-S103A-V104I-N116L-S128N-Y209A-A232V, A088L, E271W, N062E-S078D-G118D-P129E-H249R, T022A-V104I-S128N-L148I, T022Q-S101G-S103A-V104I-G159D-S188E-A230V-A232V-Q245R-N248H,

S101G-S103A-V104I-N116L-G118V-Y209A-T213A-A232V, S024R-S078G-G118D-G159D-Q245R-H249R, G097P-A098F-S099A-V104I, T022L-S024F-S078N-G118R-S166D-T213A, N062E-S078G-G118D-S188D-Q245R-N248D, T022A-S024R-T033S-S166D-S188D, T022A-T033S-R045C-G118R-A158E-S188D, T022A-S024R-N062E-S128I-S188D, T022A-S101G-S103A-V104I-P129E-G159D-S188D-A232V-Q245R-N248D-A270V-E271F, T022A-S024R-N116L-S166D, S024R-N062E-S128I-A158E, S024R-G118R-A158E-S166D, G020K-T022L-S078N-T213A, G020R-S024R-S078G-G118D-G159D-Q245R-N248D, G020K-T022L-S078N-T213A-L217E, G020R-S078D-G118D-G159D-Q245R-H249R, T022A-S024F-S101G-S103A-V104I-N116L-S128N-Y209A-G211Q-T213A-A232V, S024R-S101A-S103A-V104I-S188D-A232V-Q245R, S024R-N116L-G118R-A158E-S166D-S188D, S024F-S166D-T213A, G020R-S024R-N062E-S078D-G118S-P129E-Q245R-N248D-H249R, T022A-S024R-S128I-S166D-S188D, G020R-S024R-S078D-G118S-P129E-N248D-H249R, T022A-S024R-T033S-N116L-G118R-A158E-S166D-S188D, T022A-S024F-T033S-S101G-S103A-V104I-N116L-S128N-Y209A-T213A-A232V, T022L-S024F-L217E, G020R-S078G-G118S-G159D-S188D-Q245R-N248D-H249R, S099T-S103G, S024R-S078D-G118D-P129E-N248D-H249R, S024R-S078D-G118D-P129E-S188D-Q245R-N248D, T022A-T033S-S101G-S103A-V104I-G118R-G159D-S188D-T213A-A232V-Q245R-N248D-E271F, S024R-S078D-G118S-P129E-G159D-S188D-N248D-H249R, S078D-G118D-P129E-G159D-Q245R-H249R, A016S-T022A-S024F-S101G-S103A-V104I-N116A-Y209A-A232V, S024R-S078D-G118D-P129E-G159D-S188D-Q245R-N248D-H249R, T022A-S101G-S103A-V104I-G118R-S128L-G159D-S188D-T213A-A232V-Q245R-N248D-E271F, G020R-S078G-G118S-G159D-Q245R-N248D, S078G-G118D-G159D-S188D-Q245R, T022L-G118R-T213A-L217E, G020R-S024R-S078G-G118S-S188D-N248D-H249R, G118R-A158E-S166D-S188D, A016S-T022A-S024F-T033S-S101G-S103A-V104I-N116L-Y209V-T213A-A232V, N062E-S078G-G118S-P129E-G159D-Q245R-N248D, T022Q-A088S-S101G-S103A-V104I-G159D-S188D-A232T-Q245V-N248E, S078D-G118S-P129E-G159D-Q245R-N248D, G020K-S024F-S128D-N204K, S024F-S101G-S103A-V104I-N116A-Y209V-G211Q-A232V, S024R-S078D-G118S-S188D, S101G-S103A-V104I-N116L-Y209V-A232V, G020R-N062E-S078D-G118S-S188D-Q245R-N248D-H249R, A016S-T022A-S024F-S101G-S103A-V104I-N116L-Y209A-G211Q-A232V, S101G-S103A-V104L-L148I, T022A-S101G-S103A-V104I-G159D-S188E-A232T-Q245T-N248D-E271L, S024R-N062E-S078D-G118D-P129E-S188D-H249R, R010H-T022L-S024F-L217E, T022A-S101G-S103A-V104I-G159D-S188E-A232L-Q245R-N248D, S024R-N062E-S078G-G118D-S188D-Q245R, S024R-N116L-S128I-A158E-S166D, T022A-S101G-S103A-V104I-G159D-S188D-A232V-Q245T-N248H-E271F, G020R-S078D-G118S-P129E-G159D, G020R-S024R-S078D-G118D-P129E-Q245R-N248D, S024R-N076D-S101A-S103A-V104I-P210I-A232V-Q245R, S078D-G118D-S188D-Q245R, G020K-T022L-S024F-G118R-S166D-T213A, S078G-G118S-G159D-Q245R-N248D-H249R, T022Q-S101G-S103A-V104I-G159D-S188D-A232T-Q245R-N248E-E271F, S056R-G065P, S056K, T022A-S024R-N076D-S101G-S103A-V104I-P129E-G159D-S188D-A232V-Q245R-N248D-E271F, T022A-S024R-N062E-N116L-G118R-S128I-A158E, S024R-S078G-G118S-P129E-S188D, G020R-N062E-S078D-G118D-G159D-N248D-H249R, S024R-S078G-G118S-G159D-N248D, S024R-N062E-S078G-G118D-S188D-N248D, G020R-S024R-N062E-S078D-G118S-P129E-Q245R, S024R-S078D-G118D-G159D, T022A-S024R-T033S-G118R-S128I-S166D-S188D, A016S-T033S-S101G-S103A-V104I-N116L-S128N-Y209V-A232V, T022A-T033S-S188D, G097P-S103A-V104L, G020R-S078G-G118D-P129E, N062E-S101A-S103A-V104I-S188D-V203L-A232V-Q245R, G020R-S024R-S078G-G118S-G159D-Q245R-N248D, G020R-S078D-G118D-G159D-S188D, G020R-S024R-S078G-G118D-S188D-Q245R-N248D, G020R-N062E-S078D-G118D-S188D, G020R-S101A-P210I-G211Q, T022A-T033S-N116L-S188D, T022A-T033S-S101G-S103A-V104I-G159D-S188D-A232V-Q245R-N248D-E271F, T022A-S101G-S103A-V104I-G159D-S188D-A232L-Q245R-N248E-E271L, S024R-N062E-S078D-G118D-N248D-H249R, T022A-S024R-N116L-A158E, N062E-N076D-S101A-S103A-V104I-S188D-P210I-A232V-Q245R, S024R-S078G-G118S-S188D-N248D-H249R, G020R-S078G-G118S-P129E-S188D-N248D-H249R, S024R-S078D-G118D-G159D-S188D, A016S-S101G-S103A-V104I-N116L-Y209A-G211Q-A232V, S132D, N043K, G097P-V104L, A016S-T022A-S024F-S101G-S103A-V104I-N116A-Y209A-G211Q-A232V, S024R-N062E-S078D-G118D-G159D-S188D-H249R, S024R-S078G-G118S-G159D-S188D, S024R-S078G-G118D-G159D-S188D-N248D, S024R-N062E-S078G-G118S-G159D-S188D-Q245R-H249R, S024F-S101G-S103A-V104I-N116A-Y209V-T213A-A232V, G020K-S078N-S166D-T213A-L217E, S103A-L111V-L148I, S024F-T033S-S101G-S103A-V104I-N116L-S128N-Y209A-G211Q-T213A-A232V, S024R-S078D-G118D-G159D-S188D-Q245R-N248D, T022A-T033S-S101G-S103A-V104I-N116A-Y209V-T213A-A232V, S024R-N062E-S078G-G118D-P129E-S188D, S024R-S078D-G118D-P129E-S188D-Q245R-H249R, T022A-G118R-S166D, G020R-S024R-S078G-G118S-G159D-S188D-Q245R, T022A-S024R-T033S-N116L-G118R-A158E-S188D, T022Q-S101G-S103A-V104I-G159D-S188E-A232T-Q245V-N248D-E271F, G020R-S024R-S078D-G118S-P129E-Q245R-N248D-H249R, A016S-T022A-V104I-S128N, S024R-N062E-N076D-S101A-S103A-V104I-S188D-P210I-A232V-Q245R, T022L-G118R-S166D-T213A-L217E, S078D-G118S-P129E-G159D-S188D-Q245R-H249R, G195W-N269E, G020R-S024R-S078G-G118S-P129E-Q245V-N248E, N269W, T022A-T033S-G118R-A158E-S166D-S188D, G020R-N062E-S078G-G118D-P129E-G159D-Q245R-H249R, A016S-S101A-S103A, G097P-S099G-S103A-V104I, S024R-S078D-G118D-P129E-Q245R, T022Q-S101G-S103A-V104I-G159D-S188D-A232L-Q245R-N248E, S078G-G118D-P129E-S188D-Q245R, T033S-N062E-G118R-A158E, G020R-S078D-G118S-G159D-N248D, A016S-T022A-S103G-V104I-S128N-L148I, A016S-S101G-S103A-V104I-N116A-Y209A-A232V, S101A-S103A-V104I-S188D-M222S-A232V-Q245R, T022A-S024F-S101G-S103A-V104I-N116A-S128N-Y209V-T213A-A232V, A016S-T022A-S024F-S101G-S103A-V104I-N116A-Y209A-T213A-A232V, T022A-S101G-S103A-V104I-G159D-S188D-T213A-A232V-Q245R-N248D-E271F, A016S-S101G-S103A-V104I-N116L-Y209A-T213A-A232V, G020R-S078D-G118S-S188D, G020R-S078D-G118S-P129E-Q245R-N248D, T022L-S166D-T213A, G020R-S024R-S078D-G118S-P129E-G159D-S188D-N248D, S240G, S078G-G118S-P129E-Q245R-N248D, S024R-S078D-G118D-

P129E-G159D-Q245R-N248D, T022A-S024R-N076D-S101G-S103A-V104I-G159D-S188D-A232V-Q245R-N248D-E271F-A272V, N062E-S078G-G118S-P129E-S188D-Q245R-N248D-H249R, S024F-S078N-G118R-S166D, S078G-G118S-P129E-N248D, N155W, A016S-S024F-S101G-S103A-V104I-N116A-S128N-Y209V-G211Q-T213A-A232V, G020R-N062E-S078D-G118D-P129E-Q245R-N248D, G020R-S078D-G118D-P129E-S188D-Q236R-N248D-H249R, T022A-S024R-N116L-A158E-S188D, S101G-S103A-V104I-N116A-S128N-Y209V-G211Q-T213A-A232V, S078D-G118S-S188D-Q245R-N248D, T022L-S024F-S078N-L217E, S099A-S101A-G102A, G020R-S078D-G118D-G159D-N248D-H249R, T022A-N076D-S101G-S103A-V104I-I107V-P129E-G159D-S188D-A232V-Q245R-N248D-E271F, T033S-N116L-G118R-S166D-S188D, S024R-G118R-S128I-A158E-S166D-S188D, G020R-S024R-N062E-S078G-G118S-P129E-G159D-Q245R-N248D-H249R, N062E-S078G-G118D-N248D-H249R, N062E-S078R-P129E-S188D-Q245R-N248D, S024R-N062E-G159D-S188D-Q245R, G020R-N062E-G118R-S188D-N248D-H249R, N062E-S078R-P129E-G159D, G020R-S024R-N062E-P129E-S188D-N248D, N062E-S078R-G118R-G159D-S188D-P210L-N248D, N062E-S078R-Q245R-N248D, G020R-G159D-S188D-H249R, G020R-G118R-G159D-S188D-N248D, G118R-P129E-G159D-S188D-H249R, N062E-S078R-G118R-P129E-N248D, N062E-S078R-G159D, N062E-G118R-P129E-S188D-Q245R, G020R-S024R-P129E-G159D-S188D-N248D, S024R-N062E-S078R-G159D-N248D, G020R-P129E-S188D-H249R, G020R-P129E-G159D-S188D-Q245R, A016S-S024F-S101G-S103A-V104I-N116A-S128N-S188D-Y209V-T213A-A232V, G020R-G159D-S188D-Q245R-N248D, G118R-P129E-G159D-Q245R-N248D, G020R-N062E-S078R-P129E-S188D-N248D, G020R-P129E-S188D-Q245R, S024R-N062E-S188D-N248D, S078R-L111I-N185I-I198L-L217E, G020R-P129E-S188D-N248D-H249R, G020R-N062E-G118R-G159D-N248D, G020K-T022L-G118R-P129E-S188D, G020R-G118R-P129E-S188D, G020R-P129E-G159D-Q245R-N248D, G020R-S024R-P129E-G159D, G020R-P129E-G159D-Q245R-N248D-H249R, S024R-P129E-G159D-S188D-Q245R-N248D-H249R, G020R-P129E-Q245R-N248D, N062E-S078R-G159D-N248D, S024R-G118R-P129E-G159D-S188D-Q245R-N248D-H249R, G020R-G061W-P129E-G159D-S188D-Q245R, T022A-S101G-S103A-V104I-G159D-S188D-M222S-A232V-Q245R-N248D-A270V-E271F, N062E-G159D-S188D-H249R, A016S-S024F-S101G-S103A-V104I-N116A-S128N-S130D-Y209V-T213A-A232V, G020R-S024R-P129E-G159D-N248D-H249R, P129E-G159D-S188D-H249R, G118R-P129E-G159D-S188D-K237R-N248D-H249R, G020R-G159D-S188D-Q245R, G020R-S188D-Q245R-N248D-H249R, T022A-S101G-S103A-V104I-P129S-L217Q-A232V-Q245R, G020R-S078R-G118R-P129E-S188D-N248D, G020R-S024R-G118R-G159D-S188D-Q245R-N248D, G020R-G118R-P129E-G159D-S188D, G020R-G159D-S188D, G020R-G118R-P129E-S188D-N248D, A016S-S024R-S101G-S103A-V104I-N116A-S128N-Y209V-T213A-A232V, G020K-N062E-S188D-T213A-M222S, A016S-S024F-S101D-S103A-V104I-N116A-S128N-Y209V-T213A-A232V, S024G-S078N-S101N-Q109G-S128A-L217Q, T022A-G097S-S101N-S103A-V104I-S128A-G159D-S188D-L217Q-M222S-A232V-Q245R-N248D-E271F, T022A-S101G-S103A-V104I-G159D-S188D-M222S-A232V-Q245R-N248D-E271F, G020R-P129E-Q245R, S024R-P129E-G159D-Q245R-N248D, S024R-G118R-S188D-N248D, G020R-P129E-H249R, S024R-P129E-Q245R-N248D, T022A-S101G-S103A-V104I-L217Q-A232V-Q245R, G020R-S078R-P129E-G159D-S188D-H249R, T022A-S101G-S103A-V104I-S128A-P129S-L217Q-A232V-Q245R, G118R-P129E-H249R, G020R-N062E-G118R, G020R-G118R-P129E-G159D-Q245R-N248D, T022A-S101Q-S103A-V104I-P129S-L217Q-A232V-Q245R, S024R-S078R-G118R-P129E-G159D-S188D, P129E-Q245R-N248D-H249R, S024G-G061S-S078N-S101N-Q109G-S128A-L217Q-N243V, S078R-V084A-P129E-Q245R, S024R-G118R-G159D-S188D-N248D, G020R-G118R-P129E-G159D-H249R, S078R-P129E-G159D, G061P-S078N-G097A-S101N-S128A-V203Y-L217Q, P086S-S087G-A088V-G097A-N117S-S128A-L217Q, S024R-S078R-G159D-S188D-Q245R-N248D-H249R, S078R-G118R-P129E, S024G-S078N-S101N-S128A-L217Q-N243V, S024R-S078R-G159D-S188D, G020R-G118R-P129E, G020R-S024R-P129E-G159D-S188D-H249R, S024R-G118R-G159D-S188D, S024R-G118R-P129E-G159D-S188D-Q245R-N248D, S024G-S078N-S101N-S128A-L217Q, S024R-G159D-S188D-Q245R, S024G-S078N-S101N-Q109G-L217Q-N243V-N248A, G020R-S078R-G159D-S188D-Q245R-N248D, S078R-G118R-P129E-S188D-N248D, S024R-S188D-Q245R-N248D, G020R-S024R-S101A-P210I-G211Q, G020R-G159D-N248D-H249R, G020R-P129E, G020K-N062E-N116L-T213A-M222S, S024G-S078N-A088T-S101N-Q109G-N116T-S128A-A158S-L217Q-N218S-L257G, A016S-S024F-S101G-S103A-V104I-N116A-S128N-S166D-Y209V-T213A-A232V, S024R-N062E-S078R-P129E-H249R, N018K-G020R-S024R-R045T-S101A-P210I-G211Q-T213A, G020R-S024R-G118R-P129E-G159D-S188D-N248D-H249R, G020R-S024R-P129E-H249R, G020R-G118R-S188D-Q245R-N248D-H249R, G020R-S024R-N062E-S078G-G118S-Q245R, G020R-S024R-G118R-P129E-G159D-N248D, S024G-S078N-S101N-Q109G-S128A-L217Q-S256R, S024G-S078N-S101N-S128A-A158S-L217Q-L257G, G020R-S024R-G118R-S188D-N248D, G020R-G118R-G159D-S188D-Q245R-N248D-H249R, G159D-S188D-Q245R-N248D, S078N-G118R-S166D-L217E-M222S, G020R-G118R-P129E-G159D-Q245R-N248D-H249R, T022A-S101Q-S103A-V104I-L124V-S128A-P129S-A232V-Q245R, S024R-N062E-Q245R, S188D-Q245R-N248D, S024R-G118R-P129E-S188D-H249R, T022A-G097A-S101Q-S103A-V104I-P129S-A232V-Q245R, G020R-G118R-S188D-Q245R-N248D, S024G-S078N-S101N-Q109G-N116T-S128A-L217Q-N243V-S256R, G020R-G118R, G020R-S024R-S188D, N062E-P129E-G159D-S188D-Q245R, G020R-G159D-Q245R-N248D, G020R-N043R-S101A-P210I-G211Q, G097A-S101N-S128A-L217Q, G020R-G118R-S188D-N248D, S024R-S188D-N248D, G020R-S024R-S188D-Q245R-N248D, G020R-S024R-G118R-P129E-G159D-N248D-H249R, G020R-P129E-N248D, G159D-S188D, P129E-G159D, G020R-S188D-H249R, P129E-G159D-Q245R-N248D, G020R-G118R-G159D-N248D-H249R, G118R-S188D-N248D-H249R, G020K-S101D-G102A-L217E-S240R, N043R-G102A-L217E, N062E-S078N-S101D-S240R, G102A-L217E, G020K-S128L-L217E-S240R, G020K-N062E-S078N-L217E-S240R, N043R-S101D-S128L-L217E-S240R, G020K-S078N-S101D-G102A-P210L, N043R-S101D-L217E, G020K-G100S-L217E-S240R, S078N-G100S, G020K-N043R-S101D-G102A-L217E, G100S-S240R, G020K-G102A-L217E, G020K-S024G-N062E-S078N-S101N-Q109N-N116L-S128A-S188D,

G020K-L217E-S240R, N043R-S101D, N043R-S078N-S101D-S128L-S240R, N043R-S078N-S101D-L217E-S240R, G020K-S078N-S101D, N043R-S128L-S240R, G020K-N062E-N116L-N123G-T213A, G020K-N062E-G097S-S101G-Q109G-N116L-S128A, G020K-N062E-S078N-G097A-S101N-Q109N-N116L-S188D, N043R-S078N-S101D-G102A-L217E, G020K-S078N-S099G-S128L-L217E, G020K-N062E-S101D, G020K-S128L-L217E, G020K-S024G-N062E-S078N-G097S-S101G-Q109G-N116L-L217Q, N043R-G097A-S101D-S128L, G020K-S024G-N062E-S101Q-Q109N-N116L-S128A, G020K-S024G-N062E-S078N-S101N-N116L-S128A-L217Q, S078N-G102A-S240R, N043R-S078N-G100S-L217E-S240R, G020K-S078N-S128L-L217E-S240R, G020K-N062E-N116L-S128Q, G020K-S101G-L217E-S240R, G020K-S024G-N062E-S101N-Q109G-N116L-S128A-L217Q, G020K-N062E-S078N-G097S-S101N-N116L-L217Q, G020K-N062E-G097S-S101N-Q109G-N116L-L217Q, G020K-S024G-N062E-S078N-G097A-S101Q-Q109N-N116L-M222S, G020K-S024G-N062E-S078N-G097S-S101Q-Q109N-N116L-S28A-S188D-L217Q, G020K-N062E-S078N-S101N-Q109G-N116L-S188D-L217Q, or G020K-N062E-S105G-N116L-S128L-T213A (List 14), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from T022A-S101G-S103A-V104I-N116L-G159D-S188D-A232V-Q245R-N248D, S024R-N116L-A158E-S188D, G020K-S024F-S078N-G118R-T213A, T022A-S024R-T033S-N116L-G118R-S128I, G020R-S078D-G118D-S188D-Q245R, S024F-S101G-S103A-V104I-N116A-Y209A-T213A-A232V, S024R-N062E-S078G-G118D-G159D-S188D, T022A-N062E-N116L-G118R-A158E-S166D, G020K-T022L-S078N-S166D-L217E, G020R-S078D-G118D-G159D, T022A-S024R-T033S-N116L, G020R-S078D-G118D-P129E-G159D, G020R-S078D-G118D-G159D-H249R, S024R-N062E-S078G-G118S, S024R-S078D-G118D-S188D-Q245R-H249R, A016S-S024F-T033S-S101G-S103A-V104I-N116L-Y209V-T213A-A232V, G020R-N062E-S078D-G118D-P129E-G159D-Q245R, S024F-S101G-S103A-V104I-N116L-G118V-Y209V-G211Q-A232V, S024F-S166D-L217E, T022A-S024R-S166D, S024R-N062E-S078G-G118D-P129E-N248D, A016S-S101G-S103A-V104I-N116L-S128N-Y209V-A232V, A016S-T022A-S101G-S103A-V104I-N116A-Y209V-G211Q-A232V, S078D-G118S-G159D-N248D-H249R, S024R-S078G-G118D-P129E-G159D-S188D, T022A-S024R-N062E-N116L-G118R-S128I-S188D, S103A-S128N, T022L-S078N-G118R-S166D-T213A, S024F-T033S-S101G-S103A-V104I-N116L-S128N-Y209A-T213A-A232V, T022A-S024R-N076D-S101G-S103A-V104I-P129E-G159D-S188D-A232V-Q245R-N248D-E271F-A272V, S024R-S078D-G118S-S128N-P129E, S024R-S078G-G118S-P129E-G159D-S188D-Q245R-H249R, T022A-S024R-N076D-S101G-S103A-V104I-P129E-G159D-S188D-A232V-Q245R-N248D-A270V-E271F-A272V, T022Q-S101G-S103A-V104I-G159D-S188D-A232T-Q245T-N248D, S024R-T033S-N116L-A158E, S130E-N269K, S024R-T033S-N116L-S128I-A158E, A016V-G020R-S024R-S078D-G118D-P129E-Q245R-N248D, S099G-S101A-G102A-S103G-V104I, A016S-T022A-S101A-V104L-S128N-L148I, G020R-S024R-S078G-G118S-P129E-S188D, S259W, S259H, T022A-S101G-S103A-V104I-P129E-G159D-S188D-A232V-Q245R-N248D-E271F, N018D-S101G-S103A-V104I-N116A-Y209A-G211Q-T213A-A232V, G020K-S024F-S078N-S166D-T213A, N076D-S101A-S103A-V104I-S188D-A232V-Q245R, S078D-G118D-P129E-G159D-H249R, S024R-S078G-G118D-P129E-G159D-N248D, S024R-N062E-S101A-S103A-V104I-S188D-A232V-Q245R, E271R, G020R-S024R-S078D-G118D-P129E-G159D-S188D, T022A-S024R-N076D-S101G-S103A-V104I-G159D-S188D-A232V-Q245R-N248D-A270V-E271F, G020R-N062E-S078D-G118S-G159D-S188D-Q245R-H249R, Q012R-S101G-S103A-V104I-N116L-S128N-Y209V-A232V, G020R-S078G-G118D-P129E-G159D-S188D-Q245R-N248D, G020R-N062E-S078G-G118S-P129E-G159D-S188D-Q245R-H249R, T022A-S101G-S103A-V104I-G118R-S128L-G159D-S188D-A232V-Q245R-N248D-E271F, G020R-S078D-G118D-G159D-S188D-Q245R-N248D, T022A-S101G-S103A-V104I-G159D-S188D-A232V-Q245R-N248D-E271F-A272V, G020R-S024R-N062E-S078D-G118S-P129E-S188D-Q245R-N248D-H249R, G020R-S078G-G118S-G159D-H249R, G020K-T022L-S024F-G118R-S128D-S166D, T022A-S024R-N062E-N116L-G118R-S128I-A158E-S166D, A016S-S103G-V104L, A016S-T033S-S101G-S103A-V104I-N116L-Y209A-A232V, G020R-S024R-N062E-S078D-G118S-P129E-S188D-N248D, G020K-T022L-S078N-G118R-S166D, G020K-T213A-L217E, S024R-N062E-S078D-G118S-P129E-G159D-S188D-Q245R-N248D-H249R, S078N-S166D-T213A-L217E, S078D-G118S-P129E-G159D-Q245R-H249R, T022A-N076D-S101G-S103A-V104I-P129E-G159D-S188D-A232V-Q245R-N248D-E271F-A272V, G020K-T022L-G118R-L217E, T022A-V104L-L111V, T022A-S101G-S103A-V104I-S128A-P129E-G159D-S188D-A232V-Q245R-N248D-E271F, S024R-N062E-S078G-G118S-P129E-S188D-N248D, G020R-S024R-S078D-G118D-G159D-S188D-N248D, T022L-S078N-L217E, G020R-S024R-S078G-G118S-S188D, S024F-S101G-S103A-V104I-N116L-Y209V-G211Q-T213A-A232V, T022A-N116L-G118R-A158E-S166D, G020R-S024R-S078G-G118S-P129E-S188D-Q245R-N248D-H249R, T022A-V104I-S128N, S024R-S078G-G118D-Q245R, N062E-S078G-G118S-P129E-G159D-S188D-H249R, T022A-S101G-S103A-V104I-I107V-G159D-S188D-A232V-Q245R-N248D-A270V-E271F-A272V, S024R-N062E-S078D-G118S-P129E-G159D-Q245R-N248D-H249R, T022A-T033S-G118R-A158E-S188D, T022A-S078N-G097A-S101N-S103A-V104I-S128A-G159D-S188D-L217Q-A232V-Q245R-N248D-E271F, T022A-S024R-S166D-S188D, A016S-S024F-T033S-S101G-S103A-V104I-N116L-Y209A-A232V, T022A-T033S-S128I-A158E, S024R-T033S-N116L-S188D, N062E-N076D-S101A-S103A-V104I-P210I-A232V-Q245R, T022A-N076D-S101G-S103A-V104I-G159D-S188D-A232V-Q245R-N248D-A270V-E271F-A272V, S130D, G020K-T022L-S024F-S078N-G118R-S166D-L217E, T022Q-S101G-S103A-V104I-G159D-S188E-A232S-Q245V-N248E, S024R-T033S-N116L-S166D-S188D, S024R-S078D-G118S-S188D-Q245R-H249R, T022A-S024R-T033S-A158E-S166D-S188D, G020K-T022L-S024F-S166D-T213A-L217E, T022A-N062E-N116L-G118R-S188D, G020R-S078G-G118D-Q245R-N248D-H249R, T022A-N116L-G118R-S128I, T022L-S078N-S166D, T022L-G118R-S128D, G097P-

S099A, T022L-S024F-G118R-S128D, S242K, N062E-S078D-G118S-G159D, A016S-S103G-S128N-L148I, G097P-A098Q-S101A, T022A-S103A-V104L-S128N-L148I, T022A-S101G-S103A-V104I-G118R-G159D-S188D-T213A-A232V-Q245R-N248D-E271F, S099G-S101G-G102A, T022Q-S101G-S103A-V104I-G159D-S188D-A232L-Q245T-N248D, G100S-S101G-V104I, S078D-G118S-G159D-Q245R-N248D, A016S-S024F-T033S-S101G-S103A-V104I-N116A-Y209V-G211Q-T213A-A232V, T022A-S024R-T033S-N116L-A158E, T022A-N076D-S101G-S103A-V104I-G159D-S188D-A232V-Q245R-N248D-E271F-A272V, T022A-S024R-N116L-S128I-S166D, S101G-S103A-V104I-N116L-S128N-Y209V-A232V, S024F-S101G-S103A-V104I-N116L-Y209A-A232V, G020R-S078G-G118D-G159D-S188D-N248D, G020R-S078D-G118D-S188D-Q245R-N248D, S024F-S078N-G118R-S128D, T022L-S024F-S078N-G118R-S166D, G020R-S024R-S078D-G118S-P129E-G159D-S188D-Q245R-H249R, S103A-V104L-S128N, T022A-S024R-N062E-N116L-S128I, T022A-N062E-N116L-G118R-A158E-S188D, T022A-S024G-G097S-S101G-S103A-V104I-S128A-G159D-S188D-A232V-Q245R-N248D-E271F, G020R-S024R-N062E-S078D-G118D-G159D-S188D-Q245R-H249R, N062E-S078D-G118S-S188D-Q245R-N248D, T022A-S103A-L148I, T022A-S024R-N116L-S128I-A158E-S188D, G097P-S099T-S101G-V101I, S166D-T213A-L217E, A016S-T033S-S101G-S103A-V104I-N116L-Y209V-A232V, N062E-S078D-G118S-P129E-G159D-S188D-Q245R, T022A-S024F-S101G-S103A-V104I-N116A-S128N-Y209A-G211Q-A232V, G020K-T022L-S078N-G118R-S128D-S166D-L217E, T033S-S188D, T033S-N116L-G118R-A158E, T022A-S024G-N076D-V093I-S101N-S103A-V104I-G159D-S188D-L217Q-A232V-Q245R-N248D-E271F, G020R-S078D-G118S-P129E-Q245R-H249R, T022A-S024R-A158E-S166D-S188D, G020K-T022L-S078N-G118R-S128D, G020R-S024R-S078D-G118D-P129E-S188D, S099T-G102A, S024R-N116L-G118R-A158E-S188D, T033S-N116L-G118R-S166D, T022A-S101G-S103A-V104I-G159D-S188D-A232L-Q245V-N248H, S078D-G118D-Q245R, G020K-S078N-G118R-S166D-T213A-L217E-A272D, A016S-T022A-V104L-L111V-L148I, T022Q-S101G-S103A-V104I-G159D-S188D-A232V-Q245V-N248H, N062E-N116L-G118R-S166D, N062E-S166D, T022A-S024R-N062E-G118R-A158E-S188D, T022A-S024F-S101G-S103A-V104I-N116A-Y209V-A232V, T022A-S024R-N076D-S101G-S103A-V104I-P129E-G159D-S188D-A232V-Q245R-N248D-A270V-E271F, G020R-S024R-N062E-S078G-G118D-Q245R, S024R-N116L-S128I-A158E-S188D, S024R-N062E-S101A-S103A-V104I-P210I-A232V-Q245R, A114T, T022L-S024F-S078N-G118R-S128D, S024R-N116L-G118R-S166D, N062E-S078G-G118D-P129E, A016S-T022A-S101G-S103A-V104I-N116L-Y209A-G211Q-A232V, G020K-T022L-S078N-S166D, G020R-S024R-N062E-S078G-G118S-P129E-S188D-Q245R-N248D-H249R, T022A-S078N-G097A-S101Q-S103A-V104I-G159D-S188D-L217Q-A232V-Q245R-N248D-E271F, T022A-S101G-S103G, A016S-S024F-S101G-S103A-V104I-N116L-S128N-Y209A-G211Q-S212L-A232V, S024F-G118R-S166D-T213A, G100S-S101G, A016S-T022A-S103A-V104L-S128N, G020K-S024F-S078N-G118R-S166D, S099T-G102A-S103G, G020K-S024F-S128D-L217E, S078D-G118D-G159D-H249R, N062E-S078G-G118D-S188D, N076D-S101A-S103A-V104I-P210I-A232V-Q245R, S024R-S078G-G118D-P129E-N248D, S078G-G118S-G159D-S188D, A016S-S101G-S103A-V104I-N116L-S128N-Y209V-G211Q-T213A-A232V, G020K-S078N-G118R-S166D-T213A-L217E, T022A-S101N-S103A-V104I-L124V-P129S-G159D-S188D-A232V-Q245R-N248D-E271F, T022A-S101N-S103A-V104I-P129S-G159D-S188D-L217Q-A232V-Q245R-N248D-E271F, S024R-S078D-G118D-P129E, G020K-S024F-S128D-T213A, T022A-T033S-A158E-S188D, G020K-S024F-S128D-S166D-T274A, S024R-N062E-N116L-G118R-S128I-A158E-S166D-S188D, S078G-G118S-P129E-S188D, T022A-S024R-S128I-A158E-S188D, T022A-S024R-G118R-S128I-A158E, T022A-N116L-S166D, G020K-G118R-S128D-S166D, G020K-T022L-S024F-S078N-G118R-S128D-L217E, G020R-S024R-S078D-G118D-P129E-S188D-N248D, G020K-T022L-G118R-S128D-L217E, S024F-S078N-G118R-S128D-T213A, S024R-S078G-G118D-S188D-N248D, N062E-N076D-S101A-S103A-V104I-S188D-A232V-Q245R, T033S-G118R-S128I-A158E-S166D, A016S-S101G-S103A-V104I-N116A-S128N-Y209V-A232V, S101G-V104I-L111V-S128N, T022A-S078N-G097S-S101N-S103A-V104I-S128A-G159D-S188D-L217Q-A232V-Q245R-N248D-E271F, T022Q-S101G-S103A-V104I-G159D-S188D-A232T-Q245V-N248E, T022A-S078N-G097A-S101N-S103A-V104I-G159D-S188D-L217Q-A232V-Q245R-N248D-E271F, G020K-T022L-S024F-G118R-S128D, T022A-N076D-S078N-G097S-S101G-S103A-V104I-G159D-S188D-A232V-Q245R-N248D-E271F, T022A-S024R-S101G-S103A-V104I-P129E-G159D-S188D-A232V-Q245R-N248D-A270V-E271F, T022A-S101G-S103A-V104I-P131L-G159D-S188D-A232V-Q245R-N248D-E271F, T022Q-S101G-S103A-V104I-G159D-S188D-A232S-Q245T-N248E, T022A-N076D-S078N-S101N-S103A-V104I-S128A-G159D-S188D-A232V-Q245R-N248D-E271F, T022A-S101G-S103A-V104I-N116L-S128N-Y209V-T213A-A232V, T022A-S024R-T033S-N062E-G118R-A158E-S188D, T022A-S024R-S101G-S103A-V104I-G159D-S188D-A232V-Q245R-N248D-E271F, T022A-N116L-G118R-S188D, T022A-G097A-S101Q-S103A-V104I-L124V-S128A-P129S-G159D-S188D-A232V-Q245R-N248D-E271F, T022A-S101G-S103A-V104I-N116L-Y209V-T213A-A232V, T022A-S128I-S188D, G020R-S024R-S078G-G118D-G159D, S024R-T033S-N116L-S128I-A158E-S188D, T022A-T033S-S101G-S103A-V104I-G159D-S188D-T213A-A232V-Q245R-N248D-E271F, A016S-T033S-S101G-S103A-V104I-N116L-S128N-Y209A-A232V, A016S-S101G-S103G-V104I-L148I, S024R-T033S-G118R-S166D-S188D, T022A-T033S-S101G-S103A-V104I-N116L-Y209V-T213A-A232V, T022A-N062E-N116L-S128I, A016S-S101G-S103G-V104L-L148I, T022A-N116L-S166D-S188D, G020K-T022L-S024F-S078N-S128D-T213A, S099G-G100S-V104L, S078G-G118D-P129E-G159D-S188D-H249R-T253M, A016S-T022A-S101G-S103A-V104I-N116A-S128N-Y209A-A232V, T022A-S101G-S103A-V104I-G159D-S188D-A232V-Q245T-N248E, G020R-S078D-G118D-P129E-G159D-S188D-N248D-H249R, G118R-S166D-T213A-L217E, G020K-S024F-S128D, T022A-S024F-S101G-S103A-V104I-N116L-S128N-Y209V-G211Q-T213A-A232V, T022A-G097S-S101Q-S103A-V104I-S128A-G159D-S188D-A232V-Q245R-N248D-E271F, G020K-T022L-G118R-S128D-T213A-L217E, S024F-G118R-S128D-T213A, T022A-S101A-S103A-V104I-S128N, S024R-N062E-N076D-S101A-S103A-V104I-S188D-A232V-Q245R, T022A-S103A-S128N-L148I, G020R-N062E-S078G-G118D-G159D-S188D-N248D,

T022A-S024R-T033S-G118R-S128I-S188D, T022A-S101G-S103A-V104I-S128L-G159D-S188D-A232V-Q245R-N248D-E271F, S101G-S103A-V104I-N116L-S128N-Y209V-G211Q-A232V, T022A-S101Q-S103A-V104I-P129E-G159D-S188D-L217Q-A232V-Q245R-N248D-E271F, T022A-S024G-S078N-G097A-S101N-S103A-V104I-S128A-G159D-S188D-L217Q-A232V-Q245R-N248D-E271F, T022A-G097A-S101N-S103A-V104I-P129S-G159D-S188D-A232V-Q245R-N248D-E271F, T033S-S166D-S188D, S078D-G118S-P129E-Q245R-N248D, G020K-S024F-S078N-G118R-S166D-T213A, S024R-N062E-N116L-G118R-S166D-S188D, G020R-N062E-S078D-G118D-P129E-G159D-N248D-H249R, G020K-S078N-G118R-S128D, T022A-N062E-S166D, P014R, S240D, N155G, A016S-T022A-S024F-S101G-S103A-V104I-N116A-S128N-Y209A-T213A-A232V, A016S-T022A-T033S-S101G-S103A-V104I-N116L-Y209V-G211Q-A232V, A016S-T022A-S024F-T033S-S101G-S103A-V104I-N116L-Y209A-G211Q-T213A-A232V, T022A-G097S-S101N-S103A-V104I-G159D-S188D-A232V-Q245R-N248D-E271F, A016S-S101G-S103A-V104I-N116L-S128N-Y209V-G211Q-A232V, G118R-S128I-S166D, T022A-S078N-G097S-S101N-S103A-V104I-S128A-G159D-S188D-A232V-Q245R-N248D-E271F, S024R-A158E-S188D, T022A-S101N-S103A-V104I-L124V-P129E-G159D-S188D-L217Q-A232V-Q245R-N248D-E271F, N116L-G118R-S188D, T022A-G097A-S101N-S103A-V104I-L124V-S128A-G159D-S188D-A232V-Q245R-N248D-E271F, T022A-G118R-S128I-A158E, G097P-S101A-V104L, S103G-V104I-S128N-L148I, G020R-N062E-S078G-G118D-P129E-S188D, V026W, G020R-N062E-S078D-G118D-P129E-G159D, T022A-N076D-S101G-S103A-V104I-I107V-N123S-P129E-G159D-S188D-A232V-Q245R-N248D-E271F-A272V, S103G-S128N-L148I, T022A-S024R-N076D-S101G-S103A-V104I-G159D-S188D-A232V-Q245R-N248D-E271F, T022A-S024G-N076D-S078N-S101G-S103A-V104I-S128A-G159D-S188D-L217Q-A232V-Q245R-N248D-E271F, T022A-S078N-G097S-S101G-S103A-V104I-G159D-S188D-L217Q-A232V-Q245R-N248D-E271F, T022A-N076D-S101N-S103A-V104I-G159D-S188D-L217Q-A232V-Q245R-N248D-E271F, N062E-S078D-G118S-G159D-S188D-Q245R-H249R, S024R-N076D-S101A-S103A-V104I-A232V-Q245R, T022L-S078N, A016S-T022A-S024F-S101G-S103A-V104I-N116L-Y209V-T213A-A232V, G020K-T022L-S128D-T213A, N062E-G118R-S128I-S188D, S024R-N116L-S128I-S166D-S188D, T022A-S101N-S103A-V104I-S128A-P129E-G159D-S188D-L217Q-A232V-Q245R-N248D-E271F, S024R-T033S-N116L-G118R-A158E, T022A-N076D-G097A-S101Q-S103A-V104I-G159D-S188D-A232V-Q245R-N248D-E271F, T022L-S024F-S166D-L217E, S024R-S078D-G118S-G159D-N248D-H249R, T022A-S101Q-S103A-V104I-P129S-G159D-S188D-A232V-Q245R-N248D-E271F, T022A-N076D-S101G-S103A-V104I-S128A-G159D-S188D-A232V-Q245R-N248D-E271F, A016S-T022A-S024F-S101G-S103A-V104I-N116A-S128N-Y209A-A232V, S078G-G118D-P129E-Q245R-N248D, G020R-S078G-G118D-G159D-N248D, G020K-T022L-G118R-S128D-S166D, T022A-S024G-S101Q-S103A-V104I-S128A-G159D-S188D-L217Q-A232V-Q245R-N248D-E271F, T022A-S024G-N076D-S078N-G097A-S101G-S103A-V104I-P129E-G159D-S188D-L217Q-A232V-Q245R-N248D-E271F, T022A-S101G-S103A-V104I-G159D-S188E-A232T-Q245T-N248D, G020R-N062E-S078G-G118D-S188D-Q245R-H249R, S024F-S101G-S103A-V104I-N116L-Y209A-T213A-A232V, S024R-N062E-N076D-S101A-S103A-V104I-A232V-Q245R, T022A-S024R-N116L-G118R-S128I-A158E, A098Q-S099T-S101A-V104L, T022A-S024G-G097S-S101G-S103A-V104I-G159D-S188D-A232V-Q245R-N248D-E271F, T022A-S078N-S101G-S103A-V104I-S128A-G159D-S188D-L217Q-A232V-Q245R-N248D-E271F, T022A-S101G-S103A-V104I-P129E-G159D-S188D-L217Q-A232V-Q245R-N248D-E271F, S099G-G102A, T022A-N076D-S101G-S103A-V104I-G159D-S188D-A232V-Q245R-N248D-A270V-E271F, T022A-S078N-G097S-S101N-S103A-V104I-G159D-S188D-L217Q-A232V-Q245R-N248D-E271F, T022A-N076D-S101G-S103A-V104I-G159E-S188D-A232V-Q245R-N248D-E271F, T022A-G097A-S101G-S103A-V104I-P129E-G159D-S188D-L217Q-A232V-Q245R-N248D-E271F, T022A-N076D-S101N-S103A-V104I-S128A-G159D-S188D-L217Q-A232V-Q245R-N248D-E271F-T274A, A016S-V104I-L148I, G097P-S101A-S103A, G020K-T022L-S024F-G118R-S166D, T022A-S024R-N062E-N116L-G118R-S128I-S166D, A016S-S024F-T033S-S101G-S103A-V104I-N116A-Y209A-G211Q-T213A-A232V, T022A-S101Q-S103A-V104I-L124V-P129E-G159D-S188D-A232V-Q245R-N248D-E271F, T022A-N076D-S101G-S103A-V104I-S128A-G159D-S188D-L217Q-A232V-Q245R-N248D-E271F, T022A-S024G-N076D-S078N-S101G-S103A-V104I-G159D-S188D-L217Q-A232V-Q245R-N248D-E271F, N062E-S078G-G118S-P129E-N248D, G020R-S078D-G118S, T022A-S101Q-S103A-V104I-L124V-S128A-P129E-G159D-S188D-L217Q-A232V-Q245R-N248D-E271F, G097P-S101G-S103A-V104I, G020K-T022L-S166D-T213A-L217E, T022A-S101G-S103A-V104I-G159D-S188D-A232V-Q245R-N248D-A270V-E271F, T022A-S078N-S101N-S103A-V104I-P129E-G159D-S188D-L217Q-A232V-Q245R-N248D-E271F, A016S-S101A-S103A-S128N, T022A-S101G-S103A-V104I-G159D-S188D-L217Q-A232V-Q245R-N248D-E271F, A098Q-S099T-G102A-S103A, T022A-N076D-S078N-G097A-S101G-S103A-V104I-S128A-G159D-S188D-L217Q-A232V-Q245R-N248D-E271F, S078N-G118R-H120N-S128D-S166D, S101G-S103G-L148I, T022A-S024R-T033S-A158E-S166D, N116L-G118R-S166D, T022A-N062E-N116L-S166D, N076D-S101A-S103A-V104I-S188D-P210I-M222S-A232V-Q245R, T022A-S101G-V104L-L148I, T022A-S101G-S103A-V104I-G159D-S188E-Q245V-N248D, S024R-N076D-S101A-S103A-V104I-S188D-P210I-M222S-A232V-Q245R, T022A-S024G-N076D-G097S-S101N-S103A-V104I-G159D-S188D-L217Q-A232V-Q245R-N248D-E271F, N116L-G118R, T022A-S024G-S101N-S103A-V104I-G159D-S188D-L217Q-A232V-Q245R-N248D-E271F, T033S-S101G-S103A-V104I-N116L-S128N-Y209A-G211Q-T213A-A232V, T022L-G118R-S166D-T213A, A016S-T022A-S101G-S103A-V104I-N116A-Y209V-A232V, T022A-N076D-S101G-S103A-V104I-P129E-G159D-S188D-A232V-Q245R-N248D-A270V-E271F, T022A-S101G-S103G-V104L-L148I, S024R-S078G-G118D-S188D, T022A-S101G-S103A-V104I-G159D-S188D-A232V-N238Y-Q245R-N248D-A270V-E271F-A272V, T022A-S024G-S078N-S101Q-S103A-V104I-G159D-S188D-S216G-L217Q-A232V-Q245R-N248D-E271F, S024R-N116L-S128I, P086T-G097P-S099T-S103A-V104I, A098F-G102A, T022A-S101Q-S103A-V104I-L126I-S128A-P129E-G159D-S188D-A232V-Q245R-N248D-E271F, N062E-S078G-G118D-G159D-N248D, T022A-S024G-N076D-G097S-S101G-S103A-

V104I-S128A-G159D-S188D-L217Q-A232V-Q245R-N248D-E271F, A016S-T022A-S024F-S101G-S103A-V104I-N116L-S128N-Y209V-G211Q-A232V, G020R-S024R-S078D-G118S-H249R, G020K-S078N-G118R-S166D-T213A, G020K-T022L-S024F-G118R, S024R-S101A-S103A-V104I-P210I-A232V-Q245R, T022A-N076D-G097A-S101N-S103A-V104I-S128A-G159D-S188D-A232V-Q245R-N248D-E271F, G097P-A098Q-S099G-S103A, T022A-S024G-N076D-G097S-S101N-S103A-V104I-S128A-G159D-S188D-L217Q-A232V-Q245R-N248D-E271F, T022A-S078N-S101N-S103A-V104I-G159D-S188D-L217Q-A232V-Q245R-N248D-E271F, T022A-S024G-N076D-S078N-S101N-S103A-V104I-G159D-S188D-A232V-Q245R-N248D-E271F, G020K-G118R-S128D-L217E, A098F-S099T-G102A-S103A, T022A-S078N-G097S-S101Q-S103A-V104I-G159D-S188D-L217Q-A232V-Q245R-N248D-E271F, T022A-S024G-S101G-S103A-V104I-P129E-G159D-S188D-A232V-Q245R-N248D-E271F, G020R-S078D-G118S-Q245R, A098Q-S099T-S101A-S103A-V104L, T022A-G097A-S101N-S103A-V104I-G159D-S188D-L217Q-A232V-Q245R-N248D-E271F, G020K-S024F-S078N-S128D-T213A-L217E, T022A-G097A-S101N-S103A-V104I-G159D-S188D-A232V-Q245R-N248D-E271F, G020R-S078D-G118S-S188D-Q245R-H249R, T022A-G097A-S101N-S103A-V104I-P129E-G159D-S188D-A232V-Q245R-N248D-E271F, T022Q-S101G-S103A-V104I-G159D-S188D-A232S-Q245V-N248E, T022A-S024G-S078N-G097S-S101N-S103A-V104I-G159D-S188D-L217Q-A232V-Q245R-N248D-E271F, T022A-S101G-S103A-V104I-P129E-A158E-S188D-A232V-Q245R-N248D-E271F, T022A-S078N-S101N-S103A-V104I-G159D-S188D-A232V-Q245R-N248D-E271F, T022A-S024G-N076D-G097S-A098E-S101G-S103A-V104I-G159D-S188D-A232V-Q245R-N248D-E271F, T022A-N076D-S101G-S103A-V104I-A158E-S188D-A232V-Q245R-N248D-E271F, G020K-T022L-S078N-S166D-T213A, S101G-S103A-V104L-S128N, T022A-S101G-S103A-V104I-N116L-S128L-G159D-S188D-T213A-A232V-Q245R-N248D-E271F, T022A-S101G-S103A-V104I-G159D-S188D-A232V-Q245T-N248D, T022A-G097A-S101Q-S103A-V104I-S128A-G159D-S188D-A232V-Q245R-N248D-E271F, S099G-G100S, T022A-N076D-G097A-S101Q-S103A-V104I-S128A-G159D-S188D-L217Q-A232V-Q245R-N248D-E271F, G020R-N062E-S078D-G118D-P129E-Q245R-N248D-H249R, T022A-S078N-G097S-S101Q-S103A-V104I-Q109G-S128A-G159D-S188D-A232V-Q245R-N248D-E271F, T022A-S101N-S103A-V104I-S128A-G159D-S188D-L217Q-A232V-Q245R-N248D-E271F, T022A-S078N-G097A-S101G-S103A-V104I-S128A-G159D-S188D-A232V-Q245R-N248D-E271F, T022A-N116L-A158E-S188D, S099A-G102A-V104L, T033S-N116L-A158E-A272D, T022Q-S101G-S103A-V104I-G159D-S188E-A232T-Q245T-N248E, S101G-S103A-V104I-N116A-S128N-Y209A-G211Q-A232V, T022A-N076D-G097A-S101Q-S103A-V104I-G159D-S188D-L217Q-A232V-Q245R-N248D-E271F, T022A-S024R-T033S-N116L-G118R-S166D-S188D, T022L-S024F-G118R-S166D-T213A, T022A-S103A-V104I-L111V-S128N, T022A-N076D-S078N-G097S-S101N-S103A-V104I-G159D-S188D-L217Q-A232V-Q245R-N248D-E271F, T022A-G097A-S101N-S103A-V104I-P129S-G159D-S188D-L217Q-A232V-Q245R-N248D-E271F, T022A-S101G-S103A-V104I-G159D-S188D-A232V-V244A-Q245R-N248D-A270V-E271F-A272V, T022A-T033S-N116L-G118R-S128I, T022A-S024G-N076D-S078N-G097A-S101G-S103A-V104I-S128A-G159D-S188D-A232V-Q245R-N248D-E271F, S024R-S078G-G118S-T180N-Q245R-N248D, S099G-S103G-V104I, T022A-S101N-S103A-V104I-S128A-G159D-S188D-A232V-Q245R-N248D-E271F, T022A-G097A-S101Q-S103A-V104I-S128A-G159D-S188D-L217Q-A232V-Q245R-N248D-E271F, T022A-S024G-G097S-S101Q-S103A-V104I-S128A-G159D-S188D-L217Q-A232V-Q245R-N248D-E271F, N062E-N116L-A158E, T022A-S024G-N076D-S101N-S103A-V104I-S128A-G159D-S188D-A232V-Q245R-N248D-E271F, T022L-S024F-S078N-S166D-T213A-L217E, T022A-S101G-S103A-V104I-G159E-S188D-A232V-Q245R-N248D-E271F, T022A-S101N-S103A-V104I-P129S-G159D-S188D-A232V-Q245R-N248D-E271F, T022A-S024G-G097S-S101Q-S103A-V104I-S128A-G159D-S188D-A232V-Q245R-N248D-E271F, T022A-S024R-N076D-S101G-S103A-V104I-I107V-P129E-G159D-S188D-A232V-Q245R-N248D-A270V-E271F, S024R-N062E-N116L-G118R-S128I-A158E-S188D, A016S-S024F-S101G-S103A-V104I-N116L-Y209V-G211Q-A232V, T022A-S024R-S101G-S103A-V104I-P129E-G159D-S188D-A232V-N238Y-Q245R-N248D-E271F-A272V, T022A-S024G-N076D-G097A-S101G-S103A-V104I-G159D-S188D-L217Q-A232V-Q245R-N248D-E271F, T022A-N062Q-S101N-S103A-V104I-G159D-S188D-L217Q-A232V-Q245R-N248D-E271F, S024R-N062E-A158E-S166D-S188D, T022A-S101G-S103A-V104I-G159D-S188D-A232S-Q245V-N248E, N062E-N116L-G118R-S128I, T033S-N062E-N116L-G118R-A158E-S166D, G020R-N062E-S078G-G118D-P129E-S188D-Q245R-H249R, T022A-N076D-S078N-S101N-S103A-V104I-G159D-S188D-L217Q-A232V-Q245R-N248D-E271F, T022A-S078N-S101N-S103A-V104I-S128A-G159D-S188D-L217Q-A232V-Q245R-N248D-E271F, G020K-S166D-T213A, T022A-S024G-N076D-G097S-S101Q-S103A-V104I-S128A-G159D-S188D-L217Q-A232V-Q245R-N248D-E271F, T033S-N116L-G118R-A158E-S166D-S188D, S024R-S078D-G118S-P129E-S188D-N248D, S024R-N062E-S078G-G118D-G159D-N248D, T022A-G097A-S101N-S103A-V104I-L124V-P129E-G159D-S188D-A232V-Q245R-N248D-E271F, T022L-S024F-S078N-S166D-T213A, G020R-S024R-S078G-G118D-S188D-H249R, T022A-G097A-S101Q-S103A-V104I-P129E-G159D-S188D-A232V-Q245R-N248D-E271F, A016S-T022A-V104I-L111V, T022A-S078N-G097A-S101Q-S103A-V104I-S128A-G159D-S188D-L217Q-A232V-Q245R-N248D-E271F, S024F-T033S-S101G-S103A-V104I-N116L-Y209V-A232V, T022A-S101G-S103A-V104I-P129E-A158E-G159E-S188D-A232V-Q245R-N248D-E271F, T022A-N062E-N116L-G118R, T022A-N076D-G097S-S101G-S103A-V104I-S128A-G159D-S188D-A232V-Q245R-N248D-E271F, A016S-T022A-S101G-V104I-L111V-L148I, S024R-N116L-S128I-A158E, T022A-S024F-S101G-S103A-V104I-N116A-Y209A-A232V, T022A-S024R-N076D-S101G-S103A-V104I-G159D-S188D-A232V-Q245R-N248D-A270V-E271F-A272V, N062E-S078D-G118S-G159D-S188D-K235R-Q245R, T022A-S101Q-S103A-V104I-S128A-P129S-G159D-S188D-L217Q-A232V-Q245R-N248D-E271F, T022A-G097S-S101G-S103A-V104I-S128A-G159D-S188D-L217Q-A232V-Q245R-N248D-E271F, T022A-S103G-V104I-S128N-L148I, T022A-N076D-S078N-S101G-S103A-V104I-S128A-G159D-S188D-A232V-Q245R-N248D-E271F, T022A-N076D-S078N-G097S-S101G-S103A-V104I-G159D-S188D-L217Q-A232V-Q245R-N248D-E271F, T022A-

S024G-S078N-G097S-S101N-S103A-V104I-S128A-G159D-S188D-A232V-Q245R-N248D-E271F, T022A-S101N-S103A-V104I-L124V-S128A-P129S-G159D-S188D-A232V-Q245R-N248D-E271F, T022A-S024F-S101G-S103A-V104I-N116L-Y209V-G211Q-T213A-A232V, N076D-S101A-S103A-V104I-A232V-Q245R, T022A-S101Q-S103A-V104I-L124V-S128A-G159D-S188D-A232V-Q245R-N248D-E271F, T022A-N076D-S101Q-S103A-V104I-S128A-G159D-S188D-L217Q-A232V-Q245R-N248D-E271F, T033S-S166D, T022A-S024G-S078N-S101G-S103A-V104I-G159D-S188D-A232V-Q245R-N248D-E271F, T022A-S078N-G097S-S101N-S103A-V104I-G159D-S188D-A232V-Q245R-N248D-E271F, A114L, G020R-S024R-S078D-G118S-P129E-G159D-K237E-N248D-H249R, G020K-T022L-S024F-G118R-S128D-T213A-L217E, A016S-S101A-S103A-V104L-S128N-L148I, T022A-N076D-S078N-S101Q-S103A-V104I-G159D-S188D-L217Q-A232V-Q245R-N248D-E271F, T022A-N076D-S078N-G097S-S101N-S103A-V104I-S128A-G159D-S188D-A232V-Q245R-N248D-E271F, T022A-G097A-S101N-S103A-V104I-L124V-P129S-G159D-S188D-A232V-Q245R-N248D-E271F, T022A-S024G-S078N-S101Q-S103A-V104I-P129E-G159D-S188D-L217Q-A232V-Q245R-N248D-E271F, A016S-T022A-S101G-S103A-V104I-N116L-Y209V-A232V, T022A-G097A-S101N-S103A-V104I-L124V-S128A-P129S-G159D-S188D-A232V-Q245R-N248D-E271F, T022A-S024R-T033S-G118R-S188D, T022A-T033S-N116L-G118R-S128I-S188D, T022A-S024R-T033S-S128I-A158E-S188D, T022A-S101Q-S103A-V104I-S128A-G159D-S188D-L217Q-A232V-Q245R-N248D-E271F, A016S-T022A-S103A-L148I, T022A-N076D-S078N-G097A-S101N-S103A-V104I-S128A-G159D-S188D-A232V-Q245R-N248D-E271F, N018S-T022A-S024G-S101N-S103A-V104I-G159D-S188D-L217Q-A232V-Q245R-N248D-E271F, T022A-N076D-S078N-G097A-S101Q-S103A-V104I-G159D-S188D-A232V-Q245R-N248D-E271F, T022A-N076D-S078N-S101N-S103A-V104I-S128A-G159D-S188D-L217Q-A232V-Q245R-N248D-E271F, T022A-S024R-S101G-S103A-V104I-P129E-G159D-S188D-A232V-Q245R-N248D-E271F, T066V, T022A-G097A-S101N-S103A-V104I-S128A-P129S-G159D-S188D-L217Q-A232V-Q245R-N248D-E271F, T022A-S024G-S078N-G097S-S101Q-S103A-V104I-Q109G-G159D-S188D-L217Q-A232V-Q245R-N248D-E271F, S099T-S101A-S103G, T253L, N076D-S101A-S103A-V104I-P210I-M222S-A232V-Q245R, S099G-S101A-G102A, T022A-G097A-S101N-S103A-V104I-L124V-S128A-G159D-S188D-L217Q-A232V-Q245R-N248D-E271F, T022A-S101G-S103A-V104I-P129E-G159D-S188D-A232V-Q245R-N248D-A270V-E271F-A272V, T022A-S024G-G097A-S101N-S103A-V104I-G159D-S188D-L217Q-A232V-Q245R-N248D-E271F, S024R-S078D-G118D-S188D-Q245R, T022A-S103G-V104L-S128N, S024R-N116L-G118R, T022A-N076D-S101G-S103A-V104I-I107V-N123S-P129E-G159D-S188D-A232V-N238Y-Q245R-N248D-A270V-E271F, T022A-N076D-S078N-S101Q-S103A-V104I-S128A-G159D-S188D-A232V-Q245R-N248D-E271F, T022A-N076D-S078N-G097S-S101N-S103A-V104I-S128A-G159D-S188D-L217Q-A232V-Q245R-N248D-E271F, T022A-N043R-N076D-S101G-S103A-V104I-P129E-A158E-G159E-S188D-A232V-Q245R-N248D-E271F-A272V, T022A-S024G-N076D-S078N-S101N-S103A-V104I-S128A-G159D-S188D-A232V-Q245R-N248D-E271F, T033S-N062E, T022A-N076D-S101G-S103A-V104I-A158E-S188D-A232V-Q245R-N248D-E271F-A272V, A098Q-S099A-G102A, G118R-S128I-A158E-S188D, T022A-S024G-N076D-G097A-S101G-S103A-V104I-S128A-G159D-S188D-A232V-Q245R-N248D-E271F, T022A-G097S-S101N-S103A-V104I-Q109G-G159D-S188D-L217Q-A232V-Q245R-N248D-E271F, T022A-S103A-V104L-S128N, T022A-S101N-S103A-V104I-S128A-P129S-G159D-S188D-L217Q-A232V-Q245R-N248D-E271F, T022A-S024G-G097S-S101Q-S103A-V104I-G159D-S188D-A232V-Q245R-N248D-E271F, T022A-T033S-A158E, S024R-S188D, T022A-S101G-S103A-V104I-G159D-S188D-A232L-Q245V-N248H-E271T, S024R-T033S-N062E, S024R-T033S-S166D, T022A-T033S-S101G-S103A-V104I-G118R-G159D-S188D-A232V-Q245R-N248D-E271F, T022A-S024R-N062E-A158E-S166D-S188D, T022A-N076D-G097A-S101N-S103A-V104I-G159D-S188D-L217Q-A232V-Q245R-N248D-E271F, T022A-S024G-N076D-G097S-S101Q-S103A-V104I-G159D-S188D-L217Q-A232V-Q245R-N248D-E271F, S024R-S101A-S103A-V104I-S188D-P210I-M222S-A232V-Q245R, T022A-N076D-G097S-S101N-S103A-V104I-G159D-S188D-L217Q-A232V-Q245R-N248D-E271F, T022L-G118R-S128D-T213A, T022A-S101G-S103A-V104I-G159D-S188D-A232V-Q245V-N248E, T022A-N076D-G097S-S101Q-S103A-V104I-G159D-S188D-A232V-Q245R-N248D-E271F, T022A-S024G-N076D-G097A-S101G-S103A-V104I-G159D-S188D-A232V-Q245R-N248D-E271F, T022A-S024R-S101G-S103A-V104I-P129E-A158E-S188D-A232V-Q245R-N248D-E271F, S056G, G020R-N062E-S078D-G118S-P129E-S188D-Q245R-N248D-H249R, T022A-N076D-G097S-S101Q-S103A-V104I-Q109G-S128A-G159D-S188D-A232V-Q245R-N248D-E271F, S024R-S078D-G118S-P129E-S188D-Q245R-H249R, T022A-N076D-G097S-S101Q-S103A-V104I-S128A-G159D-S188D-L217Q-A232V-Q245R-N248D-E271F, T022A-S101Q-S103A-V104I-L124V-P129E-G159D-S188D-A232V-Q245R-N248D-E271F-R275H, T022A-S024G-S078N-G097A-S101G-S103A-V104I-S128A-G159D-S188D-A232V-Q245R-N248D-E271F, T022A-S024G-R045S-S101G-S103A-V104I-G159D-S188D-A232V-Q245R-N248D-E271F, T022A-N076D-S101G-S103A-V104I-P129E-G159D-S188D-A232V-Q245R-N248D-A270V-E271F-A272V, T022A-S101G-S103A-V104I-L126I-P129E-G159D-S188D-A232V-Q245R-N248D-E271F, T022A-S024G-N076D-S101N-S103A-V104I-G159D-S188D-L217Q-A232V-Q245R-N248D-E271F, T022A-N062D-S101G-S103A-V104I-N116L-G159D-S188D-T213A-A232V-Q245R-N248D-E271F, T022A-S024G-N076D-S078N-G097S-S101Q-S103A-V104I-G159D-S188D-A232V-Q245R-N248D-E271F, T022A-S101G-S103A-V104I-G159D-S188D-A232V-Q245R-N248D-A270V-E271F-A272V, S024R-N062E-S078G-G118D-P129E-Q245R-H249R, T022A-S101G-S103A-S128N, G020R-S024R-S078G-G118D-P129E-N248D-H249R, N116L-G118R-P129E-S188D, T022A-S101N-S103A-V104I-G159D-S188D-L217Q-A232V-Q245R-N248D-E271F, T022A-S101G-S103A-V104I-L126I-S128A-P129S-G159D-S188D-A232V-Q245R-N248D-E271F, T022A-N076D-S101G-S103A-V104I-Q109G-G159D-S188D-L217Q-A232V-Q245R-N248D-E271F, T022A-S024G-G097A-S101Q-S103A-V104I-S128A-G159D-S188D-A232V-Q245R-N248D-E271F, G020R-S078D-G118S-P129E-G159D-S188D, T022A-T033S-G118R-S166D-S188D, S078G-G118D-P129E-G159D-S188D, T022A-S024G-G097S-S101N-S103A-V104I-G159D-S188D-L217Q-A232V-Q245R-N248D-

E271F, T022A-N076D-S101Q-S103A-V104I-G159D-S188D-L217Q-A232V-Q245R-N248D-E271F, T022A-S024R-S101G-S103A-V104I-P129E-S188D-A232V-Q245R-N248D-E271F-A272V, T022A-S103A-V104I-L111V, T022A-S024G-S078N-S101N-S103A-V104I-G159D-S188D-A232V-Q245R-N248D-E271F, T022A-N076D-S101N-S103A-V104I-S128A-G159D-S188D-L217Q-A232V-Q245R-N248D-E271F, T022A-N076D-A085T-S101G-S103A-V104I-A158E-S188D-A232V-Q245R-N248D-E271F, T022A-S024G-S078N-E089G-S101Q-S103A-V104I-G159D-S188D-L217Q-A232V-Q245R-N248D-E271F, T022A-S101Q-S103A-V104I-Q109N-G159D-S188D-A232V-Q245R-N248D-E271F, T022A-N076D-S078N-S101Q-S103A-V104I-G159D-S188D-A232V-Q245R-N248D-E271F, T022A-S101N-S103A-V104I-L124V-S128A-P129E-G159D-S188D-L217Q-A232V-Q245R-N248D-E271F, T022A-S024G-G097A-S101Q-S103A-V104I-G159D-S188D-A232V-Q245R-N248D-E271F, T022A-G097A-S101Q-S103A-V104I-S128A-P129E-G159D-S188D-A232V-Q245R-N248D-E271F, T022A-S101G-S103A-V104I-P129E-G159D-S188D-A232V-Q245R-N248D-E271F-A272V, S101G-S103A, L196S, T022A-S024G-S078N-S101G-S103A-V104I-S128A-G159D-S188D-L217Q-A232V-Q245R-N248D-E271F, T022A-G097A-S101G-S103A-V104I-G159D-S188D-L217Q-A232V-Q245R-N248D-E271F, T022A-S024G-N076D-S078N-S101N-S103A-V104I-Q109N-S128A-G159D-S188D-A232V-Q245R-N248D-E271F, T022A-S078N-S101G-S103A-V104I-G159D-S188D-A232V-Q245R-N248D-E271F, T022A-G097A-S101Q-S103A-V104I-L124V-S128A-G159D-S188D-A232V-Q245R-N248D-E271F, E271S, A098Q-S099T-G100S-S101A, T022A-S024G-N076D-G097A-S101N-S103A-V104I-Q109G-G159D-S188D-L217Q-A232V-Q245R-N248D-E271F, T022A-S101Q-S103A-V104I-Q109N-S128A-G159D-S188D-L217Q-A232V-Q245R-N248D-E271F, T022A-G097A-S101Q-S103A-V104I-Q109N-G159D-S188D-A232V-Q245R-N248D-E271F, T022A-S101Q-S103A-V104I-S128A-G159D-S188D-A232V-Q245R-N248D-E271F, T022A-S024G-S078N-G097A-S101Q-S103A-V104I-S128A-G159D-S188D-L217Q-A232V-Q245R-N248D-E271F, T022A-G097S-S101N-S103A-V104I-G159D-S188D-L217Q-A232V-Q245R-N248D-E271F, T022A-S024R-N076D-S101G-S103A-V104I-P129E-G159E-S188D-A232V-Q245R-N248D-E271F, R019H-T022A-N043R-N076D-S101G-S103A-V104I-P129E-S188D-A232V-Q245R-N248D-E271F-A272V, T022A-S024G-N076D-S078N-G097S-S101Q-S103A-V104I-S128A-G159D-S188D-A232V-Q245R-N248D-E271F, T022L-S078N-S166D-T213A, G020R-S024R-S078D-G118D-Q245R-N248D, N269K, T022A-S101N-S103A-V104I-Q109G-G159D-S188D-A232V-Q245R-N248D-E27F, G097P-V139A, T022A-S101Q-S103A-V104I-S128A-P129S-G159D-S188D-A232V-Q245R-N248D-E271F, S024F-S101G-S103A-V104I-N116A-S128N-Y209V-G211Q-A232V, T022A-S101N-S103A-V104I-L124V-S128A-G159D-S188D-L217Q-A232V-Q245R-N248D-E271F, T022A-S024G-G097A-S101G-S103A-V104I-S128A-G159D-S188D-L217Q-A232V-Q245R-N248D-E271F, N062E-S078G-G118D-G159D-S188D-Q245R-H249R, T022A-S024G-S101N-S103A-V104I-S128A-G159D-S188D-L217Q-A232V-Q245R-N248D-E271F, N062E-S078D-G118D-P129E-G159D-Q245R-H249R, T022A-S078N-S101Q-S103A-V104I-G159D-S188D-L217Q-A232V-Q245R-N248D-E271F, S128I-S188D, T022A-S024G-N076D-G097S-S101Q-S103A-V104I-Q109N-S128A-G159D-S188D-L217Q-A232V-Q245R-N248D-E271F, T022A-N076D-S078N-S101G-S103A-V104I-G159D-S188D-L217Q-A232V-Q245R-N248D-E271F, S166D-L217E, T022A-S024G-N076D-G097S-S101G-S103A-V104I-G159D-S188D-A232V-Q245R-N248D-E271F, A098Q-S099G-S101A, T022A-S024R-S101G-S103A-V104I-G159D-S188D-A232V-Q245R-N248D-A270V-E271F-A272V, T022A-V068A-S101G-S103A-V104I-G118R-G159D-S188D-T213A-A232V-Q245R-N248D-E271F, T022A-S024G-S078N-S101Q-S103A-V104I-Q109N-G159D-S188D-A232V-Q245R-N248D-E271F, T022A-N076D-S101N-S103A-V104I-S128A-G159D-S188D-A232V-Q245R-N248D-E271F, T022A-S101G-S103A-V104I-P129S-G159D-S188D-L217Q-A232V-Q245R-N248D-E271F, T022A-S024G-N076D-G097S-S101Q-S103A-V104I-Q109N-G159D-S188D-A232V-Q245R-N248D-E271F, T022A-S101Q-S103A-V104I-S128A-P129E-G159D-S188D-A232V-Q245R-N248D-E271F, S128I-A158E-S166D, T022A-G097A-S101N-S103A-V104I-L124V-S128A-P129S-G159D-S188D-L217Q-A232V-Q245R-N248D-E271F, T022A-S024R-N076D-S101G-S103A-V104I-P129E-A158E-S188D-A232V-Q245R-N248D-E271F, S024R-N062E-S078D-G118D, T022A-G097A-S101N-S103A-V104I-L126I-G159D-S188D-A232V-Q245R-N248D-E271F, T022A-S101G-S103A-V104I-S128A-P129S-G159D-S188D-A232V-Q245R-N248D-E271F, S024F-S078N-G118R-N204K-T213A-L217E, G020R-N062E-S078D-G118D-G159D-N248D, T022A-S024G-N076D-G097A-S101Q-S103A-V104I-G159D-S188D-A232V-Q245R-N248D-E271F, T022A-G097A-S101Q-S103A-V104I-L124V-P129E-G159D-S188D-L217Q-A232V-Q245R-N248D-E271F, T022A-S101G-S103A-V104I-S128A-G159D-S188D-A232V-Q245R-N248D-E271F, G097P-S099G-S101G-V104I, S024R-N062E-S078D-G118D-N248D, T022A-S101Q-S103A-V104I-G159D-S188D-L217Q-A232V-Q245R-N248D-E271F, T022A-S101G-S103A-V104I-L124V-S128A-P129E-G159D-S188D-A232V-Q245R-N248D-E271F, G020K-T022L-S128D-T213A-L217E, G020K-G118R-S166D-T213A, A016S-T022A-L111V, S078D-G118D-P129E-N248D-H249R, S024R-S128I-A158E-S166D-A194T, T022A-N043R-S101G-S103A-V104I-A158E-G159E-S188D-A232V-Q245R-N248D-E271F, T022A-N076S-S101G-S103A-V104I-G159D-S188D-A232V-N238Y-Q245R-N248D-E271F-A272V, T022A-G097A-S101Q-S103A-V104I-P129S-G159D-S188D-L217Q-A232V-Q245R-N248D-E271F, T022A-S101N-S103A-V104I-Q109N-G159D-S188D-A232V-Q245R-N248D-E271F, T022A-S024R-S101G-S103A-V104I-P129E-S188D-A232V-Q245R-N248D-E271F, G020R-S078D-G118D-P129E-S188D, T022A-S101G-S103A-V104I, T022A-G097A-S101N-S103A-V104I-S128A-G159D-R186H-S188D-A232V-Q245R-N248D-E271F, T022A-S101G-S103A-V104I-L124V-S128A-P129S-G159D-S188D-A232V-Q245R-N248D-E271F, G020K-S024F-S078N-G118R-S128D-S166D-T213A, G020R-N062E-S078D-G118D-G159D-S188D, T022A-G097S-S101Q-S103A-V104I-G159D-S188D-L217Q-A232V-Q245R-N248D-E271F, T022A-S024G-S078N-G097A-S101N-S103A-V104I-S128A-G159D-S188D-A232V-Q245R-N248D-E271F, T033S-N116L-G118R-S128I-S166D, T022A-S024F-S101G-S103A-V104I-N116L-Y209A-A232V, T022L-S024F-S078N-G118R-T213A-L217E, T022A-N076D-G097A-S101Q-S103A-V104I-S128A-G159D-S188D-A232V-Q245R-N248D-E271F, T022A-N076D-S078N-S101G-S103A-V104I-G159D-S188D-A232V-Q245R-N248D-E271F,

T022A-S024G-N076D-S078N-G097S-S101N-S103A-V104I-G159D-S188D-A232V-Q245R-N248D-E271F, T022A-N076D-S101N-S103A-V104I-Q109G-S128A-G159D-S188D-A232V-Q245R-N248D-E271F, T022A-S024G-S101Q-S103A-V104I-Q109N-S128A-G159D-S188D-A232V-Q245R-N248D-E271F, N062E-S078G-G118S-P129E-S188D, G020R-N062E-S078D-G118D-G159D-Q245R-H249R, T022A-G097S-S103A-V104I-Q109N-S128A-G159D-S188D-A232V-Q245R-N248D-E271F, T022A-S024R-T033S-N062E-N116L-S166D-S188D, G020R-S078G-G118S-S188D-Q245R-N248D-H249R, T022A-G097A-S101G-S103A-V104I-S128A-G159D-S188D-A232V-Q245R-N248D-E271F, G020R-N062E-S078G-G118D-Q245R-N248D-H249R, T022A-S024G-G097A-S101Q-S103A-V104I-G159D-S188D-L217Q-A232V-Q245R-N248D-E271F, T022A-N076D-S078N-G097S-S101Q-S103A-V104I-G159D-S188D-A232V-Q245R-N248D-E271F, T022A-S078N-S101G-S103A-S128A-G159D-S188D-L217Q-A232V-Q245R-N248D-E271F, T022A-S078N-S101Q-S103A-V104I-Q109N-G159D-S188D-A232V-Q245R-N248D-E271F, G020K-T022L-S024F-S078N-S166D-T213A, A085T-G097P-A098Q, N062E-S078G-G118D-P129E-G159D-Q245R-N248D-H249R, T022A-S024G-N076S-S078N-G097A-S101N-S103A-V104I-S128A-G159D-S188D-A232V-Q245R-N248D-E271F, T022A-S078N-S101Q-S103A-V104I-S128A-G159D-S188D-A232V-Q245R-N248D-E271F, Q012R-T022A-S101G-S103A-V104I-N116L-Y209A-T213A-A232V, T022A-N076D-G097S-S101N-S103A-V104I-S128A-G159D-S188D-A232V-Q245R-N248D-E271F, T022A-S024G-S101G-S103A-V104I-G159D-S188D-A232V-Q245R-N248D-E271F, N116L-A158E-S166D-S188D, T022A-S024R-N076D-S101G-S103A-V104I-A158E-G159E-S188D-A232V-Q245R-N248D-E271F, T022A-S024G-N076D-S078N-G097A-S101Q-S103A-V104I-Q109N-G159D-S188D-A232V-Q245R-N248D-E271F, S024R-T033S-S128I-A158E, S024R-N116L-G118R-S128I-S188D, T022A-N043R-S101G-S103A-V104I-P129E-S188D-A232V-Q245R-N248D-E271F, N062E-S078D-G118D-S188D-H249R, G020R-N062E-S078D-G118S-P129E-G159D-S188D, G020K-T022L-S078D-G118D-P129E-N248D-H249R, T022A-S024R-N043R-N076D-S101G-S103A-V104I-A158E-S188D-A232V-Q245R-N248D-E271F, T022A-N076D-G097A-S101G-S103A-V104I-G159D-S188D-L217Q-A232V-Q245R-N248D-E271F, T022A-G097A-S101N-S103A-V104I-L124V-P129S-G159D-S188D-L217Q-A232V-Q245R-N248D-E271F, T022A-S101G-S103A-V104I-G159D-S188D-A232V-Q245V-N248D, N062E-S078D-G118S-P129E-S188D-Q245R, S024R-N062E-G118R-S128I-A158E-S188D, T022A-S101N-S103A-V104I-P129E-G159D-S188D-A232V-Q245R-N248D-E271F, G020K-T022L-S078N-S128D-L217E, T022A-N062E-N116L-A158E-S188D, T022A-S101A-V104I-L111V, S166D-T213A, T022A-G097A-S101N-S103A-V104I-L124V-S128A-P129E-G159D-S188D-A232V-Q245R-N248D-E271F, T022L-S024F-S166D-T213A, T022A-N076D-S101Q-S103A-V104I-G159D-S188D-A232V-Q245R-N248D-E271F, T022A-S024R-S101G-S103A-V104I-P129E-G159D-S188D-A232V-N238Y-Q245R-N248D-A270V-E271F, T022A-G097S-S101Q-S103A-V104I-Q109G-S128A-G159D-S188D-A232V-Q245R-N248D-E271F, S024R-S128I-A158E-S166D, N062E-S078D-G118S-N248D-H249R, T022A-S024G-S101Q-S103A-V104I-Q109G-G159D-S188D-A232V-Q245R-N248D-E271F, T022A-S024G-N076D-S078N-G097S-S101Q-S103A-V104I-G159D-S188D-L217Q-A232V-Q245R-N248D-E271F, T022L-S024F-S078N-S166D, T022A-S101G-S103A-V104I-P129E-A158E-S188D-A232V-Q245R-N248D-E271F-A272V, S078D-G118S-P129E-N243D-H249R, T022A-S024G-N076D-S078N-S101N-S103A-V104I-S128A-G159D-S188D-L217Q-A232V-Q245R-N248D-E271F, T022A-S078N-S101G-S103A-V104I-S128A-G159D-S188D-A232V-Q245R-N248D-E271F, T022A-S024R-N062E-G118R, T022A-N076D-S101G-S103A-V104I-P129E-S188D-A232V-Q245R-N248D-E271F-A272V, T022A-S078N-S101Q-S103A-V104I-S128A-G159D-S188D-L217Q-A232V-Q245R-N248D-E271F, S024R-S078G-G118S-Q245R, T022A-S024G-N076D-S078N-S101G-S103A-V104I-G159D-S188D-A232V-Q245R-N248D-E271F-A272T, T022A-S024G-N076D-S078N-G097A-S101Q-S103A-V104I-S128A-G159D-S188D-L217Q-A232V-Q245R-N248D-E271F, T022A-G097A-S101G-S103A-V104I-P129S-G159D-S188D-L217Q-A232V-Q245R-N248D-E271F, T022A-S024G-S078N-G097S-S101G-S103A-V104I-G159D-S188D-L217Q-A232V-Q245R-N248D-E271F, T022A-G097A-S101G-S103A-V104I-L124V-S128A-P129E-G159D-S188D-A232V-Q245R-N248D-E271F, S078N-S166D-L217E, T022A-N076D-S101G-S103A-V104I-I107V-P129E-G159D-S188D-A232V-N238Y-Q245R-N248D-A270V-E271F-A272V, Q236L, S078D-G118D-P129E-H249R, T022A-S101Q-S103A-V104I-G159D-S188D-A232V-Q245R-N248D-E271F, T022A-S101A-S103A-V104I-L111V, T022L-S024F-S078N-S128D-T213A, T022A-S024G-N076D-G097A-S101N-S103A-V104I-S128A-G159D-S188D-A232V-Q245R-N248D-E271F, G020K-S024F-S078N-G118R-S128D-L217E, T022A-S101G-S103A-V104I-G159E-S188D-A232V-Q245R-N248D-E271F-A272V, T022A-N076D-S101G-S103A-V104I-P129E-G159D-S188D-A232V-Q245R-N248D-E271F, T022A-S024G-S078N-S101G-S103A-V104I-G159D-S188D-L217Q-A232V-Q245R-N248D-E271F, T022A-G097A-S101N-S103A-V104I-P129E-G159D-S188D-L217Q-A232V-Q245R-N248D-E271F, T022A-N076D-S101N-S103A-V104I-Q109N-S128A-G159D-S188D-A232V-Q245R-N248D-E271F, T022A-N043R-N076D-S101G-S103A-V104I-A158E-G159E-S188D-A232V-Q245R-N248D-E271F-A272V, G020K-S128D-T213A-L217E, S103A-V104I-L111V-S128N, T022A-G097S-S101N-S103A-V104I-Q109N-S128A-G159D-S188D-L217Q-A232V-Q245R-N248D-E271F, T022A-S024G-S101Q-S103A-V104I-G159D-S188D-L217Q-A232V-Q245R-N248D-E271F, T022A-N076D-S101G-S103A-V104I-I107V-G159D-S188D-A232V-Q245R-N248D-A270V-E271F-A272V, V104I-L111V, T022A-N062Q-S101Q-S103A-V104I-P129E-G159D-S188D-A232V-Q245R-N248D-E271F, T022A-G097A-S101N-S103A-V104I-L124V-G159D-S188D-A232V-Q245R-N248D-E271F, A016S-S101A-L111V-S128N, T022A-S024G-N076D-S078N-G097A-S101G-S103A-V104I-G159D-S188D-L217Q-A232V-Q245R-N248D-E271F, T022A-S101G-S103A-V104I-G159D-S188E-A232L-Q245V-N248E, T022A-N076D-G097A-S101N-S103A-V104I-S128A-G159D-S188D-L217Q-A232V-Q245R-N248D-E271F, T022A-S024G-N076D-G097S-S101N-S103A-V104I-Q109G-G159D-S188D-A232V-Q245R-N248D-E271F, T022A-S101G-S103A-V104I-I107V-G159D-S188D-A232V-Q245R-N248D-E271F, T022A-N076D-G097S-S101G-S103A-V104I-G159D-S188D-A232V-Q245R-N248D-E271F, T022A-S101G-S103A-V104I-S128L-G159D-S188D-A232V-Q245R-N248D-E271F-A272D, T022A-S024G-N076D-S078N-S101Q-S103A-

V104I-S128A-G159D-S188D-L217Q-A232V-Q245R-N248D-E271F, A016S-T022A-S101G-S103A-V104I-N116L-Y209V-G211Q-T213A-A232V, T022A-S101Q-S103A-V104I-L124V-S128A-P129E-G159D-S188D-A232V-Q245R-N248D-E271F, T022A-S024G-N076D-G097A-S101N-S103A-V104I-S128A-G159D-S188D-L217Q-A232V-Q245R-N248D-E271F, T022A-S101N-S103A-V104I-Q109N-S128A-G159D-S188D-A232V-Q245R-N248D-E271F, S101G-S103A-V104I-N116A-S128N-Y209V-G211Q-A232V, S024R-S078G-G118S-G159D-S188D-Q245R-H249R, T022A-S103G-S128N-L148I, T022A-S101Q-S103A-V104I-S128A-P129E-G159D-S188D-L217Q-A232V-Q245R-N248D-E271F, T022A-N076D-G097S-S101Q-S103A-V104I-Q109N-G159D-S188D-A232V-Q245R-N248D-E271F, G020R-S024R-S078D-G118S-N248D, T022Q-S101G-S103A-V104I-G159D-S188D-A232S-Q245V-N248D-E271T, S078G-G118D-S188D-Q245R-N248D, T022A-N076D-S078N-G097S-S101N-S103A-V104I-Q109G-G159D-S188D-A232V-Q245R-N248D-E271F, G118R-S128D-S166D-L217E, G020R-S078G-G118S-P129E-Q245R-H249R, A016S-S024F-S101G-S103A-V104I-N116A-S128N-Y209V-T213A-A232V, T022A-S078N-S101Q-S103A-V104I-R145K-G159D-S188D-L217Q-A232V-Q245R-N248D-E271F, T022A-N043R-N076D-S101G-S103A-V104I-P129E-A158E-S188D-A232V-Q245R-N248D-E271F, T022A-G097A-S101Q-S103A-V104I-L126I-P129S-G159D-S188D-L217Q-A232V-Q245R-N248D-E271F, T022A-G097A-S101N-S103A-V104I-Q109N-G159D-S188D-A232V-Q245R-N248D-E271F, T022A-S024G-S078N-S101N-S103A-V104I-S128A-G159D-S188D-A232V-Q245R-N248D-E271F, T022A-S024R-N076D-S101G-S103A-V104I-P129E-S188D-A232V-Q245R-N248D-E271F-A272V, T022L-S078N-T213A, T022A-N076D-S078N-G097A-S101G-S103A-V104I-G159D-S188D-A232V-Q245R-N248D-E271F, T022A-S078N-S101G-S103A-V104I-Q109G-S128A-G159D-S188D-A232V-Q245R-N248D-E271F, N062E-S078G-G118S-P129E-G159D-Q245R-H249R, A016S-S101G-V104I-S128N-L148I, T022A-G118R-S188D, T022A-G097A-S101Q-S103A-V104I-G159D-S188D-A232V-Q245R-N248D-E271F, G020K-S024F-G118R-S128D-T213A, T022A-S101Q-S103A-V104I-P129E-G159D-S188D-A232V-Q245R-N248D-E271F, G020K-T022L-S024F-S078N-S128D-T213A-L217E, T022A-S024G-S078N-G097A-S101Q-S103A-V104I-Q109G-S128A-G159D-S188D-A232V-Q245R-N248D-E271F, A016S-S101G-S103A-V104I-N116L-Y209V-G211Q-A232V, T022A-S024G-G097A-S101Q-S103A-V104I-S128A-G159D-S188D-L217Q-A232V-Q245R-N248D-E271F, T022A-S101N-S103A-V104I-L124V-S128A-P129S-G159D-S188D-L217Q-A232V-Q245R-N248D-E271F, S099G-G100S-S103A, T022Q-S101G-S103A-V104I-S166D-S188E-A232T-Q245T-N248E, T022A-S024G-N076D-S078N-G097S-S101N-S103A-V104I-Q109N-G159D-S188D-A232V-Q245R-N248D-E271F, A098F-S099T-S103A-V104I, G020K-T022L-N062E-S078D-G118D-P129E-Q245R-N248D, T022L-S078N-G118R-S128D, T022A-S101G-S103A-V104I-N116L-Y209A-G211Q-T213A-A232V, T022A-S101Q-S103A-V104I-L126I-S128A-P129S-G159D-S188D-L217Q-A232V-Q245R-N248D-E271F, G023A-S024F-S101G-S103A-V104I-N116A-Y209V-A232V, T022A-S024R-N116L-G118R-S166D, S024R-N062E-S078D-G118D-P129E-G159D-Q245R-N248D-H249R, G020K-T022L-S024F-S078N-G118R-S128D-T213A, T022A-S024G-N076D-S078N-G097A-S101Q-S103A-V104I-S128A-

G159D-S188D-A232V-Q245R-N248D-E271F, T022A-S024G-S101N-S103A-V104I-S128A-G159D-S188D-A232V-Q245R-N248D-E271F-T274I, G097P-S099A-V104L, G097P-S099A-S103A, T022A-S024G-S078N-G097S-S101Q-S103A-V104I-G159D-S188D-A232V-Q245R-N248D-E271F, T022A-V104L-L148I, T022A-S024G-G097A-S101N-S103A-V104I-S128A-G159D-S188D-A232V-Q245R-N248D-E271F, T022A-S024R-S101G-S103A-V104I-P129E-G159S-S188D-A232V-Q245R-N248D-E271F, T022A-S024G-N076D-S078N-S101G-S103A-V104I-Q109G-G159D-S188D-A232V-Q245R-N248D-E271F, S024R-S078D-G118S-G159D-Q245R-H249R, T022W-N043R-R045T-S101A-P210I-T213A, S024G-N076D-S078N-S101N-H120Q-S128A-L217Q, G020R-S024R-G118R-P129E-G159D-H249R, G020R-S078R-G159D-S188D, PI 29E-S188D-Q245R-H249R, S078R-P129E-Q245R, S078R-P129E-N248D, T022A-S101Q-S103A-V104I-P129S-A232V-Q245R, S188D-N248D, S078R-G118R-G159D, G020R-S078G-G118S-Q245R-N248D-H249R, S024R-S078R-G118R-G159D, G020R-P129E-G159D-N248D, G020R-S024R-G159D-N248D, G097A-S128A-L217Q, S024R-P129E-G159D-N248D, T022K-S101A-S103N-V104L-A232T-Q245R, S078G-G118S-S188D-Q245R-H249R, S099T-S101G-G102A-S103A, G020R-G118R-G159D-Q245R, S024G-S078N-S101N-L217Q, S024G-S078N-S101N-S128A-L217Q-S256R, S078R-G118R-G159D-N248D, S078G-G118S-Q245R-H249R, G118R-P129E-N248D, G020K-T022L-Q245R, A098Q-S099T-S101G-S103A, G118R-H249R, S024R-G118R-N248D-H249R, G020R-S024R-S078G-G118S-Q245R-N248D-H249R, A098F-S099A-S101G-V104I, G020R-T022W-S024R-N043R-R045T-S101A-G211Q, A098Q-S099G-S101G-V104L, G020K-N062E-G097A-S101Q-Q109G-N116L-S188D-L217Q, G020K-N062E-S078N-G097A-S101Q-Q109G-N116L, G020K-N062E-G097A-S101Q-Q109N-N116L-L217Q, N043R-S078N-G102A-S128L-L217E-S240R, S078N-G097S-S101Q, N043R-N062E-S078N-S101D-S128L-S240R, S128L-L217E-E271L, G020K-S024G-N062E-G097S-S101N-Q109N-N116L-S128A-L217Q, G020K-N062E-N116L-S128L-T213A, S078N-G097A-S101G-Q109G-S188D-L217Q, S101D-S128L-L217E-S240R, G020K-S024G-N062E-G097A-S101Q-Q109G-N116L-S128A, G020K-N062E-S078N-G097S-S101N-Q109N-N116L-S128A-S188D-L217Q, G020K-N062E-G097S-S101Q-Q109G-N116L-S128A-S188D-L217Q, G020K-S024G-N062E-S078N-G097S-S101N-Q109N-N116L-S128A, S024G-S078N-G097S-S101G-S128A-S188D-L217Q, S024G-S078N-G097A-S101N-Q109G-S128A-S188D-L217Q, G020K-N043R-G102A-S128L, G020K-S078N-S101D-G102A-L217E-S240R, G020K-N062E-G100S, S078N-S128L-L217E-E271L, S128Q-L217E-E271L, G020K-S024G-N062E-S078N-G097A-S101N-N116L-S128A-L217Q, G020K-S024G-N062E-S078N-G097S-S101G-N116L-S128A-L217Q, G020K-S078N-S101D-G102A-L217E, G020K-N062E-S128L, G020K-N062E-S078N-S101G-Q109N-N116L, G020K-S024G-N062E-S078N-G097S-S101Q-N116L-S128A-L217Q, S078N-S128L-L217E-S240R, S101D-S128Q-L217E-S240R-E271L, N043R-G102A-S240R, G020K-N062E-S078N-S101N-Q109N-N116L-M222S, G020K-N062E-S101N-Q109G-N116L-S128A-L217Q, G020K-S024G-N062E-S078N-G097A-S101G-N116L-L217Q, G020K-N062E-S101G-N116L-S188D, G020K-N062E-G097S-S101Q-Q109N-N116L-S128A-S188D, G020K-I035V-G100S-S128L-L217E, N043R-S101D-G102A-S240R, N062E-S078N-G100S, G020K-N043R-R062E-

A215T, N062E-S240R, N043R-S128L-L217E-S240R, N062E-S101D-S240R, G020K-S101D-N116L-T213A, G020K-S101D-N116L-S128Q-P210S-T213A, G020K-S101D-T213A, G020K-S024G-N062E-S078N-G097S-S101Q-Q109N-N116L-S128A, G020K-N062E-S078N-G097S-S101Q-N116L-S128A-L217Q, S024G-G097S-S101N-Q109G-S188D-L217Q, G020K-S024G-N062E-S101N-Q109G-N116L-L217Q, L217E-S240R, S101D-L217E-S240R-E271L, N043R-N062E-S101D-S128L-S240R, G097A-S101N-S128A-S188D-L217Q, G020K-N062E-S078N-S101N-N116L-S128A-L217Q, G020K-N062E-S078N-G097S-S101G-Q109N-N116L-L217Q, G020K-S024G-N062E-G097S-S101N-Q109G-N116L-S128A-L217Q, G020K-S024G-N062E-G097S-S101G-Q109G-N116L-S128A-S188D-L217Q, G020K-N062E-S101N-Q109N-N116L-S128A-S188D, S078N-G097S-S101N-Q109N-S128A-S188D-L217Q-W241L, G020K-N043R-N062E-S078N-S101D, G020K-N062E-S101D-S240R, G020K-S101D-S128Q, G020K-N116L-S128Q-Y209H-T213A, G020K-N043R-S078N-G100S-L217E-N218D, S024G-S101N-Q109G-S128A-S188D-L217Q, G020K-S024G-N062E-S078N-G097S-S101N-Q109G-N116L-S128A-S188D, S078N-S101N-Q109G-S188D-L217Q, G020K-S024G-N062E-S078N-G097S-S101N-Q109G-N116L-S188D-L217Q, G020K-N062E-S078N-S101Q-Q109N-N116L-S128A-S188D-L217Q, G020K-N062E-S101G-Q109G-N116L, G020K-S024G-N062E-G097S-S101N-Q109G-N116L-S128A-S188D-M222S, S024G-G097A-S101G-S188D-L217Q, S024G-S078N-G097A-S101G-S128A-S188D, G097S-S101N-Q109G-S128A-S188D, G020K-S078N-S101D-I246T, N043R-S128L-L217E, G020K-S101D-L217E-S240R, S128L-L217E-T224A-E271L, G020K-S078N-S101D-S128Q-L217E-E271L, N062E-S078N-S101D-L217E-S240R, G020K-S101D-L217E-E271L, G020K-S078N-S128Q-L217E-S240R, G020K-N062E-S101D-N116L-T213A, G100S-S101D, S078N-G097S-S101G-S128A-L217Q, G020K-N062E-G097S-S101N-N116L-S128A-L217Q, G020K-N062E-G097S-S101N-N116L-L217Q, S101N-Q109G-S188D, G020K-S024G-N062E-G097S-S101Q-Q109N-N116L-S128A-L217Q, G020K-S024G-N062E-G097S-S101N-N116L, G020K-S024G-N062E-S101N-N116L-S128A, G020K-S024G-N062E-S078N-S101Q-Q109N-N116L-S128A, G020K-N062E-S078N-S101N-Q109G-N116L-S188D, G020K-N062E-S078N-S101N-Q109G-N116L-S128A, G020K-S024G-N062E-S078N-G097S-S101N-Q109G-N116L-S128A-M222S, G020K-S024G-N062E-S078N-G097S-S101G-N116L-S128A, S024G-S078N-G097S-S101Q-Q109G-S128A-S188D-L217Q, S024G-S078N-S101G-Q109N-S188D-L217Q, S024G-S078N-G097A-S101G-Q109G-S188D, S078N-S101D-S128Q-L217E-S240R-E271L, G020K-S128Q-L217E, S128Q-L217E-S240R-E271L, G020K-S078N-S101D-L217E, G020K-S078N-S101D-L217E-E271L, G020K-N116L-S128Q-T213A, G020K-N116L-N123G, S101G-S188D-L217Q, G020K-S024G-N062E-S078N-S101G-N116L-L217Q, S078N-G097A-S101G-Q109N-S128A-S188D, G020K-S078N-S128L-L217E-E271L, G020K-N062E-S101Q-Q109G-N116L, G020K-S101D-L217E, S024G-G097A-S101N-Q109N-S128A, G020K-S078N-S101D-S128L-L217E-S240R, 0097A-S101G-L217Q, S024G-S101Q-Q109G-S128A-L217Q, G020K-S024G-N062E-T071A-S078N-G097S-S101G-N116L-L217Q, G020K-S024G-N062E-S078N-S101G-N116L-S128A, G020K-S024G-N062E-S078N-G097A-S101N-N116L, G020K-N062E-G097A-S101N-N116L, G020K-S024G-N062E-G097A-S101N-Q109G-N116L-S128A, G020K-S024G-N062E-S078N-G097S-S101G-Q109N-N116L, G020K-N062E-S078N-G097S-S101Q-Q109G-N116L-S128A-S188D-L217Q, G020K-N062E-S101N-Q109G-N116L-L217Q, G020K-S024G-N062E-G097A-S101N-Q109G-N116L-S188D-L217Q, G020K-S024G-N062E-S101G-N116L, S078N-G097S-S101N-Q109G-G159D-L217Q, S024G-G097A-S101N-Q109G-S188D, S078N-S101G-S128A-L217Q, S078N-G097A-S101N-S128A-S188D-L217Q, S024G-G097S-S101G-S128A-S188D-L217Q, S024G-S078N-G097S-S101Q-Q109G-S128A-S188D-L217Q-V227A, G020K-N062E-S078N, S078N-S128L-L217E-S240R-E271L, G020K-N062E-I072N-S101D-N116L-S128Q, G020K-T057P-N062E-N116L-S128Q-T213A, G020K-N043R-S078N-S101D-S240R, S078N-G097S-S101N-Q109N-S128A-S188D-L217Q, S024G-S101N-Q109N-S128A-S188D, G020K-S024G-N062E-G097S-S101Q-N116L-S128A, S024G-S078N-G097S-S101N-Q109N-S128A-S188D, N043R-G100S, G020K-N062E-S078N-S101Q-Q109G-N116L-S128A, S078N-S101Q-Q109N-S188D-L217Q, G020K-N116L-S128L-T213A, G020K-S078N-S101D-L217E-S240R, G020K-N062E-S101N-Q109N-N116L-M222S, G020K-S024G-N062E-G097A-S101Q-Q109N-N116L-S128A, S078N-G097S-S101G-S128A-S188D, G097S-S101G-Q109N-S128A-M222S, S024G-S078N-G097A-S101Q-S128A-M222S, G097A-S101G-Q109N-L217Q, S024G-S078N-S101G-S128A-S188D-L217Q, S024G-G097A-S101N-Q109G-S128A-S188D, G097S-S101N-Q109G-S128A, S078N-G097A-S101Q-L217Q, G020K-N043R-S078N-S101D, G020K-N043R-E054D-N062E-S078N-S240R, G020K-S101D-S240R, S128Q-L217E-S240R, G020K-S128Q-L217E-V244A-E271L, G020K-L217E-E271L, G020K-S078N-S128L-L217E, S078N-S101D-S128Q-L217E-E271L, G020K-N062E-L217E-E271L, G020K-N062E-S101D-N116L-S128Q-T213A, G020K-N062E-S078N-N116L-S128I, G020K-N062E-S078N-S128Q-T213A, S024G-G097A-S101G-Q109G-S128A, S024G-G097S-S101N-Q109N-S128A-L217Q, G020K-S024G-N062E-S078N-S101N-N116L-S128A-S188D-L217Q, G020K-S101D, G020K-N062E-S078N-G097S-S101Q-N116L-S128A, G020K-N062E-G097S-S101G-N116L-S188D, N043R-S078N-G100S-S128L-S240R, G097S-S101N-Q109N-S188D, G097S-S101Q-Q109N-S128A-L217Q, G020K-N062E-S101N-Q109G-N116L-S128A-S188D-M222S, G020K-S024G-N062E-S078N-G097S-S101Q-Q109G-N116L, G020K-N062E-M222S, G097S-S101Q-Q109G-S188D, G020K-S078N-L217E-S240R, G020K-N062E-S078N-G097A-S101N-Q109G-N116L-S188D, G020K-S024G-N062E-G097S-S101Q-Q109G-N116L-S188D, G020K-N062E-S078N-G097A-S101Q-N116L-S128A-M222S, G020K-N062E-S078N-S101N-N116L-S188D, G020K-S024G-N062E-S078N-S101G-N116L, G020K-N062E-S078N-S101N-N116L-S128A-S188D, G020K-S024G-N062E-G097S-S101N-Q109G-N116L-S128A-S188D-L217Q, G020K-N062E-G097S-S101N-Q109N-N116L, G020K-N062E-S101G-N116L-S188D-L217Q, G097A-S101N-S128A, S101G-Q109N-S128A-M222S, S024G-G097S-S101Q-Q109G-S188D-L217Q, G097S-S101Q-Q109N-S128A-S188D, S024G-S078N-G097A-S101Q-S188D-L217Q, S024G-S078N-S101G-Q109G-S128A-L217Q, G020K-N062E-S128L-S240R, N062E-S078N-S128L-S240R, N043R-G102A-S128L-L217E-S240R, N062E-S078N-L217E-S240R-E271L, S078N-S128Q-L217E-N269S, G020K-N062E-N123G-T213A, G020K-N062E-S078N-S099G-N116L-S128Q-T213A-L217N, G020K-N062E-S078N-S128I-L217N, G097A-S101Q-S128A-S188D-

L217Q, G020K-N062E-S078N-G097S-S101N-Q109G-N116L, G020K-S024G-N062E-S078N-G097S-S101N-Q109G-N116L-S188D, G020K-N043R-S128L-S240R, S024G-S078N-G097S-S101N-Q109N-S128A, G020K-N062E-G097S-S101Q-N116L-L217Q, G020K-N062E-S078N-S128I, G020K-S024G-N062E-L090V-G097A-S101Q-N116L-M222S, G020K-N062E-S078N-S101Q-Q109G-N116L-S188D-L217Q, G020K-S024G-N062E-G097A-S101G-N116L-S128A-S188D-L217Q, G020K-N062E-G097S-S101N-Q109N-N116L-S188D-L217Q, G020K-S024G-A048V-N062E-S078N-G097A-S101N-N116L-S128A-L217Q, G020K-N062E-S078N-S101Q-Q109G-N116L, G020K-S024G-N062E-G097S-S101N-Q109N-N116L-S128A, G020K-N062E-S078N-G097A-S101Q-Q109G-N116L-S188D, G020K-N062E-S078N-G097A-S101N-Q109N-N116L-N218D, S024G-S101N-Q109G-S128A-S188D-M222S, S024G-G097A-S101Q-Q109N-S188D-L217Q, S024G-S078N-G097S-S101Q-Q109N-S128A-S188D, S101N-Q109G-M222S, S024G-I072V-G097S-S101N-S128A-L217Q, S101G-S128A, N043R-S078N-G102A-A215G, G020K-S101D-S128L-L217E-S240R, S078N-S101D-S128Q-L217E-S240R, G020K-N116L-S128L-M222S, G020K-N062E-S078N-N116L-T213A-M222S, G020K-N062E-S078N-N116L-S128Q, G020K-N062E-T213A, or G020K-N062E-S078N-N116L-N123G-M222S (List 15), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides an isolated subtilisin variant, wherein said subtilisin variant is a mature form having proteolytic activity and comprises an amino acid sequence comprising a combination of amino acid substitutions at positions selected from T022A-S024G-N076D-G097S-S101G-S103A-V104I-G159D-S188D-L217Q-A232V-Q245R-N248D-E271F, G020K-T022L-S078N-G118R-S128D-T213A, S024R-S078G-G118S-P129E-S188D-Q245R-H249R, T022A-N076D-S101G-S103A-V104I-G159D-S188D-L217Q-A232V-Q245R-N248D-E271F, T022A-S101G-S103A-V104I-S128A-G159D-S188D-L217Q-A232V-Q245R-N248D-E271F, T022A-S024G-G097S-S101Q-S103A-V104I-Q109G-G159D-S188D-A232V-Q245R-N248D-E271F, T022A-N076D-S101N-S103A-V104I-G159D-S188D-A232V-Q245R-N248D-E271F, T033S-G118R-S128I-A158E, T022A-S103A-L111V-L148I, T022A-N076D-A085T-S101G-S103A-V104I-P129E-S188D-A232V-Q245R-N248D-E271F, T022A-S024R-N076D-S101G-S103A-V104I-A158E-S188D-A232V-Q245R-N248D-E271F, G020K-T022L-S078N-S128D-T213A-L217E, T022A-T033S-P129E-S166D, T022A-S024G-N076D-G097A-S101Q-S103A-V104I-G159D-S188D-L217Q-A232V-Q245R-N248D-E271F, T022A-G097A-S101N-S103A-V104I-Q109G-G159D-S188D-L217Q-A232V-Q245R-N248D-E271F, G020K-S078N-S166D-T213A, T022A-S101Q-S103A-V104I-L124V-P129S-G159D-S188D-A232V-Q245R-N248D-E271F, T022Q-S101G-S103A-V104I-G159D-S188E-A232V-Q245T-N248D, A158E-S166D-S188D, L021S-T022A-S024G-N076D-S101Q-S103A-V104I-S128A-G159D-S188D-L217Q-A232V-Q245R-N248D-E271F, T022A-G097A-S101N-S103A-V104I-L124V-S128A-P129E-G159D-S188D-L217Q-A232V-Q245R-N248D-E271F, T022A-S101G-S103A-V104I-G159D-S188D-A232V-N238Y-Q245R-N248D-A270V-E271F, T022A-T033S-N062E-N116L-S188D, T022A-S024G-S049N-N076D-S101G-S103A-V104I-G159D-S188D-L217Q-A232V-Q245R-N248D-E271F, T022A-G097S-S101Q-S103A-V104I-G159D-S188D-A232V-Q245R-N248D-E271F, G097P-A098Q-S099A-S103G-V104I, G020K-S024F-G118R-S128D-S166D, T022A-S024G-S101G-S103A-V104I-S128A-G159D-S188D-A232V-Q245R-N248D-E271F, T022A-S024R-T033S-G118R-S166D, T022A-S024R-N076D-S101G-S103A-V104I-G159D-S188D-A232V-N238Y-Q245R-N248D-A270V-E271F, N062E-S078D-G118S-P129E-N248D-H249R, T022A-S024G-V026I-S101N-S103A-V104I-G159D-S188D-L217Q-A232V-Q245R-N248D-E271F, G097P-A098Q-S099A-S101A, S078G-G118D-P129E-S188D-Q245R-H249R, T022A-G097A-S101N-S103A-V104I-L126I-P129E-G159D-S188D-L217Q-A232V-Q245R-N248D-E271F, G020R-S024R-N062E-S078G-G118D-P129E-G159D-S188D-Q236R-Q245R-N248D, T022A-N076D-S078N-S101N-S103A-V104I-G159D-S188D-A232V-Q245R-N248D-E271F, T022A-N076D-S101G-S103A-V104I-P129E-G159D-S188D-A232V-N238Y-Q245R-N248D-E271F-A272V, T022A-N076D-N077D-S078N-G097S-S101N-S103A-V104I-S128A-G159D-S188D-A232V-Q245R-N248D-E271F, T022A-N043R-N076D-S101G-S103A-V104I-P129E-A158E-S188D-A232V-Q245R-N248D-A270V-E271F, S099G-S101A-G102A-S103A, T022A-S024G-G097A-S101N-S103A-V104I-Q109G-G159D-S188D-L217Q-A232V-Q245R-N248D-E271F, G020R-S024R-S078D-G118S-P129E-Q245R, S056C, S024R-T033S-N062E-N116L, T022A-S024G-N076D-S101G-S103A-V104I-G159D-S188D-L217Q-A232V-Q245R-N248D-E271F, T033S-S101G-S103A-V104I-N116L-S128N-Y209A-T213A-A232V, A098Q-S099A-G100S-S101G-V104I, T022A-S078N-S101N-S103A-V104I-Q109G-S128A-G159D-S188D-L217Q-A232V-Q245R-N248D-E271F, T022A-S024R-N076D-S101G-S103A-V104I-G159D-S188D-Q245R-N248D-A270V-E271F-A272V, T022A-N076D-G097S-S101Q-S103A-V104I-S128A-G159D-S188D-A232V-Q245R-N248D-E271F, T022A-S024G-S078N-S101N-S103A-V104I-Q109N-S128A-G159D-S188D-A232V-Q245R-N248D-E271F, T022A-L090I-S101G-S103A-V104I-S128A-G159D-S188D-L217Q-A232V-Q245R-N248D-E271F, G020R-N062E-S078G-G118D-P129E-G159D-S188D-N248D-H249R, A016S-T033S-S101G-S103A-V104I-N116L-S128N-Y209V-T213A-A232V, G020R-S078G-G118D-N248D-H249R, T022A-N062Q-S101G-S103A-V104I-G159D-S188D-A232V-Q245R-N248D-E271F, S024R-N062E-N116L-A158E-S166D-S188D, T022A-S024G-N076D-S101Q-S103A-V104I-G159D-S188D-L217Q-A232V-Q245R-N248D-E271F, T022A-S024R-S101G-S103A-V104I-G159D-S188D-A232V-Q245R-N248D-A270V-E271F, T022A-N062Q-S101G-S103A-V104I-P129E-G159D-S188D-A232V-Q245R-N248D-E271F, T022A-N076D-S101N-S103A-V104I-Q109G-G159D-S188D-L217Q-A232V-Q245R-N248D-E271F, T022A-S101G-S103A-V104I-P129E-S188D-A232V-Q245R-N248D-E271F, T022A-S024G-N076D-S078N-G097A-S101N-S103A-V104I-G159D-S188D-A232V-Q245R-N248D-E271F, T022A-S024R-N076D-S101G-S103A-V104I-I107V-G159D-S188D-A232V-Q245R-N248D-E271F, T022A-S024R-N116L-G118R, T022A-S024R-T033S-N062E-N116L-G118R-S128I-A158E-S188D, T022A-N076D-G097S-S101N-S103A-V104I-Q109G-S128A-G159D-S188D-A232V-Q245R-N248D-E271F, T022A-S024G-N076D-G097S-S101Q-S103A-V104I-S128A-G159D-S188D-A232V-Q245R-N248D-E271F, S024R-T033S-N062E-N116L-S128I-S188D, T022A-S024G-N076D-G097S-S101N-

S103A-V104I-G159D-S188D-A232V-Q245R-N248D-E271F, S240V, N062E-G118R, T022A-S101G-S103A-V104I-G159D-S188E-A232V-Q245T-N248E, S024R-N062E-S078G-G118D-P129E-S188D-Q245R-N248D, A016S-S103A-V104I, A088P, T022A-S101N-S103A-V104I-Q109N-G159D-S188D-L217Q-A232V-Q245R-N248D-E271F, T022A-S101N-S103A-V104I-L126I-G159D-S188D-L217Q-A232V-Q245R-N248D-E271F, G097P-A098F-V104L, T022A-G097S-S101N-S103A-V104I-S128A-G159D-S188D-A232V-Q245R-N248D-E271F, T022A-G097A-S101N-S103A-V104I-Q109N-G159D-S188D-L217Q-A232V-Q245R-N248D-E271F, G020K-T022L-S128D, T022A-S024G-S101G-S103A-V104I-G159D-S188D-L217Q-A232V-Q245R-N248D-E271F, G020R-S024R-N062E-S078D-G118D-P129E-G159D-S188D-N248D-H249R, S024F-S078N-G118R-L217E, T022A-S024G-S078N-G097S-S101Q-S103A-V104I-S128A-G159D-S188D-A232V-Q245R-N248D-E271F, T022A-S024R-S101G-S103A-V104I-A158E-G159E-S188D-A232V-Q245R-N248D-E271F-A272V, S024R-N062E-N116L-G118R-S128I-S188D, G118R-S128D-S166D-T213A, T022A-G097A-S101G-S103A-V104I-P129E-G159D-S188D-A232V-Q245R-N248D-E271F, T022A-T033S-S101G-S103A-V104I-N116L-S128L-G159D-S188D-A232V-Q245R-N248D-E271F, T022A-S078N-S101Q-S103A-V104I-Q109G-S128A-G159D-S188D-L217Q-A232V-Q245R-N248D-E271F, T022A-G097S-S101N-S103A-V104I-Q109G-S128A-G159D-S188D-L217Q-A232V-Q245R-N248D-E271F, T022A-S024G-G097S-S101N-S103A-V104I-Q109N-S128A-G159D-S188D-A232V-Q245R-N248D-E271F, T022A-N076D-G097A-S101N-S103A-V104I-G159D-S188D-A232V-Q245R-N248D-E271F, T022A-S101G-S103A-V104I-L126I-S128A-G159D-S188D-A232V-Q245R-N248D-E271F, G020R-S078G-G118S-S188D-H249R, T022A-S024G-N076D-S101Q-S103A-V104I-G159D-S188D-A232V-Q245R-N248D-E271F, T022A-S101A-S103A, T022A-N076D-S101G-S103A-V104I-P129E-G159E-S188D-A232V-Q245R-N248D, S024R-S078D-G118D-S188D-N248D-H249R, S099A-V104I, T022A-G097S-S101Q-S103A-V104I-Q109N-G159D-S188D-L217Q-A232V-Q245R-N248D-E271F, S024R-S078G-G118D-G159D-N248D, T022A-S024G-S078N-S101Q-S103A-V104I-S128A-G159D-S188D-A232V-Q245R-N248D-E271F, T022A-N076D-S101G-S103A-V104I-P129E-G159E-S188D-A232V-Q245R-N248D-E271F, T022A-G097A-S101Q-S103A-V104I-L124V-S128A-P129E-G159D-S188D-A232V-Q245R-N248D-E271F, T022A-G097A-S101Q-S103A-V104I-L124V-G159D-S188D-A232V-Q245R-N248D-E271F, S078G-G118D-P129E, S212W, T022A-S101G-S103A-V104I-I107V-P129E-G159D-S188D-A232V-N238Y-Q245R-N248D-A270V-E271F-A272V, T022A-S078N-S101Q-S103A-V104I-G159D-S188D-A232V-Q245R-N248D-E271F, T022A-G097A-S101G-S103A-V104I-S128A-G159D-S188D-L217Q-A232V-Q245R-N248D-E271F, S101G-V104L, T022A-S101G-S103A-V104I-I107V-P129E-G159D-S188D-A232V-N238Y-Q245R-N248D-E271F, T022A-S024R-S101G-S103A-V104I-P129E-G159D-S188D-A232V-Q245R-N248D-E271F-A272V, T022A-S024G-G097A-S101Q-S103A-V104I-Q109N-S128A-G159D-S188D-L217Q-A232V-Q245R-N248D-E271F, T022A-S024G-N076D-S101G-S103A-V104I-G159D-S188D-A232V-Q245R-N248D-E271F, T022A-S024R-N076D-S101G-S103A-V104I-P129E-A158E-S188D-A232V-Q245R-N248D-E271F-A272V, T022A-T033S-S101G-S103A-V104I-N116L-N117S-Y209A-G211Q-T213A-A232V, S101G-S103A-V104I-N116L-G118V-Y209A-G211Q-A232V, T022A-N062E-S101N-S103A-V104I-S128A-G159D-S188D-A232V-Q245R-N248D-E271F, T022A-S024G-G097S-S101N-S103A-V104I-S128A-G159D-S188D-L217Q-A232V-Q245R-N248D-E271F, S024F-T213A, T022A-S024G-N076D-S101N-S103A-V104I-G159D-S188D-A232V-Q245R-N248D-E271F, T022A-N076D-S101Q-S103A-V104I-Q109G-S128A-G159D-S188D-L217Q-A232V-Q245R-N248D-E271F, T022A-S078N-G097A-S099G-S101G-S103A-V104I-S128A-G159D-S188D-A232V-Q245R-N248D-E271F, T022A-N076D-S101G-S103A-V104I-G159D-S188D-L217Q-N218S-A232V-Q245R-N248D-E271F, T022A-S024G-N076D-S101N-S103A-V104I-Q109G-G159D-S188D-L217Q-A232V-Q245R-N248D-E271F, T022A-S024G-S101N-S103A-V104I-Q109N-G159D-S188D-A232V-Q245R-N248D-E271F, G020R-S024R-S078D-G118D-Q245R, T022A-S078N-I079V-S101N-S103A-V104I-G159D-S188D-L217Q-A232V-Q245R-N248D-E271F, T022A-S024R-N116L-G118R-S128I-A158E-S166D, S078G-G118D-S188D, G097P-A098Q-S099G-G102A, S099A-S103G, S078D-G118D-P129E-Q245R-N248D, T022A-S024G-S078N-S101Q-S103A-V104I-G159D-S188D-L217Q-A232V-Q245R-N248D-E271F, T022A-S078N-S101N-S103A-V104I-Q109G-G159D-S188D-L217Q-A232V-Q245R-N248D-E271F, T022A-N076D-S078N-G097S-S101Q-S103A-V104I-G159D-S188D-L217Q-A232V-Q245R-N248D-E271F, T022A-S024R-N116L-S128I-A158E-S166D-S188D, A016S-T022A-S101A-S103G-V104I, T022A-G097S-S101N-S103A-V104I-S128A-G159D-R186H-S188D-A232V-Q245R-N248D-E271F, T022A-G097A-S101Q-S103A-V104I-G159D-S188D-L217Q-A232V-Q245R-N248D-E271F, T022A-S101N-S103A-V104I-L126I-S128A-G159D-S188D-A232V-Q245R-N248D-E271F, T022A-S101Q-S103A-V104I-L126I-G159D-S188D-A232V-Q245R-N248D-E271F, T022A-N076D-G097S-S101N-S103A-V104I-G159D-S188D-A232V-Q245R-N248D-E271F, T022A-N043R-N076D-S101G-S103A-V104I-P129E-S188D-A232V-Q245R-N248D-E271F-A272V, T022A-S024R-T033S-N062E-N116L-S128I-S188D, T022A-S024G-S078N-G097S-S101G-S103A-V104I-S128A-G159D-S188D-L217Q-A232V-Q245R-N248D-E271F, T022L-S078N-G118R-S128D-T213A, T022A-N076D-G097A-A098T-S101Q-S103A-V104I-G159D-S188D-L217Q-A232V-Q245R-N248D-E271F, T022A-S024G-S078N-G097A-S101Q-S103A-V104I-S128A-G159D-S188D-A232V-Q245R-N248D-E271F, S103A-V104L, S024R-S078G-G118D-P129E-G159D-S188D-N248D, T022A-S024R-N043R-S101G-S103A-V104I-S188D-A232V-Q245R-N248D-E271F, T022A-S024R-G061W-N076D-S101G-S103A-V104I-P129E-S188D-A232V-Q245R-N248D-E271F, G020R-N062E-S078D-G118S-S188D-N248D, T022A-S101G-S103A-V104I-A158E-G159E-S188D-A232V-Q245R-N248D-E271F, G100S-V104I, T022A-S024G-N076D-S078N-G097S-S101N-S103A-V104I-G159D-S188D-L217Q-A232V-Q245R-N248D-E271F, G097P-A098F-S103A, T022A-G097S-S101Q-S103A-V104I-Q109G-G159D-S188D-A232V-Q245R-N248D-E271F, S024F-S078N-G118R-S128D-L217E, T022A-S101Q-S103A-V104I-Q109G-S128A-G159D-S188D-L217Q-A232V-Q245R-N248D-E271F, S024R-T033S-N116L-S128I-A158E-S166D, T022L-S024F-S128D, T022A-S101G-S103A-V104L, T022A-N043R-S101G-S103A-V104I-A158E-G159E-S188D-A232V-Q245R-N248D-E271F-A272V, T022A-N076D-S101G-S103A-V104I-I107V-

G159D-S188D-A232V-Q245R-N248D-E271F, T022L-S024F-S078N, T022A-N062E-A158E-S188D, G020K-T022L-S166D-T213A, T022A-S024G-T071A-S078N-S101N-S103A-V104I-G159D-S188D-A232V-Q245R-N248D-E271F, A016S-T022A-S101G-S103A-V104I-L148I, S078D-G118S-S188D-Q245R-N248D-H249R, G020K-T022L-S128D-S166D, T022A-S024G-N076D-G097S-S101N-S103A-V104I-Q109N-S128A-G159D-S188D-A232V-Q245R-N248D-E271F, T022A-N062E-S101G-S103A-V104I-P129E-S188D-A232V-Q245R-N248D-E271F, G020R-N062E-S078G-G118D-P129E-Q245R-H249R, G020R-S078G-G118D-P129E-S188D-N248D, G020K-T022L-S024F-S078N-G118R-S128D-S166D, T022A-N076D-S101G-S103A-V104I-P129E-S188D-A232V-Q245R-N248D-E271F, T022A-S101Q-S103A-V104I-L126I-P129E-G159D-S188D-L217Q-A232V-Q245R-N248D-E271F, T255G, T022A-G097A-S101N-S103A-V104I-L126I-S128A-P129E-G159D-S188D-A232V-Q245R-N248D-E271F, T022A-S024R-N076D-S101G-S103A-V104I-P129E-G159D-S188D-A232V-N238Y-Q245R-N248D-E271F, S024R-T033S-N062E-G118R-S166D-S188D, T022A-G097A-S101Q-S103A-V104I-S128A-P129S-G159D-S188D-A232V-Q245R-N248D-E271F, S024R-N062E-S078D-G118S-P129E-G159D-S188D-Q245R-H249R, T022A-S024G-S101Q-S103A-V104I-Q109N-G159D-S188D-L217Q-A232V-Q245R-N248D-E271F, A098Q-G102A, T022A-S024R-S101G-S103A-V104I-I107V-P129E-G159D-S188D-A232V-N238Y-Q245R-N248D-A270V-E271F, T022A-S024G-S078N-G097A-S101N-S103A-V104I-G159D-S188D-A232V-Q245R-N248D-E271F, T022A-S024G-S078N-S101N-S103A-V104I-Q109G-G159D-S188D-A232V-Q245R-N248D-E271F, S024R-N116L, T022A-S101G-S103A-V104I-L126I-P129E-G159D-S188D-L217Q-A232V-Q245R-N248D-E271F, G020K-S078N-S128D, T022A-S024G-S101N-S103A-V104I-S128A-G159D-S188D-A232V-Q245R-N248D-E271F, T022A-S024G-S078N-S101Q-S103A-V104I-S128A-G159D-S188D-T213A-L217Q-A232V-Q245R-N248D-E271F, T022A-S024G-S101N-S103A-V104I-G159D-S188D-A232V-Q245R-N248D-E271F, T022A-S101N-S103A-V104I-L126I-P129E-G159D-S188D-L217Q-A232V-Q245R-N248D-E271F, T022A-S024G-N076D-G097A-S101N-S103A-V104I-G159D-S188D-A232V-Q245R-N248D-E271F, T022A-S024G-N076D-S078N-G097A-S101G-S103A-V104I-G159D-S188D-A232V-Q245R-N248D-E271F, S024R-T033S-N062E-N116L-S166D, T022A-S024G-N076D-S101N-S103A-V104I-Q109G-S128A-G159D-S188D-A232V-Q245R-N248D-E271F, A016S-S024F-S101G-S103A-V104I-N116L-Y209V-A232V, G020K-S024F-S078N-S128D-S166D, G025A, T022A-S024R-N076D-S101G-S103A-V104I-G159D-S188D-A232V-N238Y-Q245R-N248D-E271F, G097P-S099T-V104I, T022A-N076D-S078N-G097A-S101N-S103A-V104I-Q109G-G159D-S188D-A232V-Q245R-N248D-E271F, G020R-S024R-S078G-G118S-G159D-Q245R-N248D-H249R, T022A-S024G-S078N-S101Q-S103A-V104I-Q109G-G159D-S188D-L217Q-A232V-Q245R-N248D-E271F, T022A-S024G-N076D-G097A-S101Q-S103A-V104I-S128A-G159D-S188D-A232V-Q245R-N248D-E271F, T022A-N076D-S078N-G097S-S101N-S103A-V104I-G159D-S188D-A232V-Q245R-N248D-E271F, T022A-S078N-G097S-S101G-S103A-V104I-S128A-G159D-S188D-A232V-Q245R-N248D-E271F, T022A-S078N-G097S-S101Q-S103A-V104I-G159D-S188D-A232V-Q245R-N248D-E271F, D041K, T022A-S024G-G097A-S101G-S103A-V104I-S128A-G159D-S188D-A232V-Q245R-N248D-E271F, T022A-S024G-G097S-S101N-S103A-V104I-G159D-S188D-A232V-Q245R-N248D-E271F, A016S-T022A-S101A-V104I-L111V-L148I, A016S-T022A-S101A-V104L-L111V, T022A-S024G-G097S-S101Q-S103A-V104I-Q109N-G159D-S188D-A232V-Q245R-N248D-E271F, S078G-G118S-S188D-N248D, G020K-T022L-S024F-S078N-S128D, G020K-T022L-S024F-G118R-S128D-T213A, T022A-S024G-G097S-S101N-S103A-V104I-S128A-G159D-S188D-A232V-Q245R-N248D-E271F, S024F-S128D, T022A-N043R-N076D-S101G-S103A-V104I-A158E-G159E-S188D-A232V-Q245R-N248D-E271F, T022A-N076D-S101G-S103A-V104I-P129E-G159D-S188D-A232V-N238Y-Q245R-N248D-A270V-E271F-A272V, T022A-S101Q-S103A-V104I-L126I-G159D-S188D-L217Q-A232V-Q245R-N248D-E271F, T022A-S101G-S103A-V104I-P129E-G159D-S188D-A232V-N238Y-Q245R-N248D-A270V-E271F, T022A-S101G-S103A-V104I-G159D-S188D-A232V-Q245R-N248D-A270V-E271F-A272V-T274A, T022A-S101N-S103A-V104I-Q109G-G159D-S188D-L217Q-A232V-Q245R-N248D-E271F, G020K-T022L-N062E-S078D-G118S-N248D, T022A-S024R-N076D-S101G-S103A-V104I-I107V-G159D-S188D-A232V-N238Y-Q245R-N248D-A270V-E271F, A016S-T022A-S101G-S103A-V104I-N116A-Y209V-T213A-A232V, T022A-S101N-S103A-V104I-L126I-P129S-G159D-S188D-L217Q-A232V-Q245R-N248D-E271F, T022A-S024G-N076D-S078N-G097A-S101Q-S103A-V104I-Q109G-G159D-S188D-L217Q-A232V-Q245R-N248D-E271F, T022A-N062E-N116L, T033S-S101G-S103A-V104I-N116A-S128N-Y209A-T213A-A232V, T022A-S101N-S103A-V104I-L126I-P129E-G159D-S188D-A232V-Q245R-N248D-E271F, T022A-S024R-S101G-S103A-V104I-I107V-G159D-S188D-A232V-Q245R-N248D-A270V-E271F, T022A-N043R-N076D-S101G-S103A-V104I-P129E-G159E-S188D-A232V-Q245R-N248D-E271F, G020R-S024R-S078D-G118D-P129E-G159D-N248D, T022A-S101G-S103A-V104I-L124V-S128A-P129E-G159D-S188D-L217Q-A232V-Q245R-N248D-E271F, T022A-S024G-S101Q-S103A-V104I-S128A-G159D-S188D-A232V-Q245R-N248D-E271F, T022A-S024R-N076D-S101G-S103A-V104I-A232V-Q245R-A270V, T022A-S101G-S103A-V104I-P129E-S188D-A232V-Q245R-N248D-E271F-A272V, T022A-N076D-S078N-G097S-S101Q-S103A-V104I-S128A-G159D-S188D-A232V-Q245R-N248D-E271F, T022A-G097A-S101Q-S103A-V104I-L126I-P129E-G159D-S188D-A232V-Q245R-N248D-E271F, T022A-G097A-S101G-S103A-V104I-G159D-S188D-A232V-Q245R-N248D-E271F, A098F-S099T-G102A, T022A-S101G-S103A-V104I-G159D-S188E-A232V-Q245T-N248D, D041L, S024R-N062E-S128I-A158E-S188D, N062E-S078D-G118D-N248D-H249R, G020K-S024F-G118R-T213A, S101G-S103G-V104I-S128N, S078N-G118R-S128D-T213A-L217E, T022A-N076D-S101G-S103A-V104I-Q109N-G159D-S188D-A232V-Q245R-N248D-E271F, T022A-N076D-G097S-S103A-V104I-Q109N-G159D-S188D-A232V-Q245R-N248D-E271F, S078G-G118S-G159D-N248D, T033S-A158E, T022A-S101G-S103A-V104I-I107V-G159D-S188D-A232V-Q245R-N248D-E271F-A272V, T022A-S101G-S103A-V104I-A158E-G159E-S188D-A232V-Q245R-N248D-E271F-A272V, T022A-S024R-T033S-S128I-S166D-S188D, T022A-N076D-S101G-S103A-V104I-A158E-G159E-S188D-A232V-Q245R-N248D-E271F, T022A-S024G-S078N-G097S-S101Q-S103A-V104I-Q109G-G159D-S188D-

A232V-Q245R-N248D-E271F, T022A-S024R-N076S-S101G-S103A-V104I-G159D-S188D-A232V-Q245R-N248D-E271F-A272V, S024R-G118R-S128I-S166D, T033S-N116L-G118R-S128I-S188D, T022A-S101G-S103A-V104I-G159D-S188D-A232V-N238Y-Q245R-N248D-E271F-A272V, T022A-S024R-T033S-N116L-G118R-V139I-S188D, T022A-S024R-N076D-S101G-S103A-V104I-P129E-A158E-G159E-S188D-A232V-Q245R-N248D-E271F, N062E-S078G-G118S-P129E-G159D-S188D-Q245R-N248D, T022A-S024G-S078N-G097A-S101N-S103A-V104I-Q109G-S128A-G159D-S188D-L217Q-A232V-Q245R-N248D-E271F, T022A-N062Q-S101Q-S103A-V104I-S128A-G159D-S188D-L217Q-A232V-Q245R-N248D-E271F, T022A-S024G-G097A-S101G-S103A-V104I-G159D-S188D-L217Q-A232V-Q245R-N248D-E271F, A016S-T022A-S024F-S101G-S103A-V104I-N116L-S128N-Y209A-T213A-A232V, T022A-G097A-S101Q-S103A-V104I-L124V-S128A-P129E-G159D-S188D-L217Q-A232V-Q245R-N248D-E271F, S024R-N062E-N116L-G118R-S128I-S166D-S188D, T022A-S024R-T033S-N116L-G118R-S128I-A158E-S166D, A108V-S128D-T213A, T022A-N043R-N076D-S101G-S103A-V104I-A158E-S188D-A232V-Q245R-N248D-E271F-A272V, T022A-S101G-S103A-V104I-I107V-G159D-S188D-A232V-Q245R-N248D-A270V-E271F, T022A-N076D-S101G-S103A-V104I-A158E-G159E-S188D-A232V-Q245R-N248D-E271F-A272V, T033S-S101G-S103A-V104I-N116L-S128N-Y209A-A232V, S024F-T033S-S101G-S103A-V104I-I107V-N116A-Y209V-T213A-A232V, T022A-S024G-G097S-S101N-S103A-V104I-Q109N-G159D-S188D-A232V-Q245R-N248D-E271F, S024R-T033S-N116L-S128I-S166D-S188D, T022A-S024R-N076D-S101G-S103A-V104I-G159D-S188D-A232V-N238Y-Q245R-N248D-E271F-A272V, T022A-G097A-S101Q-S103A-V104I-L126I-S128A-P129E-G159D-S188D-A232V-Q245R-N248D-E271F, T022A-S078N-G097A-S101Q-S103A-V104I-Q109G-G159D-S188D-A232V-Q245R-N248D-E271F, A098Q-S099G-G102A, T022A-S024G-G097A-S101G-S103A-V104I-P129E-G159D-S188D-A232V-Q245R-N248D-E271F, T022A-S024G-S101N-S103A-V104I-Q109G-G159D-S188D-A232V-Q245R-N248D-E271F, T022A-G097S-S101Q-S103A-V104I-S128A-G159D-S188D-L217Q-A232V-Q245R-N248D-E271F, T022A-S024R-S101G-S103A-V104I-I107V-G159D-S188D-A232V-Q245R-N248D-E271F, T022L-G118R-S166D, V011M-S024R-T033S-S128I-S166D, G020K-S078N-S128D-L217E, V004M, N062E-N116L-G118R-S128I-S166D, T022A-G097A-S101N-S103A-V104I-Q109G-S128A-G159D-S188D-L217Q-A232V-Q245R-N248D-E271F, G020R-S024R-N062E-S078G-G118S-P129E-Q245R-N248D-H249R, T022A-S101G-S103A-V104I-P129E-G159D-S188D-A232V-N238Y-Q245R-N248D-E271F, T022A-S101N-S103A-V104I-G159D-S188D-A232V-Q245R-N248D-E271F, T022A-T033S-N116L-S166D-S188D, T022A-S078N-G097S-S101Q-S103A-V104I-S128A-G159D-S188D-A232V-Q245R-N248D-E271F, T022A-N076D-S078N-G097S-S101N-S103A-V104I-Q109G-S128A-G159D-S188D-A232V-Q245R-N248D-E271F, G118R-T213A, T022A-S101N-S103A-V104I-L126I-G159D-S188D-A232V-Q245R-N248D-E271F, S024R-N116L-S188D, T022Q-S101G-S103A-V104I-G159D-S188E-A232V-Q245V-N248E, T022A-S024G-N076D-G097S-S101Q-S103A-V104I-G159D-S188D-A232V-Q245R-N248D-E271F, T022A-T033S-S101G-S103A-V104I-N116L-G159D-S188D-A232V-Q245R-N248D-E271F, G097P-S099T-S101A-V104L, T022A-N076D-S101G-S103A-V104I-P129E-G159D-S188D-A232V-N238Y-Q245R-N248D-A270V-E271F, T022A-S024G-G097A-S101N-S103A-V104I-G159D-S188D-A232V-Q245R-N248D-E271F, T022A-N043R-N076D-S101G-S103A-V104I-S188D-A232V-Q245R-N248D-E271F-A272V, G020R-S024R-S078G-G118D-G159D-Q245R-N248D-H249R, T022A-S101G-S103A-V104I-G159D-S188D-A232V-N238Y-Q245R-N248D-E271F, L021F-T022A-S024G-S078N-S101Q-S103A-V104I-G159D-S188D-L217Q-A232V-Q245R-N248D-E271F, N062E-S078G-G118D-G159D-S188D-Q245R-N248D, A098Q-S101A-S103A-V104L, T022A-S024G-S078N-S101Q-S103A-V104I-G159D-S188D-A232V-Q245R-N248D-E271F, N062E-G118R-A158E-S166D-S188D, T022A-S024G-S078N-S101Q-S103A-V104I-Q109N-G159D-S188D-L217Q-A232V-Q245R-N248D-E271F, N116L-S128I, T022A-N062E-S128I, T022A-S024R-T033S-N116L-S128I-A158E-S188D, T022A-S101G-S103A-V104I-L124V-S128A-G159D-S188D-L217Q-A232V-Q245R-N248D-E271F, T033S-N116L-A158E-S166D-S188D, T022A-N076D-S078N-G097A-S101N-S103A-V104I-S128A-G159D-S188D-L217Q-A232V-Q245R-N248D-E271F, T022A-S024R-N043R-S101G-S103A-V104I-A158E-S188D-A232V-Q245R-N248D-E271F, T022L-S078N-G118R-S128D-T213A-L217E, A016S-T033S-S101G-S103A-V104I-N116L-S128N-Y209A-G211Q-A232V, T022A-N043R-N076D-S101G-S103A-V104I-P129E-S188D-A232V-Q245R-N248D-E271F, T022A-N076D-S101G-S103A-V104I-P129E-A158E-G159E-S188D-A232V-Q245R-N248D-E271F-A272V, T022A-S024G-G097A-S101N-S103A-V104I-S128A-G159D-S188D-L217Q-A232V-Q245R-N248D-E271F, G020K-T022L-S024F-G118R-S128D-S166D-L217E, N062E-G118R-S128I-A158E-S188D, T022A-S024F-N043R-N076D-S101G-S103A-V104I-A158E-S188D-A232V-Q245R-N248D-E271F-A272V, T022A-S024G-N076D-S078N-S101N-S103A-V104I-G159D-S188D-L217Q-A232V-Q245R-N248D-E271F, G097P-A098Q-S099T-S103G, G097P-A098Q-S099T-S103A-V104I, N062E-S078D-G118S-S188D, T022A-N043R-N076D-S101G-S103A-V104I-P129E-A158E-S188D-A232V-Q245R-N248D-E271F-A272V, T134C, G020R-N062E-S078D-G118S-P129E-N248D, S101G-S103A-V104I-N116L-G118V-Y209A-G211Q-T213A-A232V, A016S-S101G-S103A, A016S-S103G-V104I-L111V, A098F-G100S, S101A-S103A-V104I-A232V-Q245R, T022A-G097A-S101N-S103A-V104I-L126I-S128A-G159D-S188D-A232V-Q245R-N248D-E271F, S078G-G118S-N248D-H249R, T022L-S078N-A122V-S128D, T022A-S101Q-S103A-V104I-L124V-S128A-G159D-S188D-L217Q-A232V-Q245R-N248D-E271F, T022A-G097A-S101Q-S103A-V104I-L126I-S128A-G159D-S188D-A232V-Q245R-N248D-E271F, S024F-S078N, A016S-S101G-V104I-L111V-S128N, A016S-S024F-S101G-S103A-V104I-N116L-G118V-Y209A-A232V, G097P-S099G-G100S, A098Q-S099G-G100S-V104L, S024R-S078D-G118S-L126I-P129E-N248D-H249R, T022A-S101N-S103A-V104I-Q109G-S128A-G159D-S188D-A232V-Q245R-N248D-E271F, G097P-A098Q-S103A, S099A-S101A-S103A, A016S-T022A-S101G-S103G-V104I-S128N, T022A-N076D-S101N-S103A-V104I-Q109G-S128A-G159D-S188D-L217Q-A232V-Q245R-N248D-E271F, T022A-S024G-N076D-S078N-G097A-S101N-S103A-V104I-S128A-G159D-S188D-A232V-Q245R-N248D-E271F, G020K-S024F-G118R-S166D-T213A, T022A-N076D-S078N-G097A-S101N-S103A-V104I-G159D-

S188D-L217Q-A232V-Q245R-N248D-E271F, N116L-S128I-S166D, T022A-N043R-S101G-S103A-V104I-P129E-A158E-G159E-S160P-S188D-A232V-Q245R-N248D-E271F, T033S-N116L-G118R-S128I-A158E-S166D-S188D, T022A-S024G-G097S-S101Q-S103A-V104I-Q109N-G159D-S188D-L217Q-A232V-Q245R-N248D-E271F, T022A-N043R-N076D-S101G-S103A-V104I-S188D-A232V-Q245R-N248D-E271F, T022A-S024G-N076D-S078N-G097S-S101Q-S103A-V104I-S128A-G159D-S188D-L217Q-A232V-Q245R-N248D-E271F, T022A-S024R-N043R-N076D-S101G-S103A-V104I-S188D-A232V-Q245R-N248D-E271F, R019S-T022A-S024R-N076D-S101G-S103A-V104I-G159D-S188D-A232V-N238Y-Q245R-N248D-E271F, G020K-S024F-S078N-S166D, T022A-N076D-S078N-G097A-S101Q-S103A-V104I-S128A-G159D-S188D-L217Q-A232V-Q245R-N248D-E271F, A016S-T022A-T033S-S101G-S103A-V104I-N116L-Y209V-T213A-A232V, T033S-S101G-S103A-V104I-N116L-S128N-Y209A-G211Q-A232V, G020K-T022L-S024F-G118R-S128D-S166D-T213A, T022A-S024G-N076D-S101Q-S103A-V104I-S128A-G159D-S188D-A232V-Q245R-N248D-E271F, T022A-N076D-G097S-S101N-S103A-V104I-Q109G-S128A-G159D-S188D-L217Q-A232V-Q245R-N248D-E271F, T022A-S101G-S103A-V104I-L126I-P129S-G159D-S188D-A232V-Q245R-N248D-E271F, T022A-S024R-N043R-N076D-S101G-S103A-V104I-P129E-A158E-G159E-S188D-A232V-Q245R-N248D-E271F, S024R-T033S-S128I-S166D-S188D, A098Q-S099A-G100S, S024R-T033S-N062E-N116L-A158E-S188D, G020R-S078D-G118D-P129E-N248D-H249R, T022A-S024R-N062E-N116L-S128I-S166D-S188D, A098F-S099A-V104I, T022Q-S101G-S103A-V104I-G159D-S188D-A232T-Q245T-N248E-E271F, T022A-N076D-S101G-S103A-V104I-I107V-P129E-G159D-S188D-A232V-Q245R-N248D-E271F-A272V, T022A-S024R-N076D-S101G-S103A-V104I-A158E-S188D-A232V-Q245R-N248D-E271F-A272V, S024F-G118R-S128D-S166D-A272V, S099T-G100S-S103A-V104I, T022Q-S101G-S103A-V104I-G159D-S188D-A232T-Q245T-N248E, S128D-T213A-L217E, T022A-T033S-N116L-S128I-S166D-S188D, T022L-S078N-G118R-S128D-S166D-T213A, T022A-S101G-S103A-V104I-A158E-G159E-S188D-A232V-S240E-Q245R-N248D-E271F, S078N-G118R-S128D-L217E, T022A-S024R-S101G-S103A-V104I-I107V-P129E-G159D-S188D-A232V-Q245R-N248D-E271F-A272V, T022A-S101G-S103A-V104I-L124V-S128A-P129S-G159D-S188D-L217Q-A232V-Q245R-N248D-E271F, T022L-S024F-T213A, G097P-A098Q-S103A-V104L, T022A-S078N-G097S-S101Q-S103A-V104I-Q109N-S128A-G159D-S188D-A232V-Q245R-N248D-E271F, G118R-S128I-A158E-S166D-S188D, T022A-N116L-S128I-A158E, T022A-S024F-T033S-S101G-S103A-V104I-N116L-Y209V-T213A-A232V-A272D, T022A-G118R-A158E-S166D-S188D, T022A-S024R-S101G-S103A-V104I-G159E-S188D-A232V-Q245R-N248D-E271F-A272V, T022A-S024G-S078N-G097A-S101N-S103A-V104I-Q109G-G159D-S188D-L217Q-A232V-Q245R-N248D-E271F, T022A-N043R-S101G-S103A-V104I-P129E-G159E-S188D-A232V-Q245R-N248D-E271F-A272V, T022A-G097A-S101N-S103A-V104I-Q109N-S128A-G159D-S188D-A232V-Q245R-N248D-E271F, H039C, T033S-S101G-S103A-V104I-N116A-S128N-Y209A-A232V, A016S-V104L-S128N-L148I, A098F-S101G-V104I, T022A-S024G-N076D-S101G-S103A-V104I-Q109G-S128A-G159D-S188D-A232V-Q245R-N248D-E271F, T022A-S024G-S078N-G097A-S101N-S103A-V104I-Q109G-G159D-S188D-A232V-Q245R-N248D-E271F, T022A-S024R-N076D-S101G-S103A-V104I-G159D-S188D-A232V-N238Y-Q245R-N248D-A270V-E271F-A272V, T022A-S101G-S103A-V104I-L126I-P129S-G159D-S188D-L217Q-A232V-Q245R-N248D-E271F, S078D-G118S-P129E, A098Q-S103G-V104I, A098F-S099T-S101G-G102A, T022A-S024R-N076D-S101G-S103A-V104I-P129E-S188D-A232V-Q245R-N248D-E271F, S024F-T033S-S101G-S103A-V104I-N116L-Y209V-G211Q-T213A-A232V, T022A-N062E-S101N-S103A-V104I-P129E-G159D-S188D-A232V-Q245R-N248D-E271F, S024R-S078G-G118S-Q245R-N248D, S056H, T022A-S101G-S103A-V104I-N116L-G118V-Y209A-G211Q-A232V, G097P-A098Q-S101A-S103A-V104L, T022A-N076D-S101Q-S103A-V104I-S128A-G159D-S188D-A232V-Q245R-N248D-E271F, T022A-G097A-S101Q-S103A-V104I-L126I-S128A-P129S-G159D-S188D-A232V-Q245R-N248D-E271F, T022A-S024R-T033S-N062E-N116L-G118R-S166D-S188D, S024R-T033S-N062E-N116L-A158E-S166D, A098Q-S099T-V104L, S099T-G102A-S103A, T022A-S101N-S103A-V104I-Q109G-S128A-G159D-S188D-L217Q-A232V-Q245R-N248D-E271F, T022A-N076D-S101G-S103A-V104I-P129E-A158E-G159E-S188D-A232V-Q245R-N248D-E271F, N062E-S078D-G118D-G159D, S024R-N062E-S078G-G118D-P129E-G159D-S188D, T022A-S024G-S101N-S103A-V104I-Q109N-G159D-S188D-L217Q-A232V-Q245R-N248D-E271F, S078D-G118D-H249R, T022A-G097A-S101Q-S103A-V104I-Q109G-G159D-S188D-A232V-Q245R-N248D-E271F, T022A-G097S-S101G-S103A-V104I-Q109N-G159D-S188D-A232V-Q245R-N248D-E271F, T022A-S101Q-S103A-V104I-L124T-P129S-G159D-S188D-A232V-Q245R-N248D-E271F, T022A-N062E-N116L-G118R-S128I-S166D-S188D, T022A-N076D-G097S-S101Q-S103A-V104I-G159D-S188D-L217Q-A232V-Q245R-N248D-E271F, S099G-S103A, T022A-N062E-G097A-S101N-S103A-V104I-P129S-G159D-S188D-A232V-Q245R-N248D-E271F, G020R-S024R-S078G-G118D-N238D-N248D, T022A-S024G-G097A-S101G-S103A-V104I-S128A-G159D-S188D-L217Q-A232V-Q245R-N248D-E271F-T274A, G097P-A098F-V104I, S024R-N062E-S078D-G118D-P129E-S188D-Q245R-N248D, T022A-N076D-S078N-S101N-S103A-V104I-Q109G-S128A-G159D-S188D-A232V-Q245R-N248D-E271F, T022A-S024G-G097S-S101N-S103A-V104I-Q109G-S128A-G159D-S188D-L217Q-A232V-Q245R-N248D-E271F, F050S, A016S-T022A-S101G-S103A-V104I-S128N, S101A-V104I-L111V, T022A-N076D-S101G-S103A-V104I-S188D-A232V-Q245R-N248D-E271F, T022A-S024G-G097S-S101N-S103A-V104I-Q109G-G159D-S188D-A232V-Q245R-N248D-E271F, S024F-T033S-S101G-S103A-V104I-N116L-S128N-Y209A-A232V, A098Q-S099T-G102A-S103G-V104I, T022A-T033S-G118R-S128I-S188D, S024R-N062E-S078G-G118S-Q245R, T022A-S024G-G097A-S101N-S103A-V104I-Q109N-G159D-S188D-A232V-Q245R-N248D-E271F, T022L-S024F-S128D-T213A, T022A-S101G-S103A-V104I-L126I-G159D-S188D-A232V-Q245R-N248D-E271F, A016S-T022A-S024F-S101G-S103A-V104I-N116L-Y209V-G211Q-T213A-A232V, T022A-S024R-S101G-S103A-V104I-G159D-S188D-A232V-N238Y-Q245R-N248D-A270V-E271F, G020K-T022L-S078N-S128D-A133V-T213A, T022A-S024G-N076D-G097A-S101Q-S103A-V104I-Q109G-G159D-S188D-L217Q-A232V-Q245R-N248D-E271F, T022A-

G118R-S128I-S166D, T022A-T033S-A158E-S166D, T022A-S078N-G097A-S101Q-S103A-V104I-Q109N-S128A-G159D-S188D-A232V-Q245R-N248D-E271F, G020R-S024R-S078D-G118D-N248D, A098F-S099A-S103G, T022A-N076D-S101G-S103A-V104I-P129E-G159D-S188D-A232V-N238Y-Q245R-N248D-E271F, G097P-S099T-S103A-V104L, T022A-N076D-S101G-S103A-V104I-I107V-G159D-S188D-A232V-N238Y-Q245R-N248D-E271F, S024F-S128D-T213A, T022A-S024R-N076D-S101G-S103A-V104I-P129E-G159D-S188D-A232V-N238Y-Q245R-N248D-A270V-E271F-A272V, S099A-G102A-V104I, T022A-N076D-S078N-G097A-S101N-S103A-V104I-Q109N-G159D-S188D-A232V-Q245R-N248D-E271F, S024F-T033S-S101G-S103A-V104I-I107V-N116A-Y209A-G211Q-T213A-A232V, G097P-S099A-S101A, T022A-S101G-S103A-V104I-S188D-A232V-Q245R-N248D-E271F-A272V, G020R-S024R-N062E-S078D-G118S-Q245R-N248D-H249R, S078N-G118R-S128D-T213A, T022A-G097A-S101N-S103A-V104I-L126I-P129E-G159D-S188D-A232V-Q245R-N248D-E271F, T022A-S101Q-S103A-V104I-L126I-P129S-G159D-S188D-A232V-Q245R-N248D-E271F, T022A-N076D-S101G-S103A-V104I-P129E-A158E-S188D-A232V-Q245R-N248D-E271F-A272V, T022A-S024R-N062E-S128I-A158E-S166D, T022A-N076D-S101G-S103A-V104I-P129E-G159E-S188D-A232V-Q245R-N248D-E271F-A272V, T022A-S024G-G097S-S101Q-S103A-V104I-Q109N-S128A-G159D-S188D-L217Q-A232V-Q245R-N248D-E271F, T022A-N043R-N076D-S101G-S103A-V104I-P129E-G159E-S188D-A232V-Q245R-N248D-E271F-A272V, T033S-N116L-S128I-S188D, T022L-S024F-G118R-S128D-S166D-T213A-L217E, T022A-S024G-S078N-G097S-S101N-S103A-V104I-Q109N-S128A-G159D-S188D-L217Q-A232V-Q245R-N248D-E271F, T022A-S101G-S103A-V104I-L126I-G159D-S188D-L217Q-A232V-Q245R-N248D-E271F, A016S-S101G-S103A-L148I, S024R-S078G-G118D-N248D-H249R, T022A-S024G-S078N-S101N-S103A-V104I-Q109G-S128A-G159D-S188D-A232V-Q245R-N248D-E271F, P055R, T022A-S024G-G025S-G097S-S101N-S103A-V104I-S128A-G159D-S188D-L217Q-A232V-Q245R-N248D-E271F, T022A-S101N-S103A-V104I-L124T-P129S-G159D-S188D-A232V-Q245R-N248D-E271F, S078G-G118D-G159D-Q245R, A016S-T022A-S101A-S103A-V104I-L111V, A016S-T022A-T033S-S101G-S103A-V104I-N116L-S128N-Y209A-G211Q-T213A-A232V, S024R-S078D-G118S-G159D-S188D-N248D, A016S-S101G-S103A-V104I-N116L-S128N-A133V-Y209A-G211Q-T213A-A232V, T022A-S101G-S103A-V104I-A158E-S188D-A232V-Q245R-N248D-E271F-A272V, T022A-S101Q-S103A-V104I-Q109N-S128A-G159D-S188D-A232V-Q245R-N248D-E271F, T022L-S128D, T022A-T033S-N116L-G118R-S128I-A158E-S188D, T022L-G118R-S128D-T213A-L217E, T022A-N043R-N076D-S078P-S101G-S103A-V104I-A158E-G159E-S188D-A232V-Q245R-N248D-E271F, G097P-A098F-S101A, Q002F, G097P-A098Q-S099A, S024R-T033S-N062E-S166D-S188D, G020K-S078N-S128D-T213A, T022A-S101Q-S103A-V104I-Q109G-S128A-G159D-S188D-A232V-Q245R-N248D-E271F, T022A-G097A-S101G-S103A-V104I-L126I-S128A-G159D-S188D-A232V-Q245R-N248D-E271F, G020R-N062E-S078G-G118S-P129E-G159D-S188D-N238S, G097P-S099T-S103G-V104I, T022A-N076D-S101N-S103A-V104I-Q109N-S128A-G159D-S188D-L217Q-A232V-Q245R-N248D-E271F, D181C, G020K-G118R-S128D, T022A-S101G-S103A-V104I-L126I-S128A-P129E-G159D-S188D-L217Q-A232V-Q245R-N248D-E271F, T022A-S101N-S103A-V104I-L126I-P129S-G159D-S188D-A232V-Q245R-N248D-E271F, T022A-S101Q-S103A-V104I-L124T-G159D-S188D-A232V-Q245R-N248D-E271F, T022A-G097A-S101Q-S103A-V104I-L126I-P129S-G159D-S188D-A232V-Q245R-N248D-E271F, T022L-S078N-S128D-T213A-L217E-A272D, S099T-G102A-V104I, S128I-S166D, T022A-S024R-S101G-S103A-V104I-P129E-A158E-G159E-S188D-A232V-Q245R-N248D-E271F-A272V, G020R-S078D-G118S-Q245R-H249R, G097P-S099T-G100S, G097P-S099G, G020K-S024F-S078N-S128D-S166D-T213A, A098Q-S101A-G102A-S103A, S024R-N116L-G118R-S128I, T022A-S101G-S103G-V104I-S128N, T022A-S024G-N076D-S101G-S103A-V104I-P129E-G159D-S188D-L217Q-A232V-Q245R-N248D-E271F, T022A-S101G-S103A-V104I-I107V-S153A-G159D-S188D-A232V-Q245R-N248D-A270V-E271F, S024R-N062E-S078G-G118D-S188D-Q245R-H249R, T022A-S078N-S101Q-S103A-V104I-Q109N-G159D-S188D-L217Q-A232V-Q245R-N248D-E271F, T022A-S024G-S101Q-S103A-V104I-G159D-S188D-A232V-Q245R-N248D-E271F, G020K-T022L-S024F, G020K-T022L-S078N-S128D-T213A, S078G-G118D-P129E-S188D, T022A-N076D-G097A-S101G-S103A-V104I-S128A-G159D-S188D-A232V-Q245R-N248D-E271F, A016S-S103G-V104L-S128N-L135I, T022A-N076D-S101G-S103A-V104I-G159D-S188D-A232V-N238Y-Q245R-N248D-E271F, S101G-S103A-V104I-N116L-G118V-Y209V-A232V, T022A-S101G-S103A-V104I-Q109N-G159D-S188D-A232V-Q245R-N248D-E271F, A016S-S103G-V104I-S128N-L148I, T022A-S024R-N076D-S101G-S103A-V104I-P129E-G159D-S188D-A232V-N238Y-Q245R-N248D-A270V-E271F, G025S, G020R-S078D-G118D-G159D-S188D-N248D-H249R, T033S-N116L-S188D, T022A-N043R-S101G-S103A-V104I-S188D-A232V-Q245R-N248D-E271F-A272V, G097P-A098Q-S103A-V104I, T022A-N062E-S101G-S103A-V104I-S188D-A232V-Q245R-N248D-E271F, N062E-N116L-S128I-A158E, A016S-T022A-S103G-V104L, T022A-T033S-N116L-S128I, T022L-S024F-N043H-G118R-S128D-S166D, T022A-G097A-S101N-S103A-V104I-Q109G-G159D-S188D-A232V-Q245R-N248D-E271F, S101G-S103G-V104L, G020R-N062E-S078G-G118D-P129E-G159D-S188D-Q245R-N248D, S099A-G100S-V104I, G097P-A098Q-S099G-S101A, G020R-S024R-S078G-G118S-G159D-S188D-Q245R-H249R, A016S-S103G-V104I-S128N, T022A-S024R-S101G-S103A-V104I-P129E-A158E-G159E-S188D-A232V-Q245R-N248D-E271F, T022A-S024G-G097A-S101N-S103A-V104I-Q109G-S128A-G159D-S188D-A232V-Q245R-N248D-E271F, G118R-S128D-L217E, S132H, T022A-S024F-T033S-S101G-S103A-V104I-N116L-S128N-Y209A-G211Q-T213A-A232V, T022A-G097A-S101N-S103A-V104I-L126I-P129S-G159D-S188D-L217Q-A232V-Q245R-N248D-E271F, S024k-S078D-G118D-S188D, T022A-N043R-S101G-S103A-V104I-A158E-G159E-S188D-A215V-A232V-Q245R-N248D-E271F-A272V, S024F-S078N-G118R, T022A-S101G-S103A-V104I-Q109G-S128A-G159D-S188D-A232V-Q245R-N248D-E271F, A016S-T022A-S101A-V104I, T022A-S166D-S188D, S078N-G118R-S128D-S166D-T213A, T022A-S024G-S078N-G097A-S101N-S103A-V104I-Q109N-S128A-G159D-S188D-L217Q-A232V-Q245R-N248D-E271F, T022A-N043R-S101G-S103A-V104I-G159E-S188D-A232V-Q245R-N248D-E271F, G020R-S024R-

N062E-S078D-G118D-G159D-S188D-N248D, G097P-S099T-S101A-S103G-V104I, T022A-S024R-N043R-N076D-S101G-S103A-V104I-P129E-S188D-A232V-Q245R-N248D-E271F, A016S-T022A-S103G-V104L-S128N, G020R-N062E-S078G-G118S-G159D-S188D-Q245R-H249R, G020R-S078G-G118D, G020R-S078G-G118S, Q012Y-N018G, T022A-S024R-N043R-N076D-S101G-S103A-V104I-P129E-A158E-S188D-A232V-Q245R-N248D-E271F, T033S-N062E-G118R-A158E-S166D, T022A-N076D-A088V-S101Q-S103A-V104I-G159D-S188D-A232V-Q245R-N248D-E271F, S024R-N062E-N116L-S128I-S166D-S188D, T022A-T033S-N116L-A158E, T022A-S024R-N043R-N076D-S101G-S103A-V104I-A158E-S188D-A232V-Q245R-N248D-E271F-A272V, T033S-N062E-N116L-A158E, S024R-S078G-G118D-H249R, T022A-N043R-S101G-S103A-V104I-P129E-A158E-G159E-S188D-A232V-Q245R-N248D-E271F, T022A-S024G-N076D-G097A-S101N-S103A-V104I-Q109N-G159D-S188D-A232V-Q245R-N248D-E271F, T022A-S101Q-S103A-V104I-L126I-P129E-G159D-S188D-A232V-Q245R-N248D-E271F, G020R-S078D-G118D-Q245R-H249R, G097P-S099G-V104L, T022A-N043R-N076D-S101G-S103A-V104I-A158E-S188D-A232V-Q245R-N248D-E271F, A016S-T022A-S101G-V104I-S128N-L148I, T022A-N076D-S101G-S103A-V104I-P129E-A158E-S188D-A232V-Q245R-N248D-E271F, N062E-A158E-S188D, T022A-N076D-S078N-S099R-S101Q-S103A-V104I-G159D-S188D-A232V-Q245R-N248D-E271F, A016S-T022A-S103G-V104I-L148I, S024R-T033S-N116L-A158E-S166D-S188D, T022A-S101G-S103A-V104I-N116A-G118V-Y209A-T213A-A232V, G020R-N062E-S078D-G118D-P129E-S188D-N248D-H249R, T022A-S101G-S103A-V104I-Q109N-G159D-S188D-L217Q-A232V-Q245R-N248D-E271F, G020K-T022L-S024F-S078N-G118R-S128D-S166D-T213A, T022A-S024R-T033S-N116L-S128I-S166D-S188D, T022A-S024R-S101G-S103A-V104I-S188D-A232V-Q245R-N248D-E271F, T022A-S101G-S103A-V104I-P129E-G159D-S188D-A232V-N238Y-Q245R-N248D-A270V-E271F-A272V, T022A-S024R-S101G-S103A-V104I-A158E-S188D-A232V-Q245R-N248D-E271F, T022A-T033S-S101G-S103A-V104I-S128L-G159D-S188D-T213A-A232V-Q245R-N248D-E271F, T022A-T033S-S128I-S166D, T022A-S024R-N043R-N076D-S101G-S103A-V104I-P129E-A158E-S188D-A232V-Q245R-N248D-E271F-A272V, T022A-S024R-G118R, T022A-G097A-S101N-S103A-V104I-L126I-P129S-V149I-G159D-S188D-L217Q-A232V-Q245R-N248D-E271F, T022A-N076D-S078N-G097A-S101Q-S103A-V104I-S128A-G159D-S188D-A232V-Q245R-N248D-E271F, A098Q-S101G-G102A-S103A-V104I, S078G-G118D-G159D-S188D-Q245R-N248D, G020K-S078N-S128D-S166D-T213A, T022A-S024R-S101G-S103A-V104I-A158E-G159E-S188D-A232V-Q245R-N248D-E271F, G097P-A098Q-S099T-S103A, G020K-T022L-S024F-S128D-L217E, A098Q-G100S, A016S-T033S-S101G-S103A-V104I-N116A-S128N-Y209V-A232V, A016S-S101A-L148I, A016S-S101G-V104I, T022A-N076D-S101G-S103A-V104I-G159D-S188D-A232V-N238Y-Q245R-N248D-A270V-E271F, T022A-S078N-S101G-S103A-V104I-Q109N-G159D-S188D-L217Q-A232V-Q245R-N248D-E271F, V030I-S099T-G100S, S078D-G118S-P129E-Q245R-H249R, S101G-S103A-V104I-N116L-G118V-S128N-Y209V-A232V, T022A-S024R-N043R-S101G-S103A-V104I-P129E-S188D-A232V-Q245R-N248D-E271F, G020R-S078D-G118S-P129E-S188D-N248D, T022A-S024R-N062E-G118R-S128I-A158E-S166D-S188D, T022A-T033S-N062E-G118R-S128I, T022A-S024G-G097A-S101Q-S103A-V104I-Q109N-G159D-S188D-L217Q-A232V-Q245R-N248D-E271F, G020R-S024R-S101A-S103N-V104I-G118S-P129E-Q245R, S078D-G118D-P129E-Q245R-H249R, G020R-S078D-G118D-S188D-Q245R-H249R, T022A-S024G-N076D-S101Q-S103A-V104I-Q109N-S128A-G159D-S188D-A232V-Q245R-N248D-E271F, N062E-S078D-G118D, N062E-S078D-G118S-N248D, T022A-S024R-T033S-N062E-G118R-S128I-S166D, T022A-N076D-S078N-G097S-S101Q-S103A-V104I-Q109N-S128A-G159D-S188D-A232V-Q245R-N248D-E271F, S056R, 0020R-N062E-S078G-G118D-P129E-G159D-S188D-Q245R-N248D-H249R, G097P-A098Q-S099T-V104M, T022A-S024G-S101G-S103A-V104I-L126I-P129S-G159D-S188D-L217Q-A232V-Q245R-N248D-E271F, G097P-A098Q-S099T, S128D-T213A, T022A-V068A-S101G-S103A-V104I-G118R-G159D-S188D-A232V-Q245R-N248D-E271F, G020K-T022L-S024F-G118R-T213A, S099G-S101G-G102A-S103A-V104I, S099A-G100S-S101A, T022A-N076D-S101G-S103A-V104I-G159D-S188D-A232V-N238Y-Q245R-N248D-E271F-A272V, T022A-S024G-S101N-S103A-V104I-Q109N-S128A-G159D-S188D-L217Q-A232V-Q245R-N248D-E271F, V104I-L111V-S128N-L148I, S024R-S078G-G118D-P129E-S188D-N248D, A016S-S101G-S103G-V104I-S128N, G102A-S103A, S024F-S078N-S128D-T213A, N062E-S078G-G118S-P129E-G159D-S188D, A232N, S024R-N062E-S078G-G118D-P129E-S188D-N248D-H249R, A016S-S101A-S103A-V104I-L111V, T022A-S101G-S103A-V104I-A158E-S188D-A232V-Q245R-N248D-E271F, A098Q-S099G-G100S, S101A-V104L-S128N, T022A-S024R-N043R-N076D-S101G-S103A-V104I-P129E-A158E-G159E-S188D-A232V-Q245R-N248D-E271F-A272V, T022A-S078N-S101G-S103A-V104I-Q109N-G159D-S188D-A232V-Q245R-N248D-E271F, S099A-G102A, T022A-S024F-T033S-S101G-S103A-V104I-N116L-S128N-Y209V-T213A-A232V, A098Q-S099T-G100S, T033S-N062E-N116L-G118R-S128I-S188D, T022A-N062E-S101G-S103A-V104I-A158E-G159E-S188D-A232V-Q245R-N248D-E271F, S024R-T033S-N062E-S128I-S166D, A098Q-S099T-S103A, T022A-S103G-L148I, G097P-S101A-G102A-V104I, T022A-S101G-S103A-V104I-G159D-S188D-A232V-N238Y-Q245R-N248D-A270V-E271F-A272V-R275S, N062E-N116L-S128I, G025P, G097P-S099T-G102A, A016S-S024F-T033S-S101G-S103A-V104I-N116L-S128N-Y209A-T213A-A232V, S132V, T033S-S128I-A158E, S099T-S101A-G102A-V104L, T022A-S101A-V104L-L111V-S128N, T022L-S078N-G118R, T022A-N076D-S101G-S103A-V104I-G159D-S188D-A232V-N238Y-Q245R-N248D-A270V-E271F-A272V, S024R-N116L-S128I-A158E-S166D-S188D, T033S-S101G-S103A-V104I-N116L-Y209A-A232V, T022A-S024R-N062E-N116L-G118R-S128I, G097P-S099T-S103A, T022L-S024F-S078N-G118R-S128D-S166D-T213A-L217E, S078D-G118S-P129E-S188D-Q245R-N248D, N062E-S078G-G118D-G159D-S188D-N248D-H249R, T022A-N076D-S101G-S103A-V104I-I107V-P129E-G159D-S188D-A232V-N238Y-Q245R-N248D-A270V-E271F, S078G-G118S-S188D, F050R, A016S-T022A-S024F-S101G-S103A-V104I-N116L-S128N-Y209V-T213A-L217S-A232V, T022A-S101G-S103A-V104I-P129E-G159D-S188D-A232V-N238Y-Q245R-N248D-E271F-A272V, T022A-N076D-G097A-S101Q-S103A-V104I-Q109N-P129E-G159D-S188D-

A232V-Q245R-N248D-E271F, S024F-G118R-S128D-S166D-T213A, G097P-S099A-S101G, G097P-S099A-G100S-V104I, G047I, S099T-G100S, G020K-T022L-S078N-G118R-S128D-S166D-T213A, T033S-N062E-N116L-H120N, S078D-G118D-S188D-Q245R-N248D, T022A-S024R-N076D-S101G-S103A-V104I-P129E-G159D-S188D-A215V-A232V-N238Y-Q245R-N248D-E271F, T022A-S101Q-S103A-V104I-L124T-S128A-P129S-G159D-S188D-A232V-Q245R-N248D-E271F, T022A-G097A-S101N-S103A-V104I-L124T-G159D-S188D-A232V-Q245R-N248D-E271F, G020R-S024R-S078D-G118D-P129E-G159D-S188D-N248D, T022A-S024R-N076D-S101G-S103A-V104I-S188D-A232V-Q245R-N248D-E271F, S101A-V104I-L111V-S128N, G020R-S024R-N062E-S078D-G118D-P129E-G159D-S188D, A016S-V104I-S128N, S099A-S101G-V104I, T022A-S101Q-S103A-V104I-L124T-S128A-G159D-S188D-A232V-Q245R-N248D-E271F, A098M, G097P-A098Q-G102A, T022A-S024R-N043R-N076D-S101G-S103A-V104I-P129E-S188D-A232V-Q245R-N248D-E271F-A272V, T022A-S101N-S103A-V104I-L124T-P129E-G159D-S188D-A232V-Q245R-N248D-E271F, A016S-S101A-V104I-L111V-S128N, G020R-S024R-S078G-G118S-N248D, A016S-S101G-S103A-V104I-L111V-S128N, T022L-S078N-G118R-S128D-S166D, A098Q, S024F-G118R, N062E-S078D-G118S-G159D-S188D-Q245R-N248D, W113Y, G020R-S078G-G118S-N248D, G020K-T022L-S024F-S128D-S166D-T213A, G020R-S078D-G118D-N248D, S078D-G118D-Q245R-N248D, T033S-S101G-S103A-V104I-N116L-S128N-Y209V-T213A-A232V, V051M, I035T, T022A-S101Q-S103A-V104I-L124V-L126I-S128A-P129S-G159D-S188D-A232V-Q245R-N248D-E271F, T022A-S024G-S078N-S101N-S103A-V104I-Q109N-S128A-G159D-S188D-L217Q-A232V-Q245R-N248D-E271F, T022A-S024R-N076D-S101G-S103A-V104I-P129E-G159E-S188D-A232V-Q245R-N248D-E271F-A272V, N062E-S078G-G118S-P129E-G159D-N248D, T022A-S024F-T033S-S101G-S103A-V104I-N116L-S128N-Y209V-G211Q-A232V, T022A-G097A-S101Q-S103A-V104I-L124T-P129E-G159D-S188D-A232V-Q245R-N248D-E271F, G097P-G102A, N062E-S078D-G118S-S188D-N248D, T022A-S024R-S101G-S103A-V104I-I107V-P129E-G159D-S188D-A232V-N238Y-Q245R-N248D-E271F-A272V, T022A-S101A-V104I-L148I, A016S-T022A-S024F-T033S-S101G-S103A-V104I-N116A-Y209A-G211Q-A232V, G020R-S024R-N062E-S078G-G118D-P129E-Q236R-Q245R-N248D, T022L-S024F-S078N-S128D-S166D, T022A-S024R-S101G-S103A-V104I-P129E-G159D-S188D-A232V-N238Y-Q245R-N248D-A270V-E271F-A272V, V051C, A048T-N062E-G118R-A158E-S188D, T022A-T033S-N116L-G118R-S128I-S166D-S188D, T022A-S101G-V104L-L111V-S128N, S056V, G020K-T022L-S078N-S128D, G020K-T022L-S024F-S078N-S128D-S166D, T033S-S101G-S103A-V104I-N116L-Y209V-G211Q-A232V, G097P-A098Q-S099T-S101A, T022A-S101G-S103A-V104I-S128N, T022A-S101G-S103A-V104I-I107V-G159D-S188D-A232V-N238Y-Q245R-N248D-E271F, T022A-S024R-S101G-S103A-V104I-G159E-S188D-A232V-Q245R-N248D-E271F, S024R-T033S-N062E-N116L-G118R-S128I-A158E-S188D, S024R-T033S-N116L-G118R-S128I-A158E-S166D-S188D, G097P-A098F-S099T-S101A-S103A-V104I, A098Q-G102A-S103A-V104I, T033S-S128I-S188D, T033S-S128I, T022A-S024G-N076D-G097A-S101Q-S103A-V104I-Q109N-S128A-G159D-S188D-L217Q-A232V-Q245R-N248D-E271F, W006N, A098Q-S099A-S101A-V104I, T033S-N062E-G118R-S128I, G097S-A098Q-G100S, T022L-S078N-S128D-L217E, T022A-S024R-T033S-N116L-S128I-S188D, G020K-T022L-G118R-S128D-S166D-T213A-L217E, T022A-S024G-S101G-S103A-V104I-Q109N-G159D-S188D-A232V-Q245R-N248D-E271F, A098F-V104L, A016S-S101G-V104I-S128N, A016S-T022A-V104L-L148I, T022A-S101A-L111V, T022A-S024R-S101G-S103A-V104I-A158E-S188D-A232V-Q245R-N248D-E271F-A272V, A016S-T022A-S101A-S103A-V104I, A098Q-S099T-S101G-G102A, T022A-N062E-S101Q-S103A-V104I-P129E-G159D-S188D-L217Q-A232V-Q245R-N248D-E271F, A098Q-G100S-S101A-V104I, T022A-S024R-N076D-S101G-S103A-V104I-P129E-G159D-S188D-A232V-N238Y-Q245R-N248D-E271F-A272V, G097P-A098Q-S099A-S101A-S103A-V104I, T022L-S024F-S128D-S166D, T022A-S099R-S101Q-S103A-V104I-G159D-S188D-A232V-Q245R-N248D-E271F, T022A-N076D-G097A-S101N-S103A-V104I-Q109N-S128A-G159D-S188D-L217Q-A232V-Q245R-N248D-E271F, S024F-S128D-S166D-T213A, G020K-T022L-S078N-S128D-S166D-T213A, T022A-S024R-S101G-S103A-V104I-P129E-A158E-S188D-A232V-Q245R-N248D-E271F-A272V, T022A-S101G-S103A-V104I-G159D-S188E-A232T-Q245T-N248E, G097P-S099G-G102A, A016S-S101G-S103A-V104I-N116A-S128N-Y209A-G211Q-T213A-A232V, A098Q-S099T-G102A, T022A-N043R-N076D-S101G-S103A-V104I-P129E-A158E-G159E-S188D-A232V-Q245R-N248D-E271F, T022A-N076D-S101G-S103A-V104I-I107V-G159D-S188D-A232V-N238Y-Q245R-N248D-A270V-E271F, S024R-N062E-S078D-G118S-P129E-S188D-N248D, N062E-S078D-G118S-P129E-G159D-S188D-Q245R-N248D-H249R, A016S-T022A-S101A-S103G-V104I-L148I, G097P-A098F-S099T-S103A-V104I, G020K-T022L-S024F-S078N-S128D-S166D-T213A, G020K-T213A, S024R-T033S-N062E-A158E-S166D, G020K-T022L-S078N-G118R-T213A, S024F-G118R-S128D-S166D, T022A-S024R-S101G-S103A-V104I-P129E-G159D-S188D-A232V-N238Y-Q245R-N248D-E271F, S078N-S128D-S166D-T213A, T022A-T033S-S101G-S103A-V104I-N116L-S128L-G159D-S188D-T213A-A232V-Q245R-N248D-E271F, S078D-G118S-P129E-G159D-N248D, G097P-G100S, T022A-N076D-S101G-S103A-V104I-P129E-A158E-S188D-A232V-Q245R-N248D-N269S-E271F, T022A-S101N-S103A-V104I-L124T-S128A-G159D-S188D-A232V-Q245R-N248D-E271F, T022L-S024F-S078N-S128D-S166D-T213A, G097P-A098S-S099G-G102A, G020R-N062E-S078D-G118S-G159D-S188D-N248D, S078D-G118D-G159D-S188D, T033S-S128I-S166D, A016S-T022A-S101G-S103G-V104I-L148I, D041N, A098Q-S099T-G100S-S101A-A151V, A098Q-S099A-G100S-S101A, T022A-S128I-A158E-S166D-S188D, G020R-N062E-S078G-G118D-P129E-S188D-N248D, A098Q-S099T-S101A-G102A, S024R-T033S-N062E-N116L-S128I-A158E, T022A-S024G-N076D-S101G-S103A-V104I-Q109N-S128A-G159D-S188D-A232V-Q245R-N248D-E271F, T022A-S101G-S103A-V104I-I107V-G159D-S188D-A232V-N238Y-Q245R-N248D-E271F-A272V, T022A-S024R-T033S-N062E-S128I-S188D, N062E-S078D-G118D-P129E-Q245R-N248D, S078D-G118D-G159D-Q245R-N248D, S024R-N062E-N116L-S128I-A158E-S188D, A098F-S099G, A098F-G100S-V104I, T022A-T033S-S101G-S103A-V104I-S128L-G159D-S188D-A232V-Q245R-N248D-E271F, G020K-T022L-S024F-S078N, A098F-S099T-G100S-

V104L, S024R-N076D-S101A-S103A-V104I-S188D-M222S-A232V-Q245R, T022A-S024R-N043R-S101G-S103A-V104I-P129E-A158E-G159E-S188D-A232V-Q245R-N248D-E271F, T274F, G118R-S128I-V139I-A158E-S166D-S188D, T022A-T033S-N062E-G118R-S166D-S188D, S024R-S078D-G118S-P129E-N248D, T022A-T033S-N116L-S128I-A158E, T022A-N062Q-G097A-S101N-S103A-V104I-G159D-S188D-L217Q-A232V-Q245R-N248D-E271F, N062E-N116L-S166D-S188D, T022A-S101G-S103A-V104I-I107V-G159D-S188D-A232V-N238Y-Q245R-N248D-A270V-E271F-A272V, S099A-G100S-S103A-V104I, G020K-S024F-S078N, T022L-S024F-G118R-S128D-S166D-L217E, T022A-S101A-V104L, T022A-S101G-S103A-V104I-L126I-S128A-G159D-S188D-L217Q-A232V-Q245R-N248D-E271F, A016S-T022A-S101G-S103A-V104I-N116L-G118V-Y209V-G211Q-A232V, A133T-N269E, S024R-N062E-S078G-G118D-P129E-G159D-Q245R-H249R, T022A-S024R-T033S-N062E-S128I-A158E, T022A-T033S-N062E-S128I, R275S, S024R-S078D-G118D-P129E-S188D-N248D-H249R, T022A-T033S-G118R-S128I, T033S-N116L-G118R-S128I, T022L-S024F-S078N-G118R-T213A, L075G, S099T-G100S-V104I, T033S-N062E-N116L-S128I, A016S-T022A-S103A-V104I-L148I, G097P-G102A-S103A, G097P-S099T-G100S-S101A-S103A-V104I, T253Y, T022A-N062E-N116L-G118R-S128I-S166D, T022A-N043R-S101G-S103A-V104I-P129E-A158E-S188D-A232V-Q245R-N248D-E271F, S024R-N062E-S078D-G118S-P129E-G159D-S188D-Q245R-N248D, G097P-G102A-V104I, S078N-G118R-S128D-S166D-L217E, T022A-S024R-N076D-I079T-S101G-S103A-V104I-G159D-S188D-A232V-N238Y-Q245R-N248D-A270V-E271F-A272V, T022A-S101A-V104L-S128N, G097P-A098Q-S099T-G102A-V104I, T022A-G047V-S103A-L148I, T022A-N116L-S128I-S188D, G097P-A098Q-S099T-S103A-V104L, N116L-S128I-A158E-S188D, T022A-S024R-N043R-S101G-S103A-V104I-A158E-G159E-S188D-A232V-Q245R-N248D-E271F, A016S-T022A-S101A-S103G-S128N-L148I, G097P-A098Q-S099T-S101A-V104I, L257N, G097P-S099T-S101G-S103A-V104L, A098Q-S099G-G100S-V104I, S056L, S099T-S101A-G102A-S103A-V104I, T022A-S024R-S101G-S103A-V104I-I107V-P129E-G159D-S188D-A232V-N238Y-Q245R-N248D-E271F, T022A-S103G-V104I, T022A-T033S-S101G-S103A-V104I-N116A-S128N-Y209V-G211Q-T213A-A232V, S078N-S128D, R170T, A098F-S099G-G100S, G020K-T022L-S024F-S078N-T213A, S099T-S101A-S103A, G020R-S078G-G118S-G159D-Q245R-H249R, G097P-S099G-S101G, S078D-G118S-Q245R, T033S-N062E-N116L-S188D, G097P-S099G-S101A, G020R-N062E-S078D-G118D-S188D-Q245R-H249R, S087W, A098Q-S099T-S101G-G102A-V104L, A016S-S024F-T033S-S101G-S103A-V104I-N116L-S128N-Y209V-A232V, G020K-T022L-S024F-S128D-T213A-L217E, T022A-S103A-V104I, G097P-A098Q-G100S, G020K-T022L-N062E-S078D-G118D-P129E-Q245R-H249R, G020K-S024F-S078N-T213A, A098F-S099A-S103A, S099T-G100S-S101G, N076D-S101A-S103A-V104I-S188D-M222S-A232V-Q245R, S049W, G020K-T022L-S024F-S128D-S166D-L217E, S024F-G118R-S128D-S166D-L217E, T022A-S103A-V104I-L148I, T022A-S101A-S103A-V104I, F050Q, S101G-S103A-V104I-N116A-G118V-Y209V-G211Q-A232V, S078G-G118D-H120N-H249R, A016S-S103G-L148I, G097P-S101A, S099T-S103A-V104I, S078G-G118D-P129E-G159D, T022L-S128D-S166D-T213A,

T022A-S024R-N116L-S128I, N076D-S101A-S103A-V104I-M222S-A232V-Q245R, G097P-S099T-S101A-V104I, A098Q-S099A-S101A-G102A, T022A-S024R-G025S-Q059K-N076D-S101G-S103A-V104I-P129E-A158E-G159E-S188D-A232V-Q245R-N248D-E271F, S132G, T022A-S101A-S103A-V104L-S128N, A098F-G100S-S101A, S024F-G118R-T213A, G097P-S099T-G102A-S103A, G097P-S099T-G102A-S103A-V104I, T022A-S101G-S103A-V104I-N116L-G118V-Y209V-G211Q-T213A-A232V, S024R-T033S-N116L, A098Q-S099T, A016S-T022A-S101G-S103A-V104L-S128N-L148I, A098F-S099T-S101A, A098Q-G100S-S103A, T022A-N062E-N116L-S128I-S188D, Q012E-S259N, T022A-S024F-S101G-S103A-V104I-N116L-G118V-Y209A-G211Q-T213A-A232V, T022A-S024R-N076D-S101G-S103A-V104I-I107V-G159D-S188D-A232V-N238Y-Q245R-N248D-E271F-A272V, T022A-S024G-G097A-S101G-S103A-V104I-Q109G-S128A-G159D-S188D-L217Q-A232V-Q245R-N248D-E271F, A016S-T022A-S101G-S103G-V104L-S128N, Q245D, G020K-T022L-S128D-S166D-T213A, S099T-V104I, T022A-S024F-T033S-S101G-S103A-V104I-N116L-Y209A-A232V, G020R-S078D-G118D-Q245R-N248D, S099G-S101A-V104L, G097P-S099T, S078G-G118D-Q245R, G097P-A098Q-S099A-S103A, A016S-T022A-S103A, G097P-A098Q-S101A-S103G-V104L, S078N-G118R-S128D-S166D, V026Q, G097P-A098F-S099T-S103A-V104L, T022A-S024R-S101G-S103A-V104I-G159D-S188D-A232V-N238Y-Q245R-N248D-E271F-A272V, S024R-T033S-G118R-S128I-S166D-S188D, G020K-T022L-S078N-G118R-S128D-S166D, A098F-S099T-G102A-S103G, M119L, N062E-S078G-G118D-P129E-S188D, T022L-G118R-S128D-S166D, T022A-T033S-N116L-S128I-S188D, A098F-S099T-S101G-V104L, T033S-N116L, V104L-L111V-S128N, S024R-N062E-S078D-G118D-P129E-Q245R-H249R, G097P-S099A-G100S, A016S-T022A-S103A-L111V, G097P-S099A-G102A-V104I, G097P-A098Q-S099A-S103A-V104I, T022A-G097A-S101N-S103A-V104I-L124T-P129S-G159D-S188D-A232V-Q245R-N248D-E271F, T022L-S024F-S078N-S128D-T213A-L217E, T022A-N043R-S101G-S103A-V104I-A158E-S188D-A232V-Q245R-N248D-E271F-A272V, P055V, T022A-N062E-S101Q-S103A-V104I-S128A-G159D-S188D-L217Q-A232V-Q245R-N248D-E271F, G097P-A098Q, S101G-S103A-V104I-L111V-S128N, A016S-S024F-T033S-S101G-S103A-V104I-N116L-S128N-Y209A-A232V, G020R-S078D-G118D, T022A-G097A-S101N-S103A-V104I-L124I-P129E-G159D-S188D-A232V-Q245R-N248D-E271F, T033S-G118R-S128I-S166D-S188D, N062E-S078G-G118D-P129E-G159D-S188D-H249R, V051Y, G097P-G102A-S103A-V104I, V030N, S024R-I033S-G118R-S128I-A158E-S166D, N062E-S078D-G118S-P129E-G159D-Q245V-N248E-E271T, S024R-I033S-G118R-S128I-S166D, A016S-S101G-S103G-V104L, S078N-S128D-L217E, A016S-T022A-S101A-V104I-L111V, A016M, S099T-G102A-S103A-V104I, T022A-S101A-V104I-L111V-S128N, T022A-S024R-N043R-N076D-S078P-S101G-S103A-V104I-P129E-G159E-S188D-A232V-Q245R-N248D-E271F, T022L-S078N-S128D, V051E, N062E-S078D-G118S-P129E-G159D, T022A-S101N-S103A-V104I-L124T-P129S-G159D-S188D-L217Q-A232V-Q245R-N248D-E271F, A015H, G020R-S024R-N062E-S078D-G118S-G159D-S188D-Q245R-H249R, G020K-S024F-G118R-S128D-S166D-T213A-L217E, A016S-T022A-S101G-S103G-V104I, P014N, T022A-S101Q-S103A-V104I-L124I-S128A-

P129E-G159D-S188D-A232V-Q245R-N248D-E271F, T022A-G097A-S101G-S103A-V104I-Q109N-G159D-S188D-A232V-Q245R-N248D-E271F, T022A-S024R-S101G-S103A-V104I-G159D-S188D-A232V-N238Y-Q245R-N248D-E271F, G097P-A098Q-S101A-G102A, T033S-A158E-S166D-S188D, I035C, I033S-S128I-A158E-S188D, I008S, S078N-T213A, V028T-A215V, G020K-T022L-S078N-S128D-S166D-T213A-L217E, G146C-Q236L, S101G-S103A-V104I-N116A-S128N-Y209V-T213A-A232V, S024R-S078D-G118D-G159D-K237E, S024R-T033S-N116L-S128I, T022A-S024R-S101G-S103A-V104I-I107V-G159D-S188D-A232V-N238Y-Q245R-N248D-E271F, A048G, S212D, N062E-N116L-A158E-S188D, T022A-S024F-S101G-S103A-V104I-N116L-G118V-Y209A-T213A-A232V, S024F-S078N-G118R-S128D-S166D-T213A-L217E, A098F-S101G, S132K, T022A-S101G-S103A-V104I-N116A-G118V-Y209V-T213A-A232V, T022A-T033S-S101G-S103A-V104I-N116L-Y209A-G211Q-A232V, G097P-A098Q-S099I-S101A-G102A-V104I, G097P-S099T-S101A-S103A, A016S-T022A-S024F-T033S-S101G-S103A-V104I-N116L-S128N-Y209V-A232V, A098Q-S099T-S101G-V104I, G020K-T022L-S024F-G118R-S128D-S166D-T213A-L217E, G097P-A098Q-S099G-S101G, G097P-A098Q-S099A-G100S, T033S-N062E-G118R-S166D-S188D, A016S-T022A-S024F-S101G-S103A-V104I-N116L-G118V-Y209V-T213A-A232V, N062E-S078G-G118S-P129E-S188D-Q245R-H249R, S024F-T033S-S101G-S103A-V104I-N116L-S128N-Y209V-T213A-A232V, G097P-S099G-S101G-S103A, A098F-G102A-V104I, S078D-G118S-Q245R-N248D, G097P-A098Q-S099A-G102A, G097P-A098Q-G100S-S103A, T022A-S024R-N062E-S101G-S103A-V104I-P129E-S188D-A232V-Q245R-N248D-E271F, S078G-G118D-Q245R-H249R, G097P-S099A-G100S-S101A, G097P-S099G-S103G, G020K-S024F-S128D-S166D-T213A-L217E, I008N, N269A, A088T, 1038S, A016S-T022A-S101G-S103A-V104I-N116A-G118V-Y209A-T213A-A232V, G097P-A098F-S103A-V104I, A098F-S099A, T022A-N076D-S101G-S103A-V104I-I107V-G159D-S188D-A232V-N238Y-Q245R-N248D-E271F-A272V, A098Q-S099I-G100S-V104L, G097P-S099I-V104L, A098Q-S099T-S103A-V104I, A016S-T022A-S103G-S128N, T022A-T033S-S166D-S188D, G097P-G100S-S103A, T022L-S024F-S078N-T213A-A232T, A013S, G097P-S101A-G102A-S103A, A016S-T022A-S101A-V104L-L111V-S128N, G097P-A098Q-S099I-G102A, S024R-S078G-G118D-N248D, G020K-S078N-S128D-S166D-T213A-L217E, G020R-S078G-G118D-N248D, A085S, A016S-T022A-S128N, S024F-S078N-G118R-S128D-S166D-L217E, A098Q-S099A-G100S-V104L, S024R-S078D-G118D-G159D-N248D, A098Q-S103A, N062E-A158E-S166D, G020K-S024F-G118R-S128D-S166D-L217E, G097P-A098F, G080F, G097P-S099A-S103A-V104I, T022A-S101A-L111V-S128N-L148I, A016S-S101G-S103A-V104I, T022A-N062Q-S101Q-S103A-V104I-L124V-P129S-G159D-S188D-A232V-Q245R-N248D-E271F, G097P-A098F-S099T-S101G-V104I, A073Q, K251C, A016S-T022A-S101A-S103A-V104L-L148I, G097P-A098Q-G102A-S103G, G020R-S078G-G118D-Q245R-N248D, S099A-G100S-S103A, T038A, T022A-S024R-S101G-S103A-V104I-G159D-S188D-A232V-N238Y-Q245R-N248D-A270V-E271F-A272V, T022L-S078N-S128D-T213A-L217E, T022A-S024R-N043R-N076D-S101G-S103A-V104I-P129E-G159E-S188D-A232V-Q245R-N248D-E271F, N116L-S128I-A158E-S166D, A016S-T022A-T033S-S101G-S103A-V104I-N116L-Y209A-P210Q-T213A-A232V, S049V-V199I, T022A-S103G-V104I-L148I, A016S-S101G-V104L, A098F-S099T-S101G-G102A-V104I, T022A-A158E-S166D-S188D, A016S-T022A-T033S-S101G-S103A-V104I-N116L-S128N-Y209V-G211Q-A232V, T022A-S024G-N076D-G097A-S101G-S103A-V104I-Q109G-G159D-S188D-L217Q-A232V-Q245R-N248D-E271F, A016S-S024F-T033S-S101G-S103A-V104I-N116A-Y209V-T213A-A232V, N062E-N116L-G118R-S128I-A158E-S188D, N062E-S128I-S188D, G097P, T022A-S024F-T033S-S101G-S103A-V104I-N116A-S128N-Y209A-G211Q-T213A-A232V, S024R-S078G-G118S-P129E-Q245R-H249R, S049D, G097P-A098Q-S099T-G100S, T022A-S024R-T033S-N116L-G118R-S128I-S188D, T022A-T033S-S101G-S103A-V104I-N116A-Y209A-T213A-A232V, T022L-S078N-G118R-S128D-S166D-L217E, S078G-G118D-P129E-N248D, S099A-V104L, T022A-N043R-S101G-S103A-V104I-A158E-S188D-A232V-Q245R-N248D-E271F, A098Q-V104L, T022A-T033S-G118R-S128I-S166D-S188D, G097P-S099T-S101A, W006Y, S024R-N062E-S078G-G118D-P129E-S188D-Q245R-H249R, S024R-S078D-G118D-Q245R-N248D, T022A-N076D-S101G-S103A-V104I-I107V-P129E-G159D-S188D-A232V-N238Y-Q245R-N248D-E271F, T022A-S101N-S103A-V104I-L124V-L126I-S128A-P129E-G159D-S188D-A232V-Q245R-N248D-E271F, B015T, G097P-S099T-S101G-G102A-S103A-V104I, A016S-V104L-L111V-S128N, G097P-A098F-S099T, S049I, A016S-S103G-V104L-L148I, N062E-S078G-G118D-S188D-N248D, G020R-N062E-S078D-G118S-G159D-S188D-K235R-N248D, T022A-S024R-N116L, S024R-T033S-S128I, N062E-S078D-G118D-Q245R-N248D-H249R, A098F-S099A-S103A-V104I, V004Y, T022L-S024F-S078N-T213A, A016S-S101G-S103A-V104I-N116L-G118V-Y209A-G211Q-A232V, G097P-A098Q-G102A-S103G-V104I, S078G-G118S-H249R, S024F-S101G-S103A-V104I-N116A-S128N-Y209V-A232V, G097P-V104I, S024F-T033S-S101G-S103A-V104I-N116A-S128N-Y209A-T213A-A232V, A098Q-S099G-V104L, N062E-S078D-G118D-P129E, L196K, S078G-G118D-N248D-H249R, S087M, T022A-S101G-S103A-V104I-Q109G-S128A-G159D-S188D-L217Q-A232V-Q245R-N248D-E271F, S216N-T253C, G097P-A098Q-S101G-G102A-V104I, G020K-T022L-G118R, A016S-T022A-S101A-S103G-V104I-L111V, A098F-S099A-G102A, T033S-N062E-G118R-S128I-A158E, A098Q-S099T-S101A, G020R-N062E-S078D-G118S-P129E-G159D-S188D-Q245R-N248D, V011L, A098F-S099A-S101A, F050K, N062E-S078G-G118S-G159D-S188D-N248D, V051A, T022A-T033S-G118R-S128I-A158E-S166D, V051A-S212D, P014W, Q012E, T022A-T033S-S128I-A158E-S188D, T022A-S024R-N062E-N076D-S101G-S103A-V104I-P129E-S188D-A232V-Q245R-N248D-E271F, G097P-S103A, S078G-G118D, G020R-S024R-N062E-S078G-G118D-S188D-Q245R-H249R, G097P-A098Q-G102A-V104L, T022A-S101N-S103A-V104I-L124V-S128A-G159D-S188D-A232V-Q245R-N248D-E271F, A098Q-S099T-S101A-G102A-S103A-V104I, A016S-L111V-S128N, T022A-N062E-N116L-S128I-A158E, G080C, S024R-S078D-G118S, G097P-A098F-S099G, A016S-S024F-T033S-S101G-S103A-V104I-N116L-S128N-Y209V-T213A-A232V, G097P-S099G-G100S-S103A, S212A, S024R-N062E-S078D-G118S-P129E-G159D-S188D-N248D-H249R, T022A-S103G-V104L-S128N-L148I, T022A-S101N-S103A-V104I-L124T-S128A-P129S-G159D-S188D-A232V-Q245R-

N248D-E271F, A016S-T022A-S103G-V104L-S128N-L148I, G097P-A098Q-S101A-V104I, A016S-S101A-V104I, V026D, G097P-S101A-G102A-S103A-V104I, A016S-T022A-S024F-T033S-S101G-S103A-V104I-N116L-S128N-Y209A-T213A-A232V, T033S-A158E-S188D-A272D, A048V, G020K-T022L-S078N, G020K-G118R-T213A, T022A-S103A-V104L-L148I, T022A-N062E-S128I-A158E-S166D, G097P-A098Q-S099G-G100S-V104I, S049V, G097P-A098Q-S099T-S101A-S103G, G097P-A098F-S099A-S101A-V104I, S128I-A158E-S166D-S188D, S128D-S166D, S099G-G102A-V104I, T022A-S166D, A016S-T022A-S101G-S103A-V104I-N116L-Y209V-T213A-A232V, T022A-T033S-S101G-S103A-V104I-G118R-S128L-G159D-S188D-A232V-Q245R-N248D-E271F, G097P-S099A-S103G, A016S-T033S-S101G-S103A-V104I-N116L-S128N-Y209A-G211Q-T213A-A232V, S078G-G118S, T033S-G118R-S128I-A158E-S166D-S188D, S024R-N062E-S101A-S103A-V104I-S188D-M222S-A232V-Q245R, S099T-S101A-G102A-S103A-V104L, S056F, T022A-G097A-S101Q-S103A-V104I-L124V-L126I-S128A-P129E-G159D-S188D-A232V-Q245R-N248D-E271F, T022L-S024F-S128D-L217E, T022A-S101Q-S103A-V104I-L124V-L126I-S128A-G159D-S188D-A232V-Q245R-N248D-E271F, G020R-S078G-G118S-H249R, P129E-G159D-N248D, G020R-N248D, G061E-G097A-S128A-P129E-G159K-L217Q, Q245R-N248D-H249R, P129E-G159D-S188D, S024G-N076D-S078N-S101N-S128A-L217Q-N218S, G020R-S024R-Q245R, N062E-P129E-G159D-N248D, S024G-S078N-G097A-S101N-Q109N-L217Q, G020K-G102A-S128L, G020K-S078N-S101D-S128Q, S024G-S078N-G097A-S101N-S128A, G020K-S024G-N062E-S101Q-Q109G-N116L-S188D, G020K-S078N-S101D-S240R, G020K-N043R-S128L-L217E-S240R, S078N-S101G-Q109N-L217Q, S024G-G097S-S101N-S128A-S188D, S078N-L217E-E271L, G097S-S101Q-Q109N-L217Q, G020K-N062E-N116L-M222S, G020K-N062E-S078N-N116L-S128Q-T213A, G020K-S024G-N062E-S101Q-Q109G-N116L-S188D-L217Q, S024G-S078N-G097A-S101Q-S128A-L217Q, S078N-S101D-S128L-E271L, G020K-N062E-S101N-N116L, G020K-N062E-S101Q-Q109N-N116L-M222S, G020K-N062E-S101Q-Q109G-N116L-M222S, G020K-S024G-N062E-S078N-G097S-S101G-Q109G-N116L-L217Q-M222S, G020K-S024G-N062E-S078N-S101N-N116L-S128A-M222S, G020K-N062E-S078N-S101N-Q109N-N116L-S188D-M222S, G020K-S024G-N062E-S101N-Q109N-N116L-S188D-M222S, G020K-S024G-N062E-G097S-S101Q-N116L-L217Q, G020K-N062E-G097S-S101N-Q109G-N116L-S128A-S188D, S078N-G097A-S101Q-Q109G-S128A, S024G-G097A-S101N, S024G-G097A-S101Q-Q109N-S128A-S188D, G097A-S101N-S128A-S188D, S024G-G097S-S101G-S128A-L217Q, S078N-G097A-S101G-Q109N-S128A-L217Q, S024G-G097S-S101Q-Q109N-S128A, G097A-S101N-Q109G-S128A, S024G-G097A-S101Q-Q109G-L217Q, S024G-S078N-A085G-G097A-S101N-S128A-S188D-M222S, S024G-S078N-G097S-S101Q-L217Q, S024G-S101D-S128Q-L217E, S078N-G097A-S101N-M222S, S024G-N076K-S078N-G097A-S101G-S128A-S188D-M222S, S024G-S101G-S128A-M222S, S024G-S078N-G097A-S101G-S188D, G102A-L217E-N218D, S078N-G100S-S101D, G020K-N043R-N062E-S078N-S128L-L217E, G020K-N043R-S101D-S128L, G020K-G100S-S101D-S128L-S240R, S078N-S128Q-L217E, G020K-S078N-L217E-E271L, N062E-S078N-L217E, N062E-L217E, G020K-S078N-S101D-S128Q-L217E, G020K-S078N-S101D-S128L-S240R, G020K-N123G, G020K-S128Q-T213A-M222S, S078N-L217E, G020K-N062E-S128I-L217N, G020K-N062E-S078N-S128Q-L217N, G097S-S101N-Q109G-S128A-S188D-M222S, G020K-S024G-N062E-S101Q-Q109N-N116L-S188D, G020K-N062E-S078N-N116L-S128I-L217N, S024G-S078N-G097A-S101N-Q109G-S188D, S024G-G097A-S101Q-Q109N-L217Q, G020K-S101D-S128L, S101N-Q109G-S128A, S078N-S101D-L217E, S024G-S078N-S101N-S128A-M222S, G020K-S024G-N062E-G097A-S101Q-N116L-S128A-S188D, S024G-S078N-G097A-S101N-Q109N-S128A-M222S, G020K-N062E-S078N-G097A-S101N-N116L-S128A-S188D-L217Q, G020K-S024G-N062E-S078N-G097S-S101Q-N116L-S188D, G020K-N062E-S078N-G097S-S101G-N116L-M222S, G020K-S024G-N062E-S078N-S101N-N116L-M222S, G020K-S024G-N062E-G097S-S101Q-N116L, G020K-S024G-N062E-S101Q-Q109G-N116L-S128A-S188D, G020K-S024G-N062E-G097S-S101N-Q109N-N116L-S128A-S188D-L217Q, G020K-N062E-S078N-G097S-S101N-N116L, S024G-S078N-S101G-Q109G-M222S, S078N-G097A-S101G-Q109G-S128A, S078N-G097S-S101N-Q109N-S128A, S078N-G097A-S101N-Q109N-S188D, S024G-S101N-S128A-S188D-M222S, S101Q-Q109N-S188D-M222S, S101D-G102A-L217E, G020K-N062E-S078N-S101D-L217E, G020K-S078N-S101D-I107T-S128L-S240R, G020K-S078N-G100S-L217E-N218D, G020K-N043R-S101D, N043R-G100S-S128L-L217E, G020K-S078N-S101D-S128L-L217E-E271L, G020K-S101D-S128L-E271L, G020K-S101D-N116L-S128L-T213A, G020K-N062E-S078N-T213A-L217N, G020K-N062E-N116L-L217N, G020K-N062E-S128I-T213A, N062E-S101D-S128L-S240R, G097S-S101N-S128A, G020K-N062E-S078N-N116L-T213A-L217N, G020K-S101D-M222S, S024G-S101G-Q109G, G097A-S101Q-Q109G, G097S-S101Q-Q109N-S188D, G020K-N062E-G097S-S101N-N116L-S128A-S188D-L217Q, S078N-S101Q-S128A-M222S, S078N-G097A-S101Q-Q109N, S024G-S078N-G097A-S101Q-S128A-S188D, S078N-S101D-G102A, G020K-N062E-S078N-G097S-S101Q-Q109G-N116L-S128A-S188D-M222S, G020K-S024G-N062E-S078N-G097S-S101N-Q109N-N116L-S188D-L217Q-M222S, G020K-N062E-G097S-S101Q-N116L-S128A, G020K-S024G-N062E-G097S-S101Q-N116L-S128A-S188D-L217Q, S024G-S101N-Q109N-S128A, S024G-G097S-S101Q-S128A-S188D, S024G-S101Q-L217Q, G097S-S101G-S128A, S024G-S078N-S101Q-S128A-L217Q, S024G-S078N-G097S-S101N-S188D, S024G-G097A-S101N-S128A-M222S, G097A-S101Q-Q109N-S188D-M222S, S024G-S078N-G097S-S101Q, G020K-S101D-S128L-S212P-L217E-S240R, G020K-S101D-S128L-L217E-N218S-S240R, S101D-S128Q, G020K-N062E-S078N-E271L, S101D-E271L, S101D-S240R-E271L, G020K-S101D-E271L, G020K-N116L-S128L-T213A-M222S, G020K-N116L-S128Q-M222S, G020K-N062E-V084A-S128Q-M222S, G020K-N062E-S078N-N116L, S078N-S101N-Q109G-S128A-M222S, S024G-G097S-S101Q-Q109G, G020K-N062E-T213A-L217N, G097S-S101G-S128A-S188D, G020K-S240R, N062E-S078N, G020K-S128Q-M222S, S078N-G097S-S101G-Q1090, G020R-S024G-N043R-S078N-S101Q, G097S-S101N-Q109G-S128A-M222S, S024G-G097S-S101G-Q109N, S024G-S078N-G097A-S101G-Q109N, G020K-N062E-S078N-S101N-N116L-S128A-S188D-L217Q, G020K-N062E-S101Q-Q109G-N116L-S128A-M222S, G020K-S024G-N062E-S101Q-Q109N-N116L, S024G-S078N-S101Q-M222S, S024G-G097A-S101Q-

Q109G-S128A, S101Q-Q109N-L217Q, S101Q-Q109G-S188D-L217Q, S024G-G097A-S101N-S188D-M222S, S024G-S078N-G097A-S101Q-Q109N, G097A-S101Q-S128A, G097A-S101Q-Q109G-S128A, S024G-G097S-S101Q-M222S, S078N-S101D-L217E-S240R, G020K-G100S-S128L, G020K-N043R-S078N-S128L-S240R, G020K-N043R-S101D-S240R, G020K-N043R-S078N-S128L, N062E-S128L, G020K-S078N-S101D-S128L, S078N-S101D, G020K-S101D-N116L-T213A-M222S, G020K-T213A-M222S, G020K-N116L-T213A, 0020K-N116L, G020K-N062E-S128Q-L217N, S078N-G097S-S101G-Q109N-S128A, S078N-S101Q-Q1090, N062E-S078N-S128L, G020K-N062E-N116L-S128Q-T213A-L217N, G020K-N116L-T213A-M222S, G020K-S024G-N062E-S101Q-Q109H-N116L-M222S, G020K-N116L-S128Q-T213A-M222S, S024G-G097S-S101N, G020K-P055T-N062E-N116L-L217N, S024G-S101Q-S128A-S188D-M222S, G020K-M222S, G020K-N062E-S078N-G097A-S101N-N116L-S188D-L217Q, G097S-S101G-Q109N-M222S, G020K-S024G-N062E-S078N-G097A-S101N-N116L-S128A-L217Q-M222S, G020K-S024G-N062E-G097S-S101N-Q109N-N116L-S128A-S188D-L217Q-M222S, G020K-N062E-S078N-S101Q-N116L-S128A, S024G-S078N-S10 IN-Q109G-S188D-L217Q-M222S, S101N-Q109N-S128A-M222S, S101Q-Q109G-S128A-S188D, G097A-S101G-S188D-M222S, S078N-G097S-S101N-Q109G-S128A-S188D-L217Q-M222S, S024G-G097A-S101Q-M222S, S024G-G097S-S101N-Q109N-S128A-M222S, S024G-S078N-G097S-S101N-M222S, G020K-G102A-S240R, S078N-S128Q-E271L, G020K-N062E-S078N-S128Q, G020K-N062E-S078N-T213A-M222S, G020K-N062E-S078N-S128I-T213A-L217N, S078N-G097A-S101N, G020K-N062E-N116L-S128I-T213A-L217N, S024G-G097A-S101Q-S128A-S188D-M222S, S024G-S078N-G097A-S101N, S024G-S078N-G097S-S101G-M222S, G020K-N062E-S078N-N116L-S128Q-T213A-M222S, G020K-N062E-S128Q-M222S, G020K-N062E-S101Q-N116L, G020K-N062E-S101Q-Q109G-N116L-S188D-L217Q, G020K-S024G-N062E-G097A-S101N-N116L-S128A-S188D, G020K-S024G-N062E-S078N-S101Q-Q109G-N116L-S188D-M222S, S078N-G097S-S101N-Q109G-S128A-L217Q-M222S, S024G-S078N-S101N-Q109G-S128A-L217Q-M222S, G097A-S101Q-S128A-S188D, S024G-S078N-G097A-S101N-Q109N-S128A-S188D-L217Q-M222S, S024G-S078N-G097A-S101G-L217E-M222S, S078N-G097S-S101Q-Q109G-T274I, G097A-S101G-M222S, S101N-Q109N, G020K-L217E-S240R-E271L, S128Q-S240R-E271L, G020K-S101D-N116L-S128Q-M222S, G020K-P055L-N062E-N116L-S128I, G020K-N062E-S101G-N116L-S128A-M222S, G020K-S078N-S101D-S128L-S240R-E271L, G020K-N062E-S078N-G097S-S101Q-Q109N-N116L-L217Q-M222S, S078N-S101D-S240R-E271L, S024G-S078N-S101N-Q109G-L217Q-M222S, G097A-S101G-Q109G-L217Q-M222S, G020K-S024G-N062E-S078N-G097S-S101N-N116L-S128A-L217Q-M222S, G020K-S078N-S128L-E271L, G020K-N062E-S078N-N116L-L217N, G097A-S101G-Q109G-S188D-L217Q-M222S, S024G-S078N-G097S-S101N-Q109G-S128A, G020K-S024G-N062E-S078N-G097S-S101N-N116L-S188D-M222S, G020K-S024G-N062E-G097S-S101Q-N116L-S128A-M222S, G020K-N062E-S078N-G097A-S101G-Q109G-N116L-S128A-S188D-L217Q, G020K-N062E-S101G-N116L-S128A-L217Q-M222S, S024G-G097A-S101Q-S188D-M222S, S024G-S101G, T072V-S101Q-S128A, S078N-G097S-S101N-Q109N, S024G-G097A-S101N-Q109N-S188D-L217Q-M222S, S078N-S101Q-Q109N-S188D-L217Q-M222S, G020K-N043R-N062E-S128L-L217E, N043R-G102A-S128L-S240R, 0020K-N116L-N123G-T213A-M222S, G020K-S101D-S128Q-T213A-M222S, S024G-G097A-S101Q-Q109G, G020K-S078N, G020K-N062E-S101Q-N116L-S188D, G020K-N062E-S078N-G097S-S101N-Q109G-N116L-S188D-L217Q-M222S, G020K-S024G-N062E-G097S-S101G-N116L-S128A-L217Q-M222S, G020K-N062E-G097A-S101N-N116L-S128A-L217Q-M222S, S078N-G097S-S101G-Q109N-M222S, S024G-G097A-S101Q-Q109N, S024G-G097S-S101N-Q109N-S128A-S188D-L217Q-M222S, S078N-S101N-Q109N-S188D-L217Q-M222S, S078N-S101D-S128L-L217E-S240R, G020K-N062E-S101D-N116L-S128L, G097S-S101N-S188D-M222S, G020K-S078N-S128L-S240R-E271L, G020K-N062E-N116L-S128I-T213A, G020K-S024G-N062E-S078N-G097S-S101Q-N116L-S188D-M222S, G020K-N062E-S101Q-Q109G-N116L-L217Q-M222S, G020K-S024G-N062E-G097A-S101Q-N116L-L217Q-M222S, G020K-N062E-S078N-G097S-S101Q-N116L-S128A-S188D-M222S-A232T, G020K-S024G-N062E-S078N-G097S-S101Q-Q109N-N116L-S128A-L217Q-M222S, G020K-N062E-G097A-S101Q-N116L-S188D-M222S, S024G-S078N-G097S-S101N-Q109G-S128A-L217Q-M222S, S024G-G097A-S101Q-Q109N-S128A-S188D-L217Q-M222S, G020K-N043R, G020K-N043R-S078N-G102A-S128L, G097R-S101D, G020K-N062E-S078N-I107V-N123G-S128I, G020K-N062E-S078N-N116L-N123G-T213A, G020K-N062E-N116L-S128I-M222S, G020K-N043R-S240R, S078N-S101D-S128L, G020K-S078N-S128Q-E271L, S078N-S101G-S128A-S188D-L217Q-M222S, S078N-G097S-S101G-Q109N-S128A-L217Q-M222S, or G020K-N062E-N116L-S128Q-T213A-M222S (List 16), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from G020R-T022W-S024R-R045T-S101A-N204S-G211Q, T022W-S024R-S101A-P210I-T213A, G020R-S101A-G211Q, G020R-S024R-S101A-P210I-G211Q-T213A, G020R-S101A-P210I-T213A, T022W-S024R-N043R-S101A-P210I, G020R-S024R-N043R-R045T-S101A-G211Q, T022R-S101T-S103N-V104L-A232M-Q245R, G020R-T022A-S024R-R045T-S101A-T213A, T022R-S101G-S103N-V104I-A232M-Q245R, G020R-T022W-S024R-S101A-N116L-G211Q-T213A, G020R-T022W-N043R-S101A-N116L-G211Q, G020R-T022W-N043R-R045T-S101A, T022W-N043R-R045T-S101A-P210I-T213A, G020R-S024R-R045T-S101A-Q109R-P210I-G211Q-T213A, S024R-N043K-S101A-N204D-P210I, G020R-S024R-R045T-S101A-P210I, S024R-N043R-R045T-S101A-P210I-T213A, G020R-S024R-R045T-S101A-T213A, T022R-S101A-S103N-V104I-A232T-Q245R, G020R-T022W-S024R-R045T-S101A-N204S-P210I-G211Q, T022W-N043R-S101A-P210I-G211Q, G020R-S024R-N043K-R045T-S101A-N116L-P210I, T022A-S101G-S103A-V104I-I107V-L217Q-A232V-Q245R, S024R-N043R-R045T-S101A-G211Q-T213A, T022R-S101A-S103G-V104I-A232M-Q245R, T022R-S101G-S103N-V104L-A232V-Q245R, S024R-S078G-G118S-Q245R-N248D-H249R, S024R-N043R-S101A-P210I-T213A, T022K-S101N-S103A-V104I-A232T-Q245R, G020R-N043R-S101A-P210I-G211Q, T022R-S101T-S103A-V104I-A232M-Q245R, S024R-V026A-N043R-S101A-P210I-G211Q, T022A-S078N-S101G-S103A-V104I-S128A-L217Q-A232V-Q245R, T022K-S101T-S103G-V104I-A232L-Q245R, G020R-T022W-S024R-N043R-R045T-S101A-G211Q, G020R-S024R-S078G-G118D-Q245R, T022A-S101N-S103A-V104I-S128A-P129S-A232V-Q245R, T022A-G097A-S101G-S103A-V104I-L217Q-A232V-Q245R, G020R-T022W-N043R-S101A-G211Q-T213A, N018K-G020R-S024R-R045T-S101A-P210I-G211Q-T213A, G020R-T022W-S024R-N043R-R045T-S101A, T022R-S101N-S103A-V104L-A232T-Q245R, G020R-S024R-S101A-T213A, T022R-S101N-S103G-V104I-A232V-Q245R, G020R-T022W-S024R-S101A-G211Q-T213A, T022A-S024G-S101G-S103A-V104I-S128A-L217Q-A232V-Q245R, S024R-S078G-G118D-P129E-Q245R-H249R, T022R-S101T-S103A-V104L-A232L-Q245R, G020R-S024R-S101A-G211Q-T213A, T022A-S024G-S101G-S103A-V104I-L217Q-A232V-Q245R, G020R-T022W-N043R-V051A-S101A-P210I-G211Q, S024R-S078G-G118D-Q245R, N043R-S101A-P210I, T022Y-S101G-S103N-V104I-A232L-Q245R, G020R-T022W-N043R-S101A-T213A, G020R-S024R-S078D-G118S-S188D-Q245R-H249R, T022Y-S101N-S103N-V104I-A232T-Q245R, G020R-T022W-S024R-F050L-S101A-G211Q-T213A, N018S-T022W-S024R-N043R-S101A-G211Q, T022A-S101G-S103A-V104I-S128A-P129S-L217Q-A232V-Q245R, T022R-S101N-S103N-V104I-A232V-Q245R, T022A-S024G-S078N-G097S-S101Q-S103A-V104I-L217Q-A232V-Q245R, S101A-P210I-G211Q-T213A, G020R-N043R-R045T-S101A-P210I-G211Q-T213A, T022R-S101A-S103N-V104I-A232M-Q245S, G020R-T022W-N043R-R045T-S101A-G211Q, G020R-T022W-N043R-R045T-S101A-N116L-P210I, G020R-S024R-S078D-G118S-Q245R, G020R-T022W-S024R-N043R-S101A-P210I-G211Q-T213A, G020R-S024R-N043R-R045T-V051A-S101A-P210I-G211Q, T022A-S101G-S103A-V104I-P129S-L217Q-A232V-Q245R, G020R-S078G-G118D-Q245R-N248D-H249R, T022K-S101A-S103N-V104L-A232T-Q245R, T022A-N076D-S078N-G097S-S101G-S103A-V104I-L217Q-A232V-Q245R, S024R-N043R-R045T-S101A-P210I, T022A-S024G-G061R-S078N-S101G-S103A-V104I-S128A-A232V-Q245R, T022A-S078N-S101G-S103A-V104I-L217Q-A232V-Q245R, T022A-S024G-S078N-S101Q-S103A-V104I-S128A-L217Q-A232V-Q245R, T022Q-S101T-S103A-V104L-A232V-Q245R, G020R-T022W-S024R-R045T-S101A-G211Q, PO 14R, T022R-S101A-S103N-V104L-A232M-Q245R, T022K-S101G-S103N-V104I-A232V-Q245R, G020R-S024R-S078D-G118D-Q245R, T022A-G097S-S101N-S103A-V104I-L217Q-A232V-Q245R, G020R-S024R-S101A-P210I-T213A, T022K-S101N-S103N-V104I-A232V-Q245R, T022Y-S101T-S103A-V104I-A232L-Q245R, T022A-N076D-S078N-S101G-S103A-V104I-S128A-L217Q-A232V-Q245R, G020R-S024R-N043R-R045T-S101A-P210I-G211Q-T213A, G020R-R045T-S101A-P210I-T213A, G020R-S078D-G118S-Q245R-H249R, G020R-T022W-R045T-V051A-S101A, T022R-S101T-S103A-V104I-A232V-Q245R, N043R-S101A, G020R-S024R-N043R-R045T-S101A-G211Q-T213A, T022R-S101G-S103G-V104I-A232L-Q245R, G020R-S101A-P210I, T022K-S101T-S103N-V104I-A232V-Q245R, G020R-T022W-N043R-V051A-S101A, G020R-T022W-N043R-S101A, G020R-T022W-S024R-N043R-S101A-P210I, G020R-T022W-S024R-N043R-R045T-S101A-P210I-T213A, G020R-N043R-R045T-S101A-T213A, T022A-S024G-S078N-S101N-S103A-V104I-L217Q-A232V-Q245R, T022Y-S101N-S103N-V104L-A232T-Q245R, G020R-S101A-N116L-P210I-G211Q, T022R-S101A-S103N-V104L-A232L-Q245R, G020R-S024R-N043R-S101A, T022R-S101G-S103A-V104L-A232T-Q245R, G020R-S024R-S101A-G211Q, T022A-S101Q-S103A-V104I-P129S-A232V-Q245R, T022A-S024G-G097A-S101G-S103A-V104I-L217Q-A232V-Q245R, T022A-S024G-S078N-S101G-S103A-V104I-S128A-L217Q-A232V-Q245R, T022K-S101A-S103N-V104I-A232T-Q245R, G020R-T022W-S024R-R045T-S101A, T022Y-S101G-S103A-V104I-A232V-Q245R, S024R-N043R-R045T-S101A-N116L-P210I-G211Q-T213A, T022A-S024G-S078N-S101N-S103A-V104I-S128A-L217Q-A232V-Q245R, G020R-N043R-S101A-P210I, T022A-S024G-S078N-G097A-S101G-S103A-V104I-L217Q-A232V-Q245R, T022R-S101T-S103N-V104I-A232V-Q245R, P055R, T022A-S101N-S103N-V104I-A232V-Q245R, G020R-T022W-S024R-N043R-N076D-S101A-P210I-T213A, G020R-T022W-S101A-P210I-T213A, T022Q-S101G-S103A-V104L-A232L-Q245R, T022W-S024R-N043R-R045T-S101A, T022A-S101G-S103A-V104I-L217Q-A232V-Q245R, T022K-S101N-S103A-V104I-A232L-Q245R, T022R-S101T-S103N-V104I-A232L-Q245R, G020R-S024R-N043R-R045T-S101A-P210I-T213A, T022A-S078N-S101N-S103A-V104I-S128A-A232V-Q245R, T022A-G097S-S101G-S103A-V104I-L217Q-A232V-Q245R, T022A-S078N-G097S-S101G-S103A-V104I-L217Q-A232V-Q245R, G020R-S024R-N062E-S078G-G118S-Q245R, T022K-S101A-S103N-V104I-A232L-Q245R, G020R-T022W-S024R-R045T-S101A-P210I-T213A, G020R-S024R-S078G-G118S-S188D-Q245R, T022R-S101T-S103A-V104I-A232V-Q245W, T022R-S101N-S103A-V104I-A232V-Q245R, T022K-S101T-S103N-V104I-A232T-Q245R, T022A-S024G-S078N-S101Q-S103A-V104I-L217Q-A232V-Q245R, T022A-S078N-G097A-S101N-S103A-V104I-A232V-Q245R, T022Q-S101G-S103N-V104I-A232L-Q245R, T022A-S078N-G097A-S101Q-S103A-V104I-Q109N-A232V-Q245R, T022Q-S101G-S103A-V104L-A232V-Q245R, T022A-S101G-S103A-V104I-S128A-L217Q-A232V-Q245R, G020R-T022W-N043R-R045T-S101A-P210I, T022R-S101N-S103N-V104I-A232T-Q245R, G020R-N043R-R045T-S101A-N116L-G211Q-T213A, T022Q-S101A-S103N-V104I-A232V-Q245R, T022W-S024R-N043R-R045T-S101A-N116L-P210I, T022A-S078N-G097S-S101N-S103A-V104I-L217Q-A232V-Q245R, G020R-S078D-G118D-Q245R-H249R, G020R-S024R-N043R-S101A-P210I-G211Q-T213A, T022R-S101G-S103N-V104I-A232V-Q245W, T022A-S101T-S103N-V104L-A232L-Q245R, T022A-S024G-S078N-G097S-S101N-S103A-V104I-S128A-L217Q-A232V-Q245R, T022R-S101T-S103N-V104I-A232T-Q245R, G020R-N043R-S101A-P210I-T213A, G020R-S024R-N043R-S101A-N116L-G211Q-T213A, S024R-N043R-R045T-S101A-N116L-P210I-G211Q, T022A-S024G-G097S-S101N-S103A-V104I-L217Q-A232V-Q245R, E271R, T022K-S101T-S103G-V104I-A232V-Q245R, N043R-S101A-P210I-G211Q, G020R-S024R-S078G-G118S-P129E-G159D-Q245R, T022R-S101T-S103A-V104I-A232I-Q245S, E271W, S024R-N043R-R045T-S101A-N116L-P210I-T213A, T022A-S024G-S078N-S101N-S103A-V104I-A232V-Q245R, T022A-E089G-G097A-S101N-S103A-V104I-S128A-A232V-Q245R, T022R-S101I-S103A-V104I-A232L-Q245R, T022R-S101G-S103N-

V104I-A232I-Q245S, T022A-S101G-S103A-V104I-A232M-Q245R, G020R-T022W-S024R-S101A-T213A, G020R-T022W-S024R-N043R-S101A-T213A, T022A-S024G-G097S-S101G-S103A-V104I-L217Q-A232V-Q245R, T022A-S024G-S078N-G097S-S101Q-S103A-V104I-S128A-L217Q-A232V-Q245R, G020R-S101A-T213A, E271S, G020R-S078G-G118S-Q245R-N248D-H249R, N043K, T022A-S101G-S103N-V104I-A232V-Q245R, T022Q-S101A-S103A-V104I-A232L-Q245R, G020R-T022W-S024R-R045T-S101A-T213A, G020R-S024R-S078G-G118S-Q245R-N248D-H249R, T022A-S024G-S078N-G097A-S101G-S103A-V104I-S128A-L217Q-A232V-Q245R, T022A-S024G-S078N-S101G-S103A-V104I-L217Q-A232V-Q245R, T022A-S024G-S101N-S103A-V104I-A232V-Q245R, G020R-T022W-S024R-S101A-N116L-P210I, G020R-T022W-N043R-R045T-S101A-T213A, T022A-S078N-G097A-S101N-S103A-V104I-L217Q-A232V-Q245R, T022A-S078N-S101N-S103A-V104I-L217Q-A232V-Q245R, T022R-S101N-S103G-V104L-A232V-Q245R, G020R-T022W-S024R-S101A-P210I-T213A, G020R-S024R-S078D-G118S-S188D-Q245R, G020R-S024R-S078D-G118S-G159D-Q245R, T022Y-S101T-S103A-V104I-A232M-Q245R, G020R-N043R-R045T-V051A-S101A-P210I-G211Q-T213A, G020R-T022W-S024R-N043R-R045T-S101A-T213A, T022A-S024G-S078N-G097S-S101G-S103A-V104I-L217Q-A232V-Q245R, T022A-S078N-S101Q-S103A-V104I-L217Q-A232V-Q245R, G020R-S024R-S101A-P210I-G211Q, T022Q-S101T-S103G-V104I-A232M-Q245R, G020R-N043R-S101A-G211Q-T213A, T022A-S101Q-S103A-V104I-P129S-L217Q-A232V-Q245R, T022A-S101T-S103N-V104I-A232V-Q245R, G020R-S024R-S078G-G118D-G159D-Q245R-N248D-H249R, G020R-T022W-R045T-S101A-P210I-G211Q, T022A-S078N-S101N-S103A-V104I-A232V-Q245R, T022R-S101T-S103N-V104I-S105G-A232V-Q245R, T022A-S024G-S078N-S101Q-S103A-V104I-A232V-Q245R, T022A-S101I-S103N-V104I-A232L-Q245R, T022Q-S101N-S103N-V104L-A232V-Q245R, T022R-S101N-S103N-V104L-A232M-Q245R, T022Q-S101G-S103N-V104I-A232T-Q245R, T022A-S101Q-S103A-V104I-L217Q-A232V-Q245R, T022Q-S101A-S103A-V104L-A232L-Q245R, G020R-N043R-R045T-S101A-G211Q-T213A, T022A-G097A-S101N-S103A-V104I-P129S-L217Q-A232V-Q245R, G020R-S024R-R045T-S101A-G211Q-T213A, T022A-S078N-G097A-S101G-S103A-V104I-S128A-A232V-Q245R, G020R-T022W-N043R-R045T-S101A-P210I-G211Q-T213A, T022R-S101N-S103N-V104I-A232L-Q245R, T022Y-S101G-S103A-V104I-A232M-Q245R, T022R-S101G-S103G-V104I-A232T-Q245R, T022A-S024G-S078N-G097S-S101N-S103A-V104I-L217Q-A232V-Q245R, G020R-S024R-S078G-G118D-N248D-H249R, T022A-S101A-S103N-V104L-A232V-Q245R, T022W-S024R-S101A-N116L-G211Q, G020R-S024R-S101A-T208A-P210I-G211Q, T022W-S024R-N043R-R045T-S101A-P210I-G211Q-T213A, T022Y-S101G-S103N-V104I-A232M-Q245R, T022R-S101I-S103A-V104L-A232T-Q245S, G020R-S024R-S078G-G118S-P129E-Q245R-N248D, T022A-S024G-S101Q-S103A-V104I-Q109N-A232V-Q245R, G020R-T022W-S101A, T022W-S024R-N043R-S101A-P210I-G211Q, G020R-S024R-N043R-S101A-P210I-G211Q, G020R-S024R-N062E-S078G-G118D-H249R, G020R-S024R-G047C-S101A-G211Q, G020R-S024R-S078D-G118D-P129E-Q245R-H249R, T022A-S101A-S103A-V104L-A232V-Q245R, T022A-S101T-S103N-V104L-A232M-Q245R, N018S-G020R-T022W-N043R-S101A-G211Q, T022Y-S101T-S103G-V104I-A232T-Q245R, T022K-S101A-S103A-V104I-A232M-Q245R, T022A-S024G-G097A-S101N-S103A-V104I-L217Q-A232V-Q245R, T022Y-S101N-S103N-V104L-A232V-Q245R, T022A-S101G-S103A-V104I-A232V-Q245R, T022A-G097A-S101G-S103A-V104I-P129S-A232V-Q245R, G020R-S078G-G118S-P129E-Q245R-H249R, T022A-G097S-S101G-S103A-V104I-S128A-L217Q-A232V-Q245R, T022Y-S101A-S103G-V104I-A232M-Q245R, S024R-S101A-G211Q, T022A-S024G-G097A-S101Q-S103A-V104I-Q109G-A232V-Q245R, T022A-S024G-S101G-S103A-V104I-S128A-A232V-Q245R, R045T-S101A-I107V-Q109R-P210I-G211Q-T213A, T022A-G097S-S101Q-S103A-V104I-L217Q-A232V-Q245R, T022K-S101T-S103A-V104I-A232T-Q245R, Q012R-T022A-S101G-S103A-V104I-N116L-Y209A-T213A-A232V, T022W-S024R-N043R-R045T-S101A-P210I, T022A-S101N-S103A-V104I-A232V-Q245R, T022A-S024G-S078N-G097A-S101N-S103A-V104I-A232V-Q245R, 0020R-S024R-S078G-G118S-G159D, T022Y-S101T-S103A-V104I-A232T-Q245R, T022Q-S101G-S103N-V104I-A232V-Q245R, S024R-S101A-P210I-T213A, T022A-S101N-S103A-V104I-L217Q-A232V-Q245R, T022A-S101G-S103N-V104L-A232L-Q245R, T022A-S024G-G097S-S101N-S103A-V104I-S128A-A232V-Q245R, T022A-S101G-S103A-V104I-S128A-P129S-A232V-Q245R, T022A-S101N-S103A-V104L-A232T-Q245R, S024R-S101A-P210I, T022Y-S101T-S103N-V104I-A232V-Q245R, G020R-T022W-N043R-S101A-N116L, T022Q-S101N-S103N-V104I-A232V-Q245R, S024R-S101A, T022A-S024G-S078N-S101Q-S103A-V104I-Q109N-S128A-A232V-Q245R, S024R-N043R-R045T-S101A-N116L-G211Q-T213A, S212W, T022K-S101G-S103A-V104L-A232M-Q245R, T022A-S024G-S101Q-S103A-V104I-L217Q-A232V-Q245R, S024R-N043R-R045T-S101A, G020R-S101A, G020R-S024R-S078G-G118D-P129E-Q245R-N248D-H249R, T022R-S101T-S103N-V104I-A232M-Q245R, S056K, T022A-S024R-N076D-S101G-S103A-V104I-A232V-Q245R-A270V, T022R-S101T-S103G-V104I-A232M-Q245S, G020R-T022W-R045T-S101A-P210I-G211Q-T213A, T022K-S101N-S103N-V104L-A232L-Q245R, T022W-S024R-N043R-R045T-S101A-V147I-P210I-G211Q-T213A, T022A-S101Q-S103A-V104I-Q109G-S128A-A232V-Q245R, T022A-S078N-G097S-S101Q-S103A-V104I-L217Q-A232V-Q245R, G020R-S024R-S078D-G118S-P129E-Q245R-N248D-H249R, S078G-G118D-Q245R-H249R, T022A-S101G-S103A-V104I-A232V-N238Y-Q245R-A272V, T022A-S024G-S101Q-S103A-V104I-A232V-Q245R, T022A-S078N-G097S-S101Q-S103A-V104I-A232V-Q245R, G020R-T022W-S024R-N043R-S101A-P210I-T213A, T022A-S024G-S101N-S103A-V104I-S128A-L217Q-A232V-Q245R, S056R, T022Y-S101T-S103N-V104I-A232L-Q245R, T022R-S101I-S103G-V104I-A232V-Q245S, T022W-S101A-P210I-G211Q, T022R-S101A-S103N-V104L-A232T-Q245S, T022Y-S101A-S103G-V104I-A232T-Q245R, T022R-S101I-S103A-V104L-A232T-Q245R, T022Q-S101G-S103A-V104I-A232T-Q245R, G020R-S024R-S078G-G118D-S188D-Q245R-H249R, V030I-N043R-S101A-G211Q-T213A, T022A-S101T-S103A-V104I-A232V-Q245R, T022A-S024G-S101N-S103A-V104I-S128A-A232V-Q245R, T022A-S101G-S103A-V104I-A232V-N238Y-Q245R, G020R-S078G-G118D-P129E-G159D-Q245R-H249R, S024R-S078D-G118S-S188D-Q245R-H249R, T022A-S101G-

S103A-V104I-A232V-Q245R-A270V, T022A-S024G-G097A-S101Q-S103A-V104I-A232V-Q245R, T022A-S101T-S103G-V104I-A232V-Q245R, G020R-T022W-S101A-T213A, T022A-S101G-S103A-V104I-S128A-A232V-Q245R, T022A-S101N-S103A-V104I-Q109G-A232V-Q245R, T022Q-S101N-S103N-V104L-A232L-Q245R, N018S-G020R-S101A-P210I-G211Q, G020R-S078D-G118S-S188D-Q245R-H249R, T022A-S101G-S103N-V104I-A232L-Q245R, T022R-S101T-S103G-V104L-A232V-Q245R, T022A-N076D-S101G-S103A-V104I-A232V-Q245R-A270V-A272V, T022Q-S101N-S103G-V104I-A232V-Q245S, G020R-N043R-R045T-S101A-G211Q, T022A-N076D-S101G-S103A-V104I-L217Q-A232V-Q245R, T022R-S101A-S103A-V104L-A232V-Q245S, T022A-S078N-S101Q-S103A-V104I-Q109N-A232V-Q245R, S024R-S078G-G118S-T180N-Q245R-N248D, V004M, T022A-S101T-S103N-V104I-A232T-Q245R, T022A-S078N-S101G-S103A-V104I-A230T-A232V-Q245R, T022Y-S101N-S103N-V104I-A232L-Q245R, G020R-S024R-S078D-G118S[2]G159D-Q245R-N248D, G020R-S024R-S078G-G118S-G159D-S188D-Q245R, G020R-N043R-R045T-S101A-P210I-T213A, S024R-S078D-G118D-Q245R-H249R, G020R-S024R-N043R-R045T-S101A-Q109R-T213A, T022A-S078N-S101N-S103A-V104I-Q109N-A232V-Q245R, G020R-S024R-N043R-S101A-N204D-G211Q-T213A, T022A-G097A-S101Q-S103A-V104I-A232V-Q245R, G020R-S024R-S078G-G118S-N248D, G020R-S024R-S078G-G118S-G159D-Q245R-N248D, T022A-S024G-S078N-S101N-S103A-V104I-S128A-A232V-Q245R, S024R-S078G-G118D-G159D-Q245R-H249R, T022K-S101T-S103N-V104L-A232V-Q245R, S024R-S078G-G118S-Q245R, T022A-S101A-S103G-V104I-A232L-Q245R, T022A-G097A-S101Q-S103A-V104I-S128A-A232V-Q245R, T022A-S024G-S078N-G097S-S101G-S103A-V104I-A232V-Q245R, G020R-S078D-G118S-Q245R, T022A-S024R-N076D-S101G-S103A-V104I-A232V-N238Y-Q245R-A270V-A272V, S101A-P210I-T213A, T022A-S101Q-S103A-V104I-S128A-P129S-L217Q-A232V-Q245R, A114L, A016S-T022A-S101G-S103A-V104I-N116A-Y209V-G211Q-T213A-A232V, T022A-S101N-S103A-V104I-S128A-P129S-L217Q-A232V-Q245R, T022R-S101A-S103N-V104I-A232L-Q245S, T022Q-S101N-S103A-V104I-A232M-Q245W, T022W-S024R-S101A-N204S-G211Q-T213A, T022A-S101N-S103A-V104L-A232M-Q245R, T022A-S024G-S101Q-S103A-V104I-Q109N-S128A-A232V-Q245R, G020R-S078D-G118S-P129E-Q245R-H249R, T022Q-S101T-S03A-V104I-A232T-Q245S, S024R-N043R-R045T-S101A-P210I-G211Q-T213A, T022R-S101N-S103G-V104I-A232T-Q245R, S024R-S101A-P210I-G211Q-T213A, T022A-S024G-N076D-G097A-S101G-S103A-V104I-S128A-A232V-Q245R, G020R-S024R-S078G-G118S-S188D-N248D-H249R, T022A-G097S-S101Q-S103A-V104I-Q109G-S128A-A232V-Q245R, G020R-S024R-R045T-S101A-P210I-T213A, T022A-S078N-G097S-S101N-S103A-V104I-S128A-A232V-Q245R, T022A-S024G-S078N-G097A-S101Q-S103A-V104I-A232V-Q245R, T022R-S101G-S103N-V104I-A232T-Q245W, T022K-S101G-S103A-V104I-A232V-Q245R, T022W-S024R-S101A-G211Q-T213A, S024R-N043R-S101A-P210I-G211Q, T022Q-S101T-S103G-V104I-A232T-Q245R, T022A-S101G-S103A-V104I-A232V-Q245R-A272V, T022K-S101G-S103N-V104L-A232M-Q245R, T022A-S024G-G097A-S101Q-S103A-V104I-Q109N-A232V-Q245R, S078D-G118S-G159D-Q245R-H249R, G020R-T022W-S024R-A069T-S101A-P210I-T213A, T022A-S101N-S103A-V104I-S128A-L217Q-A232V-Q245R, G020R-T022W-S024R-N043R-R045T-S101A-P210I-G211Q, G020R-S024R-S078D-G118D-G159D-S188D-Q245R-H249R, T022A-S078N-S101N-S103A-V104I-S128A-L217Q-A232V-Q245R, G020R-S078G-G118D-G159D-Q245R-N248D-H249R, T022W-R045T-S101A-T213A, G020R-S024R-S078N-G097A-S101A-Q109N-N116L-L217Q, T022R-S024F-S101G-S103A-V104I-A232V-Q245R-E271H, G020R-S024R-S078N-G097S-S101Q-S128A-L217Q, T022R-S101G-S103A-V104I-A232V-Q245R-E271H, G020R-S024R-S101G-N116L-S128A, G020R-S024R-S101A-Q109N-N116L-S128A, T022R-S024F-S101G-S103A-V104I-A232V-Q245R-T260M, G020R-S024R-S078N-S101N-N116L-S128A, G020R-S024R-G097A-S101A-Q109G-N116L, G020R-S024R-S101N-S128A, G020R-S024R-S078N-S101G-S128A-L217Q, T022R-S024F-S101G-S103A-V104I-A232V-Q245R, T022R-S078N-G097S-S101Q-S103A-V104I-Q109N-N116L-A232V-Q245R, G020R-S024R-G097A-S101A-Q109N-N116L-S128A, G020R-S024R-G097S-S101N-Q109N-S128A, T022R-S101G-S103A-V104I-A232V-P239G-Q245R, G020R-S024R-G097S-S101A-S128A, G020R-S024R-S101G-Q109N-N116L-A215V, G020R-S024R-S078N-G097S-S101Q-Q109G-N116L-S128A, G020R-S024R-S078N-G097S-S101N-Q109N, G020R-S024R-S101G-S128A, T022R-S101G-S103A-V104I-A232V-Q245R-T260K-L267N, T022R-S101G-S103A-V104I-S128A-A232V-Q245R, T022R-S024G-G097S-S101N-S103A-V104I-A232V-Q245R, T022R-S024F-S101G-S103A-V104I-V121F-A232V-Q245R, G020R-S024R-G097A-S101Q-N116L-S128A-L217Q, T022R-G097A-S101N-S103A-V104I-N116L-A232V-Q245R, G020R-S024R-S078N-G097S-S101A-N116L-S128A, G020R-S024R-G097A-S101G-S128A-L217Q, T022R-S078N-S101G-S103A-V104I-N116L-A232V-Q245R, G020R-S024G-N043R-S078N-S101Q-Q109G-N116L-S128A-Q206R-L217Q, G020R-S024R-S078N-G097S-S101Q-N116L-S128A, G020R-S024R-S078N-G097S-S101N-Q109N-N116L-S128A, G020R-S024R-S101N-Q109G-N116L, G020R-S024R-S101Q-N116L-S128A-L217Q, G020R-N043R-S078N-S101G-Q109G-N116L, G020R-S024G-N043R-S078N-G097S-S101G-S128A, T022R-S024G-S078N-S101N-S103A-V104I-S128A-A232V-Q245R, T022R-S024G-G097A-S101Q-S103A-V104I-Q109G-N116L-S128A-A232V-Q245R, T022R-S101G-S103A-V104I-A232V-P239G-Q245R-E271I, G020R-S024R-S101Q-S128A, G020R-S024R-G097A-S101N-Q109G-N116L, G020R-S024G-N043R-S078N-G097A-S101G-Q109G-N116L, G020R-S024R-G097S-S101Q-Q109N-N116L-L217Q, T022R-S024G-S078N-G097A-S101Q-S103A-V104I-A232V-Q245R, G020R-S024R-G097A-S101G-Q109N-S128A, G020R-S024R-G097S-S101A-Q109N-S128A, T022R-G097S-S101Q-S103A-V104I-Q109G-A232V-Q245R, G020R-S024R-S078N-G097A-S101N-S128A-L217Q, G020R-S024G-N043R-S078N-G097S-S101G-N116L, G020R-S024R-S078N-G097S-S101G-Q109N-N116L-L217Q, T022R-S024G-S078N-S101N-S103A-V104I-Q109N-N116L-S128A-A232V-Q245R, G020R-S024R-S078N-G097S-S101A-Q109N-S128A-L217Q, G020R-S024R-S078N-G097A-S101G-Q109N-N116L-L217Q, G020R-S024G-N043R-S078N-S101Q, G020R-S024R-S078N-G097A-S101Q-Q109G-N116L, G020R-N043R-G097A-S101N-N116L-S128A, G020R-S024R-S078N-S101G-Q109G-N116L-S128A-L217Q, G020R-S024R-S078N-S101Q-Q109G-N116L-S128A-L217Q, G020R-S024R-S078N-G097S-S101G-

Q109N-N116L-S128A, G020R-S024R-S078N-G097S-S101N-Q109N-N116L, T022R-S101N-S103A-V104I-Q109N-N116L-S128A-A232V-Q245R, T022R-S024G-G097S-S101G-S103A-V104I-Q109N-N116L-S128A-A232V-Q245R, T022R-S024G-S078N-S101G-S103A-V104I-N116L-S128A-A232V-Q245R, G020R-S024R-S078N-S101N-Q109N-N116L, G020R-S024R-S078N-S101A-Q109N-N116L-S128A, T022R-S024G-G097A-S101Q-S103A-V104I-N116L-S128A-A232V-Q245R, T022R-G097S-S101G-S103A-V104I-S128A-A232V-Q245R, T022R-G097A-S101Q-S103A-V104I-S128A-A232V-Q245R, T022R-S024G-S078N-G097S-S101Q-S103A-V104I-S128A-A232V-Q245R, T022R-S078N-G097A-S101Q-S103A-V104I-N116L-S128A-A232V-Q245R, G020R-S024R-S101G-Q109G-N116L-L217Q, G020R-S024R-S078N-S101Q-Q109N-N116L, G020R-S024R-S101G-N116L-S128A-L217Q, G020R-S024R-S101A-Q109G-N116L-S128A, T022R-S024G-S078N-G097A-S101G-S103A-V104I-N116L-L217Q-A232V-Q245R, T022R-S024G-S078N-G097S-S101Q-S103A-V104I-Q109G-N116L-S128A-A232V-Q245R, G020R-N043R-G097A-S101N-S128A-L233I, T022R-S101Q-S103A-V104I-A232V-Q245R, G020R-N043R-G097S-S101Q-Q109G-N116L-S128A, T022R-S078N-S101Q-S103A-V104I-A232V-Q245R, G020R-S024R-G097S-S101N-Q109G-N116L, T022R-S078N-G097S-S101G-S103A-V104I-S128A-A232V-Q245R, T022R-S024G-S101N-S103A-V104I-A232V-Q245R, G020R-S024R-G097A-S101N-Q109G-S128A, G020R-N043R-S101Q-N116L-S128A-L217Q, G020R-S024R-S078N-G097A-S101Q-Q109N-S128A, G020R-S024R-E089D-S101A-Q109N-N116L, G020R-S024R-G097A-S101G-Q109G-S128A, G020R-S024G-N043R-S101G-N116L-S128A-L217Q, G020R-N043R-S078N-S101Q-Q109G-L217Q, G020R-S024G-N043R-G097A-S101N-Q109N-N116L-L217Q, G020R-S024R-S078N-G097A-S101G-N116L-S128A, G020R-S024R-G097S-S101A-Q109N-N116L, G020R-S024R-S078N-S101A-Q109G-S128A, G020R-S024R-G097A-S101A-Q109G-N116L-S128A, G020R-N043R-G097A-S101Q-N116L-S128A, G020R-N043R-G097S-S101Q-S128A-L217Q, G020R-S024R-S078N-G097A-S101G-Q109G-N116L-L217Q, G020R-N043R-G097A-S101G-Q109N-N116L-S128A, G020R-N043R-S078N-G097S-S101N-Q109N-L217Q, G020R-S024R-G097S-A098E-S101A-N116L-S128A, G020R-S024R-S078N-G097S-S101A-Q109G-S128A, T022R-S024G-S078N-G097S-S101G-S103A-V104I-Q109N-N116L-L217Q-A232V-Q245R, G020R-S024R-S078N-G097A-S101Q-Q109N-N116L-L217Q, T022R-S024G-G097S-S101Q-S103A-V104I-S128A-A232V-Q245R, G020R-S024R-S101A-Q109N-N116L-S128A-L217Q, G020R-S024R-S101G-Q109G-N116L-S128A-L217Q, T022R-S078N-G097A-S101N-S103A-V104I-S128A-A232V-Q245R, G020R-S024G-N043R-S101N-N116L-S128A-L217Q, G020R-S024R-S078N-G097S-S101A-Q109N-N116L, G020R-S024R-S078N-G097A-S101N-Q109N-N116L-S128A, G020R-S024R-S078N-S101Q-Q109N-N116L-L217Q, T022R-S024G-S078N-S101N-S103A-V104I-N116L-S128A-A232V-Q245R, G020R-N043R-S101G-Q109N-N116L-S128A-L217Q, T022R-S101N-S103A-V104I-L217Q-A232V-Q245R, T022R-G097A-S101N-S103A-V104I-N116L-S128A-A232V-Q245R, G020R-S024R-G097A-S101A-S128A-L217Q, T022R-S024G-S078N-G097A-S101N-S103A-V104I-S128A-L217Q-A232V-Q245R, G020R-S024R-S078N-G097S-S101N-Q109G-N116L-S128A-L217Q, T022R-S024G-S101G-S103A-V104I-N116L-L217Q-A232V-Q245R, T022R-G097A-S101Q-S103A-V104I-N116L-S128A-A232V-Q245R, G020R-N043R-S101Q-S128A-L217Q, G020R-S024R-S078N-S101N-Q109G-S128A-L217Q, G020R-S024R-S078N-G097A-S101N-Q109N-N116L-S128A-L217Q, T022R-S024G-G097A-S101Q-S103A-V104I-N116L-L217Q-A232V-Q245R, G020R-S024R-S078N-G097S-S101G-S128A-N204S-L217Q, T022R-S024G-S078N-S101Q-S103A-V104I-N116L-S128A-A232V-Q245R, G020R-S024R-S078N-G097S-S101Q-Q109N-N116L-L217Q, G020R-S024R-S078N-S099G-S101Q-Q109N-N116L-L217Q, T022R-S024G-G097A-S101G-S103A-V104I-Q109G-N116L-L217Q-A232V-Q245R, T022R-S078N-G097A-S101Q-S103A-V104I-S128A-L217Q-A232V-Q245R, T022R-G097A-S101G-S103A-V104I-Q109G-N116L-L217Q-A232V-Q245R, G020R-S024R-G097A-S101N-Q109N-S128A-L217Q, T022R-G097S-S101N-S103A-V104I-S128A-L217Q-A232V-Q245R, G020R-S024R-K094R-S101N-N116L-S128A-L217Q, T022R-S024G-S078N-G097A-S101G-S103A-V104I-N116L-S128A-L217Q-A232V-Q245R, G020R-S024R-G097A-S101A-N116L-S128A-L217Q, G020R-S024R-S078N-G097W-S101Q-Q109N-N116L-L217Q, T022R-G097S-S101N-S103A-V104I-N116L-S128A-L217Q-A232V-Q245R, T022R-S101Q-S103A-V104I-N116L-L217Q-A232V-Q245R, T022R-S024G-S078N-G097A-S101Q-S103A-V104I-N116L-S128A-L217Q-A232V-Q245R, T022R-S078N-G097A-S101Q-S103A-V104I-Q109N-N116L-S128A-L217Q-A232V-Q245R, G020R-N043R-G097S-S101Q-Q109G-N116L-S128A-L217Q, T022R-S024G-G097A-S101G-S103A-V104I-N116L-S128A-L217Q-A232V-Q245R, T022R-G097S-S101G-S103A-V104I-L217Q-A232V-Q245R, T022R-S024G-G097A-S101Q-S103A-V104I-Q109G-N116L-L217Q-A232V-Q245R, T022R-S024G-S078N-G097A-S101Q-S103A-V104I-S128A-L217Q-A232V-Q245R, T022R-S101Q-S103A-V104I-Q109G-N116L-S128A-L217Q-A232V-Q245R, T022R-S078N-G097S-S101G-S103A-V104I-N116L-S128A-L217Q-A232V-Q245R, T022R-S024G-T071A-S078N-S101N-S103A-V104I-Q109N-N116L-S128A-A232V-Q245R, T022R-S024G-G097A-S101Q-S103A-V104I-S128A-L217Q-A232V-Q245R, T022R-S101G-S103A-V104I-Q109N-S128A-A232V-Q245R, T022R-S024G-G097S-S101G-S103A-V104I-S128A-L217Q-A232V-Q245R, T022R-S024G-S078N-S101Q-S103A-V104I-Q109N-N116L-S128A-L217Q-A232V-Q245R, T022R-S101G-S103A-A232V-Q245R, T022R-S101G-S103A-V104I-A232V-Q245R-E271A, T022R-S103A-V104I-A232V-Q245R, T022R-S101G-V104I-A232V-Q245R, T022R-S101G-S103A-V104I-Q245R, G020R-N043R-E271A, G020R-S024R-I035T-S101A-N116L, G020R-N043R-P239G, G020R-N043R-S242L, or G020R-N043R-V234F (List 17), and wherein amino acid positions of the subtilisin variant are numbered according to the numbering of corresponding amino acid positions in the amino acid sequence of *Bacillus amyloliquefaciens* subtilisin BPN' shown in SEQ ID NO: 1.

The present invention further provides an isolated subtilisin variant, wherein said subtilisin variant is a mature form having proteolytic activity and comprises an amino acid sequence comprising a combination of amino acid substitutions at positions selected from T022Y-S101N-S103A-V104I-A232T-Q245R, G020R-R045T-S101A-P210I-G211Q-L267F, T022Y-S101N-S103N-V104I-A232M-Q245R, T022A-P052T-S101G-S103A-V104I-L217Q-A232V-Q245R, T022A-S101G-S103N-V104L-A232T-Q245R, T022Y-S101A-S103N-V104L-A232V-Q245R, T022A-S101A-S103N-V104I-A232T-Q245R, T022Y-S101A-S103N-V104I-A232L-Q245R, T022Y-S101G-S103A-V104I-A232T-Q245R, T022A-S024G-N076D-S078N-G097S-S101N-S103A-V104I-L217Q-A232V-Q245R, T022A-S101N-S103N-V104I-A232M-Q245R, T022A-S101Q-S103A-V104I-S128A-P129S-A232V-Q245R, T022A-S101N-S103A-V104I-S128A-A232V-Q245R, S024R-S078D-G118S-G159D-Q245R-H249R, T022K-S101N-S103A-V104L-A232T-Q245R, T022R-S101T-S103N-V104I-A232T-Q245S, T022Q-S101N-S103N-V104I-A232M-Q245R, S024R-S078G-G118D-Q245R-H249R, T022R-S101N-S103N-V104L-A232V-Q245R, T022A-N076D-S101Q-S103A-V104I-Q109G-A232V-Q245R, G020R-S024R-S078G-G118D-S188D-Q245R-N248D, T022Y-S101N-S103A-V104I-A232V-Q245R, T022Q-S101N-S103A-V104L-A232L-Q245R, T022Q-S101N-S103N-V104I-A232L-Q245R, T022A-G097S-S101N-S103A-V104I-S128A-L217Q-A232V-Q245R, T022R-S101N-S103N-V104I-A232T-Q245S, G020R-S078D-G118D-G159D-Q245R-H249R, T022R-S101N-S103A-V104L-A232M-Q245R, T022A-N076D-G097S-S101Q-S103A-V104I-Q109N-S128A-A232V-Q245R, T022R-S101G-S103N-V104L-A232T-Q245S, G020R-T022W-N043R-R045T-S101A-G211Q-T213A, T022Q-S101T-S103N-V104I-A232T-Q245R, G020R-S024R-N043R-S101A-N204D-T213A, T022A-S024G-S101Q-S103A-V104I-Q109G-A232V-Q245R, G020R-S024R-S078D-G118D-S188D-Q245R-N248D-H249R, S024R-N043R-S101A-P210I, T022A-N076D-S101G-S103A-V104I-A232V-Q245R-A270V, G020R-S024R-S078D-G118S-H249R, S024R-S078G-G118S, T022R-S101G-S103N-V104L-A232V-Q245S, S024R-N043K-R045T-S101A, T022A-N076D-S078N-S101N-S103A-V104I-A232V-Q245R-T274A, T022A-S024G-N076D-S078N-S101G-S103A-V104I-L217Q-A232V-Q245R, T022Q-S101T-S103G-V104I-A232M-Q245W, T022A-S024R-S078G-G118S-P129E-Q245R-H249R, T022A-S024R-N076D-S101G-S103A-V104I-A232V-Q245R, V026W, T022R-S101G-S103N-V104I-A232L-Q245W, G020R-S024R-S078D-G118S-N248D, G020R-R045T-S101A-N204S-P210I, G020R-S024R-S078G-G118D-G159D-N248D-H249R, T022Y-S101A-S103N-V104I-A232V-Q245R, T022A-S024G-S078N-G097A-S101N-S103A-V104I-L217Q-A232V-Q245R, S024R-S101A-P210I-G211Q, T022R-S101N-S103N-V104I-A232V-Q245S, T022A-S024G-G097A-S101N-S103A-V104I-Q109G-A232V-Q245R, T022A-G097A-S101N-S103A-V104I-A232V-Q245R, T022A-S024G-N076D-S101Q-S103A-V104I-Q109N-A232V-Q245R, G020R-S078G-G118S-H249R, S078G-G118S-Q245R-H249R, T022A-G097A-S101N-S103A-V104I-L217Q-A232V-Q245R, T022Y-S101T-S103G-V104I-A232M-Q245R, T022K-S101G-S103N-V104I-A232L-Q245R, T022A-S024G-G097S-S101N-S103A-V104I-A232V-Q245R, S024R-S078G-G118D-G159D-S188D-Q245R-H249R, T022Q-S101N-S103A-V104I-A232V-Q245R, G020R-S024R-S078G-G118D-G159D-Q245R-N248D, T022A-S024G-S101G-S103A-V104I-A232V-Q245R, T022Q-S101G-S103A-V104L-A232T-Q245R, T022Q-S101T-S103A-V104I-A232T-Q245R, T022A-N076D-S101N-S103A-V104I-S128A-A232V-Q245R, T022A-S024G-N076D-S078N-G097A-S101G-S103A-V104I-A232V-Q245R, T022A-S101G-S103A-V104L-A232V-Q245R, T022A-S024G-S078N-G097S-S101Q-S103A-V104I-S128A-A232V-Q245R, T022A-S024G-N076D-G097S-S101G-S103A-V104I-A232V-Q245R, S024R-N043R-S101A-G211Q-T213A, T022A-G097S-S101Q-S103A-V104I-A232V-Q245R, S024R-S078G-G118S-Q245R-N248D, G020R-T022W-S024R-N043R-S101A-N204S-P210I-G211Q, T022A-S024G-S078N-G097S-S101N-S103A-V104I-Q109G-S128A-A232V-Q245R, T022A-S101G-S103A-V104I-P129S-A232V-Q245R, T022R-S101T-S103G-V104I-A232T-Q245S, T022A-S024G-T072V-G097S-S101Q-S103A-V104I-S128A-L217Q-A232V-Q245R, T022K-S101A-S103A-V104I-A232V-Q245W, G020R-T022W-S024R-R045T-S101A-N116L-P210I, T022R-S101T-S103G-V104I-A232I-Q245W, T022A-S024G-N076D-S078N-G097S-S101N-S103A-V104I-S128A-A232V-Q245R, T022A-G097A-S101N-S103A-V104I-S128A-A232V-Q245R, T022Y-S101T-S103N-V104L-A232V-Q245R, G020R-S024R-N062E-S078G-G118S-N248D, T022Q-S101G-S103A-V104I-A232V-Q245R, T022A-N076D-S078N-S101N-S103A-V104I-S128A-A232V-Q245R, T022A-S024G-G097A-S101N-S103A-V104I-S128A-A232V-Q245R, T022A-S024G-N076D-S078N-S101Q-S103A-V104I-A232V-Q245R, T022A-N076D-S078N-S101G-S103A-V104I-L217Q-A232V-Q245R, T022A-S024G-N076D-S101N-S103A-V104I-A232V-Q245R, T022R-S101N-S103A-V104I-A232L-Q245S, T022A-S078N-S101N-S103A-V104I-Q109N-L217Q-A232V-Q245R, T022R-S101A-S103A-V104I-A232V-Q245W, T022A-S101Q-S103A-V104I-A232V-Q245R, T022A-S078N-G097S-S101N-S103A-V104I-A232V-Q245R, T022A-G097A-S101Q-S103A-V104I-P129S-A232V-Q245R, T022A-S101T-S103A-V104I-A232L-Q245R, T022A-A085T-G097S-S101Q-S103A-V104I-L217Q-A232V-Q245R, T022A-S101T-S103N-V104L-S105G-A232M-Q245R, T022A-S101A-S103A-V104I-A232M-Q245S, T022Q-S101A-S103A-V104I-A232M-Q245R, T022Q-S101G-S103A-V104L-A232M-Q245R, T022A-S024G-G097A-S101Q-S103A-V104I-S128A-A232V-Q245R, T022A-S024G-G097S-S101Q-S103A-V104I-L217Q-A232V-Q245R, T022A-N076D-S078N-G097S-S101G-S103A-V104I-S128A-A232V-Q245R, T022A-G097A-S101G-S103A-V104I-H120Q-S128A-A232V-Q245R, T022A-G097A-S101N-S103A-V104I-S128A-P129S-L217Q-A232V-Q245R, G020R-S024R-N062E-S078G-G118D-Q245R, T022K-S101G-S103G-V104I-A232V-Q245R, S078G-G118S-S188D-Q245R-H249R, T022W-N043R-S101A-G211Q-T213A, T022A-S024G-N076D-G097S-S101N-S103A-V104I-Q109N-A232V-Q245R, T022Y-S101A-S103N-V104L-A232M-Q245R, G020R-T022W-S101A-N116L-G211Q-T213A, T022W-S024R-N043R-R045T-S101A-T213A, N043R-S101A-G211Q-T213A, T022Y-S101N-S103N-V104L-A232L-Q245R, T255G, T022A-G097S-S101N-S103A-V104I-S128A-A232V-Q245R, T022W-S024R-N043R-S101A-P210I-T213A, N269K, T022R-S101I-S103A-V104I-A232L-Q245S, T022A-S024G-T072V-S078N-G097S-S101N-S103A-V104I-S128X-A232V-Q245R, T022K-S101T-S103G-V104I-A232M-Q245R, H017R-N043R-R045T-S101A-P210I-T213A, T022A-S024G-G097S-S101G-S103A-V104I-S128A-A232V-Q245R, T022A-S078N-G097A-S101Q-S103A-V104I-A232V-Q245R, T022A-N076D-G097A-S101N-S103A-V104I-A232V-Q245R, T022A-S024G-V026A-S101G-S103A-V104I-S128A-A232V-Q245R, T022A-S024G-G097A-S101G-S103A-V104I-S128A-L217Q-A232V-Q245R, T022Q-S101T-S103G-V104I-A232L-Q245R, T022W-S024R-S101A-P210I-G211Q-T213A, T022Q-S101N-S103A-V104I-A232M-Q245R, G020R-R045T-S101A, T022Y-S101N-S103N-V104I-A232V-Q245R, T022R-S101G-S103A-V104I-A232L-Q245R, S024R-S078D-G118D-P129E-Q245R-H249R, T022R-S101A-S103A-V104I-A232M-Q245S, G020R-S101A-

P210I-G211Q, T022W-N043R-R045T-S101A-P210I-G211Q, T022R-S101G-S103A-V104I-A232M-Q245S, T022A-S024G-N076D-S101G-S103A-V104I-L217Q-A232V-Q245R, T022R-S101T-S103N-V104I-A232V-Q245S, T022Q-S101G-S103N-V104L-A232M-Q245R, T022K-T038I-S101G-S103A-V104I-A232T-Q245S, N043R-R045T-S101A-P210I-G211Q, T022K-S101T-S103A-V104L-A232M-Q245R, T022Y-S101T-S103N-V104I-A232I-Q245R, G020R-S024R-N043R-S101A-P210I-T213A, S099G-S101G, T022A-S101N-S103N-V104L-A232T-Q245R, T022A-S024G-N076D-S078N-G097A-S101N-S103A-V104I-A232V-Q245R, T022R-S101N-S103A-V104I-A232V-Q245W, T022W-N043R-R045T-S101A-P210I, T022K-S101A-S103G-V104I-A232I-Q245R, T022Q-S101N-S103A-V104I-A232T-Q245S, T022A-S101Q-S103A-V104I-Q109G-A232V-Q245R, T022A-G097A-S101Q-S103A-V104I-S128A-P129S-L217Q-A232V-Q245R, T022A-S078N-G097A-S101Q-S103A-V104I-L217Q-A232V-Q245R, S024R-S078G-G118S-G159D-Q245R, T022K-S101N-S103N-V104I-A232T-Q245R, A098F-S099A-V104I, G020R-R045T-S101A-G211Q-T213A, T022A-N076D-S078N-G097A-S101G-S103A-V104I-A232V-Q245R, S024R-S078D-G118S-G159D-Q245R, T022A-S024G-N076D-S101N-S103A-V104I-Q109N-A232V-Q245R, T022K-S101T-S103N-V104I-A232M-Q245R, T022A-S024G-S078N-G097S-S101N-S103A-V104I-S128A-A232V-Q245R, T022Q-S101T-S103N-V104I-A232L-Q245S, A114T, T022Q-S101N-S103N-V104L-A232I-Q245R, T022A-S078N-S101G-S103A-V104I-Q109N-A232V-Q245R, T022K-S101I-S103A-V104I-A232M-Q245R, T022A-S024G-G097S-S101Q-S103A-V104I-Q109G-S128A-L217Q-A232V-Q245R, T022A-S101G-S103A-V104I-N116L-Y209V-G211Q-A232V, T022A-S101T-S103N-V104I-A232M-Q245W, G020R-T022W-S024R-S101A-N116L-G211Q, T022A-S078N-S101Q-S103A-V104I-S128A-L217Q-A232V-Q245R, G020R-R045T-S101A-G211Q, T022A-N076D-S078N-G097A-S101G-S103A-V104I-S128A-A232V-Q245R, S024R-S101A-T213A, T022A-S078N-S101G-S103A-V104I-A232V-Q245R, G020R-S024R-S078D-G118S-G159D-S188D-Q245R-N248D-H249R, T022Y-S101N-S103N-V104I-A232V-Q245W, T022Y-S101A-S103G-V104I-A232V-Q245R, T022A-S024R-N076D-S101G-S103A-V104I-A232V-N238Y-Q245R, G020R-S078G-G118S-G159D-H249R, T022A-S024R-S101G-S103A-V104I-P129E-A232V-Q245R-A272V, T022R-S101N-S103A-V104I-A232V-Q245S, G020R-S101A-P210I-G211Q-T213A, G020R-S024R-S078D-G118S-G159D-S188D-Q245R, S087R, G020R-S024R-R045T-A048T-S101A-G211Q, T022A-S024G-G097S-S101Q-S103A-V104I-A232V-Q245R, G020R-S024R-S078G-G118S-P129E-S188D-Q245R-N248D-H249R, T022A-G097S-S101G-S103A-V104I-Q109N-A232V-Q245R, L021S-T022A-S024G-N076D-S078N-S101G-S103A-V104I-S128A-A232V-Q245R, S242K, T022K-S101A-S103A-V104I-A232V-Q245R, T022K-S101N-S103A-V104L-A232L-Q245R, T022A-N076D-S101G-S103A-V104I-A232V-N238Y-Q245R-A270V-A272V, T022R-S101T-S103A-V104I-A232V-Q245S, T022Y-S101N-S103G-V104I-A232L-Q245R, T022Q-S101N-S103G-V104I-A232V-Q245R, T022A-S101G-S103A-V104I-A232V-Q245W, T022R-S101A-S103A-V104I-A232L-Q245S, G020R-T022W-R045T-F050L-S101A-P210I-G211Q-T213A, T022A-S101Q-S103A-V104I-S128A-L217Q-A232V-Q245R, G020R-S101A-G211Q-T213A, T022A-N076D-S101G-S103A-V104I-A232V-Q245R-A272V, T022A-S101G-

S103A-V104I-A232V-N238Y-Q245R-A270V, T022A-S101N-S103G-V104I-A232V-Q245R, G020R-S101A-T208P-P210I-G211Q, D181S, S101G-S103A-V104I-N116L-Y209V-A232V, T022Q-S101A-S103N-V104I-A232I-Q245R, T022A-S101G-S103N-V104L-G211S-A232T-Q245R, T022A-G097A-S101Q-S103A-V104I-L217Q-A232V-Q245R, T022A-S101T-S103N-V104I-A232M-Q245S, T022A-S101G-S103A-V104I-Q109N-A232V-Q245R, T022Q-S101A-S103G-V104I-A232M-Q245R, G020R-S078G-G118S-G159D-N248D-H249R, T022A-N076D-S101N-S103A-V104I-A232V-Q245R, T022A-S024G-G097S-S101N-S103A-V104I-Q109G-S128A-A232V-Q245R, T022Q-S101A-S103A-V104I-A232T-Q245R, T022A-S101G-S103A-V104I-A232L-Q245R, T022A-S101G-S103A-V104I-P129E-A232V-N238Y-V244I-Q245R-A270V-A272V, G020R-S024R-S078D-G118D-G159D-Q245R-N248D-H249R, T022R-S101A-S103N-V104I-A232V-Q245W, T022Q-S101A-S103N-V104I-A232M-Q245R, T022Q-S101A-S103N-V104L-A232L-Q245R, T022A-S024G-S101Q-S103A-V104I-S128A-L217Q-A232V-Q245R, T022Q-S101G-S103G-V104I-A232M-Q245R, G020R-S078G-G118S-G159D-Q245R-H249R, T022R-S101A-S103N-V104L-A232V-Q245S, T022A-S024V-G097S-S101N-S103A-V104I-H120N-S128A-A232V-Q245R, T022A-A073V-N076D-S078N-S101N-S103A-V104I-A232V-Q245R, T022Q-S101G-S103N-V104L-A232V-Q245R-T274I, T022A-S101N-S103N-V104I-A232T-Q245R, T022W-S024R-R045P-S101A-P210I-G211Q-T213A, G020R-S024R-N062E-S078G-G118D-Q245R-N248D, T022Q-S101A-S103N-V104L-A232M-Q245R, T022Q-S101I-S103G-V104L-A232T-Q245R, T022R-S101G-S103N-A232L-Q245R, T022A-G097S-S101Q-S103A-V104I-Q109N-L217Q-A232V-Q245R, T022A-S024G-G097A-S101Q-S103A-V104I-S128A-L217Q-A232V-Q245R, S024R-S101A-G211Q-T213A, T022R-S101N-S103N-V104L-A232T-Q245S, G020R-R045T-S101A-P210I, T022R-S101A-S103A-V104I-A232M-Q245W, T022A-S101N-S103N-V104I-A232L-Q245R, T022A-S101G-S103G-V104I-A232M-Q245R, G020R-S024R-S078D-G118S-S188D-Q245R-N248D, S099T-S103G, T022W-N043R-S101A-P210I, T022W-A029V-N043R-S101A-P210I, F050R, T022A-S024G-N076D-S078N-G097S-S101Q-S103A-V104I-Q109N-A232V-Q245R, T022A-S024G-N076D-S101G-S103A-V104I-A232V-Q245R, T022R-S101G-S103N-V104L-A232L-Q245R, T022A-S101N-S103A-V104I-Q109N-S128A-A232V-Q245R, S024R-R045T-S101A, T022A-N076D-G097S-S101N-S103A-V104I-L217Q-A232V-Q245R, T022Q-S101G-S103A-V104I-A232M-Q245S, T022W-S024R-N043R-R045T-S101A-G211Q-T213A, G020R-S078G-G118S, T022W-N043R-G046C-S101A-P210I-G211Q, S101A-G211Q-T213A, T022A-N076D-S078N-S101G-S103A-V104I-A232V-Q245R, T022A-S024G-N076D-G097S-S101Q-S103A-V104I-A232V-Q245R, T022A-S101N-S103A-V104I-L126I-P129S-A232V-Q245R, T022R-S101T-S103N-V104I-A232L-Q245W, T022A-S101G-S103A-V104I-A232V-N238Y-Q245R-A270V-A272V, S078G-G118D-Q245R, T022A-S024R-S101G-S103A-V104I-P129E-A232V-N238Y-Q245R-A270V, T022A-N076D-G097S-S101N-S103A-V104I-Q109G-S128A-A232V-Q245R, T022W-S024R-R045T-S101A-N116L-P210I-T213A, T022R-S101T-S103N-V104I-A232L-Q245S, T022W-S024R-N043R-R045T-S101A-S106L-P210I-G211Q, T022A-E089G-G097A-S101Q-S103A-V104I-P129S-L217Q-A232V-Q245R, T022A-S101A-S103G-V104I-A232L-Q245S, N043R-S101A-P210I-

T213A, N043R-R045T-S101A-T213A, S078G-G118D-H120N-H249R, T022Q-S101T-S103N-V104I-A232L-Q245R-R275H, T022Y-S101A-S103A-V104I-A232T-Q245S, T022K-S101N-S103N-V104I-A232M-Q245R, T022R-S101T-S103N-V104L-A232V-Q245S, T022A-N076D-G097S-S101N-S103A-V104I-A232V-Q245R, M119L, A098F-S099A-S101G-V104I, S078D-G118S-Q245R, T022Y-S101N-S103A-V104I-A232L-Q245S, T022A-G097A-S101N-S103A-V104I-S128A-L217Q-A232V-Q245R, G020R-S078G-G118D-N248D-H249R, T022R-S101A-S103N-V104I-A232T-Q245S, T022R-S101G-S103N-V104I-A232L-Q245S, S024R-S078D-G118D-S188D-Q245R-H249R, S132H, A098Q-S099G-S101G-V104L, N043R-S101A-P210I-G211Q-T213A, T022Q-S101G-S103A-V104I-A232M-Q245W, T022A-S101Q-S103A-V104I-L126I-P129S-A232V-Q245R, T022K-S101T-S103G-V104I-A232M-Q245S, T022W-N043R-R045T-S101A-G211Q-T213A, T022Q-S101N-S103G-V104I-A232V-Q245W, DI 81T, G020R-S024R-S078D-G118S-P129E-G159D-Q245R-H249R, G020R-S024R-S078G-G118D-G159D-S188D-Q245R, T022A-S101T-S103N-V104L-A232L-Q245S, T022A-S101G-S103N-V104L-A232V-Q245S, T022A-S024G-G097A-S101N-S103A-V104I-S128A-L217Q-A232V-Q245R, T022A-S024G-N076D-S101N-S103A-V104I-S128A-A232V-Q245R, T022Y-S101T-S103A-V104L-A232M-Q245R, T022Q-S101T-S103N-V104L-A232T-Q245R, F050S, T022Y-S101G-S103N-V104I-A232V-Q245R, G020R-R045T-S101A-T213A, T022K-S101N-S103G-V104I-A232V-Q245W, S024R-S078G-G118D-P129E-G159D-Q245R-H249R, T022Q-S101T-S103N-V104I-A232M-Q245W, S049W, T022A-S101A-S103N-V104L-A232L-Q245R, T022A-N076D-S101G-S103A-V104I-I107V-P129G-A232V-Q245R-A270V, S099A-V104I, T022Q-S101A-S103G-V104I-A232V-Q245W, T022A-N076D-S101G-S103A-V104I-A232V-N238Y-Q245R, T022A-S101G-S103A-V104I-L124V-L217Q-A232V-Q245R, T022R-G097S-S101Q-S103A-V104I-S128A-L217Q-A232V-Q245R, T022R-G097A-S101Q-S103A-V104I-Q109N-S128A-A232V-Q245R, R010A-T022R-S024F-S101G-S103A-V104I-A232V-Q245R-L267N-E271H, G020R-S024G-N043R-S078N-S101G-Q109N-N116L-L217Q-M222S, G020R-N043R-E271H, G020R-N043R-E271I, G020R-S024R-S101A-N116L-N269I, T022R-S101G-S103A-V104I-A232V-Q245R-E271F, G020R-N043R-E271F, G020R-N043R-N269I, G020R-S024R-S101A-N116L-E271H, T022R-S101G-S103A-V104I-A232V-Q245R-E271H, G020R-I035T-N043R, G020R-S024R-S101A-A114T-N116L, G020R-S024R-S101A-N116L-E271I, G020R-N043R-A114T, G020R-N043R-L267N, G020R-S024R-S101A-N116L-L267N, G020R-S024R-V028A-S101A-N116L, G020R-S024R-S101A-N116L-G258R, G020R-N043R-G258R, G020R-S024R-S101A-N116L-S242L, G020R-S024R-S101A-N116L-P239G, I008N-G020R-S024R-S101A-N116L, G020R-S024R-S101A-N116L-V234F, T022R-S101G-S103A-V104I-A232V, G020R-S024R-S101A-N116L-E271A, R010A-G020R-N043R, G020R-S024R-S101A-N116L-E271F, G020R-V028A-N043R, I008N-G020R-N043R, or G020R-S024F-S101A-N116L (List 18), and wherein amino acid positions of the subtilisin variant are numbered according to the numbering of corresponding amino acid positions in the amino acid sequence of Bacillus amyloliquefaciens subtilisin BPN' shown in SEQ ID NO:1.

The present invention further provides an isolated subtilisin variant, wherein said subtilisin variant is a mature form having proteolytic activity and comprises an amino acid sequence comprising a combination of amino acid substitutions at positions selected from G020R-S024R-S078D-G118D-G159D-H249R, G020R-S024R-S078G-G118S-G159D-S188D-Q245R-N248D-H249R, T022A-S101T-S103G-V104I-A232T-Q245S, T022A-S101T-S103G-V104I-A232T-Q245R, T022Q-S101G-S103N-V104I-A232V-Q245W, T022W-N043R-S101A-T213A, T022A-N076D-S078N-G097A-S101N-S103A-V104I-S128A-A232V-Q245R, T022A-S024G-S078N-S101Q-S103A-V104I-S128A-A232V-Q245R, T022K-S101N-S103N-V104L-A232T-Q245R, T022A-S024G-S101Q-S103A-V104I-S128A-A232V-Q245R, G020R-S024R-N062E-S078G-G118D, G020R-S078G-G118D, T022Y-S101T-S103G-V104L-A232T-Q245R, R010H-T022A-S101G-S103A-V104I-A232V-Q245R-A272V, T022A-S024R-S101G-S103A-V104I-P129E-A232V-Q245R-A270V-A272V, T022A-N076D-S078N-G097S-S101Q-S103A-V104I-Q109G-A232V-Q245R, G020R-S024R-S078D-G118S-P129E-Q245R, T022A-N076D-S101G-S103A-V104I-A232V-N238Y-Q245R-A272V, T022K-S101N-S103N-V104I-A232V-Q245W, T022Q-S101T-S103N-V104I-A232M-Q245S, T022A-S078N-S101N-S103A-V104I-Q109G-L217Q-A232V-Q245R, W113Y, T022A-S101A-S103N-V104I-A232M-Q245S, T022A-S101Q-S103A-V104I-S128A-A232V-Q245R, G020R-S024R-S078G-G118D-G159D-S188D-H249R, T022A-S101N-S103G-V104I-A232T-Q245R, T022K-S101G-S103G-V104I-A232L-Q245R, T022A-N076D-G097A-S101Q-S103A-V104I-S128A-A232V-Q245R, T022Q-S101T-S103N-V104I-A232V-Q245S, T022A-S024F-S101G-S103A-V104I-N116L-Y209V-T213A-A232V, T022A-S101N-S103G-V104L-A232T-Q245R, T022A-S024R-S101G-S103A-V104I-P129E-A232V-N238Y-Q245R, T022A-N076D-G097S-S101Q-S103A-V104I-A232V-Q245R, T022A-N076D-S078N-G097A-S101N-S103A-V104I-A232V-Q245R, T022A-S101N-S103A-V104I-Q109G-S128A-A232V-Q245R, S259W, A016S-T022A-S024F-S101G-S103A-V104I-N116A-Y209V-G211Q-A232V, T022W-S101A-P210I-G211Q-T213A, T022A-S024G-N076D-G097S-S101N-S103A-V104I-A232V-Q245R, V028T-A215V, S024R-S078D-G118S-S188D-Q245R, T022Q-S101T-S103A-V104I-A232V-Q245W, T022A-S101N-S103A-V104I-Q109G-L217Q-A232V-Q245R, T022A-S024G-T071A-G097S-S101Q-S103A-V104I-S128A-A232V-Q245R, H120P, G020R-S024R-N062E-S078D-G118D-Q245R, T022A-N076D-S101Q-S103A-V104I-A232V-Q245R, T022Q-S101A-S103N-V104I-A232L-Q245W, T022Q-S101N-S103A-V104L-A232T-Q245R, T022W-S024R-N043R-R045T-S101A-N116L-P210I-G211Q, T022A-G097S-S101Q-S103A-V104I-S128A-L217Q-A232V-Q245R, G020R-S078G-G118S-G159D-S188D-H249R, A013S, A232N, T022A-N076D-S101G-S103A-V104I-A232V-Q245R, T022A-S024G-N076D-S078N-G097S-S101N-S103A-V104I-A232V-Q245R, I035T, V051M, N123A, G020R-S078G-G118S-G159D-Q245R-N248D, T022Y-S101A-S103N-V104I-A232L-Q245W, T022A-S024R-S101G-S103A-V104I-P129E-A232V-Q245R-A270V, G020R-S078D-G118S, T022R-S101N-S103N-V104L-A232M-Q245W, T022A-S024G-N076D-G097S-S101G-S103A-V104I-S128A-L217Q-A232V-Q245R, T022A-S101G-S103N-V104L-A232V-Q245R, T022A-N076D-G097A-S101Q-S103A-V104I-A232V-Q245R, T022A-S024R-N076D-S101G-S103A-V104I-I107V-P129E-A232V-Q245R, S024R-R045T-S101A-P210I-G211Q, T022A-S078N-S101N-S103A-V104I-Q109N-S128A-A232V-Q245R, T022A-S024G-S078N-G097A-S101N-S103A-

V104I-Q109N-A232V-Q245R, G020R-S024R-S078G-G118D-P129E-G159D-H249R, G020R-S078G-G118D-P129E-S188D-Q245R-H249R, PO 14W, G020R-S024R-S078G-G118S-G159D-S188D-Q245R-N248D, T022R-S101S-S103N-V104I-A232M-Q245W, T022R-A098V-S101G-S103N-V104L-A232T-Q245R, T022A-S101I-S103A-V104L-A232V-Q245W, G020R-T022W-R045T-S101A-T213A, N043R-R045T-S101A, T022K-S101N-S103A-V104I-A232V-Q245R, T022K-S101T-S103N-V104I-A232L-Q245S, S056V, G020R-T022W-R045T-S101A-G211Q, G020R-S024R-S078D-G118D-Q245R-N248D, G020R-S024R-S078D-G118S-G159D-V244L-Q245R-N248D, T022A-G097A-S101Q-S103A-V104I-Q109G-S128A-A232V-Q245R, T022A-N076D-G097S-S101G-S103A-V104I-A232V-Q245R, G020R-T022W-R045T-S101A-N116L-P210I, T022Q-S101N-S103N-V104I-A232M-Q245S, T022Y-S101G-S103N-V104I-A232V-Q245W, A114V, S141C, T022A-N076D-S078N-S101N-S103A-V104I-A232V-Q245R, S056H, S078D-G118D-Q245R, S024R-N043R-R045T-S101A-T213A, T022Y-S101T-S103G-V104I-A232V-Q245S, T022A-S024G-G097S-S101Q-S103A-V104I-S128A-L217Q-A232V-Q245R, N269W, S078G-G118S-G159D-Q245R-N248D-H249R, T022W-S024R-R045T-S101A, T022A-S024R-S101G-S103A-V104I-P129E-A232V-N238Y-Q245R-A270V-A272V, T022A-S024R-S101G-S103A-V104I-P129E-A232V-Q245R, T022A-S024R-N076D-S101G-S103A-V104I-I107V-P129E-A232V-N238Y-Q245R-A270V-A272V, A122F, S024R-S078D-G118S-P129E-G159D-Q245R-H249R, T022K-S101T-S103G-V104I-A232V-Q245S, S009G-T022A-S078N-S101Q-S103A-V104I-Q109G-S128A-L217Q-A232V-Q245R, A098Q, T022A-S101N-S103A-V104L-A232L-Q245R, T022A-S101A-S103N-V104I-A232T-Q245W, T022A-S024G-N076D-G097A-S101N-S103A-V104I-A232V-Q245R, S024R-S078G-G118D-G159D-H249R, T022A-S024G-N076D-G097S-S101N-S103A-V104I-S128A-A232V-Q245R, T022A-S024G-N076D-S078N-S101Q-S103A-V104I-S128A-A232V-Q245R, T022A-S101Q-S103A-V104I-L124V-S128A-P129S-A232V-Q245R, T022R-S101N-S103A-V104I-A232M-W241R-Q245W, R045T-S101A-P210I-G211Q, G020R-S024R-S078G-G118S-P129E-Q245V-N248E, T022Q-S101T-S103N-V104I-A232L-Q245W, T022A-S024G-S078N-S101N-S103A-V104I-Q109G-L217Q-A232V-Q245R, T022A-S024G-G097A-S101N-S103A-V104I-L217Q-A223S-A232V-Q245R, T022K-S101T-S103A-V104I-A232T-Q245W, N043R-S101A-G211Q, T022A-S101G-S103A-V104I-Q109N-S128A-A232V-Q245R, T022A-G097A-S101G-S103A-V104I-S128A-L217Q-A232V-Q245R, G020R-S078G-G118S-P129E-H249R, S024R-S078G-G118S-G159D-S188D-Q245R, N043R-R045T-S101A-N204S-P210I-T213A, T022R-S101N-S103A-V104L-A232V-Q245S, T022R-S101N-S103G-V104I-A232V-Q245S, T022K-S101T-S103N-V104I-A232M-Q245S, T022A-N076D-S101N-S103A-V104I-L217Q-A232V-Q245R, T022A-S024G-N076D-S078N-S101N-S103A-V104I-Q109G-S128A-A232V-Q245R, G020R-T022W-R045T-S101A-P210I-T213A, T022A-N076D-G097A-S101G-S103A-V104I-L217Q-A232V-Q245R, T022W-S101A-P210I, T022A-G097A-S101N-S103A-V104I-L126I-P129S-A232V-Q245R, T022A-S078D-S101N-S103A-V104I-S128A-A232V-Q245R, Q236L, T022Y-S101T-S103N-V104I-A232V-Q245S, A200D, G020R-S078G-G118S-S188D-H249R, T022A-S101G-S103N-V104I-A232T-Q245W, T022A-S024G-N076D-G097A-S101N-S103A-V104I-S128A-A232V-Q245R, G157I, G020R-S024R-S078G-G118S-P129E-G159D-S188D-Q245R, T022Y-S101A-S103G-V104L-A232T-Q245R, S024R-S078G-G118D-H249R, T022Q-S101A-S103N-V104L-A232T-Q245S, T022Y-S101A-S103N-V104I-A232T-Q245W, T022A-S024G-S101N-S103A-V104I-Q109N-L217Q-A232V-Q245R, T022A-S101G-S103N-V104I-A232M-Q245S, T022A-S024G-N076D-S078N-S101G-S103A-V104I-S128A-A232V-Q245R, T022A-S101G-S103N-V104I-A232M-Q245W, I008N, T022A-S101N-S103G-V104I-A232M-Q245S, V026A, T022R-S101N-S103A-V104L-A232T-Q245W, T022A-S101A-S103N-V104I-A232L-Q245S, T022A-S101N-S103A-V104I-A232T-Q245R, N043R-R045T-S101A-P210I-G211Q-T213A, T022A-S024G-N076D-G097A-S101Q-S103A-V104I-S128A-A232V-Q245R, A098F-S099T-S101A, A098F-S099T-S101G-V104L, P014N, A098Q-S103G-V104I, S099T-S103A-V104I, S087W, S024R-N062E-S078G-G118S-H249R, S024R-N043R-R045T-S101A-G211Q, N043R-R045T-S101A-G211Q, G020R-S078G-G118S-N248D, T022Q-S101N-S103N-V104I-A232T-Q245W, S078D-G118S-P129E-Q245R-H249R, T022Q-S101T-S103G-V104I-A232T-Q245S, T022A-S024G-S101N-S103A-V104I-Q109N-S128A-A232V-Q245R, S024F-S101G-S103A-V104I-N116L-Y209A-T213A-A232V, S101A-N116L-P210I-T213A, T022R-S101N-S103N-V104L-A232L-Q245S, B015T, T022A-S101G-S103A-V104I-L124V-A232V-Q245R, G020R-S024R-S078D-G118D-G159D-Q245R, A114I, S212A, T022A-S101T-S103N-V104I-A232L-Q245S, T022A-S024G-S078N-G097S-S101N-S103A-V104I-S128A-T143I-L217Q-A232V-Q245R, S024R-S078G-G118S-G159D-S188D-Q245R-H249R, T022K-S101A-S103N-V104L-A232L-Q245S, T022W-S101A-T213A, T022A-N076D-S078N-G097S-S101Q-S103A-V104I-A232V-Q245R, S132V, S024R-S078G-G118D-S188D-Q245R-N248D-H249R, A098Q-S101A-S103A-V104L, A098Q-S099T-S103A, T022R-S101T-S103N-V104L-A232T-Q245W, T022A-N076D-S101Q-S103A-V104I-S128A-A232V-Q245R, V051A-S101A-P210I-T213A, A098Q-S099T-S101A-V104L, T022R-S101N-S103N-V104I-A232M-Q245W, S099A-S101A-S103A, G020R-S078G-G118D-S188D-Q245R, G020R-S024R-S078D-G118S-P129E-G159D-S188D-Q245R-H249R, T022A-N076D-S078N-G097A-S101Q-S103A-V104I-L217Q-A232V-Q245R, S024R-S078G-G118D, T022Q-S101N-S103N-V104L-A232M-Q245R, T022A-S101T-S103G-V104I-A232M-Q245S, A048G, T022Q-S099G-S101A-S103N-V104I-A232V-Q245R, S024R-R045T-S101A-G211Q-T213A, S024R-R045T-S101A-I107V-A114T-N116L-P210I-G211Q-T213A, T022R-S101T-S103G-V104I-A232L-Q245S, S099G-S103A, A098F-S099A, T022R-S101N-S103G-V104I-A232V-Q245W, T022A-S103A-V104I-L124T-A232V-Q245R, T022A-S024F-S101G-S103A-V104I-N116L-Y209V-A232V, T022K-S101N-S103N-V104L-A232V-Q245S, T022K-S101A-S103A-V104L-A232M-Q245R, T022Q-S101G-S103N-VI 04I-A232T-Q245W, T022A-S101T-S103A-V104L-A232T-Q245W, T022A-S101N-S103N-V104I-A232V-Q245S, T022A-N076D-S078N-G097A-S101N-S103A-V104I-L217Q-A232V-Q245R, A098M, T022A-S101G-S103G-V104I-A232L-Q245R, G020R-S101A-S207G-P210I-T213A, T022A-S024G-G097A-S101Q-S103A-V104I-Q109G-S128A-A232V-Q245R, G020R-S024R-S078G-G118S-G159D-Q245R-N248D-H249R, G020R-S024R-S078D-G118S-P129E-G159D-Q245R, T022Y-S101G-S103N-V104I-A232L-Q245S, V026Q, S240G, G020R-S024R-S078G-G118S-S188D, G020R-S024R-S078G-

G118D-N238D-N248D, T022R-S101G-S103A-V104I-A232T-Q245S, T022W-S024R-R045T-S101A-P210I-G211Q, T022A-S024G-N076D-S078N-G097S-S101Q-S103A-V104I-A232V-Q245R, T022W-S024R-R045T-S101A-T213A, A200F, T022R-S101T-S103G-V104L-A232T-Q245S, T022A-S078N-G097S-S101Q-S103A-V104I-Q109N-L217Q-A232V-Q245R, T022A-S101G-S103N-V104I-A232T-Q245S, T022A-S101I-S103N-V104I-A232T-Q245S, T022A-S101A-S103A-V104L-A232V-Q245S, S099G-S101A-V104L, H017R-T022A-S024V-N076D-G097S-S101N-S103A-V104I-Q109N-S128A-A232V-Q245R, T022A-S101A-S103N-V104L-A232M-Q245S, T022A-S101Q-S103A-V104I-Q109G-L217Q-A232V-Q245R, T022A-S024G-N076D-S101Q-S103A-V104I-S128A-A232V-Q245R, T022A-S024G-S078N-G097S-S101N-S103A-V104I-S128A-S212P-L217Q-A232V-Q245R, S056L, T253L, T022W-R045T-S101A-G211Q-T213A, T022A-G097A-S101Q-S103A-V104I-S128A-L217Q-A232V-Q245R, T022A-S024G-N076D-S078N-G097A-S101N-S103A-V104I-S128A-A232V-Q245R, G020R-T022W-R045T-S101A-G211Q-T213A, S101A-G211Q, N123D, T022R-S101A-S103N-V104I-A232M-Q245R, T022Y-S101T-S103N-V104L-A232I-Q245R, T022A-S101G-S103A-V104I-N116L-Y209V-G211Q-T213A-A232V, G020R-S024R-S078D-G118D-N248D, A098Q-S099G-S101A, S099T-V104I, T022Q-S101G-S103A-V104I-A232V-Q245S, T022R-S101A-S103G-V104I-A232T-Q245S, T022K-S101T-S103N-V104I-A232I-Q245W, A016M, T022A-S024G-N076D-S101N-S103A-V104I-Q109G-A232V-Q245R, T022K-S101N-S103N-V104I-A232T-Q245S, G020R-N043R-R045T-S101A-N204D-P210I-G211Q, T022A-S101I-S103N-V104I-A232V-Q245S, T022Y-S101G-S103N-V104L-A232V-Q245R, T022A-S101I-S103N-V104I-A232V-Q245W, T022A-S024G-S078N-G097S-S101N-S103A-V104I-Q109G-L217Q-A232V-Q245R, A088I, T022Y-S101A-S103A-V104I-A232M-Q245S, T022W-S024R-R045T-S101A-N116L-P210I-G211Q, T022W-N043R-R045T-S101A-P210I-G211Q-T213A, 1038A, S078D-G118S-G159D-Q245R, T022K-S101T-S103A-V104L-A232V-Q245W, T022A-S024G-N076D-S078N-G097S-S101N-S103A-V104I-Q109G-A232V-Q245R, T022A-S078N-S101Q-S103A-V104I-Q109N-L217Q-A232V-Q245R, G025S, G025I, A016S-S101G-S103A-V104I-N116L-M119V-Y209V-G211Q-A232V, T022A-N076D-V084A-S101G-S103A-V104I-A232V-Q245R, V011L, T022Y-S101T-S103G-V104I-A232M-Q245S, T022R-S101N-S103A-V104L-A232I-Q245S, S240V, G020R-S024R-S078G-G118D-P129E-S188D-H249R, T022W-S024R-R045T-S101A-G211Q-T213A, T022A-S024G-N076D-G097A-S101Q-S103A-V104I-Q109G-A232V-Q245R, V004Y, V051A, G195W-N269E, S024R-S078G-G118D-N248D-H249R, T022A-S099G-S101T-S103G-V104I-A232V-Q245S, T022Q-S101T-S103G-V104I-A232L-Q245W, T022Q-S101N-S103N-V104I-A232V-Q245W; T022A-S101T-S103G-V104I-A232V-Q245W, T022K-S101N-S103G-V104I-A232V-Q245R, T022Q-S101G-S103N-V104I-A232V-Q245S, T022R-S078N-G097S-S101G-S103A-V104I-Q109G-S128A-A232V-Q245R, T022R-S101G-S103A-V104I-M222S-A232V-Q245R-E271H, G020R-S024R-S101N-Q109G-N116L-M222S, R010A-G020R-S024R-S101A-N116L, or G020R-N043R-M222S (List 19), and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides any of the above isolated subtilisin variants, wherein the subtilisin variant is a protease variant of *Bacillus lentus* subtilisin GG36 protease, wherein said *Bacillus lentus* subtilisin GG36 protease comprises the amino acid sequence shown in SEQ ID NO:2.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 1, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 2, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 3, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 4, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 5, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 6, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 7, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 8, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 9, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 10, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 11, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 12, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 13, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 14, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 15, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 16, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 17, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 18, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 19, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention further provides an isolated subtilisin variant of *Bacillus lentus* subtilisin GG36 protease, as listed above, wherein said subtilisin variant has at least 85% amino acid identity with said *Bacillus lentus* subtilisin GG36 protease comprising the amino acid sequence shown in SEQ ID NO:2.

The present invention further provides an isolated subtilisin variant of *Bacillus lentus* subtilisin GG36 protease, as listed above, wherein said subtilisin variant has at least 90% amino acid identity with said *Bacillus lentus* subtilisin GG36 protease comprising the amino acid sequence shown in SEQ ID NO:2.

The present invention further provides an isolated subtilisin variant of *Bacillus lentus* subtilisin GG36 protease, as listed above, wherein said subtilisin variant has at least 95% amino acid identity with said *Bacillus lentus* subtilisin GG36 protease comprising the amino acid sequence shown in SEQ ID NO:2.

The present invention further provides an isolated subtilisin variant of *Bacillus lentus* subtilisin GG36 protease, as listed above, wherein said subtilisin variant has at least 98% amino acid identity with said *Bacillus lentus* subtilisin GG36 protease comprising the amino acid sequence shown in SEQ ID NO:2.

The present invention further provides an isolated subtilisin variant of *Bacillus lentus* subtilisin GG36 protease, as listed above, wherein said subtilisin variant has at least 99% amino acid identity with said *Bacillus lentus* subtilisin GG36 protease comprising the amino acid sequence shown in SEQ ID NO:2.

The present invention further provides any of the isolated subtilisin variants listed above, wherein the total net charge of the variant is 0, +1, +2, +3, +4, +5, −1, −2, −3, −4, or −5 relative to the total net charge of the *Bacillus lentus* subtilisin GG36 protease. In some embodiments, the total net charge is obtained by one or more substitutions selected from: A001E, V004E, R010H/A, Q012E, A015D, N018D, R019H/S, V026D, K027E, N043D, R045C/T/S/P, S049D, V051E, G061E, N062D/E, N076D, N077D, S078D, S087D, A098E, S101D, S106E, G115E, G118D, N123D, S128D, P129E, S130D/E, S132D, A158E, G159D/E, S160D, S166D, R170T, N183D, N184D, N185E, R186H, S188D/E, A194E, A200D, Y209E, A215D, N204D, S212D, L217D/E, N218D, A230E, K235F, N237D, K237E, N238D, S240D, N243D, Q245D, R247L, N248D/E, K251C, N263D, N269D/E, A272D, A273E, R275H/S, A001R, V004R, Q012R, P014R, H017R, N018R/K, G020K/R, T022R/K, S024R/K, G025R, D032I, D041K/L/N, N043R/K, G046R, A048R, F050R/K, P055R, S056R/K, T057R, Q059K, G061R, N076K, S078R, P086R, S087R, E089G/P/I, G097R, S099R, Q109R, G115R, G118R, S132K, S144R, G159R/K, D181C/S/T, L196K, N204K, Q206R, K235R, Q236R/K, X237R, N238R, S240R, W241R, S242R/K, V244R, Q245R/K, N248R, H249R, N252R/K, S256R, G258R, T260K, N269R/K, and/or E271F/H/T/L/W/R/S/I/A/G/V, and wherein amino acid positions of the protease variant, more specifically subtilisin variants are numbered according to the numbering of corresponding amino acid positions in the amino acid sequence of *Bacillus amyloliquefaciens* subtilisin BPN' shown in SEQ ID NO:1.

The present invention also provides isolated protease variants, more specifically subtilisin variants, wherein said protease variant, more specifically subtilisin variants has at least one, or even two or more charged mutations selected from the group consisting of A001E, V004E, R010H/A, Q012E, A015D, N018D, R019H/S, V026D, K027E, N043D, R045C/T/S/P, S049D, V051E, G061E, N062D/E, N076D, N077D, S078D, S087D, A098E, S101D, S106E, G115E, G118D, N123D, S128D, P129E, S130D/E, S132D, A158E, G159D/E, S160D, S166D, R170T, N183D, N184D, N185E, R186H, S188D/E, A194E, A200D, Y209E, A215D, N204D, S212D, L217D/E, N218D, A230E, K235F, N237D, K237E, N238D, S240D; N243D, Q245D, R247L, N248D/E, K251C, N263D, N269D/E, A272D, A273E, and/or R275H/S, preferably having a charge of 0, −1, −2, −3, −4 or −5, preferably 0, −1, −2 or −3, most preferably −1 or −2 relative to the enzyme of SEQ ID NO:1. Said protease variants, more specifically subtilisin variants can also include any of the variants listed in the application.

The present invention also provides isolated protease variants, more specifically subtilisin variants, wherein said protease variant, more specifically subtilisin variants has one or two or more charged mutations selected from the group consisting of A001R, V004R, Q012R, P014R, H017R, N018R/K, G020K/R, T022R/K, S024R/K, G025R, D032I, D041K/L/N, N043R/K, G046R, A048R, F050R/K, P055R, S056R/K, T057R, Q059K, G061R, N076K, S078R, P086R, S087R, E089G/P/I, G097R, S099R, Q109R, G115R, G118R, S132K, S144R, G159R/K, D181C/S/T, L196K, N204K, Q206R, K235R, Q236R/K, K237R, N238R, S240R, W241R, S242R/K, V244R, Q245R/K, N248R, H249R, N252R/K, S256R, G258R, T260K, N269R/K, and/or E271F/H/T/L/W/R/S/I/A/V, preferably having a charge of 0, +1, +2, +3, +4 or +5, preferably +1, +2 or +3, most preferably +2 relative to the enzyme of SEQ ID NO:1. Said protease variants, more specifically subtilisin variants can also include any of the variants listed in the application.

In some embodiments, any of the above listed isolated subtilisin variants can be incorporated into a detergent composition suitable for addition to water to make a wash liquor having low ionic strength or low detergent concentration. Thus in a preferred aspect of the invention, these variants will form part of a detergent composition that is added to water, either for a handwashing or machine washing process, typically within a washing machine, to form a wash liquor, whose conductivity is from about 0.1 mS/cm to about 3 mS/cm, from about 0.3 mS/cm to about 2.5 mS/cm, or even from about 0.5 mS/cm to about 2 mS/cm. Preferred variants for use in low ionic strength or low detergent concentration are selected from the variants in any of lists 9, 14, 15 or 16, preferably list 14 or 15, most preferably list 15 above.

Without wishing to be bound by theory it is believed that these mutations to arrive at a desired net charge provide enhanced overall protease performance by ensuring optimal charge of the molecule for low ionic strength conditions, or wash liquors comprising low detergent concentration—it is only through careful combination of certain mutations, of which these are preferred, that such preferred proteases can be obtained.

In some embodiments, any of the above listed isolated subtilisin variants can be incorporated into a detergent composition suitable for addition to water to make a wash liquor having high ionic strength or high detergent concentration. Thus in a preferred aspect of the invention, these variants will form part of a detergent composition that is added to water, either for a handwashing or machine washing process, typically within a washing machine, to form a wash liquor, whose conductivity is from above about 3 mS/cm to about 30 mS/cm, from about 3.5 mS/cm to about 20 mS/cm, or even from about 4 mS/cm to about 10 mS/cm. Preferred variants for use in high ionic strength or high detergent concentration are selected from the variants in any of lists 1 or 17, 18 or 19, preferably list 17 or 18, most preferably list 17 above.

Without wishing to be bound by theory it is believed that these mutations to arrive at a desired net charge provide enhanced overall protease performance by ensuring optimal charge of the molecule for high ionic strength conditions, or wash liquors comprising high detergent concentration—it is only through careful combination of certain mutations, of which these are preferred, that such preferred proteases can be obtained.

Preferably these proteases form part of a detergent composition that is added to water either in a hand or machine washing process, typically within a washing machine, to form a wash liquor, whose conductivity is from above about 3 mS/cm to about 30 mS/cm, from about 3.5 mS/cm to about 20 mS/cm, or even from about 4 mS/cm to about 10 mS/cm.

Without wishing to be bound by theory it is believed that these mutations to arrive at a desired net charge provide enhanced overall protease performance in high ionic strength or high detergent concentration conditions—it is only through careful combination of certain mutations, of which these are preferred, that such preferred proteases can be obtained.

The present invention further provides any of the isolated subtilisin variants listed above having one or more of the following characteristics: a) a Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or e) Test Method 7 performance index of at least 1.1, at least 1.2, at least 1.3, at least 1.4, at least 1.5, at least 1.6, at least 1.7, at least 1.8, at least 1.9, at least 2, from 1.1 to about 15, from 1.1 to about 10, or even from 1.1 to about 7. Test Method 2, Test Method 3, Test Method 4, Test Method 6, and Test Method 7 are explicitly described infra in the section of Example 1 entitled "Test Methods".

Nucleic Acids of the Invention

The invention provides isolated, non-naturally occurring, or recombinant nucleic acids (also referred to herein as "polynucleotides"), which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include variant protease polypeptides, including variant subtilisin polypeptides having enzymatic activity (e.g., proteolytic activity) which are useful in cleaning applications and cleaning compositions for cleaning an item or a surface (e.g., surface of an item) in need of cleaning.

In some embodiments, the invention provides an isolated, recombinant, substantially pure, or non-naturally occurring nucleic acid comprising a nucleotide sequence encoding any polypeptide (including any fusion protein, etc.) of the invention described above in the section entitled "Polypeptides of the Invention" and elsewhere herein. The invention also provides an isolated, recombinant, substantially pure, or non-naturally-occurring nucleic acid comprising a nucleotide sequence encoding a combination of two or more of any polypeptides of the invention described above and elsewhere herein.

Also provided is an isolated, recombinant, substantially pure, or non-naturally occurring nucleic acid comprising a polynucleotide sequence which encodes a variant protease having proteolytic activity, said variant protease (e.g., variant subtilisin) comprising an amino acid sequence which differs from the amino acid sequence of SEQ ID NO:2 by no more than 50, no more than 40, no more than 30, no more than 35, no more than 25, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 amino acid residue(s), wherein amino acid positions of the variant subtilisin are numbered according to the numbering of corresponding amino acid positions in the amino acid sequence of *Bacillus amyloliquefaciens* subtilisin BPN' shown in SEQ ID NO:1 as determined by alignment of the variant protease amino acid sequence with the *Bacillus amyloliquefaciens* subtilisin BPN' amino acid sequence.

The present invention provides nucleic acids encoding an isolated subtilisin variant, wherein said subtilisin variant is a mature form having proteolytic activity and comprises an amino acid sequence comprising a combination of amino acid substitutions at positions selected from List 1, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 2, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 3, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 4, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 5, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 6, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 7, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides an isolated subtilisin variant, wherein said subtilisin variant is a mature form having proteolytic activity and comprises an amino acid sequence comprising a combination of amino acid substitutions at positions selected from List 8, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 9, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 10, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 11, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 12, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides an isolated subtilisin variant, wherein said subtilisin variant is a mature form having proteolytic activity and comprises an amino acid sequence comprising a combination of amino acid substitutions at positions selected from List 13, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 14, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 15, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 16, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 17, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides an isolated subtilisin variant, wherein said subtilisin variant is a mature form having proteolytic activity and comprises an amino acid sequence comprising a combination of amino acid substitutions at positions selected from List 18, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant, wherein said subtilisin variant is a mature form having proteolytic activity and comprises an amino acid sequence comprising a combination of amino acid substitutions at positions selected from List 19, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding any of the above isolated subtilisin variants, wherein the subtilisin variant is a protease variant of *Bacillus lentus* subtilisin GG36 protease, wherein said *Bacillus lentus* subtilisin GG36 protease comprises the amino acid sequence shown in SEQ ID NO:2.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 1, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 2, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 3, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 4, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 5, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 6, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 7, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 8, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 9, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 10, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 11, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 12, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 13, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 14, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 15, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 16, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 17, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from List 18, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, wherein said *Bacillus lentus* subtilisin GG36 protease comprises the amino acid sequence shown in SEQ ID NO:2, and wherein said subtilisin variant has at least 80% amino acid sequence identity to SEQ ID NO:2 and has proteolytic activity and comprises an amino acid sequence comprising a combination of amino acid substitutions selected from 19, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

The present invention provides nucleic acids encoding an isolated subtilisin variant of *Bacillus lentus* subtilisin GG36 protease, as listed above, wherein said subtilisin variant has at least 85% amino acid identity with said *Bacillus lentus* subtilisin GG36 protease comprising the amino acid sequence shown in SEQ ID NO:2.

The present invention provides nucleic acids encoding an isolated subtilisin variant of *Bacillus lentus* subtilisin GG36 protease, as listed above, wherein said subtilisin variant has at least 90% amino acid identity with said *Bacillus lentus* subtilisin GG36 protease comprising the amino acid sequence shown in SEQ ID NO:2.

The present invention provides nucleic acids encoding an isolated subtilisin variant of *Bacillus lentus* subtilisin GG36 protease, as listed above, wherein said subtilisin variant has at least 95% amino acid identity with said *Bacillus lentus* subtilisin GG36 protease comprising the amino acid sequence shown in SEQ ID NO:2.

The present invention provides nucleic acids encoding an isolated subtilisin variant of *Bacillus lentus* subtilisin GG36 protease, as listed above, wherein said subtilisin variant has at least 98% amino acid identity with said *Bacillus lentus* subtilisin GG36 protease comprising the amino acid sequence shown in SEQ ID NO:2.

The present invention provides nucleic acids encoding an isolated subtilisin variant of *Bacillus lentus* subtilisin GG36 protease, as listed above, wherein said subtilisin variant has at least 99% amino acid identity with said *Bacillus lentus* subtilisin GG36 protease comprising the amino acid sequence shown in SEQ ID NO:2.

The present invention further provides nucleic acids encoding any of the isolated subtilisin variants listed above, wherein the total net charge of the variant is 0, +1, +2, +3, +4, +5, −1, −2, −3, −4, or −5 relative to the total net charge of the *Bacillus lentus* subtilisin GG36 protease. In some embodiments, the total net charge is obtained by one or more substitutions selected from: A001E, V004E, R010H/A, Q012E, A015D, N018D, R019H/S, V026D, K027E, N043D, R045C/T/S/P, S049D, V051E, G061E, N062D/E, N076D, N077D, S078D, S087D, A098E, S101D, S106E, G115E, G118D, N123D, S128D, P129E, S130D/E, S132D, A158E, G159D/E, S160D, S166D, R170T, N183D, N184D, N185E, R186H, S188D/E, A194E, A200D, Y209E, A215D, N204D, S212D, L217D/E, N218D, A230E, K235F, N237D, K237E, N238D, S240D, N243D, Q245D, R247L, N248D/E, K251C, N263D, N269D/E, A272D, A273E, R275H/S, A001R, V004R, Q012R, P014R, H017R, N018R/K, G020K/R, T022R/K, S024R/K, G025R, D032I, D041K/L/N, N043R/K, G046R, A048R, F050R/K, P055R, S056R/K, T057R, Q059K, G061R, N076K, S078R, P086R, S087R, E089G/P/I, G097R, S099R, Q109R, G115R, G118R, S132K, S144R, G159R/K, D181C/S/T, L196K, N204K, Q206R, K235R, Q236R/K, K237R, N238R, S240R, W241R, S242R/K, V244R, Q245R/K, N248R, H249R, N252R/K, S256R, G258R, T260K, N269R/K, or E271F/H/T/L/W/R/S/I/A/G/V, and wherein amino acid positions of the protease variant are numbered according to the numbering of corresponding amino acid positions in the amino acid sequence of *Bacillus amyloliquefaciens* subtilisin BPN' shown in SEQ ID NO:1.

The present invention further provides nucleic acids encoding isolated protease variants, more specifically subtilisin variants, wherein said protease variant has at least one, or even two or more charged mutations selected from the group consisting of A001E, V004E, R010H/A, Q012E, A015D, N018D, R019H/S, V026D, K027E, N043D, R045C/T/S/P, S049D, V051E, G061E, N062D/E, N076D, N077D, S078D, S087D, A098E, S101D, S106E, G115E, G118D, N123D, S128D, P129E, S130D/E, S132D, A158E, G159D/E, S160D, S166D, R170T, N183D, N184D, N185E, R186H, S188D/E, A194E, A200D, Y209E, A215D, N204D, S212D, L217D/E, N218D, A230E, K235F, N237D, K237E, N238D, S240D, N243D, Q245D, R247L, N248D/E, K251C, N263D, N269D/E, A272D, A273E, and/or R275H/S, preferably having a charge of 0, −1, −2, −3, −4 or −5, preferably 0, −1, −2 or −3, most preferably −1 or −2 relative to the enzyme of SEQ ID NO:1. Said protease variants, more specifically subtilisin variants can also include any of the variants listed in the application.

The present invention also provides isolated protease variants, more specifically subtilisin variants, wherein said protease variant has one or two or more charged mutations selected from the group consisting of A001R, V004R, Q012R, P014R, H017R, N018R/K, G020K/R, T022R/K, S024R/K, G025R, D032I, D041K/L/N, N043R/K, G046R, A048R, F050R/K, P055R, S056R/K, T057R, Q059K, G061R, N076K, S078R, P086R, S087R, E089G/P/I, G097R, S099R, Q109R, G115R, G118R, S132K, S144R, G159R/K, D181C/S/T, L196K, N204K, Q206R, K235R, Q236R/K, K237R, N238R, S240R, W241R, S242R/K, V244R, Q245R/K, N248R, H249R, N252R/K, S256R, G258R, T260K, N269R/K, and/or E271F/H/T/L/W/R/S/I/A/G/V and/or N269R, preferably having a charge of 0, +1, +2, +3, +4 or +5, preferably +1, +2 or +3, most preferably +2 relative to the enzyme of SEQ ID NO:1. Said protease variants, more specifically subtilisin variants can also include any of the variants listed in the application.

As indicated herein, suitable cold water protease variants, or subtilisin variants, are variants of a parent protease, said parent protease's sequence being at least 97%, at least 99% or 100% identical to the amino acid sequence of SEQ ID NO:1, said protease variant having one or more of the following characteristics:
a) Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or e) Test Method 7 performance index of at least 1.1, at least 1.2, at least 1.3, at least 1.4, at least 1.5, at least 1.6, at least 1.7, at least 1.8, at least 1.9, at least 2, from 1.1 to about 15, from 1.1 to about 10, or even from 1.1 to about 7. Test Method 2, Test Method 3, Test Method 4, Test Method 6, and Test Method 7 are explicitly described infra in the section of Example 1 entitled "Test Methods". All mutations referenced herein utilize the BPN' numbering scheme as shown in FIG. 1. In some embodiments, the variants referenced herein refer to variants having amino acid sequences compared to the amino acid sequence of SEQ ID NO:2, using the BPN' numbering scheme.

In some embodiments, the above high ionic strength cold water protease variants, more specifically subtilisin variants form part of a detergent composition that is diluted in water, typically within a laundry washing machine, to form a laundry detergent wash liquor, whose conductivity is from about 3 mS/cm to about 30 mS/cm, from about 3.5 mS/cm to about 20 mS/cm, or even from about 4 mS/cm to about 10 mS/cm.

The charge of the cold water protease variants, more specifically subtilisin variants is expressed relative to *B. lentus* subtilisin GG36 protease wild-type having the amino acid sequence of SEQ ID NO:2. The amino acids that, impart a single negative charge are D and E and those that impart a single positive charge are R, H and K. Any amino acid change versus SEQ ID NO:2 that changes a charge is used to calculate the charge of the cold water protease variant. For example, introducing a negative charge mutation from a wild-type neutral position will add a net charge of −1 to the cold water protease variant, whereas introducing a negative charge mutation (D or E) from a wild-type positive amino acid residue (R, H or K) will add a net charge of −2. Summing the charge changes from all the amino acid residues that are different for the cold water protease variant versus *B. lentus* subtilisin GG36 protease wild-type having the amino acid sequence of SEQ ID NO:2 gives the charge change of the cold water protease variant. Without wishing to be bound by theory, it is believed that: the preferred charge range for cold water proteases to be used in low conductivity laundry detergent solutions is −5, −4, −3, −2, −1, 0, particularly −2, −1; the preferred charge range for cold water proteases to be used in high conductivity laundry detergent solutions is +5, +4, +3, +2, +1, 0, particularly +2, +1. By correctly selecting the charge unexpectedly improved levels of cold water cleaning performance can be obtained. "Low conductivity laundry detergent solutions" are defined as having a conductivity of from about 0.1 mS/cm to about 3 mS/cm, from about 0.3 mS/cm to about 2.5 mS/cm, or even from about 0.5 mS/cm to about 2 mS/cm. "High conductivity laundry detergent solutions" are defined as having a conductivity of from about 3 mS/cm to about 30 mS/cm, from about 3.5 mS/cm to about 20 mS/cm, or even from about 4 mS/cm to about 10 mS/cm. It is intended that the above examples be non-limiting. Once mutations are combined to optimize cold water performance, the enzyme charge can also be balanced by mutations in further positions.

In some embodiments, the invention provides an isolated, recombinant, substantially pure, or non-naturally occurring variant protease (e.g., variant subtilisin) having proteolytic activity, said variant protease comprising an amino acid sequence which differs from the amino acid sequence shown in SEQ ID NO:2 by no more than 50, no more than 45, no more than 40, no more than 35, no more than 30, no more than 25, no more than 20, no more than 19, no more than 18, no more than 17, no more than 16, no more than 15, no more than 14, no more than 13, no more than 12, no more than 11, no more than 10, no more than 9, or no more than 8 amino acid residues, wherein amino acid positions are numbered according to the numbering of corresponding amino acid positions in the amino acid sequence of *Bacillus amyloliquefaciens* subtilisin BPN' shown in SEQ ID NO:1, as determined by alignment of the variant protease amino acid sequence with the *Bacillus amyloliquefaciens* subtilisin BPN' amino acid sequence.

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods, or polymerase mediated recombination methods) to form essentially any desired continuous nucleic acid sequence. The synthesis of the nucleic acids of the invention can be also facilitated (or alternatively accomplished) by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984], as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 [1984]; and Itakura et al., Science 198:1056 [1984]).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. Nucleotides of the invention may also be obtained by screening cDNA libraries (e.g., cDNA libraries generated using mutagenesis techniques commonly used in the art, including those described herein) using one or more oligonucleotide probes that can hybridize to or PCR-amplify polynucleotides which encode a variant protease polypeptide(s) of the invention. Procedures for screening and isolating cDNA clones and PCR amplification procedures are well known to those of skill in the art and described in standard references known to those skilled in the art. Some nucleic acids of the invention can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination).

Methods for Making Modified Variant Proteases of the Invention

A variety of methods are known in the art that are suitable for generating modified polynucleotides of the invention that encode variant proteases of the invention, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches. Methods for making modified polynucleotides and proteins (e.g., variant proteases) include DNA shuffling methodologies, methods based on non-homologous recombination of genes, such as ITCHY (See, Ostermeier et al., 7:2139-44 [1999]), SCRACHY (See, Lutz et al. 98:11248-53 [2001]), SHIPREC (See, Sieber et al., 19:456-60 [2001]), and NRR (See, Bittker et al., 20:1024-9 [2001]; Bittker et al., 101:7011-6 [2004]), and methods that rely on the use of oligonucleotides to insert random and targeted mutations, deletions and/or insertions (See, Ness et al., 20:1251-5 [2002]; Coco et al., 20:1246-50 [2002]; Zha et al., 4:34-9 [2003]; Glaser et al., 149:3903-13 [1992]).

Vectors, Cells, and Methods for Producing Variant Proteases of the Invention

The present invention provides isolated or recombinant vectors comprising at least one polynucleotide of the invention described herein (e.g., a polynucleotide encoding a variant protease of the invention described herein), isolated or recombinant expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, cell cultures comprising cells comprising at least one polynucleotide of the invention, cell cultures comprising at least one nucleic acid or polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector. Such cells are typically referred to as host cells. Some such cells comprise bacterial cells, including, but are not limited to *Bacillus* sp. cells, such as *B. subtilis* cells. The invention also provides recombinant cells (e.g., recombinant host cells) comprising at least one variant protease of the invention.

In some embodiments, the invention provides a vector comprising a nucleic acid or polynucleotide of the invention. In some embodiments, the vector is an expression vector or expression cassette in which a polynucleotide sequence of the invention which encodes a variant protease of the invention is operably linked to one or additional nucleic acid segments required for efficient gene expression (e.g., a promoter operably linked to the polynucleotide of the invention which encodes a variant protease of the invention). A vector may include a transcription terminator and/or a selection gene, such as an antibiotic resistance gene that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pXX, pC 194, pJH 101, pE194, pHP13 (See, Harwood and Cutting [eds.], Chapter 3, *Molecular Biological Methods for Bacillus*, John Wiley & Sons [1990]; suitable replicating plasmids for *B. subtilis* include those listed on p. 92; See also, Perego, Integrational Vectors for Genetic Manipulations in *Bacillus subtilis*, in Sonenshein et al., [eds.] *Bacillus subtilis and Other Gram-Positive Bacteria: Biochemistry, Physiology and Molecular Genetics*, American Society for Microbiology, Washington, D.C. [1993], pp. 615-624).

For expression and production of a protein of interest (e.g., variant protease) in a cell, at least one expression vector comprising at least one copy of a polynucleotide encoding the modified protease, and preferably comprising multiple copies, is transformed into the cell under conditions suitable for expression of the protease. In some embodiments of the present invention, a polynucleotide sequence encoding the variant protease (as well as other sequences included in the vector) is integrated into the genome of the host cell, while in other embodiments, a plasmid vector comprising a polynucleotide sequence encoding the variant protease remains as autonomous extra-chromosomal element within the cell. The invention provides both extrachromosomal nucleic acid elements as well as incoming nucleotide sequences that are integrated into the host cell genome. The vectors described herein are useful for production of the variant proteases of the invention. In some embodiments, a polynucleotide construct encoding the variant protease is present on an integrating vector that enables the integration and optionally the amplification of the polynucleotide encoding the variant protease into the bacterial chromosome. Examples of sites for integration are well known to those skilled in the art. In some embodiments, transcription of a polynucleotide encoding a variant protease of the invention is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include, but are not limited to, for example, the amyE, amyQ, amyL, pstS, sacB, pSPAC, pAprE, pVeg, pHpaII promoters, the promoter of the *B. stearothermophilus* maltogenic amylase gene, the *B. amyloliquefaciens* (BAN) amylase gene, the *B. subtilis* alkaline protease gene, the *B. clausii* alkaline protease gene the *B. pumilis* xylosidase gene, the *B. thuringiensis* cryIIIA, and the *B. licheniformis* alpha-amylase gene. Additional promoters include, but are not limited to the A4 promoter, as well as phage Lambda $P_R$ or $P_L$ promoters, and the *E. coli* lac, trp or tac promoters.

Variant proteases of the present invention can be produced in host cells of any suitable Gram-positive microorganism, including bacteria and fungi. For example, in some embodiments, the variant protease is produced in host cells of fungal and/or bacterial origin. In some embodiments, the host cells are *Bacillus* sp., *Streptomyces* sp., *Escherichia* sp. or *Aspergillus* sp. In some embodiments, the variant proteases are produced by *Bacillus* sp. host cells. Examples of *Bacillus* sp. host cells that find use in the production of the variant proteases of the invention include, but are not limited to *B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii,* and *B. megaterium,* as well as other organisms within the genus *Bacillus*. In some embodiments, *B. subtilis* host cells are used for production of variant proteases. U.S. Pat. Nos. 5,264,366 and 4,760,025 (RE 34,606) describe various *Bacillus* host strains that can be used for producing variant proteases of the invention, although other suitable strains can be used.

Several industrial bacterial strains that can be used to produce variant proteases of the invention include non-recombinant (i.e., wild-type) *Bacillus* sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a *B. subtilis* host strain and particularly a recombinant *Bacillus subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211strain (See e.g., Hoch et al., Genetics 73:215-228 [1973]; See also, U.S. Pat. Nos. 4,450,235 and 4,302,544, and EP 0134048, each of which is incorporated by reference in its entirety). The use of *B. subtilis* as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the *Bacillus* host cell is a *Bacillus* sp. that includes a mutation or deletion in at least one of the following genes, degU, degS, degR and degQ. Preferably the mutation is in a degU gene, and more preferably the mutation is degU(Hy)32 (See e.g., Msadek et al., J. Bacteriol. 172:824-834 [1990]; and Olmos et al., Mol. Gen. Genet. 253:562-567 [1997]). One suitable host strain is a *Bacillus subtilis* carrying a degU32(Hy) mutation. In some embodiments, the *Bacillus* host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce a variant protease of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., U.S. Pat. Appln. Pub. No. 2005/0202535, incorporated herein by reference).

Host cells are transformed with at least one nucleic acid encoding at least one variant protease of the invention using any suitable method known in the art. Whether the nucleic acid is incorporated into a vector or is used without the presence of plasmid DNA, it is typically introduced into a microorganism, in some embodiments, preferably an *E. coli* cell or a competent *Bacillus* cell. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing nucleic acid or polynucleotide sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and congression, transduction, and protoplast fusion are well known and suited for use in the present invention. Methods of transformation are used to introduce a DNA construct or vector comprising a nucleic acid encoding a variant protease of the present invention into a host cell. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154: 1077-1087 [1983]; and Weinrauch et al., J. Bacteriol. 169: 1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a variant protease of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into a plasmid or vector. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one variant protease or at least one nucleic acid of the invention. Also provided are compositions comprising at least one nucleic acid, vector, or DNA construct of the invention.

In some embodiments, host cells transformed with at least one polynucleotide sequence encoding at least one variant protease of the invention are cultured in a suitable nutrient medium under conditions permitting the expression of the present protease, after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (See e.g., the catalogues of the American Type Culture Collection). In some embodiments, the protease produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Any method suitable for recovering or purifying a variant protease finds use in the present invention.

In some embodiments, a variant protease produced by a recombinant host cell is secreted into the culture medium. A nucleic acid sequence that encodes a purification facilitating domain may be used to facilitate purification of soluble proteins. A vector or DNA construct comprising a polynucleotide sequence encoding a variant protease may further comprise a nucleic acid sequence encoding a purification facilitating domain to facilitate purification of the variant protease (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system (e.g., protein A domains available from Immunex Corp., Seattle, Wash.). The inclusion of a cleavable linker sequence such as Factor XA or enterokinase (e.g., sequences available from Invitrogen, San Diego, Calif.) between the purification domain and the heterologous protein also find use to facilitate purification.

Assays for detecting and measuring the enzymatic activity of an enzyme, such as a variant protease of the invention, are well known. Various assays for detecting and measuring activity of proteases (e.g., variant proteases of the invention), are also known to those of ordinary skill in the art. In particular, assays are available for measuring protease activity that are based on the release of acid-soluble peptides from casein or hemoglobin, measured as absorbance at 280 nm or colorimetrically using the Folin method, well known to those skilled in the art. Other exemplary assays involve the solubilization of chromogenic substrates (See e.g., Ward, "Proteinases," in Fogarty (ed.)., *Microbial Enzymes and Biotechnology*, Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., mature variant proteases of the present invention) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature variant protease of the invention. A mature variant protease does not include a signal peptide or a propeptide sequence. Some methods comprise making or producing a variant protease of the invention in a recombinant bacterial host cell, such as for example, a *Bacillus* sp. cell (e.g., a *B. subtilis* cell). In some embodiments, the invention provides a method of producing a variant protease of the invention, the method comprising cultivating a recombinant host cell comprising a recombinant expression vector comprising a nucleic acid encoding a variant protease of the invention under conditions conducive to the production of the variant protease. Some such methods further comprise recovering the variant protease from the culture.

In some embodiments the invention provides methods of producing a variant protease of the invention, the methods comprising: (a) introducing a recombinant expression vector comprising a nucleic acid encoding a variant protease of the invention into a population of cells (e.g., bacterial cells, such as *B. subtilis* cells); and (b) culturing the cells in a culture medium under conditions conducive to produce the variant protease encoded by the expression vector. Some such methods further comprise: (c) isolating the variant protease from the cells or from the culture medium.

Fabric and Home Care Products

In some embodiments, the protease variants, more specifically subtilisin variants of the present invention can be used in compositions comprising an adjunct material and a protease variant, wherein the composition is a fabric and home care product.

In some embodiments, the fabric and home care product compositions comprise at least one subtilisin variant, wherein said subtilisin variant is a mature form having proteolytic activity and comprises an amino acid sequence comprising a combination of amino acid substitutions at positions selected from List 1-19, and wherein amino acid positions of the subtilisin variant are numbered according to the numbering of corresponding amino acid positions in the amino acid sequence of *Bacillus amyloliquefaciens* subtilisin BPN' shown in SEQ ID NO: 1.

The present invention further provides any of the above isolated subtilisin variants, wherein the subtilisin variant is a protease variant of *Bacillus lentus* subtilisin GG36 protease, wherein said *Bacillus lentus* subtilisin GG36 protease comprises the amino acid sequence shown in SEQ ID NO:2.

In some embodiments, the fabric and home care product compositions comprise at least one subtilisin variant of *Bacillus lentus* subtilisin GG36 protease, wherein said *Bacillus lentus* subtilisin GG36 protease comprises the amino acid sequence shown in SEQ ID NO:2, and wherein said GG36 protease is a mature form having proteolytic activity and comprises an amino acid sequence comprising a combination of amino acid substitutions selected from List 1-19, and wherein amino acid positions of the protease variant are numbered according to the numbering of corresponding amino acid positions in the amino acid sequence of *Bacillus amyloliquefaciens* subtilisin BPN' shown in SEQ ID NO:1.

In some embodiments, the fabric and home care product compositions comprise any of the isolated subtilisin variants listed above, wherein the total net charge of the variant is 0, +1, +2, +3, +4, +5, −1, −2, −3, −4, or −5 relative to the total net charge of the *Bacillus lentus* subtilisin GG36 protease. In some embodiments, the total net charge is obtained by one or more substitutions selected from: A001E, V004E, R010H/A, Q012E, A015D, N018D, R019H/S, V026D, K027E, N043D, R045C/T/S/P, S049D, V051E, G061E, N062D/E, N076D, N077D, S078D, S087D, A098E, S101D, S106E, G115E, G118D, N123D, S128D, P129E, S130D/E, S132D, A158E, G159D/E, S160D, S166D, R170T, N183D, N184D, N185E, R186H, S188D/E, A194E, A200D, Y209E, A215D, N204D, S212D, L217D/E, N218D, A230E, K235F, N237D, K237E, N238D, S240D, N243D, Q245D, R247L, N248D/E, K251C, N263D, N269D/E, A272D, A273E, R275H/S, A001R, V004R, Q012R, P014R, H017R, N018R/K, G020K/R, T022R/K, S024R/K, G025R, D032I, D041K/L/N, N043R/K, G046R, A048R, F050R/K, P055R, S056R/K, T057R, Q059K, G061R, N076K, S078R, P086R, S087R, E089G/P/I, G097R, S099R, Q109R, G115R, G118R, S132K, S144R, G159R/K, D181C/S/T, L196K, N204K, Q206R, K235R, Q236R/K, K237R, N238R, S240R, W241R, S242R/K, V244R, Q245R/K, N248R, H249R, N252R/K, S256R, G258R, T260K, N269R/K, or E271F/H/T/L/W/R/S/I/A/G/V, and wherein amino acid positions of the protease variant are numbered according to the numbering of corresponding amino acid positions in the amino acid sequence of *Bacillus amyloliquefaciens* subtilisin BPN' shown in SEQ ID NO:1.

In some embodiments, the subtilisin variant(s) of the fabric and home care product compositions are derived from a parent subtilisin that is commercially available (e.g., SAVINASE®, POLARZYME®, KANNASE®, LIQUINASE®, LIQUINASE ULTRA®, SAVINASE ULTRA®, or OVOZYME® by Novozymes A/S); MAXACAL®, PROPERASE®, PURAFECT®, FN3®, FN4® and PURAFECT OXP®, PURAFAST™, PURAFECT® PRIME, or PURAMAX® by Genencor International) and those available from Henkel/Kemira, namely BLAP (sequence shown in FIG. 29 of U.S. Pat. No. 5,352,604 with the following mutations S99D+S101R+S103A+V104I+G159S, hereinafter referred to as BLAP) and BLAP X (BLAP with S3T+V4I+V205I).

In some embodiments, the fabric and home care product compositions comprise at least one protease variant whose parent has proteolytic activity, wherein the variant protease comprises an amino acid sequence which differs from the amino acid sequence shown in SEQ ID NO:2 by no more than 50, no more than 40, no more than 35, no more than 30, no more than 25, no more than 20, no more than 19, no more than 18, no more than 17, no more than 16, no more than 15, no more than 14, no more than 13, no more than 12, no more than 11, no more than 10, no more than 9, or no more than 8 amino acid residues, wherein amino acid positions are numbered according to the numbering of corresponding amino acid positions in the amino acid sequence of *Bacillus amyloliquefaciens* subtilisin BPN' shown in SEQ ID NO:1, as determined by alignment of the variant protease amino acid sequence with the *Bacillus amyloliquefaciens* subtilisin BPN' amino acid sequence.

Cleaning and/or Treatment Compositions

In some embodiments, the consumer product which comprises a cleaning and/or treatment composition, such as fabric and home care product, comprises at least one protease variant, particularly a subtilisin variant and at least one adjunct material. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the variant proteases of the present invention. The precise nature of these additional components, and levels of incorporation thereof, will depend on the physical form of the composition and the nature of the cleaning operation for which it is to be used. The cleaning and/or treatment adjunct materials may be selected from one or more from the list including, but not limited to, surfactants, builders, bleaches, bleach activators, bleach catalysts, other enzymes, enzyme stabilizing systems, chelants, soil release polymers, dye transfer agents, dispersants, suds suppressors, dyes, perfumes, colorants, filler salts, hydrotropes, photoactivators, fluorescers, fabric conditioners, fabric softeners, hydrolyzable surfactants, preservatives, antioxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents an encapsulate comprising a perfume, a hueing agent, surfactants, builders, chelating agents, dye transfer inhibiting agents, dispersants, additional enzymes, enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, hydrotropes, solvents and mixtures thereof (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning and/or treatment adjunct materials are not compatible with the variant proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.).

In some embodiments, cleaning and/or treatment composition, such as fabric and home care product, comprises at least one protease variant further comprise at least one additional non-immunoequivalent protease selected from subtilisins (EC 3.4.21.62); trypsin-like or chymotrypsin-like proteases; metalloproteases; and mixtures thereof.

In some embodiments, cleaning and/or treatment composition, such as fabric and home care product, comprises at least one protease variant further comprise at least one additional non-immunoequivalent protease selected from: subtilisins (EC 3.4.21.62) derived from *B. subtilis, B. amyloliquefaciens, B. pumilus* and *B. gibsonii*; trypsin proteases and/or chymotrypsin proteases derived from *Cellulomonas*; metalloproteases derived from *Bacillus amyloliquefaciens*; and mixtures thereof.

In some embodiments, cleaning and/or treatment composition, such as fabric and home care product, comprises at least one protease variant further comprise at least one additional enzyme selected from hemicellulases, peroxidases, proteases, cellulases, cellobiose dehydrogenases, xyloglucanases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, lichenases glucanases, arabinosidases, hyaluronidases, chondroitinases, laccases, amylases, and mixtures thereof.

In some embodiments, cleaning and/or treatment composition, such as fabric and home care product, comprises at least one protease variant further comprise at least one additional enzyme selected from first-wash lipases; alpha-amylases; bacterial cleaning cellulases; and mixtures thereof.

In some embodiments, cleaning and/or treatment composition, such as fabric and home care product, comprises at least one protease variant further comprise at least one of the following: an encapsulate comprising a perfume comprises a perfume micro capsule; a hueing agent comprising a material selected from basic, acid, hydrophobic, direct and polymeric dyes, and dye-conjugates having a peak absorption wavelength of from 550 nm to 650 nm and mixtures thereof; a detersive surfactant comprising a material selected from anionic detersive surfactants, non-ionic detersive surfactant, cationic detersive surfactants, zwitterionic detersive surfactants and amphoteric detersive surfactants and mixtures thereof; a builder comprising a material selected from zeolites, phosphates and mixtures thereof; a silicate salt comprising a material selected from sodium silicate, potassium silicate and mixtures thereof; a brightener comprising a material selected from cold-water soluble brighteners and mixtures thereof; a carboxylate polymer comprising a material selected from maleate/acrylate random copolymer or polyacrylate homopolymer and mixtures thereof; a soil release polymer comprising a material selected from terephthalate co-polymers and mixtures thereof; a cellulosic polymer comprising a material selected from alkyl cellulose, alkyl alkoxyalkyl cellulose, carboxyalkyl cellulose, alkyl carboxyalkyl cellulose and mixtures thereof; a bleach catalyst comprising a material selected from iminium cations, iminium polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof; a bleach activator comprising a material selected from dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED), nonanoyloxybenzene sulphonate (NOBS) and mixtures thereof; a source of hydrogen peroxide comprising a material selected from inorganic perhydrate salts, including alkali metal salts such as sodium salts of perborate (usually mono- or tetra-hydrate), percarbonate, persulphate, perphosphate, persilicate salts and mixtures thereof; a chelant comprising a material selected from DTPA (diethylene triamine pentaacetic acid), HEDP (hydroxyethane diphosphonic acid), DTPMP (diethylene triamine penta(methylene phosphonic acid)), ethylenediaminedisuccinic acid (EDDS), 1,2-dihydroxybenzene-3,5-disulfonic acid disodium salt hydrate, derivatives of said chelants; and mixtures thereof.

In some embodiments, cleaning and/or treatment composition, such as fabric and home care product, comprises at least one protease variant comprise a fabric hueing agent selected from the group consisting of dyes; dye-clay conjugates comprising at least one cationic-basic dye and a smectite clay; and mixtures thereof.

In some embodiments, cleaning and/or treatment composition, such as fabric and home care product, comprises at least one protease variant comprise at least one fabric hueing agent selected from small molecule dyes and polymeric dyes and mixtures thereof optionally with a smectite clay.

In some embodiments, cleaning and/or treatment composition, such as fabric and home care product, comprises at least one protease variant are provided in single or multiple-compartment unit doses. In some embodiments, the composition is a multi-compartment unit dose, wherein the protease variant is in a different compartment than any source of hydrogen peroxide and/or chelant and/or additional enzyme.

In some embodiments, cleaning and/or treatment composition, such as fabric and home care product, comprises at least one protease variant comprise one or more of the following ingredients (based on total composition weight): from about 0.0005 wt % to about 0.1 wt %, from about 0.001 wt % to about 0.05 wt %, or even from about 0.002 wt % to about 0.03 wt % of said protease variant; and one or more of the following: from about 0.00003 wt % to about 0.1 wt % fabric hueing agent; from about 0.001 wt % to about 5 wt %, perfume capsules; from about 0.001 wt % to about 1 wt %, cold-water soluble brighteners; from about 0.00003 wt % to about 0.1 wt % bleach catalysts; from about 0.00003 wt % to about 0.1 wt % first wash lipases; from about 0.00003 wt % to about 0.1 wt % bacterial cleaning cellulases; and/or from about 0.05 wt % to about 20 wt % Guerbet nonionic surfactants.

In some embodiments, cleaning and/or treatment composition, such as fabric and home care product, is a liquid laundry detergent, a dish washing detergent.

It is intended that cleaning and/or treatment composition, such as fabric and home care product, is provided in any suitable form, including a fluid or solid. A cleaning and/or treatment composition, such as fabric and home care product, may be in the form of a unit dose pouch, especially when in the form of a liquid, and typically a cleaning and/or treatment composition, such as fabric and home care product, is at least partially, or even completely, enclosed by a water-soluble pouch. In addition, in some embodiments of a cleaning and/or treatment composition, such as fabric and home care product, comprising at least one protease variant, a cleaning and/or treatment composition, such as fabric and home care product, may have any combination of parameters and/or characteristics detailed above. Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. In the exemplified detergent compositions, the enzymes levels are expressed by pure enzyme by weight of the total composition and unless otherwise specified, the detergent ingredients are expressed by weight of the total compositions.

The cleaning compositions of the present invention are advantageously employed for example, in laundry applications, hard surface cleaning, dishwashing applications, as well as cosmetic applications such as dentures, teeth, hair and skin. In addition, due to the unique advantages of increased effectiveness in lower temperature solutions, the enzymes of the present invention are ideally suited for laundry applications. Furthermore, the enzymes of the present invention find use in granular and liquid compositions.

The variant proteases of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as premeasured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the protease variants, more specifically subtilisin variants provided herein, alone or in combination with other proteases and/or additional enzymes. The required level of enzyme is achieved by the addition of one or more protease variants, more specifically subtilisin variants of the present invention. Typically the present cleaning compositions comprise at least about 0.0001 weight percent, from about 0.0001 to about 10, from about 0.001 to about 1, or even from about 0.01 to about 0.1 weight percent of at least one of the variant proteases of the present invention.

The cleaning compositions herein are typically formulated such that, during use in aqueous cleaning operations, the wash water will have a pH of from about 5.0 to about 11.5 or even from about 7.5 to about 10.5. Liquid product formulations are typically formulated to have a neat pH from about 3.0 to about 9.0 or even from about 3 to about 5. Granular laundry products are typically formulated to have a pH from about 9 to about 11. Techniques for controlling pH at recommended usage levels include the use of buffers, alkalis, acids, etc., and are well known to those skilled in the art.

Suitable "low pH cleaning compositions" typically have a neat pH of from about 3 to about 5, and are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine or hydrochloric acid, to provide such cleaning composition with a neat pH of from about 3 to about 5. Such compositions typically comprise at least one acid stable enzyme. In some embodiments, the compositions are liquids, while in other embodiments, they are solids. The pH of such liquid compositions is typically measured as a neat pH. The pH of such solid compositions is measured as a 10% solids solution of said composition wherein the solvent is distilled water. In these embodiments, all pH measurements are taken at 20° C., unless otherwise indicated.

In some embodiments, when the variant protease(s) is/are employed in a granular composition or liquid, it is desirable for the variant protease to be in the form of an encapsulated particle to protect the variant protease from other components of the granular composition during storage. In addition, encapsulation is also a means of controlling the availability of the variant protease during the cleaning process. In some embodiments, encapsulation enhances the performance of the variant protease(s) and/or additional enzymes. In this regard, the variant proteases of the present invention are encapsulated with any suitable encapsulating material known in the art. In some embodiments, the encapsulating material typically encapsulates at least part of the catalyst for the variant protease(s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP 0 922 499; U.S. Pat. No. 4,977,252; U.S. Pat. No. 5,354,559, and U.S. Pat. No. 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

As described herein, the variant proteases of the present invention find particular use in the cleaning industry, including, but not limited to laundry and dish detergents. These applications place enzymes under various environmental stresses. The variant proteases of the present invention provide advantages over many currently used enzymes, due to their stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, European detergents typically have about 4500-5000 ppm of detergent components in the wash water, while Japanese detergents typically have approximately 667 ppm of detergent components in the wash water. In North America, particularly the United States, detergents typically have about 975 ppm of detergent components present in the wash water.

A low detergent concentration system includes detergents where less than about 800 ppm of the detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of the detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of the detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 30° C. (e.g., about 20° C.), whereas the temperature of wash water in Europe is typically between about 30 and about 60° C. (e.g., about 40° C.). However, in the interest of saving energy, many consumers are switching to using cold water washing. In addition, in some further regions, cold water is typically used for laundry, as well as dish washing applications. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Accordingly, in some embodiments, the present invention provides variant proteases that show surprising wash performance in at least one set of wash conditions (e.g., water temperature, water hardness, and/or detergent concentration). In some embodiments, the variant proteases of the present invention are comparable in wash performance to other subtilisin proteases. In some embodiments, the variant proteases of the present invention exhibit enhanced wash performance as compared to subtilisin proteases currently commercially available. Thus, in some embodiments of the present invention, the variant proteases provided herein exhibit enhanced oxidative stability, enhanced thermal stability, enhanced cleaning capabilities under various conditions, and/or enhanced chelator stability. In addition, the variant proteases of the present invention find use in cleaning compositions that do not include detergents, again either alone or in combination with builders and stabilizers.

In some embodiments of the present invention, the cleaning compositions comprise at least one variant protease of the present invention at a level from about 0.00001% to about 10% by weight of the composition and the balance (e.g., about 99.999% to about 90.0%) comprising cleaning adjunct materials by weight of composition. In some other embodiments of the present invention, the cleaning compositions of the present invention comprises at least one variant protease at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, hemicellulases, cellulases, peroxidases, proteases, xylanases, lipases, phospholipases, esterases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidases, chondroitinases, laccases, and amylases, or any combinations or mixtures thereof. In some embodiments, a combination of enzymes is used (i.e., a "cocktail")

comprising conventional applicable enzymes like protease, lipase, cutinase and/or cellulase in conjunction with amylase is used.

In addition to the protease variants, more specifically subtilisin variants provided herein, any other suitable protease finds use in the compositions of the present invention. Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, *lentus, amyloliquefaciens*, subtilisin Carlsberg, subtilisin 309, subtilisin 147 and subtilisin 168). Additional examples include those mutant proteases described in U.S. Pat. Nos. RE 34,606, 5,955,340, 5,700, 676, 6,312,936, and 6,482,628, all of which are incorporated herein by reference. Additional protease examples include, but are not limited to trypsin (e.g., of porcine or bovine origin), and the *Fusarium* protease described in WO 89/06270. In some embodiments, commercially available protease enzymes that find use in the present invention include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™, and PURAFAST™ (GenenCor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (*B. alkalophilus* subtilisin; Kao Corp., Tokyo, Japan). Various proteases are described in WO95/23221, WO 92/21760, U.S. Pat. Publ. No. 2008/0090747, and U.S. Pat. Nos. 5,801,039, 5,340,735, 5,500, 364, 5,855,625, U.S. RE 34,606, U.S. Pat. Nos. 5,955,340, 5,700,676, 6,312,936, and 6,482,628, and various other patents. In some further embodiments, metalloproteases find use in the present invention, including but not limited to the neutral metalloprotease described in WO 07/044,993.

In addition, any suitable lipase finds use in the present invention. Suitable lipases include, but are not limited to those of bacterial or fungal origin. Chemically or genetically modified mutants are encompassed by the present invention. Examples of useful lipases include *Humicola lanuginosa* lipase (See e.g., EP 258 068, and EP 305 216), *Rhizomucor miehei* lipase (See e.g., EP 238 023), *Candida* lipase, such as *C. antarctica* lipase (e.g., the *C. antarctica* lipase A or B; See e.g., EP 214 761), *Pseudomonas* lipases such as *P. alcaligenes* lipase and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipolytic enzymes such as cutinases also find use in some embodiments of the present invention, including but not limited to the cutinase derived from *Pseudomonas mendocina* (See, WO 88/09367), and the cutinase derived from *Fusarium solani pisi* (See, WO 90/09446).

Additional suitable lipases include commercially available lipases such as M1 LIPASE™, LUMA FAST™, and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001% to about 10% of additional lipase by weight of the composition and the balance of cleaning adjunct materials by weight of composition. In some other embodiments of the present invention, the cleaning compositions of the present invention also comprise lipases at a level of about 0.0001% to about 10%, about 0.001% to about 5%, about 0.001% to about 2%, about 0.005% to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296, 839). Commercially available amylases that find use in the present invention include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In some other embodiments of the present invention, the cleaning compositions of the present invention also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME®, CAREZYME® (Novozymes), and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874, 276). In some embodiments, the cleaning compositions of the present invention further comprise cellulases at a level from about 0.00001% to about 10% of additional cellulase by weight of the composition and the balance of cleaning adjunct materials by weight of composition. In some other embodiments of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. No. 6,566,114, U.S. Pat. No. 6,602,842, and U.S. Pat. No. 6,440,991, all of which are incorporated herein by reference). In some embodiments, the cleaning compositions of the present invention further comprise mannanases at a level from about 0.00001% to about 10% of additional mannanase by weight of the composition and the balance of cleaning adjunct materials by weight of composition. In some embodiments of the present invention, the cleaning compositions of the present invention also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In some other embodiments of the present invention, the cleaning compositions of the present invention also comprise, peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO 05/056782). In addition, in some embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the variant protease(s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

In some embodiments, an effective amount of one or more variant protease(s) provided herein is included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the variant proteases of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the variant proteases of the present invention. Thus, in some embodiments, the compositions comprising at least one variant protease of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one variant protease of the present invention are fabric cleaning compositions such as those described in U.S. Pat. Nos. 6,610,642 and 6,376,450. In addition, the variant proteases of the present invention find use in granular laundry detergent compositions of particular utility under European or Japanese washing conditions (See e.g., U.S. Pat. No. 6,610, 642).

In some alternative embodiments, the present invention provides hard surface cleaning compositions comprising at least one variant protease provided herein. Thus, in some embodiments, the compositions comprising at least one variant protease of the present invention is a hard surface cleaning composition such as those described in U.S. Pat. Nos. 6,610,642, 6,376,450, and 6,376,450.

In yet further embodiments, the present invention provides dishwashing compositions comprising at least one variant protease provided herein. Thus, in some embodiments, the compositions comprising at least one variant protease of the present invention is a hard surface cleaning composition such as those in U.S. Pat. Nos. 6,610,642 and 6,376,450. In some still further embodiments, the present invention provides dishwashing compositions comprising at least one variant protease provided herein. In some further embodiments, the compositions comprising at least one variant protease of the present invention comprise oral care compositions such as those in U.S. Pat. Nos. 6,376,450, and 6,376,450. The formulations and descriptions of the compounds and cleaning adjunct materials contained in the aforementioned U.S. Pat. Nos. 6,376,450, 6,605,458, 6,605, 458, and 6,610,642, find use with the variant proteases provided herein.

The cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,565,422, 5,516,448, 5,489,392, and 5,486,303, all of which are incorporated herein by reference. When a low pH cleaning composition is desired, the pH of such composition is adjusted via the addition of a material such as monoethanolamine or an acidic material such as HCl.

The cleaning compositions disclosed herein of find use in cleaning a situs (e.g., a surface, item, dishware, or fabric). Typically, at least a portion of the situs is contacted with an embodiment of the present cleaning composition, in neat form or diluted in a wash liquor, and then the situs is optionally washed and/or rinsed. For purposes of the present invention, "washing" includes but is not limited to, scrubbing, and mechanical agitation. In some embodiments, the cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

More detail regarding suitable cleaning and/or treatment adjuncts is given below.

Fabric Hueing Agents.

Although it is not preferred to incorporate additional fabric shading dyes, in addition to the thiophene azo dye, the composition may comprise one or more additional fabric hueing agents. Suitable fabric hueing agents include dyes, dye-clay conjugates, and pigments. Suitable dyes include those that deposit more onto cotton textiles compared to deposition onto synthetic textiles such as polyester and/or nylon. Further suitable dyes include those that deposit more onto synthetic fibres such as polyester and/or nylon compared to cotton. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. Examples of small molecule dyes include those selected from the group consisting of Colour Index (Society of Dyers and Colourists, Bradford, UK) numbers Direct Violet 9, Direct Violet 35, Direct Violet 48, Direct Violet 51, Direct Violet 66, Direct Violet 99, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Violet 50, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159, small molecule dyes selected from the group consisting of Colour Index (Society of Dyers and Colourists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71. Direct Violet small molecule dyes may be preferred. Dyes selected from the group consisting Acid Violet 17, Direct Blue 71, Direct Violet 51, Direct Blue 1, Acid Red 88, Acid Red 150, Acid Blue 29, Acid Blue 113 and mixtures thereof may be preferred.

Suitable polymeric dyes include polymeric dyes selected from the group consisting of polymers containing covalently bound chromogens (dye-polymer conjugates) and polymers with chromogens co-polymerized into the backbone of the polymer and mixtures thereof, and polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof. Preferred additional hueing dyes include the whitening agents found in WO 08/87497 A1. These whitening agents may be characterized by the following structure (I):

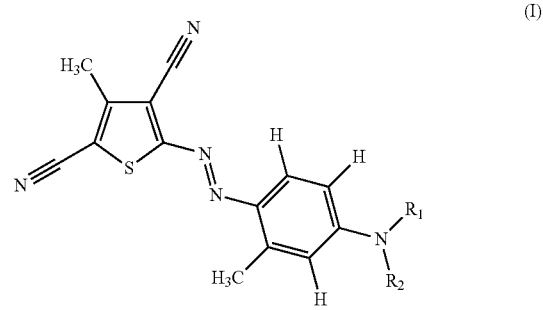

(I)

wherein $R_1$ and $R_2$ can independently be selected from:

a) $[(CH_2CR'HO)_x(CH_2CR''HO)_yH]$, wherein R' is selected from the group consisting of H, $CH_3$, $CH_2O$ $(CH_2CH_2O)_zH$, and mixtures thereof; wherein R" is selected from the group consisting of H, CH$_2$O(CH$_2$CH$_2$O)$_y$H, and mixtures thereof; wherein x+y≤5; wherein y≥1; and wherein z=0 to 5;

b) R$_1$=alkyl, aryl or aryl alkyl and R$_2$=[(CH$_2$CR'HO)(CH$_2$CR"HO)$_y$H]

wherein R' is selected from the group consisting of H, CH$_3$, CH$_2$O(CH$_2$CH$_2$O)$_z$H, and mixtures thereof; wherein R" is selected from the group consisting of H, CH$_2$O(CH$_2$CH$_2$O)$_z$H, and mixtures thereof; wherein x+y≤10; wherein y≥1; and wherein z=0 to 5;

c) R$_1$=[CH$_2$CH(OR$_3$)CH$_2$OR$_4$] and R$_2$=[CH$_2$CH(OR$_3$)CH$_2$OR$_4$]

wherein R$_3$ is selected from the group consisting of H, (CH$_2$CH$_2$O)$_z$H, and mixtures thereof; and wherein z=0 to 10;

wherein R$_4$ is selected from the group consisting of (C$_1$-C$_{16}$)alkyl, aryl groups, and mixtures thereof; and d) wherein R1 and R2 can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

A preferred additional fabric hueing agent which may be incorporated into the compositions of the invention may be characterized by the following structure (II):

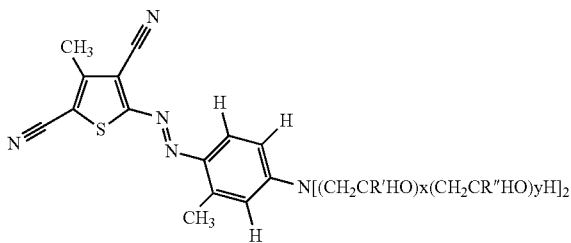

(II)

wherein R' is selected from the group consisting of H, CH$_3$, CH$_2$O(CH$_2$CH$_2$O)$_z$H, and mixtures thereof;
wherein R" is selected from the group consisting of H, CH$_2$O(CH$_2$CH$_2$O)$_z$H, and mixtures thereof;
wherein x+y≤5; wherein y≥1; and wherein z=0 to 5.

A further preferred additional hueing dye may be characterized by the following structure (III):

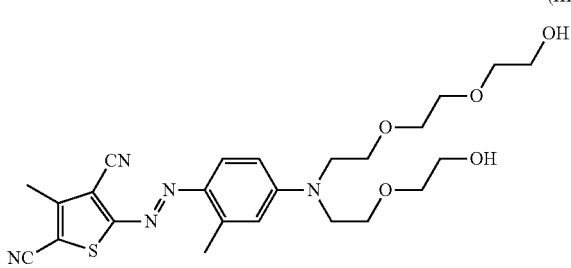

(III)

This dye is typically a mixture of compounds having an average of 3-10 EO groups, preferably 5 EO groups per molecule.

Further additional shading dyes are those described in USPN 2008 34511 A1 (Unilever). A preferred agent is "Solvent Violet 13".

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C$_1$-C$_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. Particularly preferred are Pigment Blues 15 to 20, especially Pigment Blue 15 and/or 16. Other suitable pigments include those selected from the group consisting of Ultramarine Blue (C.I. Pigment Blue 29), Ultramarine Violet (C.I. Pigment Violet 15) and mixtures thereof. Suitable hueing agents are described in more detail in U.S. Pat. No. 7,208,459 B2.

Encapsulates.

The composition may comprise an encapsulate. In one aspect, an encapsulate comprising a core, a shell having an inner and outer surface, said shell encapsulating said core. The core may comprise any laundry care adjunct, though typically the core may comprise material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polyvinylalcohols, optionally containing other co-monomers; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof. Preferred encapsulates comprise perfume. Preferred encapsulates comprise a shell which may comprise melamine formaldehyde and/or cross linked melamine formaldehyde. Preferred encapsulates comprise a core material and a shell, said shell at least partially surrounding said core material, is disclosed. At least 75%, 85% or even 90% of said encapsulates may have a fracture strength of from 0.2 MPa to 10 MPa, and a benefit agent leakage of from 0% to 20%, or even less than 10% or 5% based on total initial encapsulated benefit agent. Preferred are those in which at least 75%, 85% or even 90% of said encapsulates may have (i) a particle size of from 1 microns to 80 microns, 5 microns to 60 microns, from 10 microns to 50 microns, or even from 15 microns to 40 microns, and/or (ii) at least 75%, 85% or even 90% of said encapsulates may have a particle wall thickness of from 30 nm to 250 nm, from 80 nm to 180 nm, or even from 100 nm to 160 nm. Formaldehyde scavengers may be employed with the encapsulates, for example, in a capsule slurry and/or added to a composition before, during or after the encapsulates are added to such composition. Suitable capsules that can be made by following the teaching of USPA 2008/0305982 A1; and/or USPA 2009/0247449 A1. Alternatively, suitable capsules can be purchased from Appleton Papers Inc. of Appleton, Wis. USA.

In a preferred aspect the composition may comprise a deposition aid, preferably in addition to encapsulates. Preferred deposition aids are selected from the group consisting of cationic and nonionic polymers. Suitable polymers include cationic starches, cationic hydroxyethylcellulose, polyvinylformaldehyde, locust bean gum, mannans, xyloglucans, tamarind gum, polyethyleneterephthalate and polymers containing dimethylaminoethyl methacrylate, optionally with one or more monomers selected from the group comprising acrylic acid and acrylamide.

Perfume.

Preferred compositions of the invention comprise perfume. Typically the composition comprises a perfume that comprises one or more perfume raw materials, selected from the group as described in WO08/87497. However, any perfume useful in a laundry care composition may be used. A preferred method of incorporating perfume into the compositions of the invention is via an encapsulated perfume particle comprising either a water-soluble hydroxylic compound or melamine-formaldehyde or modified polyvinyl alcohol. In one aspect the encapsulate comprises (a) an at least partially water-soluble solid matrix comprising one or more water-soluble hydroxylic compounds, preferably starch; and (b) a perfume oil encapsulated by the solid matrix. In a further aspect the perfume may be pre-complexed with a polyamine, preferably a polyethylenimine so as to form a Schiff base.

Polymers.

The composition may comprise one or more polymers. Examples are optionally modified carboxymethylcellulose, poly(vinyl-pyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The composition may comprise one or more amphiphilic cleaning polymers such as the compound having the following general structure: bis(($C_2H_5$O)($C_2H_4$O)n)($CH_3$)—$N^+$—$C_xH_{2x}$—$N^+$—($CH_3$)-bis(($C_2H_5$O)($C_2H_4$O)n), wherein n=from 20 to 30, and x=from 3 to 8, or sulphated or sulphonated variants thereof. In one aspect, this polymer is sulphated or sulphonated to provide a zwitterionic soil suspension polymer.

The composition preferably comprises amphiphilic alkoxylated grease cleaning polymers which have balanced hydrophilic and hydrophobic properties such that they remove grease particles from fabrics and surfaces. Preferred amphiphilic alkoxylated grease cleaning polymers comprise a core structure and a plurality of alkoxylate groups attached to that core structure. These may comprise alkoxylated polyalkylenimines, preferably having an inner polyethylene oxide block and an outer polypropylene oxide block. Typically these may be incorporated into the compositions of the invention in amounts of from 0.005 to 10 wt %, generally from 0.5 to 8 wt %.

Alkoxylated polycarboxylates such as those prepared from polyacrylates are useful herein to provide additional grease removal performance. Such materials are described in WO 91/08281 and PCT 90/01815. Chemically, these materials comprise polyacrylates having one ethoxy side-chain per every 7-8 acrylate units. The side-chains are of the formula —($CH_2CH_2O$)$_m$($CH_2$)$_n$$CH_3$ wherein m is 2-3 and n is 6-12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

Mixtures of cosurfactants and other adjunct ingredients, are particularly suited to be used with an amphiphilic graft co-polymer. Preferred amphiphilic graft co-polymer(s) comprise (i) polyethyelene glycol backbone; and (ii) and at least one pendant moiety selected from polyvinyl acetate, polyvinyl alcohol and mixtures thereof. A preferred amphiphilic graft co-polymer is Sokalan HP22, supplied from BASF. Suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is preferably about 6000 and the weight ratio of the polyethylene oxide to polyvinyl acetate is about 40 to 60 and no more than 1 grafting point per 50 ethylene oxide units. Typically these are incorporated into the compositions of the invention in amounts from 0.005 to 10 wt %, more usually from 0.05 to 8 wt %. Preferably the composition comprises one or more carboxylate polymer, such as a maleate/acrylate random copolymer or polyacrylate homopolymer. In one aspect, the carboxylate polymer is a polyacrylate homopolymer having a molecular weight of from 4,000 Da to 9,000 Da, or from 6,000 Da to 9,000 Da. Typically these are incorporated into the compositions of the invention in amounts from 0.005 to 10 wt %, or from 0.05 to 8 wt %.

Preferably the composition comprises one or more soil release polymers. Examples include soil release polymers having a structure as defined by one of the following Formulae (IV), (V) or (VI):

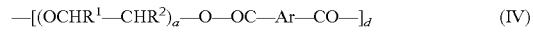  (IV)

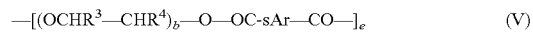  (V)

  (VI)

wherein:

a, b and c are from 1 to 200;

d, e and f are from 1 to 50;

Ar is a 1,4-substituted phenylene;

sAr is 1,3-substituted phenylene substituted in position 5 with $SO_3$Me;

Me is L1, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;

$R^1$, $R^2$, $R^3$, $R^4$, $R^5$ and $R^6$ are independently selected from H or $C_1$-$C_{18}$ n- or iso-alkyl; and $R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex SF, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

Preferably the composition comprises one or more cellulosic polymer, including those selected from alkyl cellulose, alkyl alkoxyalkyl cellulose, carboxyalkyl cellulose, alkyl carboxyalkyl cellulose. Preferred cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 Da to 300,000 Da.

Enzymes.

Preferably the composition comprises one or more enzymes. Preferred enzymes provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in the composition, the aforementioned additional enzymes may be present at levels from about 0.00001% to about 2%, from about 0.0001% to about 1% or even from about 0.001% to about 0.5% enzyme protein by weight of the composition.

Proteases.

Preferably the composition comprises one or more proteases. Suitable proteases include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus*, *B. alkalophilus*, *B. subtilis*, *B. amyloliquefaciens*, *Bacillus pumilus* and *Bacillus gibsonii* described in U.S. Pat. No. 6,312,936 B1, U.S. Pat. No. 5,679,630, U.S. Pat. No. 4,760,025, U.S. Pat. No. 7,262,042 and WO09/021,867.

(b) trypsin-type or chymotrypsin-type proteases, such as trypsin (e.g., of porcine or bovine origin), including the *Fusarium* protease described in WO 89/06270 and the chymotrypsin proteases derived from *Cellumonas* described in WO 05/052161 and WO 05/052146.

(c) metalloproteases, including those derived from *Bacillus amyloliquefaciens* described in WO 07/044,993A2.

Preferred proteases include those derived from *Bacillus gibsonii* or *Bacillus Lentus*.

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Properase®, Purafect®, Purafect Prime®, Purafect Ox®, FN3®, FN4®, Excellase® and Purafect OXP® by Genencor International, those sold under the tradename Opticlean® and Optimase® by Solvay Enzymes, those available from Henkel/Kemira, namely BLAP (sequence shown in FIG. 29 of U.S. Pat. No. 5,352,604 with the following mutations S99D+S100R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)—all from Henkel/Kemira; and KAP (*Bacillus alkalophilus* subtilisin with mutations A230V+S256G+S259N) from Kao.

Amylases.

Preferably the composition may comprise an amylase. Suitable alpha-amylases include those of bacterial or fungal origin. Chemically or genetically modified mutants (variants) are included. A preferred alkaline alpha-amylase is derived from a strain of *Bacillus*, such as *Bacillus licheniformis*, *Bacillus amyloliquefaciens*, *Bacillus stearothermophilus*, *Bacillus subtilis*, or other *Bacillus* sp., such as *Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) the variants described in WO 94/02597, WO 94/18314, WO96/23874 and WO 97/43424, especially the variants with substitutions in one or more of the following positions versus the enzyme listed as SEQ ID No. 2 in WO 96/23874: 15, 23, 105, 106, 124, 128, 133, 154, 156, 181, 188, 190, 197, 202, 208, 209, 243, 264, 304, 305, 391, 408, and 444.

(b) the variants described in U.S. Pat. No. 5,856,164 and WO99/23211, WO 96/23873, WO00/60060 and WO 06/002643, especially the variants with one or more substitutions in the following positions versus the AA560 enzyme listed as SEQ ID No. 12 in WO 06/002643:

26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with SEQ ID No. 4 in WO06/002643, the wild-type enzyme from *Bacillus* SP722, especially variants with deletions in the 183 and 184 positions and variants described in WO 00/60060, which is incorporated herein by reference.

(d) variants exhibiting at least 95% identity with the wild-type enzyme from *Bacillus* sp. 707 (SEQ ID NO:7 in U.S. Pat. No. 6,093,562), especially those comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

(e) variants described in WO 09/149,130, preferably those exhibiting at least 90% identity with SEQ ID NO: 1 or SEQ ID NO:2 in WO 09/149,130, the wild-type enzyme from *Geobacillus Stearophermophilus* or a truncated version thereof.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE® and PURASTAR OXAM® (Genencor International Inc., Palo Alto, Calif.) and KAM® (Kao, 14-10 Nihonbashi Kayabacho, 1-chome, Chuo-ku Tokyo 103-8210, Japan). In one aspect, suitable amylases include NATALASE®, STAINZYME® and STAINZYME PLUS@ and mixtures thereof.

Lipases.

Preferably the invention comprises one or more lipases, including "first cycle lipases" such as those described in U.S. Pat. No. 6,939,702 B1 and US PA 2009/0217464. Preferred lipases are first-wash lipases. In one embodiment of the invention the composition comprises a first wash lipase. First wash lipases includes a lipase which is a polypeptide having an amino acid sequence which: (a) has at least 90% identity with the wild-type lipase derived from *Humicola lanuginosa* strain DSM 4109; (b) compared to said wild-type lipase, comprises a substitution of an electrically neutral or negatively charged amino acid at the surface of the three-dimensional structure within 15A of E1 or Q249 with a positively charged amino acid; and (c) comprises a peptide addition at the C-terminal; and/or (d) comprises a peptide addition at the N-terminal and/or (e) meets the following limitations: i) comprises a negative amino acid in position E210 of said wild-type lipase; ii) comprises a negatively charged amino acid in the region corresponding to positions 90-101 of said wild-type lipase; and iii) comprises a neutral or negative amino acid at a position corresponding to N94 or said wild-type lipase and/or has a negative or neutral net electric charge in the region corresponding to positions 90-101 of said wild-type lipase. Preferred arevariants of the wild-type lipase from *Thermomyces lanuginosus* comprising one or more of the T231R and N233R mutations. The wild-type sequence is the 269 amino acids (amino acids 23-291) of the Swissprot accession number Swiss-Prot 059952 (derived from *Thermomyces lanuginosus* (*Humicola lanuginosa*)). Preferred lipases would include those sold under the tradenames Lipex® and Lipolex® and Lipoclean®.

Endoglucanases.

Other preferred enzymes include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403B2) and mixtures thereof. Suitable endoglucanases are sold under the tradenames Celluclean® and Whitezyme® (Novozymes A/S, Bagsvaerd, Denmark).

Pectate Lyases.

Other preferred enzymes include pectate lyases sold under the tradenames Pectawash®, Pectaway®, Xpect® and mannanases sold under the tradenames Mannaway® (all from Novozymes A/S, Bagsvaerd, Denmark), and Purabrite® (Genencor International Inc., Palo Alto, Calif.).

Bleaching Agents.

It may be preferred for the composition to comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent or mixtures of bleaching agents by weight of the subject composition. Examples of suitable bleaching agents include:

(1) photobleaches for example sulfonated zinc phthalocyanine sulfonated aluminium phthalocyanines, xanthene dyes and mixtures thereof;

(2) pre-formed peracids: Suitable preformed peracids include, but are not limited to compounds selected from the group consisting of pre-formed peroxyacids or salts thereof typically a percarboxylic acids and salts, percarbonic acids and salts, perimidic acids and salts, peroxymonosulfuric acids and salts, for example, Oxone®, and mixtures thereof. Suitable examples include peroxycarboxylic acids or salts thereof, or peroxysulphonic acids or salts thereof. Typical peroxycarboxylic acid salts suitable for use herein have a chemical structure corresponding to the following chemical formula:

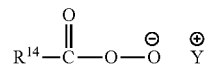

wherein: $R^{14}$ is selected from alkyl, aralkyl, cycloalkyl, aryl or heterocyclic groups; the $R^{14}$ group can be linear or branched, substituted or unsubstituted; having, when the peracid is hydrophobic, from 6 to 14 carbon atoms, or from 8 to 12 carbon atoms and, when the peracid is hydrophilic, less than 6 carbon atoms or even less than 4 carbon atoms and Y is any suitable counter-ion that achieves electric charge neutrality, preferably Y is selected from hydrogen, sodium or potassium. Preferably, $R^{14}$ is a linear or branched, substituted or unsubstituted $C_{6-9}$ alkyl. Preferably, the peroxyacid or salt thereof is selected from peroxyhexanoic acid, peroxyheptanoic acid, peroxyoctanoic acid, peroxynonanoic acid, peroxydecanoic acid, any salt thereof, or any combination thereof. Particularly preferred peroxyacids are phthalimido-peroxy-alkanoic acids, in particular ∊-phthalimido peroxy hexanoic acid (PAP). Preferably, the peroxyacid or salt thereof has a melting point in the range of from 30° C. to 60° C.

The pre-formed peroxyacid or salt thereof can also be a peroxysulphonic acid or salt thereof, typically having a chemical structure corresponding to the following chemical formula:

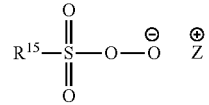

wherein: $R^{15}$ is selected from alkyl, aralkyl, cycloalkyl, aryl or heterocyclic groups; the $R^{15}$ group can be linear or branched, substituted or unsubstituted; and Z is any suitable counter-ion that achieves electric charge neutrality, preferably Z is selected from hydrogen, sodium or potassium. Preferably $R^{15}$ is a linear or branched, substituted or unsubstituted $C_{4-14}$, preferably $C_{6-14}$ alkyl. Preferably such bleach components may be present in the compositions of the invention in an amount from 0.01 to 50%, most preferably from 0.1% to 20%.

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall cleaning and/or treatment composition, such as fabric and home care product, and are typically incorporated into such cleaning and/or treatment composition, such as fabric and home care products, as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject composition may comprise NOBS, TAED or mixtures thereof.

(5) Bleach Catalysts. The compositions of the present invention may also include one or more bleach catalysts capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and alpha amino-ketones and mixtures thereof. Suitable alpha amino ketones are for example as described in WO 2012/000846 A1, WO 2008/015443 A1, and WO 2008/014965 A1. Suitable mixtures are as described in USPA 2007/0173430 A1.

Without wishing to be bound by theory, the inventors believe that controlling the electophilicity and hydrophobicity in this above described manner enables the bleach ingredient to be delivered substantially only to areas of the fabric that are more hydrophobic, and that contain electron rich soils, including visible chromophores, that are susceptible to bleaching by highly electrophilic oxidants.

In one aspect, the bleach catalyst has a structure corresponding to general formula below:

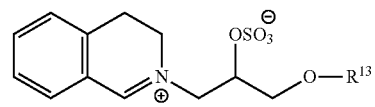

wherein $R^{13}$ is selected from the group consisting of 2-ethylhexyl, 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl;

(6) The composition may preferably comprise catalytic metal complexes. One preferred type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. No. 5,597,936; U.S. Pat. No. 5,595,967. Such cobalt catalysts are readily prepared by known procedures, such as taught for example in U.S. Pat. No. 5,597,936, and U.S. Pat. No. 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

When present, the source of hydrogen peroxide/peracid and/or bleach activator is generally present in the composition in an amount of from about 0.1 to about 60 wt %, from about 0.5 to about 40 wt % or even from about 0.6 to about 10 wt % based on the cleaning and/or treatment composition, such as fabric and home care product. One or more hydrophobic peracids or precursors thereof may be used in combination with one or more hydrophilic peracid or precursor thereof.

Typically hydrogen peroxide source and bleach activator will be incorporated together. The amounts of hydrogen peroxide source and peracid or bleach activator may be selected such that the molar ratio of available oxygen (from the peroxide source) to peracid is from 1:1 to 35:1, or even 2:1 to 10:1.

Surfactant.

Preferably the composition comprises a surfactant or surfactant system. The surfactant can be selected from nonionic, anionic, cationic, amphoteric, ampholytic, amphiphilic, zwitterionic, semi-polar nonionic surfactants and mixtures thereof. Preferred compositions comprise a mixture of surfactants/surfactant system. Preferred surfactant systems comprise one or more anionic surfactants, most preferably in combination with a co-surfactant, most preferably a nonionic and/or amphoteric and/or zwitterionic surfactant. Preferred surfactant systems comprise both anionic and nonionic surfactant, preferably in weight ratios from 90:1 to 1:90. In some instances a weight ratio of anionic to nonionic surfactant of at least 1:1 is preferred. However a ratio below 10:1 may be preferred. When present, the total surfactant level is preferably from 0.1% to 60%, from 1% to 50% or even from 5% to 40% by weight of the subject composition.

Preferably the composition comprises an anionic detersive surfactant, preferably sulphate and/or sulphonate surfactants. Preferred examples include alkyl benzene sulphonates, alkyl sulphates and alkyl alkoxylated sulphates. Preferred sulphonates are $C_{10-13}$ alkyl benzene sulphonate. Suitable alkyl benzene sulphonate (LAS) may be obtained, by sulphonating commercially available linear alkyl benzene (LAB); suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used.

Preferred sulphate detersive surfactants include alkyl sulphate, typically $C_{8-38}$ alkyl sulphate, or predominantly $C_{3-2}$ alkyl sulphate. A further preferred alkyl sulphate is alkyl alkoxylated sulphate, preferably a $C_{8-18}$ alkyl alkoxylated sulphate. Preferably the alkoxylating group is an ethoxylating group. Typically the alkyl alkoxylated sulphate has an average degree of alkoxylation of from 0.5 to 30 or 20, or from 0.5 to 10. Particularly preferred are $C_{8-18}$ alkyl ethoxylated sulphate having an average degree of ethoxylation of from 0.5 to 10, from 0.5 to 7, from 0.5 to 5 or even from 0.5 to 3.

The alkyl sulphate, alkyl alkoxylated sulphate and alkyl benzene sulphonates may be linear or branched, substituted or un-substituted. When the surfactant is branched, preferably the surfactant will comprise a mid-chain branched sulphate or sulphonate surfactant. Preferably the branching groups comprise $C_{1-4}$ alkyl groups, typically methyl and/or ethyl groups.

Preferably the composition comprises a nonionic detersive surfactant. Suitable non-ionic surfactants are selected from the group consisting of: $C_8$-$C_{18}$ alkyl ethoxylates, such as, NEODOL® non-ionic surfactants from Shell; $C_6$-$C_1$, alkyl phenol alkoxylates wherein the alkoxylate units may be ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols; $C_{14}$-$C_{22}$ mid-chain branched alkyl alkoxylates, typically having an average degree of alkoxylation of from 1 to 30; alkylpolysaccharides, in one aspect, alkylpolyglycosides; polyhydroxy fatty acid amides; ether capped poly (oxyalkylated) alcohol surfactants; and mixtures thereof.

Suitable non-ionic detersive surfactants include alkyl polyglucoside and/or an alkyl alkoxylated alcohol.

In one aspect, non-ionic detersive surfactants include alkyl alkoxylated alcohols, in one aspect $C_{8-18}$ alkyl alkoxylated alcohol, for example a $C_{8-18}$ alkyl ethoxylated alcohol, the alkyl alkoxylated alcohol may have an average degree of alkoxylation of from 1 to 80, preferably from 1 to 50, most preferably from 1 to 30, from 1 to 20, or from 1 to 10. In one aspect, the alkyl alkoxylated alcohol may be a $C_{8-18}$ alkyl ethoxylated alcohol having an average degree of ethoxylation of from 1 to 10, from 1 to 7, more from 1 to 5 or from 3 to 7, or even below 3 or 2.

The alkyl alkoxylated alcohol can be linear or branched, and substituted or un-substituted.

Suitable nonionic surfactants include those with the tradename Lutensol® from BASF.

Suitable cationic detersive surfactants include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula:

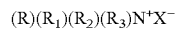

$$(R)(R_1)(R_2)(R_3)N^+X^-$$

wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, for example chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-30}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Suitable amphoteric/zwitterionic surfactants include amine oxides and betaines.

Amine-neutralized anionic surfactants—Anionic surfactants of the present invention and adjunct anionic cosurfactants, may exist in an acid form, and said acid form may be neutralized to form a surfactant salt which is desirable for use in the present detergent compositions. Typical agents for neutralization include the metal counterion base such as hydroxides, eg, NaOH or KOH. Further preferred agents for neutralizing anionic surfactants of the present invention and adjunct anionic surfactants or cosurfactants in their acid forms include ammonia, amines, or alkanolamines. Alkanolamines are preferred. Suitable non-limiting examples including monoethanolamine, diethanolamine, triethanolamine, and other linear or branched alkanolamines known in the art; for example, highly preferred alkanolamines include 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Builders.

Preferably the composition comprises one or more builders or a builder system. When a builder is used, the composition of the invention will typically comprise at least 1%, from 2% to 60% builder. It may be preferred that the composition comprises low levels of phosphate salt and/or zeolite, for example from 1 to 10 or 5 wt %. The composition may even be substantially free of strong builder; substantially free of strong builder means "no deliberately added" zeolite and/or phosphate. Typical zeolite builders include zeolite A, zeolite P and zeolite MAP. A typical phosphate builder is sodium tripolyphosphate.

Chelating Agent.

Preferably the composition comprises chelating agents and/or crystal growth inhibitor. Suitable molecules include copper, iron and/or manganese chelating agents and mixtures thereof. Suitable molecules include aminocarboxylates, aminophosphonates, succinates, salts thereof, and mixtures thereof. Non-limiting examples of suitable chelants for use herein include ethylenediaminetetracetates, N-(hydroxyethyl)ethylenediaminetriacetates, nitrilotriacetates, ethylenediamine tetraproprionates, triethylenetetraaminehexacetates, diethylenetriamine-pentaacetates, ethanoldiglycines, ethylenediaminetetrakis (methylenephosphonates), diethylenetriamine penta(methylene phosphoric acid) (DTPMP), ethylenediamine disuccinate (EDDS), hydroxyetlianedimethylenephosphonic acid (HEDP), methylglycinediacetic acid (MGDA), diethylenetriaminepentaacetic acid (DTPA), salts thereof, and mixtures thereof. Other nonlimiting examples of chelants of use in the present invention are found in U.S. Pat. Nos. 7,445,644, 7,585,376 and 2009/0176684A1. Other suitable chelating agents for use herein are the commercial DEQUEST series, and chelants from Monsanto, DuPont, and Nalco, Inc.

Dye Transfer Inhibitor (DTI).

The composition may comprise one or more dye transfer inhibiting agents. In one embodiment of the invention the inventors have surprisingly found that compositions comprising polymeric dye transfer inhibiting agents in addition to the specified dye give improved performance. This is surprising because these polymers prevent dye deposition. Suitable dye transfer inhibitors include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Suitable examples include PVP-K15, PVP-K30, ChromaBond S-400, ChromaBond S-403E and Chromabond S-100 from Ashland Aqualon, and Sokalan HP165, Sokalan HP50, Sokalan HP53, Sokalan HP59, Sokalan® HP 56K, Sokalan® HP 66 from BASF. Other suitable DTIs are as described in WO2012/004134. When present in a subject composition, the dye transfer inhibiting agents may be present at levels from about 0.0001% to about 10%, from about 0.01% to about 5% or even from about 0.1% to about 3% by weight of the composition.

Fluorescent Brightener.

Preferably the composition comprises one or more fluorescent brightener. Commercial optical brighteners which may be useful in the present invention can be classified into subgroups, which include, but are not limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Particularly preferred brighteners are selected from: sodium 2 (4-styryl-3-sulfophenyl)-2H-napthol[1,2-d]triazole, disodium 4,4'-bis{[(4-anilino-6-(N methyl-N-2 hydroxyethyl)amino 1,3,5-triazin-2-yl)]amino}stilbene-2-{2-disulfonate, disodium 4,4'-bis{[(4-anilino-6-morpholino-1,3,5-triazin-2-yl)]amino}stilbene-2-2'disulfonate, and disodium 4,4'-bis(2-sulfostyryl)biphenyl. Other examples of such brighteners are disclosed in "The Production and Application of Fluorescent Brightening Agents", M. Zahradnik, Published by John Wiley & Sons, New York (1982). Specific nonlimiting examples of optical brighteners which are useful in the present compositions are those identified in U.S. Pat. No. 4,790,856 and U.S. Pat. No. 3,646,015.

A preferred brightener has the structure below:

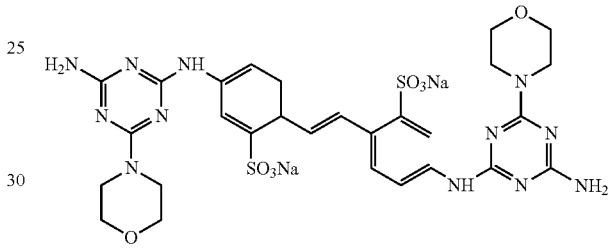

Suitable fluorescent brightener levels include lower levels of from about 0.01, from about 0.05, from about 0.1 or even from about 0.2 wt % to upper levels of 0.5 or even 0.75 wt %.

In one aspect the brightener may be loaded onto a clay to form a particle.

Preferred brighteners are totally or predominantly (typically at least 50 wt %, at least 75 wt %, at least 90 wt %, at least 99 wt %), in alpha-crystalline form. A highly preferred brightener comprises C.I. fluorescent brightener 260, preferably having the following structure:

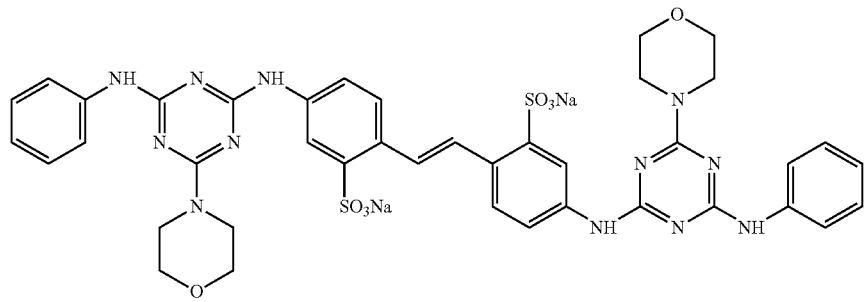

This can be particularly useful as it dissolves well in cold water, for example below 30 or 25 or even 20° C.

Preferably brighteners are incorporated in the composition in micronized particulate form, most preferably having a weight average primary particle size of from 3 to 30 micrometers, from 3 micrometers to 20 micrometers, or from 3 to 10 micrometers.

The composition may comprise C.I. fluorescent brightener 260 in beta-crystalline form, and the weight ratio of: (i) C.I. fluorescent brightener 260 in alpha-crystalline form, to (ii) C.I. fluorescent brightener 260 in beta-crystalline form may be at least 0.1, or at least 0.6.

BE680847 relates to a process for making C.I fluorescent brightener 260 in alpha-crystalline form.

Silicate Salts.

The composition may preferably also contain silicate salts, such as sodium or potassium silicate. The composition may comprise from 0 wt % to less than 10 wt % silicate salt, to 9 wt %, or to 8 wt %, or to 7 wt %, or to 6 wt %, or to 5 wt %, or to 4 wt %, or to 3 wt %, or even to 2 wt %, and preferably from above 0 wt %, or from 0.5 wt %, or even from 1 wt % silicate salt. A suitable silicate salt is sodium silicate.

Dispersants.

The composition may preferably also contain dispersants. Suitable water-soluble organic materials include the homo- or co-polymeric acids or their salts, in which the polycarboxylic acid comprises at least two carboxyl radicals separated from each other by not more than two carbon atoms.

Enzyme Stabilisers.

The composition may preferably comprise enzyme stabilizers. Any conventional enzyme stabilizer may be used, for example by the presence of water-soluble sources of calcium and/or magnesium ions in the finished fabric and home care products that provide such ions to the enzymes. In case of aqueous compositions comprising protease, a reversible protease inhibitor, such as a boron compound including borate, or preferably 4-formyl phenylboronic acid, phenylboronic acid and derivatives thereof, or compounds such as calcium formate, sodium formate and 1,2-propane diol can be added to further improve stability.

Solvent System.

The solvent system in the present compositions can be a solvent system containing water alone or mixtures of organic solvents either without or preferably with water. Preferred organic solvents include 1,2-propanediol, ethanol, glycerol, dipropylene glycol, methyl propane diol and mixtures thereof. Other lower alcohols, C1-C4 alkanolamines such as monoethanolamine and triethanolamine, can also be used. Solvent systems can be absent, for example from anhydrous solid embodiments of the invention, but more typically are present at levels in the range of from about 0.1% to about 98%, preferably at least about 1% to about 50%, more usually from about 5% to about 25%.

In some embodiments of the invention, the composition is in the form of a structured liquid. Such structured liquids can either be internally structured, whereby the structure is formed by primary ingredients (e.g. surfactant material) and/or externally structured by providing a three dimensional matrix structure using secondary ingredients (e.g. polymers, clay and/or silicate material), for use e.g. as thickeners. The composition may comprise a structurant, preferably from 0.01 wt % to 5 wt %, from 0.1 wt % to 2.0 wt % structurant. Examples of suitable structurants are given in US2006/0205631A1, US2005/0203213A1, U.S. Pat. Nos. 7,294,611, 6,855,680. The structurant is typically selected from the group consisting of diglycerides and triglycerides, ethylene glycol distearate, microcrystalline cellulose, cellulose-based materials, microfiber cellulose, hydrophobically modified alkali-swellable emulsions such as Polygel W30 (3VSigma), biopolymers, xanthan gum, gellan gum, hydrogenated castor oil, derivatives of hydrogenated castor oil such as non-ethoxylated derivatives thereof and mixtures thereof, in particular, those selected from the group of hydrogenated castor oil, derivatives of hydrogenated castor oil, microfibullar cellulose, hydroxyfunctional crystalline materials, long chain fatty alcohols, 12-hydroxystearic acids, clays and mixtures thereof. A preferred structurant is described in. U.S. Pat. No. 6,855,680 which defines suitable hydroxyfunctional crystalline materials in detail. Preferred is hydrogenated castor oil. Non-limiting examples of useful structurants include. Such structurants have a thread-like structuring system having a range of aspect ratios. Other suitable structurants and the processes for making them are described in WO2010/034736.

The composition of the present invention may comprise a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992. When present, the high melting point fatty compound is preferably included in the composition at a level of from 0.1% to 40%, preferably from 1% to 30%, more preferably from 1.5% to 16% by weight of the composition, from 1.5% to 8% in view of providing improved conditioning benefits such as slippery feel during the application to wet hair, softness and moisturized feel on dry hair.

Cationic Polymer.

The compositions of the present invention may contain a cationic polymer. Concentrations of the cationic polymer in the composition typically range from 0.05% to 3%, in another embodiment from 0.075% to 2.0%, and in yet another embodiment from 0.1% to 1.0%. Suitable cationic polymers will have cationic charge densities of at least 0.5 meq/gm, in another embodiment at least 0.9 meq/gm, in another embodiment at least 1.2 meq/gm, in yet another embodiment at least 1.5 meq/gm, but in one embodiment also less than 7 meq/gm, and in another embodiment less than 5 meq/gm, at the pH of intended use of the composition, which pH will generally range from pH 3 to pH 9, in one embodiment between pH 4 and pH 8. Herein, "cationic charge density" of a polymer refers to the ratio of the number of positive charges on the polymer to the molecular weight of the polymer. The average molecular weight of such suitable cationic polymers will generally be between 10,000 and 10 million, in one embodiment between 50,000 and 5 million, and in another embodiment between 100,000 and 3 million.

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Nonlimiting examples of such counterions include halides (e.g., chloride, fluoride, bromide, iodide), sulfate and methylsulfate.

Nonlimiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition.

Suitable cationic polymers are described in U.S. Pat. Nos. 3,962,418; 3,958,581; and U.S. Publication No. 2007/0207109A1.

Nonionic Polymer.

The composition of the present invention may include a nonionic polymer as a conditioning agent. Polyalkylene glycols having a molecular weight of more than 1000 are useful herein. Useful are those having the following general formula:

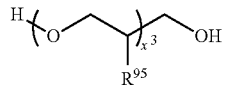

wherein R95 is selected from the group consisting of H, methyl, and mixtures thereof. Conditioning agents, and in particular silicones, may be included in the composition. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the conditioning agent in the composition should be sufficient to provide the desired conditioning benefits. Such concentration can vary with the conditioning agent, the conditioning performance desired, the average size of the conditioning agent particles, the type and concentration of other components, and other like factors.

The concentration of the silicone conditioning agent typically ranges from about 0.01% to about 10%. Non-limiting examples of suitable silicone conditioning agents, and optional suspending agents for the silicone, are described in U.S. Reissue Pat. No. 34,584, U.S. Pat. Nos. 5,104,646; 5,106,609; 4,152,416; 2,826,551; 3,964,500; 4,364,837; 6,607,717; 6,482,969; 5,807,956; 5,981,681; 6,207,782; 7,465,439; 7,041,767; 7,217,777; US Patent Application Nos. 2007/0286837A1; 2005/0048549A1; 2007/0041929A1; British Pat. No. 849,433; German Patent No. DE 10036533, which are all incorporated herein by reference; Chemistry and Technology of Silicones, New York: Academic Press (1968); General Electric Silicone Rubber Product Data Sheets SE 30, SE 33, SE 54 and SE 76; Silicon Compounds, Petrarch Systems, Inc. (1984); and in Encyclopedia of Polymer Science and Engineering, vol. 15, 2d ed., pp 204-308, John Wiley & Sons, Inc. (1989).

Organic Conditioning Oil.

The compositions of the present invention may also comprise from about 0.05% to about 3% of at least one organic conditioning oil as the conditioning agent, either alone or in combination with other conditioning agents, such as the silicones (described herein). Suitable conditioning oils include hydrocarbon oils, polyolefins, and fatty esters. Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217, 914, 4,381,919, and 4,422, 853.

Hygiene Agent.

The compositions of the present invention may also comprise components to deliver hygiene and/or malodour benefits such as one or more of zinc ricinoleate, thymol, quaternary ammonium salts such as Bardac®, polyethylenimines (such as Lupasol® from BASF) and zinc complexes thereof, silver and silver compounds, especially those designed to slowly release Ag+ or nano-silver dispersions.

Probiotics.

The composition may comprise probiotics, such as those described in WO2009/043709.

Suds Boosters.

The composition may preferably comprise suds boosters if high sudsing is desired. Suitable examples are the C10-C16 alkanolamides or C10-C14 alkyl sulphates, which are preferably incorporated at 1%-10% levels. The C10-C14 monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as MgCl2, MgSO4, CaCl2, CaSO4 and the like, can be added at levels of, typically, 0.1%-2%, to provide additional suds and to enhance grease removal performance.

Suds Supressor.

Compounds for reducing or suppressing the formation of suds may be incorporated into the compositions of the present invention. Suds suppression can be of particular importance in the so-called "high concentration cleaning process" as described in U.S. Pat. Nos. 4,489,455 and 4,489,574, and in front-loading-style washing machines. A wide variety of materials may be used as suds suppressors, and suds suppressors are well known to those skilled in the art. See, for example, Kirk Othmer Encyclopedia of Chemical Technology, Third Edition, Volume 7, pages 430-447 (John Wiley & Sons, Inc., 1979). Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic C18-C40 ketones (e.g., stearone), N-alkylated amino triazines, waxy hydrocarbons preferably having a melting point below about 100° C., silicone suds suppressors, and secondary alcohols. Suds supressors are described in U.S. Pat. Nos. 2,954,347; 4,265, 779; 4,265,779; 3,455,839; 3,933,672; 4,652,392; 4,978, 471; 4,983,316; 5,288,431; 4,639,489; 4,749,740; and 4,798,679; 4,075,118; European Patent Application No. 89307851.9; EP 150,872; and DOS 2,124,526.

For any detergent compositions to be used in automatic laundry washing machines, suds should not form to the extent that they overflow the washing machine. Suds suppressors, when utilized, are preferably present in a "suds suppressing amount. By "suds suppressing amount" is meant that the formulator of the composition can select an amount of this suds controlling agent that will sufficiently control the suds to result in a low-sudsing laundry detergent for use in automatic laundry washing machines. The compositions herein will generally comprise from 0% to 10% of suds suppressor. When utilized as suds suppressors, monocarboxylic fatty acids, and salts therein, will be present typically in amounts up to 5%, by weight, of the detergent composition. Preferably, from 0.5% to 3% of fatty monocarboxylate suds suppressor is utilized. Silicone suds suppressors are typically utilized in amounts up to 2.0%, by weight, of the detergent composition, although higher amounts may be used. Monostearyl phosphate suds suppressors are generally utilized in amounts ranging from 0.1% to 2%, by weight, of the composition. Hydrocarbon suds suppressors are typically utilized in amounts ranging from 0.01% to 5.0%, although higher levels can be used. The alcohol suds suppressors are typically used at 0.2%-3% by weight of the finished compositions.

Pearlescent Agents.

Pearlescent agents as described in WO2011/163457 may be incorporated into the compositions of the invention.

Perfume.

Preferably the composition comprises a perfume, preferably in the range from 0.001 to 3 wt %, most preferably from 0.1 to 1 wt %. Many suitable examples of perfumes are provided in the CTFA (Cosmetic, Toiletry and Fragrance Association) 1992 International Buyers Guide, published by CFTA Publications and OPD 1993 Chemicals Buyers Directory 80$^{th}$ Annual Edition, published by Schnell Publishing Co. It is usual for a plurality of perfume components to be present in the compositions of the invention, for example four, five, six, seven or more. In perfume mixtures preferably 15 to 25 wt % are top notes. Top notes are defined by Poucher (Journal of the Society of Cosmetic Chemists 6(2):80 [1995]). Preferred top notes include rose oxide, citrus oils, linalyl acetate, lavender, linalool, dihydromyrcenol and cis-3-hexanol.

Processes of Making and Using Cleaning Compositions

The present invention also provides a method of making a composition as described above comprising obtaining at least one of the variants described above and mixing it with an adjunct material or mixture thereof.

The cleaning compositions of the present invention are formulated into any suitable form such as a solid, powder, liquid, tablet or gel and the mixing of the variant and the adjunct may be by any suitable process chosen by the formulator, (See e.g., U.S. Pat. Nos. 5,879,584, 5,691,297, 5,574,005, 5,569,645, 5,565,422, 5,516,448, 5,489,392, 5,486,303, 4,515,705, 4,537,706, 4,515,707, 4,550,862, 4,561,998, 4,597,898, 4,968,451, 5,565,145, 5,929,022, 6,294,514 and 6,376,445).

In some embodiments, the cleaning compositions of the present invention are provided in unit dose form, including tablets, capsules, sachets, pouches, and multi-compartment pouches. In some embodiments, the unit dose format is designed to provide controlled release of the ingredients within a multi-compartment pouch (or other unit dose format). Suitable unit dose and controlled release formats are known in the art (See e.g., EP 2 100 949, WO 02/102955, U.S. Pat. Nos. 4,765,916 and 4,972,017, and WO 04/111178 for materials suitable for use in unit dose and controlled release formats). In some embodiments, the unit dose form is provided by tablets wrapped with a water-soluble film or water-soluble pouches. Various formats for unit doses are provided in EP 2 100 947, and are known in the art. In a preferred multi-compartment pouch, the protease variant is in a separate compartment from one or more of a further protease enzyme, a first wash lipase enzyme, a cellulase enzyme, an amylase enzyme, a bleach component, a pH modifier, a fabric hueing dye, an optical brightener and a non-ionic surfactant, or mixtures thereof.

Methods of Use

The present invention also provides a method of treating a surface, particularly a fabric, comprising contacting the surface with an aqueous liquor comprising at least one of the variants listed above and an adjunct material Typically the protease variant and adjunct material are added to water to form the wash liquor by adding the composition of the invention to water. The surface to be treated in the method of the invention may be any fabric or home care surface for cleaning such as dishware, laundry, hard surfaces, contact lenses, etc. In some embodiments, at least a portion of the surface is contacted with at least one embodiment of the cleaning compositions of the present invention, in neat form or diluted in a wash liquor, and then the surface is optionally washed and/or rinsed. For purposes of the present invention, "washing" includes, but is not limited to, soaking, scrubbing, and mechanical washing. In some embodiments, the cleaning compositions of the present invention are used at concentrations of from about 500 ppm to about 15,000 ppm in solution. In some embodiments in which the wash solvent is water, the water temperature typically ranges from about 5° C. to about 90° C.

The present invention provides methods for cleaning or washing an item or surface (e.g., hard surface) in need of cleaning, including, but not limited to methods for cleaning or washing a dishware item, a tableware item, a fabric item, a laundry item, personal care item, etc., or the like, and methods for cleaning or washing a hard or soft surface (e.g., a hard surface of an item).

In some embodiments, the present invention provides a method for cleaning an item, object, or surface in need of cleaning, the method comprising contacting the item or surface (or a portion of the item or surface desired to be cleaned) with at least one variant subtilisin protease of the present invention or a composition of the present invention for a sufficient time and/or under conditions suitable and/or effective to clean the item, object, or surface to a desired degree. Some such methods further comprise rinsing the item, object, or surface with water. For some such methods, the cleaning composition is a dishwashing detergent composition and the item or object to be cleaned is a dishware item or tableware item. As used herein, a "dishware item" is an item generally used in serving or eating food. A dishware item can be, but is not limited to for example, a dish, plate, cup, bowl, etc., and the like. As used herein, "tableware" is a broader term that includes, but is not limited to for example, dishes, cutlery, knives, forks, spoons, chopsticks, glassware, pitchers, sauce boats, drinking vessels, serving items, etc. It is intended that "tableware item" includes any of these or similar items for serving or eating food. For some such methods, the cleaning composition is an automatic dishwashing detergent composition or a hand dishwashing detergent composition and the item or object to be cleaned is a dishware or tableware item. For some such methods, the cleaning composition is a laundry detergent composition (e.g., a power laundry detergent composition or a liquid laundry detergent composition), and the item to be cleaned is a fabric item. In some other embodiments, the cleaning composition is a laundry pre-treatment composition. The cleaning composition may comprise a hard surface cleaner.

In some embodiments, the present invention provides methods for cleaning or washing a fabric item optionally in need of cleaning or washing, respectively. In some embodiments, the methods comprise providing a composition comprising the variant protease, including but not limited to fabric or laundry cleaning composition, and a fabric item or laundry item in need of cleaning, and contacting the fabric item or laundry item (or a portion of the item desired to be cleaned) with the composition under conditions sufficient or effective to clean or wash the fabric or laundry item to a desired degree.

In some embodiments, the present invention provides a method for cleaning or washing an item or surface (e.g., hard surface) optionally in need of cleaning, the method comprising providing an item or surface to be cleaned or washed and contacting the item or surface (or a portion of the item or surface desired to be cleaned or washed) with at least one subtilisin variant of the invention or a composition of the invention comprising at least one such subtilisin variant for a sufficient time and/or under conditions sufficient or effective to clean or wash the item or surface to a desired degree. Such compositions include, but are not limited to for example, a cleaning composition or detergent composition of the invention (e.g., a hand dishwashing detergent composition, hand dishwashing cleaning composition, laundry detergent or fabric detergent or laundry or fabric cleaning composition, liquid laundry detergent, liquid laundry cleaning composition, powder laundry detergent composition, powder laundry cleaning composition, automatic dishwashing detergent composition, laundry booster cleaning or detergent composition, laundry cleaning additive, and laundry pre-spotter composition, etc.). In some embodiments, the method is repeated one or more times, particularly if additional cleaning or washing is desired. For example, in some instance, the method optionally further comprises allowing the item or surface to remain in contact with the at least one variant protease or composition for a period of time sufficient or effective to clean or wash the item or surface to the desired degree. In some embodiments, the methods further comprise rinsing the item or surface with water and/or another liquid. In some embodiments, the methods further comprise contacting the item or surface with at least one variant protease of the invention or a composition of the invention again and allowing the item or surface to remain in contact with the at least one variant protease or composition for a period of time sufficient to clean or wash the item or surface to the desired degree. In some embodiments, the cleaning composition is a dishwashing detergent composition and the item to be cleaned is a dishware or tableware item. In some embodiments of the present methods, the cleaning composition is an automatic dishwashing detergent composition or a hand dishwashing detergent composition and the item to be cleaned is a dishware or tableware item. In some embodiments of the methods, the cleaning composition is a laundry detergent composition and the item to be cleaned is a fabric item.

The present invention also provides methods of cleaning a tableware or dishware item in an automatic dishwashing machine, the method comprising providing an automatic dishwashing machine, placing an amount of an automatic dishwashing composition comprising at least one subtilisin variant of the present invention or a composition of the invention sufficient to clean the tableware or dishware item in the machine (e.g., by placing the composition in an appropriate or provided detergent compartment or dispenser in the machine), putting a dishware or tableware item in the machine, and operating the machine so as to clean the tableware or dishware item (e.g., as per the manufacturer's instructions). In some embodiments, the methods include any automatic dishwashing composition described herein, which comprises, but is not limited to at least one subtilisin variant provided herein. The amount of automatic dishwashing composition to be used can be readily determined according to the manufacturer's instructions or suggestions and any form of automatic dishwashing composition comprising at least one variant protease of the invention (e.g., liquid, powder, solid, gel, tablet, etc.), including any described herein, may be employed.

The present invention also provides methods for cleaning a surface, item or object optionally in need of cleaning, the method comprises contacting the item or surface (or a portion of the item or surface desired to be cleaned) with at least one variant subtilisin of the present invention or a cleaning composition of the invention in neat form or diluted in a wash liquor for a sufficient time and/or under conditions sufficient or effective to clean or wash the item or surface to a desired degree. The surface, item, or object may then be (optionally) washed and/or rinsed if desired. For purposes of the present invention, "washing" includes, but is not limited to for example, scrubbing and mechanical agitation. In some embodiments, the cleaning compositions are employed at concentrations of from about 500 ppm to about 15,000 ppm in solution (e.g., aqueous solution). When the wash solvent is water, the water temperature typically ranges from about 5° C. to about 90° C. and when the surface, item or object comprises a fabric, the water to fabric mass ratio is typically from about 1:1 to about 30:1.

The present invention also provides methods of cleaning a laundry or fabric item in an washing machine, the method comprising providing an washing machine, placing an amount of a laundry detergent composition comprising at least one variant subtilisin of the invention sufficient to clean the laundry or fabric item in the machine (e.g., by placing the composition in an appropriate or provided detergent compartment or dispenser in the machine), placing the laundry or fabric item in the machine, and operating the machine so as to clean the laundry or fabric item (e.g., as per the manufacturer's instructions). The methods of the present invention include any laundry washing detergent composition described herein, comprising but not limited to at least one of any variant subtilisin provided herein. The amount of laundry detergent composition to be used can be readily determined according to manufacturer's instructions or suggestions and any form of laundry detergent composition comprising at least one variant protease of the invention (e.g., solid, powder, liquid, tablet, gel, etc.), including any described herein, may be employed.

EXPERIMENTAL

The present invention is described in further detail in the following examples which are not in any way intended to limit the scope of the invention as claimed.

In the experimental disclosure which follows, the following abbreviations apply: PI (Performance Index), ppm (parts per million); M (molar); mM (millimolar); μM (micromolar); nM (nanomolar); mol (moles); mmol (millimoles); pmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); rpm (revolutions per minute); GH (degrees German hardness); $H_2O$ (water); $dH_2O$ (deionized water); HCl (hydrochloric acid); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); w/w (weight to weight); g (gravity); OD (optical density); ppm (parts per million); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto-Tryptone, 24 g/l glycerol, 2.31 g/l $KH_2PO_4$, and 12.54 g/l $K2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN®-20); PEG (polyethylene glycol); PCR (polymerase chain reaction); RT-PCR (reverse transcription PCR); SDS (sodium dodecyl sulfate); Tris (tris (hydroxymethyl)aminomethane); HEPES (N-[2-Hydroxyethyl]piperazine-N-[2-ethanesulfonic acid]); HBS (HEPES buffered saline); Tris-HCl (tris[Hydroxymethyl]aminomethane-hydrochloride); Tricine (N-[tris-(hydroxymethyl)-methyl]-glycine); CHES (2-(N-cyclo-hexylamino) ethanesulfonic acid); TAPS (3-{[tris-(hydroxymethyl)-methyl]-amino}-propanesulfonic acid); CAPS (3-(cyclohexylamino)-propane-sulfonic acid; DMSO (dimethyl sulfoxide); DTT (1,4-dithio-DL-threitol); SA (sinapinic acid (s,5-dimethoxy-4-hydroxy cinnamic acid); TCA (trichloroacetic acid); Glut and GSH (reduced glutathione); GSSG (oxidized glutathione); TCEP (Tris[2-carboxyethyl]phosphine); Ci (Curies); mCi (milliCuries); µCi (microCuries); HPLC (high pressure liquid chromatography); RP-HPLC (reverse phase high pressure liquid chromatography); TLC (thin layer chromatography); MALDI-TOF (matrix-assisted laser desorption/ionization—time of flight); Ts (tosyl); Bn (benzyl); Ph (phenyl); Ms (mesyl); Et (ethyl), Me (methyl); Taq (*Thermus aquaticus* DNA polymerase); Klenow (DNA polymerase I large (Klenow) fragment); EGTA (ethylene glycol-bis(β-aminoethyl ether) N,N,N',N'-tetraacetic acid); EDTA (ethylenediaminetetracetic acid); bla (β-lactamase or ampicillin-resistance gene); MJ Research (MJ Research, Reno, Nev.); Baseclear (Baseclear BV, Inc., Leiden, the Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.); Seitz EKS (SeitzSchenk Filtersystems GmbH, Bad Kreuznach, Germany); Pall (Pall Corp., East Hills, N.Y. and Bad Kreuznach, Germany); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingen, the Netherlands); P&G and Procter & Gamble (Procter & Gamble, Inc., Cincinnati, Ohio); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); Molecular Devices (Molecular Devices, Corp., Sunnyvale, Calif.); R&D Systems (R&D Systems, Minneapolis, Minn.); Siegfried Handel (Siegfried Handel AG, Zofingen, Switzerland); Stratagene (Stratagene Cloning Systems, La Jolla, Calif.); Marsh (Marsh Biosciences, Rochester, N.Y.); Geneart (Geneart GmbH, Regensburg, Germany); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Shell Chemicals (Shell Chemicals, Inc., London, UK); Stepan (Stepan, Northfield, Ill.); Clariant (Clariant, Sulzbach, Germany); Industrial Zeolite (Industrial Zeolite Ltd., Grays, Essex, UK); Jungbunzlauer (Jungbunzlauer, Basel, Switzerland); Solvay (Solvay, Brussels, Belgium); 3V Sigma (3V Sigma, Bergamo, Italy); Innospec (Innospec, Ellesmere Port, UK); Thermphos (Thermphos, Vlissiggen-Ost, the Netherlands); Ciba Specialty (Ciba Specialty Chemicals, Basel, Switzerland); Dow Corning (Dow Corning, Barry, UK); Enichem (Enichem Iberica, Barcelona, Spain); Fluka Chemie AG (Fluka Chemie AG, Buchs, Switzerland); Gist-Brocades (Gist-Brocades, NV, Delft, the Netherlands); Dow Corning (Dow Corning Corp., Midland, Mich.); Mettler-Toledo (Mettler-Toledo Inc, Columbus, Ohio); RB (Reckitt-Benckiser, Slough, UK); and Microsoft (Microsoft, Inc., Redmond, Wash.).

As used herein, in some lists, a leading "0" is indicated, in order to provide a three number designation for each site (e.g., "001" is the same as "1," so "A001C" is the same as "A1C"). In some lists, the leading "0" is not included. In addition, as used herein, "X" refers to any amino acid.

In the exemplified detergent compositions provided herein, the enzymes levels are expressed by pure enzyme by weight of the total composition and unless otherwise specified, the detergent ingredients are expressed by weight of the total compositions. The abbreviated component identifications therein have the following meanings:

| Abbreviation | Ingredient |
|---|---|
| LAS | Sodium linear $C_{11-13}$ alkyl benzene sulfonate. |
| NaC16-17HSAS | Sodium $C_{16-17}$ highly soluble alkyl sulfate |
| TAS | Sodium tallow alkyl sulphate. |
| CxyAS | Sodium $C_{1x}$-$C_{1y}$ alkyl sulfate. |
| CxyEz | $C_{1x}$-$C_{1y}$ predominantly linear primary alcohol condensed with an average of z moles of ethylene oxide. |
| CxyAEzS | $C_{1x}$-$C_{1y}$ sodium alkyl sulfate condensed with an average of z moles of ethylene oxide. Added molecule name in the examples. |
| Nonionic | Mixed ethoxylated/propoxylated fatty alcohol e.g. Plurafac LF404 being an alcohol with an average degree of ethoxylation of 3.8 and an average degree of propoxylation of 4.5. |
| QAS | $R_2 \cdot N + (CH_3)_2(C_2H_4OH)$ with $R_2 = C_{12}$-$C_{14}$. |
| Silicate | Amorphous Sodium Silicate ($SiO_2:Na_2O$ ratio = 1.6-3.2:1). |
| Metasilicate | Sodium metasilicate ($SiO_2:Na_2O$ ratio = 1.0). |
| Zeolite A | Hydrated aluminosilicate of formula $Na_{12}(AlO_2SiO_2)_{12} \cdot 27H_2O$ |
| SKS-6 | Crystalline layered silicate of formula $\delta$-$Na_2Si_2O_5$. |
| Sulfate | Anhydrous sodium sulphate. |
| STPP | Sodium Tripolyphosphate. |
| MA/AA | Random copolymer of 4:1 acrylate/maleate, average molecular weight about 70,000-80,000. |
| AA | Sodium polyacrylate polymer of average molecular weight 4,500. |
| Polycarboxylate | Copolymer comprising mixture of carboxylated monomers such as acrylate, maleate and methacrylate with a MW ranging between 2,000-80,000 such as Sokolan commercially available from BASF, being a copolymer of acrylic acid, MW4,500. |
| BB1 | 3-(3,4-Dihydroisoquinolinium)propane sulfonate |
| BB2 | 1-(3,4-dihydroisoquinolinium)-decane-2-sulfate |
| PB1 | Sodium perborate monohydrate. |
| PB4 | Sodium perborate tetrahydrate of nominal formula $NaBO_3 \cdot 4H_2O$. |
| Percarbonate | Sodium percarbonate of nominal formula $2Na_2CO_3 \cdot 3H_2O_2$. |
| TAED | Tetraacetyl ethylene diamine. |
| NOBS | Nonanoyloxybenzene sulfonate in the form of the sodium salt. |
| DTPA | Diethylene triamine pentaacetic acid. |
| HEDP | 1,1-hydroxyethane diphosphonic acid. |
| DETPMP | Diethyltriamine penta (methylene) phosphonate, marketed by Monsanto under the Trade name Dequest 2060. |
| EDDS | Ethylenediamine-N,N'-disuccinic acid, (S,S) isomer in the form of its sodium salt |
| Diamine | Dimethyl aminopropyl amine; 1,6-hezane diamine; 1,3-propane diamine; 2-methyl-1,5-pentane diamine; 1,3-pentanediamine; 1-methyl-diaminopropane. |
| DETBCHD | 5,12-diethyl-1,5,8,12-tetraazabicyclo [6,6,2] hexadecane, dichloride, Mn(II) SALT |
| PAAC | Pentaamine acetate cobalt(III) salt. |
| Paraffin | Paraffin oil sold under the tradename Winog 70 by Wintershall. |
| Paraffin Sulfonate | A Paraffin oil or wax in which some of the hydrogen atoms have been replaced by sulfonate groups. |
| Aldose oxidase | Oxidase enzyme sold under the tradename Aldose Oxidase by Novozymes A/S |
| Galactose oxidase | Galactose oxidase from Sigma |
| nprE | The recombinant form of neutral metalloprotease expressed in *Bacillus subtilis* (See e.g., WO 07/044993) |
| PMN | Purified neutral metalloprotease from *Bacillus amyloliquefaciens*. |
| Amylase | A suitable amylolytic enzyme, such as those sold under the tradenames PURAFECT ® Ox described in WO 94/18314, WO96/05295 sold by Genencor; NATALASE ®, TERMAMYL ®, FUNGAMYI ® and DURAMYL ™, all available from Novozymes A/S. |
| Lipase | A suitable lipolytic enzyme such as those sold under the tradenames LIPEX ®, LIPOLASE ®, LIPOLASE ® Ultra by Novozymes A/S and Lipomax ™ by Gist-Brocades. |
| Cellulase | A suitable cellulytic enzyme such as those sold under the tradenames CAREZYME ®, CELLUZYME ®, and/or ENDOLASE ® by Novozymes A/S. |
| Pectin Lyase | A suitable pectin lyase, such as those sold under the tradenames PECTAWAY ® and PECTAWASH ® available from Novozymes A/S. |
| PVP | Polyvinylpyrrolidone with an average molecular weight of 60,000 |
| PVNO | Polyvinylpyridine-N-Oxide, with an average molecular weight of 50,000. |
| PVPVI | Copolymer of vinylimidazole and vinylpyrrolidone, with an average molecular weight of 20,000. |

-continued

| Abbreviation | Ingredient |
|---|---|
| Brightener 1 | Disodium 4,4'-bis(2-sulphostyryl)biphenyl. |
| Silicone antifoam | Polydimethylsiloxane foam controller with siloxane-oxyalkylene copolymer as dispersing agent with a ratio of said foam controller to said dispersing agent of 10:1 to 100:1. |
| Suds Suppressor | 12% Silicone/silica, 18% stearyl alcohol, 70% starch in granular form. |
| SRP 1 | Anionically end capped poly esters. |
| PEG X | Polyethylene glycol, of a molecular weight of x. |
| PVP K60 ® | Vinylpyrrolidone homopolymer (average MW 160,000) |
| Jeffamine ® ED-2001 | Capped polyethylene glycol from Huntsman |
| Isachem ® AS | A branched alcohol alkyl sulphate from Enichem |
| MME PEG (2000) | Monomethyl ether polyethylene glycol (MW 2000) from Fluka Chemie AG. |
| DC3225C | Silicone suds suppresser, mixture of Silicone oil and Silica from Dow Corning. |
| TEPAE | Tetraethylenepentaamine ethoxylate. |
| BTA | Benzotriazole. |
| Betaine | $(CH_3)_3N^+CH_2COO^-$ |
| Sugar | Industry grade D-glucose or food grade sugar |
| CFAA | $C_{12}$-$C_{14}$ alkyl N-methyl glucamide |
| TPKFA | $C_{12}$-$C_{14}$ topped whole cut fatty acids. |
| Clay | A hydrated aluminumu silicate in a general formula $Al_2O_3SiO_2 \cdot xH_2O$. Types: Kaolinite, montmorillonite, atapulgite, illite, bentonite, halloysite. |
| pH | Measured as a 1% solution in distilled water at 20° C. |

For North American (NA) and Western European (WE) heavy duty liquid laundry (HDL) detergents, heat inactivation of the enzymes present in commercially-available detergents is performed by placing pre-weighed liquid detergent (in a glass bottle) in a water bath at 95° C. for 2 hours. The incubation time for heat inactivation of NA and WE auto dish washing (ADW) detergents is 8 hours. Both un-heated and heated detergents are assayed within 5 minutes of dissolving the detergent to accurately determine percentage deactivated. Enzyme activity is tested by the AAPF assay.

For testing of enzyme activity in heat-inactivated detergents, working solutions of detergents are made from the heat inactivated stocks. Appropriate amounts of water hardness (e.g., 6 gpg or 12 gpg) and buffer are added to the detergent solutions to match the desired conditions. The solutions are mixed by vortexing or inverting the bottles. The following Table A provides information regarding some detergent compositions. In some experiments, additional and/or other commercially available detergents find use in the following Examples.

Table A provides granular laundry detergent compositions produced in accordance with the invention suitable for laundering fabrics.

TABLE A

Granular Laundry Detergent Compositions and Their Components

| Component | Detergent Compositions | | | | | |
|---|---|---|---|---|---|---|
| | 1 | 2 | 3 | 4 | 5 | 6 |
| Linear alkylbenzenesulfonate with aliphatic carbon chain length $C_{11}$—$C_{12}$ | 15 | 12 | 20 | 10 | 12 | 13 |
| Other surfactants | 1.6 | 1.2 | 1.9 | 3.2 | 0.5 | 1.2 |
| Phosphate builder(s) | 2 | 3 | 4 | | | |
| Zeolite | | 1 | | 1 | 4 | 1 |
| Silicate | 4 | 5 | 2 | 3 | 3 | 5 |
| Sodium Carbonate | 2 | 5 | 5 | 4 | 0 | 3 |
| Polyacrylate (MW 4500) | 1 | 0.6 | 1 | 1 | 1.5 | 1 |
| Carboxymethyl cellulose (Finnfix BDA ex CPKelco) | 1 | — | 0.3 | — | 1.1 | — |
| Celluclean ® (15.6 mg/g) | 0.23 | 0.17 | 0.5 | 0.2 | 0.2 | 0.6 |
| Cold Water Protease* | 0.23 | 0.17 | 0.05 | 0.2 | 0.03 | 0.1 |
| Stainzyme Plus ® (14 mg/g) | 0.23 | 0.17 | 0.5 | 0.2 | 0.2 | 0.6 |
| Mannaway 4.0T (4 mg/g) | 0.1 | | | 0.1 | | 0.1 |
| Lipex 100T (18.6 mg/g) | 0.2 | | 0.1 | | 0.3 | |
| Fluorescent Brightener(s) | 0.16 | 0.06 | 0.16 | 0.18 | 0.16 | 0.16 |
| Diethylenetriamine pentaacetic acid or Ethylene diamine tetraacetic acid | 0.6 | | 0.6 | 0.25 | 0.6 | 0.6 |
| $MgSO_4$ | 1 | 1 | 1 | 0.5 | 1 | 1 |
| Bleach(es) and Bleach activator(s) | 6.88 | | 6.12 | 2.09 | 1.17 | 4.66 |

TABLE A-continued

Granular Laundry Detergent Compositions and Their Components

| Component | \multicolumn{6}{c}{Detergent Compositions} |
|---|---|---|---|---|---|---|
| | 1 | 2 | 3 | 4 | 5 | 6 |
| Ethoxylated thiophene Hueing Dye[5] | 0.002 | 0.001 | 0.003 | 0.003 | — | — |
| Direct Violet 9 ex Ciba Specialty Chemicals | | | | 0.0006 | 0.0004 | 0.0006 |
| Sulfate/Citric Acid/Sodium Bicarbonate/ Moisture/perfume | \multicolumn{6}{c}{Balance to 100%} |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2]Polyethylenimine (MW = 600) with 20 ethoxylate groups per —NH.
[3]Amphiphilic alkoxylated grease cleaning polymer is a polyethylenimine (MW = 600) with 24 ethoxylate groups per —NH and 16 propoxylate groups per —NH
[4]Reversible protease inhibitor of structure:

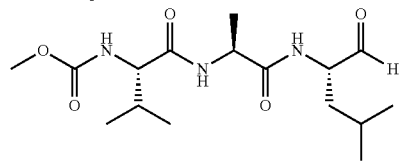

[5]Ethoxylated thiophene Hueing Dye is as described in U.S. Pat. No. 7,208,459 B2.

In Table A, all enzyme levels expressed as % enzyme raw material, except for cold water protease (of this invention) which is expressed as % of active protein added to the product.

Table B provides granular laundry detergent compositions suitable for top-loading automatic washing machines (detergent compositions 7-9) and front loading washing machines (detergent compositions 10-11). The GG36 protease variant tested and/or cold water protease of the present invention is added separately to these formulations.

TABLE B

Granular Laundry Detergent Compositions and Their Components

| Component | \multicolumn{5}{c}{Detergent Composition} |
|---|---|---|---|---|---|
| | 7 | 8 | 9 | 10 | 11 |
| Surfactants | | | | | |
| $C_{16-17}$ Branched alkyl sulfate | 3.55 | 15.8 | | | |
| $C_{12-14}$ alkyl sulphate | | | 1.5 | | |
| Sodium linear alkylbenzenesulfonate with aliphatic chain length $C_{11}$-$C_{12}$ | 9.6 | | 10.6 | 7.5 | 9 |
| Sodium $C_{14/15}$ alcohol ethoxy-3-sulfate | 1.15 | | | 2.88 | |
| Sodium $C_{14/15}$ alkyl sulphate | 2.37 | | | | |
| $C_{14/15}$ alcohol ethoxylate with average 7 moles of ethoxylation | | | | 1.17 | 1 |
| mono-$C_{8-10}$ alkyl mono-hydroxyethyl di-methyl quaternary ammonium chloride | | | | | 0.45 |
| Di methyl hydroxyl ethyl lauryl ammonium chloride | | | 0.18 | | |
| Zeolite A | 13.9 | 4.7 | 0.01 | 2.9 | 1.8 |
| Sodium Silicate 1.6.ratio | 4 | 0.2 | | 4 | 4 |
| Sodium Silicate 2.35.ratio | | | 8 | | |
| Citric Acid | | | | 2.5 | 1.4 |
| Sodium tripolyphosphate | | | 5 | | |
| Sodium Carbonate | 24.1 | 30 | 16.9 | 24.4 | 21 |
| Nonanoyloxybenzenesuplhonate | 5.78 | 2.81 | 0.96 | | |
| Oxaziridinium-based bleach booster | | | | 0.03 | 0.017 |
| Tetrasodium S,S,-ethylenediaminedisuccinate | | | | 0.2 | |
| Diethylenetriamine penta (methylene phosphonic acid), heptasodium salt | 0.61 | | | | 0.33 |
| Hydroxyethane dimethylene phosphonic acid | | | | 0.29 | 0.45 |

TABLE B-continued

Granular Laundry Detergent Compositions and Their Components

| Component | Detergent Composition | | | | |
|---|---|---|---|---|---|
| | 7 | 8 | 9 | 10 | 11 |
| Ethylene diamine tetraacetate | | | 0.27 | | |
| MgSO4 | | | 0.47 | 0.5994 | 0.782 |
| Sodium Percarbonate | 7 | 4.4 | | 15.9 | 19.1 |
| Tetra Acetyl Ethylene Diamine | | | | 3.3 | 4.6 |
| Sodium Perborate Monohydrate | | | 1.2 | | |
| Carboxymethyl cellulose (e.g. Finnfix BDA ex CPKelco) | 0.1 | | 0.17 | 1.69 | 0.23 |
| Sodium Acrylic acid/maleic acid co-polymer (70/30) | 0.0236 | 3.8 | | 2 | 2.5 |
| Sodium polyacrylate (Sokalan PA30 CL) | 4 | | 0.84 | | |
| Terephthalate polymer | | | | 0.23 | |
| Polyethylene glycol/vinyl acetate random graft co polymer | | | 0.89 | 0.89 | 0.91 |
| Photobleach-zinc phthalocyanine tetrasulfonate | | | 0.005 | 0.001 | 0.002 |
| C.I.Fluorescent Brightener 260 | 0.11 | 0.15 | 0.04 | 0.23 | 0.15 |
| C.I.Fluorescent Brightener 351 (Tinopal ® CBS) | | | 0.1 | | |
| Suds suppressor granule | | 0.25 | | 0.07 | 0.04 |
| Hydrophobically modified carboxy methyl cellulose (Finnifix ® SH-1) | | | 0.019 | 0.028 | |
| Bentonite | | | 8.35 | | |
| Miscellaneous (Dyes, perfumes, process aids, moisture and sodium sulphate) | Balance | Balance | Balance | Balance | Balance |

In Table B, surfactant ingredients can be obtained from any suitable supplier, including but not limited to BASF (e.g., LUTENSOL®), Shell Chemicals, Stepan, Huntsman, and Clariant (e.g., PRAEPAGEN®). Zeolite can be obtained from sources such as Industrial Zeolite. Citric acid and sodium citrate can be obtained from sources such as Jungbunzlauer. Sodium percarbonate, sodium carbonate, sodium bicarbonate and sodium sesquicarbonate can be obtained from sources such as Solvay. Acrylate/maleate copolymers can be obtained from sources such as BASF. Carboxymethylcellulose and hydrophobically modified carboxymethyl cellulose can be obtained from sources such as CPKelco. C.I. Fluorescent Brightener 260 can be obtained from 3V Sigma (e.g., OPTIBLANC®, OPTIBLANC® 2M/G, OPTIBLANC®0.2MG/LT Extra, or OPTIBLANC® Ecobright. Tetrasodium S,S-ethylenediamine disuccinate can be obtained from sources such as Innospec. Terephthalate copolymer can be obtained from Clariant (e.g., REPELOTEX SF 2). In addition, 1-Hydroxyethane-1,1-diphosphonic acid can be obtained from Thermphos. Oxaziridinium-based bleach booster has the following structure, where R1=2-butyloctyl, and was produced according to US 2006/0089284A1.

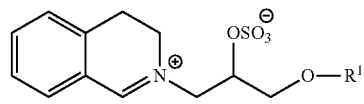

The enzymes NATALASE®, TERMAMYL®, STAINZYME PLUS®, CELLUCLEAN® and MANNAWAY®, can be obtained from Novozymes. Zinc phthalocyanine tetrasulfonate can be obtained from Ciba Specialty Chemicals (e.g., TINOLUX® BMC). Suds suppressor granule can be obtained from Dow Corning. In these detergent compositions, random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

Tables C-E provide additional granular detergent compositions suitable for washing machines (detergents 36a-n). The GG36 protease variant tested or cold water protease of the present invention is added separately to these formulations.

TABLE C

Additional Granular Laundry Detergent Compositions and Their Components

| Component | Deterent Composition | | | | |
|---|---|---|---|---|---|
| | 36a | 36b | 36c | 36d | 36e |
| Surfactants | | | | | |
| $C_{10}$ Nonionic | | | | 0.1843 | |
| $C_{16-17}$ Branched alkyl sulfate | 3.53 | 3.53 | 3.53 | | |
| $C_{12-14}$ alkyl sulphate | | | | | |
| Sodium linear alkylbenzenesulfonate with aliphatic chain length $C_{11}$-$C_{12}$ | 8.98 | 8.98 | 8.98 | 13.58 | 14.75 |

TABLE C-continued

Additional Granular Laundry Detergent Compositions and Their Components

| Component | Deterent Composition | | | | |
|---|---|---|---|---|---|
| | 36a | 36b | 36c | 36d | 36e |
| Sodium $C_{14/15}$ alcohol ethoxy-3-sulfate | 1.28 | 1.28 | 1.28 | | |
| Sodium $C_{14/15}$ alkyl sulphate | 2.36 | 2.36 | 2.36 | | |
| $C_{14/15}$ alcohol ethoxylate with average 7 moles of ethoxylation | | | | | |
| mono-$C_{8-10}$ alkyl mono-hydroxyethyl di-methyl quaternary ammonium chloride | | | | | |
| Di methyl hydroxyl ethyl lauryl ammonium chloride | | | | 0.1803 | |
| Zeolite A | 15.31 | 15.31 | 15.31 | | 4.47 |
| Bentonite | | | | 8.35 | |
| Sodium Silicate 1.6.ratio | | | | | 0.16 |
| Sodium Silicate 2.0.ratio | 3.72 | 3.72 | 3.72 | 8.41 | |
| Sodium Silicate 2.35.ratio | | | | | |
| Citric Acid | | | | 0.0066 | |
| Sodium tripolyphosphate | | | | 5.06 | |
| Sodium Carbonate | 26.1 | 26.18 | 26.1 | 15.9 | 29.0 |
| Nonanoyloxybenzenesuplhonate | 5.78 | 5.78 | 5.78 | 1.17 | 1.86 |
| Oxaziridinium-based bleach booster | 0.037 | 0.037 | 0.037 | | |
| Tetrasodium S,S,-ethylenediaminedisuccinate | | | | | |
| Diethylenetriamine penta (methylene phosphonic acid), heptasodium salt | 0.62 | 0.62 | 0.62 | | |
| Hydroxyethane dimethylene phosphonic acid | | | | | |
| Ethylene diamine tetraacetate | | | | 0.2701 | |
| MgSO4 | 0.056 | 0.056 | 0.056 | 0.47 | |
| Sodium Percarbonate | | 7.06 | 7.06 | | 3.64 |
| Tetra Acetyl Ethylene Diamine | | | | | |
| Sodium Perborate Monohydrate | | | | 1.47 | |
| Carboxymethyl cellulose (e.g. Finnfix BDA ex CPKelco) | 0.38 | 0.38 | 0.38 | 0.173 | |
| Sodium Acrylic acid/maleic acid co-polymer (70/30) | 3.79 | 3.78 | 3.79 | | 3.64 |
| Sodium polyacrylate (Sokalan PA30 CL) | 3.78 | 3.78 | 3.78 | 0.842 | |
| Terephthalate polymer | | | | | |
| Polyethylene glycol/vinyl acetate random graft co polymer | | | | 0.89 | |
| Photobleach-zinc phthalocyanine tetrasulfonate | | | | | |
| C.I.Fluorescent Brightener 260 | 0.1125 | 0.1125 | 0.1125 | 0.043 | 0.15 |
| C.I.Fluorescent Brightener 351 (Tinopal ® CBS) | | | | 0.0952 | |
| Suds suppressor granule | 0.015 | 0.015 | 0.015 | | 0.031 |
| Hyrdophobically modified carboxy methyl cellulose (Finnifix ® SH-1) | | | | | |
| Bentonite | | | | | |
| Miscellaneous (Dyes, perfumes, process aids, moisture and sodium sulphate) | Balance | Balance | Balance | Balance | Balance |

TABLE D

Additional Granular Laundry Detergent Compositions and Their Components

| Component | Detergent Composition | | | | |
|---|---|---|---|---|---|
| | 36f | 36g | 36h | 36i | 36j |
| Surfactants | | | | | |
| $C_{10}$ Nonionic | 0.1142 | 0.2894 | 0.1885 | 0.1846 | 0.1885 |
| $C_{16-17}$ Branched alkyl sulfate | | | | | |
| $C_{12-14}$ alkyl sulphate | | | | | |
| Sodium linear alkylbenzenesulfonate with aliphatic chain length $C_{11}$-$C_{12}$ | 12.94 | 15.69 | 9.01 | 8.42 | 9.51 |
| Sodium $C_{14/15}$ alcohol ethoxy-3-sulfate | | | | | |
| Sodium $C_{14/15}$ alkyl sulphate | | | | | |
| $C_{12/14}$ alcohol ethoxylate with average 7 moles of ethoxylation | 2.9 | | | | |

TABLE D-continued

Additional Granular Laundry Detergent Compositions and Their Components

| Component | 36f | 36g | 36h | 36i | 36j |
|---|---|---|---|---|---|
| $C_{12/14}$ alcohol ethoxylate with average 3 moles of ethoxylation | | | | 2.44 | |
| $C_{14/15}$ alcohol ethoxylate with average 7 moles of ethoxylation | | | 0.97 | 1.17 | 0.97 |
| mono-$C_{8-10}$ alkyl mono-hydroxyethyl di-methyl quaternary ammonium chloride | | | 0.45 | | |
| Di methyl hydroxyl ethyl lauryl ammonium chloride | | 0.195 | | | 0.45 |
| Zeolite A | 2.01 | 0.39 | 1.83 | 2.58 | 0.59 |
| Sodium Silicate 1.6.ratio | | | 4.53 | 5.62 | 4.53 |
| Sodium Silicate 2.0.ratio | | 10.1 | | | |
| Sodium Silicate 2.35.ratio | 7.05 | | | | |
| Citric Acid | | | 1.4 | 1.84 | 1.0 |
| Sodium tripolyphosphate | | 5.73 | | | |
| Sodium Carbonate | 12.65 | 15.93 | 21.0 | 27.31 | 20.2 |
| Nonanoyloxybenzenesuplhonate | | 1.73 | | | |
| Oxaziridinium-based bleach booster | | | 0.0168 | 0.0333 | 0.024 |
| Tetrasodium S,S,-ethylenediaminedisuccinate | | | | | |
| Diethylenetriamine penta (methylene phosphonic acid), heptasodium salt | | | 0.327 | | 0.3272 |
| Hydroxyethane dimethylene phosphonic acid | | | 0.45 | 0.2911 | 0.45 |
| Ethylene diamine tetraacetate | | 0.28 | | 0.1957 | |
| MgSO4 | | 0.54 | 0.79 | 0.6494 | 0.793 |
| Sodium Percarbonate | | | 19.1 | 15.85 | 22.5 |
| Tetra Acetyl Ethylene Diamine | | | 4.554 | 3.71 | 5.24 |
| Sodium Perborate Monohydrate | | 5.55 | | | |
| Carboxymethyl cellulose (e.g. Finnfix BDA ex CPKelco) | 0.62 | 0.21 | 0.23 | 1.07 | 0.2622 |
| Sodium Acrylic acid/maleic acid co-polymer (70/30) | 0.40 | 2.61 | 2.5 | 2.00 | 1.75 |
| Sodium polyacrylate (Sokalan PA30 CL) | | | 0.0055 | 0.011 | 0.008 |
| Terephthalate polymer | | | | 0.231 | |
| Polyethylene glycol/vinyl acetate random graft co polymer | 0.55 | 1.40 | 0.911 | 0.8924 | 0.911 |
| Photobleach-zinc phthalocyanine tetrasulfonate | | | | | |
| C.I.Fluorescent Brightener 260 | 0.1174 | 0.048 | 0.1455 | 0.2252 | 0.1455 |
| C.I.Fluorescent Brightener 351 (Tinopal ® CBS) | | 0.1049 | | | |
| Suds suppressor granule | | | 0.04 | 0.0658 | 0.04 |
| Hyrdophobically modified carboxy methyl cellulose (Finnifix ® SH-1) | | | | | |
| Bentonite | | | | | |
| Miscellaneous (Dyes, perfumes, process aids, moisture and sodium sulphate) | Balance | Balance | Balance | Balance | Balance |

TABLE E

Additional Granular Laundry Detergent Compositions and Their Components

| Component | 36k | 36l | 36m | 36n |
|---|---|---|---|---|
| Surfactants | | | | |
| $C_{10}$ Nonionic | 0.1979 | 0.1979 | 0.1979 | 0.1979 |
| $C_{16-17}$ Branched alkyl sulfate | | | | |
| $C_{12-14}$ alkyl sulphate | | | | |
| Sodium linear alkylbenzenesulfonate with aliphatic chain length $C_{11}$-$C_{12}$ | 8.92 | 8.92 | 11.5 | 11.5 |
| Sodium $C_{14/15}$ alcohol ethoxy-3-sulfate | 1.62 | 1.62 | 1.125 | 1.125 |
| Sodium $C_{14/15}$ alkyl sulphate | | | | |

TABLE E-continued

Additional Granular Laundry Detergent Compositions and Their Components

| Component | Detergent Composition | | | |
|---|---|---|---|---|
| | 36k | 36l | 36m | 36n |
| $C_{14/15}$ alcohol ethoxylate with average 7 moles of ethoxylation | 1.0 | 1.0 | 1.5 | 1.5 |
| mono-$C_{8-10}$ alkyl mono-hydroxyethyl di-methyl quaternary ammonium chloride | | | | |
| Di methyl hydroxyl ethyl lauryl ammonium chloride | | | | |
| Zeolite A | 1.63 | 1.63 | 2.0 | 2.0 |
| Sodium Silicate 1.6.ratio | 4.75 | 4.75 | 4.75 | 4.75 |
| Sodium Silicate 2.0.ratio | | | 0.06 | 0.06 |
| Sodium Silicate 2.35.ratio | | | | |
| Citric Acid | 1.10 | 1.10 | 1.1 | 1.1 |
| Sodium tripolyphosphate | | | | |
| Sodium Carbonate | 23.3 | 23.3 | 23.3 | 23.3 |
| Nonanoyloxybenzenesuplhonate | | | | |
| Oxaziridinium-based bleach booster | 0.021 | 0.021 | 0.015 | 0.015 |
| Tetrasodium S,S,-ethylenediaminedisuccinate | 0.26 | 0.26 | 0.26 | 0.26 |
| Diethylenetriamine penta (methylene phosphonic acid), heptasodium salt | | | | |
| Hydroxyethane dimethylene phosphonic acid | 0.47 | 0.47 | 0.47 | 0.47 |
| Ethylene diamine tetraacetate | | | | |
| MgSO4 | 0.83 | 0.83 | 0.82 | 0.82 |
| Sodium Percarbonate | 19.35 | 19.35 | 19.35 | 19.35 |
| Tetra Acetyl Ethylene Diamine | 4.51 | 4.51 | 4.51 | 4.51 |
| Sodium Perborate Monohydrate | | | | |
| Carboxymethyl cellulose (e.g. Finnfix BDA ex CPKelco) | 1.01 | 1.01 | 1.01 | 1.01 |
| Sodium Acrylic acid/maleic acid co-polymer (70/30) | 1.84 | 1.84 | 1.84 | 1.84 |
| Sodium polyacrylate (Sokalan PA30 CL) | 0.007 | 0.007 | 0.005 | 0.005 |
| Terephthalate polymer | 0.179 | 0.179 | 0.179 | 0.179 |
| Polyethylene glycol/vinyl acetate random graft co polymer | 0.96 | 0.96 | 0.96 | 0.96 |
| Photobleach-zinc phthalocyanine tetrasulfonate | | | | |
| C.I.Fluorescent Brightener 260 | 0.153 | 0.153 | 0.171 | 0.171 |
| C.I.Fluorescent Brightener 351 (Tinopal ® CBS) | | | | |
| Suds suppressor granule | 0.042 | 0.042 | 0.042 | 0.042 |
| Hyrdophobically modified carboxy methyl cellulose (Finnifix ® SH-1) | | | | |
| Bentonite | | | | |
| Miscellaneous (Dyes, perfumes, process aids, moisture and sodium sulphate) | Balance | Balance | Balance | Balance | Balance |

Notes for detergent compositions 36 a-n in Tables C, D, E:
Surfactant ingredients can be obtained from BASF, Ludwigshafen, Germany (Lutensol®); Shell Chemicals, London, UK; Stepan, Northfield, Ill., USA; Huntsman, Huntsman, Salt Lake City, Utah, USA; Clariant, Sulzbach, Germany (Praepagen®).
Zeolite can be obtained from Industrial Zeolite (UK) Ltd, Grays, Essex, UK.
Citric acid and sodium citrate can be obtained from Jungbunzlauer, Basel, Switzerland.
Sodium percarbonate, sodium carbonate, sodium bicarbonate and sodium sesquicarbonate can be obtained from Solvay, Brussels, Belgium.
Acrylate/maleate copolymers can be obtained from BASF, Ludwigshafen, Germany.
Carboxymethylcellulose and hydrophobically modified carboxymethyl cellulose can be obtained from CPKelco, Arnhem, The Netherlands.
C.I. Fluorescent Brightener 260 can be obtained from 3V Sigma, Bergamo, Italy as Optiblanc® Optiblanc® 2M/G, Optiblanc® 2MG/LT Extra, or Optiblanc® Ecobright.
Tetrasodium S,S-ethylenediamine disuccinate can be obtained from Innospec, Ellesmere Port, UK.
Terephthalate co-polymer can be obtained from Clariant under the tradename Repelotex SF 2. 1-Hydroxyethane-1,1-diphosphonic acid can be obtained from Thermphos, Vlissingen-Oost, The Netherlands.
Oxaziridinium-based bleach booster has the following structure, where R1=2-butyloctyl, and was produced according to US 2006/0089284A1.

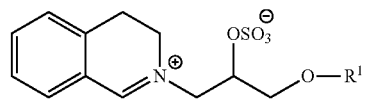

Enzymes Natalase®, Termamyl®, Stainzyme Plus®, Celluclean® and Mannaway®, can be obtained from Novozymes, Bagsvaerd, Denmark.
Zinc phthalocyanine tetrasulfonate can be obtained from Ciba Specialty Chemicals, Basel, Switzerland, as Tinolux® BMC.

Suds suppressor granule can be obtained from Dow Corning, Barry, UK.

Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

Example 1

Assays and Test Methods

This Example describes the various Test Methods and assays used in the development of the present invention. Any deviations from the protocols provided are indicated in the pertinent Examples.

The assays were performed using a Biomek FX Robot (Beckman Coulter) or a multichannel pipettor (e.g., Rainin PipetLite, Mettler-Toledo) and a SpectraMAX MTP Reader (type 340; Molecular Devices).

A. Test Methods

Test Method 1

A protocol to define whether a dye or pigment material is a fabric hueing agent for the purpose of the invention is provided below:
1) Fill two tergotometer pots with 800 ml of Newcastle upon Tyne, UK, City Water (~12 grains per US gallon total hardness, supplied by Northumbrian Water, Pity Me, Durham, Co. Durham, UK).
2) Insert pots into tergotometer, with water temperature controlled at 30° C. and agitation set at 40 rpm for the duration of the experiment.
3) Add 4.8 g of IEC-B detergent (IEC 60456 Washing Machine Reference Base Detergent Type B), supplied by wfk, Brüggen-Bracht, Germany, to each pot.
4) After two minutes, add 2.0 mg active colorant to the first pot.
5) After one minute, add 50 g of flat cotton vest (supplied by Warwick Equest, Consett, County Durham, UK), cut into 5 cm×5 cm swatches, to each pot.
6) After 10 minutes, drain the pots and re-fill with cold Water (16° C.) having a water hardness of 14.4 English Clark Degrees Hardness with a 3:1 Calcium to Magnesium molar ratio.
7) After 2 minutes rinsing, remove fabrics.
8) Repeat steps 3-7 for a further three cycles using the same treatments.
9) Collect and line dry the fabrics indoors for 12 hours.
10) Analyse the swatches using a Hunter Miniscan spectrometer fitted with D65 illuminant and UVA cutting filter, to obtain Hunter a (red-green axis) and Hunter b (yellow-blue axis) values.
11) Average the Hunter a and Hunter b values for each set of fabrics. If the fabrics treated with colorant under assessment show an average difference in hue of greater than 0.2 units on either the a axis or b axis, it is deemed to be a fabric hueing agent for the purpose of the invention.

Test Method 2

For Test Method 2, the BMI microswatch assay provided below is run using the granular detergent composition 10 (See Table D, above). The laundry detergent is dissolved in water that has a hardness of 12 gpg and adjusted to a temperature of 16° C., and the protease variant enzyme of interest is added. Performance of the protease variant enzymes is then determined as per the BMI microswatch assay described. The performance index is determined by comparing the performance of the protease variant enzyme with that of the B. lentus GG36 subtilisin enzyme having the amino acid sequence of SEQ ID NO:2, with in all cases the enzyme dosage range being 0.1-5 ppm. Protease variant enzymes having a performance index of 1.1 or greater are viewed to be cold water proteases.

Test Method 3

For Test Method 3, the BMI microswatch assay provided below is run using the granular laundry detergent composition 7 (See Table D, above). The laundry detergent is dissolved in water that has a hardness of 6 gpg and adjusted to a temperature of 16° C., the GG36 protease variant enzyme of interest is added. Performance of the GG36 protease variant enzymes is then determined as per the BMI microswatch assay described. The performance index is determined by comparing the performance of the GG36 protease variant enzyme with that of the B. lentus GG36 subtilisin enzyme having the amino acid sequence of SEQ ID NO:2, with in all cases the enzyme dosage range being 0.1-5 ppm. GG36 protease variant enzymes having a performance index of 1.1 or greater are viewed to be cold water proteases.

Test Method 4

For Test Method 4, the BMI microswatch assay is run using the granular laundry detergent composition 7 (See Table D, above). The laundry detergent is dissolved in water that has a hardness of 6 gpg and adjusted to a temperature of 16° C., and the GG36 protease variant enzyme of interest is added. Performance of the GG36 protease variant enzymes is then determined as per the BMI microswatch assay described. The performance index is determined by comparing the performance of the GG36 protease variant enzyme with that of a reference enzyme GG36-A158E, said GG36-A158E reference enzyme consisting of the B. lentus subtilisin GG36 protease amino acid sequence of SEQ ID NO:2 with a single substitution of glutamic acid for alanine at position 158 (i.e., the A158E mutation), with in all cases the enzyme dosage range being 0.1-5 ppm. GG36 protease variant enzymes having a performance index of 1.0 or greater are viewed to be cold water proteases.

Test Method 6

For Test Method 6, the BMI microswatch assay is run using one of the detergents 36a 36n in Table 1-2. The detergent is dissolved in water that has a hardness as specified in Table 1-2 and adjusted to a temperature of 16° C. Performance of the variant enzymes is then determined as per the BMI microswatch assay described. The performance index is determined by comparing the performance of the variant with that of the enzyme of SEQ ID NO:2, with the enzyme dosage range being 0.1-5 ppm in all cases. Enzymes having a performance index of 1.1 or greater are viewed to be cold water proteases.

Test Method 7

For Test Method 7, the BMI microswatch assay is run using one of the detergents in Table 1. The detergent is dissolved in water that has a hardness and buffer as specified in Table 1 and adjusted to a temperature of 16° C. or 25° C. Performance of the variant enzymes is then determined as per the BMI microswatch assay described. The performance index is determined by comparing the performance of the variant with that of the enzyme of SEQ ID NO:2, with the enzyme dosage range being 0.1-5 ppm in all cases. Enzymes having a performance index of 1.1 or greater are viewed to be cold water proteases.

B. Assays

TCA Assay for Protein Content Determination

B. subtilis cultures were grown 2-3 days at 37° C., shaking at 250-300 rpm with humidified aeration. The cells were removed from the enzyme-containing culture supernatant, by centrifugation and/or filtration. The protease/protein/enzyme concentration was determined using a TCA precipitation assay. An aliquot (20-25 ul) of culture supernatant was transferred to a 96-well flat bottom microtiter plate (MTP; Costar 9017 medium binding clear polystyrene plate) containing 100 µL/well of 0.25 N HCl. The "baseline" read was determined by light scattering/absorbance reading at 405 nm following 5 seconds of mixing. 100 µL/well of 30% (w/v) trichloroacetic acid (TCA) was added to the HCl-containing plate and incubated for 10 minutes at room temperature to facilitate protein precipitation. The light scattering/absorbance at 405 nm of this "test" plate was determined after 5 seconds of mixing. The turbidity/light scattering increase in the samples correlates to the total amount of precipitable protein in the culture supernatant. The calculations were performed by subtracting the "baseline" reading (obtained after addition of HCl) from the "test" reading (obtained after addition of TCA) to provide a relative measure of total protein present. A conversion factor relating protein precipitation with protein concentration was determined for a GG36 standard of known concentration. This conversion factor can be used for all variants since precipitation is linear with concentration. If desired, a standard curve can be created by calibrating the TCA readings with AAPF protease assays (see below) of clones with known specific activity. However, the TCA results are linear with respect to protein concentration from 50 to 500 parts per million (ppm) of protein (where 1 ppm corresponds to 1 mg/L) and can thus be plotted directly against enzyme performance for the purpose of choosing variants with desired performance.

AAPF Protease Assay

In order to determine the protease activity of the serine protease variants, more specifically subtilisin variants, the hydrolysis of N-succinyl-L-alanyl-L-alanyl-L-prolyl-L-phenyl-p-nitroanilide (suc-AAPF-pNA) was measured. The reagent solutions used were: 100 mM Tris/HCl, pH 8.6, containing 0.005% TWEEN®-80 (Tris dilution buffer); 100 mM Tris buffer, pH 8.6, containing 1 mM CaCl, and 0.005% TWEEN®-80 (Tris/Ca buffer); and 160 mM suc-AAPF-pNA in DMSO (suc-AAPF-pNA stock solution) (Sigma: S-7388). To prepare a suc-AAPF-pNA working solution, 1 ml suc-AAPF-pNA stock solution was added to 100 ml Tris/Ca buffer and mixed well for at least 10 seconds. The assay was performed by adding 10 µA of diluted protease solution to each well of a 96-well MTP, immediately followed by the addition of 190 µl of 1 mg/ml suc-AAPF-pNA working solution. The solutions were mixed for 5 sec, and the absorbance change in kinetic mode (25 readings in 5 minutes) was read at 405 nm in an MTP reader, at 25° C. The protease activity was expressed as AU (activity=$\Delta$OD·min$^{-1}$ ml$^{-1}$).

BMI Microswatch Assay (BMI Assay)

Pre-rinsed and punched blood, milk and ink (BMI) stained microswatches (EMPA116) of 5.5 millimeter circular diameter in 96 well microtiter plates (MTP; Corning 3641) were obtained from Center for Test materials BV (Vlaardingen, The Netherlands).

Detergents in Table 1 were prepared by mixing for at least 30 minutes with the appropriate level of water hardness (3:1 Ca:Mg.—CaCl$_2$:MgCl$_2$.6H$_2$O) in Milli-Q water for detergents compositions 104 and 105, and in 2 mM sodium carbonate buffer pH 10.3 for detergent compositions 101, 102, 103, 106 and 107 as described in Table 1. The detergents were centrifuged and filtered to remove precipitate and chilled on ice for 30 minutes prior to use for assays carried out at 16° C.

Enzyme concentrations were equalized to a desired fixed concentration ranging from 20-50 ppm relative to a standard of purified GG36. The specific activity of GG36 using AAPF as a substrate was used to convert baseline subtracted TCA values into enzyme concentration in ppm. Once enzyme concentration was determined in ppm, a simple formula was used to calculate the volume of each variant required to add to a fixed volume of buffer (300-600 µL) in order to achieve the desired stock enzyme concentration:

$$x = (\text{target ppm})(v_b)/(y\text{-target ppm})$$

Where x=volume enzyme, y=enzyme concentration, $v_b$=buffer volume

A Perkin-Elmer Janus robot with a Versispan 8 channel arm was used to dispense variable volumes of enzyme from the source plate (Axygen half deep well plate with pooled harvested variants used in the TCA enzyme concentration assay) into the buffer-filled destination plate using conductive tips. Samples were mixed three times by pipetting up and down. The accuracy of the enzyme dilutions was validated by measuring the AAPF activity of the equalized plate and comparing it to that of the source plate, to verify that the correct dilutions had been made.

After equalization, 5-15 µL of enzyme solution was added to a detergent-filled BMI microswatch plate to reach a final volume of ~200 µL. In some instances, the enzyme samples were not equalized, and were instead all diluted equally from the stock plate to give a working range of 0.1 to 5 ppm. Optimal target concentrations for each assay were determined from a dose response curve measuring cleaning activity over this range for a given detergent.

The MTP was sealed with foil (Bio-Rad) and incubated in iEMS incubator/shaker (Thermo/Labsystems) pre-set to 16° C. in a cold room set to 4° C. or at 25° C. on the benchtop for 15-30 minutes at 1400 rpm. Following incubation, 120 µL of supernatant was transferred to a fresh MTP (Corning 9017) and read at 600 nm using the SpectraMax reader. True absorbance readings were obtained by subtracting a blank control (no enzyme) from each value.

A performance index (PI) was calculated for each variant. The performance index is the ratio of the absorbance of the supernatant produced by variant enzyme cleaning to the absorbance produced by GG36 cleaning at a fixed enzyme concentration. PI values were calculated by dividing the absorbance of a variant by that of the control on a given plate. If multiple versions of the same variant were obtained in a library screen, their PI values were averaged to derive a single representative value. A performance index (PI) that is greater than 1 (PI>1) indicates superior cleaning by a variant as compared to the standard (e.g., GG36), while a PI of 1 (PI=1) identifies a variant that performs the same as the standard, and a PI that is less than 1 (PI<1) identifies a variant that performs worse than the standard.

TABLE 1-1

Detergent Compositions

| Detergent Compositions | 101 | 102 | 103 | 104 | 105 | 106 | 107 |
|---|---|---|---|---|---|---|---|
| Sodium $C_{12-17}$ alkyl sulfate | | 0.8 | 5.88 | 6.93 | 6.93 | | |
| Sodium linear alkylbenzenesulfonate with aliphatic chain length $C_{11}$-$C_{12}$ | 14.47 | 13.6 | 8.98 | 8.2 | 7.02 | 11.5 | 8.78 |
| Sodium $C_{12-17}$ alcohol ethoxy sulfate | | 2 | 1.28 | 1.51 | 1.51 | 1.12 | |
| $C_{10-15}$ alcohol ethoxylate with average 7 moles ethoxylation | 0.06 | 0.12 | | | | 1.7 | 1.33 |
| Zeolite | 2.7 | | 15.21 | 17.78 | 20.54 | 2.04 | 1.57 |
| Sodium Silicate | 5.7 | 8 | 3.72 | 3.44 | 2.94 | 4.76 | 5.87 |
| Citric Acid | | | 0 | 0.5 | 0 | 1.08 | 1 |
| Sodium tripolyphosphate | | | | | | | |
| Sodium Carbonate | 11.93 | 13.47 | 26.09 | 29.7 | 28 | 23.28 | 23.77 |
| Nonanoyloxybenzenesuplhonate | | | 5.77 | 2.74 | 0.63 | | |
| Oxaziridinium-based bleach booster | | | 0.04 | 0 | 0 | 0.01 | 0.01 |
| Tetrasodium S,S,-ethylenediaminedisuccinate | | | | | | 0.26 | 0 |
| Diethylenetriamine penta (methylene phosphonic acid), heptasodium salt (DTPA) | | | 0.61 | 0.49 | 1.6 | | |
| Hydroxyethane dimethylene phosphonic acid | | | | | | 0.47 | 0.55 |
| Ethylene diamine tetraacetate | | | | | | | |
| MgSO4 | | | 0.05 | 0 | 0 | 0.81 | 2 |
| Sodium Percarbonate | | 1.53 | 7.05 | 6.53 | 10.4 | 19.35 | 14.11 |
| Tetra Acetyl Ethylene Diamine | | 1.15 | | | | 4.51 | 3.26 |
| Sodium Perborate Monohydrate | | | | | | | |
| Carboxymethyl cellulose (e.g. Finnfix BDA ex CPKelco) | 0.21 | 0.21 | 0.38 | 0 | 0 | 1.01 | 0.91 |
| Sodium acrylic acid/acrylic-maleic acid copolymer | 1.55 | 0.75 | 3.79 | 3.48 | 2.98 | 1.84 | 1.75 |
| Polyethylene glycol/vinyl acetate random graft copolymer | 0.3 | 0.6 | | | | 0.96 | 0.91 |
| Photobleach- zinc phthalocyanine tetrasulfonate | | 0.0066 | | | | 0.0022 | 0.0012 |
| Fluorescent Brightener | 0.2 | 0.13 | 0.11 | 0.11 | 0.11 | 0.11 | 0.11 |
| Suds suppressor granule | | | 0.01 | 0.16 | 0.01 | 0.05 | 0.05 |
| Miscellaneous (Dyes, perfumes, process aids, moisture and sodium sulphate) | Balance | Balance | Balance | Balance | Balance | Balance | Balance |

TABLE 1-2

Final Detergent, Water Hardness, and Buffer Concentrations Used for BMI Microswatch Assays

| Detergent Composition | Final Detergent Concentration (g/L) | Final Water Hardness* (gpg) | Final Sodium Carbonate Buffer Concentration (mM) |
|---|---|---|---|
| 1 | 1.2 | 12 | 2 |
| 2 | 2.25 | 12 | 2 |
| 3 | 0.719 | 6 | 2 |
| 4 | 0.625 | 6 | 0 |
| 5 | 0.625 | 6 | 0 |
| 6 | 7.69 | 20 | 2 |
| 7 | 7.69 | 20 | 2 |

*(3:1 Ca:Mg) Concentration as detailed in text.

Performance Index

The performance index compares the performance of the variant (measured value) and the standard enzyme (theoretical value) at the same protein concentration. In addition, the theoretical values can be calculated, using the parameters of a performance dose response curve of the standard protease Example 2

Construction of Variants and Combinatorial Libraries of GG36

This Example describes the cold water cleaning of GG36 variants and libraries constructed in *B. subtilis* using the pHPLT-GG36 *B. subtilis* expression plasmid. This *B. subtilis* expression plasmid contains the GG36 expression cassette shown below, the *B. licheniformis* LAT promoter (Plat), and additional elements from pUB110 (McKenzie et al., Plasmid, 15:93-103, 1986) including a replicase gene (reppUB), a neomycin/kanamycin resistance gene (neo) and a bleomycin resistance marker (bleo) (FIG. 4 in U.S. Pat. No. 6,566,112). The pHPLT-GG36 plasmid map was provided in WO2011140364. The GG36 expression cassette sequence is provided below.

The DNA sequence of GG36 (the signal sequence is shown in lower case letters, propeptide in lower case, underlined text, and GG36 mature sequence in uppercase letters) is provided below:

(SEQ ID NO: 3)
gtgagaagcaaaaaattgtggatcgtcgcgtcgaccgcactactcatt tctgttgctttcagttcatcgatcgcatcggctgctgaagaagcaaaa gaaaaatatttaattggctttaatgagcaggaagctgtcagtgagttt gtagaacaagtagaggcaaatgacgaggtcgccattctctctgaggaa gaggaagtcgaaattgaattgcttcatgaatttgaaacgattcctgtt ttatccgttgagttaagcccagaagatgtggacgcgcttgagctcgat ccagcgatttcttatattgaagaggatgcagaagtaacgacattgGCG

CAATCAGTGCCATGGGGAATTAGCCGTGTGCAAGCCCCAGCTGCCCAT

AACCGTGGATTGACAGGTTCTGGTGTAAAAGTTGCTGTCCTCGATACA

GGTATTTCCACTCATCCAGACTTAAATATTCGTGGTGGCGCTAGCTTT

GTACCAGGGGAACCATCCACTCAAGATGGGAATGGGCATGGCACGCAT

GTGGCCGGGACGATTGCTGCTTTAAACAATTCGATTGGCGTTCTTGGC

GTAGCGCCGAGCGCGGAACTATACGCTGTTAAAGTATTAGGGGCGAGC

```
GGTTCAGGTTCGGTCAGCTCGATTGCCCAAGGATTGGAATGGGCAGGG

AACAATGGCATGCACGTTGCTAATTTGAGTTTAGGAAGCCCTTCGCCA

AGTGCCACACTTGAGCAAGCTGTTAATAGCGCGACTTCTAGAGGCGTT

CTTGTTGTAGCGGCATCTGGAAATTCAGGTGCAGGCTCAATCAGCTAT

CCGGCCCGTTATGCGAACGCAATGGCAGTCGGAGCTACTGACCAAAAC

AACAACCGCGCCAGCTTTTCACAGTATGGCGCAGGGCTTGACATTGTC

GCACCAGGTGTAAACGTGCAGAGCACATACCCAGGTTCAACGTATGCC

AGCTTAAACGGTACATCGATGGCTACTCCTCATGTTGCAGGTGCAGCA

GCCCTTGTTAAACAAAAGAACCCATCTTGGTCCAATGTACAAATCCGC

AATCATCTAAAGAATACGGCAACGAGCTTAGGAAGCACGAACTTGTAT

GGAAGCGGACTTGTCAATGCAGAAGCTGCAACTCGTTAA
```

The protein sequence of GG36 (the signal sequence is shown in lower case letters, propeptide in lower case, underlined text, and GG36 mature protease sequence in uppercase letters) is provided below:

(SEQ ID NO: 4)
vrskklwivastallisvafsssiasa<u>aeeakekyliqfneqeaysef</u>

<u>veqveandevailseeeeveiellhefetipvlsvelspedvdaleld</u>

<u>paisyieedaevttm</u>AQSVPWGISRVQAPAAHNRGLTGSGVKVAVLDT

GISTHPDLNIRGGASFVPGEPSTQDGNGHGTHVAGTIAALNNSIGVLG

VAPSAELYAVKVLGASGSGSVSSIAQGLEWAGNNGMHVANLSLGSPSP

SATLEQAVNSATSRGVLVVAASGNSGAGSISYPARYANAMAVGATDQN

NNRASFSQYGAGLDIVAPGVNVQSTYPGSTYASLNGTSMATPHVAGAA

ALVKQKNPSWSNVQIRNHLKNTATSLGSTNLYGSGLVNAEAATR.

The DNA libraries and variants were created by extension PCR (WO2011140364), QuickChange mutagenesis (Stratagene), or they were synthesized at DNA2.0, Inc. or GeneArt. The pHPLT GG36 plasmid was used for cloning of the GG36 variant genes or for the mutagenesis reactions. For efficient transformation of the libraries and variants in *B. subtilis*, 1 microliter of the ligated library products or mutagenesis reactions was amplified using rolling circle amplification by Illustra Templiphi kit according to the manufacturer's instructions (GE Healthcare) to generate multimeric DNA for transformation into *Bacillus subtilis*. Products of the rolling circle amplification were diluted 100-times and used to transform *B. subtilis* cells (genotype: ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, the colonies with halos were inoculated in 120 μl of Luria broth medium containing 10 μg/mL neomycin for plasmid DNA extraction (QIAprep Spin Miniprep kit, Qiagen). The extracted plasmids were sequenced to confirm the presence of the desired mutations. The variants were expressed in *B. subtilis* cells (genotype: ΔaprE, ΔprE, amyE::xylRPxylAcomK-phleo) as described in Example 1 (TCA assay), and were further characterized using the BMI microswatch cleaning assay as described in Example 1. In the following tables, the detergent compositions ("Detergents") correspond to those shown in Table 1 above. Also, as indicated, the amino acid position is listed according to BPN' numbering.

TABLE 2-1

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| G020R-N062E-S078G-G118S-S188D-N248D-H249R | +++ |
| S024R-N062E-G118R-A158E-S188D | +++ |
| T022A-S024R-T033S-G118R-S166D-S188D | +++ |
| S024R-N062E-S078G-G118S-S188D-Q245R-N248D | +++ |
| G020R-S024R-N062E-S078D-G118S-P129E-G159D | +++ |
| G020R-S024R-N062E-S078G-G118D-P129E | +++ |
| G020R-S024R-N062E-S078G-G118S-P129E-G159D-S188D-Q245R-N248D | +++ |
| G020R-N062E-S078G-G118S-G159D-Q245R-N248D | +++ |
| S024R-N116L-A158E-S166D | +++ |
| G020R-N062E-S078G-G118S-G159D-S188D-H249R | +++ |
| G020R-S024R-S078G-G118D-P129E-G159D-S188D | +++ |
| S024R-G118R-S166D | +++ |
| T022A-S024R-T033S-G118R-A158E-S166D-A273V | +++ |
| G020R-N062E-S078G-G118S-P129E-G159D-S188D-Q245R | +++ |
| T022A-G118R-A158E-S166D | +++ |
| G020R-S024R-N062E-S078D-G118S-G159D-S188D-Q245R-N248D | +++ |
| T022A-S024R-G118R-S166D-S188D | +++ |
| N062E-S078G-G118S-G159D | +++ |
| T022A-S101G-S103A-V104I-G159D-S188D-A232V-Q245R-N248E-E271H | +++ |
| G020R-S024R-N062E-S078G-G118D-Q245R-N248D | +++ |
| S024R-T033S-N116L-A158E-S166D | +++ |
| S024R-N062E-S078G-G118D-P129E-G159D-Q245R | +++ |
| G020R-N062E-S078D-G118S-Q245R | +++ |
| T022A-S024R-N062E-N116L-A158E | +++ |
| G020R-N062E-S078G-G118D-P129E | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024R-T033S-N062E-N116L-G118R-S188D | +++ |
| G020R-N062E-S078G-G118D-P129E-G159D-S188D-H249R | +++ |
| S024R-S078G-G118S-P129E-G159D-Q245R-N248D | +++ |
| G020R-N062E-S078G-G118D-S188D-H249R | +++ |
| T022Q-S101G-S103A-V104I-G159D-S188D-A232L-Q245T-N248D-E271T | +++ |
| S078G-G118S-P129E-G159D-S188D-Q245R-N248D-H249R | +++ |
| T022Q-S101G-S103A-V104I-G159D-S188E-A232V-Q245T-N248H-E271T | +++ |
| G020R-S024R-S078D-G118S-G159D-S188D-H249R | +++ |
| G020R-S078D-G118S-P129E-G159D-Q245R-N248D-H249R | +++ |
| S024R-N062E-N116L-G118R | +++ |
| T022A-S024R-N116L-G118R-A158E-S188D | +++ |
| S024R-N062E-S078G-G118S-P129E-Q245R | +++ |
| S024R-N062E-G118R-A158E | +++ |
| G020R-N062E-S078G-G118S-G159D-S188D | +++ |
| G020R-S024R-S078D-G118S-G159D-S188D-Q245R-N248D-H249R | +++ |
| S024R-S078D-G118S-P129E-G159D-Q245R | +++ |
| A098Q-S099T-G102A-S103G | +++ |
| T022A-G118R-S166D-S188D | +++ |
| S024R-S078D-G118S-G159D-S188D-H249R | +++ |
| T022A-S024R-N116L-G118R-S166D-S188D | +++ |
| T022A-N062E-G118R-A158E | +++ |
| G020R-S078G-G118D-G159D-S188D-Q245R | +++ |
| S024R-N062E-S078G-G118D-G159D-S188D-Q245R | +++ |
| T022Q-S101G-S103A-V104I-G159D-S188D-A232V-Q245R-N248E-E271F | +++ |
| T022A-S101G-S103A-V104I-G159D-S188E-A232S-Q245R-N248E-E271F | +++ |
| G020R-N062E-S078G-G118S-P129E-N248D-H249R | +++ |
| S024R-N116L-G118R-S128I-S166D-S188D | +++ |
| G020R-S024R-N062E-S078G-G118D-P129E-G159D-S188D-H249R | +++ |
| G020R-S024R-N062E-S078G-G118D-G159D-S188D-N248D | +++ |
| G020R-S024R-S078G-G118D-P129E-S188D-Q245R-N248D | +++ |
| S024R-N062E-S078D-G118S-S188D-H249R | +++ |
| T033S-N062E-G118R | +++ |
| T022Q-S101G-S103A-V104I-G159D-S188D-A232S-Q245T-N248E-E271H | +++ |
| T033S-G118R-A158E-S166D | +++ |
| T022Q-S101G-S103A-V104I-G159D-S188E-A232S-Q245V-N248H | +++ |
| G020R-S024R-S078D-G118D-S188D-Q245R-N248D-H249R | +++ |
| T022A-S024R-N062E | +++ |
| G020R-S024R-N062E-S078D-G118D-G159D-S188D-R247L | +++ |
| T022Q-S101G-S103A-V104I-G159D-S188D-A232S-Q245R-N248E-E271T | +++ |
| G020R-N062E-S078G-G118S-P129E-G159D-Q245R-N248D | +++ |
| T022Q-S101G-S103A-V104I-G159D-S188E-A232S-Q245R-N248H | +++ |
| P014S-G020R-S024R-S078G-G118S-P129E-S188D-Q245R-N248D | +++ |
| T022A-S101G-S103A-V104I-G159D-S188E-A232V-Q245R-N248E-E271L | +++ |
| G020R-S078D-G118D-G159D-S188D-H249R | +++ |
| T022Q-S101G-S103A-V104I-G159D-S188E-A232L-Q245R-N248D-E271T | +++ |
| T022A-S101G-S103A-V104I-G159D-S188E-A232T-Q245T-N248E-E271L | +++ |
| S024R-N062E-S078D-G118S-S188D-Q245R | +++ |
| T022Q-S101G-S103A-V104I-G159D-S188E-A232L-Q245R-N248E-E271H | +++ |
| G020R-S078D-G118S-P129E-G159D-H249R | +++ |
| T022A-S101G-S103A-V104I-G159D-S188D-A232S-Q245R-N248H-E271F | +++ |
| T022A-S101G-S103A-V104I-G159D-S188D-A232L-Q245R-N248H-E271H | +++ |
| S024F-T033S-S101G-S103A-V104I-N116A-Y209A-T213A-A232V | +++ |
| S024F-S101G-S103A-V104I-N116L-S128N-Y209V-G211Q-T213A-A232V | +++ |
| S024R-S078G-G118S-G159D-S188D-Q245R-N248D | +++ |
| G020R-S024R-S078G-G118S-S188D-Q245R | +++ |
| G020R-S024R-N062E-S078D-G118D-P129E-G159D-Q245R | +++ |
| S024R-S078D-G118D-G159D-S188D-H249R | +++ |
| G020R-S078G-G118S-G159D-S188D-H249R | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| G020R-S024R-N062E-S078G-G118S-S188D-N248D | +++ |
| S078D-G118S-G159D-Q245R | +++ |
| G020R-S024R-N062E-S078G-G118D-P129E-G159D-N248D-H249R | +++ |
| S024R-N062E-S078G-G118S-P129E-Q245R-N248D | +++ |
| G020R-S078G-G118S-P129E-S188D-Q245R-N248D | +++ |
| S024R-N062E-S078G-G118S-G159D-Q245R | +++ |
| G020R-N062E-S078D-G118D-P129E-Q245R | +++ |
| T022A-S101G-S103A-V104I-G159D-S188E-P210L-A232T-Q245T-N248D-E271T | +++ |
| G020R-S024R-N062E-S078G-G118S-P129E | +++ |
| G020R-S024R-N062E-S078G-G118D-G159D-S188D-H249R | +++ |
| T022Q-S101G-S103A-V104I-G159D-S188D-A232T-Q245V-N248D-E271L | +++ |
| A016S-T022A-S101G-S103A-V104I-N116L-S128N-Y209V-A232V | +++ |
| T022A-S101G-S103A-V104I-G159D-S188E-A232S-Q245T-N248H-E271H | +++ |
| G020R-N062E-S078G-G118D-P129E-G159D-H249R | +++ |
| T022A-S101G-S103A-V104I-G159D-S188D-A232L-Q245R-N248E | +++ |
| G020R-S024R-S078G-G118D-G159D-S188D-Q245R | +++ |
| S024R-N062E-S078G-G118S-G159D-Q245R-N248D | +++ |
| G020R-S078G-G118S-G159D-S188D-Q245R | +++ |
| S024R-N062E-S078G-G118S-G159D-S188D | +++ |
| T022A-S101G-S103A-V104I-G159D-S188E-A232V-Q245R-N248H-E271H | +++ |
| G020R-S024R-N062E-S078G-G118D-G159D | +++ |
| T022A-S101G-S103A-V104I-G159D-S188D-A232T-V244A-Q245R-N248H-E271H | +++ |
| S024R-S078G-G118S-P129E-G159D-S188D-Q245R | +++ |
| T022Q-S101G-S103A-V104I-G159D-S188E-A232V-Q245V-N248D-E271F | +++ |
| G020R-S024R-N062E-S078G-G118D-G159D-S188D-Q245R | +++ |
| T022A-S024R-N062E-S128I-A158E | +++ |
| G020R-S024R-S078G-G118D-N248D-H249R | +++ |
| S024R-S078G-G118D-P129E-Q245R-H249R | +++ |
| T022A-S101G-S103A-V104I-G159D-S188D-A232T-Q236K-Q245T-N248E | +++ |
| N062E-S078G-G118S-G159D-Q245R-N248D | +++ |
| T033S-G118R-S166D | +++ |
| G020R-S024R-S078G-G118D-P129E-S188D-N248D | +++ |
| G020R-S078G-G118S-P129E-G159D-S188D-Q245R-N248D | +++ |
| A016S-T022A-S101G-S103A-V104I-L111V | +++ |
| T022Q-S101G-S103A-V104I-G159D-S188D-A232V-Q245R-N248E-E271H | +++ |
| S024R-N116L-G118R-S128I-A158E-S188D-V199I | +++ |
| G020R-S024R-S078D-G118D-G159D-H249R | +++ |
| T022A-S101G-S103A-V104I-G159D-S188E-A232S-Q245R-N248E-E271T | +++ |
| G020R-S024R-S078D-G118S-S188D-N248D-H249R | +++ |
| T022A-S101G-S103A-V104I-G159D-S188D-A232T-Q245R-N248D-E271T | +++ |
| G020R-S024R-S078G-G118D-P129E-S188D-H249R | +++ |
| S024R-N062E-S078G-G118S-S188D-N248D | +++ |
| T022A-S101G-S103A-V104I-N116L-S128N-Y209A-G211Q-T213A-A232V | +++ |
| T022Q-S101G-S103A-V104I-G159D-S188D-A232T-Q245R-N248D-E271L | +++ |
| S024R-A048V-S078G-G118D-G159D-S188D-H249R | +++ |
| G020R-S024R-N062E-S078D-G118D | +++ |
| G102A-S103G-V104I | +++ |
| G020R-S024R-S078D-G118D-G159D-Q245R-N248D-H249R | +++ |
| T022A-T033S-G118R-A158E | +++ |
| T022A-S024R-N116L-S128I-S188D | +++ |
| G020R-S024R-S078D-G118D-P129E-G159D-Q245R-N248D-H249R | +++ |
| T022Q-S101G-S103A-V104I-G159D-S188E-A232T-Q245T-N248E-E271F | +++ |
| S024R-N062E-S078G-G118S-S188D-Q245R | +++ |
| S024R-N062E-S078G-G118D-G159D | +++ |
| G020R-S024R-N062E-S078D-G118S-P129E-G159D-Q245R | +++ |
| T022Q-S101G-S103A-V104I-G159D-S188E-A232S-Q245V-N248E-E271T | +++ |
| G020R-S078G-G118D-S188D-N248D-H249R | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S024R-N062E-N116L-G118R-A158E-S166D-S188D | +++ |
| S078G-G118S-G159D-S188D-H249R | +++ |
| T022Q-S101G-S103A-V104I-G159D-S188E-A232T-Q245V-N248H-E271F | +++ |
| G020R-S078G-G118S-P129E-G159D-S240E-N248D-H249R | +++ |
| S024F-T033S-S101G-S103A-V104I-N116A-Y209A-G211Q-T213A-A232V | +++ |
| N062E-S078D-G118S-S188D-H249R | +++ |
| T022A-S101G-S103A-V104I-G159D-S188E-A232V-Q245V-N248D-E271T | +++ |
| G020R-S078G-G118S-G159D-S188D-Q245R-N248D | +++ |
| T022Q-S101G-S103A-V104I-G159D-S188D-A232T-Q245R-N248D-E271F | +++ |
| S024R-S078G-G118D-G159D-S188D-Q245R-N248D-H249R | +++ |
| G020R-S024R-N062E-S078D-G118D-Q245R | +++ |
| S024R-S078G-G118D-P129E-S188D-Q245R | +++ |
| N062E-S078G-G118S-S188D-Q245R-N248D-H249R | +++ |
| S024R-N062E-S078G-G118D-G159D-H249R | +++ |
| G020R-S078G-G118S-P129E-G159D-S188D-H249R | +++ |
| S024R-N062E-S078G-G118S-P129E-S188D-H249R | +++ |
| T022Q-S101G-S103A-V104I-G159D-S188D-A232L-Q245R-N248H | +++ |
| T022Q-S101G-S103A-V104I-G159D-S188D-A232V-Q245V-N248H-E271L | +++ |
| G020R-S101G-S103A-V104I-N116A-S128N-Y209V-G211Q-T213A-A232V | +++ |
| S024R-N062E-S078D-G118S-P129E-G159D-H249R | +++ |
| T022A-S101G-S103A-V104I-G159D-S188E-A232V-Q245R-N248D-E271H | +++ |
| G020R-N062E-S078G-G118D-P129E-S188D-H249R | +++ |
| T022Q-S101G-S103A-V104I-G159D-S188E-A232L-Q245V-N248E-E271L | +++ |
| G020K-T022L-S078G-G118S-P129E-G159D | +++ |
| S078G-G118S-S188D-Q245R-N248D | +++ |
| T022A-S024F-S101G-S103A-V104I-N116A-S128N-Y209A-A232V | +++ |
| G020R-S024R-N062E-S078G-G118S-G159D-N248D | +++ |
| N062E-G118R-S166D-S188D | +++ |
| T022Q-S101G-S103A-V104I-G159D-S188E-A232T-Q245R-N248E-E271T | +++ |
| T022A-S101G-S103A-V104I-G159D-S188D-A232S-Q245T-N248H-E271F | +++ |
| G020R-N062E-S078G-G118S-G159D-H249R | +++ |
| S024R-N062E-N116L-A158E | +++ |
| S024R-S078G-G118D-P129E-Q245R-N248D-H249R | +++ |
| G020R-S024R-N062E-S078D-G118S-P129E-S188D-Q245R | +++ |
| S024R-S078G-G118D-P129E-G159D-S188D-H249R | +++ |
| T022Q-S101G-S103A-V104I-G159D-S188E-A232L-Q245R-N248D-E271H | +++ |
| S024R-S078D-G118D-P129E-S188D-Q245R-N248D-H249R | +++ |
| G020R-S024R-S078G-G118D-P129E-G159D-N248D-H249R | +++ |
| T022A-S101G-S103A-V104I-G159D-S188E-A232V-Q245T-N248E-E271F | +++ |
| T022Q-S101G-S103A-V104I-G159D-S188D-A232L-Q245T-N248H-E271T | +++ |
| S024R-S078D-G118S-P129E-G159D | +++ |
| G020R-N062E-S078G-G118S-P129E-S188D-Q245R | +++ |
| T022A-S024R-N116L-G118R-S128I-S188D | +++ |
| T022A-S101G-S103A-V104I-G159D-S188E-A232L-Q245T-N248E-E271H | +++ |
| G020R-S024R-S078D-G118S-P129E-G159D-S188D-Q245R-N248D | +++ |
| G020R-S024R-N062E-S078G-G118S-P129E-S188D-N248D-H249R | +++ |
| T022A-S101G-S103A-V104I-G159D-S188E-A232V-Q245V-N248H-E271H | +++ |
| G020R-S078G-G118D-P129E-G159D-S188D-H249R | +++ |
| G020R-S024R-S078D-G118S-S188D-Q245R-H249R | +++ |
| T022A-S101G-S103A-V104I-G159D-S188D-A232V-Q245R-N248E-E271F | +++ |
| T022A-S101G-S103A-V104I-G159D-S188D-A232T-Q245R-N248D-E271F | +++ |
| S024R-N062E-S078G-G118S-S188D-N248D-H249R | +++ |
| G020R-N062E-S078G-G118S-G159D-Q245R | +++ |
| S024R-N062E-G118R-A158E-S166D-S188D | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024R-N062E-S078G-G118S-P129E-G159D-N248D-H249R | +++ |
| G020R-S024R-N062E-S078G-G118S-P129E-A158T-G159D-Q245R-N248D | +++ |
| T022Q-S101G-S103A-V104I-G159D-S188E-A232T-Q245R-N248E-E271L | +++ |
| G020R-S024R-N062E-S078D-G118S-S188D-H249R | +++ |
| S024R-S078G-G118S-S188D-N248D | +++ |
| T022A-S101G-S103A-V104I-G159D-S188E-A232L-Q245V-N248E-E271H | +++ |
| T022Q-S101G-S103A-V104I-G159D-S188D-A232L-Q245T-N248H-E271H | +++ |
| S099G-S101G | +++ |
| T022Q-S101G-S103A-V104I-G159D-S188D-A232T-Q245V-N248D-E271F | +++ |
| G020R-N062E-S078D-G118S-P129E-G159D-Q245R | +++ |
| T022A-S101G-S103A-V104I-G159D-S188E-A232T-Q245T-N248H-E271H | +++ |
| T022Q-S101G-S103A-V104I-G159D-S188E-A232V-Q245V-N248H-E271L | +++ |
| T022A-S101G-S103A-V104I-G159D-S188D-A232V-Q245R-N248E-E271T | +++ |
| T022Q-S101G-S103A-V104I-G159D-S188E-A232L-Q245T-N248E-E271T | +++ |
| T022Q-S101G-S103A-V104I-G159D-S188E-A232L-Q245V-N248E-E271H | +++ |
| T022Q-S101G-S103A-V104I-G159D-S188D-A232T-Q245R-N248H-E271L | +++ |
| G020R-S078G-G118S-P129E-G159D-S188D-Q245R-N248D-H249R | +++ |
| G020R-S024R-N062E-S078G-G118S-S188D-N248D | +++ |
| S024R-N062E-S078G-G118S-P129E-G159D | +++ |
| A016S-T022A-S101G-S103A-V104I-N116A-S128N-Y209V-G211Q-A232V | +++ |
| S024R-S078G-G118D-S188D-Q245R-N248D-H249R | +++ |
| G020R-S024R-S078D-G118D-G159D-S188D-Q245R-N248D-H249R | +++ |
| A016S-T022A-S101G-S103A-V104I-N116A-Y209V-G211Q-T213A-A232V | +++ |
| S024R-N062E-S078G-G118D-S188D-H249R | +++ |
| T022L-S078N-G118R-S166D-T213A-L217E | +++ |
| T022A-S101G-S103A-V104I-G159D-S188D-A232S-Q245R-N248E-E271H | +++ |
| S024R-S078G-G118D-G159D-N248D-H249R | +++ |
| S024R-S078G-G118D-P129E-S188D-Q245R-N248D | +++ |
| T022Q-S101G-S103A-V104I-G159D-S188E-A232T-Q245T-N248H-E271T | +++ |
| T022A-S101G-S103A-V104I-G159D-S188D-A232S-Q245R-N248H-E271H | +++ |
| G020R-S024R-S078G-G118S-G159D-S188D-Q245R-N248D | +++ |
| T022A-S101G-S103A-V104I-G159D-S188D-A232V-Q245R-N248D-E271L | +++ |
| S024R-N062E-S078G-G118D-P129E-G159D-H249R | +++ |
| T022A-S101G-S103A-V104I-G159D-S188E-A232T-Q245T-N248H-E271F | +++ |
| G020R-S024R-N062E-S078G-G118S-P129E-G159D-S188D-N248D-H249R | +++ |
| T022Q-S101G-S103A-V104I-G159D-S188E-A232T-Q245R-N248H-E271T | +++ |
| T022A-S101G-S103A-V104I-G159D-S188D-A232S-Q245R-N248E-E271F | +++ |
| G020R-S024R-S078D-G118S-P129E-G159D-H249R | +++ |
| S024R-N062E-S078G-G118S-P129E-G159D-S188D-Q245R | +++ |
| T022A-S101G-S103A-V104I-G159D-S188E-A232S-Q245R-N248D-E271H | +++ |
| G020R-S024R-S078D-G118S-S188D | +++ |
| T022A-S101G-S103A-V104I-G159D-S188D-A232T-Q245R-N248E | +++ |
| T022Q-S101G-S103A-V104I-G159D-S188D-A232T-Q245R-N248D-E271H | +++ |
| T022A-S101G-S103A-V104I-G159D-S188E-A232T-Q245R-N248H-E271F | +++ |
| T022Q-S101G-S103A-V104I-G159D-S188E-A232S-Q245T-N248H-E271T | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S101G-S103A-V104I-G159D-S188D-A232S-Q245T-N248H-E271T | +++ |
| N062E-S078G-G118D-G159D-N248D-H249R | +++ |
| G020R-S078G-G118S-S188D-N248D | +++ |
| S024R-S078D-G118S-P129E-S188D | +++ |
| G020R-S078G-G118D-P129E-S188D-H249R | +++ |
| G020R-N062E-S078D-G118D-G159D-S188D-H249R | +++ |
| T022Q-S101G-S103A-V104I-G159D-S188D-A232T-Q245T-N248D-E271L | +++ |
| T022A-S101G-S103A-V104I-G159D-S188E-A232V-Q245V-N248H-E271T | +++ |
| G020R-N062E-S078G-G118S-P129E-G159D-Q245R | +++ |
| A001E-G020R-S024R-S078G-G118D-G159D-S188D | +++ |
| T022Q-S101G-S103A-V104I-G159D-S188D-A232S-Q245T-N248E-E271L | +++ |
| G020R-S078D-G118S-G159D-N248D-H249R | +++ |
| T022Q-S101G-S103A-V104I-G159D-S188E-A232T-Q245V-N248E-E271L | +++ |
| G020R-N062E-S078D-G118S-P129E-H249R | +++ |
| T022Q-S101G-S103A-V104I-G159D-S188D-A232S-Q245R-N248E-E271F | +++ |
| S024F-T033S-S101G-S103A-V104I-N116A-Y209V-A232V | +++ |
| S024R-N062E-N116L-G118R-S128I-A158E | +++ |
| S024R-S078G-G118D-P129E-G159D-S188D-Q245R | +++ |
| T022Q-S101G-S103A-V104I-G159D-S188E-A232L-Q245V-N248D-E271L | +++ |
| T022Q-S101G-S103A-V104I-G159D-S188D-A232S-Q245V-N248E-E271H | +++ |
| S024R-N062E-S078G-G118S-G159D-N248D | +++ |
| G020R-S078G-G118S-P129E-S188D-H249R | +++ |
| S024R-S078G-G118S-P129E-S188D-Q245R | +++ |
| S024R-N062E-S078D-G118D-G159D-H249R | +++ |
| T022Q-S101G-S103A-V104I-G159D-S188D-A232S-Q245T-N248H-E271H | +++ |
| S024R-S078G-G118S-P129E-Q245R-N248D | +++ |
| S024R-T033S-G118R-A158E | +++ |
| G020R-S024R-S078D-G118S-S188D-Q245R-N248D | +++ |
| G020R-N062E-S078G-G118S-P129E-S188D-Q245R-N248D | +++ |
| T022A-S101G-S103A-V104I-G159D-S188E-A232S-Q245R-N248D-E271T | +++ |
| T022Q-S101G-S103A-V104I-G159D-S188D-A232S-Q245R-N248H-E271T | +++ |
| T022A-S101G-S103A-V104I-G159D-S188E-A232L-Q245T-N248D-E271H | +++ |
| G020R-S024R-N062E-S078G-G118D-P129E-S188D-Q245R-N248D | +++ |
| G020R-S024R-S078G-G118D-P129E-G159D-S188D-Q245R | +++ |
| T022A-S101G-S103A-V104I-G159D-S188D-A232S-Q245R-N248D-E271H | +++ |
| S024R-S078D-G118D-G159D-S188D-Q245R | +++ |
| G020R-S024R-S078G-G118D-P129E-S188D-N248D-H249R | +++ |
| S024R-S078G-G118S-G159D-S188D-Q245R-N248D-H249R | +++ |
| G020R-N062E-S078G-G118S-P129E | +++ |
| T022Q-S101G-S103A-V104I-G159D-S188E-A232V-Q245V-N248D | +++ |
| T022A-S101G-S103A-V104I-G159D-S188E-A232V-Q245R-N248D-E271L | +++ |
| A016S-T022A-S024F-S101G-S103A-V104I-N116L-Y209A-G211Q-T213A-A232V | +++ |
| T022A-S024R-T033S-S188D | +++ |
| G020R-S024R-S078D-G118S-G159D-Q245R-N248D | +++ |
| G020R-S024R-N062E-S078G-G118D-G159D-H249R | +++ |
| G020R-S024R-S078G-G118D-P129E-G159D-S188D-Q245R-N248D | +++ |
| T022Q-S101G-S103A-V104I-G159D-S188E-A232L-Q245T-N248D-E271H | +++ |
| N062E-S078G-G118S-N248D | +++ |
| T022A-S024R-N062E-S128I | +++ |
| G020R-S024R-N062E-S078D-G118D-G159D-S188D-Q245R-N248D | +++ |
| G020R-S024R-N062E-S078G-G118D-P129E-G159D-H249R | +++ |
| G020R-S024R-S078D-G118D-S188D-N248D-H249R | +++ |
| S024R-S078G-G118D-G159D-S188D | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024F-S101G-S103A-V104I-N116A-Y209A-G211Q-A232V | +++ |
| T022Q-S101G-S103A-V104I-G159D-S188D-A232L-Q245R-N248E-E271L | +++ |
| T022A-S024R-T033S-N062E-G118R-S188D | +++ |
| G020R-S078D-G118D-P129E-G159D-S188D-Q245R-H249R | +++ |
| T022Q-S101G-S103A-V104I-G159D-S188D-A232T-Q245R-N248D-T255M-E271T | +++ |
| S024R-N062E-S078D-G118S-N248D-H249R | +++ |
| T022A-S101G-S103A-V104I-G159D-S188E-A232L-Q245R-N248D-E271H | +++ |
| G020R-S024R-S078D-G118D-P129E-G159D-S188D-H249R | +++ |
| T022Q-S101G-S103A-V104I-G159D-S188E-A232S-Q245T-N248D-E271L | +++ |
| G020R-S024R-N062E-S078G-G118D-P129E-Q245R-N248D | +++ |
| T022A-S101G-S103A-V104I-G159D-S188D-A232L-Q245R-N248H-E271F | +++ |
| S024R-G118R-S128I-A158E-S188D | +++ |
| S024R-N062E-S078G-G118S-P129E-G159D-S188D-Q245R-N248D-H249R | +++ |
| T022Q-S101G-S103A-V104I-G159D-S188D-A232S-Q245V-N248H | +++ |
| T022A-S101G-S103A-V104I-G159D-S188D-A232L-Q245T-N248E-E271H | +++ |
| T022A-G118R-S128I-A158E-S188D | +++ |
| T022Q-S101G-S103A-V104I-G159D-S188E-A232V-Q245R-N248E-E271T | +++ |
| S078G-G118S-P129E-G159D-S188D-Q245R-H249R | +++ |
| S024R-N062E-S078G-G118D-P129E-G159D | +++ |
| N116L-G118R-S128I-A158E | +++ |
| T022A-S101G-S103A-V104I-G159D-S188E-A232T-Q245R-N248H-E271T | +++ |
| G020R-S024R-S078G-G118D-P129E-G159D-S188D-N248D-H249R | +++ |
| G020R-S024R-N062E-S078D-G118S-G159D-Q245R-N248D | +++ |
| S024R-S078D-G118S-P129E-G159D-Q245R-H249R | +++ |
| S024R-N062E-S078D-G118D-G159D | +++ |
| S024R-T033S-G118R-S188D | +++ |
| T022A-S101G-S103A-V104I-G159D-S188E-A232L-Q245R-N248H-E271L | +++ |
| T022Q-S101G-S103A-V104I-G159D-S188D-A232S-Q245V-N248E-E271L | +++ |
| S024R-S078G-G118D-P129E-S188D | +++ |
| S078G-G118D-G159D-S188D-H249R | +++ |
| T022A-S101G-S103A-V104I-G159D-S188E-A232V-Q245T-N248H-E271H | +++ |
| T022A-S101G-S103A-V104I-G159D-S188D-A232T-Q245V-N248D-E271L | +++ |
| A016S-T033S-S101G-S103A-V104I-N116A-Y209V-G211Q-T213A-A232V | +++ |
| T022A-S024R-N062E-N116L-S128I-A158E | +++ |
| T022Q-S101G-S103A-V104I-G159D-S188D-A232L-Q245T-N248H-E271F | +++ |
| S024R-G118R-S128I-S188D | +++ |
| G020R-S078G-G118D-G159D-Q245R-N248D-H249R | +++ |
| N062E-S101A-S103A-V104I-S188D-P210I-A232V-Q245R | +++ |
| S024R-N062E-S078G-G118S-P129E-G159D-S188D-Q245R-N248D | +++ |
| S024R-N062E-S078G-G118D-N248D-H249R | +++ |
| S024R-N062E-S078G-G118S-G159D-S188D-N248D | +++ |
| S024R-N062E-S078G-G118S-P129E-S188D-Q245R | +++ |
| T022A-T033S-G118R-S166D | +++ |
| T022Q-S101G-S103A-V104I-G159D-S188E-A232L-Q245R-N248E-E271T | +++ |
| S078G-G118D-S188D-Q245R-N248D-H249R | +++ |
| T022A-S024R-G118R-S128I | +++ |
| T022Q-S101G-S103A-V104I-G159D-S188D-A232L-Q245T-N248E-E271L | +++ |
| G020R-N062E-S078D-G118S-S188D | +++ |
| T022A-T033S-S101G-S103A-V104I-N116L-G159D-S188D-T213A-A232V-Q245R-N248D-E271F | +++ |
| T022Q-S101G-S103A-V104I-G159D-S188D-A232V-Q245V-N248H-E271T | +++ |
| S024R-S078D-G118S-P129E-G159D-N248D-H249R | +++ |
| G020R-S078G-G118S-G159D-N248D-H249R | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| G020R-N062E-S078G-G118S-S188D | +++ |
| T022Q-S101G-S103A-V104I-G159D-S188D-A232T-Q245R-N248D-E271T | +++ |
| T022A-S101G-S103A-V104I-G159D-S188E-A232T-Q245T-N248H | +++ |
| G020R-S024R-N062E-S078D-G118S-P129E-G159D-Q245R-N248D | +++ |
| G020R-N062E-S078D-G118S-G159D-Q245R | +++ |
| S024R-S128I-A158E | +++ |
| T022Q-S101G-S103A-V104I-G159D-S188E-A232L-Q245R-N248H-E271H | +++ |
| S024R-N062E-S078D-G118S-S188D-N248D-H249R | +++ |
| A016S-S024F-S101G-S103A-V104I-N116L-Y209A-L217S-A232V | +++ |
| S003T-S024R-N062E-S078D-G118S-N248D | +++ |
| G020R-S024R-N062E-S078D-G118D-S188D | +++ |
| T022A-S101G-S103A-V104I-G159D-S188E-A232T-Q245V-N248D-E271H | +++ |
| T022Q-S101G-S103A-V104I-G159D-S188D-A232S-Q245V-N248D-E271H | +++ |
| G020R-N062E-S078D-G118S-P129E-S188D-Q245R | +++ |
| T022A-S101G-S103A-V104I-G159D-S188D-A232S-Q245R-N248D-S265G-E271H | +++ |
| G020R-S078G-G118D-P129E-G159D-Q245R-H249R | +++ |
| T022Q-S101G-S103A-V104I-G159D-S188D-A232L-Q245V-N248E-E271L | +++ |
| G020R-S024R-S078G-G118S-G159D-S188D-N248D | +++ |
| S078G-G118D-G159D-S188D-Q245R-N248D-H249R | +++ |
| G020R-N062E-S078D-G118S-G159D-Q245R-N248D | +++ |
| T022A-S101G-S103A-V104I-G159D-S188D-A232L-Q245T-N248H-E271H | +++ |
| S024R-N062E-S078D-G118S-P129E-S188D-Q245R-N248D-H249R | +++ |
| T022A-S101G-S103A-V104I-G159D-S188E-A232T-Q245R-N248E | +++ |
| T022Q-S101G-S103A-V104I-G159D-S188E-A232T-Q245R-N248D-E271L | +++ |
| G020K-T022L-S078N-S166D-T213A-L217E | +++ |
| G020R-S078D-G118S-P129E-G159D-Q245R | +++ |
| T022A-T033S-N116L-G118R-A158E | +++ |
| G020R-S024R-S078G-G118S-P129E-G159D-S188D-Q245R | +++ |
| A001G-T022A-S101G-S103A-V104I-G159D-S188D-A232L-Q245T-N248H-E271L | +++ |
| S024R-S078D-G118S-G159D-Q245R | +++ |
| G020K-T022L-S078N-G118R-S166D-T213A-L217E | +++ |
| S078G-G118S-P129E-S188D-Q245R | +++ |
| T022Q-S101G-S103A-V104I-G159D-S188E-A232L-Q245T-N248E | +++ |
| T022Q-S101G-S103A-V104I-G159D-S188E-A232V-Q245V-N248E-E271F | +++ |
| S188D | +++ |
| S024R-N062E-S078G-G118D-H249R | +++ |
| T022Q-S101G-S103A-V104I-G159D-S188D-A232T-Q245T-N248H-E271L | +++ |
| T022A-S101G-S103A-V104I-G159D-S188E-A232T-Q245V-N248E-E271F | +++ |
| G020R-S024R-N062E-S078D-G118S-P129E-S188D | +++ |
| T022A-S101G-S103A-V104I-G159D-S188D-A232V-Q245T-N248H-E271L | +++ |
| S024R-S078D-G118D-P129E-S188D-H249R | +++ |
| T022A-S101G-S103A-V104I-G159D-S188D-A232V-Q245V-N248D-E271H | +++ |
| G020R-S078G-G118D-G159D | +++ |
| T022Q-S101G-S103A-V104I-G159D-S188E-A232V-Q245V-N248D-E271L | +++ |
| T022A-N062E-G118R-S128I-S188D | +++ |
| T022A-N116L-G118R-A158E-S166D-S188D | +++ |
| S024R-N062E-N116L | +++ |
| T022A-S024R-N116L-S128I-S166D-S188D | +++ |
| T022Q-S101G-S103A-V104I-G159D-S188E-A232V-Q245T-N248D-E271F | +++ |
| N116L-A158E-S166D | +++ |
| G020R-S024R-S078D-G118S-P129E-N248D | +++ |
| T022A-S101G-S103A-V104I-G159D-S188D-A232S-Q245R-N248D-E271T | +++ |
| T022A-S101G-S103A-V104I-G159D-S188D-A232L-Q245R-N248E-E271H | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022Q-S101G-S103A-V104I-G159D-S188D-A232T-Q245R-N248H | +++ |
| T022A-S024R-N062E-N116L-A158E-S166D | +++ |
| G020R-N062E-S078D-G118S-P129E | +++ |
| T022A-S101G-S103A-V104I-N116L-H120Q-S128N-Y209A-G211Q-T213A-A232V | +++ |
| T022A-S101G-S103A-V104I-G159D-S188D-A232L-Q245V-N248E-E271F | +++ |
| A016S-S024F-S101G-S103A-V104I-N116L-S128N-Y209A-G211Q-T213A-A232V | +++ |
| T022Q-S101G-S103A-V104I-G159D-S188D-A232V-Q245T-N248H-E271L | +++ |
| G020R-S024R-N062E-S078G-G118D-P129E-S188D | +++ |
| T022Q-S101G-S103A-V104I-G159D-S188E-A232S-Q245R-N248E-E271F | +++ |
| N062E-S101A-S103A-V104I-A232V-Q245R | +++ |
| T022A-S101G-S103A-V104I-G159D-S188E-A232S-Q245R-N248H | +++ |
| T022A-S101G-S103A-V104I-G159D-S188D-A232L-Q245T-N248E-E271L | +++ |
| S024R-N062E-N116L-G118R-S128I | +++ |
| T022Q-S101G-S103A-V104I-G159D-S188E-A232T-Q245T-N248H-E271F | +++ |
| T022A-S101G-S103A-V104I-G159D-S188E-A232V-Q245T-N248E-E271H | +++ |
| T022A-S101G-S103A-V104I-G159D-S188E-A232V-Q245V-N248D-E271F | +++ |
| T022A-S101G-S103A-V104I-G159D-S188E-A232T-Q245R-N248E-E271F | +++ |
| T022A-S101G-S103A-V104I-G159D-S188E-A232S-Q245T-N248E-E271H | +++ |
| T022Q-S101G-S103A-V104I-G159D-S188D-A232T-Q245R-N248H-E271H | +++ |
| N062E-G118R-S128I-A158E | +++ |
| T022Q-S101G-S103A-V104I-G159D-S188E-A232T-Q245T-N248H-E271H | +++ |
| S078D-G118S-G159D-Q245R-H249R | +++ |
| S103A-V104I-S128N-L148I | +++ |
| G020R-S024R-N062E-S078D-G118D-P129E-S188D-H249R | +++ |
| T022Q-S101G-S103A-V104I-G159D-S188D-A232S-Q245R-N248H-E271H | +++ |
| S024R-G118R-S188D | +++ |
| T022Q-S101G-S103A-V104I-G159D-S188D-A232L-Q245V-N248E-E271F | +++ |
| T033S-N062E-G118R-A158E-S188D | +++ |
| T022A-S024F-S101G-S103A-V104I-N116A-S128N-Y209V-G211Q-T213A-A232V | +++ |
| S024R-N062E-S078G-G118S-P129E-G159D-S188D-H249R | +++ |
| S078G-G118S-P129E-G159D-H249R | +++ |
| T022A-S101G-S103A-V104I-G159D-S188D-A232T-Q245V-N248E-E271H | +++ |
| N062E-N076D-S101A-S103A-V104I-A232V-Q245R | +++ |
| G020K-S024F-S078N-L217E | +++ |
| S103A-S128N-L148I | +++ |
| S024F-S101G-S103A-V104I-N116L-Y209A-G211Q-T213A-A232V | +++ |
| G020R-S024R-S078D-G118S-P129E-G159D-S188D-Q245R-N248D-H249R | +++ |
| G020R-N062E-S078D-G118D-P129E-G159D-H249R | +++ |
| S078G-G118D-P129E-G159D-Q245R-H249R | +++ |
| G020R-N062E-S078D-G118S-G159D-Q245R-N248D-H249R | +++ |
| G020R-N062E-S078G-G118S-N248D-H249R | +++ |
| T022A-S101G-S103A-V104I-G159D-S188D-A232S-Q245R-N248E-E271L | +++ |
| G020R-S024R-S078D-G118D-G159D-S188D | +++ |
| T033S-N116L-A158E | +++ |
| G020K-S024F-S166D-L217E | +++ |
| S024R-S078D-G118D-G159D-S188D-Q245R-H249R | +++ |
| G020R-S024R-N062E-S078G-G118S-G159D-N248D-H249R | +++ |
| T022A-S101G-S103A-V104I-G159D-S188D-A232V-Q245T-N248H-E271H | +++ |
| T022A-S024R-T033S-G118R-A158E-S166D | +++ |
| N062E-S078D-G118D-G159D-Q245R | +++ |
| S078G-G118S-P129E-G159D-S188D-H249R | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| G020R-N062E-S078G-G118S-P129E-G159D | +++ |
| T022Q-S101G-S103A-V104I-G159D-S188E-A232L-Q245T-N248H-E271F | +++ |
| S078D-G118S-G159D-H249R | +++ |
| S078G-G118D-P129E-G159D-H249R | +++ |
| G020R-S024R-S078D-G118D-P129E-S188D-N248D-H249R | +++ |
| S024R-N062E-S078G-G118S-G159D-S188D-H249R | +++ |
| G020R-S078D-G118S-G159D-S188D-Q245R | +++ |
| G020R-N062E-S078D-G118S-G159D-S188D-H249R | +++ |
| G020R-S024R-N062E-S078G-G118S-P129E-Q245R-N248D | +++ |
| G020R-N062E-S078G-G118D-S188D-Q245R-N248D | +++ |
| S024R-N062E-S078D-G118S-G159D-S188D | +++ |
| G020R-S024R-N062E-S078G-G118S-P129E-Q245R | +++ |
| G020R-S024R-S078D-G118D-G159D | +++ |
| G020R-S078G-G118S-G159D-S188D-N248D-H249R | +++ |
| T022Q-S101G-S103A-V104I-G159D-S188E-A232T-Q245T-N248H | +++ |
| T022Q-S101G-S103A-V104I-G159D-S188D-A232S-Q245R-N248E-E271L | +++ |
| T022A-S101G-S103A-V104I-G159D-S188D-A232V-Q245R-N248H | +++ |
| T022A-S024R-N116L-G118R-S128I-S166D-S188D | +++ |
| S024R-N062E-S078G-G118S-G159D-S188D-Q245R-N248D | +++ |
| A016S-S024F-S101G-S103A-V104I-N116L-S128N-Y209V-G211Q-A232V | +++ |
| T022A-S101G-S103A-V104I-G159D-S188D-A232V-Q245V-N248H-E271L | +++ |
| S024R-S078G-G118S-P129E-S188D-Q245R-N248D-H249R | +++ |
| S024R-S078D-G118D-P129E-Q245R-H249R | +++ |
| T022Q-S101G-S103A-V104I-G159D-S188E-A232S-Q245V-N248D-E271F | +++ |
| G020K-S024F-S078N-G118R-S166D-L217E | +++ |
| S024F-G118R-S166D-T213A-L217E | +++ |
| G020R-S024R-S078D-G118S-P129E-S188D-Q245R-N248D-H249R | +++ |
| T022A-S024R-T033S-S078N-S166D-S188D | +++ |
| G020R-S024R-S078G-G118D-Q245R | +++ |
| G020K-S024F-S078N-G118R-S166D-T213A-L217E | +++ |
| G020K-T022L-S078G-G118S-G159D-S188D-H249R | +++ |
| T022A-S101G-S103A-V104I-G159D-S188E-A232V-Q245T-N248D-E271L | +++ |
| S024R-T033S-G118R-A158E-S166D-S188D | +++ |
| T022Q-S101G-S103A-V104I-G159D-S188D-A232L-Q245T-N248D-E271L | +++ |
| T022V-S024F-T033S-S101G-S103A-V104I-N116L-Y209A-G211Q-T213A-A232V | +++ |
| G020R-S024R-S078G-G118D-G159D-S188D | +++ |
| S078N-G118R-S166D-L217E | +++ |
| S024R-S078G-G118S-G159D-Q245R-N248D | +++ |
| T022A-S024R-G118R-S128I-A158E-S166D-S188D | +++ |
| T022A-S101G-S103A-V104I-G159D-S188E-A232L-Q245R-N248H-E271H | +++ |
| T022A-S101G-S103A-V104I-G159D-S188E-A232T-Q245T-N248H-E271T | +++ |
| G020R-S024R-S078G-G118D-G159D-N248D-H249R | +++ |
| T022Q-S101G-S103A-V104I-G159D-S188D-A232V-Q245V-N248D-E271F | +++ |
| A016S-T022A-S101G-S103A-V104L-L148I | +++ |
| G020R-S024R-N062E-S078D-G118S-G159D-N248D | +++ |
| T022Q-S101G-S103A-V104I-G159D-S188E-A232T-Q245R-N248E-E271H | +++ |
| S078G-G118D-P129E-G159D-Q245R | +++ |
| S024R-S078G-G118S-S188D-Q245R-N248D | +++ |
| G020R-N062E-S078D-G118D-G159D-S188D | +++ |
| G020R-S024R-N062E-S078D-G118D-G159D-S188D-Q245R | +++ |
| T022A-T033S-S101G-S103A-V104I-N116L-Y209A-G211Q-T213A-A232V | +++ |
| T022A-S101G-S103A-V104I-G159D-S188D-A232V-Q245R-N248H-E271H | +++ |
| T022A-S024R-T033S-S128I-S188D | +++ |
| T022Q-S101G-S103A-V104I-G159D-S188E-A232V-Q245T-N248D-E271H | +++ |
| T022Q-S101G-S103A-V104I-G1159D-S188D-A232L-Q245R-N248E-E271F | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024R-S078G-G118S-P129E-S188D-N248D | +++ |
| G020R-N062E-S078D-G118S-P129E-Q245R | +++ |
| T022Q-S101G-S103A-V104I-G159D-S188D-A232T-Q245T-N248D-E271F | +++ |
| T022Q-S101G-S103A-V104I-G159D-S188D-A232T-Q245T-N248H | +++ |
| G020R-S024R-S078D-G118D-G159D-Q245R | +++ |
| T022Q-S101G-S103A-V104I-G159D-S188D-A232T-Q245T-N248E-E271L | +++ |
| S101A-N116L-P210I-T213A | +++ |
| T022Q-S101G-S103A-V104I-G159D-S188D-A232V-Q245R-N248H-E271F | +++ |
| G020R-S024R-N062E-S078D-G118D-P129E-Q245R-N248D | +++ |
| T022A-S024R-N062E-A158E | +++ |
| T022Q-S101G-S103A-V104I-G159D-S188E-A232V-Q245T-N248D-E271H | +++ |
| G020R-S024R-N062E-S078D-G118D-G159D-S188D-Q245R-N248D-H249R | +++ |
| G020R-N062E-S078G-G118S-G159D-S188D-Q245R-N248D | +++ |
| N062E-S078G-G118S-S188D-H249R | +++ |
| A016S-S024F-T033S-S101G-S103A-V104I-N116L-Y209V-G211Q-T213A-A232V | +++ |
| G020R-S078G-G118D-S188D-H249R | +++ |
| T022A-S024F-S101G-S103A-V104I-N116L-S128N-Y209A-G211Q-A232V | +++ |
| G020R-N062E-S078D-G118S-G159D-N248D-H249R | +++ |
| T022Q-S101G-S103A-V104I-G159D-S188D-A232T-Q245T-N248D-E271H | +++ |
| T022A-S024R-N116L-G118R-A158E-S166D-S188D | +++ |
| G020R-S024R-S078G-G118S-P129E-G159D-S188D-Q245R-N248D-H249R | +++ |
| S024R-N062E-N076D-S101A-S103A-V104I-P210I-A232V-Q245R | +++ |
| N062E-S078D-G118S-G159D-Q245R-N248D-H249R | +++ |
| G020R-S024R-S078G-G118D-G159D-S188D-N248D-H249R | +++ |
| T022Q-S101G-S103A-V104I-G159D-S188D-A232S-Q245V-N248E-E271T | +++ |
| T022A-S101G-S103A-V104I-G159D-S188D-A232L-Q245V-N248E-E271T | +++ |
| S024R-S101A-S103A-V104I-S188D-P210I-A232V-Q245R | +++ |
| S024R-N062E-N116L-G118R-A158E | +++ |
| G020R-S078G-G118D-S188D-Q245R | +++ |
| T022A-S101G-S103A-V104I-G159D-S188D-A232L-Q245V-N248E-E271L | +++ |
| T022Q-S101G-S103A-V104I-G159D-S188D-A232L-Q245R-N248E-E271H | +++ |
| S024R-S166D-S188D | +++ |
| T022A-S101G-S103A-V104I-G159D-S188D-A232V-Q245T-N248D-E271F | +++ |
| A016S-T022A-S024F-S101G-S103A-V104I-N116A-Y209V-G211Q-A232V | +++ |
| T022Q-S101G-S103A-V104I-G159D-S188E-A232L-Q245T-N248D-E271F | +++ |
| G020R-N062E-S078G-G118D-G159D-S188D-Q245R-N248D | +++ |
| T022A-N062E-N116L-G118R-A158E | +++ |
| S024R-N062E-N116L-G118R-S128I-S166D | +++ |
| T022Q-S101G-S103A-V104I-G159D-S188E-A232V-Q245R-N248H | +++ |
| G020R-S024R-N062E-S078D-G118D-H249R | +++ |
| T022A-S101G-S103A-V104I-G159D-S188E-A232T-Q245R-N248E-E271L | +++ |
| S024R-N062E-G118R-S128I-S188D | +++ |
| N062E-S078G-G118S-G159D-N248D-H249R | +++ |
| G020K-T022L-N062E-S078D-G118S-G159D-H249R | +++ |
| N062E-S078G-G118D-Q245R-N248D | +++ |
| G020R-S024R-N062E-S078D-G118D-G159D-S188D-H249R | +++ |
| T022A-S024F-S101G-S103A-V104I-N116L-Y209V-T213A-A232V | +++ |
| T022A-S101G-S103A-V104I-G159D-S188D-A232T-Q245R-N248D-E271L | +++ |
| S024R-N116L-G118R-S128I-A158E | +++ |
| T022A-S101G-S103A-V104I-G159D-S188E-A232V-Q245R-N248E-E271F | +++ |
| T022Q-S101G-S103A-V104I-G159D-S188D-A232V-Q245V-N248E-E271T | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022Q-S101G-S103A-V104I-G159D-S188D-A232S-Q245V-N248D-E271L | +++ |
| A016S-S101G-S103A-V104L-L148I | +++ |
| T022Q-S101G-S103A-V104I-G159D-S188E-A232L-Q245T-N248H-E271T | +++ |
| G020R-N062E-S078G-G118S-S188D-Q245R | +++ |
| T022A-S101G-S103A-V104I-G159D-S188E-A232V-Q245V-N248E-E271H | +++ |
| S024R-S078D-G118D-S188D-Q245R-N248D-H249R | +++ |
| G020R-S024R-S078D-G118S-P129E-Q245R-N248D | +++ |
| G020R-S078G-G118D-G159D-S188D | +++ |
| T022Q-S101G-S103A-V104I-G159D-S188D-A232L-Q245T-N248E-E271T | +++ |
| G020R-S024R-S078D-G118D-G159D-N248D-H249R | +++ |
| S024R-N062E-S078G-G118S-P129E-S188D-Q245R-N248D | +++ |
| T022A-S101G-S103A-V104I-G159D-S188E-A232L-Q245T-N248D-E271T | +++ |
| T022A-S101G-S103A-V104I-G159D-S188D-A232V-Q245R-N248E | +++ |
| T022Q-S101G-S103A-V104I-G159D-S188D-A232V-Q245T-N248H-E271F | +++ |
| T022Q-S101G-S103A-V104I-G159D-S188D-A232S-Q245T-N248E-E271F | +++ |
| T022A-S101G-S103A-V104I-G159D-S188D-A232L-Q245R-N248D-E271L | +++ |
| G020R-S024R-N062E-S078D-G118S-P129E-N248D | +++ |
| S024R-N062E-S078D-G118S-P129E-G159D-N248D-H249R | +++ |
| T022Q-S101G-S103A-V104I-G159D-S188E-S212L-A232S-Q245V-N248D-E271T | +++ |
| S024R-S078G-G118D-G159D-H249R | +++ |
| T022A-N116L-G118R-S128I-S188D | +++ |
| T022A-S101G-S103A-V104I-G159D-S188E-A232V-Q245R-N248D | +++ |
| N062E-S078G-G118D-S188D-Q245R | +++ |
| G020K-S078N-S166D-L217E | +++ |
| N062E-S078G-G118S-P129E-S188D-Q245R | +++ |
| T022Q-S101G-S103A-V104I-G159D-S188E-A232S-Q245V-N248E-E271F | +++ |
| N062E-N116L-G118R-S166D-S188D | +++ |
| G020R-S024R-S078D-G118S-G159D-N248D | +++ |
| T022A-S024F-S101G-S103A-V104I-N116L-S128N-Y209V-A232V | +++ |
| S078G-G118S-P129E-G159D-Q245R | +++ |
| T022A-T033S-S101G-S103A-V104I-N116L-Y209V-G211Q-T213A-A232V | +++ |
| S078D-G118S-P129E-G159D-S188D-Q245R-N248D-H249R | +++ |
| S101G-S103A-V104I-N116L-S128N-Y209A-G211Q-T213A-A232V | +++ |
| G097P-S101A-S103G | |
| S024R-N062E-S078G-G118S-S188D | +++ |
| G020R-S024R-S078D-G118D-P129E-S188D-H249R | +++ |
| S024R-N062E-S078G-G118S-G159D | +++ |
| A016S-T022A-T033S-S101G-S103A-V104I-N116A-Y209A-A232V | +++ |
| T022A-N116L-G118R-S128I-A158E-S166D | +++ |
| T022Q-S101G-S103A-V104I-G159D-S188E-A232T-Q245R-N248D-E271T | +++ |
| S024R-T033S | +++ |
| S024R-G118R-S128I | +++ |
| T022A-S101G-S103A-V104I-G159D-S188E-A232L-Q245T-N248E-E271L | +++ |
| S024R-N062E-A158E | +++ |
| S024R-S078D-G118S-P129E | +++ |
| G020R-S024R-S078D-G118S-P129E-G159D-S188D-H249R | +++ |
| T022Q-S101G-S103A-V104I-G159D-S188E-A232V-Q245V-N248H-E271F | +++ |
| T022Q-S101G-S103A-V104I-G159D-S188E-A232V-Q245R-N248H-E271F | +++ |
| G020R-S024R-N062E-S078G-G118S-G159D | +++ |
| T022Q-S101G-S103A-V104I-G159D-S188D-A232S-Q245V-N248H-E271L | +++ |
| S024R-S078D-G118S-P129E-S188D-Q245R-N248D | +++ |
| N062E-S078G-G118S-S188D-Q245R-N248D | +++ |
| N062E-N116L-G118R-S128I-S188D | +++ |
| T022A-S101G-S103A-V104I-G159D-S188D-A232S-Q245V-N248D-E271F | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| G020R-S024R-S078D-G118S-G159D-S188D-Q245R-N248D | +++ |
| T022A-S101G-S103A-V104I-G159D-S188E-A232V-Q245T-N248D-E271T | +++ |
| T022A-S101G-S103A-V104I-G159D-S188D-A232S-Q245V-N248E-E271T | +++ |
| T022A-T033S-N116L-G118R-S188D | +++ |
| G020R-S024R-N062E-S078G-G118S-P129E-S188D-N248D | +++ |
| G020R-N062E-S078G-G118S-P129E-G159D-N248D | +++ |
| S078G-G118S-P129E-G159D-S188D-Q245R | +++ |
| N062E-S078D-G118S-G159D-H249R | +++ |
| T022A-S101G-S103A-V104I-G159D-S188E-A232T-Q245R-N248D | +++ |
| T022A-S024R-T033S-N062E-N116L | +++ |
| T022Q-S101G-S103A-V104I-G159D-S188E-A232S-Q245T-N248E-E271T | +++ |
| N062E-S078D-G118S-H249R | +++ |
| T022A-S024R-N062E-N116L-G118R-A158E | +++ |
| T022L-S078N-G118R-S166D-L217E | +++ |
| G020R-S024R-N062E-S078D-G118D-S188D-Q245R-N248D-H249R | +++ |
| T022A-S101G-S103A-V104I-G159D-S188E-A232S-Q245R-N248H-E271L | +++ |
| G020R-S024R-S078G-G118D-P129E-Q245R-N248D-H249R | +++ |
| T022A-S101G-S103A-V104I-G159D-S188E-A232T-Q245V-N248D-E271L | +++ |
| S078D-G118S-P129E-S188D-Q245R | +++ |
| S024R-S078G-G118D-G159D-S188D-Q245R-H249R | +++ |
| S078D-G118D-G159D-S188D-Q245R-H249R | +++ |
| S024F-T213A-L217E | +++ |
| S024F-T033S-S101G-S103A-V104I-N116L-S128N-Y209V-G211Q-A232V | +++ |
| T022Q-S101G-S103A-V104I-G159D-S188D-A232S-Q245T-N248D-E271H | +++ |
| T022Q-S101G-S103A-V104I-G159D-S188D-A232S-Q245T-N248E-E271T | +++ |
| T022Q-S101G-S103A-V104I-G159D-S188D-A232V-Q245R-N248H-E271H | +++ |
| G020R-S078D-G118D-P129E-G159D-Q245R-H249R | +++ |
| T022A-S101G-S103A-V104I-G159D-S188D-A232L-Q245R-N248D | +++ |
| T022A-S101G-S103A-V104I-G159D-S188D-A232L-Q245R-N248D-E271T | +++ |
| N062E-S078G-G118S-P129E-Q245R | +++ |
| S078G-G118S-S188D-Q245R-N248D-H249R | +++ |
| S101A-S103G-V104I-L148I | +++ |
| T022A-S101G-S103A-V104I-G159D-S188E-A232V-Q245R-N248H-E271F | +++ |
| T022Q-S101G-S103A-V104I-G159D-S188E-A232T-Q245V-N248H-E271H | +++ |
| T022A-N116L-G118R-A158E | +++ |
| T022A-S024F-T033S-S101G-S103A-V104I-I107V-N116L-S128N-Y209A-G211Q-T213A-A232V | +++ |
| T022Q-S101G-S103A-V104I-G159D-S188E-A232S-Q245R-N248H-E271T | +++ |
| G020R-N062E-S078D-G118D-G159D | +++ |
| G020R-N062E-S078D-G118S | +++ |
| S024R-N062E-S078D-G118D-P129E-G159D-Q245R | +++ |
| T022A-S101G-S103A-V104I-G159D-S188E-A232T-Q245V-N248E-E271T | +++ |
| T022A-S101G-S103A-V104I-G159D-S188D-A232T-Q245V-N248D-E271H | +++ |
| S078G-G118S-G159D | +++ |
| S024F-G118R-T213A-L217E | +++ |
| S024R-N062E-S078D-G118S-P129E-Q245R-N248D | +++ |
| G020R-S024R-S078D-G118S-P129E-G159D-Q245R | +++ |
| S024R-S078D-G118D-G159D-H249R | +++ |
| S024R-N076D-S101A-S103A-V104I-S188D-P210I-A232V-Q245R | +++ |
| G020R-S024R-N062E-S078D-G118D-P129E-G159D-H249R | +++ |
| G020R-S024R-N062E-S078G-G118D-S188D-N248D-H249R | +++ |
| G020R-S024R-N062E-S078G-G118S-P129E-S188D-H249R | +++ |
| T022Q-S101G-S103A-V104I-G159D-S188E-A232S-Q245V-N248D | +++ |
| T022A-S101G-S103A-V104I-G159D-S188D-A232V-Q245T-N248E-E271H | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022Q-S101G-S103A-V104I-G159D-S188D-A232V-Q245V-N248D-E271T | +++ |
| G020R-S024R-S078D-G118D-P129E-G159D-N248D-H249R | +++ |
| G020R-S024R-N062E-S078D-G118S-P129E-G159D-N248D | +++ |
| N062E-S078G-G118D-P129E-H249R | +++ |
| G020K-T022L-S078N-G118R-T213A-L217E | +++ |
| G020R-S024R-N062E-S078G-G118D-P129E-S188D-H249R | +++ |
| T022A-S024R-T033S-N116L-S166D-S188D | +++ |
| S024R-S078G-G118D-G159D-S188D-H249R | +++ |
| T033S-N116L-G118R-A158E-S188D | +++ |
| T022A-S101G-S103A-V104I-G159D-S188E-A232V-Q245V-N248H | +++ |
| S101A-S103A-V104I-S188D-P210I-A232V-Q245R | +++ |
| G020R-S024R-N062E-S078G-G118D-S188D-Q245R | +++ |
| T022A-S024R-T033S-N062E-N116L-G118R-P129E-S188D | +++ |
| T022A-S101G-S103A-V104I-G159D-S188E-A232S-Q245T-N248E | +++ |
| S024R-S078G-G118S | +++ |
| N062E-S101A-S103A-V104I-P210I-A232V-Q245R | +++ |
| N062E-S078G-G118D-G159D | +++ |
| T022A-S024R-N062E-N116L-G118R-S128I-S166D-S188D | +++ |
| S024R-S078D-G118D-G159D-Q245R | +++ |
| G020R-N062E-S078G-G118S-G159D-S188D-N248D-H249R | +++ |
| T022Q-S101G-S103A-V104I-G159D-S188E-A232S-Q245R-N248E-E271H | +++ |
| T022Q-S101G-S103A-V104I-G159D-S188D-A232T-V244I-Q245R-N248H-E271L | +++ |
| S024R-S078G-G118S-P129E-G159D-N248D | +++ |
| S024R-N062E-S078G-G118S-G159D-H249R | +++ |
| T022A-S024F-T033S-S101G-S103A-V104I-N116L-Y209V-G211Q-A232V | +++ |
| A016S-S101G-S103A-V104I-N116A-S128N-Y209V-G211Q-T213A-A232V | +++ |
| G020R-N062E-S078G-G118D-S188D | +++ |
| T022A-S101G-S103A-V104I-G159D-S188E-A232S-Q245V-N248E-E271H | +++ |
| T022A-S101G-S103A-V104I-G159D-S188D-A232V-Q245V-N248E-E271L | +++ |
| G020K-S166D-L217E | +++ |
| T022A-S101G-S103A-V104I-G159D-S188D-A232S-Q245T-N248E-E271T | +++ |
| G020R-N062E-S078G-G118D-Q245R | +++ |
| S024R-N062E-S078D-G118S-P129E-S188D-Q245R-N248D | +++ |
| A016S-T022A-S024F-S101G-S103A-V104I-N116A-S128N-Y209A-G211Q-A232V | +++ |
| S024F-T033S-S101G-S103A-V104I-N116L-Y209A-A232V | +++ |
| T033S-G118R-S188D | +++ |
| T022A-S101G-S103A-V104I-G159D-S188D-A232S-Q245T-N248E-E271H | +++ |
| T022Q-S101G-S103A-V104I-G159D-S188D-A232S-Q245T-N248D-E271T | +++ |
| G020R-S024R-S078G-G118S-P129E-G159D-S188D-N248D | +++ |
| T022Q-S101G-S103A-V104I-G159D-S188D-A232V-Q245T-N248H-E271F | +++ |
| G020R-S078G-G118D-P129E-S188D-Q245R | +++ |
| G020R-S078G-G118D-G159D-S188D-Q245R-N248D | +++ |
| S024R-S078G-G118D-P129E-N248D-H249R | +++ |
| G020R-S024R-S078D-G118D-P129E | +++ |
| N062E-S078D-G118S-S188D-Q245R | +++ |
| G020R-S024R-S078G-G118S-G159D-S188D | +++ |
| T022Q-S101G-S103A-V104I-G159D-S188D-A232T-Q245V-N248H-E271L | +++ |
| T022A-S101G-S103A-V104I-G159D-S188E-A232T-Q245R-N248D-E271L | +++ |
| N062E-S078G-G118S-G159D-H249R | +++ |
| G020R-S078D-G118S-P129E-G159D-N248D | +++ |
| G020R-S024R-S078D-G118S-G159D-S188D-Q245R | +++ |
| G020R-N062E-S078G-G118D-P129E-S188D-Q245R-N248D | +++ |
| T022Q-S101G-S103A-V104I-G159D-S188D-A232L-Q245R-N248H | +++ |
| G020R-S024R-S078G-G118S-G159D-V244L-Q245R-N248D | +++ |
| G020R-S024R-S078G-G118D-P129E-S188D-Q245R-N248D-H249R | +++ |
| T022A-S024F-T033S-S101G-S103A-V104I-N116A-Y209A-A232V | +++ |
| G020R-S024R-N062E-S078D-G118S-P129E-G159D-A272D | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| N116L-G118R-S128I-A158E-S166D | +++ |
| S024R-S078D-G118S-P129E-H249R | +++ |
| S024R-N062E-S078G-G118S-P129E-N248D | +++ |
| G020R-S078G-G118S-P129E-G159D-S188D | +++ |
| G020R-S024R-S078D-G118S-G159D-N248D-H249R | +++ |
| S024R-S078D-G118D-G159D-S188D-Q245R-N248D-H249R | +++ |
| T033S-S101G-S103A-V104I-N116L-Y209A-G211Q-T213A-A232V | +++ |
| T033S-S101G-S103A-V104I-N116A-Y209A-T213A-A232V | +++ |
| T022A-S101G-S103A-V104I-G159D-S188E-A232S-Q245V-N248H | +++ |
| N062E-S078G-G118S-N248D-H249R | +++ |
| G020R-N062E-S078D-G118D-G159D-S188D-Q245R | +++ |
| T022A-S024F-S101G-S103A-V104I-N116A-Y209A-T213A-A232V | +++ |
| N043F-S101G-S103A-V104I-G159D-S188D-A232V-Q245R-N248D-E271F | +++ |
| S024R-S078G-G118D-P129E-G159D | +++ |
| G020R-N062E-S078G-G118D-G159D-Q245R-N248D | +++ |
| S024R-S166D | +++ |
| S024R-S078G-G118S-P129E-N248D | +++ |
| A016S | +++ |
| N076D-S101A-S103A-V104I-S188D-P210I-A232V-Q245R | +++ |
| G020K-L217E | +++ |
| G118S-S166D-S188D | +++ |
| S024R-S078D-G118S-G159D-S188D | +++ |
| S024R-S078D-G118S-P129E-S188D-Q245R | +++ |
| A016S-S101G-S103A-V104I-N116A-S128N-Y209A-T213A-A232V | +++ |
| N116L-S166D | +++ |
| S024R-N062E-S078G-G118D-P129E-G159D-S188D-Q245R | +++ |
| G020R-S024R-S078D-G118D-P129E-N248D-H249R | +++ |
| N062E-S078G-G118S-G159D-S188D-Q245R | +++ |
| T022A-S101G-S103A-V104I-G159D-S188D-A232L-Q245V-N248E-E271H | +++ |
| S024R-N062E-S078G-G118S-P129E-H249R | +++ |
| G118R-S166D-T213A | +++ |
| G020R-S024R-N062E-S078G-G118S-P129E-G159D | +++ |
| G020R-S024R-S078D-G115W-G118D-G159D-N248D | +++ |
| A016S-S024F-S101G-S103A-V104I-N116A-Y209A-A232V | +++ |
| S024R-N062E-N116L-S128I-A158E | +++ |
| T022Q-S101G-S103A-V104I-G159D-S188E-A232V-Q245V-N248D-E271L | +++ |
| S024R-N062E-S078G-G118S-P129E-H249R | +++ |
| S024R-N062E-S078D-G118D-P129E-N248D-H249R | +++ |
| G020K-T022L-S024F-S078N-G118R-L217E | +++ |
| S101G-G102A-S103A | +++ |
| G020R-S078G-G118S-P129E-Q245R-N248D | +++ |
| G020K-S078N-S166D | +++ |
| T022A-G118R-A158E | +++ |
| G020K-T022L-S024F-S078N-S166D | +++ |
| T022A-T033S-N062E-N116L-G118R-A158E-S188D | +++ |
| S024R-S078G-G118S-P129E-G159D-H249R | +++ |
| S101G-S103A-V104I-N116L-Y209V-G211Q-A232V | +++ |
| A015D-A016S-S101G-S103A-V104I-N116L-S128N-Y209V-T213A-A232V | +++ |
| G020R-N062E-S078D-G118D-P129E-S188D-H249R | +++ |
| G020K-S024F-S078N-S128D | +++ |
| T033S-N116L-S166D-S188D | +++ |
| G020R-S078G-G118S-P129E-G159D | +++ |
| T022A-S024R-T033S-L082I-G118R-S128I-A158E-S188D | +++ |
| G020R-S024R-S078D-G118S-S188D-N248D | +++ |
| G020R-S078G-G118D-P129E-S188D-Q245R-H249R | +++ |
| N062E-S078G-G118D-Q245R | +++ |
| G020K-T022L-S078N-L217E | +++ |
| T022A-S101G-S103A-V104I-G159D-S188D-A232T-Q245V-N248E-E271L | +++ |
| T022Q-S101G-S103A-V104I-G159D-S188D-A232S-Q245V-N248E-E271H | +++ |
| T022Q-S101G-S103A-V104I-G159D-S188E-A232T-Q245T-N248E-E271T | +++ |
| A016S-T033S-S101G-S103A-V104I-N116L-Y209V-G211Q-T213A-A232V | +++ |
| T022Q-S101G-S103A-V104I-G159D-S188E-A232L-Q245K-N248H | +++ |
| N062E-S078G-G118D-Q245R | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S024R-G118R-A158E-S166D | +++ |
| A016S-S101A-S103A-S128N-L148I | +++ |
| T022A-S101G-S103A-V104I-G159D-S188D-A232S-Q245R-N248E | +++ |
| S024R-N062E-S078G-G118D | +++ |
| S024R-N062E-S078G-G118S-P129E-G159D-S188D | +++ |
| S078G-G118D-P129E-G159D-S188D-Q245R-N248D-H249R | +++ |
| G020R-S078D-G118D-P129E-G159D-Q245R | +++ |
| T022A-S101G-S103A-V104I-G159D-S188D-A232S-Q245V-N248H | +++ |
| T022Q-S101G-S103A-V104I-G159D-S188D-A232V-Q245R-N248D-E271H | +++ |
| G020R-S024R-N062E-S078G-G118D-H249R | +++ |
| S078D-G118S-P129E-G159D-H249R | +++ |
| T022Q-S101G-S103A-V104I-G159D-S188E-A232S-Q245T-N248D-E271H | +++ |
| S024R-S078D-G118D-P129E-G159D-S188D-Q245R | +++ |
| T022L-T213A-L217E | +++ |
| G020R-N062E-S078G-G118S-P129E-G159D-S188D-N248D-H249R | +++ |
| T022Q-S101G-S103A-V104I-G159D-S188D-A232T-Q245R-N248H-E271T | +++ |
| G020R-N062E-S078G-G118D-Q245R | +++ |
| G020R-S024R-N062E-S078G-G118D-N248D-H249R | +++ |
| T022A-S101G-S103A-V104I-G159D-S188D-A232V-Q245R-N248H-E271T | +++ |
| S024R-S078D-G118D-P129E-H249R | +++ |
| S024R-N062E-N116L-G118R-S188D | +++ |
| S024R-N062E-G118R | +++ |
| T022A-S101G-S103A-V104I-G159D-S188D-A232V-Q245R-N248E | +++ |
| G020R-S024R-S078G-G118S-P129E-G159D-S188D-H249R | +++ |
| T022A-S101G-S103A-V104I-G159D-S188E-A232L-Q245R-N248H | +++ |
| S024R-S078D-G118S-P129E-G159D-N248D | +++ |
| T022Q-S101G-S103A-V104I-G159D-S188D-A232L-Q245V-N248D-E271T | +++ |
| G020R-S078G-G118D-P129E-Q245R-N248D-H249R | +++ |
| G020R-S024R-N062E-S078G-G118D-P129E-S188D-Q245R-N248D | +++ |
| A016S-S024F-T033S-S101G-S103A-V104I-N116L-Y209V-A232V | +++ |
| G097P-A098Q-S099G-V104L | +++ |
| T022A-S101G-S103A-V104I-G159D-S188D-A232S-Q245T-N248D-E271F | +++ |
| G020R-S024R-N062E-S078G-G118S-N248D | +++ |
| A016S-S103A-S128N | +++ |
| S024R-S078G-G118D-P129E-Q245R | +++ |
| S078D-G118D-P129E-S188D-H249R | +++ |
| T022A-S024R-T033S-N062E-N116L-A158E | +++ |
| A016S-T022A-S101G-S103A-V104I-N116A-S128N-Y209V-T213A-A232V | +++ |
| S024R-S078G-G118S-G159D-S188D-Q245R | +++ |
| T033S-N062E-N116L-G118R-A158E-S188D | +++ |
| G020R-S024R-N062E-S078D-G118S-G159D-Q245R-A272V | +++ |
| G118R-S128I-A158E-S166D | +++ |
| G020K-T022L-S024F-S078N-S166D-D181E-L217E | +++ |
| N062E-G118R-S188D | +++ |
| S024F-S101G-S103A-V104I-N116L-S128N-Y209A-T213A-A232V | +++ |
| G020R-S078D-G118D-G159D-S188D-Q245R | +++ |
| S024R-N062E-S078G-G118D-P129E-N248D-H249R | +++ |
| G020R-S024R-N062E-S078G-G118D-N248D | +++ |
| T022A-V068A-S101G-S103A-V104I-G159D-S188D-T213A-A232V-Q245R-N248D-E271F | +++ |
| G020R-N062E-S078D-G118S-P129E-G159D-S188D-Q245R | +++ |
| S024R-S078G-G118S-P129E-N248D-H249R | +++ |
| T022Q-S101G-S103A-V104I-G159D-S188D-A232V-Q245R-N248H-E271L | +++ |
| T033S-N116L-G118R-S188D | +++ |
| N062E-S078G-G118S-S188D-N248D-H249R | +++ |
| A016S-T022A-S101G-S103A-V104I-S128N-L148I | +++ |
| G020R-S078G-G118S-S188D-N248D-H249R | +++ |
| G020R-S024R-S078D-G118D-P129E-G159D-Q245R-N248D | +++ |
| S024F-T033S-S101G-S103A-V104I-N116L-Y209A-T213A-A232V | +++ |
| S024R-N062E-G118R-S128I-A158E | +++ |
| G020R-S024R-S078D-G118S-G159D-S188D | +++ |
| S024R-N062E-S078G-G118D-G159D-Q245R-N248D-H249R | +++ |
| N062E-G118R-A158E-S166D | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| G020R-S024R-S078D-G118S-P129E-S188D | +++ |
| S078G-G118D-G159D | +++ |
| G020R-S024R-S078D-G118D-P129E-G159D-S188D-Q245R-N248D | +++ |
| G020R-S078G-G118D-S188D-N248D | +++ |
| G020K-T022L-S078G-G118D-G159D-N248D-H249R | +++ |
| S103G-L148I-M175T | +++ |
| G020R-S024R-S078G-G118S-P129E-Q245R-N248D | +++ |
| T022A-S101G-S103A-V104I-G159D-S188D-A232S-Q245R-N248D-H249R-E271F | +++ |
| T022A-S024F-S101G-S103A-V104I-N116A-S128N-Y209A-G211Q-T213A-A232V | +++ |
| A016S-T033S-S101G-S103A-V104I-N116A-Y209A-G211Q-A232V | +++ |
| T022A-S024R-N062E-S166D | +++ |
| G020R-S078D-G118S-G159D-S188D-Q245R-N248D-H249R | +++ |
| T022A-S024F-S101G-S103A-V104I-N116A-S128N-Y209V-A232V | +++ |
| T022A-S024R-N062E-N116L-A158E-S188D | +++ |
| T022Q-S101G-S103A-V104I-G159D-S188E-A232S-Q245T-N248E-E271L | +++ |
| S024R-T033S-N116L-G118R-A158E-S188D | +++ |
| T022Q-S101G-S103A-V104I-G159D-S188D-A232S-Q245V-N248H-E271H | +++ |
| G020R-N062E-S078D-G118S-G159D-N248D | +++ |
| T022A-S024R-N116L-G118R-A158E | +++ |
| G020K-T022L-S024F-G118R-L217E | +++ |
| S024R-S078D-G118S-G159D-S188D-N248D-H249R | +++ |
| G020R-S024R-N062E-S078G-G118D-P129E-S188D-N248D | +++ |
| T022Q-S101G-S103A-V104I-G159D-S188D-A232V-Q245R-N248D-E271L | +++ |
| G020R-S024R-N062E-S078D-G118S-P129E-G159D-S188D-N248D-H249R | +++ |
| N062E-G118R-S166D | +++ |
| T022Q-S101G-S103A-V104I-G159D-S188D-A232S-Q245R-N248D | +++ |
| G020R-N062E-S078D-G118S-P129E-G159D-N248D-H249R | +++ |
| T022A-S101G-S103A-V104I-G159D-S188D-A232T-Q245V-N248H-E271T | +++ |
| T022L-S024F-G118R-S166D | +++ |
| T022Q-S101G-S103A-V104I-G159D-S188D-A232V-Q245R-N248D | +++ |
| G020K-S024F-S166D-T213A-L217E | +++ |
| N062E-S078G-G118S-G159D-S188D | +++ |
| S024R-N062E-S078G-G118D-Q245R-N248D | +++ |
| G020K-T022L-S024F-S078N-T213A-L217E | +++ |
| T022A-V068A-S101G-S103A-V104I-N116L-G159D-S188D-T213A-A232V-Q245R-N248D-E271F | +++ |
| N062E-S078G-G118S-P129E-G159D | +++ |
| G020R-S024R-N062E-S078G-G118S-G159D-H249R | +++ |
| G020K-T022L-S024F-S078N-G118R-S166D-T213A-L217E | +++ |
| T022A-N062E-N116L-A158E | +++ |
| T022Q-S101G-S103A-V104I-G159D-S188D-A232T-Q245V-N248E-E271L | +++ |
| T022A-S024R-N062E-S128I-S166D | +++ |
| S024R-S078G-G118D-G159D-Q245R-N248D-H249R | +++ |
| G020R-S024R-N062E-S078G-G118S-P129E-G159D-H249R | +++ |
| G020R-S078G-G118D-S188D-Q245R-N248D | +++ |
| G020R-S024R-N062E-S078G-G118D-P129E-S188D-Q245R-N248D-H249R | +++ |
| S024R-S078G-G118S-G159D-Q245R | +++ |
| T022A-S024R-N062E-G118R-S128I-A158E | +++ |
| G020R-S078D-G118S-P129E-G159D-S188D-Q245R | +++ |
| S024R-S078G-G118S-Q245R-N248D-H249R | +++ |
| G118R-A158E-S188D | +++ |
| G020K-S024F-G118R-S166D-L217E | +++ |
| G020K-S024F-S078N-G118R-T213A-L217E | +++ |
| T022A-S101G-S103A-V104I-G159D-S188E-A232S-Q245V-N248D-E271L | +++ |
| T022A-S101G-S103A-V104I-G159D-S188D-A232S-Q245V-N248D | +++ |
| S024R-N062E-S078G-G118S-H249R | +++ |
| G020R-S024R-S078G-G118S-G159D-S188D-Q245R-N248D-H249R | +++ |
| A016S-S024F-S101G-S103A-V104I-N116L-S128N-Y209V-A232V | +++ |
| T033S-A158E-S166D | +++ |
| S024R-S078G-G118S-S188D-N248D-H249R | +++ |
| S024R-N062E-S078G-G118S-S188D-Q245R-N248D | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| N062E-S078G-G118D-G159D-Q245R-N248D | +++ |
| N062E-S078G-G118D-S188D-Q245R-N248D-H249R | +++ |
| S024R-N116L-G118R-S128I-A158E-S166D | +++ |
| G020R-N062E-S078D-G118S-P129E-G159D-Q245R-N248D | +++ |
| S024R-N062E-S101A-S103A-V104I-S188D-P210I-A232V-Q245R | +++ |
| N062E-S078D-G118S-P129E-H249R | +++ |
| S024R-S078G-G118S-P129E-G159D-S188D | +++ |
| A016S-S101G-S103A-V104I-N116A-S128N-Y209V-T213A-A232V | +++ |
| G020K-T022L-S024F-S078N-S166D-T213A-L217E | +++ |
| G020R-S024R-N062E-S078D-G118D-S188D-N248D | +++ |
| G020R-S024R-N062E-S078G-G118S-G159D-A272D | +++ |
| T022A-S024R-A158E | +++ |
| G020R-S078G-G118S-G159D-N248D | +++ |
| T022A-S101G-S103A-V104I-G159D-S188E-A232V-Q245V-N248E-E271T | +++ |
| S101G-S103A-V104I-N116A-Y209A-G211Q-T213A-A232V | +++ |
| G020K-T022L-S024F-S166D-L217E | +++ |
| G020R-S024R-S078D-G118S-Q245R | +++ |
| G020R-S078D-G118D-P129E-S188D-Q245R | +++ |
| G020R-S024R-N062E-S078G-G118S-S188D-Q245R-N248D | +++ |
| G020R-S024R-S078D-G118D-G159D-N248D | +++ |
| T022A-S101G-S103A-V104I-G159D-S188D-A232S-Q245T-N248H | +++ |
| G020R-S024R-S078D-G118S-S188D-Q245R | +++ |
| G020R-N062E-S078D-G118D-S188D-Q245R | +++ |
| G020R-S024R-S078D-G118D-G159D-S188D-Q245R-H249R | +++ |
| T022A-S128I-A158E-S188D | +++ |
| A016S-S024F-S101G-S103A-V104I-N116A-S128N-Y209V-T213A-A232V-V244G | +++ |
| T022L-S078N-T213A-L217E | +++ |
| S078D-G118S-P129E-H249R | +++ |
| G020K-T022L-S024F-S078N-G118R-T213A-L217E | +++ |
| N062E-S078D-G118S-G159D-Q245R | +++ |
| G020K-S024F-S166D | +++ |
| S024R-N062E-S078G-G118D-Q245R-N248D-H249R | +++ |
| G020K-S024F-S078N-G118R-L2l7E | +++ |
| T022L-S024F-S078N-G118R-S166D-L217E | +++ |
| T022A-S024R-T033S-A158E-S188D | +++ |
| T022Q-S101G-S103A-V104I-G159D-S188D-A232L-Q245T-N248D-E271H | +++ |
| S087R | +++ |
| T022A-S101G-S103A-V104I-G159D-S188E-A232T-Q245V-N248H | +++ |
| G020R-S078G-G118D-P129E-G159D-Q245R-N248D-H249R | +++ |
| S078G-G118S-P129E-G159D-Q245R-N248D | +++ |
| S024R-S078D-G118D-P129E-G159D-Q245R-N248D-H249R | +++ |
| G020R-S078G-G118S-P129E | +++ |
| S024R-N116L-G118R-S166D-S188D | +++ |
| G020R-S024R-S078G-G118S-P129E-G159D-Q245R | +++ |
| T022A-S101G-S103G-V104I | +++ |
| G020R-S024R-N062E-S078D-G118D-P129E-G159D | +++ |
| G020R-S024R-N062E-S078D-G118D-P129E-Q245R-N248D-H249R | +++ |
| T022A-S024R-N062E-N116L-G118R-S188D | +++ |
| T022Q-S101G-S103A-V104I-G159D-S188E-A232L-Q245T-N248E-E271L | +++ |
| A016S-S101G-S103A-V104I-N116L-M119V-Y209V-G211Q-A232V | +++ |
| G020R-S024R-N062E-S078G-G118D | +++ |
| T022Q-S101G-S103A-V104I-G159D-S188E-A232V-Q245T-N248H-E271L | +++ |
| T022A-S101G-S103A-V104I-G159D-S188D-A232S-Q245T-N248D-E271T | +++ |
| T033S-S101G-S103A-V104I-N116L-Y209A-G211Q-A232V | +++ |
| G020R-S024R-N062E-S078D-G118S-P129E-G159D-N248D-H249R | +++ |
| G020R-S078G-G118S-P129E-N248D-H249R | +++ |
| G020K-T022L-G118R-S128D | +++ |
| T022Q-S101G-S103A-V104I-G159D-S188D-A232L-Q245V-N248D-E271L | +++ |
| G020R-S024R-S078D-G118S-G159D-S188D-N248D-H249R | +++ |
| S101G-S103A-V104I-N116L-Y209A-T213A-A232V | +++ |
| T022A-S101G-S103A-V104I-G159D-S188D-A232L-Q245T-N248E-E271T | +++ |
| S024R-N062E-S078D-G118D-G159D-Q245R-N248D-H249R | +++ |
| G020K-S024F-T213A-L217E | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| G118R-S128I-S188D | +++ |
| G020R-S078G-G118S-P129E-H249R | +++ |
| T022A-N062E-G118R-S188D | +++ |
| S024R-S078G-G118S-P129E-G159D-Q245R | +++ |
| T022A-S024F-S101G-S103A-V104I-N116L-Y209A-G211Q-T213A-A232V | +++ |
| T022A-S024R-N116L-A158E-S166D | +++ |
| T022A-S101G-S103A-V104I-G159D-S188D-A232L-Q245T-N248H-E271T | +++ |
| T022Q-S101G-S103A-V104I-G159D-S188D-A232L-Q245T-N248H-E271L | +++ |
| S024R-N062E-A158E-S188D | +++ |
| G020K-S024F-G118R-S166D-T213A-L217E | +++ |
| T022A-S101G-S103A-V104I-G159D-S188E-A232S-Q245T-N248H-E271T | +++ |
| S078D-G118D-P129E-G159D-Q245R | +++ |
| S101A-S103A-V104I-S188D-A232V-Q245R | +++ |
| N062E-N116L-G118R-A158E | +++ |
| T022A-T033S-S101G-S103A-V104I-N116L-Y209A-T213A-A232V | +++ |
| T022L-S024F-G118R-S128D-T213A | +++ |
| A016S-S024F-S101G-S103A-V104I-N116L-S128N-Y209A-A232V | +++ |
| S078D-G118S-G159D-S188D-N248D-H249R | +++ |
| G020R-S078G-G118S-P129E-S188D | +++ |
| T022A-T033S-N116L-S166D | +++ |
| S024R-N062E-G118R-S188D | +++ |
| S024R-T033S-N116L-G118R-S128I-A158E | +++ |
| S101A-S103A-V104I-P210I-A232V-Q245R | +++ |
| G020R-S024R-N062E-S078G-G118S-S188D-H249R | +++ |
| T022A-S024R-N116L-G118R-S128I-A158E-S166D-S188D | +++ |
| A016S-S024F-S101G-S103A-V104I-N116L-Y209V-G211Q-T213A-A232V | +++ |
| T022A-S101G-S103A-V104I-G159D-S188E-A232S-Q245V-N248D-E271H | +++ |
| S078G-G118S-G159D-S188D-N248D-H249R | +++ |
| S024R-S078D-G118D-P129E-G159D-S188D-H249R | +++ |
| T022Q-S101G-S103A-V104I-G159D-S188D-A232L-Q245T-N248E-E271F | +++ |
| G020R-N062E-S078D-G118D | +++ |
| S024R-T033S-N116L-G118R-S128I-A158E-S188D | +++ |
| T033S-N062E-N116L-G118R-S188D | +++ |
| T022A-T033S-N116L-G118R-A158E-S188D | +++ |
| S078N-G118R-S166D | +++ |
| T022Q-S101G-S103A-V104I-G159D-S188E-A232V-Q245T-N248E-E271L | +++ |
| T022Q-S101G-S103A-V104I-G159D-S188E-A232L-Q245T-N248H-E271L | +++ |
| S024F-S101G-S103A-V104I-N116A-Y209A-G211Q-T213A-A232V | +++ |
| G020R-S024R-S078D-G118D-G159D-S188D-Q245R-N248D | +++ |
| T022A-S101G-S103A-V104I-N116L-G159D-S188D-T213A-A232V-Q245R-N248D-E271F | +++ |
| T022A-G118R-A158E-S188D | +++ |
| S024R-S078D-G118S-G159D-H249R | +++ |
| S101G-S103A-V104I-N116L-Y209A-G211Q-A232V | +++ |
| T022A-S101G-S103A-V104I-G159D-S188E-A232S-Q245V-N248E-E271F | +++ |
| S024R-N062E-S078D-G118S-P129E-Q245R | +++ |
| G020K-S024F-S078N-T213A-L217E | +++ |
| G020R-S024R-S078G-G118D-P129E-G159D-H249R | +++ |
| G020R-S024R-S078D-G118S-G159D-S188D-N248D | +++ |
| T022A-S101G-S103A-V104I-G118R-G159D-S188D-A232V-Q245R-N248D-E271F | +++ |
| G020R-S078G-G118S-S188D-Q245R-N248D | +++ |
| G020R-S024R-N062E-S078G-G118D-P129E-S188D-N248D-H249R | +++ |
| G020R-S078D-G118S-P129E-G159D-S188D-Q245R-N248D | +++ |
| T022A-S101G-S103A-V104I-G159D-S188E-A232T-Q245V-N248D-E271T | +++ |
| T022A-S101G-S103A-V104I-G159D-S188E-A232V-Q245T-N248H | +++ |
| S024R-S078D-G118S-P129E-G159D-S188D-Q245R-N248D | +++ |
| S101G-S103A-L148I | +++ |
| T022A-S101G-S103A-V104I-G159D-S188E-A232S-Q245T-N248D-E271L | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S101G-S103A-V104I-G159D-S188D-A232T-Q245T-N248D-S265G-E271L | +++ |
| V104I-L111V-L148I | +++ |
| T022A-G118R-S128I | +++ |
| G020R-S024R-S078G-G118D-P129E-G159D-N248D | +++ |
| G020K-T022L-G118R-S166D-T213A-L217E | +++ |
| G020R-S078D-G118D-P129E-Q245R-N248D | +++ |
| G097P-S099A-S101A-S103A | +++ |
| N062E-S078G-G118S-P129E-G159D-Q245R-N248D-H249R | +++ |
| A016S-V104L-L111V | +++ |
| T022Q-S101G-S103A-V104I-G159D-S188E-A232T-Q245V-N248D-E271T | +++ |
| N062E-S078G-G118D-P129E-Q245R-N248D | +++ |
| T022Q-S101G-S103A-V104I-G159D-S188E-A232L-Q245V-N248E | +++ |
| T022A-S024R-T033S-G118R-A158E-S188D | +++ |
| S078N-G118R-T213A-L217E | +++ |
| T022A-S024F-S101G-S103A-V104I-N116L-Y209A-G211Q-A232V | +++ |
| G020R-S024R-S078G-G118D-S188D-Q245R-H249R | +++ |
| T022A-S101G-S103A-V104I-N116L-S128L-G159D-S188D-A232V-Q245R-N248D-E271F | +++ |
| G020K-T022L-S078N-G118R-S128D-L217E | +++ |
| T022Q-S101G-S103A-V104I-G159D-S188E-A232V-Q245R-N248H-E271T | +++ |
| T022A-S024R-T033S-N116L-A158E-S188D | +++ |
| S024R-N062E-S128I-S188D | +++ |
| S024R-S078G-G118S-S188D | +++ |
| T022Q-S101G-S103A-V104I-G159D-S188E-A232V-Q245T-N248D-E271L | +++ |
| G020K-S024F-G118R-T213A-L217E | +++ |
| T022A-S024R-S101G-S103A-V104I-P129E-G159D-S188D-A232V-Q245R-N248D-A270V-E271F-A272V | +++ |
| S103A-V104I-L111V-L148I | +++ |
| T022A-S024F-T033S-S101G-S103A-V104I-N116L-Y209V-G211Q-T213A-A232V | +++ |
| T022A-S101G-S103A-V104I-G159D-S188D-A232S-Q245V-N248H-E271T | +++ |
| S078D-G118D-G159D-Q245R | +++ |
| G020K-T022L-S078D-G118D-P129E-G159D-Q245R-H249R | +++ |
| A016S-T022A-T033S-S101G-S103A-V104I-N116A-Y209V-G211Q-T213A-A232V | +++ |
| T022A-S024R-T033S-S166D | +++ |
| S024R-S078D-G118D-G159D-S188D-N248D-H249R | +++ |
| A016S-S024F-S101G-S103A-V104I-N116L-Y209A-T213A-A232V | +++ |
| S024R-T033S-A158E | +++ |
| G020R-S024R-N062E-S078G-G118D-G159D-S188D-Q245R-N248D-H249R | +++ |
| T022Q-S101G-S103A-V104I-G159D-S188D-A232V-Q245T-N248D-E271T | +++ |
| G020R-N062E-S078D-G118D-S188D-Q245R-N248D | +++ |
| S078G-G118D-S188D-Q245R | +++ |
| T022Q-S101G-S103A-V104I-G159D-S188D-A232V-Q245T-N248D-E271L | +++ |
| G020R-S024R-N062E-S078G-G118D-P129E-G159D-S188D-N248D | +++ |
| S024R-N116L-S128I-S166D | +++ |
| S024R-S078D-G118D-G159D-Q245R-N248D | +++ |
| A016S-T022A-S024F-S101G-S103A-V104I-N116L-S128N-Y209A-G211Q-T213A-A232V | +++ |
| S078G-G118D-P129E-G159D-Q245V-N248E-E271F | +++ |
| G020K-S024F-S078N-G118R-S128D-T213A-L217E | +++ |
| T022L-S024F-T213A-L217E | +++ |
| T022A-S024F-S101G-S103A-V104I-N116L-G118V-Y209A-A232V | +++ |
| N062E-S101A-S103A-V104I-S188D-A232V-Q245R | +++ |
| T022A-N062E-A158E | +++ |
| S024R-T033S-S128I-A158E-S188D | +++ |
| S024R-S078D-G118S-S188D-Q245R | +++ |
| T022Q-S101G-S103A-V104I-G159D-S188E-A232L-Q245R-N248D | +++ |
| G020R-S024R-S078G-G118D-G159D-S188D-H249R | +++ |
| S024R-S078G-G118D-P129E-G159D-Q245R-H249R | +++ |
| S024R-N062E-S078G-G118D-P129E-G159D-S188D-N248D-H249R | +++ |
| S024R-T033S-A158E-S188D | +++ |
| T022A-S101G-S103A-V104I-L148I | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| N116L-G118R-S128I-S166D | +++ |
| S024R-N062E-S078D-G118S-S188D-N248D | +++ |
| S078G-G118S-P129E-H249R | +++ |
| S101A-S103A-V104I-S188D-P210I-Q245R | +++ |
| T022A-S101G-S103A-V104I-N116L-G118V-Y209V-T213A-A232V | +++ |
| G020K-T022L-S024F-S078N-G118R-S166D | +++ |
| T022A-G118R-S128I-S188D | +++ |
| G020R-N062E-S078G-G118S-N248D | +++ |
| G020R-S078D-G118D-S188D-H249R | +++ |
| N062E-S078G-G118D | +++ |
| G020K-T022L-G118R-S166D-T213A | +++ |
| G061E-S101G-S103A-V104I-N116A-Y209V-G211Q-T213A-A232V | +++ |
| T022A-S101G-S103A-V104I-G159D-S188E-A232S-Q245V-N248E-E271L | +++ |
| T022A-S024F-T033S-S101G-S103A-V104I-N116A-Y209V-T213A-A232V | +++ |
| T022A-S024R-N076D-S101G-S103A-V104I-G159D-S188D-A232V-Q245R-N248D-N269D-A270V-E271F-A272V | +++ |
| T022A-V068A-S101G-S103A-V104I-G159D-S188D-A232V-Q245R-N248D-E271F | +++ |
| T022A-S101G-S103A-V104I-G159D-S188E-A232L-Q245T-N248E-E271T | +++ |
| S078G-G118S-P129E-S188D-N248D-H249R | +++ |
| G020K-T022L-S166D-L217E | +++ |
| T213A-L217E | +++ |
| T022A-S101G-S103A-V104I-G159D-S188D-A232S-Q245V-N248D-E271T | +++ |
| T022A-S101G-S103A-V104I-G159D-S188D-A232S-Q245R-N248D | +++ |
| T022A-S101G-S103A-V104I-G159D-S188E-A232L-Q245V-N248H | +++ |
| G020R-S078D-G118S-G159D-Q245R-N248D-H249R | +++ |
| S024F-S101G-S103A-V104I-N116A-Y209V-A232V | +++ |
| T022L-S024F-G118R-S166D-L217E | +++ |
| S024R-T033S-S188D | +++ |
| G020R-N062E-S078G-G118D-G159D-S188D-H249R-A272D | +++ |
| T033S-A158E-S188D | +++ |
| S101G-S103A-V104I-N116L-S128N-Y209A-G211Q-A232V | +++ |
| T022Q-S101G-S103A-V104I-G159D-S188D-A232V-Q245T-N248E | +++ |
| G020R-S078D-G118D-G159D-Q245R | +++ |
| A016S-S024F-T033S-S101G-S103A-V104I-N116L-Y209V-G211Q-A232V | +++ |
| N062E-S078D-G118S-S188D | +++ |
| G020R-S024R-S078D-G118S-P129E-S188D-Q245R | +++ |
| A016S-S101G-S128N-L148I | +++ |
| G118R-S128I-S166D-S188D | +++ |
| N062E-S078D-G118D-P129E-G159D-H249R | +++ |
| T022A-T033S-N062E-N116L | +++ |
| N062E-S078G-G118D-P129E-Q245R | +++ |
| T022A-S024F-T033S-S101G-S103A-V104I-N116L-Y209V-T213A-A232V | +++ |
| T022A-S101G-S103A-V104I-G159D-S188D-A232T-Q245T-N248E-E271L | +++ |
| S078G-G118S-S188D-H249R | +++ |
| S024R-N062E-S078D-G118S-H249R | +++ |
| S078G-G118S-P129E-S188D-N248D | +++ |
| S101G-S103A-V104I-N116L-S128N-Y209V-T213A-A232V | +++ |
| T022A-S024R-N062E-N116L-G118R-A158E-S188D | +++ |
| G020K-S024F-S078N-S166D-L217E | +++ |
| S024R-S078G-G118S-P129E-H249R | +++ |
| T022A-S024R-S128I-A158E-S166D | +++ |
| S101G-S103A-V104I-N116L-Y209V-G211Q-T213A-A232V | +++ |
| T022A-S024F-T033S-S101G-S103A-V104I-N116L-Y209A-G211Q-A232V | +++ |
| G020R-S078D-G118D-P129E-G159D-S188D-Q245R | +++ |
| N062E-S078G-G118S-P129E-G159D-N248D-H249R | +++ |
| A016S-V104I-S128N-L148I | +++ |
| T022A-S101G-S103A-V104I-G159D-S188E-A232T-Q245V-N248E | +++ |
| T022A-G023A-T033S-S101G-S103A-V104I-N116A-Y209A-G211Q-T213A-A232V | +++ |
| T022A-N116L-S188D | +++ |
| G020R-N062E-S078D-G118D-P129E-G159D-S188D-Q245R | +++ |
| S024R-N062E-S078G-G118D-P129E-H249R | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024F-T033S-S101G-S103A-V104I-N116L-Y209V-T213A-A232V | +++ |
| S024R-S078G-G118S-G159D-S188D-N248D | +++ |
| T022A-S024F-S101G-S103A-V104I-N116L-Y209V-A232V | +++ |
| T022A-S101G-S103A-V104I-N116L-S128N-Y209V-G211Q-A232V | +++ |
| S024R-N062E-S166D-S188D | +++ |
| S024R-S078D-G118S-G159D-S188D-Q245R-N248D | +++ |
| S101G-S103A-V104I-N116A-Y209V-T213A-A232V | +++ |
| T022A-S024R-G118R-A158E-S166D-S188D | +++ |
| T022A-T033S-S101G-S103A-V104I-N116L-Y209A-A232V | +++ |
| G020K-T022L-S024F-S078N-G118R-S128D | +++ |
| A016S-T022A-S024F-T033S-S101G-S103A-V104I-N116A-Y209V-T213A-A232V | +++ |
| S024R-N062E-N116L-S128I | +++ |
| T022A-S024F-S101G-S103A-V104I-N116L-Y209A-T213A-A232V | +++ |
| T022A-V068A-S101G-S103A-V104I-N116L-G159D-S188D-A232V-Q245R-N248D-E271F | +++ |
| T022A-S024R-T033S-N062E-G118R-A158E | +++ |
| S024R-N062E-S078D-G118D-P129E-Q245R-N248D-H249R | +++ |
| T022Q-S101G-S103A-V104I-G159D-S188D-A232T-Q245R-N248D | +++ |
| T022A-S024R-A158E-S188D | +++ |
| G020K-T022L-S078N-G118R-S166D-L217E | +++ |
| G020R-S078D-G118D-P129E | +++ |
| A016S-S101G-S103A-V104I-N116A-S128N-Y209V-G211Q-A232V | +++ |
| G020K-T022L-S024F-G118R-S166D-T213A-L217E | +++ |
| G118R-T213A-L217E | +++ |
| T022L-S024F-S166D-T213A-L217E | +++ |
| S024R-N076D-S101A-S103A-V104I-S188D-A232V-Q245R | +++ |
| T022A-T033S-G118R-P129E | +++ |
| S024R-S078G-G118S-P129E-G159D-S188D-N248D | +++ |
| T022A-S024R-S101G-S103A-V104I-I107V-P129E-G159D-S188D-A232V-Q245R-N248D-A270V-E271F | +++ |
| T022A-S101G-S103A-V104I-N116L-Y209V-G211Q-T213A-A232V | +++ |
| T022A-S101A-S103G-V104I-S128N | +++ |
| T022A-S024R-N062E-N116L-G118R-S166D | +++ |
| A016S-T022A-S024F-S101G-S103A-V104I-N116L-Y209A-T213A-A232V | +++ |
| A016S-S101G-S103A-V104I-N116L-Y209V-G211Q-T213A-A232V | +++ |
| S024F-G118R-S128D-T213A-L217E | +++ |
| T022L-S024F-G118R-T213A-L217E | +++ |
| N062E-S078D-G118S | +++ |
| S024R-G118R-A158E-S188D | +++ |
| S024F-S101G-S103A-V104I-N116L-S128N-Y209A-A232V | +++ |
| A088L | +++ |
| E271W | +++ |
| N062E-S078D-G118D-P129E-H249R | +++ |
| T022A-V104I-S128N-L148I | +++ |
| T022Q-S101G-S103A-V104I-G159D-S188E-A230V-A232V-Q245R-N248H | +++ |
| S101G-S103A-V104I-N116L-G118V-Y209A-T213A-A232V | +++ |
| S024R-S078D-G118D-G159D-Q245R-H249R | +++ |
| G097P-A098F-S099A-V104I | +++ |
| T022A-S101G-S103A-V104I-G159D-S188D-A232V-Q245R-N248D-E271F | +++ |
| T022L-S024F-S078N-G118R-S166D-T213A | +++ |
| N062E-S078G-G118D-S188D-Q245R-N248D | +++ |
| T022A-S024R-T033S-S166D-S188D | +++ |
| T022A-T033S-R045C-G118R-A158E-S188D | +++ |
| T022A-S024R-N062E-S128I-S188D | +++ |
| T022A-S101G-S103A-V104I-P129E-G159D-S188D-A232V-Q245R-N248D-A270V-E271F | +++ |
| T022A-S024R-N116L-S166D | +++ |
| S024R-N062E-S128I-A158E | +++ |
| S024R-G118R-A158E-S166D | +++ |
| G020K-T022L-S078N-T213A | +++ |
| G020R-S024R-S078G-G118D-G159D-Q245R-N248D | +++ |
| G020K-T022L-S078N-T213A-L217E | +++ |
| G020R-S078D-G118D-G159D-Q245R-H249R | +++ |
| T022A-S024F-S101G-S103A-V104I-N116L-S128N-Y209A-G211Q-T213A-A232V | +++ |
| S024R-S101A-S103A-V104I-S188D-A232V-Q245R | +++ |
| S024R-N116L-G118R-A158E-S166D-S188D | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024F-S166D-T213A | +++ |
| G020R-S024R-N062E-S078D-G118S-P129E-Q245R-N248D-H249R | +++ |
| T022A-S024R-S128I-S166D-S188D | +++ |
| G020R-S024R-S078D-G118S-P129E-N248D-H249R | +++ |
| T022A-S024R-T033S-N116L-G118R-A158E-S166D-S188D | +++ |
| T022A-S024F-T033S-S101G-S103A-V104I-N116L-S128N-Y209A-T213A-A232V | +++ |
| T022L-S024F-L217E | +++ |
| G020R-S078G-G118S-G159D-S188D-Q245R-N248D-H249R | +++ |
| T022A-S101G-S103A-V104I-N116L-G159D-S188D-A232V-Q245R-N248D-E271F | +++ |
| S099T-S103G | +++ |
| S024R-S078D-G118D-P129E-N248D-H249R | +++ |
| S024R-S078D-G118D-P129E-S188D-Q245R-N248D | +++ |
| T022A-T033S-S101G-S103A-V104I-G118R-G159D-S188D-T213A-A232V-Q245R-N248D-E271F | +++ |
| S024R-S078D-G118S-P129E-G159D-S188D-N248D-H249R | +++ |
| S078D-G118D-P129E-G159D-Q245R-H249R | +++ |
| A016S-T022A-S024F-S101G-S103A-V104I-N116A-Y209A-A232V | +++ |
| S024R-S078D-G118D-P129E-G159D-S188D-Q245R-N248D-H249R | +++ |
| T022A-S101G-S103A-V104I-G118R-S128L-G159D-S188D-T213A-A232V-Q245R-N248D-E271F | +++ |
| G020R-S078G-G118S-G159D-Q245R-N248D | +++ |
| S078G-G118D-G159D-S188D-Q245R | +++ |
| T022L-G118R-T213A-L217E | +++ |
| G020R-S024R-S078G-G118S-S188D-N248D-H249R | +++ |
| G118R-A158E-S166D-S188D | +++ |
| A016S-T022A-S024F-T033S-S101G-S103A-V104I-N116L-Y209V-T213A-A232V | +++ |
| N062E-S078D-G118S-P129E-G159D-Q245R-N248D | +++ |
| T022Q-A088S-S101G-S103A-V104I-G159D-S188D-A232T-Q245V-N248E | +++ |
| S078D-G118S-P129E-G159D-Q245R-N248D | +++ |
| G020K-S024F-S128D-N204K | +++ |
| S024F-S101G-S103A-V104I-N116A-Y209V-G211Q-A232V | +++ |
| S024R-S078D-G118S-S188D | +++ |
| S101G-S103A-V104I-N116L-Y209V-A232V | +++ |
| G020R-N062E-S078D-G118S-S188D-Q245R-N248D-H249R | +++ |
| A016S-T022A-S024F-S101G-S103A-V104I-N116L-Y209A-G211Q-A232V | +++ |
| S101G-S103A-V104L-L148I | +++ |
| T022A-S101G-S103A-V104I-G159D-S188E-A232T-Q245T-N248D-E271L | +++ |
| S024R-N062E-S078D-G118D-P129E-S188D-H249R | +++ |
| R010H-T022L-S024F-L217E | +++ |
| T022A-S101G-S103A-V104I-G159D-S188E-A232L-Q245R-N248D | +++ |
| S024R-N062E-S078G-G118D-S188D-Q245R | +++ |
| S024R-N116L-S128I-A158E-S166D | +++ |
| T022A-S101G-S103A-V104I-G159D-S188D-A232V-Q245T-N248H-E271F | +++ |
| G020R-S078D-G118S-P129E-G159D | +++ |
| G020R-S024R-S078D-G118D-P129E-Q245R-N248D | +++ |
| S024R-N076D-S101A-S103A-V104I-P210I-A232V-Q245R | +++ |
| S078D-G118S-S188D-Q245R | +++ |
| G020K-T022L-S024F-G118R-S166D-T213A | +++ |
| S078G-G118S-G159D-Q245R-N248D-H249R | +++ |
| T022Q-S101G-S103A-V104I-G159D-S188D-A232T-Q245R-N248E-E271F | +++ |
| S056R-G065P | +++ |
| S056K | +++ |
| T022A-S024R-N076D-S101G-S103A-V104I-P129E-G159D-S188D-A232V-Q245R-N248D-E271F | +++ |
| T022A-S024R-N062E-N116L-G118R-S128I-A158E | +++ |
| S024R-S078G-G118S-P129E-S188D | +++ |
| G020R-N062E-S078D-G118D-G159D-N248D-H249R | +++ |
| S024R-S078G-G118S-G159D-N248D | +++ |
| S024R-N062E-S078G-G118D-S188D-N248D | +++ |
| G020R-S024R-N062E-S078D-G118S-P129E-Q245R | +++ |
| S024R-S078D-G118D-G159D | +++ |
| T022A-S024R-T033S-G118R-S128I-S166D-S188D | +++ |
| A016S-T033S-S101G-S103A-V104I-N116L-S128N-Y209V-A232V | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-T033S-S188D | +++ |
| G097P-S103A-V104L | +++ |
| G020R-S078G-G118D-P129E | +++ |
| N062E-S101A-S103A-V104I-S188D-V203L-A232V-Q245R | +++ |
| G020R-S024S-S078G-G118S-G159D-Q245R-N248D | +++ |
| G020R-S078D-G118D-G159D-S188D | +++ |
| G020R-S024R-S078G-G118D-S188D-Q245R-N248D | +++ |
| G020R-N062E-S078D-G118D-S188D | +++ |
| G020R-S101A-P210I-G211Q | +++ |
| T022A-T033S-N116L-S188D | +++ |
| T022A-T033S-S101G-S103A-V104I-G159D-S188D-A232V-Q245R-N248D-E271F | +++ |
| T022A-S101G-S103A-V104I-G159D-S188D-A232L-Q245R-N248E-E271L | +++ |
| S024R-N062E-S078D-G118D-N248D-H249R | +++ |
| T022A-S024R-N116L-A158E | +++ |
| N062E-N076D-S101A-S103A-V104I-S188D-P210I-A232V-Q245R | +++ |
| S024R-S078G-G118S-S188D-N248D-H249R | +++ |
| G020R-S078G-G118S-P129E-S188D-N248D-H249R | +++ |
| S024R-S078G-G118D-G159D-S188D | +++ |
| A016S-S101G-S103A-V104I-N116L-Y209A-G211Q-A232V | +++ |
| S132D | +++ |
| N043K | +++ |
| G097P-V104L | +++ |
| A016S-T022A-S024F-S101G-S103A-V104I-N116A-Y209A-G211Q-A232V | +++ |
| S024R-N062E-S078D-G118D-G159D-S188D-H249R | +++ |
| S024R-S078G-G118S-G159D-S188D | +++ |
| S024R-S078G-G118D-G159D-S188D-N248D | +++ |
| S024R-N062E-S078G-G118S-G159D-S188D-Q245R-H249R | +++ |
| S024F-S101G-S103A-V104I-N116A-Y209V-T213A-A232V | +++ |
| G020K-S078N-S166D-T213A-L217E | +++ |
| S103A-L111V-L148I | +++ |
| S024F-T033S-S101G-S103A-V104I-N116L-S128N-Y209A-G211Q-T213A-A232V | +++ |
| S024R-S078D-G118D-G159D-S188D-Q245R-N248D | +++ |
| T022A-T033S-S101G-S103A-V104I-N116A-Y209V-T213A-A232V | +++ |
| S024R-N062E-S078G-G118D-P129E-S188D | +++ |
| S024R-S078D-G118D-P129E-S188D-Q245R-H249R | +++ |
| T022A-G118R-S166D | +++ |
| G020R-S024R-S078G-G118S-G159D-S188D-Q245R | +++ |
| T022A-S024R-T033S-N116L-G118R-A158E-S188D | +++ |
| T022Q-S101G-S103A-V104I-G159D-S188E-A232T-Q245V-N248D-E271F | +++ |
| G020R-S024R-S078D-G118S-P129E-Q245R-N248D-H249R | +++ |
| A016S-T022A-V104I-S128N | +++ |
| S024R-N062E-N076D-S101A-S103A-V104I-S188D-P210I-A232V-Q245R | +++ |
| T022L-G118R-S166D-T213A-L217E | +++ |
| S078D-G118S-P129E-G159D-S188D-Q245R-H249R | +++ |
| G195W-N269E | +++ |
| G020R-S024R-S078G-G118S-P129E-Q245V-N248E | +++ |
| N269W | +++ |
| T022A-T033S-G118R-A158E-S166D-S188D | +++ |
| G020R-N062E-S078G-G118D-P129E-G159D-Q245R-H249R | +++ |
| A016S-S101A-S103A | +++ |
| G097P-S099G-S103A-V104I | +++ |
| S024R-S078D-G118D-P129E-Q245R | +++ |
| T022Q-S101G-S103A-V104I-G159D-S188D-A232L-Q245R-N248E | +++ |
| S078G-G118D-P129E-S188D-Q245R | +++ |
| T033S-N062E-G118R-A158E | +++ |
| G020R-S078D-G118S-G159D-S188D-N248D | +++ |
| A016S-T022A-S103G-V104I-S128N-L148I | +++ |
| A016S-S101G-S103A-V104I-N116A-Y209A-A232V | +++ |
| S101A-S103A-V104I-S188D-M222S-A232V-Q245R | +++ |
| T022A-S024F-S101G-S103A-V104I-N116A-S128N-Y209V-T213A-A232V | +++ |
| A016S-T022A-S024F-S101G-S103A-V104I-N116A-Y209A-T213A-A232V | +++ |
| T022A-S101G-S103A-V104I-G159D-S188D-T213A-A232V-Q245R-N248D-E271F | +++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| A016S-S101G-S103A-V104I-N116L-Y209A-T213A-A232V | +++ |
| G020R-S078D-G118S-S188D | +++ |
| G020R-S078D-G118S-P129E-Q245R-N248D | +++ |
| T022L-S166D-T213A | +++ |
| G020R-S024R-S078D-G118S-P129E-G159D-S188D-N248D | +++ |
| S240G | +++ |
| L217E | +++ |
| S078G-G118S-P129E-Q245R-N248D | +++ |
| S024R-S078D-G118D-P129E-G159D-Q245R-N248D | +++ |
| S024R-S078G-G118S-G159D | +++ |
| T022A-S024R-N076D-S101G-S103A-V104I-G159D-S188D-A232V-Q245R-N248D-E271F-A272V | +++ |
| N062E-S078G-G118S-P129E-S188D-Q245R-N248D-H249R | +++ |
| S024F-S078N-G118R-S166D | +++ |
| S078G-G118S-P129E-N248D | +++ |
| N155W | +++ |
| A016S-S024F-S101G-S103A-V104I-N116A-S128N-Y209V-G211Q-T213A-A232V | +++ |
| G020R-N062E-S078D-G118D-P129E-Q245R-N248D | +++ |
| G020R-S078D-G118D-P129E-S188D-Q236R-N248D-H249R | +++ |
| T022A-S024R-N116L-A158E-S188D | +++ |
| S101G-S103A-V104I-N116A-S128N-Y209V-G211Q-T213A-A232V | +++ |
| S078D-G118S-S188D-Q245R-N248D | +++ |
| T022L-S024F-S078N-L217E | +++ |
| S099A-S101A-G102A | +++ |
| G020R-S078D-G118D-G159D-N248D-H249R | +++ |
| T022A-N076D-S101G-S103A-V104I-I107V-P129E-G159D-S188D-A232V-Q245R-N248D-E271F | +++ |
| T033S-N116L-G118R-S166D-S188D | +++ |
| S024R-G118S-S128I-A158E-S166D-S188D | +++ |
| G020R-S024R-N062E-S078G-G118S-P129E-G159D-Q245R-N248D-H249R | +++ |
| N062E-S078G-G118D-N248D-H249R | +++ |
| S024R-N116L-A158E-S188D | ++ |
| G020K-S024F-S078N-G118R-T213A | ++ |
| T022A-S024R-T033S-N116L-G118R-S128I | ++ |
| G020R-S078D-G118D-S188D-Q245R | ++ |
| S024F-S101G-S103A-V104I-N116A-Y209A-T213A-A232V | ++ |
| S024F-N062E-S078G-G118D-G159D-S188D | ++ |
| T022A-N062E-N116L-G118R-A158E-S166D | ++ |
| G020K-T022L-S078N-S166D-L217E | ++ |
| G020R-S078D-G118D-G159D | ++ |
| T022A-S024R-T033S-N116L | ++ |
| G020R-S078D-G118D-P129E-G159D | ++ |
| S166D | ++ |
| G020R-S078D-G118D-G159D-H249R | ++ |
| S024R-N062E-S078G-G118S | ++ |
| S024R-S078D-G118D-S188D-Q245R-H249R | ++ |
| A016S-S024F-T033S-S101G-S103A-V104I-N116L-Y209V-T213A-A232V | ++ |
| G020R-N062E-S078D-G118D-P129E-G159D-Q245R | ++ |
| S024F-S101G-S103A-V104I-N116L-G118V-Y209V-G211Q-A232V | ++ |
| S024F-S166D-L217E | ++ |
| T022A-S024R-S166D | ++ |
| S024R-N062E-S078G-G118D-P129E-N248D | ++ |
| A016S-S101G-S103A-V104I-N116L-S128N-Y209V-A232V | ++ |
| A016S-T022A-S101G-S103A-V104I-N116A-Y209V-G211Q-A232V | ++ |
| S078D-G118S-G159D-N248D-H249R | ++ |
| S024R-S078G-G118D-P129E-G159D-S188D | ++ |
| T022A-S024R-N062E-N116L-G118R-S128I-S188D | ++ |
| S103A-S128N | ++ |
| T022L-S078N-G118R-S166D-T213A | ++ |
| S024F-T033S-S101G-S103A-V104I-N116L-S128N-Y209A-T213A-A232V | ++ |
| T022A-S024R-N076D-S101G-S103A-V104I-P129E-G159D-S188D-A232V-Q245R-N248D-E271F-A272V | ++ |
| S024R-S078D-G118S-S128N-P129E | ++ |
| S024R-S078G-G118S-P129E-G159D-S188D-Q245R-H249R | ++ |
| T022A-S024R-N076D-S101G-S103A-V104I-P129E-G159D-S188D-A232V-Q245R-N248D-A270V-E271F-A272V | ++ |
| T022Q-S101G-S103A-V104I-G159D-S188D-A232T-Q245T-N248D | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024R-T033S-N116L-A158E | ++ |
| S130E-N269K | ++ |
| S024R-T033S-N116L-S128I-A158E | ++ |
| A016V-G020R-S024R-S078D-G118D-P129E-Q245R-N248D | ++ |
| S099G-S101A-G102A-S103G-V104I | ++ |
| A016S-T022A-S101A-V104L-S128N-L148I | ++ |
| G020R-S024R-S078G-G118S-P129E-S188D | ++ |
| S259W | ++ |
| S259H | ++ |
| T022A-S101G-S103A-V104I-P129E-G159D-S188D-A232V-Q245R-N248D-E271F | ++ |
| N018D-S101G-S103A-V104I-N116A-Y209A-G211Q-T213A-A232V | ++ |
| G020K-S024F-S078N-S166D-T213A | ++ |
| N076D-S101A-S103A-V104I-S188D-A232V-Q245R | ++ |
| S078D-G118D-P129E-G159D-H249R | ++ |
| S024R-S078G-G118D-P129E-G159D-N248D | ++ |
| S024R-N062E-S101A-S103A-V104I-S188D-A232V-Q245R-E271R | ++ |
| G020R-S024R-S078D-G118D-P129E-G159D-S188D | ++ |
| T022A-S024R-N076D-S101G-S103A-V104I-G159D-S188D-A232V-Q245R-N248D-A270V-E271F | ++ |
| G020R-N062E-S078D-G118S-G159D-S188D-Q245R-H249R | ++ |
| Q012R-S101G-S103A-V104I-N116L-S128N-Y209V-A232V | ++ |
| G020R-S078G-G118D-P129E-G159D-S188D-Q245R-N248D | ++ |
| G020R-N062E-S078G-G118S-P129E-G159D-S188D-Q245R-H249R | ++ |
| T022A-S101G-S103A-V104I-G118R-S128L-G159D-S188D-A232V-Q245R-N248D-E271F | ++ |
| G020R-S078D-G118D-G159D-S188D-Q245R-N248D | ++ |
| T022A-S101G-S103A-V104I-G159D-S188D-A232V-Q245R-N248D-E271F-A272V | ++ |
| G020R-S024R-N062E-S078D-G118S-P129E-S188D-Q245R-N248D-H249R | ++ |
| G020R-S078G-G118S-G159D-H249R | ++ |
| G020K-T022L-S024F-G118R-S128D-S166D | ++ |
| T022A-S024R-N062E-N116L-G118R-S128I-A158E-S166D | ++ |
| A016S-S103G-V104L | ++ |
| A016S-T033S-S101G-S103A-V104I-N116L-Y209A-A232V | ++ |
| G020R-S024R-N062E-S078D-G118S-P129E-S188D-N248D | ++ |
| G020K-T022L-S078N-G118R-S166D | ++ |
| G020K-T213A-L217E | ++ |
| S024R-N062E-S078D-G118S-P129E-G159D-S188D-Q245R-N248D-H249R | ++ |
| S078N-S166D-T213A-L217E | ++ |
| S078D-G118S-P129E-G159D-Q245R-H249R | ++ |
| T022A-N076D-S101G-S103A-V104I-P129E-G159D-S188D-A232V-Q245R-N248D-E271F-A272V | ++ |
| G020K-T022L-G118R-L217E | ++ |
| T022A-V104L-L111V | ++ |
| T022A-S101G-S103A-V104I-S128A-P129E-G159D-S188D-A232V-Q245R-N248D-E271F | ++ |
| S024R-N062E-S078G-G118S-P129E-S188D-N248D | ++ |
| G020R-S024R-S078D-G118D-G159D-S188D-N248D | ++ |
| T022L-S078N-L217E | ++ |
| G020R-S024R-S078G-G118S-S188D | ++ |
| S024F-S101G-S103A-V104I-N116L-Y209V-G211Q-T213A-A232V | ++ |
| T022A-N116L-G118R-A158E-S166D | ++ |
| G020R-S024R-S078G-G118S-P129E-S188D-Q245R-N248D-H249R | ++ |
| T022A-V104I-S128N | ++ |
| T022A-S101G-S103A-V104I-N116L-S128N-Y209V-G211Q-T213A-A232V | ++ |
| S024R-S078G-G118D-Q245R | ++ |
| N062E-S078G-G118S-P129E-G159D-S188D-H249R | ++ |
| T022A-S101G-S103A-V104I-I107V-G159D-S188D-A232V-Q245R-N248D-A270V-E271F-A272V | ++ |
| S024R-N062E-S078D-G118S-P129E-G159D-Q245R-N248D-H249R | ++ |
| T022A-T033S-G118R-A158E-S188D | ++ |
| T022A-S078N-G097A-S101N-S103A-V104I-S128A-G159D-S188D-L217Q-A232V-Q245R-N248D-E271F | ++ |
| T022A-S024R-S166D-S188D | ++ |
| A016S-S024F-T033S-S101G-S103A-V104I-N116L-Y209A-A232V | ++ |
| T022A-T033S-S128I-A158E | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024R-T033S-N116L-S188D | ++ |
| N062E-N076D-S101A-S103A-V104I-P210I-A232V-Q245R | ++ |
| T022A-N076D-S101G-S103A-V104I-G159D-S188D-A232V-Q245R-N248D-A270V-E271F-A272V | ++ |
| S130D | ++ |
| G020K-T022L-S024F-S078N-G118R-S166D-L217E | ++ |
| T022Q-S101G-S103A-V104I-G159D-S188E-A232S-Q245V-N248E | ++ |
| S024R-T033S-N116L-S166D-S188D | ++ |
| S024F-S078N-T213A-L217E | ++ |
| S024R-S078D-G118S-S188D-Q245R-H249R | ++ |
| T022A-S024R-T033S-A158E-S166D-S188D | ++ |
| N116L | ++ |
| G020K-T022L-S024F-S166D-T213A-L217E | ++ |
| T022A-N062E-N116L-G118R-S188D | ++ |
| G020R-S024R-S078G-G118S-G159D | ++ |
| G020R-S078G-G118D-Q245R-N248D-H249R | ++ |
| T022A-N116L-G118R-S128I | ++ |
| T022L-S078N-S166D | ++ |
| T022L-G118R-S128D | ++ |
| G097P-S099A | ++ |
| T022L-S024F-G118R-S128D | ++ |
| S242K | ++ |
| N062E-S078D-G118S-G159D | ++ |
| A016S-S103G-S128N-L148I | ++ |
| G097P-A098Q-S101A | ++ |
| T022A-S103A-V104L-S128N-L148I | ++ |
| T022A-S101G-S103A-V104I-G118R-G159D-S188D-T213A-A232V-Q245R-N248D-E271F | ++ |
| S099G-S101G-G102A | ++ |
| T022Q-S101G-S103A-V104I-G159D-S188D-A232L-Q245T-N248D | ++ |
| G100S-S101G-V104I | ++ |
| S078D-G118S-G159D-Q245R-N248D | ++ |
| A016S-S024F-T033S-S101G-S103A-V104I-N116A-Y209V-G211Q-T213A-A232V | ++ |
| T022A-S024R-T033S-N116L-A158E | ++ |
| T022A-N076D-S101G-S103A-V104I-G159D-S188D-A232V-Q245R-N248D-E271F-A272V | ++ |
| T022A-S024R-N116L-S128I-S166D | ++ |
| S101G-S103A-V104I-N116L-S128N-Y209V-A232V | ++ |
| S024F-S101G-S103A-V104I-N116L-Y209A-A232V | ++ |
| G020R-S078G-G118D-G159D-S188D-N248D | ++ |
| G020R-S078D-G118D-S188D-Q245R-N248D | ++ |
| S024F-S078N-G118R-S128D | ++ |
| T022L-S024F-S078N-G118R-S166D | ++ |
| G020R-S024R-S078D-G118S-P129E-G159D-S188D-Q245R-H249R | ++ |
| S103A-V104L-S128N | ++ |
| T022A-S024R-N062E-N116L-S128I | ++ |
| T022A-N062E-N116L-G118R-A158E-S188D | ++ |
| T022A-S024G-G097S-S101G-S103A-V104I-S128A-G159D-S188D-A232V-Q245R-N248D-E271F | ++ |
| G020R-S024R-N062E-S078D-G118D-G159D-S188D-Q245R-H249R | ++ |
| N062E-S078D-G118S-S188D-Q245R-N248D | ++ |
| T022A-S103A-L148I | ++ |
| T022A-S024R-N116L-S128I-A158E-S188D | ++ |
| G097P-S099T-S101G-V104I | ++ |
| S166D-T213A-L217E- | ++ |
| A016S-T033S-S101G-S103A-V104I-N116L-Y209V-A232V | ++ |
| N062E-S078D-G118S-P129E-G159D-S188D-Q245R | ++ |
| T022A-S024F-S101G-S103A-V104I-N116A-S128N-Y209A-G211Q-A232V | ++ |
| G020K-T022L-S078N-G118R-S128D-S166D-L217E | ++ |
| T033S-S188D | ++ |
| T033S-N116L-G118R-A158E | ++ |
| T022A-S024G-N076D-V093I-S101N-S103A-V104I-G159D-S188D-L217Q-A232V-Q245R-N248D-E271F | ++ |
| G020R-S078D-G118S-P129E-Q245R-H249R | ++ |
| T022A-S024R-A158E-S166D-S188D | ++ |
| G020K-T022L-S078N-G118R-S128D | ++ |
| G020R-S024R-S078D-G118D-P129E-S188D | ++ |
| S099T-G102A | ++ |
| S024R-N116L-G118R-A158E-S188D | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T033S-N116L-G118R-S166D | ++ |
| T022A-S101G-S103A-V104I-G159D-S188D-A232L-Q245V-N248H | ++ |
| G020R-S024R-S078D-G118S-G159D-Q245R | ++ |
| S078D-G118D-Q245R | ++ |
| G020K-S078N-G118R-S166D-T213A-L217E-A272D | ++ |
| A016S-T022A-V104L-L111V-L148I | ++ |
| T022Q-S101G-S103A-V104I-G159D-S188D-A232V-Q245V-N248H | ++ |
| N062E-N116L-G118R-S166D | ++ |
| N062E-S166D | ++ |
| T022A-S024R-N062E-G118R-A158E-S188D | ++ |
| T022A-S024F-S101G-S103A-V104I-N116A-Y209V-A232V | ++ |
| T022A-S024R-N076D-S101G-S103A-V104I-P129E-G159D-S188D-A232V-Q245R-N248D-A270V-E271F | ++ |
| G020R-S024R-N062E-S078G-G118D-Q245R | ++ |
| S024R-N116L-S128I-A158E-S188D | ++ |
| S024R-N062E-S101A-S103A-V104I-P210I-A232V-Q245R | ++ |
| A114T | ++ |
| T022L-S024F-S078N-G118R-S128D | ++ |
| S024R-N116L-G118R-S166D | ++ |
| N062E-S078G-G118D-P129E | ++ |
| A016S-T022A-S101G-S103A-V104I-N116L-Y209A-G211Q-A232V | ++ |
| G020K-T022L-S078N-S166D | ++ |
| G020R-S024R-N062E-S078G-G118S-P129E-S188D-Q245R-N248D-H249R | ++ |
| T022A-S078N-G097A-S101Q-S103A-V104I-G159D-S188D-L217Q-A232V-Q245R-N248D-E271F | ++ |
| T022A-S101G-S103G | ++ |
| A016S-S024F-S101G-S103A-V104I-N116L-S128N-Y209A-G211Q-S212L-A232V | ++ |
| S024F-G118R-S166D-T213A | ++ |
| G100S-S101G | ++ |
| T022A-S101G-S103A-V104I-S128L-G159D-S188D-T213A-A232V-Q245R-N248D-E271F | ++ |
| A016S-T022A-S103A-V104L-S128N | ++ |
| G020K-S024F-S078N-G118R-S166D | ++ |
| S099T-G102A-S103G | ++ |
| G020K-S024F-S128D-L217E | ++ |
| S078D-G118D-G159D-H249R | ++ |
| N062E-S078G-G118D-S188D | ++ |
| N076D-S101A-S103A-V104I-P210I-A232V-Q245R | ++ |
| S024R-S078G-G118D-P129E-N248D | ++ |
| S078G-G118S-G159D-S188D | ++ |
| A016S-S101G-S103A-V104I-N116L-S128N-Y209V-G211Q-T213A-A232V | ++ |
| G020K-S078N-G118R-S166D-T213A-L217E | ++ |
| T022A-S101N-S103A-V104I-L124V-P129S-G159D-S188D-A232V-Q245R-N248D-E271F | ++ |
| T022A-S101N-S103A-V104I-P129S-G159D-S188D-L217Q-A232V-Q245R-N248D-E271F | ++ |
| S024R-S078D-G118D-P129E | ++ |
| G020K-S024F-S128D-T213A | ++ |
| T022A-T033S-A158E-S188D | ++ |
| G020K-S024F-S128D-S166D-T274A | ++ |
| S024R-N062E-N116L-G118R-S128I-A158E-S166D-S188D | ++ |
| S078G-G118S-P129E-S188D | ++ |
| T022A-S024R-S128I-A158E-S188D | ++ |
| T022A-S024R-G118R-S128I-A158E | ++ |
| T022A-N116L-S166D | ++ |
| G020K-G118R-S128D-S166D | ++ |
| G020K-T022L-S024F-S078N-G118R-S128D-L217E | ++ |
| G020R-S024R-S078D-G118D-P129E-S188D-N248D | ++ |
| G020K-T022L-G118R-S128D-L217E | ++ |
| S024F-S078N-G118R-S128D-T213A | ++ |
| S024R-S078G-G118D-S188D-N248D | ++ |
| N062E-N076D-S101A-S103A-V104I-S188D-A232V-Q245R | ++ |
| T033S-G118R-S128I-A158E-S166D | ++ |
| A016S-S101G-S103A-V104I-N116A-S128N-Y209V-A232V | ++ |
| T022L-S078N-G118R-S128D-L217E | ++ |
| S101G-V104I-L111V-S128N | ++ |
| T022A-S078N-G097S-S101N-S103A-V104I-S128A-G159D-S188D-L217Q-A232V-Q245R-N248D-E271F | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022Q-S101G-S103A-V104I-G159D-S188D-A232T-Q245V-N248E | ++ |
| T022A-S078N-G097A-S101N-S103A-V104I-G159D-S188D-L217Q-A232V-Q245R-N248D-E271F | ++ |
| G020K-T022L-S024F-G118R-S128D | ++ |
| T022A-N076D-S078N-G097S-S101G-S103A-V104I-G159D-S188D-A232V-Q245R-N248D-E271F | ++ |
| T022A-S024R-S101G-S103A-V104I-P129E-G159D-S188D-A232V-Q245R-N248D-A270V-E271F | ++ |
| V104I | ++ |
| T022A-S101G-S103A-V104I-P131L-G159D-S188D-A232V-Q245R-N248D-E271F | ++ |
| T022Q-S101G-S103A-V104I-G159D-S188D-A232S-Q245T-N248E | ++ |
| T022A-N076D-S078N-S101N-S103A-V104I-S128A-G159D-S188D-A232V-Q245R-N248D-E271F | ++ |
| A016S-S024F-T033S-S101G-S103A-V104I-N116L-Y209A-T213A-A232V | ++ |
| T022A-S101G-S103A-V104I-N116L-S128N-Y209V-T213A-A232V | ++ |
| T022A-S024R-T033S-N062E-G118R-A158E-S188D | ++ |
| T022A-S024R-S101G-S103A-V104I-G159D-S188D-A232V-Q245R-N248D-E271F | ++ |
| T022A-N116L-G118R-S188D | ++ |
| T022A-G097A-S101Q-S103A-V104I-L124V-S128A-P129S-G159D-S188D-A232V-Q245R-N248D-E271F | ++ |
| T022A-S101G-S103A-V104I-N116L-Y209V-T213A-A232V | ++ |
| T022A-S128I-S188D | ++ |
| G020R-S024S-S078G-G118D-G159D | ++ |
| S024R-T033S-N116L-S128I-A158E-S188D | ++ |
| T022A-T033S-S101G-S103A-V104I-G159D-S188D-T213A-A232V-Q245R-N248D-E271F | ++ |
| A016S-T033S-S101G-S103A-V104I-N116L-S128N-Y209A-A232V | ++ |
| A016S-S101G-S103G-V104I-L148I | ++ |
| S024R-T033S-G118R-S166D-S188D | ++ |
| T022A-T033S-S101G-S103A-V104I-N116L-Y209V-T213A-A232V | ++ |
| T022A-N062E-N116L-S128I | ++ |
| A016S-S101G-S103G-V104L-L148I | ++ |
| T022A-N116L-S166D-S188D | ++ |
| G020K-T022L-S024F-S078N-S128D-T213A | ++ |
| T022A-S101G-S103A-V104I-N116L-Y209V-G211Q-A232V | ++ |
| S099G-G100S-V104L | ++ |
| S078G-G118D-P129E-G159D-S188D-H249R-T253M | ++ |
| A016S-T022A-S101G-S103A-V104I-N116A-S128N-Y209A-A232V | ++ |
| T022A-S101G-S103A-V104I-G159D-S188D-A232V-Q245T-N248E | ++ |
| G020R-S078D-G118D-P129E-G159D-S188D-N248D-H249R | ++ |
| G118R-S166D-T213A-L217E | ++ |
| G020K-S024F-S128D | ++ |
| T022A-S024F-S101G-S103A-V104I-N116L-S128N-Y209V-G211Q-T213A-A232V | ++ |
| T022A-G097S-S101Q-S103A-V104I-S128A-G159D-S188D-A232V-Q245R-N248D-E271F | ++ |
| G020K-T022L-G118R-S128D-T213A-L217E | ++ |
| S024F-G118R-S128D-T213A | ++ |
| T022A-S101A-S103A-V104I-S128N | ++ |
| S024R-N062E-N076D-S101A-S103A-V104I-S188D-A232V-Q245R | ++ |
| T022A-S103A-S128N-L148I | ++ |
| G020R-N062E-S078G-G118D-G159D-S188D-N248D | ++ |
| T022A-S024R-T033S-G118R-S128I-S188D | ++ |
| T022A-S101G-S103A-V104I-S128L-G159D-S188D-A232V-Q245R-N248D-E271F | ++ |
| S101G-S103A-V104I-N116L-S128N-Y209V-G211Q-A232V | ++ |
| T022A-S101Q-S103A-V104I-P129E-G159D-S188D-L217Q-A232V-Q245R-N248D-E271F | ++ |
| T022A-S024G-S078N-G097A-S101N-S103A-V104I-S128A-G159D-S188D-L217Q-A232V-Q245R-N248D-E271F | ++ |
| T022A-G097A-S101N-S103A-V104I-P129S-G159D-S188D-A232V-Q245R-N248D-E271F | ++ |
| T033S-S166D-S188D | ++ |
| S078D-G118S-P129E-Q245R-N248D | ++ |
| G020K-S024F-S078N-G118R-S166D-T213A | ++ |
| S024R-N062E-N116L-G118R-S166D-S188D | ++ |
| G020R-N062E-S078D-G118D-P129E-G159D-N248D-H249R | ++ |
| G020K-S078N-G118R-S128D | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-N062E-S166D | ++ |
| P014R | ++ |
| S240D | ++ |
| N155G | ++ |
| A016S-T022A-S024F-S101G-S103A-V104I-N116A-S128N-Y209A-T213A-A232V | ++ |
| A016S-T022A-T033S-S101G-S103A-V104I-N116L-Y209V-G211Q-A232V | ++ |
| A016S-T022A-S024F-T033S-S101G-S103A-V104I-N116L-Y209A-G211Q-T213A-A232V | ++ |
| T022A-G097S-S101N-S103A-V104I-G159D-S188D-A232V-Q245R-N248D-E271F | ++ |
| A016S-S101G-S103A-V104I-N116L-S128N-Y209V-G211Q-A232V | ++ |
| G118R-S128I-S166D | ++ |
| T022A-S078N-G097S-S101N-S103A-V104I-S128A-G159D-S188D-A232V-Q245R-N248D-E271F | ++ |
| T022A-S101G-S103A-V104I-M119V-P129E-G159D-S188D-L217Q-A232V-Q245R-N248D-E271F | ++ |
| S024R-A158E-S188D | ++ |
| T022A-S101N-S103A-V104I-L124V-P129E-G159D-S188D-L217Q-A232V-Q245R-N248D-E271F | ++ |
| N116L-G118R-S188D | ++ |
| T022A-G097A-S101N-S103A-V104I-L124V-S128A-G159D-S188D-A232V-Q245R-N248D-E271F | ++ |
| T022A-G118R-S128I-A158E | ++ |
| G097P-S101A-V104L | ++ |
| S103G-V104I-S128N-L148I | ++ |
| G020R-N062E-S078G-G118D-P129E-S188D | ++ |
| V026W | ++ |
| G020R-N062E-S078D-G118D-P129E-G159D | ++ |
| T022A-N076D-S101G-S103A-V104I-I107V-N123S-P129E-G159D-S188D-A232V-Q245R-N248D-E271F-A272V | ++ |
| S103G-S128N-L148I | ++ |
| T022A-S024R-N076D-S101G-S103A-V104I-G159D-S188D-A232V-Q245R-N248D-E271F | ++ |
| T022A-S024G-N076D-S078N-S101G-S103A-V104I-S128A-G159D-S188D-L217Q-A232V-Q245R-N248D-E271F | ++ |
| T022A-S078N-G097S-S101G-S103A-V104I-G159D-S188D-L217Q-A232V-Q245R-N248D-E271F | ++ |
| T022A-N076D-S101N-S103A-V104I-G159D-S188D-L217Q-A232V-Q245R-N248D-E271F | ++ |
| N062E-S078D-G118S-G159D-S188D-Q245R-H249R | ++ |
| S024R-N076D-S101A-S103A-V104I-A232V-Q245R | ++ |
| T022L-S078N | ++ |
| A016S-T022A-S024F-S101G-S103A-V104I-N116L-Y209V-T213A-A232V | ++ |
| G020K-T022L-S128D-T213A | ++ |
| N062E-G118R-S128I-S188D | ++ |
| S024R-N116L-S128I-S166D-S188D | ++ |
| T022A-S101N-S103A-V104I-S128A-P129E-G159D-S188D-L217Q-A232V-Q245R-N248D-E271F | ++ |
| S024R-T033S-N116L-G118R-A158E | ++ |
| T022A-N076D-G097A-S101Q-S103A-V104I-G159D-S188D-A232V-Q245R-N248D-E271F | ++ |
| T022L-S024F-S166D-L217E | ++ |
| S024R-S078D-G118S-G159D-N248D-H249R | ++ |
| T022A-S101Q-S103A-V104I-P129S-G159D-S188D-A232V-Q245R-N248D-E271F | ++ |
| T022A-N076D-S101G-S103A-V104I-S128A-G159D-S188D-A232V-Q245R-N248D-E271F | ++ |
| A016S-T022A-S024F-S101G-S103A-V104I-N116A-S128N-Y209A-A232V | ++ |
| S078G-G118D-P129E-Q245R-N248D | ++ |
| G020R-S078G-G118D-G159D-N248D | ++ |
| G020K-T022L-G118R-S128D-S166D | ++ |
| T022A-S024G-S101Q-S103A-V104I-S128A-G159D-S188D-L217Q-A232V-Q245R-N248D-E271F | ++ |
| T022A-S024G-N076D-S078N-G097A-S101G-S103A-V104I-P129E-G159D-S188D-L217Q-A232V-Q245R-N248D-E271F | ++ |
| T022A-S101G-S103A-V104I-G159D-S188E-A232T-Q245T-N248D | ++ |
| G020R-N062E-S078G-G118D-S188D-Q245R-H249R | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024F-S101G-S103A-V104I-N116L-Y209A-T213A-A232V | ++ |
| S024R-N062E-N076D-S101A-S103A-V104I-A232V-Q245R | ++ |
| T022A-S024R-N116L-G118R-S128I-A158E | ++ |
| A098Q-S099T-S101A-V104L | ++ |
| T022A-S024G-G097S-S101G-S103A-V104I-G159D-S188D-A232V-Q245R-N248D-E271F | ++ |
| T022A-S078N-S101G-S103A-V104I-S128A-G159D-S188D-L217Q-A232V-Q245R-N248D-E271F | ++ |
| T022A-S101G-S103A-V104I-P129E-G159D-S188D-L217Q-A232V-Q245R-N248D-E271F | ++ |
| S099G-G102A | ++ |
| T022A-N076D-S101G-S103A-V104I-G159D-S188D-A232V-Q245R-N248D-A270V-E271F | ++ |
| T022A-S078N-G097S-S101N-S103A-V104I-G159D-S188D-L217Q-A232V-Q245R-N248D-E271F | ++ |
| T022A-N076D-S101G-S103A-V104I-G159E-S188D-A232V-Q245R-N248D-E271F | ++ |
| T022A-G097A-S101G-S103A-V104I-P129E-G159D-S188D-L217Q-A232V-Q245R-N248D-E271F | ++ |
| T022A-N076D-S101N-S103A-V104I-S128A-G159D-S188D-L217Q-A232V-Q245R-N248D-E271F-T274A | ++ |
| A016S-V104I-L148I | ++ |
| G097P-S101A-S103A | ++ |
| G020K-T022L-S024F-G118R-S166D | ++ |
| T022A-S024R-N062E-N116L-G118R-S128I-S166D | ++ |
| A016S-S024F-T033S-S101G-S103A-V104I-N116A-Y209A-G211Q-T213A-A232V | ++ |
| T022A-S101Q-S103A-V104I-L124V-P129E-G159D-S188D-A232V-Q245R-N248D-E271F | ++ |
| T022A-N076D-S101G-S103A-V104I-S128A-G159D-S188D-L217Q-A232V-Q245R-N248D-E271F | ++ |
| T022A-S024G-N076D-S078N-S101G-S103A-V104I-G159D-S188D-L217Q-A232V-Q245R-N248D-E271F | ++ |
| N062E-S078G-G118S-P129E-N248D | ++ |
| G020R-S078D-G118S | ++ |
| T022A-S101Q-S103A-V104I-L124V-S128A-P129E-G159D-S188D-L217Q-A232V-Q245R-N248D-E271F | ++ |
| G097P-S101G-S103A-V104I | ++ |
| G020K-T022L-S166D-T213A-L217E | ++ |
| T022A-S101G-S103A-V104I-G159D-S188D-A232V-Q245R-N248D-A270V-E271F | ++ |
| T022A-S078N-S101N-S103A-V104I-P129E-G159D-S188D-L217Q-A232V-Q245R-N248D-E271F | ++ |
| A016S-S101A-S103A-S128N | ++ |
| T022A-S101G-S103A-V104I-G159D-S188D-L217Q-A232V-Q245R-N248D-E271F | ++ |
| A098Q-S099T-G102A-S103A | ++ |
| T022A-N076D-S078N-G097A-S101G-S103A-V104I-S128A-G159D-S188D-L217Q-A232V-Q245R-N248D-E271F | ++ |
| S078N-G118R-H120N-S128D-S166D | ++ |
| S101G-S103G-L148I | ++ |
| T022A-S024R-T033S-A158E-S166D | ++ |
| N116L-G118R-S166D | ++ |
| T022A-N062E-N116L-S166D | ++ |
| N076D-S101A-S103A-V104I-S188D-P210I-M222S-A232V-Q245R | ++ |
| T022A-S101G-V104L-L148I | ++ |
| T022A-S101G-S103A-V104I-G159D-S188E-Q245V-N248D | ++ |
| S024R-N076D-S101A-S103A-V104I-S188D-P210I-M222S-A232V-Q245R | ++ |
| T022A-S024G-N076D-G097S-S101N-S103A-V104I-G159D-S188D-L217Q-A232V-Q245R-N248D-E271F | ++ |
| N116L-G118R | ++ |
| T022A-S024G-S101N-S103A-V104I-G159D-S188D-L217Q-A232V-Q245R-N248D-E271F | ++ |
| T033S-S101G-S103A-V104I-N116L-S128N-Y209A-G211Q-T213A-A232V | ++ |
| T022L-G118R-S166D-T213A | ++ |
| A016S-T022A-S101G-S103A-V104I-N116A-Y209V-A232V | ++ |
| T022A-N076D-S101G-S103A-V104I-P129E-G159D-S188D-A232V-Q245R-N248D-A270V-E271F | ++ |
| T022A-S101G-S103G-V104L-L148I | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024R-S078G-G118D-S188D | ++ |
| T022A-S101G-S103A-V104I-G159D-S188D-A232V-N238Y-Q245R-N248D-A270V-E271F-A272V | ++ |
| T022A-S024G-S078N-S101Q-S103A-V104I-G159D-S188D-S216G-L217Q-A232V-Q245R-N248D-E271F | ++ |
| S024R-N116L-S128I | ++ |
| P086T-G097P-S099T-S103A-V104I | ++ |
| A098F-G102A | ++ |
| T022A-S101Q-S103A-V104I-L126I-S128A-P129E-G159D-S188D-A232V-Q245R-N248D-E271F | ++ |
| N062E-S078G-G118D-G159D-N248D | ++ |
| T022A-S024G-N076D-G097S-S101G-S103A-V104I-S128A-G159D-S188D-L217Q-A232V-Q245R-N248D-E271F | ++ |
| A016S-T022A-S024F-S101G-S103A-V104I-N116L-S128N-Y209V-G211Q-A232V | ++ |
| G020R-S024R-S078D-G118S-H249R | ++ |
| G020K-S078N-G118R-S166D-T213A | ++ |
| G020K-T022L-S024F-G118R | ++ |
| S024R-S101A-S103A-V104I-P210I-A232V-Q245R | ++ |
| T022A-N076D-G097A-S101N-S103A-V104I-S128A-G159D-S188D-A232V-Q245R-N248D-E271F | ++ |
| G097P-A098Q-S099G-S103A | ++ |
| T022A-S024G-N076D-G097S-S101N-S103A-V104I-S128A-G159D-S188D-L217Q-A232V-Q245R-N248D-E271F | ++ |
| T022A-S078N-S101N-S103A-V104I-G159D-S188D-L217Q-A232V-Q245R-N248D-E271F | ++ |
| T022A-S024G-N076D-S078N-S101N-S103A-V104I-G159D-S188D-A232V-Q245R-N248D-E271F | ++ |
| G020K-G118R-S128D-L217E | ++ |
| A098F-S099T-G102A-S103A | ++ |
| T022A-S078N-G097S-S101Q-S103A-V104I-G159D-S188D-L217Q-A232V-Q245R-N248D-E271F | ++ |
| T022A-S024G-S101G-S103A-V104I-P129E-G159D-S188D-A232V-Q245R-N248D-E271F | ++ |
| G020R-S078D-G118S-Q245R | ++ |
| A098Q-S099T-S101A-S103A-V104L | ++ |
| T022A-G097A-S101N-S103A-V104I-G159D-S188D-L217Q-A232V-Q245R-N248D-E271F | ++ |
| G020K-S024F-S078N-S128D-T213A-L217E | ++ |
| T022A-G097A-S101N-S103A-V104I-G159D-S188D-A232V-Q245R-N248D-E271F | ++ |
| G020R-S078D-G118S-S188D-Q245R-H249R | ++ |
| T022A-G097A-S101N-S103A-V104I-P129E-G159D-S188D-A232V-Q245R-N248D-E271F | ++ |
| T022Q-S101G-S103A-V104I-G159D-S188D-A232S-Q245V-N248E | ++ |
| T022A-S024G-S078N-G097S-S101N-S103A-V104I-G159D-S188D-L217Q-A232V-Q245R-N248D-E271F | ++ |
| T022A-S101G-S103A-V104I-P129E-A158E-S188D-A232V-Q245R-N248D-E271F | ++ |
| T022A-S078N-S101N-S103A-V104I-G159D-S188D-A232V-Q245R-N248D-E271F | ++ |
| T022A-S024G-N076D-G097S-A098E-S101G-S103A-V104I-G159D-S188D-A232V-Q245R-N248D-E271F | ++ |
| T022A-N076D-S101G-S103A-V104I-A158E-S188D-A232V-Q245R-N248D-E271F | ++ |
| G020K-T022L-S078N-S166D-T213A | ++ |
| S101G-S103A-V104L-S128N | ++ |
| T022A-S101G-S103A-V104I-N116L-S128L-G159D-S188D-T213A-A232V-Q245R-N248D-E271F | ++ |
| T022A-S101G-S103A-V104I-G159D-S188D-A232V-Q245T-N248D | ++ |
| T022A-G097A-S101Q-S103A-V104I-S128A-G159D-S188D-A232V-Q245R-N248D-E271F | ++ |
| S099G-G100S | ++ |
| T022A-N076D-G097A-S101Q-S103A-V104I-S128A-G159D-S188D-L217Q-A232V-Q245R-N248D-E271F | ++ |
| G020R-N062E-S078D-G118D-P129E-Q245R-N248D-H249R | ++ |
| T022A-S078N-G097S-S101Q-S103A-V104I-Q109G-S128A-G159D-S188D-A232V-Q245R-N248D-E271F | ++ |
| T022A-S101N-S103A-V104I-S128A-G159D-S188D-L217Q-A232V-Q245R-N248D-E271F | ++ |
| T022A-S078N-G097A-S101G-S103A-V104I-S128A-G159D-S188D- | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| A232V-Q245R-N248D-E271F | |
| T022A-N116L-A158E-S188D | ++ |
| S099A-G102A-V104L | ++ |
| T033S-N116L-A158E-A272D | ++ |
| T022Q-S101G-S103A-V104I-G159D-S188E-A232T-Q245T-N248E | ++ |
| S101G-S103A-V104I-N116A-S128N-Y209A-G211Q-A232V | ++ |
| G020K-T022L-S078N-G118R-S128D-T213A-L217E | ++ |
| T022A-N076D-G097A-S101Q-S103A-V104I-G159D-S188D-L217Q-A232V-Q245R-N248D-E271F | ++ |
| T022A-S024R-T033S-N116L-G118R-S166D-S188D | ++ |
| T022L-S024F-G118R-S166D-T213A | ++ |
| T022A-S103A-V104I-L111V-S128N | ++ |
| T022A-N076D-S078N-G097S-S101N-S103A-V104I-G159D-S188D-L217Q-A232V-Q245R-N248D-E271F | ++ |
| T022A-G097A-S101N-S103A-V104I-P129S-G159D-S188D-L217Q-A232V-Q245R-N248D-E271F | ++ |
| T022A-S024G-S078N-S101N-S103A-V104I-G159D-S188D-L217Q-A232V-Q245R-N248D-E271F | ++ |
| T022A-S101G-S103A-V104I-G159D-S188D-A232V-V244A-Q245R-N248D-A270V-E271F-A272V | ++ |
| T022A-T033S-N116L-G118R-S128I | ++ |
| T022A-S024G-N076D-S078N-G097A-S101G-S103A-V104I-S128A-G159D-S188D-A232V-Q245R-N248D-E271F | ++ |
| S024R-S078G-G118S-T180N-Q245R-N248D | ++ |
| S099G-S103G-V104I | ++ |
| T022A-S101N-S103A-V104I-S128A-G159D-S188D-A232V-Q245R-N248D-E271F | ++ |
| T022A-G097A-S101Q-S103A-V104I-S128A-G159D-S188D-L217Q-A232V-Q245R-N248D-E271F | ++ |
| T022A-S024G-G097S-S101Q-S103A-V104I-S128A-G159D-S188D-L217Q-A232V-Q245R-N248D-E271F | ++ |
| N062E-N116L-A158E | ++ |
| T022A-S024G-N076D-S101N-S103A-V104I-S128A-G159D-S188D-A232V-Q245R-N248D-E271F | ++ |
| T022L-S024F-S078N-S166D-T213A-L217E | ++ |
| T022A-S101G-S103A-V104I-G159E-S188D-A232V-Q245R-N248D-E271F | ++ |
| T022A-S101N-S103A-V104I-P129S-G159D-S188D-A232V-Q245R-N248D-E271F | ++ |
| T022A-S024G-G097S-S101Q-S103A-V104I-S128A-G159D-S188D-A232V-Q245R-N248D-E271F | ++ |
| T022A-S024R-N076D-S101G-S103A-V104I-I107V-P129E-G159D-S188D-A232V-Q245R-N248D-A270V-E271F | ++ |
| S024R-N062E-N116L-G118R-S128I-A158E-S188D | ++ |
| A016S-S024F-S101G-S103A-V104I-N116L-Y209V-G211Q-A232V | ++ |
| T022A-S024R-S101G-S103A-V104I-P129E-G159D-S188D-A232V-N238Y-Q245R-N248D-E271F-A272V | ++ |
| T022A-S024G-N076D-G097A-S101G-S103A-V104I-G159D-S188D-L217Q-A232V-Q245R-N248D-E271F | ++ |
| T022A-N062Q-S101N-S103A-V104I-G159D-S188D-L217Q-A232V-Q245R-N248D-E271F | ++ |
| S024R-N062E-A158E-S166D-S188D | ++ |
| T022A-S101G-S103A-V104I-G159D-S188D-A232S-Q245V-N248E | ++ |
| N062E-N116L-G118R-S128I | ++ |
| T033S-N062E-N116L-G118R-A158E-S166D | ++ |
| G020R-N062E-S078G-G118D-P129E-S188D-Q245R-H249R | ++ |
| T022A-N076D-S078N-S101N-S103A-V104I-G159D-S188D-L217Q-A232V-Q245R-N248D-E271F | ++ |
| T022A-S078N-S101N-S103A-V104I-S128A-G159D-S188D-L217Q-A232V-Q245R-N248D-E271F | ++ |
| G020K-S166D-T213A | ++ |
| T022A-S024G-N076D-G097S-S101Q-S103A-V104I-S128A-G159D-S188D-L217Q-A232V-Q245R-N248D-E271F | ++ |
| T033S-N116L-G118R-A158E-S166D-S188D | ++ |
| S024R-S078D-G118S-P129E-S188D-N248D | ++ |
| S024R-N062E-S078G-G118D-G159D-N248D | ++ |
| T022A-G097A-S101N-S103A-V104I-L124V-P129E-G159D-S188D-A232V-Q245R-N248D-E271F | ++ |
| T022L-S024F-S078N-S166D-T213A | ++ |
| G020R-S024R-S078G-G118D-S188D-H249R | ++ |
| T022A-G097A-S101Q-S103A-V104I-P129E-G159D-S188D-A232V- | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| Q245R-N248D-E271F | |
| A016S-T022A-V104I-L111V | ++ |
| T022A-S078N-G097A-S101Q-S103A-V104I-S128A-G159D-S188D-L217Q-A232V-Q245R-N248D-E271F | ++ |
| S024F-T033S-S101G-S103A-V104I-N116L-Y209V-A232V | ++ |
| T022A-S101G-S103A-V104I-P129E-A158E-G159E-S188D-A232V-Q245R-N248D-E271F | ++ |
| T022A-N062E-N116L-G118R | ++ |
| T022A-N076D-G097S-S101G-S103A-V104I-S128A-G159D-S188D-A232V-Q245R-N248D-E271F | ++ |
| A016S-T022A-S101G-V104I-L111V-L148I | ++ |
| S024R-N116L-S128I-A158E | ++ |
| T022A-S024F-S101G-S103A-V104I-N116A-Y209A-A232V | ++ |
| T022A-S024R-N076D-S101G-S103A-V104I-G159D-S188D-A232V-Q245R-N248D-A270V-E271F-A272V | ++ |
| N062E-S078D-G118S-G159D-S188D-K235R-Q245R | ++ |
| T022A-S101Q-S103A-V104I-S128A-P129S-G159D-S188D-L217Q-A232V-Q245R-N248D-E271F | ++ |
| T022A-G097S-S101G-S103A-V104I-S128A-G159D-S188D-L217Q-A232V-Q245R-N248D-E271F | ++ |
| T022A-S103G-V104I-S128N-L148I | ++ |
| T022A-N076D-S078N-S101G-S103A-V104I-S128A-G159D-S188D-A232V-Q245R-N248D-E271F | ++ |
| T022A-N076D-S078N-G097S-S101G-S103A-V104I-G159D-S188D-L217Q-A232V-Q245R-N248D-E271F | ++ |
| T022A-S024G-S078N-G097S-S101N-S103A-V104I-S128A-G159D-S188D-A232V-Q245R-N248D-E271F | ++ |
| T022A-S101N-S103A-V104I-L124V-S128A-P129S-G159D-S188D-A232V-Q245R-N248D-E271F | ++ |
| T022A-S024F-S101G-S103A-V104I-N116L-Y209V-G211Q-T213A-A232V | ++ |
| S024F-G118R-S128D | ++ |
| N076D-S101A-S103A-V104I-A232V-Q245R | ++ |
| T022A-S101Q-S103A-V104I-L124V-S128A-G159D-S188D-A232V-Q245R-N248D-E271F | ++ |
| T022A-N076D-S101Q-S103A-V104I-S128A-G159D-S188D-L217Q-A232V-Q245R-N248D-E271F | ++ |
| T033S-S166D | ++ |
| T022A-S024G-S078N-S101G-S103A-V104I-G159D-S188D-A232V-Q245R-N248D-E271F | ++ |
| T022A-S078N-G097S-S101N-S103A-V104I-G159D-S188D-A232V-Q245R-N248D-E271F | ++ |
| A114L | ++ |
| G020R-S024R-S078D-G118S-P129E-G159D-K237E-N248D-H249R | ++ |
| G020K-T022L-S024F-G118R-S128D-T213A-L217E | ++ |
| A016S-S101A-S103A-V104L-S128N-L148I | ++ |
| T022A-N076D-S078N-S101Q-S103A-V104I-G159D-S188D-L217Q-A232V-Q245R-N248D-E271F | ++ |
| T022A-N076D-S078N-G097S-S101N-S103A-V104I-S128A-G159D-S188D-A232V-Q245R-N248D-E271F | ++ |
| T022A-G097A-S101N-S103A-V104I-L124V-P129S-G159D-S188D-A232V-Q245R-N248D-E271F | ++ |
| T022A-S024G-S078N-S101Q-S103A-V104I-P129E-G159D-S188D-L217Q-A232V-Q245R-N248D-E271F | ++ |
| A016S-T022A-S101G-S103A-V104I-N116L-Y209V-A232V | ++ |
| T022A-G097A-S101N-S103A-V104I-L124V-S128A-P129S-G159D-S188D-A232V-Q245R-N248D-E271F | ++ |
| T022A-S024R-T033S-G118R-S188D | ++ |
| T022A-T033S-N116L-G118R-S128I-S188D | ++ |
| T022A-S024R-T033S-S128I-A158E-S188D | ++ |
| T022A-S101Q-S103A-V104I-S128A-G159D-S188D-L217Q-A232V-Q245R-N248D-E271F | ++ |
| A016S-T022A-S103A-L148I | ++ |
| T022A-N076D-S078N-G097A-S101N-S103A-V104I-S128A-G159D-S188D-A232V-Q245R-N248D-E271F | ++ |
| N018S-T022A-S024G-S101N-S103A-V104I-G159D-S188D-L217Q-A232V-Q245R-N248D-E271F | ++ |
| T022A-N076D-S078N-G097A-S101Q-S103A-V104I-G159D-S188D-A232V-Q245R-N248D-E271F | ++ |
| T022A-G097S-S101N-S103A-V104I-S128A-G159D-S188D-L217Q-A232V-Q245R-N248D-E271F | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-N076D-S078N-S101N-S103A-V104I-S128A-G159D-S188D-L217Q-A232V-Q245R-N248D-E271F | ++ |
| T022A-S024R-S101G-S103A-V104I-P129E-G159D-S188D-A232V-Q245R-N248D-E271F | ++ |
| V104L-L111V | ++ |
| T066V | ++ |
| T022A-G097A-S101N-S103A-V104I-S128A-P129S-G159D-S188D-L217Q-A232V-Q245R-N248D-E271F | ++ |
| T022A-S024G-S078N-G097S-S101Q-S103A-V104I-Q109G-G159D-S188D-L217Q-A232V-Q245R-N248D-E271F | ++ |
| S099T-S101A-S103G | ++ |
| T253L | ++ |
| N076D-S101A-S103A-V104I-P210I-M222S-A232V-Q245R | ++ |
| S099G-S101A-G102A | ++ |
| T022A-G097A-S101N-S103A-V104I-L124V-S128A-G159D-S188D-L217Q-A232V-Q245R-N248D-E271F | ++ |
| T022A-S101G-S103A-V104I-P129E-G159D-S188D-A232V-Q245R-N248D-A270V-E271F-A272V | ++ |
| T022A-S024G-G097A-S101N-S103A-V104I-G159D-S188D-L217Q-A232V-Q245R-N248D-E271F | ++ |
| S024R-S078D-G118D-S188D-Q245R | ++ |
| T022A-S103G-V104L-S128N | ++ |
| S024R-N116L-G118R | ++ |
| T022A-N076D-S101G-S103A-V104I-I107V-N123S-P129E-G159D-S188D-A232V-N238Y-Q245R-N248D-A270V-E271F | ++ |
| T022A-N076D-S078N-S101Q-S103A-V104I-S128A-G159D-S188D-A232V-Q245R-N248D-E271F | ++ |
| T022A-N076D-S078N-G097S-S101N-S103A-V104I-S128A-G159D-S188D-L217Q-A232V-Q245R-N248D-E271F | ++ |
| T022A-N043R-N076D-S101G-S103A-V104I-P129E-A158E-G159E-S188D-A232V-Q245R-N248D-E271F-A272V | ++ |
| T022A-S024G-N076D-S078N-S101N-S103A-V104I-S128A-G159D-S188D-A232V-Q245R-N248D-E271F | ++ |
| T033S-N062E | ++ |
| T022A-N076D-S101G-S103A-V104I-A158E-S188D-A232V-Q245R-N248D-E271F-A272V | ++ |
| A098Q-S099A-G102A | ++ |
| G118R-S128I-A158E-S188D | ++ |
| T022A-S024G-N076D-G097A-S101G-S103A-V104I-S128A-G159D-S188D-A232V-Q245R-N248D-E271F | ++ |
| T022A-G097S-S101N-S103A-V104I-Q109G-G159D-S188D-L217Q-A232V-Q245R-N248D-E271F | ++ |
| T022A-S103A-V104L-S128N | ++ |
| T022A-S101N-S103A-V104I-S128A-P129S-G159D-S188D-L217Q-A232V-Q245R-N248D-E271F | ++ |
| T022A-S024G-G097S-S101Q-S103A-V104I-G159D-S188D-A232V-Q245R-N248D-E271F | ++ |
| T022A-T033S-A158E | ++ |
| S024R-S188D | ++ |
| T022A-S101G-S103A-V104I-G159D-S188D-A232L-Q245V-N248H-E271T | ++ |
| S024R-T033S-N062E | ++ |
| S024R-T033S-S166D | ++ |
| T022A-T033S-S101G-S103A-V104I-G118R-G159D-S188D-A232V-Q245R-N248D-E271F | ++ |
| T022A-S024R-N062E-A158E-S166D-S188D | ++ |
| T022A-N076D-G097A-S101N-S103A-V104I-G159D-S188D-L217Q-A232V-Q245R-N248D-E271F | ++ |
| T022A-S024G-N076D-G097S-S101Q-S103A-V104I-G159D-S188D-L217Q-A232V-Q245R-N248D-E271F | ++ |
| S024R-S101A-S103A-V104I-S188D-P210I-M222S-A232V-Q245R | ++ |
| T022A-N076D-G097S-S101N-S103A-V104I-G159D-S188D-L217Q-A232V-Q245R-N248D-E271F | ++ |
| T022L-G118R-S128D-T213A | ++ |
| T022A-S101G-S103A-V104I-G159D-S188D-A232V-Q245V-N248E | ++ |
| T022A-N076D-G097S-S101Q-S103A-V104I-G159D-S188D-A232V-Q245R-N248D-E271F | ++ |
| T022A-S024G-N076D-G097A-S101G-S103A-V104I-G159D-S188D-A232V-Q245R-N248D-E271F | ++ |
| T022A-S024R-S101G-S103A-V104I-P129E-A158E-S188D-A232V-Q245R-N248D-E271F | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S056G | ++ |
| G020R-N062E-S078D-G118S-P129E-S188D-Q245R-N248D-H249R | ++ |
| T022A-N076D-G097S-S101Q-S103A-V104I-Q109G-S128A-G159D-S188D-A232V-Q245R-N248D-E271F | ++ |
| S024R-S078D-G118S-P129E-S188D-Q245R-H249R | ++ |
| T022A-N076D-G097S-S101Q-S103A-V104I-S128A-G159D-S188D-L217Q-A232V-Q245R-N248D-E271F | ++ |
| T022A-S101Q-S103A-V104I-L124V-P129E-G159D-S188D-A232V-Q245R-N248D-E271F-R275H | ++ |
| T022A-S024G-S078N-G097A-S101G-S103A-V104I-S128A-G159D-S188D-A232V-Q245R-N248D-E271F | ++ |
| T022A-S024G-R045S-S101G-S103A-V104I-G159D-S188D-A232V-Q245R-N248D-E271F | ++ |
| T022A-N076D-S101G-S103A-V104I-P129E-G159D-S188D-A232V-Q245R-N248D-A270V-E271F-A272V | ++ |
| T022A-S101G-S103A-V104I-L126I-P129E-G159D-S188D-A232V-Q245R-N248D-E271F | ++ |
| T022A-S024G-N076D-S101N-S103A-V104I-G159D-S188D-L217Q-A232V-Q245R-N248D-E271F | ++ |
| T022A-N062D-S101G-S103A-V104I-N116L-G159D-S188D-T213A-A232V-Q245R-N248D-E271F | ++ |
| T022A-S024G-N076D-S078N-G097S-S101Q-S103A-V104I-G159D-S188D-A232V-Q245R-N248D-E271F | ++ |
| T022A-S101G-S103A-V104I-G159D-S188D-A232V-Q245R-N248D-A270V-E271F-A272V | ++ |
| S024R-N062E-S078G-G118D-P129E-Q245R-H249R | ++ |
| T022A-S101G-S103A-S128N | ++ |
| G020R-S024R-S078G-G118D-P129E-N248D-H249R | ++ |
| N116L-G118R-P129E-S188D | ++ |
| T022A-S101N-S103A-V104I-G159D-S188D-L217Q-A232V-Q245R-N248D-E271F | ++ |
| T022A-S101A-S103A-V104I-L126I-S128A-P129S-G159D-S188D-A232V-Q245R-N248D-E271F | ++ |
| T022A-N076D-S101G-S103A-V104I-Q109G-G159D-S188D-L217Q-A232V-Q245R-N248D-E271F | ++ |
| T022A-S024G-G097A-S101Q-S103A-V104I-S128A-G159D-S188D-A232V-Q245R-N248D-E271F | ++ |
| G020R-S078D-G118S-P129E-G159D-S188D | ++ |
| T022A-T033S-G118R-S166D-S188D | ++ |
| S078G-G118D-P129E-G159D-SI88D | ++ |
| T022A-S024G-G097S-S101N-S103A-V104I-G159D-S188D-L217Q-A232V-Q245R-N248D-E271F | ++ |
| T022A-N076D-S101Q-S103A-V104I-G159D-S188D-L217Q-A232V-Q245R-N248D-E271F | ++ |
| T022A-S024R-S101G-S103A-V104I-P129E-S188D-A232V-Q245R-N248D-E271F-A272V | ++ |
| T022A-S103A-V104I-L111V | ++ |
| T022A-S024G-S078N-S101N-S103A-V104I-G159D-S188D-A232V-Q245R-N248D-E271F | ++ |
| T022A-N076D-S101N-S103A-V104I-S128A-G159D-S188D-L217Q-A232V-Q245R-N248D-E271F | ++ |
| T022A-N076D-A085T-S101G-S103A-V104I-A158E-S188D-A232V-Q245R-N248D-E271F | ++ |
| T022A-S024G-S078N-E089G-S101Q-S103A-V104I-G159D-S188D-L217Q-A232V-Q245R-N248D-E271F | ++ |
| T022A-S101Q-S103A-V104I-Q109N-G159D-S188D-A232V-Q245R-N248D-E271F | ++ |
| T022A-N076D-S078N-S101Q-S103A-V104I-G159D-S188D-A232V-Q245R-N248D-E271F | ++ |
| T022A-S101N-S103A-V104I-L124V-S128A-P129E-G159D-S188D-L217Q-A232V-Q245R-N248D-E271F | ++ |
| T022A-S024G-G097A-S101Q-S103A-V104I-G159D-S188D-A232V-Q245R-N248D-E271F | ++ |
| T022A-G097A-S101Q-S103A-V104I-S128A-P129E-G159D-S188D-A232V-Q245R-N248D-E271F | ++ |
| T022A-S101G-S103A-V104I-P129E-G159D-S188D-A232V-Q245R-N248D-E271F-A272V | ++ |
| S101G-S103A | ++ |
| L196S | ++ |
| T022A-S024G-S078N-S101G-S103A-V104I-S128A-G159D-S188D-L217Q-A232V-Q245R-N248D-E271F | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-G097A-S101G-S103A-V104I-G159D-S188D-L217Q-A232V-Q245R-N248D-E271F | ++ |
| T022A-S024G-N076D-S078N-S101N-S103A-V104I-Q109N-S128A-0159D-S188D-A232V-Q245R-N248D-E271F | ++ |
| T022A-S078N-S101G-S103A-V104I-G159D-S188D-A232V-Q245R-N248D-E271F | ++ |
| T022A-G097A-S101Q-S103A-V104I-L124V-S128A-G159D-S188D-A232V-Q245R-N248D-E271F | ++ |
| E271S | ++ |
| A098Q-S099T-G100S-S101A | ++ |
| T022A-S024G-N076D-G097A-S101N-S103A-V104I-Q109G-G159D-S188D-L217Q-A232V-Q245R-N248D-E271F | ++ |
| T022A-S101Q-S103A-V104I-Q109N-S128A-G159D-S188D-L217Q-A232V-Q245R-N248D-E271F | ++ |
| T022A-G097A-S101Q-S103A-V104I-Q109N-G159D-S188D-A232V-Q245R-N248D-E271F | ++ |
| T022A-S101Q-S103A-V104I-S128A-G159D-S188D-A232V-Q245R-N248D-E271F | ++ |
| T022A-S024G-S078N-G097A-S101Q-S103A-V104I-S128A-G159D-S188D-L217Q-A232V-Q245R-N248D-E271F | ++ |
| T022A-G097S-S101N-S103A-V104I-G159D-S188D-L217Q-A232V-Q245R-N248D-E271F | ++ |
| T022A-S024R-N076D-S101G-S103A-V104I-P129E-G159E-S188D-A232V-Q245R-N248D-E271F | ++ |
| R019H-T022A-N043R-N076D-S101G-S103A-V104I-P129E-S188D-A232V-Q245R-N248D-E271F-A272V | ++ |
| T022A-S024G-N076D-S078N-G097S-S101Q-S103A-V104I-S128A-G159D-S188D-A232V-Q245R-N248D-E271F | ++ |
| T022L-S078N-S166D-T213A | ++ |
| G020R-S024R-S078D-G118D-Q245R-N248D | ++ |
| N269K | ++ |
| T022A-S101N-S103A-V104I-Q109G-G159D-S188D-A232V-Q245R-N248D-E271F | ++ |
| G097P-V139A | ++ |
| T022A-S101Q-S103A-V104I-S128A-P129S-G159D-S188D-A232V-Q245R-N248D-E271F | ++ |
| S024F-S101G-S103A-V104I-N116A-S128N-Y209V-G211Q-A232V | ++ |
| T022A-S101N-S103A-V104I-L124V-S128A-G159D-S188D-L217Q-A232V-Q245R-N248D-E271F | ++ |
| T022A-S024G-G097A-S101G-S103A-V104I-S128A-G159D-S188D-L217Q-A232V-Q245R-N248D-E271F | ++ |
| N062E-S078G-G118D-G159D-S188D-Q245R-H249R | ++ |
| T022A-S024G-S101N-S103A-V104I-S128A-G159D-S188D-L217Q-A232V-Q245R-N248D-E271F | ++ |
| N062E-S078D-G118D-P129E-G159D-Q245R-H249R | ++ |
| T022A-G097A-S101N-S103A-V104I-S128A-G159D-S188D-A232V-Q245R-N248D-E271F | ++ |
| T022A-S078N-S101Q-S103A-V104I-G159D-S188D-L217Q-A232V-Q245R-N248D-E271F | ++ |
| S128I-S188D | ++ |
| T022A-S024G-N076D-G097S-S101Q-S103A-V104I-Q109N-S128A-G159D-S188D-L217Q-A232V-Q245R-N248D-E271F | ++ |
| T022A-N076D-S078N-S101G-S103A-V104I-G159D-S188D-L217Q-A232V-Q245R-N248D-E271F | ++ |
| S166D-L217E | ++ |
| T022A-S024G-N076D-G097S-S101G-S103A-V104I-G159D-S188D-A232V-Q245R-N248D-E271F | ++ |
| A098Q-S099G-S101A | ++ |
| T022A-S024R-S101G-S103A-V104I-G159D-S188D-A232V-Q245R-N248D-A270V-E271F-A272V | ++ |
| T022A-V068A-S101G-S103A-V104I-G118R-G159D-S188D-T213A-A232V-Q245R-N248D-E271F | ++ |
| T022A-S024G-S078N-S101Q-S103A-V104I-Q109N-G159D-S188D-A232V-Q245R-N248D-E271F | ++ |
| T022A-N076D-S101N-S103A-V104I-S128A-G159D-S188D-A232V-Q245R-N248D-E271F | ++ |
| T022A-S101G-S103A-V104I-P129S-G159D-S188D-L217Q-A232V-Q245R-N248D-E271F | ++ |
| T022A-S024G-N076D-G097S-S101Q-S103A-V104I-Q109N-G159D-S188D-A232V-Q245R-N248D-E271F | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S101Q-S103A-V104I-S128A-P129E-G159D-S188D-A232V-Q245R-N248D-E271F | ++ |
| S128I-A158E-S166D | ++ |
| T022A-G097A-S101N-S103A-V104I-L124V-S128A-P129S-G159D-S188D-L217Q-A232V-Q245R-N248D-E271F | ++ |
| T022A-S024R-N076D-S101G-S103A-V104I-P129E-A158E-S188D-A232V-Q245R-N248D-E271F | ++ |
| S024R-N062E-S078D-G118D | ++ |
| T022A-G097A-S101N-S103A-V104I-L126I-G159D-S188D-A232V-Q245R-N248D-E271F | ++ |
| T022A-S101G-S103A-V104I-S128A-P129S-G159D-S188D-A232V-Q245R-N248D-E271F | ++ |
| S024F-S078N-G118R-N204K-T213A-L217E | ++ |
| G020R-N062E-S078D-G118D-G159D-N248D | ++ |
| T022A-S024G-N076D-G097A-S101Q-S103A-V104I-G159D-S188D-A232V-Q245R-N248D-E271F | ++ |
| T022A-G097A-S101Q-S103A-V104I-L124V-P129E-G159D-S188D-L217Q-A232V-Q245R-N248D-E271F | ++ |
| T022A-S101G-S103A-V104I-S128A-G159D-S188D-A232V-Q245R-N248D-E271F | ++ |
| G097P-S099G-S101G-V104I | ++ |
| S024R-N062E-S078D-G118D-N248D | ++ |
| T022A-S101Q-S103A-V104I-G159D-S188D-L217Q-A232V-Q245R-N248D-E271F | ++ |
| T022A-S101G-S103A-V104I-L124V-S128A-P129E-G159D-S188D-A232V-Q245R-N248D-E271F | ++ |
| S128I | ++ |
| G020K-T022L-S128D-T213A-L217E | ++ |
| G020K-G118R-S166D-T213A | ++ |
| A016S-T022A-L111V | ++ |
| S078D-G118D-P129E-N248D-H249R | ++ |
| T022A-N076D-S101G-S103A-V104I-G159D-S188D-A232V-Q245R-N248D-E271F | ++ |
| S024R-S128I-A158E-S166D-A194T | ++ |
| T022A-N043R-S101G-S103A-V104I-A158E-G159E-S188D-A232V-Q245R-N248D-E271F | ++ |
| T022A-N076S-S101G-S103A-V104I-G159D-S188D-A232V-N238Y-Q245R-N248D-E271F-A272V | ++ |
| T022A-G097A-S101Q-S103A-V104I-P129S-G159D-S188D-L217Q-A232V-Q245R-N248D-E271F | ++ |
| I022A-S101N-S103A-V104I-Q109N-G159D-S188D-A232V-Q245R-N248D-E271F | ++ |
| T022A-S024R-S101G-S103A-V104I-P129E-S188D-A232V-Q245R-N248D-E271F | ++ |
| G020R-S078D-G118D-P129E-S188D | ++ |
| T022A-S101G-S103A-V104I | ++ |
| T022A-G097A-S101N-S103A-V104I-S128A-G159D-R186H-S188D-A232V-Q245R-N248D-E271F | ++ |
| T022A-S101G-S103A-V104I-L124V-S128A-P129S-G159D-S188D-A232V-Q245R-N248D-E271F | ++ |
| G020K-S024F-S078N-G118R-S128D-S166D-T213A | ++ |
| G020R-N062E-S078D-G118D-G159D-S188D | ++ |
| T022A-G097S-S101Q-S103A-V104I-G159D-S188D-L217Q-A232V-Q245R-N248D-E271F | ++ |
| T022A-S024G-S078N-G097A-S101N-S103A-V104I-S128A-G159D-S188D-A232V-Q245R-N248D-E271F | ++ |
| T033S-N116L-G118R-S128I-S166D | ++ |
| T022A-S024F-S101G-S103A-V104I-N116L-Y209A-A232V | ++ |
| T022L-S024F-S078N-G118R-T213A-L217E | ++ |
| T022A-N076D-G097A-S101Q-S103A-V104I-S128A-G159D-S188D-A232V-Q245R-N248D-E271F | ++ |
| T022A-N076D-S078N-S101G-S103A-V104I-G159D-S188D-A232V-Q245R-N248D-E271F | ++ |
| T022A-S024G-N076D-S078N-G097S-S101N-S103A-V104I-G159D-S188D-A232V-Q245R-N248D-E271F | ++ |
| T022A-N076D-S101N-S103A-V104I-Q109G-S128A-G159D-S188D-A232V-Q245R-N248D-E271F | ++ |
| T022A-S024G-S101Q-S103A-V104I-Q109N-S128A-G159D-S188D-A232V-Q245R-N248D-E271F | ++ |
| N062E-S078G-G118S-P129E-S188D | ++ |
| G020R-N062E-S078D-G118D-G159D-Q245R-H249R | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-G097S-S103A-V104I-Q109N-S128A-G159D-S188D-A232V-Q245R-N248D-E271F | ++ |
| T022A-S024R-T033S-N062E-N116L-S166D-S188D | ++ |
| G020R-S078G-G118S-S188D-Q245R-N248D-H249R | ++ |
| T022A-G097A-S101G-S103A-V104I-S128A-G159D-S188D-A232V-Q245R-N248D-E271F | ++ |
| G020R-N062E-S078G-G118D-Q245R-N248D-H249R | ++ |
| T022A-S024G-G097A-S101Q-S103A-V104I-G159D-S188D-L217Q-A232V-Q245R-N248D-E271F | ++ |
| T022A-N076D-S078N-G097S-S101Q-S103A-V104I-G159D-S188D-A232V-Q245R-N248D-E271F | ++ |
| T022A-S078N-S101G-S103A-S128A-G159D-S188D-L217Q-A232V-Q245R-N248D-E271F | ++ |
| T022A-S078N-S101Q-S103A-V104I-Q109N-G159D-S188D-A232V-Q245R-N248D-E271F | ++ |
| G020K-T022L-S024F-S078N-S166D-T213A | ++ |
| A085T-G097P-A098Q | ++ |
| N062E-S078G-G118D-P129E-G159D-Q245R-N248D-H249R | ++ |
| T022A-S024G-N076S-S078N-G097A-S101N-S103A-V104I-S128A-G159D-S188D-A232V-Q245R-N248D-E271F | ++ |
| T022A-S078N-S101Q-S103A-V104I-S128A-G159D-S188D-A232V-Q245R-N248D-E271F | ++ |
| Q012R-T022A-S101G-S103A-V104I-N116L-Y209A-T213A-A232V | ++ |
| T022A-N076D-G097S-S101N-S103A-V104I-S128A-G159D-S188D-A232V-Q245R-N248D-E271F | ++ |
| T022A-S024G-S101G-S103A-V104I-G159D-S188D-A232V-Q245R-N248D-E271F | ++ |
| N116L-A158E-S166D-S188D | ++ |
| T022A-S024R-N076D-S101G-S103A-V104I-A158E-G159E-S188D-A232V-Q245R-N248D-E271F | ++ |
| T022A-S024G-N076D-S078N-G097A-S101Q-S103A-V104I-Q109N-G159D-S188D-A232V-Q245R-N248D-E271F | ++ |
| S024R-T033S-S128I-A158E | ++ |
| S024R-N116L-G118R-S128I-S188D | ++ |
| T022A-N043R-S101G-S103A-V104I-P129E-S188D-A232V-Q245R-N248D-E271F | ++ |
| N062E-S078D-G118D-S188D-H249R | ++ |
| G020R-N062E-S078D-G118S-P129E-G159D-S188D | ++ |
| G020K-T022L-S078D-G118D-P129E-N248D-H249R | ++ |
| T022A-S024R-N043R-N076D-S101G-S103A-V104I-A158E-S188D-A232V-Q245R-N248D-E271F | ++ |
| T022A-N076D-G097A-S101G-S103A-V104I-G159D-S188D-L217Q-A232V-Q245R-N248D-E271F | ++ |
| T022A-G097A-S101N-S103A-V104I-L124V-P129S-G159D-S188D-L217Q-A232V-Q245R-N248D-E271F | ++ |
| T022A-S101G-S103A-V104I-G159D-S188D-A232V-Q245V-N248D | ++ |
| N062E-S078D-G118S-P129E-S188D-Q245R | ++ |
| S024R-N062E-G118R-S128I-A158E-S188D | ++ |
| T022A-S101N-S103A-V104I-P129E-G159D-S188D-A232V-Q245R-N248D-E271F | ++ |
| G020K-T022L-S078N-S128D-L217E | ++ |
| T022A-N062E-N116L-A158E-S188D | ++ |
| T022A-S101A-V104I-L111V | ++ |
| S166D-T213A | ++ |
| T022A-G097A-S101N-S103A-V104I-L124V-S128A-P129E-G159D-S188D-A232V-Q245R-N248D-E271F | ++ |
| T022L-S024F-S166D-T213A | ++ |
| T022A-N076D-S101Q-S103A-V104I-G159D-S188D-A232V-Q245R-N248D-E271F | ++ |
| T022A-S024R-S101G-S103A-V104I-P129E-G159D-S188D-A232V-N238Y-Q245R-N248D-A270V-E271F | ++ |
| T022A-G097S-S101Q-S103A-V104I-Q109G-S128A-G159D-S188D-A232V-Q245R-N248D-E271F | ++ |
| S024R-S128I-A158E-S166D | ++ |
| N062E-S078D-G118S-N248D-H249R | ++ |
| T022A-S024G-S101Q-S103A-V104I-Q109G-G159D-S188D-A232V-Q245R-N248D-E271F | ++ |
| T022A-S024G-N076D-S078N-G097S-S101Q-S103A-V104I-G159D-S188D-L217Q-A232V-Q245R-N248D-E271F | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022L-S024F-S078N-S166D | ++ |
| T022A-S101G-S103A-V104I-P129E-A158E-S188D-A232V-Q245R-N248D-E271F-A272V | ++ |
| S078D-G118S-P129E-N243D-H249R | ++ |
| T022A-S024G-N076D-S078N-S101N-S103A-V104I-S128A-G159D-S188D-L217Q-A232V-Q245R-N248D-E271F | ++ |
| T022A-S078N-S101G-S103A-V104I-S128A-G159D-S188D-A232V-Q245R-N248D-E271F | ++ |
| T022A-S024R-N062E-G118R | ++ |
| T022A-N076D-S101G-S103A-V104I-P129E-S188D-A232V-Q245R-N248D-E271F-A272V | ++ |
| T022A-S078N-S101Q-S103A-V104I-S128A-G159D-S188D-L217Q-A232V-Q245R-N248D-E271F | ++ |
| S024R-S078G-G118S-Q245R | ++ |
| T022A-S024G-N076D-S078N-S101G-S103A-V104I-G159D-S188D-A232V-Q245R-N248D-E271F-A272T | ++ |
| T022A-S024G-N076D-S078N-G097A-S101Q-S103A-V104I-S128A-G159D-S188D-L217Q-A232V-Q245R-N248D-E271F | ++ |
| T022A-G097A-S101G-S103A-V104I-P129S-G159D-S188D-L217Q-A232V-Q245R-N248D-E271F | ++ |
| T022A-S024G-S078N-G097S-S101G-S103A-V104I-G159D-S188D-L217Q-A232V-Q245R-N248D-E271F | ++ |
| T022A-G097A-S101G-S103A-V104I-L124V-S128A-P129E-G159D-S188D-A232V-Q245R-N248D-E271F | ++ |
| S078N-S166D-L217E | ++ |
| T022A-N076D-S101G-S103A-V104I-I107V-P129E-G159D-S188D-A232V-N238Y-Q245R-N248D-A270V-E271F-A272V | ++ |
| Q236L | ++ |
| S078D-G118D-P129E-H249R | ++ |
| T022A-S101Q-S103A-V104I-G159D-S188D-A232V-Q245R-N248D-E271F | ++ |
| T022A-S101A-S103A-V104I-L111V | ++ |
| T022L-S024F-S078N-S128D-T213A | ++ |
| T022A-S024G-N076D-G097A-S101N-S103A-V104I-S128A-G159D-S188D-A232V-Q245R-N248D-E271F | ++ |
| G020K-S024F-S078N-G118R-S128D-L217E | ++ |
| T022A-S101G-S103A-V104I-G159E-S188D-A232V-Q245R-N248D-E271F-A272V | ++ |
| T022A-N076D-S101G-S103A-V104I-P129E-G159D-S188D-A232V-Q245R-N248D-E271F | ++ |
| T022A-S024G-S078N-S101G-S103A-V104I-G159D-S188D-L217Q-A232V-Q245R-N248D-E271F | ++ |
| T022A-G097A-S101N-S103A-V104I-P129E-G159D-S188D-L217Q-A232V-Q245R-N248D-E271F | ++ |
| T022A-N076D-S101N-S103A-V104I-Q109N-S128A-G159D-S188D-A232V-Q245R-N248D-E271F | ++ |
| T022A-N043R-N076D-S101G-S103A-V104I-A158E-G159E-S188D-A232V-Q245R-N248D-E271F-A272V | ++ |
| G020K-S128D-T213A-L217E | ++ |
| S103A-V104I-L111V-S128N | ++ |
| T022A-G097S-S101N-S103A-V104I-Q109N-S128A-G159D-S188D-L217Q-A232V-Q245R-N248D-E271F | ++ |
| T022A-S024G-S101Q-S103A-V104I-G159D-S188D-L217Q-A232V-Q245R-N248D-E271F | ++ |
| T022A-N076D-S101G-S103A-V104I-I107V-G159D-S188D-A232V-Q245R-N248D-A270V-E271F-A272V | ++ |
| V104I-L111V | ++ |
| T022A-N062Q-S101Q-S103A-V104I-P129E-G159D-S188D-A232V-Q245R-N248D-E271F | ++ |
| T022A-G097A-S101N-S103A-V104I-L124V-G159D-S188D-A232V-Q245R-N248D-E271F | ++ |
| A016S-S101A-L111V-S128N | ++ |
| T022A-S024G-N076D-S078N-G097A-S101G-S103A-V104I-G159D-S188D-L217Q-A232V-Q245R-N248D-E271F | ++ |
| T022A-S101G-S103A-V104I-G159D-S188E-A232L-Q245V-N248E | ++ |
| T022A-N076D-G097A-S101N-S103A-V104I-S128A-G159D-S188D-L217Q-A232V-Q245R-N248D-E271F | ++ |
| T022A-S024G-N076D-G097S-S101N-S103A-V104I-Q109G-G159D-S188D-A232V-Q245R-N248D-E271F | ++ |
| T022A-S101G-S103A-V104I-I107V-G159D-S188D-A232V-Q245R-N248D-E271F | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-N076D-G097S-S101G-S103A-V104I-G159D-S188D-A232V-Q245R-N248D-E271F | ++ |
| T022A-S101G-S103A-V104I-S128L-G159D-S188D-A232V-Q245R-N248D-E271F-A272D | ++ |
| T022A-S101Q-S103A-V104I-L126I-P129S-G159D-S188D-L217Q-A232V-Q245R-N248D-E271F | ++ |
| T022A-S024G-N076D-S078N-S101Q-S103A-V104I-S128A-G159D-S188D-L217Q-A232V-Q245R-N248D-E271F | ++ |
| A016S-T022A-S101G-S103A-V104I-N116L-Y209V-G211Q-T213A-A232V | ++ |
| T022A-S101Q-S103A-V104I-L124V-S128A-P129E-G159D-S188D-A232V-Q245R-N248D-E271F | ++ |
| T022A-S024G-N076D-G097S-S101N-S103A-V104I-S128A-G159D-S188D-L217Q-A232V-Q245R-N248D-E271F | ++ |
| T022A-S101N-S103A-V104I-Q109N-S128A-G159D-S188D-A232V-Q245R-N248D-E271F | ++ |
| S101G-S103A-V104I-N116A-S128N-Y209V-G211Q-A232V | ++ |
| S024R-S078G-G118S-G159D-S188D-Q245R-H249R | ++ |
| T022A-S103G-S128N-L148I | ++ |
| T022A-S101Q-S103A-V104I-S128A-P129E-G159D-S188D-L217Q-A232V-Q245R-N248D-E271F | ++ |
| T022A-N076D-G097S-S101Q-S103A-V104I-Q109N-G159D-S188D-A232V-Q245R-N248D-E271F | ++ |
| G020R-S024R-S078D-G118S-N248D | ++ |
| T022Q-S101G-S103A-V104I-G159D-S188D-A232S-Q245V-N248D-E271T | ++ |
| S078G-G118D-S188D-Q245R-N248D | ++ |
| T022A-N076D-S078N-G097S-S101N-S103A-V104I-Q109G-G159D-S188D-A232V-Q245R-N248D-E271F | ++ |
| G118R-S128D-S166D-L217E | ++ |
| G020R-S078G-G118S-P129E-Q245R-H249R | ++ |
| A016S-S024F-S101G-S103A-V104I-N116A-S128N-Y209V-T213A-A232V | ++ |
| T022A-S078N-S101Q-S103A-V104I-R145K-G159D-S188D-L217Q-A232V-Q245R-N248D-E271F | ++ |
| T022A-N043R-N076D-S101G-S103A-V104I-P129E-A158E-S188D-A232V-Q245R-N248D-E271F | ++ |
| T022A-G097A-S101Q-S103A-V104I-L126I-P129S-G159D-S188D-L217Q-A232V-Q245R-N248D-E271F | ++ |
| T022A-G097A-S101N-S103A-V104I-Q109N-G159D-S188D-A232V-Q245R-N248D-E271F | ++ |
| T022A-S024G-S078N-S101N-S103A-V104I-S128A-G159D-S188D-A232V-Q245R-N248D-E271F | ++ |
| T022A-S024R-N076D-S101G-S103A-V104I-P129E-S188D-A232V-Q245R-N248D-E271F-A272V | ++ |
| T022L-S078N-T213A | ++ |
| T022A-N076D-S078N-G097A-S101G-S103A-V104I-G159D-S188D-A232V-Q245R-N248D-E271F | ++ |
| T022A-S078N-S101G-S103A-V104I-Q109G-S128A-G159D-S188D-A232V-Q245R-N248D-E271F | ++ |
| N062E-S078G-G118S-P129E-G159D-Q245R-H249R | ++ |
| A016S-S101G-V104I-S128N-L148I | ++ |
| T022A-G118R-S188D | ++ |
| T022A-G097A-S101Q-S103A-V104I-G159D-S188D-A232V-Q245R-N248D-E271F | ++ |
| G020K-S024F-G118R-S128D-T213A | ++ |
| T022A-S101Q-S103A-V104I-P129E-G159D-S188D-A232V-Q245R-N248D-E271F | ++ |
| G020K-T022L-S024F-S078N-S128D-T213A-L217E | ++ |
| T022A-S024G-S078N-G097A-S101Q-S103A-V104I-Q109G-S128A-G159D-S188D-A232V-Q245R-N248D-E271F | ++ |
| A016S-S101G-S103A-V104I-N116L-Y209V-G211Q-A232V | ++ |
| T022A-S024G-G097A-S101Q-S103A-V104I-S128A-G159D-S188D-L217Q-A232V-Q245R-N248D-E271F | ++ |
| T022A-S101N-S103A-V104I-L124V-S128A-P129S-G159D-S188D-L217Q-A232V-Q245R-N248D-E271F | ++ |
| S099G-G100S-S103A | ++ |
| T022Q-S101G-S103A-V104I-S166D-S188E-A232T-Q245T-N248E | ++ |
| T022A-S024G-N076D-S078N-G097S-S101N-S103A-V104I-Q109N-G159D-S188D-A232V-Q245R-N248D-E271F | ++ |
| A098F-S099T-S103A-V104I | ++ |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| G020K-T022L-N062E-S078D-G118D-P129E-Q245R-N248D | ++ |
| T022L-S078N-G118R-S128D | ++ |
| T022A-S101G-S103A-V104I-N116L-Y209A-G211Q-T213A-A232V | ++ |
| T022A-S101Q-S103A-V104I-L126I-S128A-P129S-G159D-S188D-L217Q-A232V-Q245R-N248D-E271F | ++ |
| G023A-S024F-S101G-S103A-V104I-N116A-Y209V-A232V | ++ |
| T022A-S024R-N116L-G118R-S166D | ++ |
| S024R-N062E-S078D-G118D-P129E-G159D-Q245R-N248D-H249R | ++ |
| G020K-T022L-S024F-S078N-G118R-S128D-T213A | ++ |
| T022A-S024G-N076D-S078N-G097A-S101Q-S103A-V104I-S128A-G159D-S188D-A232V-Q245R-N248D-E271F | ++ |
| T022A-S024G-S101N-S103A-V104I-S128A-G159D-S188D-A232V-Q245R-N248D-E271F-T274I | ++ |
| G097P-S099A-V104L | ++ |
| G097P-S099A-S103A | ++ |
| T022A-S024G-S078N-G097S-S101Q-S103A-V104I-G159D-S188D-A232V-Q245R-N248D-E271F | ++ |
| T022A-V104L-L148I | ++ |
| T022A-S024G-G097A-S101N-S103A-V104I-S128A-G159D-S188D-A232V-Q245R-N248D-E271F | ++ |
| T022A-S024R-S101G-S103A-V104I-P129E-G159S-S188D-A232V-Q245R-N248D-E271F | ++ |
| S103G | ++ |
| T022A-S024G-N076D-S078N-S101G-S103A-V104I-Q109G-G159D-S188D-A232V-Q245R-N248D-E271F | ++ |
| T022A-S024G-N076D-G097S-S101G-S103A-V104I-G159D-S188D-L217Q-A232V-Q245R-N248D-E271F | + |
| G020K-T022L-S078N-G118R-S128D-T213A | + |
| S024R-S078G-G118S-P129E-S188D-Q245R-H249R | + |
| T022A-N076D-S101G-S103A-V104I-G159D-S188D-L217Q-A232V-Q245R-N248D-E271F | + |
| T022A-S101G-S103A-V104I-S128A-G159D-S188D-L217Q-A232V-Q245R-N248D-E271F | + |
| T022A-S024G-G097S-S101Q-S103A-V104I-Q109G-G159D-S188D-A232V-Q245R-N248D-E271F | + |
| T022A-N076D-S101N-S103A-V104I-G159D-S188D-A232V-Q245R-N248D-E271F | + |
| T033S-G118R-S128I-A158E | + |
| T022A-S103A-L111V-L148I | + |
| T022A-N076D-A085T-S101G-S103A-V104I-P129E-S188D-A232V-Q245R-N248D-E271F | + |
| T022A-S024R-N076D-S101G-S103A-V104I-A158E-S188D-A232V-Q245R-N248D-E271F | + |
| T022A-G097A-S101N-S103A-V104I-S128A-G159D-S188D-L217Q-A232V-Q245R-N248D-E271F | + |
| G020K-T022L-S078N-S128D-T213A-L217E | + |
| T022A-T033S-P129E-S166D | + |
| T022A-S024G-N076D-G097A-S101Q-S103A-V104I-G159D-S188D-L217Q-A232V-Q245R-N248D-E271F | + |
| T022A-G097A-S101N-S103A-V104I-Q109G-G159D-S188D-L217Q-A232V-Q245R-N248D-E271F | + |
| G020K-S078N-S166D-T213A | + |
| T022A-S101Q-S103A-V104I-L124V-P129S-G159D-S188D-A232V-Q245R-N248D-E271F | + |
| T022Q-S101G-S103A-V104I-G159D-S188E-A232V-Q245T-N248D | + |
| A158E-S166D-S188D | + |
| L021S-T022A-S024G-N076D-S101Q-S103A-V104I-S128A-G159D-S188D-L217Q-A232V-Q245R-N248D-E271F | + |
| T022A-G097A-S101N-S103A-V104I-L124V-S128A-P129E-G159D-S188D-L217Q-A232V-Q245R-N248D-E271F | + |
| T022A-S101G-S103A-V104I-G159D-S188D-A232V-N238Y-Q245R-N248D-A270V-E271F | + |
| T022A-T033S-N062E-N116L-S188D | + |
| T022A-S024G-S049N-N076D-S101G-S103A-V104I-G159D-S188D-L217Q-A232V-Q245R-N248D-E271F | + |
| T022A-G097S-S101Q-S103A-V104I-G159D-S188D-A232V-Q245R-N248D-E271F | + |
| G097P-A098Q-S099A-S103G-V104I | + |
| G020K-S024F-G118R-S128D-S166D | + |
| T022A-S024G-S101G-S103A-V104I-S128A-G159D-S188D-A232V-Q245R-N248D-E271F | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-G097A-S101Q-S103A-V104I-L124V-P129S-G159D-S188D-A232V-Q245R-N248D-E271F | + |
| T022A-S024R-T033S-G118R-S166D | + |
| T022A-S024R-N076D-S101G-S103A-V104I-G159D-S188D-A232V-N238Y-Q245R-N248D-A270V-E271F | + |
| N062E-S078D-G118S-P129E-N248D-H249R | + |
| T022A-S024G-V026I-S101N-S103A-V104I-G159D-S188D-L217Q-A232V-Q245R-N248D-E271F | + |
| G097P-A098Q-S099A-S101A | + |
| S078G-G118D-P129E-S188D-Q245R-H249R | + |
| T022A-G097A-S101N-S103A-V104I-L126I-P129E-G159D-S188D-L217Q-A232V-Q245R-N248D-E271F | + |
| G020R-S024R-N062E-S078G-G118D-P129E-G159D-S188D-Q236R-Q245R-N248D | + |
| T022A-N076D-S078N-S101N-S103A-V104I-G159D-S188D-A232V-Q245R-N248D-E271F | + |
| T022A-N076D-S101G-S103A-V104I-P129E-G159D-S188D-A232V-N238Y-Q245R-N248D-E271F-A272V | + |
| T022A-N076D-N077D-S078N-G097S-S101N-S103A-V104I-S128A-G159D-S188D-A232V-Q245R-N248D-E271F | + |
| T022A-N043R-N076D-S101G-S103A-V104I-P129E-A158E-S188D-A232V-Q245R-N248D-A270V-E271F | + |
| S099G-S101A-G102A-S103A | + |
| A016S-T022A-S024F-S101G-S103A-V104I-N116A-S128N-Y209V-T213A-A232V | + |
| T022A-S024G-G097A-S101N-S103A-V104I-Q109G-G159D-S188D-L217Q-A232V-Q245R-N248D-E271F | + |
| G020R-S024R-S078D-G118S-P129E-Q245R | + |
| S056C | + |
| S024R-T033S-N062E-N116L | + |
| T022A-S024G-N076D-S101G-S103A-V104I-G159D-S188D-L217Q-A232V-Q245R-N248D-E271F | + |
| T033S-S101G-S103A-V104I-N116L-S128N-Y209A-T213A-A232V | + |
| A098Q-S099A-G100S-S101G-V104I | + |
| T022A-S078N-S101N-S103A-V104I-Q109G-S128A-G159D-S188D-L217Q-A232V-Q245R-N248D-E271F | + |
| T022A-S024R-N076D-S101G-S103A-V104I-G159D-S188D-Q245R-N248D-A270V-E271F-A272V | + |
| T022A-N076D-G097S-S101Q-S103A-V104I-S128A-G159D-S188D-A232V-Q245R-N248D-E271F | + |
| T022A-S024G-S078N-S101N-S103A-V104I-Q109N-S128A-G159D-S188D-A232V-Q245R-N248D-E271F | + |
| T022A-L090I-S101G-S103A-V104I-S128A-G159D-S188D-L217Q-A232V-Q245R-N248D-E271F | + |
| G020R-N062E-S078G-G118D-P129E-G159D-S188D-N248D-H249R | + |
| A016S-T033S-S101G-S103A-V104I-N116L-S128N-Y209V-T213A-A232V | + |
| G020R-S078G-G118D-N248D-H249R | + |
| T022A-N062Q-S101G-S103A-V104I-G159D-S188D-A232V-Q245R-N248D-E271F | + |
| S024R-N062E-N116L-A158E-S166D-S188D | + |
| T022A-S024G-N076D-S101Q-S103A-V104I-G159D-S188D-L217Q-A232V-Q245R-N248D-E271F | + |
| T022A-S024R-S101G-S103A-V104I-G159D-S188D-A232V-Q245R-N248D-A270V-E271F | + |
| T022A-N062Q-S101G-S103A-V104I-P129E-G159D-S188D-A232V-Q245R-N248D-E271F | + |
| T022A-N076D-S101N-S103A-V104I-Q109G-G159D-S188D-L217Q-A232V-Q245R-N248D-E271F | + |
| T022A-S101G-S103A-V104I-P129E-S188D-A232V-Q245R-N248D-E271F | + |
| T022A-S024G-N076D-S078N-G097A-S101N-S103A-V104I-G159D-S188D-A232V-Q245R-N248D-E271F | + |
| T022A-S024G-N076D-S101G-S103A-V104I-I107V-G159D-S188D-A232V-Q245R-N248D-E271F | + |
| T022A-S024R-N116L-G118R | + |
| T022A-S024R-T033S-N062E-N116L-G118R-S128I-A158E-S188D | + |
| T022A-N076D-G097S-S101N-S103A-V104I-Q109G-S128A-G159D-S188D-A232V-Q245R-N248D-E271F | + |
| T022A-S024G-N076D-G097S-S101Q-S103A-V104I-S128A-G159D-S188D-A232V-Q245R-N248D-E271F | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S024R-T033S-N062E-N116L-S128I-S188D | + |
| T022A-S024G-N076D-G097S-S101N-S103A-V104I-G159D-S188D-A232V-Q245R-N248D-E271F | + |
| S240V | + |
| N062E-G118R | + |
| T022A-S101G-S103A-V104I-G159D-S188E-A232V-Q245T-N248E | + |
| S024R-N062E-S078G-G118D-P129E-S188D-Q245R-N248D | + |
| A016S-S103A-V104I | + |
| A088P | + |
| T022A-S101N-S103A-V104I-Q109N-G159D-S188D-L217Q-A232V-Q245R-N248D-E271F | + |
| T022A-S101N-S103A-V104I-L126I-G159D-S188D-L217Q-A232V-Q245R-N248D-E271F | + |
| G097P-A098F-V104L | + |
| T022A-G097S-S101N-S103A-V104I-S128A-G159D-S188D-A232V-Q245R-N248D-E271F | + |
| T022A-G097A-S101N-S103A-V104I-Q109N-G159D-S188D-L217Q-A232V-Q245R-N248D-E271F | + |
| G020K-T022L-S128D | + |
| T022A-S024G-S101G-S103A-V104I-G159D-S188D-L217Q-A232V-Q245R-N248D-E271F | + |
| G020R-S024R-N062E-S078D-G118D-P129E-G159D-S188D-N248D-H249R | + |
| S024F-S078N-G118R-L217E | + |
| T022A-S024G-S078N-G097S-S101Q-S103A-V104I-S128A-G159D-S188D-A232V-Q245R-N248D-E271F | + |
| T022A-S024R-S101G-S103A-V104I-A158E-G159E-S188D-A232V-Q245R-N248D-E271F-A272V | + |
| S024R-N062E-N116L-G118R-S128I-S188D | + |
| G118R-S128D-S166D-T213A | + |
| T022A-G097A-S101G-S103A-V104I-P129E-G159D-S188D-A232V-Q245R-N248D-E271F | + |
| T022A-T033S-S101G-S103A-V104I-N116L-S128L-G159D-S188D-A232V-Q245R-N248D-E271F | + |
| T022A-S078N-S101Q-S103A-V104I-Q109G-S128A-G159D-S188D-L217Q-A232V-Q245R-N248D-E271F | + |
| T022A-G097S-S101N-S103A-V104I-Q109G-S128A-G159D-S188D-L217Q-A232V-Q245R-N248D-E271F | + |
| T022A-S024G-G097S-S101N-S103A-V104I-Q109N-S128A-G159D-S188D-A232V-Q245R-N248D-E271F | + |
| T022A-N076D-G097A-S101N-S103A-V104I-G159D-S188D-A232V-Q245R-N248D-E271F | + |
| T022A-S101G-S103A-V104I-L126I-S128A-G159D-S188D-A232V-Q245R-N248D-E271F | + |
| G020R-S078G-G118S-S188D-H249R | + |
| T022A-S024G-N076D-S101Q-S103A-V104I-G159D-S188D-A232V-Q245R-N248D-E271F | + |
| T022A-S101A-S103A | + |
| T022A-N076D-S101G-S103A-V104I-P129E-G159E-S188D-A232V-Q245R-N248D | + |
| S024R-S078D-G118D-S188D-N248D-H249R | + |
| S099A-V104I | + |
| T022A-G097S-S101Q-S103A-V104I-Q109N-G159D-S188D-L217Q-A232V-Q245R-N248D-E271F | + |
| S024R-S078G-G118D-G159D-N248D | + |
| T022A-S024G-S078N-S101Q-S103A-V104I-S128A-G159D-S188D-A232V-Q245R-N248D-E271F | + |
| T022A-N076D-S101G-S103A-V104I-P129E-G159E-S188D-A232V-Q245R-N248D-E271F | + |
| T022A-G097A-S101Q-S103A-V104I-L124V-S128A-P129E-G159D-S188D-A232V-Q245R-N248D-E271F | + |
| T022A-G097A-S101Q-S103A-V104I-L124V-G159D-S188D-A232V-Q245R-N248D-E271F | + |
| S078G-G118D-P129E | + |
| S212W | + |
| T022A-S101G-S103A-V104I-V107V-P129E-G159D-S188D-A232V-N238Y-Q245R-N248D-A270V-E271F-A272V | + |
| T022A-S078N-S101Q-S103A-V104I-G159D-S188D-A232V-Q245R-N248D-E271F | + |
| T022A-G097A-S101G-S103A-V104I-S128A-G159D-S188D-L217Q-A232V-Q245R-N248D-E271F | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S101G-V104L | + |
| T022A-S101G-S103A-V104I-I107V-P129E-G159D-S188D-A232V-N238Y-Q245R-N248D-E271F | + |
| T022A-S024R-S101G-S103A-V104I-P129E-G159D-S188D-A232V-Q245R-N248D-E271F-A272V | + |
| T022A-S024G-G097A-S101Q-S103A-V104I-Q109N-S128A-G159D-S188D-L217Q-A232V-Q245R-N248D-E271F | + |
| T022A-S024G-N076D-S101G-S103A-V104I-G159D-S188D-A232V-Q245R-N248D-E271F | + |
| T022A-S024R-N076D-S101G-S103A-V104I-P129E-A158E-S188D-A232V-Q245R-N248D-E271F-A272V | + |
| T022A-T033S-S101G-S103A-V104I-N116L-N117S-Y209A-G211Q-T213A-A232V | + |
| S101G-S103A-V104I-N116L-G118V-Y209A-G211Q-A232V | + |
| T022A-N062E-S101N-S103A-V104I-S128A-G159D-S188D-A232V-Q245R-N248D-E271F | + |
| T022A-S024G-G097S-S101N-S103A-V104I-S128A-G159D-S188D-L217Q-A232V-Q245R-N248D-E271F | + |
| S024F-T213A | + |
| T022A-S024G-N076D-S101N-S103A-V104I-G159D-S188D-A232V-Q245R-N248D-E271F | + |
| G020R-S024R-S078D-G118S-P129E-G159D-Q245R-H249R | + |
| T022A-N076D-S101Q-S103A-V104I-Q109G-S128A-G159D-S188D-L217Q-A232V-Q245R-N248D-E271F | + |
| T022A-S078N-G097A-S099G-S101G-S103A-V104I-S128A-G159D-S188D-A232V-Q245R-N248D-E271F | + |
| T022A-N076D-S101G-S103A-V104I-G159D-S188D-L217Q-N218S-A232V-Q245R-N248D-E271F | + |
| T022A-S024G-N076D-S101N-S103A-V104I-Q109G-G159D-S188D-L217Q-A232V-Q245R-N248D-E271F | + |
| T022A-S024G-S101N-S103A-V104I-Q109N-G159D-S188D-A232V-Q245R-N248D-E271F | + |
| G020R-S024R-S078D-G118D-Q245R | + |
| T022A-S078N-I079V-S101N-S103A-V104I-G159D-S188D-L217Q-A232V-Q245R-N248D-E271F | + |
| T022A-S024R-N116L-G118R-S128I-A158E-S166D | + |
| S078G-G118D-S188D | + |
| G097P-A098Q-S099G-G102A | + |
| S099A-S103G | + |
| S078D-G118D-P129E-Q245R-N248D | + |
| T022A-S024G-S078N-S101Q-S103A-V104I-G159D-S188D-L217Q-A232V-Q245R-N248D-E271F | + |
| T022A-S078N-S101N-S103A-V104I-Q109G-G159D-S188D-L217Q-A232V-Q245R-N248D-E271F | + |
| T022A-N076D-S078N-G097S-S101Q-S103A-V104I-G159D-S188D-L217Q-A232V-Q245R-N248D-E271F | + |
| T022A-S024R-N116L-S128I-A158E-S166D-S188D | + |
| A016S-T022A-S101A-S103G-V104I | + |
| T022A-G097S-S101N-S103A-V104I-S128A-G159D-R186H-S188D-A232V-Q245R-N248D-E271F | + |
| T022A-G097A-S101Q-S103A-V104I-G159D-S188D-L217Q-A232V-Q245R-N248D-E271F | + |
| T022A-S101N-S103A-V104I-L126I-S128A-G159D-S188D-A232V-Q245R-N248D-E271F | + |
| T022A-S101Q-S103A-V104I-L126I-G159D-S188D-A232V-Q245R-N248D-E271F | + |
| T022A-N076D-G097S-S101N-S103A-V104I-G159D-S188D-A232V-Q245R-N248D-E271F | + |
| T022A-N043R-N076D-S101G-S103A-V104I-P129E-S188D-A232V-Q245R-N248D-E271F-A272V | + |
| T022A-S024R-T033S-N062E-N116L-S128I-S188D | + |
| T022A-S024G-S078N-G097S-S101G-S103A-V104I-S128A-G159D-S188D-L217Q-A232V-Q245R-N248D-E271F | + |
| T022L-S078N-G118R-S128D-T213A | + |
| T022A-N076D-G097A-A098T-S101Q-S103A-V104I-G159D-S188D-L217Q-A232V-Q245R-N248D-E271F | + |
| T022A-S024G-S078N-G097A-S101Q-S103A-V104I-S128A-G159D-S188D-A232V-Q245R-N248D-E271F | + |
| S103A-V104L | + |
| G020R-S024R-S078D-G118D-P129E-Q245R-H249R | + |
| S024R-S078G-G118D-P129E-G159D-S188D-N248D | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S024R-N043R-S101G-S103A-V104I-S188D-A232V-Q245R-N248D-E271F | + |
| T022A-S024R-G061W-N076D-S101G-S103A-V104I-P129E-S188D-A232V-Q245R-N248D-E271F | + |
| G020R-N062E-S078D-G118S-S188D-N248D | + |
| T022A-S101G-S103A-V104I-A158E-G159E-S188D-A232V-Q245R-N248D-E271F | + |
| G100S-V104I | + |
| T022A-S024G-N076D-S078N-G097S-S101N-S103A-V104I-G159D-S188D-L217Q-A232V-Q245R-N248D-E271F | + |
| G097P-A098F-S103A | + |
| T022A-G097S-S101Q-S103A-V104I-Q109G-G159D-S188D-A232V-Q245R-N248D-E271F | + |
| S024F-S078N-G118R-S128D-L217E | + |
| T022A-S101Q-S103A-V104I-Q109G-S128A-G159D-S188D-L217Q-A232V-Q245R-N248D-E271F | + |
| S024R-T033S-N116L-S128I-A158E-S166D | + |
| T022L-S024F-S128D | + |
| T022A-S101G-S103A-V104L | + |
| TO22A-N043R-S101G-S103A-V104I-A158E-G159E-S188D-A232V-Q245R-N248D-E271F-A272V | + |
| T022A-N076D-S101G-S103A-V104I-I107V-G159D-S188D-A232V-Q245R-N248D-E271F | + |
| T022L-S024F-S078N | + |
| T022A-N062E-A158E-S188D | + |
| G020A-T022L-S166D-T213A | + |
| T022A-S024G-T071A-S078N-S101N-S103A-V104I-G159D-S188D-A232V-Q245R-N248D-E271F | + |
| A016S-T022A-S101G-S103A-V104I-L148I | + |
| S078D-G118S-S188D-Q245R-N248D-H249R | + |
| G020K-T022L-S128D-S166D | + |
| T022A-S024G-N076D-G097S-S101N-S103A-V104I-Q109N-S128A-G159D-S188D-A232V-Q245R-N248D-E271F | + |
| T022A-N062E-S101G-S103A-V104I-P129E-S188D-A232V-Q245R-N248D-E271F | + |
| G020R-N062E-S078G-G118D-P129E-Q245R-H249R | + |
| G020R-S078G-G118D-P129E-S188D-N248D | + |
| G020K-T022L-S024F-S078N-G118R-S128D-S166D | + |
| T022A-N076D-S101G-S103A-V104I-P129E-S188D-A232V-Q245R-N248D-E271F | + |
| T022A-S101Q-S103A-V104I-L126I-P129E-G159D-S188D-L217Q-A232V-Q245R-N248D-E271F | + |
| T255G | + |
| T022A-G097A-S101N-S103A-V104I-L126I-S128A-P129E-G159D-S188D-A232V-Q245R-N248D-E271F | + |
| T033S-G118R | + |
| T022A-S024R-N076D-S101G-S103A-V104I-P129E-G159D-S188D-A232V-N238Y-Q245R-N248D-E271F | + |
| S024R-T033S-N062E-G118R-S166D-S188D | + |
| T022A-G097A-S101Q-S103A-V104I-S128A-P129S-G159D-S188D-A232V-Q245R-N248D-E271F | + |
| S024R-N062E-S078D-G118S-P129E-G159D-S188D-Q245R-H249R | + |
| T022A-S024G-S101Q-S103A-V104I-Q109N-G159D-S188D-L217Q-A232V-Q245R-N248D-E271F | + |
| A098Q-G102A | + |
| T022A-S024R-S101G-S103A-V104I-I107V-P129E-G159D-S188D-A232V-N238Y-Q245R-N248D-A270V-E271F | + |
| T022A-S024G-S078N-G097A-S101N-S103A-V104I-G159D-S188D-A232V-Q245R-N248D-E271F | + |
| T022A-S024G-S078N-S101N-S103A-V104I-Q109G-G159D-S188D-A232V-Q245R-N248D-E271F | + |
| S024R-N116L | + |
| T022A-S101G-S103A-V104I-L126I-P129E-G159D-S188D-L217Q-A232V-Q245R-N248D-E271F | + |
| G020K-S078N-S128D | + |
| T022A-S024G-S101N-S103A-V104I-S128A-G159D-S188D-A232V-Q245R-N248D-E271F | + |
| T022A-S024G-S078N-S101Q-S103A-V104I-S128A-G159D-S188D-T213A-L217Q-A232V-Q245R-N248D-E271F | + |
| T022A-S024G-S101N-S103A-V104I-G159D-S188D-A232V-Q245R-N248D-E271F | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S101N-S103A-V104I-L126I-P129E-G159D-S188D-L217Q-A232V-Q245R-N248D-E271F | + |
| T022A-S024G-N076D-G097A-S101N-S103A-V104I-G159D-S188D-A232V-Q245R-N248D-E271F | + |
| T022A-S024G-N076D-S078N-G097A-S101G-S103A-V104I-G159D-S188D-A232V-Q245R-N248D-E271F | + |
| S024R-T033S-N062E-N116L-S166D | + |
| T022A-S024G-N076D-S101N-S103A-V104I-Q109G-S128A-G159D-S188D-A232V-Q245R-N248D-E271F | + |
| A016S-S024F-S101G-S103A-V104I-N116L-Y209V-A232V | + |
| G020K-S024F-S078N-S128D-S166D | + |
| G025A | + |
| T022A-S024R-N076D-S101G-S103A-V104I-G159D-S188D-A232V-N238Y-Q245R-N248D-E271F | + |
| G097P-S099T-V104I | + |
| T022A-N076D-S078N-G097A-S101N-S103A-V104I-Q109G-G159D-S188D-A232V-Q245R-N248D-E271F | + |
| G020R-S024S-S078G-G118S-G159D-Q245R-N248D-H249R | + |
| T022A-S024G-S078N-S101Q-S103A-V104I-Q109G-G159D-S188D-L217Q-A232V-Q245R-N248D-E271F | + |
| T022A-S024G-N076D-G097A-S101Q-S103A-V104I-S128A-G159D-S188D-A232V-Q245R-N248D-E271F | + |
| T022A-N076D-S078N-G097S-S101N-S103A-V104I-G159D-S188D-A232V-Q245R-N248D-E271F | + |
| T022A-S078N-G097S-S101G-S103A-V104I-S128A-G159D-S188D-A232V-Q245R-N248D-E271F | + |
| T022A-S078N-G097S-S101Q-S103A-V104I-G159D-S188D-A232V-Q245R-N248D-E271F | + |
| D041K | + |
| T022A-S024G-G097A-S101G-S103A-V104I-S128A-G159D-S188D-A232V-Q245R-N248D-E271F | + |
| T022A-S024G-G097S-S101N-S103A-V104I-G159D-S188D-A232V-Q245R-N248D-E271F | + |
| A016S-T022A-S101A-V104I-L111V-L148I | + |
| A016S-T022A-S101A-V104L-L111V | + |
| T022A-S024G-G097S-S101Q-S103A-V104I-Q109N-G159D-S188D-A232V-Q245R-N248D-E271F | + |
| S078G-G118S-S188D-N248D | + |
| G020K-T022L-S024F-S078N-S128D | + |
| G020K-T022L-S024F-G118R-S128D-T213A | + |
| T022A-S024G-G097S-S101N-S103A-V104I-S128A-G159D-S188D-A232V-Q245R-N248D-E271F | + |
| S024F-S128D | + |
| T022A-N043R-N076D-S101G-S103A-V104I-A158E-G159E-S188D-A232V-Q245R-N248D-E271F | + |
| T022A-N076D-S101G-S103A-V104I-P129E-G159D-S188D-A232V-N238Y-Q245R-N248D-A270V-E271F-A272V | + |
| T022A-S101Q-S103A-V104I-L126I-G159D-S188D-L217Q-A232V-Q245R-N248D-E271F | + |
| T022A-S101G-S103A-V104I-P129E-G159D-S188D-A232V-N238Y-Q245R-N248D-A270V-E271F | + |
| T022A-S101G-S103A-V104I-G159D-S188D-A232V-Q245R-N248D-A270V-E271F-A272V-T274A | + |
| T022A-S101G-S103A-V104I-S188D-A232V-Q245R-N248D-E271F | + |
| T022A-S101N-S103A-V104I-Q109G-G159D-S188D-L217Q-A232V-Q245R-N248D-E271F | + |
| G020K-T022L-N062E-S078D-G118S-N248D | + |
| T022A-S024R-N076D-S101G-S103A-V104I-I107V-G159D-S188D-A232V-N238Y-Q245R-N248D-A270V-E271F | + |
| A016S-T022A-S101G-S103A-V104I-N116A-Y209V-T213A-A232V | + |
| T022A-S101N-S103A-V104I-L126I-P129S-G159D-S188D-L217Q-A232V-Q245R-N248D-E271F | + |
| T022A-S024G-N076D-S078N-G097A-S101Q-S103A-V104I-Q109G-G159D-S188D-L217Q-A232V-Q245R-N248D-E271F | + |
| T022A-N062E-N116L | + |
| T033S-S101G-S103A-V104I-N116A-S128N-Y209A-T213A-A232V | + |
| T022A-S101N-S103A-V104I-L126I-P129E-G159D-S188D-A232V-Q245R-N248D-E271F | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S024R-S101G-S103A-V104I-I107V-G159D-S188D-A232V-Q245R-N248D-A270V-E271F | + |
| T022A-N043R-N076D-S101G-S103A-V104I-P129E-G159E-S188D-A232V-Q245R-N248D-E271F | + |
| G020R-S024R-S078D-G118D-P129E-G159D-N248D | + |
| T022A-S101G-S103A-V104I-L124V-S128A-P129E-G159D-S188D-L217Q-A232V-Q245R-N248D-E271F | + |
| T022A-S024G-S101Q-S103A-V104I-S128A-G159D-S188D-A232V-Q245R-N248D-E271F | + |
| T022A-S024R-N076D-S101G-S103A-V104I-A232V-Q245R-A270V | + |
| T022A-S101G-S103A-V104I-P129E-S188D-A232V-Q245R-N248D-E271F-A272V | + |
| T022A-N076D-S078N-G097S-S101Q-S103A-V104I-S128A-G159D-S188D-A232V-Q245R-N248D-E271F | + |
| S099T | + |
| T022A-G097A-S101Q-S103A-V104I-L126I-P129E-G159D-S188D-A232V-Q245R-N248D-E271F | + |
| T022A-G097A-S101G-S103A-V104I-G159D-S188D-A232V-Q245R-N248D-E271F | + |
| A098F-S099T-G102A | + |
| T022A-S101G-S103A-V104I-G159D-S188E-A232V-Q245T-N248D | + |
| D041L | + |
| S024R-N062E-S128I-A158E-S188D | + |
| N062E-S078D-G118D-N248D-H249R | + |
| G020K-S024F-G118R-T213A | + |
| S101G-S103G-V104I-S128N | + |
| S078N-G118R-S128D-T213A-L217E | + |
| T022A-N076D-S101G-S103A-V104I-Q109N-G159D-S188D-A232V-Q245R-N248D-E271F | + |
| T022A-N076D-G097S-S103A-V104I-Q109N-G159D-S188D-A232V-Q245R-N248D-E271F | + |
| S078G-G118S-G159D-N248D | + |
| T033S-A158E | + |
| T022A-S101G-S103A-V104I-I107V-G159D-S188D-A232V-Q245R-N248D-E271F-A272V | + |
| T022A-S101G-S103A-V104I-A158E-G159E-S188D-A232V-Q245R-N248D-E271F-A272V | + |
| T022A-S024R-T033S-S128I-S166D-S188D | + |
| A158E-S188D | + |
| T022A-N076D-S101G-S103A-V104I-A158E-G159E-S188D-A232V-Q245R-N248D-E271F | + |
| T022A-S024G-S078N-G097S-S101Q-S103A-V104I-Q109G-G159D-S188D-A232V-Q245R-N248D-E271F | + |
| T022A-S024R-N076S-S101G-S103A-V104I-G159D-S188D-A232V-Q245R-N248D-E271F-A272V | + |
| S024R-G118R-S128I-S166D | + |
| T033S-N116L-G118R-S128I-S188D | + |
| T022A-S101G-S103A-V104I-G159D-S188D-A232V-N238Y-Q245R-N248D-E271F-A272V | + |
| T022A-S024R-T033S-N116L-G118R-V139I-S188D | + |
| T022A-S024R-N076D-S101G-S103A-V104I-P129E-A158E-G159E-S188D-A232V-Q245R-N248D-E271F | + |
| N062E-S078G-G118S-P129E-G159D-S188D-Q245R-N248D | + |
| T022A-S024G-S078N-G097A-S101N-S103A-V104I-Q109G-S128A-G159D-S188D-L217Q-A232V-Q245R-N248D-E271F | + |
| T022A-N062Q-S101Q-S103A-V104I-S128A-G159D-S188D-L217Q-A232V-Q245R-N248D-E271F | + |
| T022A-S024G-G097A-S101G-S103A-V104I-G159D-S188D-L217Q-A232V-Q245R-N248D-E271F | + |
| S101A-S103G | + |
| A016S-T022A-S024F-S101G-S103A-V104I-N116L-S128N-Y209A-T213A-A232V | + |
| T022A-G097A-S101Q-S103A-V104I-L124V-S128A-P129E-G159D-S188D-L217Q-A232V-Q245R-N248D-E271F | + |
| S024R-N062E-N116L-G118R-S128I-S166D-S188D | + |
| T022A-S024R-T033S-N116L-G118R-S128I-A158E-S166D | + |
| A108V-S128D-T213A | + |
| T022A-N043R-N076D-S101G-S103A-V104I-A158E-S188D-A232V-Q245R-N248D-E271F-A272V | + |
| T022A-S101G-S103A-V104I-I107V-G159D-S188D-A232V-Q245R-N248D-A270V-E271F | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-N076D-S101G-S103A-V104I-A158E-G159E-S188D-A232V-Q245R-N248D-E271F-A272V | + |
| T033S-S101G-S103A-V104I-N116L-S128N-Y209A-A232V | + |
| S024F-T033S-S101G-S103A-V104I-I107V-N116A-Y209V-T213A-A232V | + |
| T022A-S024G-G097S-S101N-S103A-V104I-Q109N-G159D-S188D-A232V-Q245R-N248D-E271F | + |
| S024R-T033S-N116L-S128I-S166D-S188D | + |
| T022A-S024R-N076D-S101G-S103A-V104I-G159D-S188D-A232V-N238Y-Q245R-N248D-E271F-A272V | + |
| T022A-G097A-S101Q-S103A-V104I-L126I-S128A-P129E-G159D-S188D-A232V-Q245R-N248D-E271F | + |
| T022A-S078N-G097A-S101Q-S103A-V104I-Q109G-G159D-S188D-A232V-Q245R-N248D-E271F | + |
| A098Q-S099G-G102A | + |
| T022A-S024G-G097A-S101G-S103A-V104I-P129E-G159D-S188D-A232V-Q245R-N248D-E271F | + |
| T022A-S024G-S101N-S103A-V104I-Q109G-G159D-S188D-A232V-Q245R-N248D-E271F | + |
| T022A-G097S-S101Q-S103A-V104I-S128A-G159D-S188D-L217Q-A232V-Q245R-N248D-E271F | + |
| T022A-S024R-S101G-S103A-V104I-I107V-G159D-S188D-A232V-Q245R-N248D-E271F | + |
| T022L-G118R-S166D | + |
| V011M-S024R-T033S-S128I-S166D | + |
| G020K-S078N-S128D-L217E | + |
| V004M | + |
| N062E-N116L-G118R-S128I-S166D | + |
| T022A-G097A-S101N-S103A-V104I-Q109G-S128A-G159D-S188D-L217Q-A232V-Q245R-N248D-E271F | + |
| G020R-S024R-N062E-S078G-G118S-P129E-Q245R-N248D-H249R | + |
| T022A-S101G-S103A-V104I-P129E-G159D-S188D-A232V-N238Y-Q245R-N248D-E271F | + |
| T022A-S101N-S103A-V104I-G159D-S188D-A232V-Q245R-N248D-E271F | + |
| T022A-T033S-N116L-S166D-S188D | + |
| T022A-S078N-G097S-S101Q-S103A-V104I-S128A-G159D-S188D-A232V-Q245R-N248D-E271F | + |
| T033S | + |
| T022A-N076D-S078N-G097S-S101N-S103A-V104I-Q109G-S128A-G159D-S188D-A232V-Q245R-N248D-E271F | + |
| G118R-T213A | + |
| T022A-S101N-S103A-V104I-L126I-G159D-S188D-A232V-Q245R-N248D-E271F | + |
| S024R-N116L-S188D | + |
| T022Q-S101G-S103A-V104I-G159D-S188E-A232V-Q245V-N248E | + |
| T022A-S024G-N076D-G097S-S101Q-S103A-V104I-G159D-S188D-A232V-Q245R-N248D-E271F | + |
| T022A-T033S-S101G-S103A-V104I-N116L-G159D-S188D-A232V-Q245R-N248D-E271F | + |
| G097P-S099T-S101A-V104L | + |
| T022A-N076D-S101G-S103A-V104I-P129E-G159D-S188D-A232V-N238Y-Q245R-N248D-A270V-E271F | + |
| T022A-S024G-G097A-S101N-S103A-V104I-G159D-S188D-A232V-Q245R-N248D-E271F | + |
| T022A-N043R-N076D-S101G-S103A-V104I-S188D-A232V-Q245R-N248D-E271F-A272V | + |
| G020R-S024R-S078G-G118D-G159D-Q245R-N248D-H249R | + |
| T022A-S101G-S103A-V104I-G159D-S188D-A232V-N238Y-Q245R-N248D-E271F | + |
| L021F-T022A-S024G-S078N-S101Q-S103A-V104I-G159D-S188D-L217Q-A232V-Q245R-N248D-E271F | + |
| N062E-S078G-G118D-G159D-S188D-Q245R-N248D | + |
| A098Q-S101A-S103A-V104L | + |
| T022A-S024G-S078N-S101Q-S103A-V104I-G159D-S188D-A232V-Q245R-N248D-E271F | + |
| N062E-G118R-A158E-S166D-S188D | + |
| T022A-S024G-S078N-S101Q-S103A-V104I-Q109N-G159D-S188D-L217Q-A232V-Q245R-N248D-E271F | + |
| N116L-S128I | + |
| T022A-N062E-S128I | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S024R-T033S-N116L-S128I-A158E-S188D | + |
| T022A-S101G-S103A-V104I-L124V-S128A-G159D-S188D-L217Q-A232V-Q245R-N248D-E271F | + |
| T033S-N116L-A158E-S166D-S188D | + |
| T022A-N076D-S078N-G097A-S101N-S103A-V104I-S128A-G159D-S188D-L217Q-A232V-Q245R-N248D-E271F | + |
| T022A-S024R-N043R-S101G-S103A-V104I-A158E-S188D-A232V-Q245R-N248D-E271F | + |
| T022L-S078N-G118R-S128D-T213A-L217E | + |
| A016S-T033S-S101G-S103A-V104I-N116L-S128N-Y209A-G211Q-A232V | + |
| T022A-N043R-N076D-S101G-S103A-V104I-P129E-S188D-A232V-Q245R-N248D-E271F | + |
| T022A-N076D-S101G-S103A-V104I-P129E-A158E-G159E-S188D-A232V-Q245R-N248D-E271F-A272V | + |
| T022A-S024G-G097A-S101N-S103A-V104I-S128A-G159D-S188D-L217Q-A232V-Q245R-N248D-E271F | + |
| G020K-T022L-S024F-G118R-S128D-S166D-L217E | + |
| N062E-G118R-S128I-A158E-S188D | + |
| T022A-S024F-N043R-N076D-S101G-S103A-V104I-A158E-S188D-A232V-Q245R-N248D-E271F-A272V | + |
| T022A-S024G-N076D-S078N-S101N-S103A-V104I-G159D-S188D-L217Q-A232V-Q245R-N248D-E271F | + |
| G097P-A098Q-S099T-S103G | + |
| G097P-A098Q-S099T-S103A-V104I | + |
| N062E-S078D-G118S-S188D | + |
| T022A-N043R-N076D-S101G-S103A-V104I-P129E-A158E-S188D-A232V-Q245R-N248D-E271F-A272V | + |
| T134C | + |
| G020R-N062E-S078D-G118S-P129E-N248D | + |
| S101G-S103A-V104I-N116L-G118V-Y209A-G211Q-T213A-A232V | + |
| T022A-S024R-T033S-N116L-A158E-S166D-S188D | + |
| A016S-S101G-S103A | + |
| A016S-S103G-V104I-L111V | + |
| A098F-G100S | + |
| S101A-S103A-V104I-A232V-Q245R | + |
| T022A-G097A-S101N-S103A-V104I-L126I-S128A-G159D-S188D-A232V-Q245R-N248D-E271F | + |
| S078G-G118S-N248D-H249R | + |
| T022L-S078N-A122V-S128D | + |
| T022A-S101Q-S103A-V104I-L124V-S128A-G159D-S188D-L217Q-A232V-Q245R-N248D-E271F | + |
| T022A-G097A-S101Q-S103A-V104I-L126I-S128A-G159D-S188D-A232V-Q245R-N248D-E271F | + |
| S024F-S078N | + |
| A016S-S101G-V104I-L111V-S128N | + |
| A016S-S024F-S101G-S103A-V104I-N116L-G118V-Y209A-A232V | + |
| G097P-S099G-G100S | + |
| A098Q-S099G-G100S-V104L | + |
| S024R-S078D-G118S-L126I-P129E-N248D-H249R | + |
| T022A-S101N-S103A-V104I-Q109G-S128A-G159D-S188D-A232V-Q245R-N248D-E271F | + |
| G097P-A098Q-S103A | + |
| S099A-S101A-S103A | + |
| A016S-T022A-S101G-S103G-V104I-S128N | + |
| T022A-N076D-S101N-S103A-V104I-Q109G-S128A-G159D-S188D-L217Q-A232V-Q245R-N248D-E271F | + |
| T022A-S024G-N076D-S078N-G097A-S101N-S103A-V104I-S128A-G159D-S188D-A232V-Q245R-N248D-E271F | + |
| G020K-S024F-G118R-S166D-T213A | + |
| S024R-S078D-G118S-G159D-Q245R-H249R | + |
| T022A-N076D-S078N-G097A-S101N-S103A-V104I-G159D-S188D-L217Q-A232V-Q245R-N248D-E271F | + |
| N116L-S128I-S166D | + |
| T022A-N043R-S101G-S103A-V104I-P129E-A158E-G159E-S160P-S188D-A232V-Q245R-N248D-E271F | + |
| T033S-N116L-G118R-S128I-A158E-S166D-S188D | + |
| T022A-S024G-G097S-S101Q-S103A-V104I-Q109N-G159D-S188D-L217Q-A232V-Q245R-N248D-E271F | + |
| T022A-N043R-N076D-S101G-S103A-V104I-S188D-A232V-Q245R-N248D-E271F | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S024G-N076D-S078N-G097S-S101Q-S103A-V104I-S128A-G159D-S188D-L217Q-A232V-Q245R-N248D-E271F | + |
| T022A-S024R-N043R-N076D-S101G-S103A-V104I-S188D-A232V-Q245R-N248D-E271F | + |
| R019S-T022A-S024R-N076D-S101G-S103A-V104I-G159D-S188D-A232V-N238Y-Q245R-N248D-E271F | + |
| G020K-S024F-S078N-S166D | + |
| T022A-N076D-S078N-G097A-S101Q-S103A-V104I-S128A-G159D-S188D-L217Q-A232V-Q245R-N248D-E271F | + |
| A016S-T022A-T033S-S101G-S103A-V104I-N116L-Y209V-T213A-A232V | + |
| T033S-S101G-S103A-V104I-N116L-S128N-Y209A-G211Q-A232V | + |
| G020K-T022L-S024F-G118R-S128D-S166D-T213A | + |
| T022A-S024G-N076D-S101Q-S103A-V104I-S128A-G159D-S188D-A232V-Q245R-N248D-E271F | + |
| T022A-N076D-G097S-S101N-S103A-V104I-Q109G-S128A-G159D-S188D-L217Q-A232V-Q245R-N248D-E271F | + |
| T022A-S101G-S103A-V104I-L126I-P129S-G159D-S188D-A232V-Q245R-N248D-E271F | + |
| T022A-S024R-N043R-N076D-S101G-S103A-V104I-P129E-A158E-G159E-S188D-A232V-Q245R-N248D-E271F | + |
| S024R-T033S-S128I-S166D-S188D | + |
| A098Q-S099A-G100S | + |
| S024R-T033S-N062E-N116L-A158E-S188D | + |
| G020R-S078D-G118D-P129E-N248D-H249R | + |
| T022A-S024R-N062E-N116L-S128I-S166D-S188D | + |
| A098Q-S099G-S101G-V104L | + |
| A098F-S099A-V104I | + |
| T022Q-S101G-S103A-V104I-G159D-S188D-A232T-Q245T-N248E-E271F | + |
| T022A-N076D-S101G-S103A-V104I-I107V-P129E-G159D-S188D-A232V-Q245R-N248D-E271F-A272V | + |
| T022A-S024R-N076D-S101G-S103A-V104I-A158E-S188D-A232V-Q245R-N248D-E271F-A272V | + |
| S024F-G118R-S128D-S166D-A272V | + |
| S099T-G100S-S103A-V104I | + |
| T022Q-S101G-S103A-V104I-G159D-S188D-A232T-Q245T-N248E | + |
| S128D-T213A-L217E | + |
| T022A-T033S-N116L-S128I-S166D-S188D | + |
| T022L-S078N-G118R-S128D-S166D-T213A | + |
| T022A-S101G-S103A-V104I-A158E-G159E-S188D-A232V-S240F-Q245R-N248D-E271F | + |
| S078N-G118R-S128D-L217E | + |
| T022A-S024R-S101G-S103A-V104I-I107V-P129E-G159D-S188D-A232V-Q245R-N248D-E271F-A272V | + |
| T022A-S101G-S103A-V104I-L124V-S128A-P129S-G159D-S188D-L217Q-A232V-Q245R-N248D-E271F | + |
| T022L-S024F-T213A | + |
| G097P-A098Q-S103A-V104L | + |
| T022A-S078N-G097S-S101Q-S103A-V104I-Q109N-S128A-G159D-S188D-A232V-Q245R-N248D-E271F | + |
| G118R-S128I-A158E-S166D-S188D | + |
| T022A-N116L-S128I-A158E | + |
| T022A-S024F-T033S-S101G-S103A-V104I-N116L-Y209V-T213A-A232V-A272D | + |
| T022A-G118R-A158E-S166D-S188D | + |
| T022A-S024R-S101G-S103A-V104I-G159E-S188D-A232V-Q245R-N248D-E271F-A272V | + |
| T022A-S024G-S078N-G097A-S101N-S103A-V104I-Q109G-G159D-S188D-L217Q-A232V-Q245R-N248D-E271F | + |
| T022A-N043R-S101G-S103A-V104I-P129E-G159E-S188D-A232V-Q245R-N248D-E271F-A272V | + |
| T022A-G097A-S101N-S103A-V104I-Q109N-S128A-G159D-S188D-A232V-Q245R-N248D-E271F | + |
| H039C | + |
| T033S-S101G-S103A-V104I-N116A-S128N-Y209A-A232V | + |
| A016S-V104L-S128N-L148I | + |
| A098F-S101G-V104I | + |
| T022A-S024G-N076D-S101G-S103A-V104I-Q109G-S128A-G159D-S188D-A232V-Q245R-N248D-E271F | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S024G-S078N-G097A-S101N-S103A-V104I-Q109G-G159D-S188D-A232V-Q245R-N248D-E271F | + |
| T022A-S024R-N076D-S101G-S103A-V104I-G159D-S188D-A232V-N238Y-Q245R-N248D-A270V-E271F-A272V | + |
| T022A-S101G-S103A-V104I-L126I-P129S-G159D-S188D-L217Q-A232V-Q245R-N248D-E271F | + |
| S078D-G118S-P129E | + |
| A098Q-S103G-V104I | + |
| A098F-S099T-S101G-G102A | + |
| T022A-S024R-N076D-S101G-S103A-V104I-P129E-S188D-A232V-Q245R-N248D-E271F | + |
| S024F-T033S-S101G-S103A-V104I-N116L-Y209V-G211Q-T213A-A232V | + |
| T022A-N062E-S101N-S103A-V104I-P129E-G159D-S188D-A232V-Q245R-N248D-E271F | + |
| S024R-S078G-G118S-Q245R-N248D | + |
| S056H | + |
| T022A-S101G-S103A-V104I-N116L-G118V-Y209A-G211Q-A232V | + |
| G097P-A098Q-S101A-S103A-V104L | + |
| T022A-N076D-S101Q-S103A-V104I-S128A-G159D-S188D-A232V-Q245R-N248D-E271F | + |
| T022A-G097A-S101Q-S103A-V104I-L126I-S128A-P129S-G159D-S188D-A232V-Q245R-N248D-E271F | + |
| T022A-S024R-T033S-N062E-N116L-G118R-S166D-S188D | + |
| S024R-T033S-N062E-N116L-A158E-S166D | + |
| A098Q-S099T-V104L | + |
| S099T-G102A-S103A | + |
| T022A-S101N-S103A-V104I-Q109G-S128A-G159D-S188D-L217Q-A232V-Q245R-N248D-E271F | + |
| T022A-N076D-S101G-S103A-V104I-P129E-A158E-G159E-S188D-A232V-Q245R-N248D-E271F | + |
| N062E-S078D-G118D-G159D | + |
| S024R-N062E-S078G-G118D-P129E-G159D-S188D | + |
| T022A-S024G-S101N-S103A-V104I-Q109N-G159D-S188D-L217Q-A232V-Q245R-N248D-E271F | + |
| S078D-G118D-I-I249R | + |
| T022A-G097A-S101Q-S103A-V104I-Q109G-G159D-S188D-A232V-Q245R-N248D-E271F | + |
| T022A-G097S-S101G-S103A-V104I-Q109N-G159D-S188D-A232V-Q245R-N248D-E271F | + |
| T022A-S101Q-S103A-V104I-L124T-P129S-G159D-S188D-A232V-Q245R-N248D-E271F | + |
| T022A-N062E-N116L-G118R-S128I-S166D-S188D | + |
| T022A-N076D-G097S-S101Q-S103A-V104I-G159D-S188D-L217Q-A232V-Q245R-N248D-E271F | + |
| S099G-S103A | + |
| T022A-N062E-G097A-S101N-S103A-V104I-P129S-G159D-S188D-A232V-Q245R-N248D-E271F | + |
| G020R-S024R-S078G-G118D-N238D-N248D | + |
| T022A-S024G-G097A-S101G-S103A-V104I-S128A-G159D-S188D-L217Q-A232V-Q245R-N248D-E271F-T274A | + |
| T022R-S101G-S103A-V104I-A232V-Q245R | + |
| G097P-A098F-V104I | + |
| S024R-N062E-S078D-G118D-P129E-S188D-Q245R-N248D | + |
| T022A-N076D-S078N-S101N-S103A-V104I-Q109G-S128A-G159D-S188D-A232V-Q245R-N248D-E271F | + |
| T022A-S024G-G097S-S101N-S103A-V104I-Q109G-S128A-G159D-S188D-L217Q-A232V-Q245R-N248D-E271F | + |
| F050S | + |
| A016S-T022A-S101G-S103A-V104I-S128N | + |
| T022A-G097A-S101G-S103A-V104I-L124V-P129S-G159D-S188D-A232V-Q245R-N248D-E271F | + |
| S101A-V104I-L111V | + |
| T022A-N076D-S101G-S103A-V104I-S188D-A232V-Q245R-N248D-E271F | + |
| T022A-S024G-G097S-S101N-S103A-V104I-Q109G-G159D-S188D-A232V-Q245R-N248D-E271F | + |
| S024F-T033S-S101G-S103A-V104I-N116L-S128N-Y209A-A232V | + |
| A098Q-S099T-G102A-S103G-V104I | + |
| T022A-T033S-G118R-S128I-S188D | |
| S024R-N062E-S078G-G118S-Q245R | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S024G-G097A-S101N-S103A-V104I-Q109N-G159D-S188D-A232V-Q245R-N248D-E271F | + |
| T022L-S024F-S128D-T213A | + |
| T022A-S101G-S103A-V104I-L126I-G159D-S188D-A232V-Q245R-N248D-E271F | + |
| A016S-T022A-S024F-S101G-S103A-V104I-N116L-Y209V-G211Q-T213A-A232V | + |
| T022A-S024R-S101G-S103A-V104I-G159D-S188D-A232V-N238Y-Q245R-N248D-A270V-E271F | + |
| G020K-T022L-S078N-S128D-A133V-T213A | + |
| T022A-S024G-N076D-G097A-S101Q-S103A-V104I-Q109G-G159D-S188D-L217Q-A232V-Q245R-N248D-E271F | + |
| T022A-G118R-S128I-S166D | + |
| T022A-T033S-A158E-S166D | + |
| T022A-S078N-G097A-S101Q-S103A-V104I-Q109N-S128A-G159D-S188D-A232V-Q245R-N248D-E271F | + |
| G020R-S024R-S078D-G118D-N248D | + |
| A098F-S099A-S103G | + |
| T022A-N076D-S101G-S103A-V104I-P129E-G159D-S188D-A232V-N238Y-Q245R-N248D-E271F | + |
| G097P-S099T-S103A-V104L | + |
| T022A-N076D-S101G-S103A-V104I-I107V-G159D-S188D-A232V-N238Y-Q245R-N248D-E271F | + |
| S024F-S128D-T213A | + |
| T022A-S024R-N076D-S101G-S103A-V104I-P129E-G159D-S188D-A232V-N238Y-Q245R-N248D-A270V-E271F-A272V | + |
| S099A-G102A-V104I | + |
| T022A-N076D-S078N-G097A-S101N-S103A-V104I-Q109N-G159D-S188D-A232V-Q245R-N248D-E271F | + |
| S024F-T033S-S101G-S103A-V104I-I107V-N116A-Y209A-G211Q-T213A-A232V | + |
| G097P-S099A-S101A | + |
| T022A-S101G-S103A-V104I-S188D-A232V-Q245R-N248D-E271F-A272V | + |
| G020R-S024R-N062E-S078D-G118S-Q245R-N248D-H249R | + |
| G118R | + |
| S078N-G118R-S128D-T213A | + |
| T022A-G097A-S101N-S103A-V104I-L126I-P129E-G159D-S188D-A232V-Q245R-N248D-E271F | + |
| T022A-S101Q-S103A-V104I-L126I-P129S-G159D-S188D-A232V-Q245R-N248D-E271F | + |
| T022A-N076D-S101G-S103A-V104I-P129E-A158E-S188D-A232V-Q245R-N248D-E271F-A272V | + |
| T022A-S024R-N062E-S128I-A158E-S166D | + |
| S128D | + |
| T022A-N076D-S101G-S103A-V104I-P129E-G159E-S188D-A232V-Q245R-N248D-E271F-A272V | + |
| T022A-S024G-G097S-S101Q-S103A-V104I-Q109N-S128A-G159D-S188D-L217Q-A232V-Q245R-N248D-E271F | + |
| T022A-N043R-N076D-S101G-S103A-V104I-P129E-G159E-S188D-A232V-Q245R-N248D-E271F-A272V | + |
| T033S-N116L-S128I-S188D | + |
| T022L-S024F-G118R-S128D-S166D-T213A-L217E | + |
| T022A-S024G-S078N-G097S-S101N-S103A-V104I-Q109N-S128A-G159D-S188D-L217Q-A232V-Q245R-N248D-E271F | + |
| T022A-S101G-S103A-V104I-L126I-G159D-S188D-L217Q-A232V-Q245R-N248D-E271F | + |
| A016S-S101G-S103A-L148I | + |
| S024R-S078G-G118D-N248D-H249R | + |
| T022A-S024G-S078N-S101N-S103A-V104I-Q109G-S128A-G159D-S188D-A232V-Q245R-N248D-E271F | + |
| P055R | + |
| T022A-S024G-G025S-G097S-S101N-S103A-V104I-S128A-G159D-S188D-L217Q-A232V-Q245R-N248D-E271F | + |
| T022A-S101N-S103A-V104I-L124T-P129S-G159D-S188D-A232V-Q245R-N248D-E271F | + |
| S078G-G118D-G159D-Q245R | + |
| T022A | + |
| A016S-T022A-S101A-S103A-V104I-L111V | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S078G-G118S-S188D-Q245R-H249R | + |
| A016S-T022A-T033S-S101G-S103A-V104I-N116L-S128N-Y209A-G211Q-T213A-A232V | + |
| S024R-S078D-G118S-G159D-S188D-N248D | + |
| A016S-S101G-S103A-V104I-N116L-S128N-A133V-Y209A-G211Q-T213A-A232V | + |
| T022A-S101G-S103A-V104I-A158E-S188D-A232V-Q245R-N248D-E271F-A272V | + |
| T022A-S101Q-S103A-V104I-Q109N-S128A-G159D-S188D-A232V-Q245R-N248D-E271F | + |
| T022L-S128D | + |
| T022A-T033S-N116L-G118R-S128I-A158E-S188D | + |
| T022L-G118R-S128D-T213A-L217E | + |
| T022A-N043R-N076D-S078P-S101G-S103A-V104I-A158E-G159E-S188D-A232V-Q245R-N248D-E271F | + |
| G097P-A098F-S101A | + |
| Q002F | + |
| G097P-A098Q-S099A | + |
| S024R-T033S-N062E-S166D-S188D | + |
| G020K-S078N-S128D-T213A | + |
| T022A-S101Q-S103A-V104I-Q109G-S128A-G159D-S188D-A232V-Q245R-N248D-E271F | + |
| T022A-G097A-S101G-S103A-V104I-L126I-S128A-G159D-S188D-A232V-Q245R-N248D-E271F | + |
| G020R-N062E-S078G-G118S-P129E-G159D-S188D-N238S | + |
| G097P-S099T-S103G-V104I | + |
| T022A-N076D-S101N-S103A-V104I-Q109N-S128A-G159D-S188D-L217Q-A232V-Q245R-N248D-E271F | + |
| D181C | + |
| G020K-G118R-S128D | + |
| T022A-S101G-S103A-V104I-L126I-S128A-P129E-G159D-S188D-L217Q-A232V-Q245R-N248D-E271F | + |
| T022A-S101N-S103A-V104I-L126I-P129S-G159D-S188D-A232V-Q245R-N248D-E271F | + |
| T022A-S101Q-S103A-V104I-L124T-G159D-S188D-A232V-Q245R-N248D-E271F | + |
| T022A-G097A-S101Q-S103A-V104I-L126I-P129S-G159D-S188D-A232V-Q245R-N248D-E271F | + |
| T022L-S078N-S128D-T213A-L217E-A272D | + |
| S099T-G102A-V104I | + |
| S128I-S166D | + |
| T022A-S024R-S101G-S103A-V104I-P129E-A158E-G159E-S188D-A232V-Q245R-N248D-E271F-A272V | + |
| G020R-S078D-G118S-Q245R-H249R | + |
| G097P-S099T-G100S | + |
| G097P-S099G | + |
| G020K-S024F-S078N-S128D-S166D-T213A | + |
| A098Q-S101A-G102A-S103A | + |
| S024R | + |
| S024R-N116L-G118R-S128I | + |
| T022A-S101G-S103G-V104I-S128N | + |
| T022A-S024G-N076D-S101G-S103A-V104I-P129E-G159D-S188D-L217Q-A232V-Q245R-N248D-E271F | + |
| T022A-S101G-S103A-V104I-I107V-S153A-G159D-S188D-A232V-Q245R-N248D-A270V-E271F | + |
| S024R-N062E-S078G-G118D-S188D-Q245R-H249R | + |
| T022A-S078N-S101Q-S103A-V104I-Q109N-G159D-S188D-L217Q-A232V-Q245R-N248D-E271F | + |
| T022A-S024G-S101Q-S103A-V104I-G159D-S188D-A232V-Q245R-N248D-E271F | + |
| G020K-T022L-S024F | + |
| G020K-T022L-S078N-S128D-T213A | + |
| S078G-G118D-P129E-S188D | + |
| T022A-N076D-G097A-S101G-S103A-V104I-S128A-G159D-S188D-A232V-Q245R-N248D-E271F | + |
| A016S-S103G-V104L-S128N-L135I | + |
| T022A-N076D-S101G-S103A-V104I-G159D-S188D-A232V-N238Y-Q245R-N248D-E271F | + |
| S101G-S103A-V104I-N116L-G118V-Y209V-A232V | + |
| T022A-S101G-S103A-V104I-Q109N-G159D-S188D-A232V-Q245R-N248D-E271F | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| A016S-S103G-V104I-S128N-L148I | + |
| T022A-S024R-N076D-S101G-S103A-V104I-P129E-G159D-S188D-A232V-N238Y-Q245R-N248D-A270V-E271F | + |
| G025S | + |
| G020R-S078D-G118D-G159D-S188D-N248D-H249R | + |
| S099T-S101G-G102A-S103A | + |
| T033S-N116L-S188D | + |
| T022A-N043R-S101G-S103A-V104I-S188D-A232V-Q245R-N248D-E271F-A272V | + |
| G097P-A098Q-S103A-V104I | + |
| T022A-N062E-S101G-S103A-V104I-S188D-A232V-Q245R-N248D-E271F | + |
| N062E-N116L-S128I-A158E | + |
| A016S-T022A-S103G-V104L | + |
| T022A-T033S-N116L-S128I | + |
| T022L-S024F-N043H-G118R-S128D-S166D | + |
| T022A-G097A-S101N-S103A-V104I-Q109G-G159D-S188D-A232V-Q245R-N248D-E271F | + |
| S101G-S103G-V104L | + |
| G020R-N062E-S078G-G118D-P129E-G159D-S188D-Q245R-N248D | + |
| S099A-G100S-V104I | + |
| G097P-A098Q-S099G-S101A | + |
| G020R-S024G-S078G-G118S-G159D-S188D-Q245R-H249R | + |
| A016S-S103G-V104I-S128N | + |
| T022A-S024R-S101G-S103A-V104I-P129E-A158E-G159E-S188D-A232V-Q245R-N248D-E271F | + |
| T022A-S024G-G097A-S101N-S103A-V104I-Q109G-S128A-G159D-S188D-A232V-Q245R-N248D-E271F | + |
| G118R-S128D-L217E | + |
| S132H | + |
| T022A-S024F-T033S-S101G-S103A-V104I-N116L-S128N-Y209A-G211Q-T213A-A232V | + |
| T022A-G097A-S101N-S103A-V104I-L126I-P129S-G159D-S188D-L217Q-A232V-Q245R-N248D-E271F | + |
| S024R-S078D-G118D-S188D | + |
| T022A-N043R-S101G-S103A-V104I-A158E-G159E-S188D-A215V-A232V-Q245R-N248D-E271F-A272V | + |
| S024F-S078N-G118R | + |
| T022A-S101G-S103A-V104I-Q109G-S128A-G159D-S188D-A232V-Q245R-N248D-E271F | + |
| A016S-T022A-S101A-V104I | + |
| T022A-S166D-S188D | + |
| S078N-G118R-S128D-S166D-T213A | + |
| T022A-S024G-S078N-G097A-S101N-S103A-V104I-Q109N-S128A-G159D-S188D-L217Q-A232V-Q245R-N248D-E271F | + |
| T022A-N043R-S101G-S103A-V104I-G159E-S188D-A232V-Q245R-N248D-E271F | + |
| G020R-S024R-N062E-S078D-G118D-G159D-S188D-N248D | + |
| G097P-S099T-S101A-S103G-V104I | + |
| T022A-S024R-N043R-N076D-S101G-S103A-V104I-P129E-S188D-A232V-Q245R-N248D-E271F | + |
| A016S-T022A-S101A-S103G-V104L-S128N | + |
| G020R-N062E-S078G-G118S-G159D-S188D-Q245R-H249R | + |
| G020R-S078G-G118D | + |
| G020R-S078G-G118S | + |
| Q012Y-N018G | + |
| T022A-S024R-N043R-N076D-S101G-S103A-V104I-P129E-A158E-S188D-A232V-Q245R-N248D-E271F | + |
| T033S-N062E-G118R-A158E-S166D | + |
| T022A-N076D-A088V-S101Q-S103A-V104I-G159D-S188D-A232V-Q245R-N248D-E271F | + |
| G097P-A098Q-S099A-V104I | + |
| S024R-N062E-N116L-S128I-S166D-S188D | + |
| T022A-T033S-N116L-A158E | + |
| T022A-S024R-N043R-N076D-S101G-S103A-V104I-A158E-S188D-A232V-Q245R-N248D-E271F-A272V | + |
| T033S-N062E-N116L-A158E | + |
| S024R-S078G-G118D-H249R | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-N043R-S101G-S103A-V104I-P129E-A158E-G159E-S188D-A232V-Q245R-N248D-E271F | + |
| T022A-S024G-N076D-G097A-S101N-S103A-V104I-Q109N-G159D-S188D-A232V-Q245R-N248D-E271F | + |
| T022A-S101Q-S103A-V104I-L126I-P129E-G159D-S188D-A232V-Q245R-N248D-E271F | + |
| G020R-S078D-G118D-Q245R-H249R | + |
| G097P-S099G-V104L | + |
| T022A-N043R-N076D-S101G-S103A-V104I-A158E-S188D-A232V-Q245R-N248D-E271F | + |
| A016S-T022A-S101G-V104I-S128N-L148I | + |
| T022A-N076D-S101G-S103A-V104I-P129E-A158E-S188D-A232V-Q245R-N248D-E271F | + |
| N062E-A158E-S188D | + |
| T022A-N076D-S078N-S099R-S101Q-S103A-V104I-G159D-S188D-A232V-Q245R-N248D-E271F | + |
| A016S-T022A-S103G-V104I-L148I | + |
| S024R-T033S-N116L-A158E-S166D-S188D | + |
| T022A-S101G-S103A-V104I-N116A-G118V-Y209A-T213A-A232V | + |
| G020R-N062E-S078D-G118D-P129E-S188D-N248D-H249R | + |
| T022A-S101G-S103A-V104I-Q109N-G159D-S188D-L217Q-A232V-Q245R-N248D-E271F | + |
| G020K-T022L-S024F-S078N-G118R-S128D-S166D-T213A | + |
| T022A-S024R-T033S-N116L-S128I-S166D-S188D | + |
| T022A-S024R-S101G-S103A-V104I-S188D-A232V-Q245R-N248D-E271F | + |
| T022A-S101G-S103A-V104I-P129E-G159D-S188D-A232V-N238Y-Q245R-N248D-E271F-A272V | + |
| T022A-S024R-S101G-S103A-V104I-A158E-S188D-A232V-Q245R-N248D-E271F | + |
| T022A-T033S-S101G-S103A-V104I-S128L-G159D-S188D-T213A-A232V-Q245R-N248D-E271F | + |
| T022A-T033S-S128I-S166D | + |
| G097P-A098Q-S099T-S101G | + |
| T022A-S024R-N043R-N076D-S101G-S103A-V104I-P129E-A158E-S188D-A232V-Q245R-N248D-E271F-A272V | + |
| T022A-S024R-G118R | + |
| T022A-G097A-S101N-S103A-V104I-L126I-P129S-V149I-G159D-S188D-L217Q-A232V-Q245R-N248D-E271F | + |
| T022A-N076D-S078N-G097A-S101Q-S103A-V104I-S128A-G159D-S188D-A232V-Q245R-N248D-E271F | + |
| A098Q-S101G-G102A-S103A-V104I | + |
| S078G-G118D-G159D-S188D-Q245R-N248D | + |
| G020K-S078N-S128D-S166D-T213A | + |
| T022A-S024R-S101G-S103A-V104I-A158E-G159E-S188D-A232V-Q245R-N248D-E271F | + |
| G097P-A098Q-S099T-S103A | + |
| G020K-T022L-S024F-S128D-L217E | + |
| A098Q-G100S | + |
| A016S-T033S-S101G-S103A-V104I-N116A-S128N-Y209V-A232V | + |
| A016S-S101A-L148I | + |
| A016S-S101G-V104I | + |
| T022A-N076D-S101G-S103A-V104I-G159D-S188D-A232V-N238Y-Q245R-N248D-A270V-E271F | + |
| T022A-S078N-S101G-S103A-V104I-Q109N-G159D-S188D-L217Q-A232V-Q245R-N248D-E271F | + |
| V030I-S099T-G100S | + |
| S078D-G118S-P129E-Q245R-H249R | + |
| S101G-S103A-V104I-N116L-G118V-S128N-Y209V-A232V | + |
| T022A-S024R-N043R-S101G-S103A-V104I-P129E-S188D-A232V-Q245R-N248D-E271F | + |
| G020R-S078D-G118S-P129E-S188D-N248D | + |
| T022A-S024R-N062E-G118R-S128I-A158E-S166D-S188D | + |
| T022A-T033S-N062E-G118R-S128I | + |
| T022A-S024G-G097A-S101Q-S103A-V104I-Q109N-G159D-S188D-L217Q-A232V-Q245R-N248D-E271F | + |
| G020R-S024R-S101A-S103N-V104I-G118S-P129E-Q245R | + |
| S078D-G118D-P129E-Q245R-H249R | + |
| G020R-S078D-G118D-S188D-Q245R-H249R | + |
| T022A-S024G-N076D-S101Q-S103A-V104I-Q109N-S128A-G159D-S188D-A232V-Q245R-N248D-E271F | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| N062E-S078D-G118D | + |
| N062E-S078D-G118S-N248D | + |
| T022A-S024R-T033S-N062E-G118R-S128I-S166D | + |
| T022A-N076D-S078N-G097S-S101Q-S103A-V104I-Q109N-S128A-G159D-S188D-A232V-Q245R-N248D-E271F | + |
| S056R | + |
| G020R-N062E-S078G-G118D-P129E-G159D-S188D-Q245R-N248D-H249R | + |
| G097P-A098Q-S099T-V104M | + |
| T022A-S024G-S101G-S103A-V104I-L126I-P129S-G159D-S188D-L217Q-A232V-Q245R-N248D-E271F | + |
| G097P-A098Q-S099T | + |
| S128D-T213A | + |
| G020R-S024R-S078G-G118S-Q245R-N248D-H249R | + |
| T022A-V068A-S101G-S103A-V104I-G118R-G159D-S188D-A232V-Q245R-N248D-E271F | + |
| G020K-T022L-S024F-G118R-T213A | + |
| S099G-S101G-G102A-S103A-V104I | + |
| S099A-G100S-S101A | + |
| T022A-N076D-S101G-S103A-V104I-G159D-S188D-A232V-N238Y-Q245R-N248D-E271F-A272V | + |
| T022A-S024G-S101N-S103A-V104I-Q109N-S128A-G159D-S188D-L217Q-A232V-Q245R-N248D-E271F | + |
| V104I-L111V-S128N-L148I | + |
| S024R-S078G-G118D-P129E-S188D-N248D | + |
| A016S-S101G-S103G-V104I-S128N | + |
| G102A-S103A | + |
| S024F-S078N-S128D-T213A | + |
| N062E-S078G-G118S-P129E-G159D-S188D | + |
| A232N | + |
| S024R-N062E-S078G-G118D-P129E-S188D-N248D-H249R | + |
| A016S-S101A-S103A-V104I-L111V | + |
| T022A-S101G-S103A-V104I-A158E-S188D-A232V-Q245R-N248D-E271F | + |
| A098Q-S099G-G100S | + |
| S024R-G118R | + |
| S101A-V104L-S128N | + |
| T022A-S024R-N043R-N076D-S101G-S103A-V104I-P129E-A158E-G159E-S188D-A232V-Q245R-N248D-E271F-A272V | + |
| T022A-S078N-S101G-S103A-V104I-Q109N-G159D-S188D-A232V-Q245R-N248D-E271F | + |
| S099A-G102A | + |
| T022A-S024F-T033S-S101G-S103A-V104I-N116L-S128N-Y209V-T213A-A232V | + |
| A098Q-S099T-G100S | + |
| T033S-N062E-N116L-G118R-S128I-S188D | + |
| T022A-N062E-S101G-S103A-V104I-A158E-G159E-S188D-A232V-Q245R-N248D-E271F | + |
| S024R-T033S-N062E-S128I-S166D | + |
| A098Q-S099T-S103A | + |
| T022A-S103G-L148I | + |
| G097P-S101A-G102A-V104I | + |
| T022A-S101G-S103A-V104I-G159D-S188D-A232V-N238Y-Q245R-N248D-A270V-E271F-A272V-R275S | + |
| N062E-N116L-S128I | + |
| G025P | + |
| G097P-S099T-G102A | + |
| A016S-S024F-T033S-S101G-S103A-V104I-N116L-S128N-Y209A-T213A-A232V | + |
| S132V | + |
| T033S-S128I-A158E | + |
| S099T-S101A-G102A-V104L | + |
| T022A-S101A-V104L-L111V-S128N | + |
| T022L-S078N-G118R | + |
| T022A-N076D-S101G-S103A-V104I-G159D-S188D-A232V-N238Y-Q245R-N248D-A270V-E271F-A272V | + |
| S024R-N116L-S128I-A158E-S166D-S188D | + |
| T033S-S101G-S103A-V104I-N116L-Y209A-A232V | + |
| T022A-S024R-N062E-N116L-G118R-S128I | + |
| G097P-S099T-S103A | + |
| T022L-S024F-S078N-G118R-S128D-S166D-T213A-L217E | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S078D-G118S-P129E-S188D-Q245R-N248D | + |
| N062E-S078G-G118D-G159D-S188D-N248D-H249R | + |
| A098F-S099A-S101G-V104I | + |
| T022A-N076D-S101G-S103A-V104I-I107V-P129E-G159D-S188D-A232V-N238Y-Q245R-N248D-A270V-E271F | + |
| S078G-G118S-S188D | + |
| F050R | + |
| A016S-T022A-S024F-S101G-S103A-V104I-N116L-S128N-Y209V-T213A-L217S-A232V | + |
| T022A-S101G-S103A-V104I-P129E-G159D-S188D-A232V-N238Y-Q245R-N248D-E271F-A272V | + |
| T022A-N076D-G097A-S101Q-S103A-V104I-Q109N-P129E-G159D-S188D-A232V-Q245R-N248D-E271F | + |
| S024F-G118R-S128D-S166D-T213A | + |
| G097P-S099A-S101G | + |
| G097P-S099A-G100S-V104I | + |
| G047I | + |
| S099T-G100S | + |
| G020K-T022L-S078N-G118R-S128D-S166D-T213A | + |
| T033S-N062E-N116L-H120N | + |
| S078D-G118D-S188D-Q245R-N248D | + |
| T022A-S024R-N076D-S101G-S103A-V104I-P129E-G159D-S188D-A215V-A232V-N238Y-Q245R-N248D-E271F | + |
| T022A-S101Q-S103A-V104I-L124T-S128A-P129S-G159D-S188D-A232V-Q245R-N248D-E271F | + |
| T022A-G097A-S101N-S103A-V104I-L124T-G159D-S188D-A232V-Q245R-N248D-E271F | + |
| G020R-S024R-S078D-G118D-P129E-G159D-S188D-N248D | + |
| T022A-S024R-N076D-S101G-S103A-V104I-S188D-A232V-Q245R-N248D-E271F | + |
| S101A-V104I-L111V-S128N | + |
| G020R-S024R-N062E-S078D-G118D-P129E-G159D-S188D | + |
| A016S-V104I-S128N | + |
| G020R-S078G-G118S-Q245R-N248D-H249R | + |
| S099A-S101G-V104I | + |
| T022A-S101Q-S103A-V104I-L124T-S128A-G159D-S188D-A232V-Q245R-N248D-E271F | + |
| A098M | + |
| G097P-A098Q-G102A | + |
| T022A-S024R-N043R-N076D-S101G-S103A-V104I-P129E-S188D-A232V-Q245R-N248D-E271F-A272V | + |
| T022A-S101N-S103A-V104I-L124T-P129E-G159D-S188D-A232V-Q245R-N248D-E271F | + |
| A016S-S101A-V104I-L111V-S128N | + |
| G020R-S024R-S078G-G118S-N248D | + |
| A016S-S101G-S103A-V104I-L111V-S128N | + |
| T022L-S078N-G118R-S128D-S166D | + |
| A098Q | + |
| S024F-G118R | + |
| N062E-S078D-G118S-G159D-S188D-Q245R-N248D | + |
| W113Y | + |
| G020R-S078G-G118S-N248D | + |
| G020K-T022L-S024F-S128D-S166D-T213A | + |
| G020R-S078D-G118D-N248D | + |
| S078D-G118D-Q245R-N248D | + |
| T033S-S101G-S103A-V104I-N116L-S128N-Y209V-T213A-A232V | + |
| V051M | + |
| I035T | + |
| T022A-S101Q-S103A-V104I-L124V-L126I-S128A-P129S-G159D-S188D-A232V-Q245R-N248D-E271F | + |
| T022A-S024G-S078N-S101N-S103A-V104I-Q109N-S128A-G159D-S188D-L217Q-A232V-Q245R-N248D-E271F | + |
| T022A-S024R-N076D-S101G-S103A-V104I-P129E-G159E-S188D-A232V-Q245R-N248D-E271F-A272V | + |
| N062E-S078G-G118S-P129E-G159D-N248D | + |
| T022A-S024F-T033S-S101G-S103A-V104I-N116L-S128N-Y209V-G211Q-A232V | + |
| T022A-G097A-S101Q-S103A-V104I-L124I-P129E-G159D-S188D-A232V-Q245R-N248D-E271F | + |
| G097P-G102A | + |
| N062E-S078D-G118S-S188D-N248D | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-S024R-S101G-S103A-V104I-I107V-P129E-G159D-S188D-A232V-N238Y-Q245R-N248D-E271F-A272V | + |
| T022A-S101A-V104I-L148I | + |
| A016S-T022A-S024F-T033S-S101G-S103A-V104I-N116A-Y209A-G211Q-A232V | + |
| G020R-S024R-N062E-S078G-G118D-P129E-Q236R-Q245R-N248D | + |
| T022L-S024F-S078N-S128D-S166D | + |
| T022A-S024R-S101G-S103A-V104I-P129E-G159D-S188D-A232V-N238Y-Q245R-N248D-A270V-E271F-A272V | + |
| V051C | + |
| A048T-N062E-G118R-A158E-S188D | + |
| T022A-T033S-N116L-G118R-S128I-S166D-S188D | + |
| T022A-S101G-V104L-L111V-S128N | + |
| S056V | + |
| G020K-T022L-S078N-S128D | + |
| G020K-T022L-S024F-S078N-S128D-S166D | + |
| T033S-S101G-S103A-V104I-N116L-Y209V-G211Q-A232V | + |
| G097P-A098Q-S099T-S101A | + |
| T022A-S101G-S103A-V104I-S128N | + |
| T022A-S101G-S103A-V104I-I107V-G159D-S188D-A232V-N238Y-Q245R-N248D-E271F | + |
| T022A-S024R-S101G-S103A-V104I-G159E-S188D-A232V-Q245R-N248D-E271F | + |
| S024R-T033S-N062E-N116L-G118R-S128I-A158E-S188D | + |
| S024R-T033S-N116L-G118R-S128I-A158E-S166D-S188D | + |
| G097P-A098F-S099T-S101A-S103A-V104I | + |
| A098Q-G102A-S103A-V104I | + |
| T033S-S128I-S188D | + |
| T033S-S128I | + |
| T022A-S024G-N076D-G097A-S101Q-S103A-V104I-Q109N-S128A-G159D-S188D-L217Q-A232V-Q245R-N248D-E271F | + |
| W006N | + |
| A098Q-S099A-S101A-V104I | + |
| T033S-N062E-G118R-S128I | + |
| G097S-A098Q-G100S | + |
| T022L-S078N-S128D-L217E | + |
| T022A-S024R-T033S-N116L-S128I-S188D | + |
| G020K-T022L-G118R-S128D-S166D-T213A-L217E | + |
| G102A | + |
| T022A-S024G-S101G-S103A-V104I-Q109N-G159D-S188D-A232V-Q245R-N248D-E271F | + |
| A098F-V104L | + |
| A016S-S101G-V104I-S128N | + |
| A016S-T022A-V104L-L148I | + |
| T022A-S101A-L111V | + |
| T022A-S024R-S101G-S103A-V104I-A158E-S188D-A232V-Q245R-N248D-E271F-A272V | + |
| A016S-T022A-S101A-S103A-V104I | + |
| A098Q-G102A-S103G | + |
| A098Q-S099T-S101G-G102A | + |
| T022A-N062E-S101Q-S103A-V104I-P129E-G159D-S188D-L217Q-A232V-Q245R-N248D-E271F | + |
| A098Q-G100S-S101A-V104I | + |
| T022A-S024R-N076D-S101G-S103A-V104I-P129E-G159D-S188D-A232V-N238Y-Q245R-N248D-E271F-A272V | + |
| G097P-A098Q-S099A-S101A-S103A-V104I | + |
| T022L-S024F-S128D-S166D | + |
| T022A-S099R-S101Q-S103A-V104I-G159D-S188D-A232V-Q245R-N248D-E271F | + |
| T022A-N076D-G097A-S101N-S103A-V104I-Q109N-S128A-G159D-S188D-L217Q-A232V-Q245R-N248D-E271F | + |
| S024F-S128D-S166D-T213A | + |
| G020K-T022L-S078N-S128D-S166D-T213A | + |
| T022A-S024R-S101G-S103A-V104I-P129E-A158E-S188D-A232V-Q245R-N248D-E271F-A272V | + |
| T022A-S101G-S103A-V104I-G159D-S188E-A232T-Q245T-N248E | + |
| G097P-S099G-G102A | + |
| A016S-S101G-S103A-V104I-N116A-S128N-Y209A-G211Q-T213A-A232V | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| A098Q-S099T-G102A | + |
| T022A-N043R-N076D-S101G-S103A-V104I-P129E-A158E-G159E-S188D-A232V-Q245R-N248D-E271F | + |
| T022A-N076D-S101G-S103A-V104I-I107V-G159D-S188D-A232V-N238Y-Q245R-N248D-A270V-E271F | + |
| S024R-N062E-S078D-G118S-P129E-S188D-N248D | + |
| N062E-S078D-G118S-P129E-G159D-S188D-Q245R-N248D-H249R | + |
| A016S-T022A-S101A-S103G-V104I-L148I | + |
| G097P-A098F-S099T-S103A-V104I | + |
| G020K-T022L-S024F-S078N-S128D-S166D-T213A | + |
| G020K-T213A | + |
| S024R-T033S-N062E-A158E-S166D | + |
| G020K-T022L-S078N-G118R-T213A | + |
| S024F-G118R-S128D-S166D | + |
| T022A-S024R-S101G-S103A-V104I-P129E-G159D-S188D-A232V-N238Y-Q245R-N248D-E271F | + |
| S078N-S128D-S166D-T213A | + |
| T022A-T033S-S101G-S103A-V104I-N116L-S128L-G159D-S188D-T213A-A232V-Q245R-N248D-E271F | + |
| S078D-G118S-P129E-G159D-N248D | + |
| S099T-S101A-G102A-S103A | + |
| G097P-G100S | + |
| T022A-N076D-S101G-S103A-V104I-P129E-A158E-S188D-A232V-Q245R-N248D-N269S-E271F | + |
| T022A-S101N-S103A-V104I-L124T-S128A-G159D-S188D-A232V-Q245R-N248D-E271F | + |
| T022L-S024F-S078N-S128D-S166D-T213A | + |
| G097P-A098S-S099G-G102A | + |
| T022A-S128N | + |
| G100S | + |
| G020R-N062E-S078D-G118S-G159D-S188D-N248D | + |
| S078D-G118D-G159D-S188D | + |
| T033S-S128I-S166D | + |
| A016S-T022A-S101G-S103G-V104I-L148I | + |
| D041N | + |
| A098Q-S099T-G100S-S101A-A151V | + |
| A098Q-S099A-G100S-S101A | + |
| T022A-S128I-A158E-S166D-S188D | + |
| G020R-N062E-S078G-G118D-P129E-S188D-N248D | + |
| A098Q-S099T-S101A-G102A | + |
| S024R-T033S-N062E-N116L-S128I-A158E | + |
| T022A-S024G-N076D-S101G-S103A-V104I-Q109N-S128A-G159D-S188D-A232V-Q245R-N248D-E271F | + |
| T022A-S101G-S103A-V104I-I107V-G159D-S188D-A232V-N238Y-Q245R-N248D-E271F-A272V | + |
| G097P-S099A-G102A | + |
| T022A-S024R-T033S-N062E-S128I-S188D | + |
| N062E-S078D-G118D-P129E-Q245R-N248D | + |
| S078D-G118D-G159D-Q245R-N248D | + |
| S024R-N062E-N116L-S128I-A158E-S188D | + |
| A098F-S099G | + |
| A098F-G100S-V104I | + |
| T022A-T033S-S101G-S103A-V104I-S128L-G159D-S188D-A232V-Q245R-N248D-E271F | + |
| G020K-T022L-S024F-S078N | + |
| A098F-S099T-G100S-V104L | + |
| S024R-N076D-S101A-S103A-V104I-S188D-M222S-A232V-Q245R | + |
| T022A-S024R-N043R-S101G-S103A-V104I-P129E-A158E-G159E-S188D-A232V-Q245R-N248D-E271F | + |
| T274F | + |
| G118R-S128I-V139I-A158E-S166D-S188D | + |
| T022A-T033S-N062E-G118R-S166D-S188D | + |
| A016S-S101G-S103A-V104I-N116L-S128N-Y209A-G211Q-A232V | + |
| S024R-S078D-G118S-P129E-N248D | + |
| T022A-T033S-N116L-S128I-A158E | + |
| T022A-N062Q-G097A-S101N-S103A-V104I-G159D-S188D-L217Q-A232V-Q245R-N248D-E271F | + |
| N062E-N116L-S166D-S188D | + |
| T022A-S101G-S103A-V104I-I107V-G159D-S188D-A232V-N238Y-Q245R-N248D-A270V-E271F-A272V | + |
| S099A-G100S-S103A-V104I | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| G020K-S024F-S078N | + |
| T022L-S024F-G118R-S128D-S166D-L217E | + |
| T022A-S101A-V104L | + |
| T022A-S101G-S103A-V104I-L126I-S128A-G159D-S188D-L217Q-A232V-Q245R-N248D-E271F | + |
| A016S-T022A-S101G-S103A-V104I-N116L-G118V-Y209V-G211Q-A232V | + |
| A133T-N269E | + |
| S024R-N062E-S078G-G118D-P129E-G159D-Q245R-H249R | + |
| T022A-S024R-T033S-N062E-S128I-A158E | + |
| T022A-T033S-N062E-S128I | + |
| R275S | + |
| S024R-S078D-G118D-P129E-S188D-N248D-H249R | + |
| T022A-T033S-G118R-S128I | + |
| T033S-N116L-G118R-S128I | + |
| T022L-S024F-S078N-G118R-T213A | + |
| L075G | + |
| S099T-G100S-V104I | + |
| T033S-N062E-N116L-S128I | + |
| S101A | + |
| A016S-T022A-S103A-V104I-L148I | + |
| G097P-G102A-S103A | + |
| G097P-S099T-G100S-S101A-S103A-V104I | + |
| T253Y | + |
| T022A-N062E-N116L-G118R-S128I-S166D | + |
| T022A-N043R-S101G-S103A-V104I-P129E-A158E-S188D-A232V-Q245R-N248D-E271F | + |
| S024R-N062E-S078D-G118S-P129E-G159D-S188D-Q245R-N248D | + |
| G097P-G102A-V104I | + |
| S078N-G118R-S128D-S166D-L217E | + |
| T022A-S024R-N076D-I079T-S101G-S103A-V104I-G159D-S188D-A232V-N238Y-Q245R-N248D-A270V-E271F-A272V | + |
| T022A-S101A-V104L-S128N | + |
| G097P-A098Q-S099T-G102A-V104I | + |
| T022A-G047V-S103A-L148I | + |
| T022A-N116L-S128I-S188D | + |
| G097P-A098Q-S099T-S103A-V104L | + |
| N116L-S128I-A158E-S188D | + |
| T022A-S024R-N043R-S101G-S103A-V104I-A158E-G159E-S188D-A232V-Q245R-N248D-E271F | + |
| A016S-T022A-S101A-S103G-S128N-L148I | + |
| G097P-A098Q-S099T-S101A-V104I | + |
| L257N | + |
| G097P-S099T-S101G-S103A-V104L | + |
| A098Q-S099G-G100S-V104I | + |
| S056L | + |
| S099T-S101A-G102A-S103A-V104I | + |
| T022A-S024R-S101G-S103A-V104I-I107V-P129E-G159D-S188D-A232V-N238Y-Q245R-N248D-E271F | + |
| T022A-S103G-V104I | + |
| T022A-T033S-S101G-S103A-V104I-N116A-S128N-Y209V-G211Q-T213A-A232V | + |
| S078N-S128D | + |
| R170T | + |
| A098F-S099G-G100S | + |
| G020K-T022L-S024F-S078N-T213A | + |
| S099T-S101A-S103A | + |
| G020R-S078G-G118S-G159D-Q245R-H249R | + |
| G097P-S099G-S101G | + |
| S078D-G118S-Q245R | + |
| T022L-S078N-S128D-T213A | + |
| T033S-N062E-N116L-S188D | + |
| G097P-S099G-S101A | + |
| G020R-N062E-S078D-G118D-S188D-Q245R-H249R | + |
| S087W | + |
| A098Q-S099T-S101G-S103A | + |
| A098Q-S099T-S101G-G102A-V104L | + |
| A016S-S024F-T033S-S101G-S103A-V104I-N116L-S128N-Y209V-A232V | + |
| G020K-T022L-S024F-S128D-T213A-L217E | + |
| T022A-S103A-V104I | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| G097P-A098Q-G100S | + |
| G020K-T022L-N062E-S078D-G118D-P129E-Q245R-H249R | + |
| G020K-S024F-S078N-T213A | + |
| A098F-S099A-S103A | + |
| S099T-G100S-S101G | + |
| N076D-S101A-S103A-V104I-S188D-M222S-A232V-Q245R | + |
| S049W | + |
| G020K-T022L-S024F-S128D-S166D-L217E | + |
| S024F-G118R-S128D-S166D-L217E | + |
| T022A-S103A-V104I-L148I | + |
| T022A-S101A-S103A-V104I | + |
| F050Q | + |
| S101G-S103A-V104I-N116A-G118V-Y209V-G211Q-A232V | + |
| S078G-G118D-H120N-H249R | + |
| A016S-S103G-L148I | + |
| G097P-S101A | + |
| S099T-S103A-V104I | + |
| S078G-G118D-P129E-G159D | + |
| T022L-S128D-S166D-T213A | + |
| T022A-S024R-N116L-S128I | + |
| N076D-S101A-S103A-V104I-M222S-A232V-Q245R | + |
| G097P-S099T-S101A-V104I | + |
| A098Q-S099A-S101A-G102A | + |
| T022A-S024R-G025S-Q059K-N076D-S101G-S103A-V104I-P129E-A158E-G159E-S188D-A232V-Q245R-N248D-E271F | + |
| S132G | + |
| T022A-S101A-S103A-V104L-S128N | + |
| A098F-G100S-S101A | + |
| S024F-G118R-T213A | + |
| G097P-S099T-G102A-S103A | + |
| G097P-S099T-G102A-S103A-V104I | + |
| T022A-S101G-S103A-V104I-N116L-G118V-Y209V-G211Q-T213A-A232V | + |
| S024R-T033S-N116L | + |
| A098Q-S099T | + |
| A016S-T022A-S101G-S103A-V104L-S128N-L148I | + |
| A098F-S099T-S101A | + |
| A098Q-G100S-S103A | + |
| T022A-N062E-N116L-S128I-S188D | + |
| Q012E-S259N | + |
| T022A-S024F-S101G-S103A-V104I-N116L-G118V-Y209A-G211Q-T213A-A232V | + |
| T022A-S024R-N076D-S101G-S103A-V104I-I107V-G159D-S188D-A232V-N238Y-Q245R-N248D-E271F-A272V | + |
| T022A-S024G-G097A-S101G-S103A-V104I-Q109G-S128A-G159D-S188D-L217Q-A232V-Q245R-N248D-E271F | + |
| A016S-T022A-S101G-S103G-V104L-S128N | + |
| Q245D | + |
| G020K-T022L-S128D-S166D-T213A | + |
| S099T-V104I | + |
| T022A-S024F-T033S-S101G-S103A-V104I-N116L-Y209A-A232V | + |
| G020R-S078D-G118D-Q245R-N248D | + |
| S099G-S101A-V104L | + |
| G097P-S099T | + |
| S078G-G118D-Q245R | + |
| G097P-A098Q-S099A-S103A | + |
| A016S-T022A-S103A | + |
| G097P-A098Q-S101A-S103G-V104L | + |
| S078N-G118R-S128D-S166D | + |
| V026Q | + |
| G097P-A098F-S099T-S103A-V104L | + |
| T022A-S024R-S101G-S103A-V104I-G159D-S188D-A232V-N238Y-Q245R-N248D-E271F-A272V | + |
| S024R-T033S-G118R-S128I-S166D-S188D | + |
| G020K-T022L-S078N-G118R-S128D-S166D | + |
| A098F-S099T-G102A-S103G | + |
| M119L | + |
| N062E-S078G-G118D-P129E-S188D | + |
| T022L-G118R-S128D-S166D | + |
| T022A-T033S-N116L-S128I-S188D | + |
| A098F-S099T-S101G-V104L | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T033S-N116L | + |
| V104L-L111V-S128N | + |
| S024R-N062E-S078D-G118D-P129E-Q245R-H249R | + |
| G097P-S099A-G100S | + |
| A016S-T022A-S103A-L111V | + |
| G097P-S099A-G102A-V104I | + |
| G097P-A098Q-S099A-S103A-V104I | + |
| T022A-G097A-S101N-S103A-V104I-L124T-P129S-G159D-S188D-A232V-Q245R-N248D-E271F | + |
| T022L-S024F-S078N-S128D-T213A-L217E | + |
| T022A-N043R-S101G-S103A-V104I-A158E-S188D-A232V-Q245R-N248D-E271F-A272V | + |
| P055V | + |
| T022A-N062E-S101Q-S103A-V104I-S128A-G159D-S188D-L217Q-A232V-Q245R-N248D-E271F | + |
| G097P-A098Q | + |
| S101G-S103A-V104I-L111V-S128N | + |
| A016S-S024F-T033S-S101G-S103A-V104I-N116L-S128N-Y209A-A232V | + |
| G020R-S078D-G118D | + |
| T022A-G097A-S101N-S103A-V104I-L124T-P129E-G159D-S188D-A232V-Q245R-N248D-E271F | + |
| T033S-G118R-S128I-S166D-S188D | + |
| N062E-S078G-G118D-P129E-G159D-S188D-H249R | + |
| V051Y | + |
| G097P-G102A-S103A-V104I | + |
| V030N | + |
| V104L | + |
| S024R-T033S-G118R-S128I-A158E-S166D | + |
| N062E-S078D-G118S-P129E-G159D-Q245V-N248E-E271T | + |
| S024R-T033S-G118R-S128I-S166D | + |
| A016S-S101G-S103G-V104L | + |
| S078N-S128D-L217E | + |
| A016S-T022A-S101A-V104I-L111V | + |
| A016M | + |
| S099T-G102A-S103A-V104I | + |
| T022A-S101A-V104I-L111V-S128N | + |
| T022A-S024R-N043R-N076D-S078P-S101G-S103A-V104I-P129E-G159E-S188D-A232V-Q245R-N248D-E271F | + |
| T022L-S078N-S128D | + |
| V051E | + |
| N062E-S078D-G118S-P129E-G159D | + |
| T022A-S101N-S103A-V104I-L124T-P129S-G159D-S188D-L217Q-A232V-Q245R-N248D-E271F | + |
| A015H | + |
| G020R-S024R-N062E-S078D-G118S-G159D-S188D-Q245R-H249R | + |
| G020K-S024F-G118R-S128D-S166D-T213A-L217E | + |
| A016S-T022A-S101G-S103G-V104I | + |
| P014N | + |
| T022A-S101Q-S103A-V104I-L124T-S128A-P129E-G159D-S188D-A232V-Q245R-N248D-E271F | + |
| T022A-G097A-S101G-S103A-V104I-Q109N-G159D-S188D-A232V-Q245R-N248D-E271F | + |
| T022A-S024R-S101G-S103A-V104I-G159D-S188D-A232V-N238Y-Q245R-N248D-E271F | + |
| G097P-A098Q-S101A-G102A | + |
| T033S-A158E-S166D-S188D | + |
| I035C | + |
| T033S-S128I-A158E-S188D | + |
| I008S | + |
| S078N-T213A | + |
| V028T-A215V | + |
| G020K-T022L-S078N-S128D-S166D-T213A-L217E | + |
| G146C-Q236L | + |
| G020K | + |
| S101G-S103A-V104I-N116A-S128N-Y209V-T213A-A232V | + |
| S024R-S078D-G118D-G159D-K237E | + |
| S024R-T033S-N116L-S128I | + |
| T022A-S024R-S101G-S103A-V104I-I107V-G159D-S188D-A232V-N238Y-Q245R-N248D-E271F | + |
| A048G | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S212D | + |
| N062E-N116L-A158E-S188D | + |
| T022A-S024F-S101G-S103A-V104I-N116L-G118V-Y209A-T213A-A232V | + |
| S024F-S078N-G118R-S128D-S166D-T213A-L217E | + |
| A098F-S101G | + |
| S132K | + |
| T022A-S101G-S103A-V104I-N116A-G118V-Y209V-T213A-A232V | + |
| T022A-T033S-S101G-S103A-V104I-N116L-Y209A-G211Q-A232V | + |
| G097P-A098Q-S099T-S101A-G102A-V104I | + |
| G097P-S099T-S101A-S103A | + |
| A016S-T022A-S024F-T033S-S101G-S103A-V104I-N116L-S128N-Y209V-A232V | + |
| A098Q-S099T-S101G-V104I | + |
| G020K-T022L-S024F-G118R-S128D-S166D-T213A-L217E | + |
| G097P-A098Q-S099G-S101G | + |
| G097P-A098Q-S099A-G100S | + |
| T033S-N062E-G118R-S166D-S188D | + |
| A016S-T022A-S024F-S101G-S103A-V104I-N116L-G118V-Y209V-T213A-A232V | + |
| N062E-S078G-G118S-P129E-S188D-Q245R-H249R | + |
| S024F-T033S-S101G-S103A-V104I-N116L-S128N-Y209V-T213A-A232V | + |
| G097P-S099G-S101G-S103A | + |
| A098F-G102A-V104I | + |
| S078D-G118S-Q245R-N248D | + |
| G097P-A098Q-S099A-G102A | + |
| G097P-A098Q-G100S-S103A | + |
| T022A-S024R-N062E-S101G-S103A-V104I-P129E-S188D-A232V-Q245R-N248D-E271F | + |
| S078G-G118D-Q245R-H249R | + |
| G097P-S099A-G100S-S101A | + |
| G097P-S099G-S103G | + |
| G020K-S024F-S128D-S166D-T213A-L217E | + |
| I008N | + |
| N269A | + |
| A088T | + |
| T038S | + |
| A016S-T022A-S101G-S103A-V104I-N116A-G118V-Y209A-T213A-A232V | + |
| G097P-A098F-S103A-V104I | + |
| A098F-S099A | + |
| T022A-N076D-S101G-S103A-V104I-I107V-G159D-S188D-A232V-N238Y-Q245R-N248D-E271F-A272V | + |
| A098Q-S099T-G100S-V104L | + |
| G097P-S099T-V104L | + |
| A098Q-S099T-S103A-V104I | + |
| A016S-T022A-S103G-S128N | + |
| T022A-T033S-S166D-S188D | + |
| G097P-G100S-S103A | + |
| T022L-S024F-S078N-T213A-A232T | + |
| A013S | + |
| G097P-S101A-G102A-S103A | + |
| A016S-T022A-S101A-V104L-L111V-S128N | + |
| G097P-A098Q-S099T-G102A | + |
| S024R-S078G-G118D-N248D | + |
| G020K-S078N-S128D-S166D-T213A-L217E | + |
| G020R-S078G-G118D-N248D | + |
| A085S | + |
| A016S-T022A-S128N | + |
| S024F-S078N-G118R-S128D-S166D-L217E | + |
| A098Q-S099A-G100S-V104L | + |
| S024R-S078D-G118D-G159D-N248D | + |
| A098Q-S103A | + |
| N062E-A158E-S166D | + |
| G020K-S024F-G118R-S128D-S166D-L217E | + |
| G097P-A098F | + |
| G080F | + |
| G097P-S099A-S103A-V104I | + |
| T022A-S101A-L111V-S128N-L148I | + |
| A016S-S101G-S103A-V104I | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| T022A-N062Q-S101Q-S103A-V104I-L124V-P129S-G159D-S188D-A232V-Q245R-N248D-E271F | + |
| G097P-A098F-S099T-S101G-V104I | + |
| A073Q | + |
| K251C | + |
| A016S-T022A-S101A-S103A-V104L-L148I | + |
| G097P-A098Q-G102A-S103G | + |
| G020R-S078G-G118D-Q245R-N248D | + |
| S099A-G100S-S103A | + |
| T038A | + |
| T022A-S024R-S101G-S103A-V104I-G159D-S188D-A232V-N238Y-Q245R-N248D-A270V-E271F-A272V | + |
| T022L-S078N-S128D-T213A-L217E | + |
| T022A-S024R-N043R-N076D-S101G-S103A-V104I-P129E-G159E-S188D-A232V-Q245R-N248D-E271F | + |
| N116L-S128I-A158E-S166D | + |
| A016S-T022A-T033S-S101G-S103A-V104I-N116L-Y209A-P210Q-T213A-A232V | + |
| S049V-V199I | + |
| T022A-S103G-V104I-L148I | + |
| A016S-S101G-V104L | + |
| A098F-S099T-S101G-G102A-V104I | + |
| T022A-A158E-S166D-S188D | + |
| A016S-T022A-T033S-S101G-S103A-V104I-N116L-S128N-Y209V-G211Q-A232V | + |
| T022A-S024G-N076D-G097A-S101G-S103A-V104I-Q109G-G159D-S188D-L217Q-A232V-Q245R-N248D-E271F | + |
| A016S-S024F-T033S-S101G-S103A-V104I-N116A-Y209V-T213A-A232V | + |
| N062E-N116L-G118R-S128I-A158E-S188D | + |
| N062E-S128I-S188D | + |
| G097P | + |
| T022A-S024F-T033S-S101G-S103A-V104I-N116A-S128N-Y209A-G211Q-T213A-A232V | + |
| S024R-S078G-G118S-P129E-Q245R-H249R | + |
| S049D | + |
| G097P-A098Q-S099T-G100S | + |
| T022A-S024R-T033S-N116L-G118R-S128I-S188D | + |
| T022A-T033S-S101G-S103A-V104I-N116A-Y209A-T213A-A232V | + |
| T022L-S078N-G118R-S128D-S166D-L217E | + |
| S078G-G118D-P129E-N248D | + |
| S099A-V104L | + |
| T022A-N043R-S101G-S103A-V104I-A158E-S188D-A232V-Q245R-N248D-E271F | + |
| A098Q-V104L | + |
| T022A-T033S-G118R-S128I-S166D-S188D | + |
| G097P-S099T-S101A | + |
| W006Y | + |
| S024R-N062E-S078G-G118D-P129E-S188D-Q245R-H249R | + |
| S024R-S078D-G118D-Q245R-N248D | + |
| T022A-N076D-S101G-S103A-V104I-I107V-P129E-G159D-S188D-A232V-N238Y-Q245R-N248D-E271F | + |
| T022A-S101N-S103A-V104I-L124V-L126I-S128A-P129E-G159D-S188D-A232V-Q245R-N248D-E271F | + |
| B015T | + |
| G097P-S099T-S101G-G102A-S103A-V104I | + |
| A016S-V104L-L111V-S128N | + |
| G097P-A098F-S099T | + |
| S099G | + |
| S049I | + |
| A016S-S103G-V104L-L148I | + |
| N062E-S078G-G118D-S188D-N248D | + |
| G020R-N062E-S078D-G118S-G159D-S188D-K235R-N248D | + |
| T022A-S024R-N116L | + |
| S024R-T033S-S128I | + |
| N062E-S078D-G118D-Q245R-N248D-H249R | + |
| A098F-S099A-S103A-V104I | + |
| V004Y | + |
| T022L-S024F-S078N-T213A | + |
| A016S-S101G-S103A-V104I-N116L-G118V-Y209A-G211Q-A232V | + |
| G097P-A098Q-G102A-S103G-V104I | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S078G-G118S-H249R | + |
| S024F-S101G-S103A-V104I-N116A-S128N-Y209V-A232V | + |
| G097P-V104I | + |
| S024F-T033S-S101G-S103A-V104I-N116A-S128N-Y209A-T213A-A232V | + |
| A098Q-S099G-V104L | + |
| N062E-S078D-G118D-P129E | + |
| L196K | + |
| S078G-G118D-N248D-H249R | + |
| S087M | + |
| T022A-S101G-S103A-V104I-Q109G-S128A-G159D-S188D-L217Q-A232V-Q245R-N248D-E271F | + |
| S216N-T253C | + |
| G097P-A098Q-S101G-G102A-V104I | + |
| G020K-T022L-G118R | + |
| A016S-T022A-S101A-S103G-V104I-L111V | + |
| A098F-S099A-G102A | + |
| T033S-N062E-G118R-S128I-A158E | + |
| A098Q-S099T-S101A | + |
| G020R-N062E-S078D-G118S-P129E-G159D-S188D-Q245R-N248D | + |
| V011L | + |
| S101A-L148I | + |
| A098F-S099A-S101A | + |
| F050K | + |
| N062E-S078G-G118S-G159D-S188D-N248D | + |
| V051A | + |
| T022A-T033S-G118R-S128I-A158E-S166D | + |
| V051A-S212D | + |
| P014W | + |
| Q012E | + |
| T022A-T033S-S128I-A158E-S188D | + |
| T022A-S024R-N062E-N076D-S101G-S103A-V104I-P129E-S188D-A232V-Q245R-N248D-E271F | + |
| G097P-S103A | + |
| S078G-G118D | + |
| G020R-S024R-N062E-S078G-G118D-S188D-Q245R-H249R | + |
| G097P-A098Q-G102A-V104L | + |
| T022A-S101N-S103A-V104I-L124V-S128A-G159D-S188D-A232V-Q245R-N248D-E271F | + |
| A098Q-S099T-S101A-G102A-S103A-V104I | + |
| A016S-L111V-S128N | + |
| T022A-N062E-N116L-S128I-A158E | + |
| G080C | + |
| S024R-S078D-G118S | + |
| G097P-A098F-S099G | + |
| A016S-S024F-T033S-S101G-S103A-V104I-N116L-S128N-Y209V-T213A-A232V | + |
| G097P-S099G-G100S-S103A | + |
| S212A | + |
| S024R-N062E-S078D-G118S-P129E-G159D-S188D-N248D-H249R | + |
| T022A-S103G-V104L-S128N-L148I | + |
| T022A-S101N-S103A-V104I-L124T-S128A-P129S-G159D-S188D-A232V-Q245R-N248D-E271F | + |
| A016S-T022A-S103G-V104L-S128N-L148I | + |
| G097P-A098Q-S101A-V104I | + |
| A016S-S101A-V104I | + |
| V026D | + |
| G097P-S101A-G102A-S103A-V104I | + |
| A016S-T022A-S024F-T033S-S101G-S103A-V104I-N116L-S128N-Y209A-T213A-A232V | + |
| T033S-A158E-S188D-A272D | + |
| A048V | + |
| G020K-T022L-S078N | + |
| G020K-G118R-T213A | + |
| T022A-S103A-V104L-L148I | + |
| T022A-N062E-S128I-A158E-S166D | + |
| G097P-A098Q-S099G-G100S-V104I | + |
| S049V | + |
| G097P-A098Q-S099T-S101A-S103G | + |
| G097P-A098F-S099A-S101A-V104I | + |
| S128I-A158E-S166D-S188D | + |

TABLE 2-1-continued

BMI cleaning performance of Group D1 variants.
PI = Performance Index
PI > or = 3 is +++; PI between 2.9 and 2 = ++; PI between
1.9 and 1.1 = + in a Detergent
Composition as described in Table 1

| Sequence of GG36 Variants (BPN' numbering) | PI Relative to GG36; BMI assay at 25° C. |
|---|---|
| S128D-S166D | + |
| S099G-G102A-V104I | + |
| T022A-S166D | + |
| A016S-T022A-S101G-S103A-V104I-N116L-Y209V-T213A-A232V | + |
| T022A-T033S-S101G-S103A-V104I-G118R-S128L-G159D-S188D-A232V-Q245R-N248D-E271F | + |
| G097P-S099A-S103G | + |
| A016S-T033S-S101G-S103A-V104I-N116L-S128N-Y209A-G211Q-T213A-A232V | + |
| S078G-G118S | + |
| T033S-G118R-S128I-A158E-S166D-S188D | + |
| S024R-N062E-S101A-S103A-V104I-S188D-M222S-A232V-Q245R | + |
| S099T-S101A-G102A-S103A-V104L | + |
| S056F | + |
| T022A-G097A-S101Q-S103A-V104I-L124V-L126I-S128A-P129E-G159D-S188D-A232V-Q245R-N248D-E271F | + |
| T022L-S024F-S128D-L217E | + |
| T022A-S101Q-S103A-V104I-L124V-L126I-S128A-G159D-S188D-A232V-Q245R-N248D-E271F | + |
| G020R-S078G-G118S-H249R | + |

TABLE 2-2

BMI cleaning performance of Group D2 variants.
PI = Performance Index
PI > or = 3 is +++; PI between 2.9 and 2 = ++; PI between 1.9 and 1.1 = + in Detergent
Composition 104 as described in Table 1

| Sequence of GG36 Variants (BPN' numbering) | PI Relative to GG36; BMI assay, Detergent 104 at 25° C. |
|---|---|
| A016S-S024F-S101D-S103A-V104I-N116A-S128N-Y209V-T213A-A232V | +++ |
| A016S-S024F-S101G-S103A-V104I-N116A-S128N-S130D-Y209V-T213A-A232V | +++ |
| A016S-S024F-S101G-S103A-V104I-N116A-S128N-S166D-Y209V-T213A-A232V | +++ |
| A016S-S024F-S101G-S103A-V104I-N116A-S128N-S188D-Y209V-T213A-A232V | +++ |
| A016S-S024F-T033S-S101G-S103A-V104I-N116L-Y209A-T213A-A232V | +++ |
| A016S-S024R-S101G-S103A-V104I-N116A-S128N-Y209V-T213A-A232V | +++ |
| A016S-S101G-S103A-V104I-N116L-S128N-Y209A-G211Q-A232V | +++ |
| A016S-T022A-S024F-S101G-S103A-V104I-N116A-S128N-Y209V-T213A-A232V | +++ |
| A016S-T022A-S101G-S103A-V104I-N116A-Y209V-G211Q-T213A-A232V | +++ |
| A016S-T033S-S101G-S103A-V104I-N116A-Y209A-G211Q-A232V | +++ |
| A098Q-G102A-S103G | +++ |
| A098Q-S099T-G102A-S103G | +++ |
| G020K-N062E-N116L-T213A | +++ |
| G020K-N062E-N116L-T213A-M222S | +++ |
| G020K-N062E-S188D-T213A-M222S | +++ |
| G020K-S024F-S166D-T213A-L217E | +++ |
| G020K-S166D-L217E | +++ |
| G020K-T022L-G118R-P129E-S188D | +++ |
| G020K-T022L-S024F-S078N-G118R-S166D-T213A-L217E | +++ |
| G020K-T022L-S078N-G118R-S128D-T213A-L217E | +++ |
| G020R-G061W-P129E-G159D-S188D-Q245R | +++ |
| G020R-G118R | +++ |
| G020R-G118R-G159D-N248D-H249R | +++ |
| G020R-G118R-G159D-S188D-N248D | +++ |
| G020R-G118R-G159D-S188D-Q245R-N248D-H249R | +++ |
| G020R-G118R-P129E | +++ |
| G020R-G118R-P129E-G159D-H249R | +++ |
| G020R-G118R-P129E-GI59D-Q245R-N248D | +++ |

TABLE 2-2-continued

BMI cleaning performance of Group D2 variants.
PI = Performance Index
PI > or = 3 is +++; PI between 2.9 and 2 = ++; PI between 1.9 and 1.1 = + in Detergent
Composition 104 as described in Table 1

| Sequence of GG36 Variants (BPN' numbering) | PI Relative to GG36; BMI assay, Detergent 104 at 25° C. |
|---|---|
| G020R-G118R-P129E-G159D-Q245R-N248D-H249R | +++ |
| G020R-G118R-P129E-G159D-S188D | +++ |
| G020R-G118R-P129E-S188D | +++ |
| G020R-G118R-P129E-S188D-N248D | +++ |
| G020R-G118R-S188D-N248D | +++ |
| G020R-G118R-S188D-Q245R-N248D | +++ |
| G020R-G118R-S188D-Q245R-N248D-H249R | +++ |
| G020R-G159D-N248D-H249R | +++ |
| G020R-G159D-Q245R-N248D | +++ |
| G020R-G159D-S188D | +++ |
| G020R-G159D-S188D-H249R | +++ |
| G020R-G159D-S188D-Q245R | +++ |
| G020R-G159D-S188D-Q245R-N248D | +++ |
| G020R-N043R-S101A-P210I-G211Q | +++ |
| G020R-N062E-G118R | +++ |
| G020R-N062E-G118R-G159D-N248D | +++ |
| G020R-N062E-G118R-S188D-N248D-H249R | +++ |
| G020R-N062E-S078G-G118S-G159D-S188D | +++ |
| G020R-N062E-S078G-G118S-S188D-Q245R | +++ |
| G020R-N062E-S078R-P129E-S188D-N248D | +++ |
| G020R-P129E | +++ |
| G020R-P129E-G159D-Q245R-N248D | +++ |
| G020R-P129E-G159D-Q245R-N248D-H249R | +++ |
| G020R-P129E-G159D-S188D-Q245R | +++ |
| G020R-P129E-H249R | +++ |
| G020R-P129E-N248D | +++ |
| G020R-P129E-Q245R | +++ |
| G020R-P129E-Q245R-N248D | +++ |
| G020R-P129E-S188D-H249R | +++ |
| G020R-P129E-S188D-N248D-H249R | +++ |
| G020R-P129E-S188D-Q245R | +++ |
| G020R-S024R-G118R-G159D-S188D-Q245R-N248D | +++ |
| G020R-S024R-G118R-P129E-G159D-N248D | +++ |
| G020R-S024R-G118R-P129E-G159D-N248D-H249R | +++ |
| G020R-S024R-G118R-P129E-G159D-S188D-N248D-H249R | +++ |
| G020R-S024R-G118R-S188D-N248D | +++ |
| G020R-S024R-N062E-P129E-S188D-N248D | +++ |
| G020R-S024R-N062E-S078D-G118S-P129E-Q245R-N248D-H249R | +++ |
| G020R-S024R-N062E-S078D-G118S-P129E-S188D-Q245R | +++ |
| G020R-S024R-N062E-S078G-G118S-S188D-N248D | +++ |
| G020R-S024R-N062E-S078G-G118S-G159D-N248D | +++ |
| G020R-S024R-N062E-S078G-G118S-P129E | +++ |
| G020R-S024R-N062E-S078G-G118S-Q245R | +++ |
| G020R-S024R-P129E-G159D | +++ |
| G020R-S024R-P129E-G159D-N248D-H249R | +++ |
| G020R-S024R-P129E-G159D-S188D-H249R | +++ |
| G020R-S024R-P129E-G159D-S188D-N248D | +++ |
| G020R-S024R-P129E-H249R | +++ |
| G020R-S024R-S078D-G118D-P129E-Q245R-H249R | +++ |
| G020R-S024R-S078D-G118S-G159D-Q245R | +++ |
| G020R-S024R-S078D-G118S-P129E-G159D-Q245R-H249R | +++ |
| G020R-S024R-S078D-G118S-S188D-Q245R | +++ |
| G020R-S024R-S078G-G118S-G159D | +++ |
| G020R-S024R-S078G-G118S-G159D-Q245R-N248D | +++ |
| G020R-S024R-S101A-P210I-G211Q | +++ |
| G020R-S024R-S188D | +++ |
| G020R-S024R-S188D-Q245R-N248D | +++ |
| G020R-S078G-G118S-P129E-G159D-S240E-N248D-H249R | +++ |
| G020R-S078R-G118R-P129E-S188D-N248D | +++ |
| G020R-S078R-G159D-S188D-Q245R-N248D | +++ |
| G020R-S078R-P129E-G159D-S188D-H249R | +++ |
| G020R-S188D-H249R | +++ |
| G020R-S188D-Q245R-N248D-H249R | +++ |
| G061P-S078N-G097A-S101N-S128A-V203Y-L217Q | +++ |
| G097A-S101N-S128A-L217Q | +++ |
| G097P-A098Q-S099A-V104I | +++ |
| G097P-A098Q-S099T-S101G | +++ |
| G097P-S099A-G102A | +++ |
| G118R-P129E-G159D-Q245R-N248D | +++ |
| G118R-P129E-G159D-S188D-H249R | +++ |
| G118R-P129E-G159D-S188D-K237R-N248D-H249R | +++ |

TABLE 2-2-continued

BMI cleaning performance of Group D2 variants.
PI = Performance Index
PI > or = 3 is +++; PI between 2.9 and 2 = ++; PI between 1.9 and 1.1 = + in Detergent Composition 104 as described in Table 1

| Sequence of GG36 Variants (BPN' numbering) | PI Relative to GG36; BMI assay, Detergent 104 at 25° C. |
|---|---|
| G118R-P129E-H249R | +++ |
| G118R-S188D-N248D-H249R | +++ |
| G159D-S188D | +++ |
| G159D-S188D-Q245R-N248D | +++ |
| N018K-G020R-S024R-R045T-S101A-P210I-G211Q-T213A | +++ |
| N062E-G118R-P129E-S188D-Q245R | +++ |
| N062E-G159D-S188D-H249R | +++ |
| N062E-P129E-G159D-S188D-Q245R | +++ |
| N062E-S078G-G118D-N248D-H249R | +++ |
| N062E-S078G-G118R-G159D-S188D-P210L-N248D | +++ |
| N062E-S078G-G118R-P129E-N248D | +++ |
| N062E-S078R-G159D | +++ |
| N062E-S078R-G159D-N248D | +++ |
| N062E-S078R-P129E-G159D | +++ |
| N062E-S078R-P129E-S188D-Q245R-N248D | +++ |
| N062E-S078R-Q245R-N248D | +++ |
| P086S-S087G-A088V-G097A-N117S-S128A-L217Q | +++ |
| P129E-G159D | +++ |
| P129E-G159D-Q245R-N248D | +++ |
| P129E-G159D-S188D-H249R | +++ |
| P129E-Q245R-N248D-H249R | +++ |
| S024F-G118R-S128D | +++ |
| S024F-S078N-T213A-L217E | +++ |
| S024G-G061S-S078N-S101N-Q109G-S128A-L217Q-N243V | +++ |
| S024G-S078N-A088T-S101N-Q109G-N116T-S128A-A158S-L217Q-N218S-L257G | +++ |
| S024G-S078N-S101N-Q109G-L217Q-N243V-N248A | +++ |
| S024G-S078N-S101N-Q109G-N116T-S128A-L217Q-N243V-S256R | +++ |
| S024G-S078N-S101N-Q109G-S128A-L217Q | +++ |
| S024G-S078N-S101N-Q109G-S128A-L217Q-S256R | +++ |
| S024G-S078N-S101N-S128A-A158S-L217Q-L257G | +++ |
| S024G-S078N-S101N-S128A-L217Q | +++ |
| S024G-S078N-S101N-S128A-L217Q-N243V | +++ |
| S024R-G118R-G159D-S188D | +++ |
| S024R-G118R-G159D-S188D-N248D | +++ |
| S024R-G118R-P129E-G159D-S188D-Q245R-N248D | +++ |
| S024R-G118R-P129E-G159D-S188D-Q245R-N248D-H249R | +++ |
| S024R-G118R-P129E-S188D-H249R | +++ |
| S024R-G118R-S188D | +++ |
| S024R-G118R-S188D-N248D | +++ |
| S024R-G159D-S188D-Q245R | +++ |
| S024R-N062E-G159D-S188D-Q245R | +++ |
| S024R-N062E-N116L-G118R-S128I-A158E | +++ |
| S024R-N062E-N116L-G118R-S128I-S166D | +++ |
| S024R-N062E-Q245R | +++ |
| S024R-N062E-S078D-G118S-S188D-Q245R | +++ |
| S024R-N062E-S078G-G118D-N248D-H249R | +++ |
| S024R-N062E-S078G-G118S-S188D-Q245R-N248D | +++ |
| S024R-N062E-S078R-G159D-N248D | +++ |
| S024R-N062E-S078R-P129E-H249R | +++ |
| S024R-N062E-S188D-N248D | +++ |
| S024R-P129E-G159D-Q245R-N248D | +++ |
| S024R-P129E-G159D-S188D-Q245R-N248D-H249R | +++ |
| S024R-P129E-Q245R-N248D | +++ |
| S024R-S078R-G118R-P129E-G159D-S188D | +++ |
| S024R-S078R-G159D-S188D | +++ |
| S024R-S078R-G159D-S188D-Q245R-N248D-H249R | +++ |
| S024R-S188D-N248D | +++ |
| S024R-S188D-Q245R-N248D | +++ |
| S078N-G118R-S166D-L217E-M222S | +++ |
| S078R-G118R-P129E | +++ |
| S078R-G118R-P129E-S188D-N248D | +++ |
| S078R-L111I-N185I-I198L-L217E | +++ |
| S078R-P129E-G159D | +++ |
| S078R-V084A-P129E-Q245R | +++ |
| S099T-S101A-G102A-S103A | +++ |
| S101G-S103A-V104I-G159D-S188D-A232V-Q245R-N248D-E271F | +++ |
| S101G-S103A-V104I-N116L-G159D-S188D-A232V-Q245R-N248D-E271F | +++ |

TABLE 2-2-continued

BMI cleaning performance of Group D2 variants.
PI = Performance Index
PI > or = 3 is +++; PI between 2.9 and 2 = ++; PI between 1.9 and 1.1 = + in Detergent
Composition 104 as described in Table 1

| Sequence of GG36 Variants (BPN' numbering) | PI Relative to GG36; BMI assay, Detergent 104 at 25° C. |
|---|---|
| S188D-Q245R-N248D | +++ |
| T022A-G097A-S101G-S103A-V104I-L124V-P129S-G159D-S188D-A232V-Q245R-N248D-E271F | +++ |
| T022A-G097A-S101N-S103A-V104I-S128A-G159D-S188D-A232V-Q245R-N248D-E271F | +++ |
| T022A-G097A-S101N-S103A-V104I-S128A-G159D-S188D-L217Q-A232V-Q245R-N248D-E271F | +++ |
| T022A-G097A-S101Q-S103A-V104I-L124V-P129S-G159D-S188D-A232V-Q245R-N248D-E271F | +++ |
| T022A-G097A-S101Q-S103A-V104I-P129S-A232V-Q245R | +++ |
| T022A-G097S-S101N-S103A-V104I-S128A-G159D-S188D-L217Q-A232V-Q245R-N248D-E271F | +++ |
| T022A-G097S-S101N-S103A-V104I-S128A-G159D-S188D-L217Q-M222S-A232V-Q245R-N248D-E271F | +++ |
| T022A-S024F-S101G-S103A-V104I-N116L-S128N-Y209A-G211Q-T213A-A232V | +++ |
| T022A-S024G-S078N-S101N-S103A-V104I-G159D-S188D-L217Q-A232V-Q245R-N248D-E271F | +++ |
| T022A-S024R-N062E-N116L-G118R-A158E | +++ |
| T022A-S024R-T033S-N062E-N116L-G118R-P129E-S188D | +++ |
| T022A-S024R-T033S-N116L-A158E-S166D-S188D | +++ |
| T022A-S101G-S103A-G159D-S188D-A232V-Q245R-N248D-E271F | +++ |
| T022A-S101G-S103A-N116L-G159D-S188D-A232V-Q245R-N248D-E271F | +++ |
| T022A-S101G-S103A-V104I-G159D-A232V-Q245R-N248D-E271F | +++ |
| T022A-S101G-S103A-V104I-G159D-S188D-A232V-N248D-E271F | +++ |
| T022A-S101G-S103A-V104I-G159D-S188D-A232V-Q245R-E271F | +++ |
| T022A-S101G-S103A-V104I-G159D-S188D-A232V-Q245R-N248D | +++ |
| T022A-S101G-S103A-V104I-G159D-S188D-A232V-Q245R-N248D-E271F | +++ |
| T022A-S101G-S103A-V104I-G159D-S188D-M222S-A232V-Q245R-N248D-A270V-E271F | +++ |
| T022A-S101G-S103A-V104I-G159D-S188D-M222S-A232V-Q245R-N248D-E271F | +++ |
| T022A-S101G-S103A-V104I-G159D-S188D-Q245R-N248D-E271F | +++ |
| T022A-S101G-S103A-V104I-G159D-S188E-A232V-Q245R-N248D | +++ |
| T022A-S101G-S103A-V104I-L217Q-A232V-Q245R | +++ |
| T022A-S101G-S103A-V104I-M119V-P129E-G159D-S188D-L217Q-A232V-Q245R-N248D-E271F | +++ |
| T022A-S101G-S103A-V104I-N116L-G159D-A232V-Q245R-N248D-E271F | +++ |
| T022A-S101G-S103A-V104I-N116L-G159D-S188D-A232V-N248D-E271F | +++ |
| T022A-S101G-S103A-V104I-N116L-G159D-S188D-A232V-Q245R-E271F | +++ |
| T022A-S101G-S103A-V104I-N116L-G159D-S188D-A232V-Q245R-N248D-E271F | +++ |
| T022A-S101G-S103A-V104I-N116L-G159D-S188D-Q245R-N248D-E271F | +++ |
| T022A-S101G-S103A-V104I-N116L-S128N-Y209V-G211Q-T213A-A232V | +++ |
| T022A-S101G-S103A-V104I-N116L-S188D-A232V-Q245R-N248D-E271F | +++ |
| T022A-S101G-S103A-V104I-N116L-Y209V-G211Q-A232V | +++ |
| T022A-S101G-S103A-V104I-P129S-L217Q-A232V-Q245R | +++ |
| T022A-S101G-S103A-V104I-S128A-P129S-L217Q-A232V-Q245R | +++ |
| T022A-S101G-S103A-V104I-S128L-G159D-S188D-T213A-A232V-Q245R-N248D-E271F | +++ |
| T022A-S101G-S103A-V104I-S188D-A232V-Q245R-N248D-E271F | +++ |
| T022A-S101G-V104I-G159D-S188D-A232V-Q245R-N248D-E271F | +++ |
| T022A-S101G-V104I-N116L-G159D-S188D-A232V-Q245R-N248D-E271F | +++ |
| T022A-S101Q-S103A-V104I-L124V-S128A-P129S-A232V-Q245R | +++ |
| T022A-S101Q-S103A-V104I-L126I-P129S-G159D-S188D-L217Q-A232V-Q245R-N248D-E271F | +++ |
| T022A-S101Q-S103A-V104I-P129S-L217Q-A232V-Q245R | +++ |
| T022A-S103A-V104I-G159D-S188D-A232V-Q245R-N248D-E271F | +++ |
| T022A-S103A-V104I-N116L-G159D-S188D-A232V-Q245R-N248D-E271F | +++ |

TABLE 2-2-continued

BMI cleaning performance of Group D2 variants.
PI = Performance Index
PI > or = 3 is +++; PI between 2.9 and 2 = ++; PI between 1.9 and 1.1 = + in Detergent
Composition 104 as described in Table 1

| Sequence of GG36 Variants (BPN' numbering) | PI Relative to GG36; BMI assay, Detergent 104 at 25° C. |
|---|---|
| T022A-S101Q-S103A-V104I-L124V-S128A-P129S-A232V-Q245R | +++ |
| T022A-S101Q-S103A-V104I-L126I-P129S-G159D-S188D-L217Q-A232V-Q245R-N248D-E271F | +++ |
| T022A-S101Q-S103A-V104I-P129S-L217Q-A232V-Q245R | +++ |
| T022A-S103A-V104I-G159D-S188D-A232V-Q245R-N248D-E271F | +++ |
| T022A-S103A-V104I-N116L-G159D-S188D-A232V-Q245R-N248D-E271F | +++ |
| T022A-T033S-S101G-S103A-V104I-N116L-Y209A-G211Q-T213A-A232V | +++ |
| T022L-S078N-G118R-S128D-L217E | +++ |
| T022Q-S101G-S103A-V104I-G159D-S188D-A232L-Q245R-N248E-E271H | +++ |
| T022R-S101G-S103A-V104I-A232V-Q245R | +++ |
| A098F-S099A-S101G-V104I | ++ |
| A098Q-S099G-S101G-V104L | ++ |
| A098Q-S099T-S101G-S103A | ++ |
| G020K-T022L-Q245R | ++ |
| G020R-G118R-G159D-Q245R | ++ |
| G020R-P129E-G159D-N248D | ++ |
| G020R-S024R-G118R-P129E-G159D-H249R | ++ |
| G020R-S024R-G159D-N248D | ++ |
| G020R-S024R-S078D-G118S-Q245R | ++ |
| G020R-S024R-S078G-G118S-Q245R-N248D-H249R | ++ |
| G020R-S078D-G118S-P129E-Q245R-H249R | ++ |
| G020R-S078D-G118S-Q245R | ++ |
| G020R-S078G-G118S-Q245R-N248D-H249R | ++ |
| G020R-S078R-G159D-S188D | ++ |
| G020R-T022W-S024R-N043R-R045T-S101A-G211Q | ++ |
| G097A-S128A-L217Q | ++ |
| G100S | ++ |
| G118R-H249R | ++ |
| G118R-P129E-N248D | ++ |
| P129E-S188D | ++ |
| P129E-S188D-Q245R-H249R | ++ |
| S024G-N076D-S078N-S101N-H120Q-S128A-L217Q | ++ |
| S024G-S078N-S101N-L217Q | ++ |
| S024G-S078N-S101N-S128A-L217Q-S256R | ++ |
| S024R-G118R-N248D-H249R | ++ |
| S024R-P129E-G159D-N248D | ++ |
| S024R-S078D-G118S-G159D-Q245R-H249R | ++ |
| S024R-S078R-G118R-G159D | ++ |
| S078G-G118S-Q245R-H249R | ++ |
| S078G-G118S-S188D-Q245R-H249R | ++ |
| S078R-G118R-G159D | ++ |
| S078R-G118R-G159D-N248D | ++ |
| S078R-P129E-N248D | ++ |
| S078R-P129E-Q245R | ++ |
| S099T-G102A | ++ |
| S099T-S101G-G102A-S103A | ++ |
| S188D | ++ |
| S188D-N248D | ++ |
| T022A-S101G-S103A-V104I-N116L-G159D-S188D-A232V-Q245R-N248D | ++ |
| T022A-S101Q-S103A-V104I-P129S-A232V-Q245R | ++ |
| T022K-S101A-S103N-V104L-A232T-Q245R | ++ |
| T022W-N043R-R045T-S101A-P210I-T213A | ++ |
| A098F-S099A | + |
| A098F-S099A-V104I | + |
| A098Q-S099A-G100S | + |
| A098Q-V104L | + |
| G020R-N248D | + |
| G020R-S024R-Q245R | + |
| G020R-S024R-S078D-G118S-H249R | + |
| G020R-S078D-G118S-Q245R-H249R | + |
| G061E-G097A-S128A-P129E-G159K-L217Q | + |
| G097P-S099G-G100S | + |
| N062E-P129E-G159D-N248D | + |
| P129E-G159D-N248D | + |
| P129E-G159D-S188D | + |
| Q245R | + |
| Q245R-N248D-H249R | + |

TABLE 2-2-continued

BMI cleaning performance of Group D2 variants.
PI = Performance Index
PI > or = 3 is +++; PI between 2.9 and 2 = ++; PI between 1.9 and 1.1 = + in Detergent
Composition 104 as described in Table 1

| Sequence of GG36 Variants (BPN' numbering) | PI Relative to GG36; BMI assay, Detergent 104 at 25° C. |
|---|---|
| S024G-N076D-S078N-S101N-S128A-L217Q-N218S | + |
| S024R | + |
| S024R-S078G-G118S-Q245R | + |
| S099T-G100S-S103A-V104I | + |
| S099T-S101A-S103A | + |
| S099T-S103A-V104I | + |
| V104I | + |

TABLE 2-3

BMI cleaning performance of Group D3 variants.
PI = Performance Index
PI > or = 3 is +++; PI between 2.9 and 2 = ++; PI between 1.9 and 1.1 = + in Detergent
Composition 105 as described in Table 1

| Sequence of GG36 Variants (BPN' numbering) | PI Relative to GG36; BMI assay, Detergent 105, 25° C. |
|---|---|
| G020K-S101D-G102A-L217E-S240R | +++ |
| N043R-G102A-L217E | +++ |
| N062E-S078N-S101D-S240R | +++ |
| G102A-L217E | +++ |
| G020K-S128L-L217E-S240R | +++ |
| G020K-N062E-S078N-L217E-S240R | +++ |
| N043R-S101D-S128L-L217E-S240R | +++ |
| G020K-S078N-S101D-G102A-P210L | +++ |
| N043R-S101D-L217E | +++ |
| G020K-G100S-L217E-S240R | +++ |
| S078N-G100S | +++ |
| G020K-N043R-S101D-G102A-L217E | +++ |
| G100S-S240R | +++ |
| G020K-G102A-L217E | +++ |
| G020K-S024G-N062E-S078N-S101N-Q109N-N116L-S128A-S188D | +++ |
| G020K-L217E-S240R | +++ |
| N043R-S101D | +++ |
| N043R-S078N-S101D-S128L-S240R | +++ |
| N043R-S078N-S101D-L217E-S240R | +++ |
| G020K-S078N-S101D | +++ |
| N043R-S128L-S240R | +++ |
| G020K-N062E-N116L-N123G-T213A | +++ |
| G020K-N062E-G097S-S101G-Q109G-N116L-S128A | +++ |
| G020K-N062E-S078N-G097A-S101N-Q109N-N116L-S188D | +++ |
| N043R-S078N-S101D-G102A-L217E | +++ |
| G020K-S078N-S099G-S128L-L217E | +++ |
| G020K-N062E-S101D | +++ |
| G020K-S128L-L217E | +++ |
| G020K-S024G-N062E-S078N-G097S-S101G-Q109G-N116L-L217Q | +++ |
| N043R-G097A-S101D-S128L | +++ |
| G020K-S024G-N062E-S101Q-Q109N-N116L-S128A | +++ |
| G020K-S024G-N062E-S078N-S101N-N116L-S128A-L217Q | +++ |
| S078N-G102A-S240R | +++ |
| N043R-S078N-G100S-L217E-S240R | +++ |
| G020K-S078N-S128L-L217E-S240R | +++ |
| G020K-N062E-N116L-S128Q | +++ |
| G020K-S101G-L217E-S240R | +++ |
| G020K-S024G-N062E-S101N-Q109N-N116L-S128A-L217Q | +++ |
| G020K-N062E-S078N-G097S-S101N-N116L-L217Q | +++ |
| G020K-N062E-G097S-S101N-Q109G-N116L-L217Q | +++ |
| G020K-S024G-N062E-S078N-G097A-S101Q-Q109N-N116L-M222S | +++ |
| G020K-S024G-N062E-S078N-G097S-S101Q-Q109N-N116L-S128A-S188D-L217Q | +++ |
| G020K-N062E-S078N-S101N-Q109N-N116L-S188D-L217Q | +++ |
| G020K-N062E-S105G-N116L-S128L-T213A | +++ |
| G020K-N062E-G097A-S101Q-Q109G-N116L-S188D-L217Q | ++ |
| G020K-N062E-S078N-G097A-S101Q-Q109G-N116L | ++ |
| G020K-N062E-G097A-S101Q-Q109N-N116L-L217Q | ++ |
| N043R-S078N-G102A-S128L-L217E-S240R | ++ |

TABLE 2-3-continued

BMI cleaning performance of Group D3 variants.
PI = Performance Index
PI > or = 3 is +++; PI between 2.9 and 2 = ++; PI between 1.9 and 1.1 = + in Detergent
Composition 105 as described in Table 1

| Sequence of GG36 Variants (BPN' numbering) | PI Relative to GG36; BMI assay, Detergent 105, 25° C. |
|---|---|
| S078N-G097S-S101Q | ++ |
| N043R-N062E-S078N-S101D-S128L-S240R | ++ |
| S128L-L217E-E271L | ++ |
| G020K-S024G-N062E-G097S-S101N-Q109N-N116L-S128A-L217Q | ++ |
| G020K-N062E-N116L-S128L-T213A | ++ |
| S078N-G097A-S101G-Q109G-S188D-L217Q | ++ |
| S101D-S128L-L217E-S240R | ++ |
| G020K-S024G-N062E-G097A-S101Q-Q109G-N116L-S128A | ++ |
| G020K-N062E-S078N-G097S-S101N-Q109N-N116L-S128A-S188D-L217Q | ++ |
| G020K-N062E-G097S-S101Q-Q109G-N116L-S128A-S188D-L217Q | ++ |
| G020K-S024G-N062E-S078N-G097S-S101N-Q109N-N116L-S128A | ++ |
| S024G-S078N-G097S-S101G-S128A-S188D-L217Q | ++ |
| S024G-S078N-G097A-S101N-Q109G-S128A-S188D-L217Q | ++ |
| G020K-N043R-G102A-S128L | ++ |
| G020K-S078N-S101D-G102A-L217E-S240R | ++ |
| G020K-N062E-G100S | ++ |
| S078N-S128L-L217E-E271L | ++ |
| S128Q-L217E-E271L | ++ |
| G020K-L217E | ++ |
| G020K-S024G-N062E-S078N-G097A-S101N-N116L-S128A-L217Q | ++ |
| G020K-S024G-N062E-S078N-G097S-S101G-N116L-S128A-L217Q | ++ |
| G020K-S078N-S101D-G102A-L217E | ++ |
| G020K-N062E-S128L | ++ |
| G020K-N062E-S078N-S101G-Q109N-N116L | ++ |
| G020K-S024G-N062E-S078N-G097S-S101Q-N116L-S128A-L217Q | ++ |
| S078N-S128L-L217E-S240R | ++ |
| S101D-S128Q-L217E-S240R-E271L | ++ |
| N043R-G102A-S240R | ++ |
| G020K-N062E-S078N-S101N-Q109N-N116L-M222S | ++ |
| G020K-N062E-S101N-Q109G-N116L-S128A-L217Q | ++ |
| G020K-S024G-N062E-S078N-G097A-S101G-N116L-L217Q | ++ |
| G020K-N062E-S101G-N116L-S188D | ++ |
| G020K-N062E-G097S-S101Q-Q109N-N116L-S128A-S188D | ++ |
| G020K-I035V-G100S-S128L-L217E | ++ |
| N043R-S101D-G102A-S240R | ++ |
| N062E-S078N-G100S | ++ |
| G020K-N043R-N062E-A215T | ++ |
| N062E-S240R | ++ |
| N043R-S128L-L217E-S240R | ++ |
| N062E-S101D-S240R | ++ |
| G020K-S101D-N116L-T213A | ++ |
| G020K-S101D-N116L-S128Q-P210S-T213A | ++ |
| G020K-S101D-T213A | ++ |
| G020K-S024G-N062E-S078N-G097S-S101Q-Q109N-N116L-S128A | ++ |
| G020K-N062E-S078N-G097S-S101Q-N116L-S128A-L217Q | ++ |
| T022A-S101G-S103A-V104I-G159D-S188D-A232V-Q245R-N248D-E271F | ++ |
| S024G-G097S-S101N-Q109G-S188D-L217Q | ++ |
| G020K-S024G-N062E-S101N-Q109G-N116L-L217Q | ++ |
| L217E-S240R | ++ |
| S101D-L217E-S240R-E271L | ++ |
| N043R-N062E-S101D-S128L-S240R | ++ |
| G097A-S101N-S128A-S188D-L217Q | ++ |
| G020K-N062E-S078N-S101N-N116L-S128A-L217Q | ++ |
| G020K-N062E-S078N-G097S-S101G-Q109N-N116L-L217Q | ++ |
| G020K-S024G-N062E-G097S-S101N-Q109G-N116L-S128A-L217Q | ++ |
| G020K-S024G-N062E-G097S-S101G-Q109G-N116L-S128A-S188D-L217Q | ++ |
| G020K-N062E-S101N-Q109N-N116L-S128A-S188D | ++ |
| S078N-G097S-S101N-Q109N-S128A-S188D-L217Q-W241L | ++ |
| G020K-N043R-N062E-S078N-S101D | ++ |
| G020K-N062E-S101D-S240R | ++ |
| G020K-S101D-S128Q | ++ |
| G020K-N116L-S128Q-Y209H-T213A | ++ |
| G020K-N043R-S078N-G100S-L217E-N218D | ++ |
| S024G-S101N-Q109G-S128A-S188D-L217Q | ++ |
| G020K-S024G-N062E-S078N-G097S-S101N-Q109G-N116L-S128A-S188D | ++ |

TABLE 2-3-continued

BMI cleaning performance of Group D3 variants.
PI = Performance Index
PI > or = 3 is +++; PI between 2.9 and 2 = ++; PI between 1.9 and 1.1 = + in Detergent
Composition 105 as described in Table 1

| Sequence of GG36 Variants (BPN' numbering) | PI Relative to GG36; BMI assay, Detergent 105, 25° C. |
|---|---|
| S078N-S101N-Q109G-S188D-L217Q | ++ |
| G020K-S024G-N062E-S078N-G097S-S101N-Q109G-N116L-S188D-L217Q | ++ |
| G020K-N062E-S078N-S101Q-Q109N-N116L-S128A-S188D-L217Q | ++ |
| G020K-N062E-S101G-Q109G-N116L | ++ |
| G020K-S024G-N062E-G097S-S101N-Q109G-N116L-S128A-S188D-M222S | ++ |
| S024G-G097A-S101G-S188D-L217Q | ++ |
| S024G-S078N-G097A-S101G-S128A-S188D | ++ |
| G097S-S101N-Q109G-S128A-S188D | ++ |
| G020K-S078N-S101D-I246T | ++ |
| N043R-S128L-L217E | ++ |
| G020K-S101D-L217E-S240R | ++ |
| S128L-L217E-T224A-E271L | ++ |
| G020K-S078N-S101D-S128Q-L217E-E271L | ++ |
| N062E-S078N-S101D-L217E-S240R | ++ |
| G020K-S101D-L217E-E271L | ++ |
| G020K-S078N-S128Q-L217E-S240R | ++ |
| G020K-N062E-S101D-N116L-T213A | ++ |
| G100S-S101D | ++ |
| S078N-G097S-S101G-S128A-L217Q | ++ |
| G020K-N062E-G097S-S101N-N116L-S128A-L217Q | ++ |
| G020K-N062E-G097S-S101N-N116L-L217Q | ++ |
| S101N-Q109G-S188D | ++ |
| G020K-S024G-N062E-G097S-S101Q-Q109N-N116L-S128A-L217Q | ++ |
| G020K-S024G-N062E-G097S-S101N-N116L | ++ |
| G020K-S024G-N062E-S101N-N116L-S128A | ++ |
| G020K-S024G-N062E-S078N-S101Q-Q109N-N116L-S128A | ++ |
| G020K-N062E-S078N-S101N-Q109G-N116L-S188D | ++ |
| G020K-N062E-S078N-S101N-Q109G-N116L-S128A | ++ |
| G020K-S024G-N062E-S078N-G097S-S101N-Q109G-N116L-S128A-M222S | ++ |
| G020K-S024G-N062E-S078N-G097S-S101G-N116L-S128A | ++ |
| S024G-S078N-G097S-S101Q-Q109G-S128A-S188D-L217Q | ++ |
| S024G-S078N-S101G-Q109N-S188D-L217Q | ++ |
| S024G-S078N-G097A-S101G-Q109G-S188D | ++ |
| S078N-S101D-S128Q-L217E-S240R-E271L | ++ |
| G020K-S128Q-L217E | ++ |
| S128Q-L217E-S240R-E271L | ++ |
| G020K-S078N-S101D-L217E | ++ |
| G020K-S078N-S101D-L217E-E271L | ++ |
| G020K-N116L-S128Q-T213A | ++ |
| G020K-N116L-N123G | ++ |
| S101G-S188D-L217Q | ++ |
| L217E | ++ |
| G020K-S024G-N062E-S078N-S101G-N116L-L217Q | ++ |
| S078N-G097A-S101G-Q109N-S128A-S188D | ++ |
| G020K-S078N-S128L-L217E-E271L | ++ |
| G020K-N062E-S101Q-Q109G-N116L | ++ |
| G020K-S101D-L217E | ++ |
| S024G-G097A-S101N-Q109N-S128A | ++ |
| G020K-S078N-S101D-S128L-L217E-S240R | ++ |
| G097A-S101G-L217Q | ++ |
| S024G-S101Q-Q109G-S128A-L217Q | ++ |
| G020K-N062E-N116L-T213A-M222S | ++ |
| G020K-S024G-N062E-T071A-S078N-G097S-S101G-N116L-L217Q | ++ |
| G020K-S024G-N062E-S078N-S101G-N116L-S128A | ++ |
| G020K-S024G-N062E-S078N-G097A-S101N-N116L | ++ |
| G020K-N062E-G097A-S101N-N116L | ++ |
| G020K-S024G-N062E-G097A-S101N-Q109G-N116L-S128A | ++ |
| G020K-S024G-N062E-S078N-G097S-S101G-Q109N-N116L | ++ |
| G020K-N062E-S078N-G097S-S101Q-Q109G-N116L-S128A-S188D-L217Q | ++ |
| G020K-N062E-S101N-Q109G-N116L-L217Q | ++ |
| G020K-S024G-N062E-G097A-S101N-Q109G-N116L-S188D-L217Q | ++ |
| G020K-S024G-N062E-S101G-N116L | ++ |
| S078N-G097S-S101N-Q109G-G159D-L217Q | ++ |
| S024G-G097A-S101N-Q109G-S188D | ++ |
| S078N-S101G-S128A-L217Q | ++ |
| S078N-G097A-S101N-S128A-S188D-L217Q | ++ |
| S024G-G097S-S101G-S128A-S188D-L217Q | ++ |

TABLE 2-3-continued

BMI cleaning performance of Group D3 variants.
PI = Performance Index
PI > or = 3 is +++; PI between 2.9 and 2 = ++; PI between 1.9 and 1.1 = + in Detergent
Composition 105 as described in Table 1

| Sequence of GG36 Variants (BPN' numbering) | PI Relative to GG36; BMI assay, Detergent 105, 25° C. |
|---|---|
| S024G-S078N-G097S-S101Q-Q109G-S128A-S188D-L217Q-V227A | ++ |
| G020K-N062E-S078N | ++ |
| S078N-S128L-L217E-S240R-E271L | ++ |
| G020K-N062E-I072N-S101D-N116L-S128Q | ++ |
| G020K-T057P-N062E-N116L-S128Q-T213A | ++ |
| G020K-N043R-S078N-S101D-S240R | ++ |
| S078N-G097S-S101N-Q109N-S128A-S188D-L217Q | ++ |
| S024G-S101N-Q109N-S128A-S188D | ++ |
| G020K-S024G-N062E-G097S-S101Q-N116L-S128A | ++ |
| S024G-S078N-G097S-S101N-Q109N-S128A-S188D | ++ |
| N043R-G100S | ++ |
| G020K-N062E-S078N-S101Q-Q109G-N116L-S128A | ++ |
| S078N-S101Q-Q109N-S188D-L217Q | ++ |
| G020K-N116L-S128L-T213A | ++ |
| G020K-S078N-S101D-L217E-S240R | ++ |
| G020K-N062E-S101N-Q109N-N116L-M222S | ++ |
| G020K-S024G-N062E-G097A-S101Q-Q109N-N116L-S128A | ++ |
| S078N-G097S-S101G-S128A-S188D | ++ |
| G097S-S101G-Q109N-S128A-M222S | ++ |
| S024G-S078N-G097A-S101Q-S128A-M222S | ++ |
| G097A-S101G-Q109N-L217Q | ++ |
| S024G-S078N-S101G-S128A-S188D-L217Q | ++ |
| S024G-G097A-S101N-Q109G-S128A-S188D | ++ |
| G097S-S101N-Q109G-S128A | ++ |
| S078N-G097A-S101Q-L217Q | ++ |
| G020K-N043R-S078N-S101D | ++ |
| G020K-N043R-E054D-N062E-S078N-S240R | ++ |
| G020K-S101D-S240R | ++ |
| S128Q-L217E-S240R | ++ |
| G020K-S128Q-L217E-V244A-E271L | ++ |
| G020K-L217E-E271L | ++ |
| G020K-S078N-S128L-L217E | ++ |
| S078N-S101D-S128Q-L217E-E271L | ++ |
| G020K-N062E-L217E-E271L | ++ |
| G020K-N062E-S101D-N116L-S128Q-T213A | ++ |
| G020K-N062E-S078N-N116L-S128I | ++ |
| G020K-N062E-S078N-S128Q-T213A | ++ |
| S024G-G097A-S101G-Q109G-S128A | ++ |
| S024G-G097S-S101N-Q109N-S128A-L217Q | ++ |
| G020K-S024G-N062E-S078N-S101N-N116L-S128A-S188D-L217Q | ++ |
| G020K-S101D | ++ |
| G020K-N062E-S078N-G097S-S101Q-N116L-S128A | ++ |
| G020K-N062E-G097S-S101G-N116L-S188D | ++ |
| N043R-S078N-G100S-S128L-S240R | ++ |
| G097S-S101N-Q109N-S188D | ++ |
| G097S-S101Q-Q109N-S128A-L217Q | ++ |
| G020K-N062E-S101N-Q109G-N116L-S128A-S188D-M222S | ++ |
| G020K-S024G-N062E-S078N-G097S-S101Q-Q109G-N116L | ++ |
| G020K-N062E-M222S | ++ |
| G097S-S101Q-Q109G-S188D | ++ |
| G020K-N062E-N116L-T213A | ++ |
| G020K-S078N-L217E-S240R | ++ |
| G020K-N062E-S078N-G097A-S101N-Q109G-N116L-S188D | ++ |
| G020K-S024G-N062E-G097S-S101Q-Q109G-N116L-S188D | ++ |
| G020K-N062E-S078N-G097A-S101Q-N116L-S128A-M222S | ++ |
| G020K-N062E-S078N-S101N-N116L-S188D | ++ |
| G020K-S024G-N062E-S078N-S101G-N116L | ++ |
| G020K-N062E-S078N-S101N-N116L-S128A-S188D | ++ |
| G020K-S024G-N062E-G097S-S101N-Q109G-N116L-S128A-S188D-L217Q | ++ |
| G020K-N062E-G097S-S101N-Q109N-N116L | ++ |
| G020K-N062E-S101G-N116L-S188D-L217Q | ++ |
| G097A-S101N-S128A | ++ |
| S101G-Q109N-S128A-M222S | ++ |
| S024G-G097S-S101Q-Q109G-S188D-L217Q | ++ |
| G097S-S101Q-Q109N-S128A-S188D | ++ |
| S024G-S078N-G097A-S101Q-S188D-L217Q | ++ |
| S024G-S078N-S101G-Q109G-S128A-L217Q | ++ |
| G020K-N062E-S128L-S240R | ++ |
| N062E-S078N-S128L-S240R | ++ |
| N043R-G102A-S128L-L217E-S240R | ++ |

TABLE 2-3-continued

BMI cleaning performance of Group D3 variants.
PI = Performance Index
PI > or = 3 is +++; PI between 2.9 and 2 = ++; PI between 1.9 and 1.1 = + in Detergent Composition 105 as described in Table 1

| Sequence of GG36 Variants (BPN' numbering) | PI Relative to GG36; BMI assay, Detergent 105, 25° C. |
|---|---|
| N062E-S078N-L217E-S240R-E271L | ++ |
| S078N-S128Q-L217E-N269S | ++ |
| G020K-N062E-N123G-T213A | ++ |
| G020K-N062E-S078N-S099G-N116L-S128Q-T213A-L217N | ++ |
| G020K-N062E-S078N-S128I-L217N | ++ |
| G097A-S101Q-S128A-S188D-L217Q | ++ |
| G020K-N062E-N116L | ++ |
| G020K-N062E-S078N-G097S-S101N-Q109G-N116L | ++ |
| G020K-S024G-N062E-S078N-G097S-S101N-Q109G-N116L-S188D | ++ |
| G020K-N043R-S128L-S240R | ++ |
| S024G-S078N-G097A-S101N-Q109N-S128A | ++ |
| G020K-N062E-G097S-S101Q-N116L-L217Q | ++ |
| G020K-N062E-S078N-S128I | ++ |
| G020K-S024G-N062E-L090V-G097A-S101Q-N116L-M222S | ++ |
| G020K-N062E-S078N-S101Q-Q109G-N116L-S188D-L217Q | ++ |
| G020K-S024G-N062E-G097A-S101Q-N116L-S128A-S188D-L217Q | ++ |
| G020K-N062E-G097S-S101N-Q109N-N116L-S188D-L217Q | ++ |
| G020K-S024G-A048V-N062E-S078N-G097A-S101N-N116L-S128A-L217Q | ++ |
| G020K-N062E-S078N-S101Q-Q109G-N116L | ++ |
| G020K-S024G-N062E-G097S-S101N-Q109N-N116L-S128A | ++ |
| G020K-N062E-S078N-G097A-S101Q-Q109G-N116L-S188D | ++ |
| G020K-N062E-S078N-G097A-S101N-Q109N-N116L-N218D | ++ |
| S024G-S101N-Q109G-S128A-S188D-M222S | ++ |
| S024G-G097A-S101Q-Q109N-S188D-L217Q | ++ |
| S024G-S078N-G097S-S101Q-Q109N-S128A-S188D | ++ |
| S101N-Q109G-M222S | ++ |
| S024G-I072V-G097S-S101N-S128A-L217Q | ++ |
| S101G-S128A | ++ |
| N043R-S078N-G102A-A215G | ++ |
| G020K-S101D-S128L-L217E-S240R | ++ |
| S078N-S101D-S128Q-L217E-S240R | ++ |
| G020K-N116L-S128L-M222S | ++ |
| G020K-N062E-S078N-N116L-T213A-M222S | ++ |
| G020K-N062E-S078N-N116L-S128Q | ++ |
| G020K-N062E-T213A | ++ |
| G020K-N062E-S078N-N116L-N123G-M222S | ++ |
| S024G-S078N-G097A-S101N-Q109N-L217Q | + |
| G020K-G102A-S128L | + |
| G020K-S078N-S101D-S128Q | + |
| S024G-S078N-G097A-S101N-S128A | + |
| G020K-S024G-N062E-S101Q-Q109G-N116L-S188D | + |
| G020K-S078N-S101D-S240R | + |
| G020K-N043R-S128L-L217E-S240R | + |
| S078N-S101G-Q109N-L217Q | + |
| S024G-G097S-S101N-S128A-S188D | + |
| S078N-L217E-E271L | + |
| G097S-S101Q-Q109N-L217Q | + |
| G020K-N062E-N116L-M222S | + |
| G020K-N062E-S078N-N116L-S128Q-T213A | + |
| G020K-S024G-N062E-S101Q-Q109G-N116L-S188D-L217Q | + |
| S024G-S078N-G097A-S101Q-S128A-L217Q | + |
| S078N-S101D-S128L-E271L | + |
| G020K-N062E | + |
| G020K-N062E-S101N-N116L | + |
| G020K-N062E-S101Q-Q109N-N116L-M222S | + |
| G020K-N062E-S101Q-Q109G-N116L-M222S | + |
| G020K-S024G-N062E-S078N-G097S-S101G-Q109G-N116L-L217Q-M222S | + |
| G020K-S024G-N062E-S078N-S101N-N116L-S128A-M222S | + |
| G020K-N062E-S078N-S101N-Q109N-N116L-S188D-M222S | + |
| G020K-S024G-N062E-S101N-Q109N-N116L-S188D-M222S | + |
| G020K-S024G-N062E-G097S-S101Q-N116L-L217Q | + |
| G020K-N062E-G097S-S101N-Q109G-N116L-S128A-S188D | + |
| S078N-G097A-S101Q-Q109G-S128A | + |
| S024G-G097A-S101N | + |
| S024G-G097A-S101Q-Q109N-S128A-S188D | + |
| G097A-S101N-S128A-S188D | + |
| S024G-G097S-S101G-S128A-L217Q | + |
| S078N-G097A-S101G-Q109N-S128A-L217Q | + |
| S024G-G097S-S101Q-Q109N-S128A | + |

TABLE 2-3-continued

BMI cleaning performance of Group D3 variants.
PI = Performance Index
PI > or = 3 is +++; PI between 2.9 and 2

TABLE 2-3-continued

BMI cleaning performance of Group D3 variants.
PI = Performance Index
PI > or = 3 is +++; PI between 2.9 and 2 = ++; PI between 1.9 and 1.1 = + in Detergent
Composition 105 as described in Table 1

| Sequence of GG36 Variants (BPN' numbering) | PI Relative to GG36; BMI assay, Detergent 105, 25° C. |
|---|---|
| G020K-N062E-G097S-S101N-N116L-S128A-S188D-L217Q | + |
| S078N-S101Q-S128A-M222S | + |
| S078N-G097A-S101Q-Q109N | + |
| S024G-S078N-G097A-S101Q-S128A-S188D | + |
| S078N-S101D-G102A | + |
| G020K-N062E-S078N-G097S-S101Q-Q109G-N116L-S128A-S188D-M222S | + |
| G020K-S024G-N062E-S078N-G097S-S101N-Q109N-N116L-S188D-L217Q-M222S | + |
| G020K-N062E-G097S-S101Q-N116L-S128A | + |
| G020K-S024G-N062E-G097S-S101Q-N116L-S128A-S188D-L217Q | + |
| S024G-S101N-Q109N-S128A | + |
| S024G-G097S-S101Q-S128A-S188D | + |
| S024G-S101Q-L217Q | + |
| G097S-S101G-S128A | + |
| S024G-S078N-S101Q-S128A-L217Q | + |
| S024G-S078N-G097S-S101N-S188D | + |
| S024G-G097A-S101N-S128A-M222S | + |
| G097A-S101Q-Q109N-S188D-M222S | + |
| S024G-S078N-G097S-S101Q | + |
| G020K-S101D-S128L-S212P-L217E-S240R | + |
| G020K-S101D-S128L-L217E-N218S-S240R | + |
| S101D-S128Q | + |
| G020K-N062E-S078N-E271L | + |
| S101D-E271L | + |
| S101D-S240R-E271L | + |
| G020K-S101D-E271L | + |
| G020K-N116L-S128L-T213A-M222S | + |
| G020K-N116L-S128Q-M222S | + |
| G020K-N062E-V084A-S128Q-M222S | + |
| G020K-N062E-S078N-N116L | + |
| S078N-S101N-Q109G-S128A-M222S | + |
| S024G-G097S-S101Q-Q109G | + |
| G020K-N062E-T213A-L217N | + |
| G097S-S101G-S128A-S188D | + |
| G020K-S240R | + |
| N062E-S078N | + |
| G020K-S128Q-M222S | + |
| S078N-G097S-S101G-Q109G | + |
| G020R-S024G-N043R-S078N-S101Q | + |
| G097S-S101N-Q109G-S128A-M222S | + |
| S024G-G097S-S101G-Q109N | + |
| S024G-S078N-G097A-S101G-Q109N | + |
| G020K-N062E-S078N-S101N-N116L-S128A-S188D-L217Q | + |
| G020K-N062E-S101Q-Q109G-N116L-S128A-M222S | + |
| G020K-S024G-N062E-S101Q-Q109N-N116L | + |
| S024G-S078N-S101Q-M222S | + |
| S024G-G097A-S101Q-Q109G-S128A | + |
| S101Q-Q109N-L217Q | + |
| S101Q-Q109G-S188D-L217Q | + |
| S024G-G097A-S101N-S188D-M222S | + |
| S024G-S078N-G097A-S101Q-Q109N | + |
| G097A-S101Q-S128A | + |
| G097A-S101Q-Q109G-S128A | + |
| S024G-G097S-S101Q-M222S | + |
| S078N-S101D-L217E-S240R | + |
| G020K-G100S-S128L | + |
| G020K-N043R-S078N-S128L-S240R | + |
| G020K-N043R-S101D-S240R | + |
| G020K-N043R-S078N-S128L | + |
| N062E-S128L | + |
| G020K-S078N-S101D-S128L | + |
| S078N-S101D | + |
| S101D | + |
| G020K-S101D-N116L-T213A-M222S | + |
| G020K-T213A-M222S | + |
| G020K-N116L-T213A | + |
| G020K-N116L | + |
| G020K-N062E-S128Q-L217N | + |
| S078N-G097S-S101G-Q109N-S128A | + |
| S078N-S101Q-Q109G | + |

TABLE 2-3-continued

BMI cleaning performance of Group D3 variants.
PI = Performance Index
PI > or = 3 is +++; PI between 2.9 and 2 = ++; PI between 1.9 and 1.1 = + in Detergent
Composition 105 as described in Table 1

| Sequence of GG36 Variants (BPN' numbering) | PI Relative to GG36; BMI assay, Detergent 105, 25° C. |
|---|---|
| N062E-S078N-S128L | + |
| G020K-N062E-N116L-S128Q-T213A-L217N | + |
| G020K-N116L-T213A-M222S | + |
| G020K-S024G-N062E-S101Q-Q109H-N116L-M222S | + |
| G020K-N116L-S128Q-T213A-M222S | + |
| S024G-G097S-S101N | + |
| G020K-P055T-N062E-N116L-L217N | + |
| S024G-S101Q-S128A-S188D-M222S | + |
| G020K-M222S | + |
| G020K-N062E-S078N-G097A-S101N-N116L-S188D-L217Q | + |
| G097S-S101G-Q109N-M222S | + |
| G020K-S024G-N062E-S078N-G097A-S101N-N116L-S128A-L217Q-M222S | + |
| G020K-S024G-N062E-G097S-S101N-Q109N-N116L-S128A-S188D-L217Q-M222S | + |
| G020K-N062E-S078N-S101Q-N116L-S128A | + |
| S024G-S078N-S101N-Q109G-S188D-L217Q-M222S | + |
| S101N-Q109N-S128A-M222S | + |
| S101Q-Q109G-S128A-S188D | + |
| G097A-S101G-S188D-M222S | + |
| S078N-G097S-S101N-Q109G-S128A-S188D-L217Q-M222S | + |
| S024G-G097A-S101Q-M222S | + |
| S024G-G097S-S101N-Q109N-S128A-M222S | + |
| S024G-S078N-G097S-S101N-M222S | + |
| G020K-G102A-S240R | + |
| S078N-S128Q-E271L | + |
| G020K-N062E-S078N-S128Q | + |
| G020K-N062E-S078N-T213A-M222S | + |
| G020K-N062E-S078N-S128I-T213A-L217N | + |
| S078N-G097A-S101N | + |
| G020K-N062E-N116L-S128I-T213A-L217N | + |
| S024G-G097A-S101Q-S128A-S188D-M222S | + |
| S024G-S078N-G097A-S101N | + |
| S024G-S078N-G097S-S101G-M222S | + |
| G020K-N062E-S078N-N116L-S128Q-T213A-M222S | + |
| G020K-N062E-S128Q-M222S | + |
| G020K-N062E-S101Q-N116L | + |
| G020K-N062E-S101Q-Q109N-N116L-S188D-L217Q | + |
| G020K-S024G-N062E-G097A-S101N-N116L-S128A-S188D | + |
| G020K-S024G-N062E-S078N-S101Q-Q109G-N116L-S188D-M222S | + |
| S078N-G097S-S101N-Q109G-S128A-L217Q-M222S | + |
| S024G-S078N-S101N-Q109G-S128A-L217Q-M222S | + |
| G097A-S101Q-S128A-S188D | + |
| S024G-S078N-G097A-S101N-Q109N-S128A-S188D-L217Q-M222S | + |
| S024G-S078N-G097A-S101G-L217E-M222S | + |
| S078N-G097S-S101Q-Q109G-T274I | + |
| G097A-S101G-M222S | + |
| S101N-Q109N | + |
| G020K-L217E-S240R-E271L | + |
| S128Q-S240R-E271L | + |
| G020K-S101D-N116L-S128Q-M222S | + |
| G020K-P055L-N062E-N116L-S128I | + |
| G020K-N062E-S101G-N116L-S128A-M222S | + |
| G020K-S078N-S101D-S128L-S240R-E271L | + |
| G020K-T213A | + |
| G020K-N062E-S078N-G097S-S101Q-Q109N-N116L-L217Q-M222S | + |
| S078N-S101D-S240R-E271L | + |
| S024G-S078N-S101N-Q109G-L217Q-M222S | + |
| G097A-S101G-Q109G-L217Q-M222S | + |
| G020K-S024G-N062E-S078N-G097S-S101N-N116L-S128A-L217Q-M222S | + |
| G020K-S078N-S128L-E271L | + |
| G020K-N062E-S078N-N116L-L217N | + |
| G097A-S101G-Q109G-S188D-L217Q-M222S | + |
| S024G-S078N-G097S-S101N-Q109G-S128A | + |
| G020K-S024G-N062E-S078N-G097S-S101N-N116L-S188D-M222S | + |
| G020K-S024G-N062E-G097S-S101Q-N116L-S128A-M222S | + |
| G020K-N062E-S078N-G097A-S101G-Q109N-N116L-S128A-S188D-L217Q | + |
| G020K-N062E-S101G-N116L-S128A-L217Q-M222S | + |
| S024G-G097A-S101Q-S188D-M222S | + |

TABLE 2-3-continued

BMI cleaning performance of Group D3 variants.
PI = Performance Index
PI > or = 3 is +++; PI between 2.9 and 2 = ++; PI between 1.9 and 1.1 = + in Detergent
Composition 105 as described in Table 1

| Sequence of GG36 Variants (BPN' numbering) | PI Relative to GG36; BMI assay, Detergent 105, 25° C. |
|---|---|
| S024G-S101G | + |
| I072V-S101Q-S128A | + |
| S078N-G097S-S101N-Q109N | + |
| S024G-G097A-S101N-Q109N-S188D-L217Q-M222S | + |
| S078N-S101Q-Q109N-S188D-L217Q-M222S | + |
| G020K-N043R-N062E-S128L-L217E | + |
| N043R-G102A-S128L-S240R | + |
| G020K-N116L-N123G-T213A-M222S | + |
| G020K-S101D-S128Q-T213A-M222S | + |
| S024G-G097A-S101Q-Q109G | + |
| G020K-S078N | + |
| G020K-N062E-S101Q-N116L-S188D | + |
| G020K-N062E-S078N-G097S-S101N-Q109G-N116L-S188D-L217Q-M222S | + |
| G020K-S024G-N062E-G097S-S101G-N116L-S128A-L217Q-M222S | + |
| G020K-N062E-G097A-S101N-N116L-S128A-L217Q-M222S | + |
| S078N-G097S-S101G-Q109N-M222S | + |
| S024G-G097A-S101Q-Q109N | + |
| S024G-G097S-S101N-Q109N-S128A-S188D-L217Q-M222S | + |
| S078N-S101N-Q109N-S188D-L217Q-M222S | + |
| S078N-S101D-S128L-L217E-S240R | + |
| G020K-N062E-S101D-N116L-S128L | + |
| G097S-S101N-S188D-M222S | + |
| G020K-S078N-S128L-S240R-E271L | + |
| G020K-N062E-N116L-S128I-T213A | + |
| G020K-S024G-N062E-S078N-G097S-S101Q-N116L-S188D-M222S | + |
| G020K-N062E-S101Q-Q109G-N116L-L217Q-M222S | + |
| G020K-S024G-N062E-G097A-S101Q-N116L-L217Q-M222S | + |
| G020K-N062E-S078N-G097S-S101Q-N116L-S128A-S188D-M222S-A232T | + |
| G020K-S024G-N062E-S078N-G097S-S101Q-Q109N-N116L-S128A-L217Q-M222S | + |
| G020K-N062E-G097A-S101Q-N116L-S188D-M222S | + |
| S024G-S078N-G097S-S101N-Q109G-S128A-L217Q-M222S | + |
| S024G-G097A-S101Q-Q109N-S128A-S188D-L217Q-M222S | + |
| G020K-N043R | + |
| G020K-N043R-S078N-G102A-S128L | + |
| G097R-S101D | + |
| G020K-N062E-S078N-I107V-N123G-S128I | + |
| G020K-N062E-S078N-N116L-N123G-T213A | + |
| G020K-N062E-N116L-S128I-M222S | + |
| G020K-N043R-S240R | + |
| S078N-S101D-S128L | + |
| G020K-S078N-S128Q-E271L | + |
| S078N-S101G-S128A-S188D-L217Q-M222S | + |
| S078N-G097S-S101G-Q109N-S128A-L217Q-M222S | + |
| S240R | + |
| G020K-N062E-N116L-S128Q-T213A-M222S | + |

TABLE 2-4

BMI cleaning performance of Group C1 variants.
PI = Performance Index
PI > or = 1.50 is +++; PI between 1.49 and 1.20 = ++; PI between 1.19
and 1.1 = + in Detergent Composition 106 as described in Table 1

| Sequence of GG36 Variants (BPN' numbering) | PI Relative to GG36; BMI assay, Detergent 106 at 25° C. |
|---|---|
| G020R-T022W-S024R-R045T-S101A-N204S-G211Q | +++ |
| T022W-S024R-S101A-P210I-T213A | +++ |
| G020R-S101A-G211Q | +++ |
| G020R-S024R-S101A-P210I-G211Q-T213A | +++ |
| G020R-S101A-P210I-T213A | +++ |
| T022W-S024R-N043R-S101A-P210I | +++ |
| G020R-S024R-N043R-R045T-S101A-G211Q | +++ |
| T022R-S101T-S103N-V104L-A232M-Q245R | +++ |

TABLE 2-4-continued

BMI cleaning performance of Group C1 variants.
PI = Performance Index
PI > or = 1.50 is +++; PI between 1.49 and 1.20 = ++; PI between 1.19
and 1.1 = + in Detergent Composition 106 as described in Table 1

| Sequence of GG36 Variants (BPN' numbering) | PI Relative to GG36; BMI assay, Detergent 106 at 25° C. |
|---|---|
| G020R-T022A-S024R-R045T-S101A-T213A | +++ |
| T022R-S101G-S103N-V104I-A232M-Q245R | +++ |
| G020R-T022W-S024R-S101A-N116L-G211Q-T213A | +++ |
| G020R-T022W-N043R-S101A-N116L-G211Q | +++ |
| G020R-T022W-N043R-R045T-SI0IA | +++ |
| T022W-N043R-R045T-S101A-P210I-T213A | +++ |
| G020R-S024R-R045T-S101A-Q109R-P210I-G211Q-T213A | +++ |
| S024R-N043K-S101A-N204D-P210I | +++ |
| G020R-S024R-R045T-S101A-P210I | +++ |
| S024R-N043R-R045T-S101A-P210I-T213A | +++ |
| G020R-S024R-R045T-S101A-T213A | +++ |
| T022R-S101A-S103N-V104I-A232T-Q245R | +++ |
| G020R-T022W-S024R-R045T-S101A-N204S-P210I-G211Q | +++ |
| T022W-N043R-S101A-P210I-G211Q | +++ |
| G020R-S024R-N043K-R045T-S101A-N116L-P210I | +++ |
| T022A-S101G-S103A-V104I-I107V-L217Q-A232V-Q245R | +++ |
| S024R-N043R-R045T-S101A-G211Q-T213A | +++ |
| T022R-S101A-S103G-V104I-A232M-Q245R | +++ |
| T022R-S101G-S103N-V104L-A232V-Q245R | +++ |
| S024R-S078G-G118S-Q245R-N248D-H249R | +++ |
| S024R-N043R-S101A-P210I-T213A | +++ |
| G020R-S024R-N043R-R045T-S101A-T213A | +++ |
| T022K-S101N-S103A-V104I-A232T-Q245R | +++ |
| G020R-N043R-S101A-P210I-G211Q | +++ |
| T022R-S101T-S103A-V104I-A232M-Q245R | +++ |
| S024R-V026A-N043R-S101A-P210I-G211Q | +++ |
| T022A-S078N-S101G-S103A-V104I-S128A-L217Q-A232V-Q245R | +++ |
| T022K-S101T-S103G-V104I-A232L-Q245R | +++ |
| G020R-T022W-S024R-N043R-R045T-S101A-G211Q | +++ |
| G020R-S024R-S078G-G118D-Q245R | +++ |
| T022A-S101N-S103A-V104I-S128A-P129S-A232V-Q245R | +++ |
| T022A-G097A-S101G-S103A-V104I-L217Q-A232V-Q245R | +++ |
| G020R-T022W-N043R-S101A-G211Q-T213A | +++ |
| N018K-G020R-S024R-N043R-R045T-S101A-P210I-G211Q-T213A | +++ |
| G020R-T022W-S024R-N043R-R045T-S101A | +++ |
| T022R-S101N-S103A-V104L-A232T-Q245R | +++ |
| G020R-S024R-S101A-T213A | +++ |
| T022R-S101N-S103G-V104I-A232V-Q245R | +++ |
| G020R-T022W-S024R-S101A-G211Q-T213A | +++ |
| T022A-S024G-S101G-S103A-V104I-S128A-L217Q-A232V-Q245R | +++ |
| S024R-S078G-G118D-P129E-Q245R-H249R | +++ |
| T022R-S101T-S103A-V104L-A232L-Q245R | +++ |
| G020R-S024R-S101A-G211Q-T213A | +++ |
| T022A-S024G-S101G-S103A-V104I-L217Q-A232V-Q245R | +++ |
| G020R-T022W-N043R-V051A-S101A-P210I-G211Q | +++ |
| S024R-S078G-G118D-Q245R | +++ |
| N043R-S101A-P210I | +++ |
| T022Y-S101G-S103N-V104I-A232L-Q245R | +++ |
| G020R-T022W-N043R-S101A-T213A | +++ |
| G020R-S024R-S078D-G118S-S188D-Q245R-H249R | +++ |
| T022Y-S101N-S103N-V104I-A232T-Q245R | +++ |
| G020R-T022W-S024R-F050L-S101A-G211Q-T213A | +++ |
| N018S-T022W-S024R-N043R-S101A-G211Q | +++ |
| T022A-S101G-S103A-V104I-S128A-P129S-L217Q-A232V-Q245R | +++ |
| T022R-S101N-S103N-V104I-A232V-Q245R | +++ |
| T022A-S024G-S078N-G097S-S101Q-S103A-V104I-L217Q-A232V-Q245R | +++ |
| S101A-P210I-G211Q-T213A | +++ |
| G020R-N043R-R045T-S101A-P210I-G211Q-T213A | +++ |
| T022R-S101A-S103N-V104I-A232M-Q245S | +++ |
| G020R-T022W-N043R-R045T-S101A-G211Q | +++ |
| G020R-T022W-N043R-R045T-S101A-N116L-P210I | +++ |
| G020R-S024R-S078D-G118S-Q245R | +++ |
| G020R-T022W-S024R-N043R-S101A-P210I-G211Q-T213A | +++ |
| G020R-S024R-N043R-R045T-V051A-S101A-P210I-G211Q | +++ |
| T022A-S101G-S103A-V104I-P129S-L217Q-A232V-Q245R | +++ |
| G020R-S078G-G118D-Q245R-N248D-H249R | +++ |
| T022K-S101A-S103N-V104L-A232T-Q245R | +++ |
| T022A-N076D-S078N-G097S-S101G-S103A-V104I-L217Q-A232V-Q245R | +++ |
| S024R-N043R-R045T-S101A-P210I | +++ |

TABLE 2-4-continued

BMI cleaning performance of Group C1 variants.
PI = Performance Index
PI > or = 1.50 is +++; PI between 1.49 and 1.20 = ++; PI between 1.19
and 1.1 = + in Detergent Composition 106 as described in Table 1

| Sequence of GG36 Variants (BPN' numbering) | PI Relative to GG36; BMI assay, Detergent 106 at 25° C. |
|---|---|
| T022A-S024G-G061R-S078N-S101G-S103A-V104I-S128A-A232V-Q245R | +++ |
| T022A-S078N-S101G-S103A-V104I-L217Q-A232V-Q245R | +++ |
| T022A-S024G-S078N-S101Q-S103A-V104I-S128A-L217Q-A232V-Q245R | +++ |
| T022Q-S101T-S103A-V104L-A232V-Q245R | +++ |
| G020R-T022W-S024R-R045T-S101A-G211Q | +++ |
| P014R | +++ |
| T022R-S101A-S103N-V104L-A232M-Q245R | +++ |
| T022K-S101G-S103N-V104I-A232V-Q245R | +++ |
| G020R-S024R-S078D-G118D-Q245R | +++ |
| T022A-G097S-S101N-S103A-V104I-L217Q-A232V-Q245R | +++ |
| G020R-S024R-S101A-P210I-T213A | +++ |
| T022K-S101N-S103N-V104I-A232V-Q245R | +++ |
| T022Y-S101T-S103A-V104I-A232L-Q245R | +++ |
| T022A-N076D-S078N-S101G-S103A-V104I-S128A-L217Q-A232V-Q245R | +++ |
| G020R-S024R-N043R-R045T-S101A-P210I-G211Q-T213A | +++ |
| G020R-R045T-S101A-P210I-T213A | +++ |
| G020R-S078D-G118S-Q245R-H249R | +++ |
| G020R-T022W-R045T-V051A-S101A | +++ |
| T022R-S101T-S103A-V104I-A232V-Q245R | +++ |
| N043R-S101A | +++ |
| G020R-S024R-N043R-R045T-S101A-G211Q-T213A | +++ |
| T022R-S101G-S103G-V104I-A232L-Q245R | +++ |
| G020R-S101A-P210I | +++ |
| T022K-S101T-S103N-V104I-A232V-Q245R | +++ |
| G020R-T022W-N043R-V051A-S101A | +++ |
| G020R-T022W-N043R-S101A | +++ |
| G020R-T022W-S024R-N043R-S101A-P210I | +++ |
| G020R-T022W-S024R-N043R-R045T-S101A-P210I-T213A | +++ |
| G020R-N043R-R045T-S101A-T213A | +++ |
| T022A-S024G-S078N-S101N-S103A-V104I-L217Q-A232V-Q245R | +++ |
| T022Y-S101N-S103N-V104L-A232T-Q245R | +++ |
| G020R-S101A-N116L-P210I-G211Q | +++ |
| T022R-S101A-S103N-V104L-A232L-Q245R | +++ |
| G020R-S024R-N043R-S101A | +++ |
| T022R-S101G-S103A-V104L-A232T-Q245R | +++ |
| G020R-S024R-S101A-G211Q | +++ |
| T022A-S101Q-S103A-V104I-P129S-A232V-Q245R | +++ |
| T022A-S024G-G097A-S101G-S103A-V104I-L217Q-A232V-Q245R | +++ |
| T022A-S024G-S078N-S101G-S103A-V104I-S128A-L217Q-A232V-Q245R | +++ |
| T022K-S101A-S103N-V104I-A232T-Q245R | +++ |
| G020R-T022W-S024R-R045T-S101A | +++ |
| T022Y-S101G-S103A-V104I-A232V-Q245R | +++ |
| S024R-N043R-R045T-S101A-N116L-P210I-G211Q-T213A | +++ |
| T022A-S024G-S078N-S101N-S103A-V104I-S128A-L217Q-A232V-Q245R | +++ |
| G020R-N043R-S101A-P210I | +++ |
| T022A-S024G-S078N-G097A-S101G-S103A-V104I-L217Q-A232V-Q245R | +++ |
| T022R-S101T-S103N-V104I-A232V-Q245R | +++ |
| P055R | +++ |
| T022A-S101N-S103N-V104I-A232V-Q245R | +++ |
| G020R-T022W-S024R-N043R-N076D-S101A-P210I-T213A | +++ |
| G020R-T022W-S101A-P210I-T213A | +++ |
| T022Q-S101G-S103A-V104L-A232L-Q245R | +++ |
| T022W-S024R-N043R-R045T-S101A | +++ |
| T022A-S101G-S103A-V104I-L217Q-A232V-Q245R | +++ |
| T022K-S101N-S103A-V104I-A232L-Q245R | +++ |
| T022R-S101T-S103N-V104I-A232L-Q245R | +++ |
| G020R-S024R-N043R-R045T-S101A-P210I-T213A | +++ |
| T022A-S078N-S101N-S103A-V104I-S128A-A232V-Q245R | +++ |
| T022A-G097S-S101G-S103A-V104I-L217Q-A232V-Q245R | +++ |
| T022A-S078N-G097S-S101G-S103A-V104I-L217Q-A232V-Q245R | +++ |
| G020R-S024R-N062E-S078G-G118S-Q245R | +++ |
| T022K-S101A-S103N-V104I-A232L-Q245R | +++ |
| G020R-T022W-S024R-R045T-S101A-P210I-T213A | +++ |
| G020R-S024R-S078G-G118S-S188D-Q245R | +++ |
| T022R-S101T-S103A-V104I-A232V-Q245W | +++ |

TABLE 2-4-continued

BMI cleaning performance of Group C1 variants.
PI = Performance Index
PI > or = 1.50 is +++; PI between 1.49 and 1.20 = ++; PI between 1.19
and 1.1 = + in Detergent Composition 106 as described in Table 1

| Sequence of GG36 Variants (BPN' numbering) | PI Relative to GG36; BMI assay, Detergent 106 at 25° C. |
|---|---|
| T022R-S101N-S103A-V104I-A232V-Q245R | +++ |
| T022K-S101T-S103N-V104I-A232I-Q245R | +++ |
| T022A-S024G-S078N-S101Q-S103A-V104I-L217Q-A232V-Q245R | +++ |
| T022A-S078N-G097A-S101N-S103A-V104I-A232V-Q245R | +++ |
| T022Q-S101G-S103N-V104I-A232L-Q245R | +++ |
| T022A-S078N-G097A-S101Q-S103A-V104I-Q109N-A232V-Q245R | +++ |
| T022Q-S101G-S103A-V104L-A232V-Q245R | +++ |
| T022A-S101G-S103A-V104I-S128A-L217Q-A232V-Q245R | +++ |
| G020R-T022W-N043R-R045T-S101A-P210I | +++ |
| T022R-S101N-S103N-V104I-A232T-Q245R | +++ |
| G020R-N043R-R045T-S101A-N116L-G211Q-T213A | +++ |
| T022Q-S101A-S103N-V104I-A232V-Q245R | +++ |
| T022W-S024R-N043R-R045T-S101A-N116L-P210I | +++ |
| T022A-S078N-G097S-S101N-S103A-V104I-L217Q-A232V-Q245R | +++ |
| G020R-S078D-G118D-Q245R-H249R | +++ |
| G020R-S024R-N043R-S101A-P210I-G211Q-T213A | +++ |
| T022R-S101G-S103N-V104I-A232V-Q245W | +++ |
| T022A-S101T-S103N-V104L-A232L-Q245R | +++ |
| T022A-S024G-S078N-G097S-S101N-S103A-V104I-S128A-L217Q-A232V-Q245R | +++ |
| T022R-S101T-S103N-V104I-A232I-Q245R | +++ |
| G020R-N043R-S101A-P210I-T213A | +++ |
| G020R-S024R-N043R-S101A-N116L-G211Q-T213A | +++ |
| S024R-N043R-R045T-S101A-N116L-P210I-G211Q | +++ |
| T022A-S024G-G097S-S101N-S103A-V104I-L217Q-A232V-Q245R | +++ |
| E271R | +++ |
| T022K-S101T-S103G-V104I-A232V-Q245R | +++ |
| N043R-S101A-P210I-G211Q | +++ |
| G020R-S024R-S078G-G118S-P129E-G159D-Q245R | +++ |
| T022R-S101T-S103A-V104I-A232T-Q245S | +++ |
| E271W | +++ |
| S024R-N043R-R045T-S101A-N116L-P210I-T213A | +++ |
| T022A-S024G-S078N-S101N-S103A-V104I-A232V-Q245R | +++ |
| T022A-E089G-G097A-S101N-S103A-V104I-S128A-A232V-Q245R | +++ |
| T022R-S101T-S103A-V104I-A232L-Q245R | +++ |
| T022R-S101G-S103N-V104I-A232T-Q245S | +++ |
| T022A-S101G-S103A-V104I-A232M-Q245R | +++ |
| G020R-T022W-S024R-S101A-T213A | +++ |
| G020R-T022W-S024R-R045T-S101A-P210I | +++ |
| G020R-T022W-S024R-N043R-S101A-T213A | +++ |
| T022A-S024G-G097S-S101G-S103A-V104I-L217Q-A232V-Q245R | +++ |
| T022A-S024G-S078N-G097S-S101Q-S103A-V104I-S128A-L217Q-A232V-Q245R | +++ |
| G020R-S101A-T213A | +++ |
| E271S | +++ |
| G020R-S078G-G118S-Q245R-N248D-H249R | +++ |
| N043K | +++ |
| T022A-S101G-S103N-V104I-A232V-Q245R | +++ |
| T022Q-S101A-S103A-V104I-A232L-Q245R | +++ |
| G020R-T022W-S024R-R045T-S101A-T213A | +++ |
| G020R-S024R-S078G-G118S-Q245R-N248D-H249R | +++ |
| T022A-S024G-S078N-G097A-S101G-S103A-V104I-S128A-L217Q-A232V-Q245R | +++ |
| T022A-S024G-S078N-S101G-S103A-V104I-L217Q-A232V-Q245R | +++ |
| T022A-S024G-S101N-S103A-V104I-A232V-Q245R | +++ |
| G020R-T022W-S024R-S101A-N116L-P210I | +++ |
| G020R-T022W-N043R-R045T-S101A-T213A | +++ |
| T022A-S078N-G097A-S101N-S103A-V104I-L217Q-A232V-Q245R | +++ |
| T022A-S078N-S101N-S103A-V104I-L217Q-A232V-Q245R | +++ |
| T022R-S101N-S103G-V104L-A232V-Q245R | +++ |
| G020R-T022W-S024R-S101A-P210I-T213A | +++ |
| G020R-S024R-S078D-G118S-S188D-Q245R | +++ |
| G020R-S024R-S078D-G118S-G159D-Q245R | +++ |
| T022Y-S101T-S103A-V104I-A232M-Q245R | +++ |
| G020R-N043R-R045T-V051A-S101A-P210I-G211Q-T213A | +++ |
| G020R-T022W-S024R-N043R-R045T-S101A-T213A | +++ |
| T022A-S024G-S078N-G097S-S101G-S103A-V104I-L217Q-A232V-Q245R | +++ |
| T022A-S078N-S101Q-S103A-V104I-L217Q-A232V-Q245R | +++ |
| G020R-S024R-S101A-P210I-G211Q | +++ |
| T022Q-S101T-S103G-V104I-A232M-Q245R | +++ |

TABLE 2-4-continued

BMI cleaning performance of Group C1 variants.
PI = Performance Index
PI > or = 1.50 is +++; PI between 1.49 and 1.20 = ++; PI between 1.19
and 1.1 = + in Detergent Composition 106 as described in Table 1

| Sequence of GG36 Variants (BPN' numbering) | PI Relative to GG36; BMI assay, Detergent 106 at 25° C. |
|---|---|
| G020R-N043R-S101A-G211Q-T213A | +++ |
| T022A-S101Q-S103A-V104I-P129S-L217Q-A232V-Q245R | +++ |
| T022A-S101T-S103N-V104I-A232V-Q245R | +++ |
| G020R-S024R-S078G-G118D-G159D-Q245R-N248D-H249R | +++ |
| G020R-T022W-R045T-S101A-P210I-G211Q | +++ |
| T022A-S078N-S101N-S103A-V104I-A232V-Q245R | +++ |
| T022R-S101T-S103N-V104I-S105G-A232V-Q245R | +++ |
| T022A-S024G-S078N-S101Q-S103A-V104I-A232V-Q245R | +++ |
| T022A-S101T-S103N-V104I-A232L-Q245R | +++ |
| T022Q-S101N-S103N-V104L-A232V-Q245R | +++ |
| T022R-S101N-S103N-V104L-A232M-Q245R | +++ |
| T022Q-S101G-S103N-V104I-A232T-Q245R | +++ |
| T022A-S101Q-S103A-V104I-L217Q-A232V-Q245R | +++ |
| T022Q-S101A-S103A-V104I-A232L-Q245R | +++ |
| G020R-N043R-R045T-S101A-G211Q-T213A | +++ |
| T022A-G097A-S101N-S103A-V104I-P129S-L217Q-A232V-Q245R | +++ |
| G020R-S024R-R045T-S101A-G211Q-T213A | +++ |
| T022A-S078N-G097A-S101G-S103A-V104I-S128A-A232V-Q245R | +++ |
| G020R-T022W-N043R-R045T-S101A-P210I-G211Q-T213A | +++ |
| T022R-S101N-S103N-V104I-A232L-Q245R | +++ |
| T022Y-S101G-S103A-V104I-A232M-Q245R | +++ |
| T022R-S101G-S103G-V104I-A232T-Q245R | +++ |
| T022A-S024G-S078N-G097S-S101N-S103A-V104I-L217Q-A232V-Q245R | +++ |
| G020R-S024R-S078G-G118D-N248D-H249R | +++ |
| T022A-S101A-S103N-V104L-A232V-Q245R | +++ |
| T022W-S024R-S101A-N116L-G211Q | +++ |
| G020R-S024R-S101A-T208A-P210I-G211Q | +++ |
| T022W-S024R-N043R-R045T-S101A-P210I-G211Q-T213A | +++ |
| T022Y-S101G-S103N-V104I-A232M-Q245R | +++ |
| T022R-S101T-S103A-V104L-A232T-Q245S | +++ |
| G020R-S024R-S078G-G118S-P129E-Q245R-N248D | +++ |
| T022A-S024G-S101Q-S103A-V104I-Q109N-A232V-Q245R | +++ |
| G020R-T022W-S101A | +++ |
| T022W-S024R-N043R-S101A-P210I-G211Q | +++ |
| G020R-S024R-N043R-S101A-P210I-G211Q | +++ |
| G020R-S024R-N062E-S078G-G118D-H249R | +++ |
| G020R-S024R-G047C-S101A-G211Q | +++ |
| G020R-S024R-S078D-G118D-P129E-Q245R-H249R | +++ |
| T022A-S101A-S103A-V104L-A232V-Q245R | +++ |
| T022A-S101T-S103N-V104I-A232M-Q245R | +++ |
| N018S-G020R-T022W-N043R-S101A-G211Q | +++ |
| T022Y-S101T-S103G-V104I-A232T-Q245R | +++ |
| T022K-S101A-S103A-V104I-A232M-Q245R | +++ |
| T022A-S024G-G097A-S101N-S103A-V104I-L217Q-A232V-Q245R | +++ |
| T022Y-S101N-S103N-V104I-A232V-Q245R | +++ |
| T022A-S101G-S103A-V104I-A232V-Q245R | +++ |
| T022A-G097A-S101G-S103A-V104I-P129S-A232V-Q245R | +++ |
| G020R-S078G-G118S-P129E-Q245R-H249R | +++ |
| T022A-G097S-S101G-S103A-V104I-S128A-L217Q-A232V-Q245R | +++ |
| T022Y-S101A-S103G-V104I-A232M-Q245R | +++ |
| S024R-S101A-G211Q | +++ |
| T022A-S024G-G097A-S101Q-S103A-V104I-Q109G-A232V-Q245R | +++ |
| T022A-S024G-S101G-S103A-V104I-S128A-A232V-Q245R | +++ |
| R045T-S101A-I107V-Q109R-P210I-G211Q-T213A | +++ |
| T022A-G097S-S101Q-S103A-V104I-L217Q-A232V-Q245R | +++ |
| T022K-S101T-S103A-V104I-A232T-Q245R | +++ |
| Q012R-T022A-S101G-S103A-V104I-N116L-Y209A-T213A-A232V | +++ |
| T022W-S024R-N043R-R045T-S101A-P210I | +++ |
| T022A-S101N-S103A-V104I-A232V-Q245R | +++ |
| T022A-S024G-S078N-G097A-S101N-S103A-V104I-A232V-Q245R | +++ |
| G020R-S024R-S078G-G118S-G159D | +++ |
| T022Y-S101T-S103A-V104I-A232T-Q245R | +++ |
| T022Q-S101G-S103N-V104I-A232V-Q245R | +++ |
| S024R-S101A-P210I-T213A | +++ |
| T022A-S101N-S103A-V104I-L217Q-A232V-Q245R | +++ |
| T022A-S101G-S103N-V104L-A232L-Q245R | +++ |
| T022A-S024G-G097S-S101N-S103N-V104I-S128A-A232V-Q245R | +++ |
| T022A-S101G-S103A-V104I-S128A-P129S-A232V-Q245R | +++ |
| T022A-S101N-S103A-V104L-A232T-Q245R | +++ |
| S024R-S101A-P210I | +++ |

TABLE 2-4-continued

BMI cleaning performance of Group C1 variants.
PI = Performance Index
PI > or = 1.50 is +++; PI between 1.49 and 1.20 = ++; PI between 1.19
and 1.1 = +in Detergent Composition 106 as described in Table 1

| Sequence of GG36 Variants (BPN' numbering) | PI Relative to GG36; BMI assay, Detergent 106 at 25° C. |
|---|---|
| T022Y-S101T-S103N-V104I-A232V-Q245R | +++ |
| G020R-T022W-N043R-S101A-N116L | +++ |
| T022Q-S101N-S103N-V104I-A232V-Q245R | +++ |
| S024R-S101A | +++ |
| T022A-S024G-S078N-S101Q-S103A-V104I-Q109N-S128A-A232V-Q245R | +++ |
| S024R-N043R-R045T-S101A-N116L-G211Q-T213A | +++ |
| S212W | +++ |
| T022K-S101G-S103A-V104L-A232M-Q245R | +++ |
| T022A-S024G-S101Q-S103A-V104I-L217Q-A232V-Q245R | +++ |
| S024R-N043R-R045T-S101A | +++ |
| G020R-S101A | +++ |
| G020R-S024R-S078G-G118D-P129E-Q245R-N248D-H249R | +++ |
| T022-S101T-S103N-V104I-A232M-Q245R | +++ |
| S056K | +++ |
| T022A-S024R-N076D-S101G-S103A-V104I-A232V-Q245R-A270V | +++ |
| T022-S101T-S103G-V104I-A232M-Q245S | +++ |
| G020R-T022W-R045T-S101A-P210I-G211Q-T213A | +++ |
| T022K-S101N-S103N-V104L-A232L-Q245R | +++ |
| T022W-S024R-N043R-R045T-S101A-V147I-P210I-G211Q-T213A | +++ |
| T022A-S101Q-S103A-V104I-Q109G-S128A-A232V-Q245R | +++ |
| T022A-S078N-G097S-S101Q-S103A-V104I-L217Q-A232V-Q245R | +++ |
| G020R-S024R-S078D-G118S-P129E-Q245R-N248D-H249R | +++ |
| S078G-G118D-Q245R-H249R | +++ |
| T022A-S101G-S103A-V104I-A232V-N238Y-Q245R-A272V | +++ |
| T022A-S024G-S101Q-S103A-V104I-A232V-Q245R | +++ |
| T022A-S078N-G097S-S101Q-S103A-V104I-A232V-Q245R | +++ |
| G020R-T022W-S024R-N043R-S101A-P210I-T213A | +++ |
| T022A-S024G-S101N-S103A-V104I-S128A-L217Q-A232V-Q245R | +++ |
| S056R | +++ |
| T022Y-S101T-S103N-V104I-A232L-Q245R | +++ |
| T022R-S101T-S103G-V104I-A232V-Q245S | +++ |
| T022W-S101A-P210I-G211Q | +++ |
| T022A-S101A-S103N-V104L-A232T-Q245S | +++ |
| T022Y-S101A-S103G-V104I-A232T-Q245R | +++ |
| T022R-S101T-S103A-V104L-A232T-Q245R | +++ |
| T022Q-S101G-S103A-V104I-A232T-Q245R | +++ |
| G020R-S024R-S078G-G118D-S188D-Q245R-H249R | +++ |
| V030I-N043R-S101A-G211Q-T213A | +++ |
| T022A-S101T-S103A-V104I-A232V-Q245R | +++ |
| T022A-S024G-S101N-S103A-V104I-S128A-A232A-Q245R | +++ |
| T022A-S101G-S103A-V104I-A232V-N238Y-Q245R | +++ |
| G020R-S078G-G118D-P129E-G159D-Q245R-H249R | +++ |
| T022R-S101G-S103A-V104I-A232V-Q245R | +++ |
| S024R-S078D-G118S-S188D-Q245R-H249R | +++ |
| T022A-S101G-S103A-V104I-A232V-Q245R-A270V | +++ |
| T022A-S024G-G097A-S101Q-S103A-V104I-A232V-Q245R | +++ |
| T022A-S101T-S103G-V104I-A232V-Q245R | +++ |
| G020R-T022W-S101A-T213A | +++ |
| T022A-S101G-S103A-V104I-S128A-A232V-Q245R | +++ |
| T022A-S101N-S103A-V104I-Q109G-A232V-Q245R | +++ |
| T022Q-S101N-S103N-V104L-A232L-Q245R | +++ |
| N018S-G020R-S101A-P210I-G211Q | +++ |
| G020R-S078D-G118S-S188D-Q245R-H249R | +++ |
| T022A-S101G-S103N-V104I-A232L-Q245R | +++ |
| T022R-S101T-S103G-V104L-A232V-Q245R | +++ |
| T022A-N076D-S101G-S103A-V104I-A232V-Q245R-A270V-A272V | +++ |
| T022Q-S101N-S103G-V104I-A232V-Q245S | +++ |
| G020R-N043R-R045T-S101A-G211Q | +++ |
| T022A-N076D-S101G-S103A-V104I-L217Q-A232V-Q245R | +++ |
| T022R-S101A-S103A-V104L-A232V-Q245S | +++ |
| T022A-S078N-S101Q-S103A-V104I-Q109N-A232V-Q245R | +++ |
| S024R-S078G-G118S-T180N-Q245R-N248D | +++ |
| V004M | +++ |
| T022A-S101T-S103N-V104I-A232T-Q245R | +++ |
| T022A-S078N-S101G-S103A-V104I-A230T-A232V-Q245R | +++ |
| T022Y-S101N-S103N-V104I-A232L-Q245R | +++ |
| G020R-S024R-S078D-G118S-G159D-Q245R-N248D | +++ |
| G020R-S024R-S078G-G118S-G159D-S188D-Q245R | +++ |
| G020R-N043R-R045T-S101A-P210I-T213A | +++ |
| S024R-S078D-G118D-Q245R-H249R | +++ |

TABLE 2-4-continued

BMI cleaning performance of Group C1 variants.
PI = Performance Index
PI > or = 1.50 is +++; PI between 1.49 and 1.20 = ++; PI between 1.19 and 1.1 = + in Detergent Composition 106 as described in Table 1

| Sequence of GG36 Variants (BPN' numbering) | PI Relative to GG36; BMI assay, Detergent 106 at 25° C. |
|---|---|
| G020R-S024R-N043R-R045T-S101A-Q109R-T213A | +++ |
| T022A-S078N-S101N-S103A-V104I-Q109N-A232V-Q245R | +++ |
| G020R-S024R-N043R-S101A-N204D-G211Q-T213A | +++ |
| T022A-G097A-S101Q-S103A-V104I-A232V-Q245R | +++ |
| G020R-S024R-S078G-G118S-N248D | +++ |
| G020R-S024R-S078G-G118S-G159D-Q245R-N248D | +++ |
| T022A-S024G-S078N-S101N-S103A-V104I-S128A-A232V-Q245R | +++ |
| S024R-S078G-G118D-G159D-Q245R-H249R | +++ |
| T022K-S101T-S103N-V104L-A232V-Q245R | +++ |
| S024R-S078G-G118S-Q245R | +++ |
| T022A-S101A-S103G-V104I-A232L-Q245R | +++ |
| T022A-G097A-S101Q-S103A-V104I-S128A-A232V-Q245R | +++ |
| T022A-S024G-S078N-G097S-S101G-S103A-V104I-A232V-Q245R | +++ |
| G020R-S078D-G118S-Q245R | +++ |
| T022A-S024R-N076D-S101G-S103A-V104I-A232V-N238Y-Q245R-A270V-A272V | +++ |
| S101A-P210I-T213A | +++ |
| T022A-S101Q-S103A-V104I-S128A-P129S-L217Q-A232V-Q245R | +++ |
| A114L | +++ |
| A016S-T022A-S101G-S103A-V104I-N116A-Y209V-G211Q-T213A-A232V | +++ |
| T022A-S101N-S103A-V104I-S128A-P129S-L217Q-A232V-Q245R | +++ |
| T022R-S101A-S103N-V104I-A232L-Q245S | +++ |
| T022Q-S101N-S103A-V104I-A232M-Q245W | +++ |
| T022W-S024R-S101A-N204S-G211Q-T213A | +++ |
| T022A-S101N-S103A-V104L-A232M-Q245R | +++ |
| T022A-S024G-S101Q-S103A-V104I-Q109N-S128A-A232V-Q245R | +++ |
| G020R-S078D-G118S-P129E-Q245R-H249R | +++ |
| T022Q-S101T-S103A-V104I-A232T-Q245S | +++ |
| S024R-N043R-R045T-S101A-P210I-G211Q-T213A | +++ |
| T022R-S101N-S103G-V104I-A232T-Q245R | +++ |
| S024R-S101A-P210I-G211Q-T213A | +++ |
| T022A-S024G-N076D-G097A-S101G-S103A-V104I-S128A-A232V-Q245R | +++ |
| G020R-S024R-S078G-G118S-S188D-N248D-H249R | +++ |
| T022A-G097S-S101Q-S103A-V104I-Q109G-S128A-A232V-Q245R | +++ |
| G020R-S024R-R045T-S101A-P210I-T213A | +++ |
| T022A-S078N-G097S-S101N-S103A-V104I-S128A-A232V-Q245R | +++ |
| T022A-S024G-S078N-G097A-S101Q-S103A-V104I-A232V-Q245R | +++ |
| T022R-S101G-S103N-V104I-A232T-Q245W | +++ |
| T022K-S101G-S103A-V104I-A232V-Q245R | +++ |
| T022W-S024R-S101A-G211Q-T213A | +++ |
| S024R-N043R-S101A-P210I-G211Q | +++ |
| T022Q-S101T-S103G-V104I-A232T-Q245R | +++ |
| T022A-S101G-S103A-V104I-A232V-Q245R-A272V | +++ |
| T022K-S101G-S103N-V104L-A232M-Q245R | +++ |
| T022A-S024G-G097A-S101Q-S103A-V104I-Q109N-A232V-Q245R | +++ |
| S078D-G118S-G159D-Q245R-H249R | +++ |
| G020R-T022W-S024R-A069T-S101A-P210I-T213A | +++ |
| T022A-S101N-S103A-V104I-S128A-L217Q-A232V-Q245R | +++ |
| G020R-T022W-S024R-N043R-R045T-S101A-P210I-G211Q | +++ |
| G020R-S024R-S078D-G118D-G159D-S188D-Q245R-H249R | +++ |
| T022A-S078N-S101N-S103A-V104I-S128A-L217Q-A232V-Q245R | +++ |
| G020R-S078G-G118D-G159D-Q245R-N248D-H249R | +++ |
| T022W-R045T-S101A-T213A | +++ |
| T022Y-S101N-S103A-V104I-A232T-Q245R | ++ |
| G020R-R045T-S101A-P210I-G211Q-L267F | ++ |
| T022Y-S101N-S103N-V104L-A232M-Q245R | ++ |
| T022A-P052T-S101G-S103A-V104I-L217Q-A232V-Q245R | ++ |
| T022A-S101G-S103N-V104L-A232T-Q245R | ++ |
| T022Y-S101A-S103N-V104L-A232V-Q245R | ++ |
| T022A-S101A-S103N-V104I-A232T-Q245R | ++ |
| T022Y-S101A-S103N-V104I-A232L-Q245R | ++ |
| T022Y-S101G-S103A-V104I-A232T-Q245R | ++ |
| T022A-S024G-N076D-S078N-G097S-S101N-S103A-V104I-L217Q-A232V-Q245R | ++ |
| T022A-S101N-S103N-V104L-A232M-Q245R | ++ |
| T022A-S101Q-S103A-V104I-S128A-P129S-A232V-Q245R | ++ |
| T022A-S101N-S103A-V104I-S128A-A232V-Q245R | ++ |
| S024R-S078D-G118S-G159D-Q245R-H249R | ++ |
| T022K-S101N-S103A-V104L-A232T-Q245R | ++ |

TABLE 2-4-continued

BMI cleaning performance of Group C1 variants.
PI = Performance Index
PI > or = 1.50 is +++; PI between 1.49 and 1.20 = ++; PI between 1.19
and 1.1 = +in Detergent Composition 106 as described in Table 1

| Sequence of GG36 Variants (BPN' numbering) | PI Relative to GG36; BMI assay, Detergent 106 at 25° C. |
|---|---|
| T022R-S101T-S103N-V104I-A232T-Q245S | ++ |
| T022Q-S101N-S103N-V104I-A232M-Q245R | ++ |
| S024R-S078G-G118D-Q245R-H249R | ++ |
| T022R-S101N-S103N-V104I-A232V-Q245R | ++ |
| T022A-N076D-S101Q-S103A-V104I-Q109G-A232V-Q245R | ++ |
| G020R-S024R-S078G-G118D-S188D-Q245R-N248D | ++ |
| T022Y-S101N-S103A-V104I-A232V-Q245R | ++ |
| T022Q-S101N-S103A-V104L-A232L-Q245R | ++ |
| T022Q-S101N-S103N-V104I-A232L-Q245R | ++ |
| T022A-G097S-S101N-S103A-V104I-S128A-L217Q-A232V-Q245R | ++ |
| T022R-S101N-S103N-V104I-A232T-Q245S | ++ |
| G020R-S078D-G118D-G159D-Q245R-H249R | ++ |
| T022R-S101N-S103A-V104L-A232M-Q245R | ++ |
| T022A-N076D-G097S-S101Q-S103A-V104I-Q109N-S128A-A232V-Q245R | ++ |
| T022R-S101G-S103N-V104L-A232T-Q245S | ++ |
| G020R-T022W-N043R-R045T-S101A-G211Q-T213A | ++ |
| T022Q-S101T-S103N-V104I-A232T-Q245R | ++ |
| G020R-S024R-N043R-S101A-N204D-T213A | ++ |
| T022A-S024G-S101Q-S103A-V104I-Q109G-A232V-Q245R | ++ |
| G020R-S024R-S078D-G118D-S188D-Q245R-N248D-H249R | ++ |
| S024R-N043R-S101A-P210I | ++ |
| T022A-N076D-S101G-S103A-V104I-A232V-Q245R-A270V | ++ |
| G020R-S024R-S078D-G118S-H249R | ++ |
| S024R-S078G-G118S | ++ |
| T022R-S101G-S103N-V104L-A232V-Q245S | ++ |
| S024R-N043K-R045T-S101A | ++ |
| T022A-N076D-S078N-S101N-S103A-V104I-A232V-Q245R-T274A | ++ |
| T022A-S024G-N076D-S078N-S101G-S103A-V104I-L217Q-A232V-Q245R | ++ |
| T022Q-S101T-S103G-V104I-A232M-Q245W | ++ |
| S024R-S078G-G118S-P129E-Q245R-H249R | ++ |
| T022A-S024R-N076D-S101G-S103A-V104I-A232V-Q245R V026W | ++ |
| T022R-S101G-S103N-V104I-A232L-Q245W | ++ |
| G020R-S024R-S078D-G118S-N248D | ++ |
| G020R-R045T-S101A-N204S-P210I | ++ |
| G020R-S024R-S078G-G118D-G159D-N248D-H249R | ++ |
| T022Y-S101A-S103N-V104I-A232V-Q245R | ++ |
| T022A-S024G-S078N-G097A-S101N-S103A-V104I-L217Q-A232V-Q245R | ++ |
| S024R-S101A-P210I-G211Q | ++ |
| T022R-S101N-S103N-V104I-A232V-Q245S | ++ |
| T022A-S024G-G097A-S101N-S103A-V104I-Q109G-A232V-Q245R | ++ |
| T022A-G097A-S101N-S103A-V104I-A232V-Q245R | ++ |
| T022A-S024G-N076D-S101Q-S103A-V104I-Q109N-A232V-Q245R | ++ |
| G020R-S024G-S078G-G118S-H249R | ++ |
| S078G-G118S-Q245R-H249R | ++ |
| T022A-G097A-S101N-S103A-V104I-L217Q-A232V-Q245R | ++ |
| T022Y-S101T-S103G-V104I-A232M-Q245R | ++ |
| T022K-S101G-S103N-V104I-A232L-Q245R | ++ |
| T022A-S024G-G097S-S101N-S103A-V104I-A232V-Q245R | ++ |
| S024R-S078G-G118D-G159D-S188D-Q245R-H249R | ++ |
| T022Q-S101N-S103A-V104I-A232V-Q245R | ++ |
| G020R-S024R-S078G-G118D-G159D-Q245R-N248D | ++ |
| T022A-S024G-S101G-S103A-V104I-A232V-Q245R | ++ |
| T022Q-S101G-S103A-V104L-A232T-Q245R | ++ |
| T022Q-S101T-S103A-V104I-A232T-Q245R | ++ |
| T022A-N076D-S101N-S103A-V104I-S128A-A232V-Q245R | ++ |
| T022A-S024G-N076D-S078N-G097A-S101G-S103A-V104I-A232V-Q245R | ++ |
| T022A-S101G-S103A-V104L-A232V-Q245R | ++ |
| T022A-S024G-S078N-G097S-S101Q-S103A-V104I-S128A-A232V-Q245R | ++ |
| T022A-S024G-N076D-G097S-S101G-S103A-V104I-A232V-Q245R | ++ |
| S024R-N043R-S101A-G211Q-T213A | ++ |
| T022A-G097S-S101Q-S103A-V104I-A232V-Q245R | ++ |
| S024R-S078G-G118S-Q245R-N248D | ++ |
| G020R-T022W-S024R-N043R-S101A-N204S-P210I-G211Q | ++ |
| T022A-S024G-S078N-G097S-S101N-S103A-V104I-Q109G-S128A-A232V-Q245R | ++ |

TABLE 2-4-continued

BMI cleaning performance of Group C1 variants.
PI = Performance Index
PI > or = 1.50 is +++; PI between 1.49 and 1.20 = ++; PI between 1.19
and 1.1 = +in Detergent Composition 106 as described in Table 1

| Sequence of GG36 Variants (BPN' numbering) | PI Relative to GG36; BMI assay, Detergent 106 at 25° C. |
|---|---|
| T022A-S101G-S103A-V104I-P129S-A232V-Q245R | ++ |
| T022R-S101T-S103G-V104I-A232T-Q245S | ++ |
| T022A-S024G-I072V-G097S-S101Q-S103A-V104I-S128A-L217Q-A232V-Q245R | ++ |
| T022K-S101A-S103A-V104I-A232V-Q245W | ++ |
| G020R-T022W-S024R-R045T-S101A-N116L-P210I | ++ |
| T022R-S101T-S103G-V104I-A232T-Q245W | ++ |
| T022A-S024G-N076D-S078N-G097S-S101N-S103A-V104I-S128A-A232V-Q245R | ++ |
| T022A-G097A-S101N-S103A-V104I-S128A-A232V-Q245R | ++ |
| T022Y-S101T-S103N-V104L-A232V-Q245R | ++ |
| G020R-S024R-N062E-S078G-G118S-N248D | ++ |
| T022Q-S101G-S103A-V104I-A232V-Q245R | ++ |
| T022A-N076D-S078N-S101N-S103A-V104I-S128A-A232V-Q245R | ++ |
| T022A-S024G-G097A-S101N-S103A-V104I-S128A-A232V-Q245R | ++ |
| T022A-S024G-N076D-S078N-S101Q-S103A-V104I-A232V-Q245R | ++ |
| T022A-N076D-S078N-S101G-S103A-V104I-L217Q-A232V-Q245R | ++ |
| T022A-S024G-N076D-S101N-S103A-V104I-A232V-Q245R | ++ |
| T022R-S101N-S103A-V104I-A232L-Q245S | ++ |
| T022A-S078N-S101N-S103A-V104I-Q109N-L217Q-A232V-Q245R | ++ |
| T022R-S101A-S103A-V104I-A232V-Q245W | ++ |
| T022R-S101Q-S103A-V104I-A232V-Q245R | ++ |
| T022A-S078N-G097S-S101N-S103A-V104I-A232V-Q245R | ++ |
| T022A-G097A-S101Q-S103A-V104I-P129S-A232V-Q245R | ++ |
| T022A-S101T-S103A-V104I-A232L-Q245R | ++ |
| T022A-A085T-G097S-S101Q-S103A-V104I-L217Q-A232V-Q245R | ++ |
| T022A-S101T-S103N-V104L-S105G-A232M-Q245R | ++ |
| T022A-S101A-S103A-V104I-A232M-Q245S | ++ |
| T022Q-S101A-S103A-V104I-A232M-Q245R | ++ |
| T022Q-S101G-S103A-V104L-A232M-Q245R | ++ |
| T022A-S024G-G097A-S101Q-S103A-V104I-S128A-A232V-Q245R | ++ |
| T022A-S024G-G097S-S101Q-S103A-V104I-L217Q-A232V-Q245R | ++ |
| T022A-N076D-S078N-G097S-S101G-S103A-V104I-S128A-A232V-Q245R | ++ |
| T022A-G097A-S101G-S103A-V104I-H120Q-S128A-A232V-Q245R | ++ |
| T022A-G097A-S101N-S103A-V104I-S128A-P129S-L217Q-A232V-Q245R | ++ |
| G020R-S024R-N062E-S078G-G118D-Q245R | ++ |
| T022K-S101G-S103G-V104I-A232V-Q245R | ++ |
| S078G-G118S-S188D-Q245R-H249R | ++ |
| T022W-N043R-S101A-G211Q-T213A | ++ |
| T022A-S024G-N076D-G097S-S101N-S103A-V104I-Q109N-A232V-Q245R | ++ |
| T022Y-S101A-S103N-V104L-A232M-Q245R | ++ |
| G020R-T022W-S101A-N116L-G211Q-T213A | ++ |
| T022W-S024R-N043R-R045T-S101A-T213A | ++ |
| N043R-S101A-G211Q-T213A | ++ |
| T022Y-S101N-S103N-V104L-A232L-Q245R | ++ |
| T255G | ++ |
| T022A-G097S-S101N-S103A-V104I-S128A-A232V-Q245R | ++ |
| T022W-S024R-N043R-S101A-P210I-T213A | ++ |
| N269K | ++ |
| T022R-S101T-S103A-V104I-A232L-Q245S | ++ |
| T022A-S024G-I072V-S078N-G097S-S101N-S103A-V104I-S128A-A232V-Q245R | ++ |
| T022K-S101T-S103G-V104I-A232M-Q245R | ++ |
| H017R-N043R-R045T-S101A-P210I-T213A | ++ |
| T022A-S024G-G097S-S101G-S103A-V104I-S128A-A232V-Q245R | ++ |
| T022A-S078N-G097A-S101Q-S103A-V104I-A232V-Q245R | ++ |
| T022A-N076D-G097A-S101N-S103A-V104I-A232V-Q245R | ++ |
| T022A-S024G-V026A-S101G-S103A-V104I-S128A-A232V-Q245R | ++ |
| T022A-S024G-G097A-S101G-S103A-V104I-S128A-L217Q-A232V-Q245R | ++ |
| T022Q-S101T-S103G-V104I-A232L-Q245R | ++ |
| T022W-S024R-S101A-P210I-G211Q-T213A | ++ |
| T022Q-S101N-S103A-V104I-A232M-Q245R | ++ |
| G020R-R045I-S101A | ++ |
| T022Y-S101N-S103N-V104I-A232V-Q245R | ++ |
| T022R-S101G-S103A-V104I-A232L-Q245R | ++ |
| S024R-S078D-G118D-P129E-Q245R-H249R | ++ |
| T022R-S101A-S103A-V104I-A232M-Q245S | ++ |

TABLE 2-4-continued

BMI cleaning performance of Group C1 variants.
PI = Performance Index
PI > or = 1.50 is +++; PI between 1.49 and 1.20 = ++; PI between 1.19
and 1.1 = +in Detergent Composition 106 as described in Table 1

| Sequence of GG36 Variants (BPN' numbering) | PI Relative to GG36; BMI assay, Detergent 106 at 25° C. |
|---|---|
| G020R-S101A-P210I-G211Q | ++ |
| T022W-N043R-R045T-S101A-P210I-G211Q | ++ |
| T022R-S101G-S103A-V104I-A232M-Q245S | ++ |
| T022A-S024G-N076D-S101G-S103A-V104I-L217Q-A232V-Q245R | ++ |
| T022R-S101T-S103N-V104I-A232V-Q245S | ++ |
| T022Q-S101G-S103N-V104L-A232M-Q245R | ++ |
| T022K-T038I-S101G-S103A-V104I-A232T-Q245S | ++ |
| N043R-R045T-S101A-P210I-G211Q | ++ |
| T022K-S101T-S103A-V104L-A232M-Q245R | ++ |
| T022Y-S101T-S103N-V104I-A232T-Q245R | ++ |
| G020R-S024R-N043R-S101A-P210I-T213A | ++ |
| S099G-S101G | ++ |
| T022A-S101N-S103N-V104L-A232T-Q245R | ++ |
| T022A-S024G-N076D-S078N-G097A-S101N-S103A-V104I-A232V-Q245R | ++ |
| T022R-S101N-S103A-V104I-A232V-Q245W | ++ |
| T022W-N043R-R045T-S101A-P210I | ++ |
| T022K-S101A-S103G-V104I-A232T-Q245R | ++ |
| T022Q-S101N-S103A-V104I-A232T-Q245S | ++ |
| T022A-S101Q-S103A-V104I-Q109G-A232V-Q245R | ++ |
| T022A-G097A-S101Q-S103A-V104I-S128A-P129S-L217Q-A232V-Q245R | ++ |
| T022A-S078N-G097A-S101Q-S103A-V104I-L217Q-A232V-Q245R | ++ |
| S024R-S078G-G118S-G159D-Q245R | ++ |
| T022K-S101N-S103N-V104I-A232I-Q245R | ++ |
| A098F-S099A-V104I | ++ |
| G020R-R045T-S101A-G211Q-T213A | ++ |
| T022A-N076D-S078N-G097A-S101G-S103A-V104I-A232V-Q245R | ++ |
| S024R-S078D-G118S-G159D-Q245R | ++ |
| T022A-S024G-N076D-S101N-S103A-V104I-Q109N-A232V-Q245R | ++ |
| T022K-S101T-S103N-V104I-A232M-Q245R | ++ |
| T022A-S024G-S078N-G097S-S101N-S103A-V104I-S128A-A232V-Q245R | ++ |
| T022Q-S101T-S103N-V104I-A232L-Q245S | ++ |
| A114T | ++ |
| T022Q-S101N-S103N-V104L-A232T-Q245R | ++ |
| T022A-S078N-S101G-S103A-V104I-Q109N-A232V-Q245R | ++ |
| T022K-S101T-S103A-V104I-A232M-Q245R | ++ |
| T022A-S024G-G097S-S101Q-S103A-V104I-Q109G-S128A-L217Q-A232V-Q245R | ++ |
| T022A-S101G-S103A-V104I-N116L-Y209V-G211Q-A232V | ++ |
| T022A-S101T-S103N-V104I-A232M-Q245W | ++ |
| G020R-T022W-S024R-S101A-N116L-G211Q | ++ |
| T022A-S078N-S101Q-S103A-V104I-S128A-L217Q-A232V-Q245R | ++ |
| G020R-R045T-S101A-G211Q | ++ |
| T022A-N076D-S078N-G097A-S101G-S103A-V104I-S128A-A232V-Q245R | ++ |
| S024R-S101A-T213A | ++ |
| T022A-S078N-S101G-S103A-V104I-A232V-Q245R | ++ |
| G020R-S024R-S078D-G118S-G159D-S188D-Q245R-N248D-H249R | ++ |
| T022Y-S101N-S103N-V104I-A232V-Q245W | ++ |
| T022Y-S101A-S103G-V104I-A232V-Q245R | ++ |
| T022A-S024R-N076D-S101G-S103A-V104I-A232V-N238Y-Q245R | ++ |
| G020R-S078G-G118S-GI59D-H249R | ++ |
| T022A-S024G-S101G-S103A-V104I-P129E-A232V-Q245R-A272V | ++ |
| T022R-S101N-S103A-V104I-A232V-Q245S | ++ |
| G020R-S101A-P210I-G211Q-T213A | ++ |
| G020R-S024R-S078D-G118S-G159D-S188D-Q245R | ++ |
| S087R | ++ |
| G020R-S024R-R045T-A048T-S101A-G211Q | ++ |
| T022A-S024G-G097S-S101Q-S103A-V104I-A232V-Q245R | ++ |
| G020R-S024R-S078G-G118S-P129E-S188D-Q245R-N248D-H249R | ++ |
| T022A-G097S-S101G-S103A-VI04I-Q109N-A232V-Q245R | ++ |
| L021S-T022A-S024G-N076D-S078N-S101G-S103A-V104I-S128A-A232V-Q245R | ++ |
| S242K | ++ |
| T022K-S101A-S103A-V104I-A232V-Q245R | ++ |
| T022K-S101N-S103A-V104L-A232L-Q245R | ++ |
| T022A-N076D-S101G-S103A-V104I-A232V-N238Y-Q245R-A270V-A272V | ++ |
| T022R-S101T-S103A-V104I-A232V-Q245S | ++ |

TABLE 2-4-continued

BMI cleaning performance of Group C1 variants.
PI = Performance Index
PI > or = 1.50 is +++; PI between 1.49 and 1.20 = ++; PI between 1.19
and 1.1 = + in Detergent Composition 106 as described in Table 1

| Sequence of GG36 Variants (BPN' numbering) | PI Relative to GG36; BMI assay, Detergent 106 at 25° C. |
|---|---|
| T022Y-S101N-S103G-V104I-A232L-Q245R | ++ |
| T022Q-S101N-S103G-V104I-A232V-Q245R | ++ |
| T022A-S101G-S103A-V104I-A232V-Q245W | ++ |
| T022R-S101A-S103A-V104I-A232L-Q245S | ++ |
| G020R-T022W-R045T-F050L-S101A-P210I-G211Q-T213A | ++ |
| T022A-S101Q-S103A-V104I-S128A-L217Q-A232V-Q245R | ++ |
| G020R-S101A-G211Q-T213A | ++ |
| T022A-N076D-S101G-S103A-V104I-A232V-Q245R-A272V | ++ |
| T022A-S101G-S103A-V104I-A232V-N238Y-Q245R-A270V | ++ |
| T022A-S101N-S103G-V104I-A232V-Q245R | ++ |
| G020R-S101A-T208P-P210I-G211Q | ++ |
| D181S | ++ |
| S101G-S103A-V104I-N116L-Y209V-A232V | ++ |
| T022Q-S101A-S103N-V104I-A232T-Q245R | ++ |
| T022A-S101G-S103N-V104L-G211S-A232T-Q245R | ++ |
| T022A-G097A-S101Q-S103A-V104I-L217Q-A232V-Q245R | ++ |
| T022A-S101T-S103N-V104I-A232M-Q245S | ++ |
| T022A-S101G-S103A-V104I-Q109N-A232V-Q245R | ++ |
| T022Q-S101A-S103G-V104I-A232M-Q245R | ++ |
| G020R-S078G-G118S-G159D-N248D-H249R | ++ |
| T022A-N076D-S101N-S103A-V104I-A232V-Q245R | ++ |
| T022A-S024G-G097S-S101N-S103A-V104I-Q109G-S128A-A232V-Q245R | ++ |
| T022Q-S101A-S103A-V104I-A232T-Q245R | ++ |
| T022A-S101G-S103A-V104I-A232L-Q245R | ++ |
| T022A-S101G-S103A-V104I-P129E-A232V-N238Y-V244I-Q245R-A270V-A272V | ++ |
| G020R-S024R-S078D-G118D-G159D-Q245R-N248D-H249R | ++ |
| T022R-S101A-S103N-V104I-A232V-Q245W | ++ |
| T022Q-S101A-S103N-V104I-A232M-Q245R | ++ |
| T022Q-S101A-S103N-V104L-A232L-Q245R | ++ |
| T022A-S024G-S101Q-S103A-V104I-S128A-L217Q-A232V-Q245R | ++ |
| T022Q-S101G-S103G-V104I-A232M-Q245R | ++ |
| G020R-S078G-G118S-G159D-Q245R-H249R | ++ |
| T022R-S101A-S103N-V104L-A232V-Q245S | ++ |
| T022A-S024V-G097S-S101N-S103A-V104I-H120N-S128A-A232V-Q245R | ++ |
| T022A-A073V-N076D-S078N-S101N-S103A-V104I-A232V-Q245R | ++ |
| T022Q-S101G-S103N-V104L-A232V-Q245R-T274I | ++ |
| T022A-S101N-S103N-V104I-A232T-Q245R | ++ |
| T022W-S024R-R045P-S101A-P210I-G211Q-T213A | ++ |
| G020R-S024R-N062E-S078G-G118D-Q245R-N248D | ++ |
| T022Q-S101A-S103N-V104I-A232M-Q245R | ++ |
| T022Q-S101T-S103G-V104L-A232T-Q245R | ++ |
| T022R-S101G-S103N-A232L-Q245R | ++ |
| T022A-G097S-S101Q-S103A-V104I-Q109N-L217Q-A232V-Q245R | ++ |
| T022A-S024G-G097A-S101Q-S103A-V104I-S128A-L217Q-A232V-Q245R | ++ |
| S024R-S101A-G211Q-T213A | ++ |
| T022R-S101N-S103N-V104L-A232T-Q245S | ++ |
| G020R-R045T-S101A-P210I | ++ |
| T022R-S101A-S103A-V104I-A232M-Q245W | ++ |
| T022A-S101N-S103N-V104I-A232L-Q245R | ++ |
| T022A-S101G-S103G-V104I-A232M-Q245R | ++ |
| G020R-S024R-S078D-G118S-S188D-Q245R-N248D | ++ |
| S099T-S103G | ++ |
| T022W-N043R-S101A-P210I | ++ |
| T022W-A029V-N043R-S101A-P210I | ++ |
| F050R | ++ |
| T022A-S024G-N076D-S078N-G097S-S101Q-S103A-V104I-Q109N-A232V-Q245R | ++ |
| T022A-S024G-N076D-S101G-S103A-V104I-A232V-Q245R | ++ |
| T022R-S101G-S103N-V104L-A232L-Q245R | ++ |
| T022A-S101N-S103A-V104I-Q109N-S128A-A232V-Q245R | ++ |
| S024R-R045T-S101A | ++ |
| T022A-N076D-G097S-S101N-S103A-V104I-L217Q-A232V-Q245R | ++ |
| T022Q-S101G-S103A-V104I-A232M-Q245S | ++ |
| T022W-S024R-N043R-R045T-S101A-G211Q-T213A | ++ |
| G020R-S078G-G118S | ++ |
| T022W-N043R-G046C-S101A-P210I-G211Q | ++ |
| S101A-G211Q-T213A | ++ |

TABLE 2-4-continued

BMI cleaning performance of Group C1 variants.
PI = Performance Index
PI > or = 1.50 is +++; PI between 1.49 and 1.20 = ++; PI between 1.19
and 1.1 = + in Detergent Composition 106 as described in Table 1

| Sequence of GG36 Variants (BPN' numbering) | PI Relative to GG36; BMI assay, Detergent 106 at 25° C. |
|---|---|
| T022A-N076D-S078N-S101G-S103A-V104I-A232V-Q245R | ++ |
| T022A-S024G-N076D-G097S-S101Q-S103A-V104I-A232V-Q245R | ++ |
| T022A-S101N-S103A-V104I-L126I-P129S-A232V-Q245R | ++ |
| T022R-S101T-S103N-V104I-A232L-Q245W | ++ |
| T022A-S101G-S103A-V104I-A232V-N238Y-Q245R-A270V-A272V | ++ |
| S078G-G118D-Q245R | ++ |
| T022A-S024R-S101G-S103A-V104I-P129E-A232V-N238Y-Q245R-A270V | ++ |
| T022A-N076D-G097S-S101N-S103A-V104I-Q109G-S128A-A232V-Q245R | ++ |
| T022W-S024R-R045T-S101A-N116L-P210I-T213A | ++ |
| T022R-S101T-S103N-V104I-A232L-Q245S | ++ |
| T022W-S024R-N043R-R045T-S101A-S106L-P210I-G211Q | ++ |
| T022A-E089G-G097A-S101Q-S103A-V104I-P129S-L217Q-A232V-Q245R | ++ |
| V104I | ++ |
| T022A-S101A-S103G-V104I-A232L-Q245S | ++ |
| N043R-S101A-P210I-T213A | ++ |
| N043R-R045T-S101A-T213A | ++ |
| S078G-G118D-H120N-H249R | ++ |
| T022Q-S101T-S103N-V104I-A232L-Q245R-R275H | ++ |
| T022Y-S101A-S103A-V104I-A232T-Q245S | ++ |
| T022K-S101N-S103N-V104I-A232M-Q245R | ++ |
| T022R-S101T-S103N-V104L-A232V-Q245S | ++ |
| T022A-N076D-G097S-S101N-S103A-V104I-A232V-Q245R | ++ |
| M119L | ++ |
| A098F-S099A-S101G-V104I | ++ |
| S078D-G118S-Q245R | ++ |
| T022Y-S101N-S103A-V104I-A232L-Q245S | ++ |
| T022A-G097A-S101N-S103A-V104I-S128A-L217Q-A232V-Q245R | ++ |
| G020R-S078G-G118D-N248D-H249R | ++ |
| T022R-S101A-S103N-V104I-A232T-Q245S | ++ |
| T022R-S101G-S103N-V104I-A232L-Q245S | ++ |
| S024R-S078D-G118D-S188D-Q245R-H249R | ++ |
| S132H | ++ |
| A098Q-S099G-S101G-V104L | ++ |
| N043R-S101A-P210I-G211Q-T213A | ++ |
| T022Q-S101G-S103A-V104I-A232M-Q245W | ++ |
| T022A-S101Q-S103A-V104I-L126I-P129S-A232V-Q245R | ++ |
| T022K-S101I-S103G-V104I-A232M-Q245S | ++ |
| T022W-N043R-R045T-S101A-G211Q-T213A | ++ |
| T022Q-S101N-S103G-V104I-A232V-Q245W | ++ |
| D181T | ++ |
| G020R-S024R-S078D-G118S-P129E-G159D-Q245R-H249R | ++ |
| G020R-S024R-S078G-G118D-G159D-S188D-Q245R | ++ |
| T022A-S101T-S103N-V104L-A232L-Q245S | ++ |
| T022A-S101G-S103N-V104L-A232V-Q245S | ++ |
| T022A-S024G-G097A-S101N-S103A-V104I-S128A-L217Q-A232V-Q245R | ++ |
| T022A-S024G-N076D-S101N-S103A-V104I-S128A-A232V-Q245R | ++ |
| T022Y-S101T-S103A-V104L-A232M-Q245R | ++ |
| T022Q-S101T-S103N-V104L-A232T-Q245R | ++ |
| F050S | ++ |
| T022Y-S101G-S103N-V104I-A232V-Q245R | ++ |
| G020R-R045T-S101A-T213A | ++ |
| T022K-S101N-S103G-V104I-A232V-Q245W | ++ |
| S024R-S078G-G118D-P129E-G159D-Q245R-H249R | ++ |
| T022Q-S101T-S103N-V104I-A232M-Q245W | ++ |
| S049W | ++ |
| T022A-S101A-S103N-V104L-A232L-Q245R | ++ |
| T022A-N076D-S101G-S103A-V104I-I107V-P129G-A232V-Q245R-A270V | ++ |
| S099A-V104I | ++ |
| T022Q-S101A-S103G-V104I-A232V-Q245W | ++ |
| T022A-N076D-S101G-S103A-V104I-A232V-N238Y-Q245R | ++ |
| T022A-S101G-S103A-V104I-L124V-L217Q-A232V-Q245R | ++ |
| G020R-S024R-S078D-G118D-G159D-H249R | + |
| G020R-S024R-S078G-G118S-G159D-S188D-Q245R-N248D-H249R | + |
| T022A-S101T-S103G-V104I-A232T-Q245S | + |
| T022A-S101I-S103G-V104I-A232T-Q245R | + |
| T022Q-S101G-S103N-V104I-A232V-Q245W | + |

TABLE 2-4-continued

BMI cleaning performance of Group C1 variants.
PI = Performance Index
PI > or = 1.50 is +++; PI between 1.49 and 1.20 = ++; PI between 1.19
and 1.1 = + in Detergent Composition 106 as described in Table 1

| Sequence of GG36 Variants (BPN' numbering) | PI Relative to GG36; BMI assay, Detergent 106 at 25° C. |
|---|---|
| T022W-N043R-S101A-T213A | + |
| T022A-N076D-S078N-G097A-S101N-S103A-V104I-S128A-A232V-Q245R | + |
| T022A-S024G-S078N-S101Q-S103A-V104I-S128A-A232V-Q245R | + |
| T022K-S101N-S103N-V104L-A232T-Q245R | + |
| T022A-S024G-S101Q-S103A-V104I-S128A-A232V-Q245R | + |
| G020R-S024R-N062E-S078G-G118D | + |
| G020R-S078G-G118D | + |
| T022Y-S101T-S103G-V104L-A232T-Q245R | + |
| R010H-T022A-S101G-S103A-V104I-A232V-Q245R-A272V | + |
| T022A-S024R-S101G-S103A-V104I-P129E-A232V-Q245R-A270V-A272V | + |
| T022A-N076D-S078N-G097S-S101Q-S103A-V104I-Q109G-A232V-Q245R | + |
| G020R-S024R-S078D-G118S-P129E-Q245R | + |
| T022A-N076D-S101G-S103A-V104I-A232V-N238Y-Q245R-A272V | + |
| T022K-S101N-S103N-V104I-A232V-Q245W | + |
| T022Q-S101T-S103N-V104I-A232M-Q245S | + |
| T022A-S078N-S101N-S103A-V104I-Q109G-L217Q-A232V-G245R | + |
| W113Y | + |
| T022A-S101A-S103N-V104I-A232M-Q245S | + |
| T022A-S101Q-S103A-V104I-S128A-A232V-Q245R | + |
| G020R-S024R-S078G-G118D-G159D-S188D-H249R | + |
| T022A-S101N-S103G-V104I-A232T-Q245R | + |
| T022K-S101G-S103G-V104I-A232L-Q245R | + |
| T022A-N076D-G097A-S101Q-S103A-V104I-S128A-A232V-Q245R | + |
| T022Q-S101T-S103N-V104I-A232V-Q245S | + |
| T022A-S024F-S101G-S103A-V104I-N116L-Y209V-T213A-A232V | + |
| T022A-S101N-S103G-V104L-A232T-Q245R | + |
| T022A-S024G-S101G-S103A-V104I-P129E-A232V-N238Y-Q245R | + |
| T022A-N076D-G097S-S101Q-S103A-V104I-A232V-Q245R | + |
| T022A-N076D-S078N-G097A-S101N-S103A-V104I-A232V-Q245R | + |
| T022A-S101N-S103A-V104I-Q109G-S128A-A232V-Q245R | + |
| S259W | + |
| A016S-T022A-S024F-S101G-S103A-V104I-N116A-Y209V-G211Q-A232V | + |
| T022W-S101A-P210I-G211Q-T213A | + |
| T022A-S024G-N076D-G097S-S101N-S103A-V104I-A232V-Q245R | + |
| V028T-A215V | + |
| S024R-S078D-G118S-S188D-Q245R | + |
| T022Q-S101T-S103A-V104I-A232V-Q245W | + |
| T022A-S101N-S103A-V104I-Q109G-L217Q-A232V-Q245R | + |
| T022A-S024G-T071A-G097S-S101Q-S103A-V104I-S128A-A232V-Q245R | + |
| H120P | + |
| G020R-S024R-N062E-S078D-G118D-Q245R | + |
| T022A-N076D-S101Q-S103A-V104I-A232V-Q245R | + |
| T022Q-S101A-S103N-V104I-A232L-Q245W | + |
| T022Q-S101N-S103A-V104L-A232T-Q245R | + |
| T022W-S024R-N043R-R045T-S101A-N116L-P210I-G211Q | + |
| T022A-G097S-S101Q-S103A-V104I-S128A-L217Q-A232V-Q245R | + |
| G020R-S078G-G118S-G159D-S188D-H249R | + |
| A013S | + |
| A232N | + |
| T022A-N076D-S101G-S103A-V104I-A232V-Q245R | + |
| T022A-S024G-N076D-S078N-G097S-S101N-S103A-V104I-A232V-Q245R | + |
| I035T | + |
| V051M | + |
| N123A | + |
| G020R-S078G-G118S-G159D-Q245R-N248D | + |
| T022Y-S101A-S103N-V104I-A232L-Q245W | + |
| T022A-S024R-S101G-S103A-V104I-P129E-A232V-Q245R-A270V | + |
| G020R-S078D-G118S | + |
| T022R-S101N-S103N-V104L-A232M-Q245W | + |
| T022A-S024G-N076D-G097S-S101G-S103A-V104I-S128A-L217Q-A232V-Q245R | + |
| T022A-S101G-S103N-V104L-A232V-Q245R | + |
| T022A-N076D-G097A-S101Q-S103A-V104I-A232V-Q245R | + |
| T022A-S024R-N076D-S101G-S103A-V104I-I107V-P129E-A232V-Q245R | + |

TABLE 2-4-continued

BMI cleaning performance of Group C1 variants.
PI = Performance Index
PI > or = 1.50 is +++; PI between 1.49 and 1.20 = ++; PI between 1.19
and 1.1 = + in Detergent Composition 106 as described in Table 1

| Sequence of GG36 Variants (BPN' numbering) | PI Relative to GG36; BMI assay, Detergent 106 at 25° C. |
|---|---|
| S024R-R045T-S101A-P210I-G211Q | + |
| T022A-S078N-S101N-S103A-V104I-Q109N-S128A-A232V-Q245R | + |
| T022A-S024G-S078N-G097A-S101N-S103A-V104I-Q109N-A232V-Q245R | + |
| G020R-S024R-S078G-G118D-P129E-G159D-H249R | + |
| G020R-S078G-G118D-P129E-S188D-Q245R-H249R | + |
| P014W | + |
| G020R-S024R-S078G-G118S-G159D-S188D-Q245R-N248D | + |
| T022R-S101G-S103N-V104I-A232M-Q245W | + |
| T022R-A098V-S101G-S103N-V104L-A232T-Q245R | + |
| T022A-S101T-S103A-V104I-A232V-Q245W | + |
| G020R-T022W-R045T-S101A-T213A | + |
| N043R-R045T-S101A | + |
| T022K-S101N-S103A-V104I-A232V-Q245R | + |
| T022K-S101I-S103N-V104I-A232L-Q245S | + |
| S056V | + |
| G020R-T022W-R045I-S101A-G211Q | + |
| G020R-S024R-S078D-G118D-Q245R-N248D | + |
| G020R-S024R-S078D-G118S-G159D-V244L-Q245R-N248D | + |
| T022A-G097A-S101Q-S103A-V104I-Q109G-S128A-A232V-Q245R | + |
| T022A-N076D-G097S-S101G-S103A-V104I-A232V-Q245R | + |
| G020R-T022W-R045T-S101A-N116L-P210I | + |
| T022Q-S101N-S103N-V104I-A232M-Q245S | + |
| T022Y-S101G-S103N-V104I-A232V-Q245W | + |
| A114V | + |
| S141C | + |
| T022A-N076D-S078N-S101N-S103A-V104I-A232V-Q245R | + |
| S056H | + |
| S078D-G118D-Q245R | + |
| S024R-N043R-R045T-S101A-T213A | + |
| T022Y-S101T-S103G-V104I-A232V-Q245S | + |
| T022A-S024G-G097S-S101Q-S103A-V104I-S128A-L217Q-A232V-Q245R | + |
| N269W | + |
| S078G-G118S-G159D-Q245R-N248D-H249R | + |
| T022W-S024R-R045T-S101A | + |
| T022A-S024R-S101G-S103A-V104I-P129E-A232V-N238Y-Q245R-A270V-A272V | + |
| T022A-S024R-S101G-S103A-V104I-P129E-A232V-Q245R | + |
| T022A-S024R-N076D-S101G-S103A-V104I-I107V-P129E-A232V-N238Y-Q245R-A270V-A272V | + |
| A122F | + |
| S024R-S078D-G118S-P129E-G159D-Q245R-H249R | + |
| S099G | + |
| T022K-S101T-S103G-V104I-A232V-Q245S | + |
| S009G-T022A-S078N-S101Q-S103A-V104I-Q109G-S128A-L217Q-A232V-Q245R | + |
| A098Q | + |
| T022A-S101N-S103A-V104L-A232L-Q245R | + |
| T022A-S101A-S103N-V104I-A232T-Q245W | + |
| T022A-S024G-N076D-G097A-S101N-S103A-V104I-A232V-Q245R | + |
| S024R-S078G-G118D-G159D-H249R | + |
| T022A-S024G-N076D-G097S-S101N-S103A-V104I-S128A-A232V-Q245R | + |
| T022A-S024G-N076D-S078N-S101Q-S103A-V104I-S128A-A232V-Q245R | + |
| T022A-S101Q-S103A-V104I-L124V-S128A-P129S-A232V-Q245R | + |
| T022R-S101N-S103A-V104I-A232M-W241R-Q245W | + |
| R045T-S101A-P210I-G211Q | + |
| G020R-S024R-S078G-G118S-P129E-Q245V-N248E | + |
| T022Q-S101T-S103N-V104I-A232L-Q245W | + |
| T022A-S024G-S078N-S101N-S103A-V104I-Q109G-L217Q-A232V-Q245R | + |
| T022A-S024G-G097A-S101N-S103A-V104I-L217Q-A223S-A232V-Q245R | + |
| T022K-S101T-S103A-V104I-A232T-Q245W | + |
| N043R-S101A-G211Q | + |
| T022A-S101G-S103A-V104I-Q109N-S128A-A232V-Q245R | + |
| T022A-G097A-S101G-S103A-V104I-S128A-L217Q-A232V-Q245R | + |
| G020R-S078G-G118S-P129E-H249R | + |
| S024R-S078G-G118S-G159D-S188D-Q245R | + |

TABLE 2-4-continued

BMI cleaning performance of Group C1 variants.
PI = Performance Index
PI > or = 1.50 is +++; PI between 1.49 and 1.20 = ++; PI between 1.19
and 1.1 = +in Detergent Composition 106 as described in Table 1

| Sequence of GG36 Variants (BPN' numbering) | PI Relative to GG36; BMI assay, Detergent 106 at 25° C. |
|---|---|
| N043R-R045T-S101A-N204S-P210I-T213A | + |
| T022R-S101N-S103A-V104L-A232V-Q245S | + |
| T022R-S101N-S103G-V104I-A232V-Q245S | + |
| T022K-S101T-S103N-V104I-A232M-Q245S | + |
| T022A-N076D-S101N-S103A-V104I-L217Q-A232V-Q245R | + |
| T022A-S024G-N076D-S078N-S101N-S103A-V104I-Q109G-S128A-A232V-Q245R | + |
| G020R-T022W-R045T-S101A-P210I-T213A | + |
| T022A-N076D-G097A-S101G-S103A-V104I-L217Q-A232V-Q245R | + |
| T022W-S101A-P210I | + |
| T022A-G097A-S101N-S103A-V104I-L126I-P129S-A232V-Q245R | + |
| T022A-S078D-S101N-S103A-V104I-S128A-A232V-Q245R | + |
| Q236L | + |
| T022Y-S101T-S103N-V104I-A232V-Q245S | + |
| A200D | + |
| G020R-S078G-G118S-S188D-H249R | + |
| T022A-S101G-S103N-V104I-A232T-Q245W | + |
| T022A-S024G-N076D-G097A-S101N-S103A-V104I-S128A-A232V-Q245R | + |
| G157I | + |
| G020R-S024R-S078G-G118S-P129E-G159D-S188D-Q245R | + |
| T022Y-S101A-S103G-V104L-A232T-Q245R | + |
| S024R-S078G-G118D-H249R | + |
| T022Q-S101A-S103L-V104L-A232T-Q245S | + |
| T022Y-S101A-S103N-V104I-A232T-Q245W | + |
| T022A-S024G-S101N-S103A-V104I-Q109N-L217Q-A232V-Q245R | + |
| T022A-S101G-S103N-V104I-A232M-Q245S | + |
| T022A-S024G-N076D-S078N-S101G-S103A-V104I-S128A-A232V-Q245R | + |
| T022A-S101G-S103N-V104I-A232M-Q245W | + |
| I008N | + |
| T022A-S101N-S103G-V104I-A232M-Q245S | + |
| V026A | + |
| T022R-S101N-S103A-V104I-A232T-Q245W | + |
| T022A-S101A-S103N-V104I-A232L-Q245S | + |
| T022A-S101N-S103A-V104I-A232T-Q245R | + |
| N043R-R045T-S101A-P210I-G211Q-T213A | + |
| T022A-S024G-N076D-G097A-S101Q-S103A-V104I-S128A-A232V-Q245R | + |
| A098F-S099T-S101A | + |
| A098F-S099T-S101G-V104L | + |
| P014N | + |
| A098Q-S103G-V104I | + |
| S099T-S103A-V104I | + |
| S087W | + |
| S024R-N062E-S078G-G118S-H249R | + |
| S024R-N043R-R045T-S101A-G211Q | + |
| N043R-R045T-S101A-G211Q | + |
| G020R-S078G-G118S-N248D | + |
| T022Q-S101N-S103N-V104I-A232T-Q245W | + |
| S078D-G118S-P129E-Q245R-H249R | + |
| T022Q-S101T-S103G-V104I-A232T-Q245S | + |
| T022A-S024G-S101N-S103A-V104I-Q109N-S128A-A232V-Q245R | + |
| S024F-S101G-S103A-V104I-N116L-Y209A-T213A-A232V | + |
| S101A-N116L-P210I-T213A | + |
| T022R-S101N-S103N-V104L-A232L-Q245S | + |
| B015T | + |
| S099T | + |
| T022A-S101G-S103A-V104I-L124V-A232V-Q245R | + |
| G020R-S024R-S078D-G118D-G159D-Q245R | + |
| A114I | + |
| S212A | + |
| T022A-S101T-S103N-V104I-A232L-Q245S | + |
| T022A-S024G-S078N-G097S-S101N-S103A-V104I-S128A-T143I-L217Q-A232V-Q245R | + |
| S024R-S078G-G118S-G159D-S188D-Q245R-H249R | + |
| T022K-S101A-S103N-V104L-A232L-Q245S | + |
| T022W-S101A-T213A | + |
| T022A-N076D-S078N-G097S-S101Q-S103A-V104I-A232V-Q245R | + |
| S132V | + |
| S024R-S078G-G118D-S188D-Q245R-N248D-H249R | + |

TABLE 2-4-continued

BMI cleaning performance of Group C1 variants.
PI = Performance Index
PI > or = 1.50 is +++; PI between 1.49 and 1.20 = ++; PI between 1.19
and 1.1 = +in Detergent Composition 106 as described in Table 1

| Sequence of GG36 Variants (BPN' numbering) | PI Relative to GG36; BMI assay, Detergent 106 at 25° C. |
|---|---|
| A098Q-S101A-S103A-V104L | + |
| A098Q-S099T-S103A | + |
| T022R-S101T-S103N-V104L-A232T-Q245W | + |
| T022A-N076D-S101Q-S103A-V104I-S128A-A232V-Q245R | + |
| V051A-S101A-P210I-T213A | + |
| A098Q-S099T-S101A-V104L | + |
| T022R-S101N-S103N-V104I-A232M-Q245W | + |
| S099A-S101A-S103A | + |
| G020R-S078G-G118D-S188D-Q245R | + |
| G020R-S024R-S078D-G118S-P129E-G159D-S188D-Q245R-H249R | + |
| T022A-N076D-S078N-G097A-S101Q-S103A-V104I-L217Q-A232V-Q245R | + |
| S024R-S078G-G118D | + |
| T022Q-S101N-S103N-V104L-A232M-Q245R | + |
| T022A-S101T-S103G-V104I-A232M-Q245S | + |
| A048G | + |
| T022Q-S099G-S101A-S103N-V104I-A232V-Q245R | + |
| S024R-R045T-S101A-G211Q-T213A | + |
| S024R-R045T-S101A-I107V-A114T-N116L-P210I-G211Q-T213A | + |
| T022R-S101T-S103G-V104I-A232L-Q245S | + |
| S099G-S103A | + |
| A098F-S099A | + |
| T022R-S101N-S103G-V104I-A232V-Q245W | + |
| T022A-S103A-V104I-L124T-A232V-Q245R | + |
| T022A-S024F-S101G-S103A-V104I-N116L-Y209V-A232V | + |
| T022K-S101N-S103N-V104I-A232V-Q245S | + |
| T022K-S101A-S103A-V104L-A232M-Q245R | + |
| T022Q-S101G-S103N-V104I-A232T-Q245W | + |
| T022A-S101T-S103A-V104L-A232T-Q245W | + |
| T022A-S101N-S103N-V104I-A232V-Q245S | + |
| T022A-N076D-S078N-G097A-S101N-S103A-V104I-L217Q-A232V-Q245R | + |
| A098M | + |
| T022A-S101G-S103G-V104I-A232L-Q245R | + |
| G020R-S101A-S207G-P210I-T213A | + |
| T022A-S024G-G097A-S101Q-S103A-V104I-Q109G-S128A-A232V-Q245R | + |
| G020R-S024R-S078G-G118S-G159D-Q245R-N248D-H249R | + |
| G020R-S024R-S078D-G118S-P129E-G159D-Q245R | + |
| T022Y-S101G-S103N-V104I-A232L-Q245S | + |
| V026Q | + |
| S240G | + |
| G020R-S024R-S078G-G118S-S188D | + |
| G020R-S024R-S078G-G118D-N238D-N248D | + |
| T022R-S101G-S103A-V104I-A232T-Q245S | + |
| T022W-S024R-R045T-S101A-P210I-G211Q | + |
| T022A-S024G-N076D-S078N-G097S-S101Q-S103A-V104I-A232V-Q245R | + |
| T022W-S024R-R045T-S101A-T213A | + |
| A200F | + |
| T022R-S101T-S103G-V104L-A232T-Q245S | + |
| T022A-S078N-G097S-S101Q-S103A-V104I-Q109N-L217Q-A232V-Q245R | + |
| T022A-S101G-S103N-V104I-A232T-Q245S | + |
| T022A-S101T-S103N-V104L-A232T-Q245S | + |
| T022A-S101A-S103A-V104L-A232V-Q245S | + |
| S099G-S101A-V104L | + |
| H017R-T022A-S024V-N076D-G097S-S101N-S103A-V104I-Q109N-S128A-A232V-Q245R | + |
| T022A-S101A-S103N-V104L-A232M-Q245S | + |
| T022A-S101Q-S103A-V104I-Q109G-L217Q-A232V-Q245R | + |
| T022A-S024G-N076D-S101Q-S103A-V104I-S128A-A232V-Q245R | + |
| T022A-S024G-S078N-G097S-S101N-S103A-V104I-S128A-S212P-L217Q-A232V-Q245R | + |
| S056L | + |
| T253L | + |
| T022W-R045T-S101A-G211Q-T213A | + |
| T022A-G097A-S101Q-S103A-V104I-S128A-L217Q-A232V-Q245R | + |
| T022A-S024G-N076D-S078N-G097A-S101N-S103A-V104I-S128A-A232V-Q245R | + |
| G020R-T022W-R045T-S101A-G211Q-T213A | + |

TABLE 2-4-continued

BMI cleaning performance of Group C1 variants.
PI = Performance Index
PI > or = 1.50 is +++; PI between 1.49 and 1.20 = ++; PI between 1.19
and 1.1 = +in Detergent Composition 106 as described in Table 1

| Sequence of GG36 Variants (BPN' numbering) | PI Relative to GG36; BMI assay, Detergent 106 at 25° C. |
|---|---|
| S101A-G211Q | + |
| N123D | + |
| T022R-S101A-S103N-V104I-A232M-Q245W | + |
| T022Y-S101T-S103N-V104L-A232T-Q245R | + |
| T022A-S101G-S103A-V104I-N116L-Y209V-G211Q-T213A-A232V | + |
| G020R-S024R-S078D-G118D-N248D | + |
| A098Q-S099G-S101A | + |
| S099T-V104I | + |
| T022Q-S101G-S103A-V104I-A232V-Q245S | + |
| T022R-S101A-S103G-V104I-A232T-Q245S | + |
| T022K-S101T-S103N-V104I-A232T-Q245W | + |
| A016M | + |
| T022A-S024G-N076D-S101N-S103A-V104I-Q109G-A232V-Q245R | + |
| T022K-S101N-S103N-V104I-A232T-Q245S | + |
| G020R-N043R-R045T-S101A-N204D-P210I-G211Q | + |
| T022A-S101T-S103N-V104I-A232V-Q245S | + |
| T022Y-S101G-S103N-V104L-A232V-Q245R | + |
| T022A-S101T-S103N-V104I-A232V-Q245W | + |
| T022A-S024G-S078N-G097S-S101N-S103A-V104I-Q109G-L217Q-A232V-Q245R | + |
| A088T | + |
| T022Y-S101A-S103A-V104I-A232M-Q245S | + |
| T022W-S024R-R045T-S101A-N116L-P210I-G211Q | + |
| T022W-N043R-R045T-S101A-P210I-G211Q-T213A | + |
| T038A | + |
| S078D-G118S-G159D-Q245R | + |
| T022K-S101T-S103A-V104L-A232V-Q245W | + |
| T022A-S024G-N076D-S078N-G097S-S101N-S103A-V104I-Q109G-A232V-Q245R | + |
| T022A-S078N-S101Q-S103A-V104I-Q109N-L217Q-A232V-Q245R | + |
| G025S | + |
| G025T | + |
| A016S-S101G-S103A-V104I-N116L-M119V-Y209V-G211Q-A232V | + |
| T022A-N076D-V084A-S101G-S103A-V104I-A232V-Q245R | + |
| V011L | + |
| T022Y-S101T-S103G-V104I-A232M-Q245S | + |
| T022R-S101N-S103A-V104L-A232T-Q245S | + |
| S240V | + |
| G020R-S024R-S078G-G118D-P129E-S188D-H249R | + |
| T022W-S024R-R045T-S101A-G211Q-T213A | + |
| T022A-S024G-N076D-G097A-S101Q-S103A-V104I-Q109G-A232V-Q245R | + |
| V004Y | + |
| V051A | + |
| G195W-N269E | + |
| S024R-S078G-G118D-N248D-H249R | + |
| T022A-S099G-S101T-S103G-V104I-A232V-Q245S | + |
| T022Q-S101T-S103G-V104I-A232L-Q245W | + |
| T022Q-S101N-S103N-V104I-A232V-Q245W | + |
| T022A-S101T-S103G-V104I-A232V-Q245W | + |
| T022K-S101N-S103G-V104I-A232V-Q245R | + |
| T022Q-S101G-S103N-V104I-A232V-Q245S | + |

TABLE 2-5

BMI cleaning performance of Group C2 variants.

| Sequence of GG36 Variants (BPN' numbering) | PI Relative to GG36; BMI assay, Detergent 107 at 25° C. |
|---|---|
| G020R-S024R-S078N-G097A-S101A-Q109N-N116L-L217Q | +++ |
| T022R-S024F-S101G-S103A-V104I-A232V-Q245R-E271H | +++ |
| G020R-S024R-S078N-G097S-S101Q-S128A-L217Q | +++ |
| T022R-S101G-S103A-V104I-A232V-Q245R-E271H | +++ |
| G020R-S024R-S101G-N116L-S128A | +++ |
| G020R-S024R-S101A-Q109N-N116L-S128A | +++ |
| T022R-S024F-S101G-S103A-V104I-A232V-Q245R-T260M | +++ |

TABLE 2-5-continued

BMI cleaning performance of Group C2 variants.

| Sequence of GG36 Variants (BPN' numbering) | PI Relative to GG36; BMI assay, Detergent 107 at 25° C. |
|---|---|
| G020R-S024R-S078N-S101N-N116L-S128A | +++ |
| G020R-S024R-G097A-S101A-Q109G-N116L | +++ |
| G020R-S024R-S101N-S128A | +++ |
| G020R-S024R-S078N-S101G-S128A-L217Q | +++ |
| T022R-S024F-S101G-S103A-V104I-A232V-Q245R | +++ |
| T022R-S078N-G097S-S101Q-S103A-V104I-Q109N-N116L-A232V-Q245R | +++ |
| G020R-S024R-G097A-S101A-Q109N-N116L-S128A | +++ |
| G020R-S024R-G097S-S101N-Q109N-S128A | +++ |
| T022R-S101G-S103A-V104I-A232V-P239G-Q245R | +++ |
| G020R-S024R-G097S-S101A-S128A | +++ |
| G020R-S024R-S101G-Q109N-N116L-A215V | +++ |
| G020R-S024R-S078N-G097S-S101Q-Q109G-N116L-S128A | +++ |
| G020R-S024R-S078N-G097S-S101N-Q109N | +++ |
| G020R-S024R-S101G-S128A | +++ |
| T022R-S101G-S103A-V104I-A232V-Q245R-T260K-L267N | +++ |
| T022R-S101G-S103A-V104I-S128A-A232V-Q245R | +++ |
| T022R-S024G-G097S-S101N-S103A-V104I-A232V-Q245R | +++ |
| T022R-S024F-S101G-S103A-V104I-V121F-A232V-Q245R | +++ |
| G020R-S024R-G097A-S101Q-N116L-S128A-L217Q | +++ |
| T022R-S101G-S103A-V104I-A232V-Q245R | +++ |
| T022R-G097A-S101N-S103A-V104I-N116L-A232V-Q245R | +++ |
| G020R-S024R-S078N-G097S-S101A-N116L-S128A | +++ |
| G020R-S024R-G097A-S101G-S128A-L217Q | +++ |
| T022R-S078N-S101G-S103A-V104I-N116L-A232V-Q245R | +++ |
| G020R-S024G-N043R-S078N-S101Q-Q109G-N116L-S128A-Q206R-L217Q | +++ |
| G020R-S024R-S078N-G097S-S101Q-N116L-S128A | +++ |
| G020R-S024R-S078N-G097S-S101N-Q109N-N116L-S128A | +++ |
| G020R-S024R-S101N-Q109G-N116L | +++ |
| G020R-S024R-S101Q-N116L-S128A-L217Q | +++ |
| G020R-N043R-S078N-S101G-Q109G-N116L | +++ |
| G020R-S024G-N043R-S078N-G097S-S101G-S128A | +++ |
| T022R-S024G-S078N-S101N-S103A-V104I-S128A-A232V-Q245R | +++ |
| T022R-S024G-G097A-S101Q-S103A-V104I-Q109G-N116L-S128A-A232V-Q245R | +++ |
| T022R-S101G-S103A-V104I-A232V-P239G-Q245R-E271I | +++ |
| G020R-S024R-S101Q-S128A | +++ |
| G020R-S024R-G097A-S101N-Q109G-N116L | +++ |
| G020R-S024G-N043R-S078N-G097A-S101G-Q109G-N116L | +++ |
| G020R-S024R-G097S-S101Q-Q109N-N116L-L217Q | +++ |
| T022R-S024G-S078N-G097A-S101Q-S103A-V104I-A232V-Q245R | +++ |
| G020R-S024R-G097A-S101G-Q109N-S128A | +++ |
| G020R-S024R-G097S-S101A-Q109N-S128A | +++ |
| T022R-G097S-S101Q-S103A-V104I-Q109G-A232V-Q245R | +++ |
| G020R-S024R-S078N-G097A-S101N-S128A-L217Q | +++ |
| G020R-S024G-N043R-S078N-G097S-S101G-N116L | +++ |
| G020R-S024R-S078N-G097S-S101G-Q109N-N116L-L217Q | +++ |
| T022R-S024G-S078N-S101N-S103A-V104I-Q109N-N116L-S128A-A232V-Q245R | +++ |
| G020R-S024R-S078N-G097S-S101A-Q109N-S128A-L217Q | +++ |
| G020R-S024R-S078N-G097A-S101G-Q109N-N116L-L217Q | +++ |
| G020R-S024G-N043R-S078N-S101Q | +++ |
| G020R-S024R-S078N-G097A-S101Q-Q109G-N116L | +++ |
| G020R-N043R-G097A-S101N-N116L-S128A | +++ |
| G020R-S024R-S078N-S101G-Q109G-N116L-S128A-L217Q | +++ |
| G020R-S024R-S078N-S101Q-Q109G-N116L-S128A-L217Q | +++ |
| G020R-S024R-S078N-G097S-S101G-Q109N-N116L-S128A | +++ |
| G020R-S024R-S078N-G097S-S101N-Q109N-N116L | +++ |
| T022R-S101N-S103A-V104I-Q109N-N116L-S128A-A232V-Q245R | +++ |
| T022R-S024G-G097S-S101G-S103A-V104I-Q109G-N116L-S128A-A232V-Q245R | +++ |
| T022R-S024G-S078N-S101G-S103A-V104I-N116L-S128A-A232V-Q245R | +++ |
| G020R-S024R-S078N-S101N-Q109N-N116L | +++ |
| G020R-S024R-S078N-S101A-Q109N-N116L-S128A | +++ |
| T022R-S024G-G097A-S101Q-S103A-V104I-N116L-S128A-A232V-Q245R | +++ |
| T022R-G097S-S101G-S103A-V104I-S128A-A232V-Q245R | +++ |
| T022R-G097A-S101Q-S103A-V104I-S128A-A232V-Q245R | +++ |
| T022R-S024G-S078N-G097S-S101Q-S103A-V104I-S128A-A232V-Q245R | +++ |
| T022R-S078N-G097A-S101Q-S103A-V104I-N116L-S128A-A232V-Q245R | +++ |

TABLE 2-5-continued

BMI cleaning performance of Group C2 variants.

| Sequence of GG36 Variants (BPN' numbering) | PI Relative to GG36; BMI assay, Detergent 107 at 25° C. |
|---|---|
| G020R-S024R-S101G-Q109G-N116L-L217Q | +++ |
| G020R-S024R-S078N-S101Q-Q109N-N116L | +++ |
| G020R-S024R-S101G-N116L-S128A-L217Q | +++ |
| G020R-S024R-S101A-Q109G-N116L-S128A | +++ |
| T022R-S024G-S078N-G097A-S101G-S103A-V104I-N116L-L217Q-A232V-Q245R | +++ |
| T022R-S024G-S078N-G097S-S101Q-S103A-V104I-Q109G-N116L-S128A-A232V-Q245R | +++ |
| G020R-N043R-G097A-S101N-S128A-L233I | +++ |
| T022R-S101Q-S103A-V104I-A232V-Q245R | +++ |
| G020R-N043R-G097S-S101Q-Q109G-N116L-S128A | +++ |
| T022R-S078N-S101Q-S103A-V104I-A232V-Q245R | +++ |
| G020R-S024R-G097S-S101N-Q109G-N116L | +++ |
| T022R-S078N-G097S-S101G-S103A-V104I-S128A-A232V-Q245R | +++ |
| T022R-S024G-S101N-S103A-V104I-A232V-Q245R | +++ |
| G020R-S024R-G097A-S101N-Q109G-S128A | +++ |
| G020R-N043R-S101Q-N116L-S128A-L217Q | +++ |
| G020R-S024R-S078N-G097A-S101Q-Q109N-S128A | +++ |
| G020R-S024R-E089D-S101A-Q109N-N116L | +++ |
| G020R-S024R-G097A-S101G-Q109G-S128A | +++ |
| G020R-S024G-N043R-S101G-N116L-S128A-L217Q | +++ |
| G020R-N043R-S078N-S101Q-Q109G-L217Q | +++ |
| G020R-S024G-N043R-G097A-S101N-Q109N-N116L-L217Q | +++ |
| G020R-S024R-S078N-G097A-S101G-N116L-S128A | +++ |
| G020R-S024R-G097S-S101A-Q109N-N116L | +++ |
| G020R-S024R-S078N-S101A-Q109G-S128A | +++ |
| G020R-S024R-G097A-S101A-Q109G-N116L-S128A | +++ |
| G020R-N043R-G097A-S101Q-N116L-S128A | +++ |
| G020R-N043R-G097S-S101Q-S128A-L217Q | +++ |
| G020R-S024R-S078N-G097A-S101G-Q109G-N116L-L217Q | +++ |
| G020R-N043R-G097A-S101G-Q109N-N116L-S128A | +++ |
| G020R-N043R-S078N-G097S-S101N-Q109N-L217Q | +++ |
| G020R-S024R-G097S-A098E-S101A-N116L-S128A | +++ |
| G020R-S024R-S078N-G097S-S101A-Q109G-S128A | +++ |
| T022R-S024G-S078N-G097S-S101G-S103A-V104I-Q109N-N116L-L217Q-A232V-Q245R | +++ |
| G020R-S024R-S078N-G097A-S101Q-Q109N-N116L-L217Q | +++ |
| T022R-S024G-G097S-S101Q-S103A-V104I-S128A-A232V-Q245R | +++ |
| G020R-S024R-S101A-Q109N-N116L-S128A-L217Q | +++ |
| G020R-S024R-S101G-Q109G-N116L-S128A-L217Q | +++ |
| T022R-S078N-G097A-S101N-S103A-V104I-S128A-A232V-Q245R | +++ |
| G020R-S024G-N043R-S101N-N116L-S128A-L217Q | +++ |
| G020R-S024R-S078N-G097S-S101A-Q109N-N116L | +++ |
| G020R-S024R-S078N-G097A-S101N-Q109N-N116L-S128A | +++ |
| G020R-S024R-S078N-S101Q-Q109N-N116L-L217Q | +++ |
| T022R-S024G-S078N-S101N-S103A-V104I-N116L-S128A-A232V-Q245R | +++ |
| G020R-N043R-S101G-Q109N-N116L-S128A-L217Q | +++ |
| T022R-S101N-S103A-V104I-L217Q-A232V-Q245R | +++ |
| T022R-G097A-S101N-S103A-V104I-N116L-S128A-A232V-Q245R | +++ |
| G020R-S024R-G097A-S101A-S128A-L217Q | +++ |
| T022R-S024G-S078N-G097A-S101N-S103A-V104I-S128A-L217Q-A232V-Q245R | +++ |
| G020R-S024R-S078N-G097S-S101N-Q109G-N116L-S128A-L217Q | +++ |
| T022R-S024G-S101G-S103A-V104I-N116L-L217Q-A232V-Q245R | +++ |
| T022R-G097A-S101Q-S103A-V104I-N116L-S128A-A232V-Q245R | +++ |
| G020R-N043R-S101Q-S128A-L217Q | +++ |
| G020R-S024R-S078N-S101N-Q109G-S128A-L217Q | +++ |
| G020R-S024R-S078N-G097A-S101N-Q109N-N116L-S128A-L217Q | +++ |
| T022R-S024G-G097A-S101Q-S103A-V104I-N116L-L217Q-A232V-Q245R | +++ |
| G020R-S024R-S078N-G097S-S101G-S128A-N204S-L217Q | +++ |
| T022R-S024G-S078N-S101Q-S103A-V104I-N116L-S128A-A232V-Q245R | +++ |
| G020R-S024R-S078N-G097S-S101Q-Q109N-N116L-L217Q | +++ |
| G020R-S024R-S078N-S099G-S101Q-Q109N-N116L-L217Q | +++ |
| T022R-S024G-G097A-S101G-S103A-V104I-Q109G-N116L-L217Q-A232V-Q245R | +++ |
| T022R-S078N-G097A-S101Q-S103A-V104I-S128A-L217Q-A232V-Q245R | +++ |
| T022R-G097A-S101G-S103A-V104I-Q109G-N116L-L217Q-A232V-Q245R | +++ |
| G020R-S024R-G097A-S101N-Q109N-S128A-L217Q | +++ |
| T022R-G097S-S101N-S103A-V104I-S128A-L217Q-A232V-Q245R | +++ |

TABLE 2-5-continued

BMI cleaning performance of Group C2 variants.

| Sequence of GG36 Variants (BPN' numbering) | PI Relative to GG36; BMI assay, Detergent 107 at 25° C. |
|---|---|
| G020R-S024R-K094R-S101N-N116L-S128A-L217Q | +++ |
| T022R-S024G-S078N-G097A-S101G-S103A-V104I-N116L-S128A-L217Q-A232V-Q245R | +++ |
| G020R-S024R-G097A-S101A-N116L-S128A-L217Q | +++ |
| G020R-S024R-S078N-G097W-S101Q-Q109N-N116L-L217Q | +++ |
| T022R-G097S-S101N-S103A-V104I-N116L-S128A-L217Q-A232V-Q245R | +++ |
| T022R-S101Q-S103A-V104I-N116L-L217Q-A232V-Q245R | +++ |
| T022R-S024G-S078N-G097A-S101Q-S103A-V104I-N116L-S128A-L217Q-A232V-Q245R | +++ |
| T022R-S078N-G097A-S101Q-S103A-V104I-Q109N-N116L-S128A-L217Q-A232V-Q245R | +++ |
| G020R-N043R-G097S-S101Q-Q109G-N116L-S128A-L217Q | +++ |
| T022R-S024G-G097A-S101G-S103A-V104I-N116L-S128A-L217Q-A232V-Q245R | +++ |
| T022R-G097S-S101G-S103A-V104I-L217Q-A232V-Q245R | +++ |
| T022R-S024G-G097A-S101Q-S103A-V104I-Q109G-N116L-L217Q-A232V-Q245R | +++ |
| T022R-S024G-S078N-G097A-S101Q-S103A-V104I-S128A-L217Q-A232V-Q245R | +++ |
| T022R-S101Q-S103A-V104I-Q109G-N116L-S128A-L217Q-A232V-Q245R | +++ |
| T022R-S078N-G097S-S101G-S103A-V104I-N116L-S128A-L217Q-A232V-Q245R | +++ |
| T022R-S024G-T071A-S078N-S101N-S103A-V104I-Q109N-N116L-S128A-A232V-Q245R | +++ |
| T022R-S024G-G097A-S101Q-S103A-V104I-N116L-S128A-L217Q-A232V-Q245R | +++ |
| T022R-S101G-S103A-V104I-Q109N-S128A-A232V-Q245R | +++ |
| T022R-S024G-G097S-S101G-S103A-V104I-S128A-L217Q-A232V-Q245R | +++ |
| T022R-S024G-S078N-S101Q-S103A-V104I-Q109N-N116L-S128A-L217Q-A232V-Q245R | +++ |
| T022R-G097S-S101Q-S103A-V104I-S128A-L217Q-A232V-Q245R | ++ |
| T022R-G097A-S101Q-S103A-V104I-Q109N-S128A-A232V-Q245R | ++ |
| R010A-T022R-S024F-S101G-S103A-V104I-A232V-Q245R-L267N-E271H | ++ |
| G020R-S024G-N043R-S078N-S101G-Q109N-N116L-L217Q-M222S | ++ |
| T022R-S078N-G097S-S101G-S103A-V104I-Q109G-S128A-A232V-Q245R | + |
| T022R-S101G-S103A-V104I-M222S-A232V-Q245R-E271H | + |
| G020R-S024R-S101N-Q109G-N116L-M222S | + |

PI = Performance Index
PI > or = 1.50 is +++; PI between 1.49 and 1.20 = ++; PI between 1.19 and 1.1 = + in Detergent Composition 107 as described in Table 1

TABLE 2-6

BMI cleaning performance of Group C3 variants.

| Sequence of GG36 Variants (BPN' numbering) | PI Relative to GG36; BMI assay, Detergent 107 at 25° C. |
|---|---|
| T022R-S101G-S103A-A232V-Q245R | +++ |
| T022R-S101G-S103A-V104I-A232V-Q245R-E271A | +++ |
| T022R-S103A-V104I-A232V-Q245R | +++ |
| T022R-S101G-V104I-A232V-Q245R | +++ |
| T022R-S101G-S103A-V104I-Q245R | +++ |
| G020R-N043R-E271A | +++ |
| G020R-S024R-I035T-S101A-N116L | +++ |
| G020R-N043R-P239G | +++ |
| G020R-N043R-S242L | +++ |
| G020R-N043R-V234F | +++ |
| G020R-N043R-E271H | ++ |
| G020R-N043R-E271I | ++ |
| G020R-S024R-S101A-N116L-N269I | ++ |
| T022R-S101G-S103A-V104I-A232V-Q245R-E271F | ++ |
| G020R-N043R-E271F | ++ |
| G020R-N043R-N269I | ++ |
| G020R-S024R-S101A-N116L-E271H | ++ |
| T022R-S101G-S103A-V104I-A232V-Q245R-E271H | ++ |
| G020R-I035T-N043R | ++ |
| G020R-S024R-S101A-A114T-N116L | ++ |
| G020R-S024R-S101A-N116L-E271I | ++ |
| G020R-N043R-A114T | ++ |
| S101G-S103A-V104I-A232V-Q245R | ++ |
| G020R-N043R-L267N | ++ |
| G020R-S024R-S101A-N116L-L267N | ++ |
| G020R-S024R-V028A-S101A-N116L | ++ |
| G020R-S024R-S101A-N116L-G258R | ++ |
| G020R-N043R-G258R | ++ |
| G020R-S024R-S101A-N116L-S242L | ++ |
| G020R-S024R-S101A-N116L-P239G | ++ |
| I008N-G020R-S024R-S101A-N116L | ++ |
| G020R-S024R-S101A-N116L-V234F | ++ |
| T022R-S101G-S103A-V104I-A232V | ++ |

TABLE 2-6-continued

BMI cleaning performance of Group C3 variants.

| Sequence of GG36 Variants (BPN' numbering) | PI Relative to GG36; BMI assay, Detergent 107 at 25° C. |
|---|---|
| G020R-S024R-S101A-N116L-E271A | ++ |
| R010A-G020R-N043R | ++ |
| G020R-S024R-S101A-N116L-E271F | ++ |
| G020R-V028A-N043R | ++ |
| I008N-G020R-N043R | ++ |
| G020R-S024F-S101A-N116L | ++ |
| R010A-G020R-S024R-S101A-N116L | + |
| G020R-N043R-M222S | + |

PI = Performance Index
PI > or = 1.50 is +++; PI between 1.49 and 1.20 = ++; PI between 1.19 and 1.1 = + in Detergent Composition 107

We claim:

1. An isolated subtilisin variant, wherein said subtilisin variant is a mature form having proteolytic activity and comprises an amino acid sequence comprising a combination of amino acid substitutions at positions selected from T022R+S101G+Q245R, wherein said subtilisin variant has at least 80% amino acid identity with a *Bacillus lentus* subtilisin GG36 protease comprising the amino acid sequence shown in SEQ ID NO:2, and wherein amino acid positions of the subtilisin variant are numbered according to the numbering of corresponding amino acid positions in the amino acid sequence of *Bacillus amyloliquefaciens* subtilisin BPN' shown in SEQ ID NO:1.

2. The isolated subtilisin variant of claim 1, wherein the subtilisin variant is a subtilisin variant of *Bacillus lentus* subtilisin GG36 protease, wherein said *Bacillus lentus* subtilisin GG36 protease comprises the amino acid sequence shown in SEQ ID NO:2.

3. The isolated subtilisin variant of claim 1, wherein the total net charge of the variant is 0, +1, +2, +3, +4, +5, −1, −2, −3, −4, or −5 relative to the total net charge of the *Bacillus lentus* subtilisin GG36 protease.

4. The isolated subtilisin variant of claim 3, wherein the total net charge is obtained by one or more substitutions selected from: A001E, V004E, R010H/A, Q012E, A015D, N018D, R019H/S, V026D, K027E, N043D, R045C/T/S/P, S049D, V051E, G061E, N062D/E, N076D, N077D, S078D, S087D, A098E, S101D, S106E, G115E, G118D, N123D, S128D, P129E, S130D/E, S132D, A158E, G159D/E, S160D, S166D, R170T, N183D, N184D, N185E, R186H, S188D/E, A194E, A200D, Y209E, A215D, N204D, S212D, L217D/E, N218D, A230E, K235F, K237E, N238D, S240D, N243D, Q245D, R247L, N248D/E, K251C, N263D, N269D/E, A272D, A273E, or R275H/S, and wherein amino acid positions of the protease variant are numbered according to the numbering of corresponding amino acid positions in the amino acid sequence of *Bacillus amyloliquefaciens* subtilisin BPN' shown in SEQ ID NO:1.

5. The isolated subtilisin variant of claim 3, wherein the total net charge is obtained by one or more substitutions selected from: A001R, V004R, Q012R, P014R, H017R, N018R/K, G020K/R, T022R/K, S024R/K, G025R, D032I, D041K/L/N, N043R/K, G046R, A048R, F050R/K, P055R, S056R/K, T057R, Q059K, G061R, N076K, S078R, P086R, S087R, E089G/P/I, G097R, S099R, Q109R, G115R, G118R, S132K, S144R, G159R/K, D181C/S/T, L196K, N204K, Q206R, K235R, Q236R/K, K237R, N238R, S240R, W241R, S242R/K, V244R, Q245R/K, N248R, H249R, N252R/K, S256R, G258R, T260K, N269R/K, or E271F/H/T/L/W/R/S/I/A/G/V, and wherein amino acid positions of the protease variant are numbered according to the numbering of corresponding amino acid positions in the amino acid sequence of *Bacillus amyloliquefaciens* subtilisin BPN' shown in SEQ ID NO:1.

6. The isolated subtilisin variant of claim 1, wherein the subtilisin variant has one or more of the following characteristics: a) a Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or e) Test Method 7 performance index of at least 1.1, at least 1.2, at least 1.3, at least 1.4, at least 1.5, at least 1.6, at least 1.7, at least 1.8, at least 1.9, at least 2, from 1.1 to about 15, from 1.1 to about 10, or even from 1.1 to about 7.

7. A composition comprising at least one subtilisin variant of claim 1, wherein said composition is not a fabric and home care product.

8. The composition of claim 7, wherein said composition is a cleaning composition.

9. The composition of claim 8, wherein said cleaning composition is a granular, powder, solid, bar, liquid, tablet, gel, or paste composition.

10. The composition of claim 7, further comprising at least one bleaching agent.

11. The composition of claim 7, wherein said cleaning composition is phosphate-free.

12. The composition of claim 7, wherein said cleaning composition contains phosphate.

13. The composition of claim 7, further comprising at least one additional enzyme.

14. The composition of claim 13, wherein said at least one additional enzyme is selected from hemicellulases, cellulases, peroxidases, proteases, metalloproteases, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidases, chondroitinases, laccases, and amylases, or any combination thereof.

15. The composition of claim 7, wherein said subtilisin variant is not a cold water protease variant, wherein said cold water protease variant has one or more of the following characteristics: a) a Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or e) Test Method 7 performance index of at least 1.1, at least 1.2, at least 1.3, at least 1.4, at least 1.5, at least 1.6, at least 1.7, at least 1.8, at least 1.9, at least 2, from 1.1 to about 15, from 1.1 to about 10, or even from 1.1 to about 7.

16. A method of cleaning, comprising contacting a surface or an item with a cleaning composition comprising at least one subtilisin variant of claim 1.

17. A method of cleaning comprising contacting a surface or an item with a cleaning composition set forth in claim 7.

18. The method of claim 16, wherein said subtilisin variant is not a cold water protease variant, wherein said cold water protease variant has one or more of the following characteristics: a) a Test Method 2 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; b) a Test Method 3 performance index of at least 1.1, at least 1.2, at least 1.3, at least 1.4, at least 1.5, at least 1.6, at least 1.7, at least 1.8, at least 1.9, at least 2, from 1.1 to about 10, from 1.1 to about 8, or even from 1.1 to about 5; c) a Test Method 4 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or d) a Test Method 6 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8, or even from 1.0 to about 5; and/or e) Test Method 7 performance index of at least 1.1, at least 1.2, at least 1.3, at least 1.4, at least 1.5, at least 1.6, at least 1.7, at least 1.8, at least 1.9, at least 2, from 1.1 to about 15, from 1.1 to about 10, or even from 1.1 to about 7.

19. The isolated subtilisin variant of claim 1, wherein said variant is selected from T022R-S101G-S103A-V104I-A232V-Q245R;
T022R-S024F-S101G-S103A-V104I-A232V-Q245R-E271H;
T022R-S101G-S103A-V104I-A232V-Q245R-E271H;
T022R-S024F-S101G-S103A-V104I-A232V-Q245R-T260M;
T022R-S024F-S101G-S103A-V104I-A232V-Q245R;
T022R-S101G-S103A-V104I-A232V-P239G-Q245R;
T022R-S101G-S103A-V104I-A232V-Q245R-T260K-L267N;
T022R-S101G-S103A-V104I-S128A-A232V-Q245R;
T022R-S024F-S101G-S103A-V104I-V121F-A232V-Q245R;
T022R-S078N-S101G-S103A-V104I-N116L-A232V-Q245R;
T022R-S101G-S103A-V104I-A232V-P239G-Q245R-E271I;
T022R-S024G-G097S-S101G-S103A-V104I-Q109G-N116L-S128A-A232V-Q245R;
T022R-S024G-S078N-S101G-S103A-V104I-N116L-S128A-A232V-Q245R;
T022R-G097S-S101G-S103A-V104I-S128A-A232V-Q245R;
T022R-S024G-S078N-G097A-S101G-S103A-V104I-N116L-L217Q-A232V-Q245R;
T022R-S024G-S078N-G097S-S101G-S103A-V104I-Q109N-N116L-L217Q-A232V-Q245R;
T022R-S024G-S101G-S103A-V104I-N116L-L217Q-A232V-Q245R;
T022R-S024G-G097A-S101G-S103A-V104I-Q109G-N116L-L217Q-A232V-Q245R;
T022R-G097A-S101G-S103A-V104I-Q109G-N116L-L217Q-A232V-Q245R;

T022R-S024G-S078N-G097A-S101G-S103A-V104I-N116L-S128A-L217Q-A232V-Q245R;
T022R-S024G-G097A-S101G-S103A-V104I-N116L-S128A-L217Q-A232V-Q245R;
T022R-G097S-S101G-S103A-V104I-L217Q-A232V-Q245R;
T022R-S078N-G097S-S101G-S103A-V104I-N116L-S128A-L217Q-A232V-Q245R;
T022R-S101G-S103A-V104I-Q109N-S128A-A232V-Q245R;
T022R-S024G-G097S-S101G-S103A-V104I-S128A-L217Q-A232V-Q245R;

T022R-S101G-S103A-V104I-A232V-Q245R-E271A;

R010A-T022R-S024F-S101G-S103A-V104I-A232V-Q245R-L267N-E271H;

T022R-S101G-S103A-V104I-A232V-Q245R-E271F;

T022R-S101G-S103A-V104I-A232V-Q245R-E271H;

T022R-S078N-G097S-S101G-S103A-V104I-Q109G-S128A-A232V-Q245R; and

T022R-S101G-S103A-V104I-M222S-A232V-Q245R-E271H.

* * * * *

SEQUENCE LISTING

<160> NUMBER OF SEQ ID NOS: 5

<210> SEQ ID NO 1
<211> LENGTH: 275
<212> TYPE: PRT
<213> ORGANISM: Bacillus amyloliquefaciens

<400> SEQUENCE: 1

```
Ala Gln Ser Val Pro Tyr Gly Val Ser Gln Ile Lys Ala Pro Ala Leu
 1               5                  10                  15

His Ser Gln Gly Tyr Thr Gly Ser Asn Val Lys Val Ala Val Ile Asp
             20                  25                  30

Ser Gly Ile Asp Ser Ser His Pro Asp Leu Lys Val Ala Gly Gly Ala
         35                  40                  45

Ser Met Val Pro Ser Glu Thr Asn Pro Phe Gln Asp Asn Asn Ser His
 50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
```

275

<210> SEQ ID NO 2
<211> LENGTH: 269
<212> TYPE: PRT
<213> ORGANISM: Bacillus lentus

<400> SEQUENCE: 2

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 3
<211> LENGTH: 1143
<212> TYPE: DNA
<213> ORGANISM: Bacillus lentus

<400> SEQUENCE: 3

```
gtgagaagca aaaaattgtg gatcgtcgcg tcgaccgcac tactcatttc tgttgctttc      60
agttcatcga tcgcatcggc tgctgaagaa gcaaaagaaa aatatttaat tggctttaat     120
gagcaggaag ctgtcagtga gtttgtagaa caagtagagg caaatgacga ggtcgccatt     180
ctctctgagg aagaggaagt cgaaattgaa ttgcttcatg aatttgaaac gattcctgtt     240
ttatccgttg agttaagccc agaagatgtg gacgcgcttg agctcgatcc agcgatttct     300
```

```
tatattgaag aggatgcaga agtaacgaca atggcgcaat cagtgccatg gggaattagc    360
cgtgtgcaag ccccagctgc ccataaccgt ggattgacag gttctggtgt aaaagttgct    420
gtcctcgata caggtatttc cactcatcca gacttaaata ttcgtggtgg cgctagcttt    480
gtaccagggg aaccatccac tcaagatggg aatgggcatg gcacgcatgt ggccgggacg    540
attgctgctt taaacaattc gattggcgtt cttggcgtag cgccgagcgc ggaactatac    600
gctgttaaag tattaggggc gagcggttca ggttcggtca gctcgattgc ccaaggattg    660
gaatgggcag ggaacaatgg catgcacgtt gctaatttga gtttaggaag cccttcgcca    720
agtgccacac ttgagcaagc tgttaatagc gcgacttcta gaggcgttct tgttgtagcg    780
gcatctggaa attcaggtgc aggctcaatc agctatccgg cccgttatgc gaacgcaatg    840
gcagtcggag ctactgacca aaacaacaac cgcgccagct tttcacagta tggcgcaggg    900
cttgacattg tcgcaccagg tgtaaacgtg cagagcacat acccaggttc aacgtatgcc    960
agcttaaacg gtacatcgat ggctactcct catgttgcag gtgcagcagc ccttgttaaa   1020
caaaagaacc catcttggtc caatgtacaa atccgcaatc atctaaagaa tacggcaacg   1080
agcttaggaa gcacgaactt gtatggaagc ggacttgtca atgcagaagc tgcaactcgt   1140
taa                                                                 1143
```

<210> SEQ ID NO 4
<211> LENGTH: 380
<212> TYPE: PRT
<213> ORGANISM: Bacillus lentus

<400> SEQUENCE: 4

```
Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Ser Gly Ser Val Ser Ser Ile Ala Gln Gly Leu Glu Trp Ala Gly
    210                 215                 220
```

```
Asn Asn Gly Met His Val Ala Asn Leu Ser Leu Gly Ser Pro Ser Pro
225             230             235             240

Ser Ala Thr Leu Glu Gln Ala Val Asn Ser Ala Thr Ser Arg Gly Val
            245             250             255

Leu Val Val Ala Ala Ser Gly Asn Ser Gly Ala Gly Ser Ile Ser Tyr
            260             265             270

Pro Ala Arg Tyr Ala Asn Ala Met Ala Val Gly Ala Thr Asp Gln Asn
        275             280             285

Asn Asn Arg Ala Ser Phe Ser Gln Tyr Gly Ala Gly Leu Asp Ile Val
    290             295             300

Ala Pro Gly Val Asn Val Gln Ser Thr Tyr Pro Gly Ser Thr Tyr Ala
305             310             315             320

Ser Leu Asn Gly Thr Ser Met Ala Thr Pro His Val Ala Gly Ala Ala
            325             330             335

Ala Leu Val Lys Gln Lys Asn Pro Ser Trp Ser Asn Val Gln Ile Arg
            340             345             350

Asn His Leu Lys Asn Thr Ala Thr Ser Leu Gly Ser Thr Asn Leu Tyr
            355             360             365

Gly Ser Gly Leu Val Asn Ala Glu Ala Ala Thr Arg
        370             375             380

<210> SEQ ID NO 5
<211> LENGTH: 4
<212> TYPE: PRT
<213> ORGANISM: Artificial Sequence
<220> FEATURE:
<223> OTHER INFORMATION: synthetic reagent

<400> SEQUENCE: 5

Ala Ala Pro Phe
1
```